United States Patent
Chen et al.

(10) Patent No.: US 10,711,004 B2
(45) Date of Patent: Jul. 14, 2020

(54) OXADIAZOLE TRANSIENT RECEPTOR POTENTIAL CHANNEL INHIBITORS

(71) Applicant: Genentech, Inc., South San Francisco, CA (US)

(72) Inventors: Huifen Chen, South San Francisco, CA (US); Brian Safina, South San Francisco, CA (US); Daniel Shore, South San Francisco, CA (US); Jack Terrett, South San Francisco, CA (US); Elisia Villemure, South San Francisco, CA (US); Matthew Volgraf, South San Francisco, CA (US); Stuart Ward, Harlow (GB); Aijun Lu, Beijing (CN); Robin Larouche-Gauthier, Montreal (CA); Francis Beaumier, Montreal (CA); Martin Dery, Montreal (CA); Lea Constantineau-Forget, Montreal (CA); Chantal Grand-Maitre, Montreal (CA); Luce Lepissier, Montreal (CA)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/558,718

(22) Filed: Sep. 3, 2019

(65) Prior Publication Data
US 2020/0002340 A1    Jan. 2, 2020

Related U.S. Application Data

(63) Continuation of application No. PCT/EP2018/055690, filed on Mar. 7, 2018.

(51) Int. Cl.
*C07D 473/30* (2006.01)
*C07D 471/04* (2006.01)
*C07D 487/04* (2006.01)
*C07D 473/08* (2006.01)

(52) U.S. Cl.
CPC ......... *C07D 473/30* (2013.01); *C07D 471/04* (2013.01); *C07D 473/08* (2013.01); *C07D 487/04* (2013.01)

(58) Field of Classification Search
CPC .. C07D 473/30; C07D 471/04; C07D 473/08; C07D 487/04
USPC ....................................................... 514/249
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regan |
| 4,544,545 A | 10/1985 | Ryan et al. |
| 5,004,697 A | 4/1991 | Pardridge et al. |
| 5,112,596 A | 5/1992 | Malfroy-Camine |
| 5,268,164 A | 12/1993 | Kozarich et al. |
| 5,506,206 A | 4/1996 | Kozarich et al. |
| 5,686,416 A | 11/1997 | Kozarich et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0162695 A1 | 8/2003 | Schatzberg et al. |
| 2004/0131692 A1 | 7/2004 | Kreuter et al. |
| 2004/0204354 A1 | 10/2004 | Nelson et al. |
| 2005/0089473 A1 | 4/2005 | Black et al. |
| 2005/0124533 A1 | 6/2005 | Schatzberg et al. |
| 2015/0376173 A1 | 12/2015 | Paek et al. |

FOREIGN PATENT DOCUMENTS

| | | |
|---|---|---|
| EP | 0102324 A2 | 3/1984 |
| EP | 0133988 A2 | 8/1984 |
| EP | 0438230 A2 | 7/1991 |
| WO | 2008/119741 A2 | 10/2008 |
| WO | 2011/114181 A1 | 9/2011 |
| WO | 2017/060488 A1 | 4/2017 |
| WO | 2018/096159 A1 | 5/2018 |

OTHER PUBLICATIONS (Database PubChem Compound [Online] NCBI, Sep. 8, 2005, Database accession No. CID 3437423 abstract).
Ackley, David C., et al. Optimization in Drug Discovery: In Vitro Methods "Metabolic Stability Assessed by Liver Microsomes and Hepatoeytes" Yan, Zhengyin, ed., Totowa, New Jersey:Humana Press,:151-162 (Jan. 1, 2004).
Agopyan, N., et al., "TRPV1 receptors mediate particulate matter-induced apoptosis" Am J Physiol Lung Cell Mol Physiol 286:L563-L572 (Oct. 30, 2003).
Agopyan, N., et al., "Vanilloid receptor activation by 2- and 10-μm particles induces responses leading to apoptosis in human airway epithelial cells" Toxicol Appl Pharm 192:21-35 (May 28, 2003).
Ansel, et al. Ansel's Pharmaceutical Dosage Forms And Drug Delivery Systems (Table of Contents only, in 6 pages), Allen et al., 8th edition, Philadelphia, PA:Lippincott Williams & Wilkins, ( 2004).

(Continued)

*Primary Examiner* — Kristin A Vajda
(74) *Attorney, Agent, or Firm* — Robert C. Hall

(57) ABSTRACT

The invention relates to compounds of formula I:

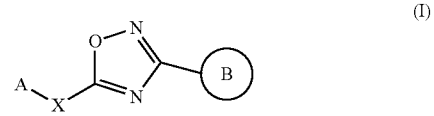

and pharmaceutically acceptable salts thereof. In addition, the present invention relates to methods of manufacturing and methods of using the compounds of formula I as well as pharmaceutical compositions containing such compounds. The compounds may be useful in treating diseases and conditions mediated by TRPA1, such as pain.

23 Claims, No Drawings

(56) References Cited

OTHER PUBLICATIONS

Asai, Hideaki, et al., "Heat and mechanical hyperalgesia in mice model of cancer pain" Pain 117:19-29 (May 3, 2005).
Barton, N.J., et al., "Attenuation of experimental arthritis in TRPV1R knockout mice" Exp Mol Pathol 81:166-170 (Jun. 16, 2006).
Bobo et al., "Convection-enhanced delivery of macromolecules in the brain" PNAS Sci. USA 91:2076-2080 ( 1994).
Bolcskei, Kata, et al., "Investigation of the role of TRPV1 receptors in acute and chronic nociceptive processes using gene-deficient mice" Pain 117:368-376 (Jun. 27, 2005).
Bundgaard A Textbook of Drug Design and Development; Chapter 5 "Design and Application of Prodrugs":113-191( 1991).
Bundgaard et al., "(C) Means to Enhance Penetration (1) Prodrugs as a means to improve the delivery of peptide drugs" Adv Drug Deliver Rev 8:1-38 ( 1992).
Bundgaard, "Design of prodrugs: Bioreversible derivatives for various functional groups and chemical entities" Design of Prodrugs:1 ( 1985).
Bundgaard, "Formation of Prodrugs of Amines, Amides, Ureides and Imides" Methods in Enzymology 112:347 ( 1985).
CAS Registry Database, 1069804-72-3, Nov. 2, 2008.
CAS Registry Database, 1309241-92-6, Jun. 13, 2011.
CAS Registry Database, 1309344-12-4, Jun. 14, 2011.
CAS Registry Database, 1381342-13-7, abstract (Database Registry [Online] Chemical Abstracts Service, Columbus, Ohio, US; Jul. 4, 2012 Database accession No. 1381342-13-7 abstract), pp. 1 Jul. 4, 2012.
CAS Registry Database, 887037-04-9, abstract (Database Registry [online] Chemical Abstracts Service, Columbus, Ohio, US; Jun. 7, 2006, Database accession No. 887037-04-9 abstract) Jun. 7, 2006.
Chan, C.L.H., et al., "Sensory fibres expressing capsaicin receptor TRPV1 in patients with rectal hypersensitivity and faecal urgency" Lancet 361:385-391 (Feb. 1, 2003).
Coffey, S. Rodd's Chemistry of Carbon Compounds Coffey, S., Second edition, Elsevier B.V.:Elsevier B.V., vol. I-IV ( 2008).
Database STN RN1309116-79-7, (STN Registry Database No. RN1309116-79-7, registry entry compound, Jun. 13, 2011), pp. 1Creation Date Jun. 13, 2011.
De Yebenes et al., "Continuous Intracerebroventricular Infusion of Dopamine and Dopamine Agonists Through a Totally Implanted Drug Delivery System in Animal Models of Parkinson's Disease" Movement Disorders 2(3):143-158 ( 1987).
Derong Ding et al., "Exploration of the structure-activity relationship of 1,2,4-oxadiazole antibiotics" Bioorg Med Chem Lett 25(21):4854-4857 (Nov. 1, 2015).
Dinis, Paulo, et al., "Anandamide-Evoked Activation of Vanilloid Receptor 1 Contributes to the Development of Bladder Hyperreflexia and Nociceptive Transmission to Spinal Dorsal Horn Neurons in Cystitis" J Neurol Sci 24(50):11253-11263 (Dec. 15, 2004).
Eppstein, D. et al., "Biological activity of liposome-encapsulated murine interferon y is mediated by a cell membrane receptor" PNAS 82(11):3688-3692 (Jun. 1, 1985).
Fleisher et al., "Improved oral drug delivery: solubility limitations overcome by the use of prodrugs" Adv Drug Deliver Rev 19:115-130 ( 1996).
Gennaro et al. Remington: The Science and Practive of Pharmacy (Press), Philadelphia: Lippincott, Williams & Wilkins, ( 2000).
Geppetti, P., et al., "Activation and sensitisation of the vanilloid receptor: role in gastrointestinal inflammation and function" Brit J Pharmacol 141:1313-1320 (Mar. 29, 2004).
Ghilardi, J.R., et al., "Selective Blockade of the Capsaicin Receptor TRPV1 Attenuates Bone Cancer Pain" J Neurol Sci 25(12):3126-3131 (Mar. 23, 2005).
Gill et al., "Direct Brain Infusion of Glial Cell Line-Derived Neurotrophic Factor in Parkinson Disease" Nat Med. 9:589-595 (Mar. 31, 2003).
Goadsby, P. J., "Post-triptan Era for the Treatment of Acute Migraine" Curr Pain Head Reports 8:393-398 (Jan. 1, 2004).

Harbaugh, "Intracerebroventricular cholinergic drug administration in Alzheimer's disease: preliminary results of a double-blind study" J. Neural. Transm. 24 Suppl.:271-277 ( 1987).
Ho Fiesers' Reagents for Organic Synthesis (Table of Contents, in 5 pages), Hoboken, New Jersey: John Wiley & Sons, Inc., vol. 23 ( 2007).
Honore, P., et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats" J Pharmacol Exp Ther 314(1):410-421 (Apr. 14, 2005).
Hwang et al., "Hepatic uptake and degradation of unilamellar sphingomyelin/cholesterol liposomes: A kinetic study" PNAS Sci. USA 77(7):4030-4034 ( 1980).
"International Preliminary Report on Patentability—PCT/EP2017/080571":pp. 1-28 (dated Feb. 7, 2018).
"International Preliminary Report on Patentability—PCT/EP2018/055690":pp. 1-9 (dated Sep. 19, 2019).
"International Search Report—PCT/EP2017/080571":pp. 1-5 (dated Jan. 26, 2017).
"International Search Report—PCT/EP2018/055690":pp. 1-6 (dated May 15, 2018).
Kakeya et al., "Studies on Prodrugs of Cephalosporins.I. ///superscript:1)/// Synthesis and Biological Properties of Glycyloxybenzoyloxymethyl and Glycylaminobenzoyloxymethyl Esters of 7β-[2-(2-Aminothiazol-4yl)-(Z)-2-methoxyiminoacetamido]-3-3-methyl-3-cephem-4-carboxylic Acid" Chem. Pharm. Bull. 32(2):692-698 ( 1984).
Kimball, E.S., et al., "Vanilloid receptor 1 antagonists attenuate disease severity in dextran sulphate sodium-induced colitis in mice" Neurogastroent Motil 16:811-818 (Jan. 5, 2004).
Kosugi, Masafumi, et al., "Activation of TRPA1 Channel Facilitates Excitatory Synaptic Transmission in Substantia Gelatinosa Neurons of the Adult Rat Spinal Cord" J Neurol Sci 27(16):4443-4451 (Apr. 18, 2007).
Kremeyer, Barbara, et al., "A Gain-of-Function Mutation in TRPA1 Causes Familial Episodic Pain Syndrome" Neuro 66:671-680 (Jun. 10, 2010).
Lalloo, Umesh G., et al., "Capsazepine inhibits cough induced by capsaicin and citric acid but not by hypertonic saline in guinea pigs" J Appl Physiol:1082-1087 (May 23, 1995).
Langer et al., "Biocompatibility of polymeric delivery systems for macromolecules" J Biomed Mater Res 15:267-277 ( 1981).
Menendez, L., et al., "Analgesic effects of capsazepine and resiniferatoxin on bone cancer pain in mice" Neurosci Lett 393:70-73 (Sep. 19, 2005).
Monge et al., "The Reaction of 2-Indolecarbohydrazones With Ethoxycarbonylchloride. New Syntheses of 2,3-Dihydro-2-oxo-1,3,4-oxadiazoles and 1,2,3,4-Tetrahydro-4-oxo-5H-pyridazino [4,5-b]indoles" J Heterocyclic Chem 21(2):397-400 (Jan. 1, 1984).
Musser et al., "Synthesis of 2-/2,3-Dihydro-2-oxo-1,3,4-oxadiazol-5-yl) Benzo Heterocyles. A Novel Series of Orally Active Antiallergic Agents" J. Med. Chem. 27:121-125 (Jan. 1, 1984).
Neuwelt, E. A. Implications of the Blood-Brain Barrier and Its Manipulation Neuwelt, E.A., ed., Plenum Publishing Corporation-Springer, vol. vols. 1-2:1-434, (Jan. 1, 1989).
Nielsen, N., et al., "Glycolamide Esters as Biolabile Prodrugs of Carboxylic Acid Agents: Synthesis, Stability, Bioconversion, and Physicochemical Properties" J Pharmacol Sci 77(4):285 (Apr. 1, 1988).
Notari, Robert, et al. Methods of Enzymology: Drug and Enzyme Targeting "Theory and Practice of Prodrug Kinetics" Widder, Kenneth J., eds, First edition, Waltham, MA: Academic Press, vol. 112:309-396 (Jun. 11, 1985).
Papanastassiou et al., "The Potential for Efficacy of The Modified (ICP 34.5) Herpes Simplex Virus HSV1716 Following Intratumoural Injection into Human Malignant Glioma: A Proof of Principle Study" Gene Ther 9:398-406 (Apr. 2, 2002).
Patel, S., et al., "I 2 mediated synthesis of 5-substituted-3-methyl/benzyl-1,3,4-oxadiazol-2(3H)-ones via sequential condensation/oxidative cyclization and rearrangement" Bioorg Chem 14(24):5683-5689 (Jan. 1, 2016).

(56) References Cited

OTHER PUBLICATIONS

Pomonis, J.D., et al., "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain" J Pharmacol Exp Ther 306(1):387-393 (Apr. 31, 2003).

Remington Remington's Pharmaceutical Sciences (Table of Contents, total in 6 pages), Osol et al., 15th edition, Easton, PA: Mack Publishing Company, ( 1975).

Robinson et al., "Discovery of the Hemifumarate and (α-L-Alanyloxy)methyl Ether as Prodrugs of an Antirheumatic Oxindole: Prodrugs for the Enolic OH Group" J. Med. Chem. 39:10-18 ( 1996).

Rowe. R. C. et al. Handbook of Pharmaceutical Excipients, [GB] "Chemical Industry Press" (in Chinese with English Abstract),:137-139, 530-532,667-669, 2001.

Sanchez, Maria, et al., "Expression of the transient receptor potential vanilloid 1 (TRPV1) in LNCaP and PC-3 prostate cancer cells and in human prostate tissue" Eur J Pharmacol 515:20-27 (Apr. 8, 2005).

Schenkel et al., "Optimization of a Novel Quinazolinone-Based Series of Transient Receptor Potential A1 (TRA1) Antagonists Demonstrating Potent in Vivo Activity" J Med Chem 59(6):2794-2809 (Mar. 24, 2016).

Sculptoreanu, A., et al., "Protein kinase C contributes to abnormal capsaicin responses in DRG neurons from cats with feline interstitial cystitis" Neurosci Lett 381:42-46 (Jan. 28, 2005).

Sidman, K., et al., "Controlled Release of Macromolecules and Pharmaceuticals from Synthetic Polypeptides Based on Glutamic Acid" Biopolymers 22:547-556 ( 1983).

Sugimoto, O., et al., "The use of a Mitsunobu reagent for the formation of heterocycles: a simple method for the preparation of 3-alkyl-e-aryl-1,3,4-oxadiazol-2(3H)-ones from carboxylic acids" Chem Commun 50(55):7314-7317 (Jan. 1, 2014).

Szabo, A., et al., "Role of Transient Receptor Potential Vanilloid 1 Receptors in Adjuvant-Induced Chronic Arthritis: In Vivo Study Using Gene-Deficient Mice" J Pharmacol Exp Ther 314(1):111-119 (Apr. 5, 2005).

Wael, et al., "Synthesis and Antimicrobial Activity of New 1,2,3-Triazolopyrimide Derivatives and Their Glycoside and Acyclic Nucleoside Analogs" J Heterocyclic Chem 49(3):607-612 (May 1, 2012).

Walker, Katherine, et al., "The VR1 Antagonist Capsazepine Reverses Mechanical Hyperalgesia in Models of Inflammatory and Neuropathic Pain" J Pharmacol Exp Ther 304(1):56-62 (Jan. 1, 2003).

Wei, Hong, et al., "Spinal transient receptor potential ankyrin 1 channel contributes to central pain hypersensitivity in various pathophysiological conditions in the rat" Pain 152:582-591 (Nov. 29, 2010).

Wei, Hong, et al., "Spinal TRPA1 ion channels contribute to cutaneous neurogenic inflammation in the rat" Neurosci Lett 479:253-256 (May 23, 2010).

Xu, Li, et al., "Discovery and Modification of in Vivo Active Nrf2 Hits Identification and Structure-Activity Relationship Study" J Med Chem 58(14):5419-5436 (Jul. 23, 2015).

Yiangou, Y., et al., "Vanilloid receptor 1 immunoreactivity in inflamed human bowel" Lancet 357:1338-1339 (Apr. 28, 2001).

OXADIAZOLE TRANSIENT RECEPTOR POTENTIAL CHANNEL INHIBITORS

CROSS REFERENCE TO RELATED APPLICATIONS

This application is a continuation of International Application No. PCT/EP2018/055690 filed on Mar. 7, 2018, which claims the priority of International Application Nos. PCT/CN2017/075843 filed on Mar. 7, 2017 and PCT/CN2018/074543 filed on Jan. 30, 2018, the disclosures of which are incorporated herein by reference.

FIELD OF THE INVENTION

The present invention relates to oxadiazole compounds, their manufacture, pharmaceutical compositions containing them and their use as Transient Receptor Potential (TRP) cation channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. Transient receptor potential cation channel, subfamily A, member 1 (TRPA1) is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a chemosensor.

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress (e.g., 4-hydroxynonenal and related compounds) activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., J. Neurosci 27, (2007) 4443-4451; Kremayer et al., Neuron 66 (2010) 671-680; Wei et al., Pain 152 (2011) 582-591); Wei et al., Neurosci Lett 479 (2010) 253-256)), providing additional rationale for the utility of small molecule TRPA1 inhibitors in the treatment of pain disorders.

BRIEF DESCRIPTION OF THE INVENTION

In some embodiments, a compound of formula (I), stereoisomers thereof, tautomers thereof, and salts thereof are provided:

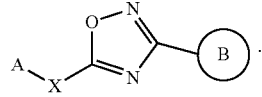

A is selected from substituted and unsubstituted 6-6 fused bicyclic heteroaryl, substituted and unsubstituted 5-6 fused bicyclic heteroaryl, and substituted and unsubstituted 6-5 fused bicyclic heteroaryl. X is selected from a bond, $C_{1-4}$ alkylene, —O—, —S—, —SO$_2$—, and —N(R$^1$)—, wherein R$^1$ is selected from H and $C_{1-6}$ alkyl. B is selected from: (a) substituted and unsubstituted $C_{4-6}$ cycloalkyl wherein, when substituted, the bond to the oxadiazole moiety and the bond to the substituent are on other than adjacent ring carbon atoms; (b) substituted and unsubstituted fused bicyclic bound to the oxadiazole moiety by a carbon-carbon bond; and (c) substituted and unsubstituted fused tricyclic.

In other embodiments, the following compounds, stereoisomers thereof, and pharmaceutically acceptable salts thereof are provided:

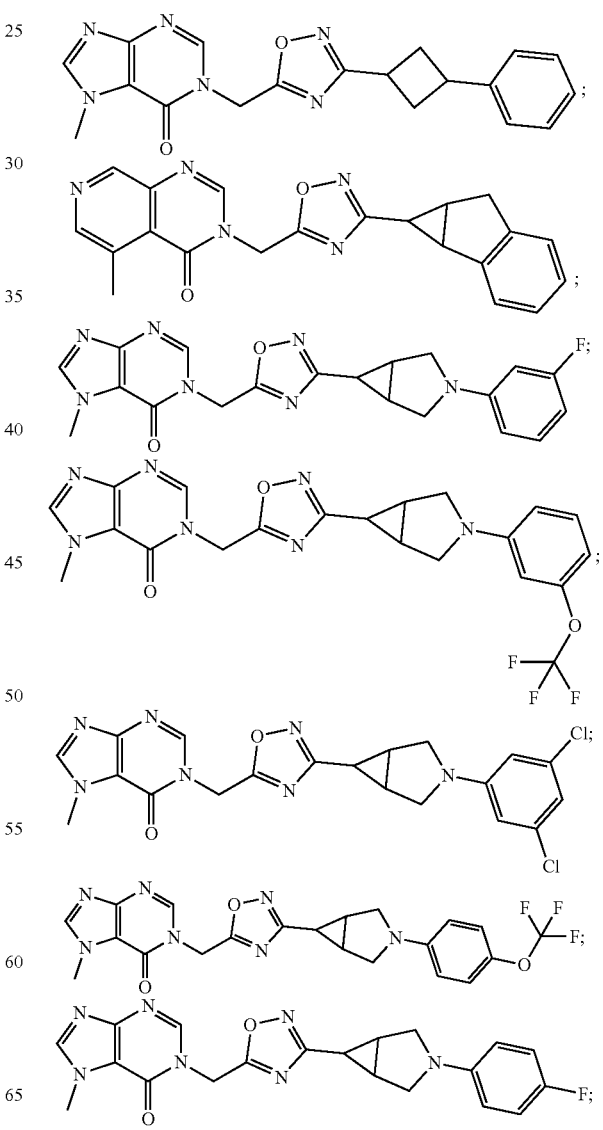

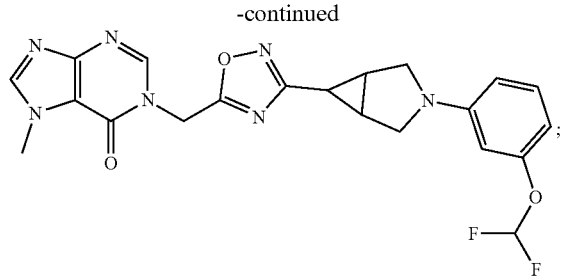
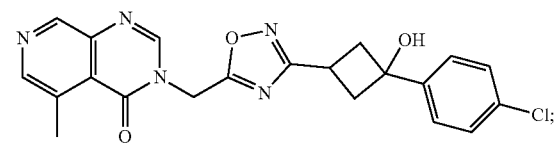
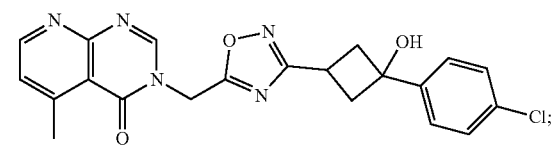
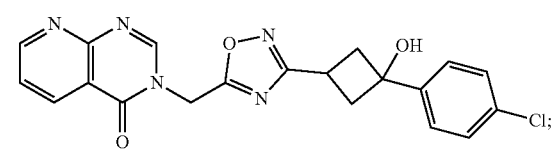
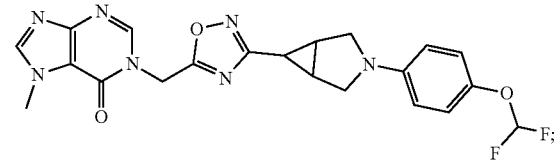
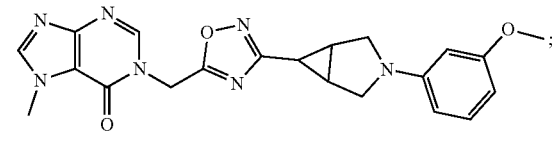
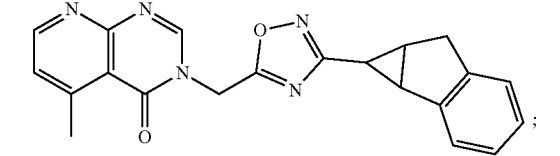
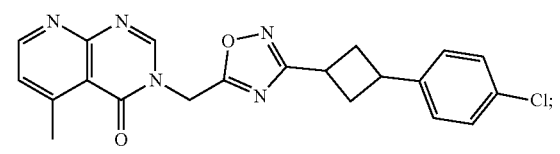
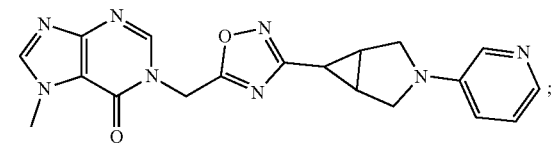
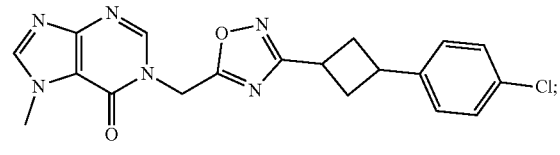
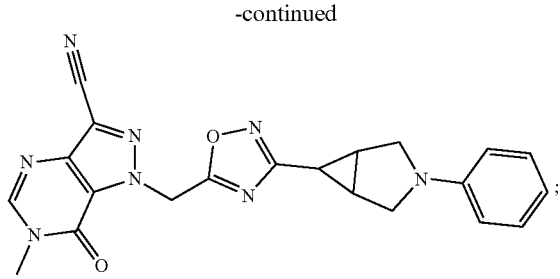
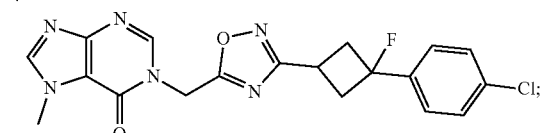
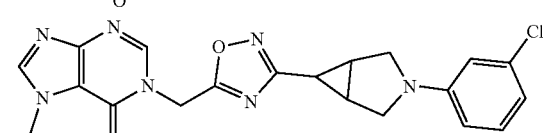
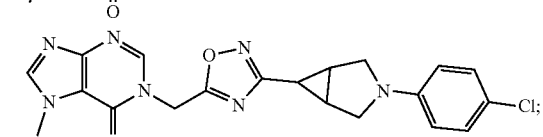
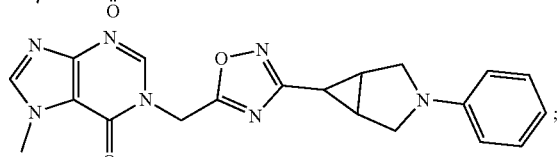
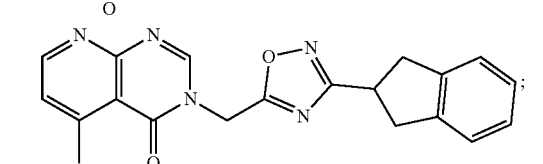
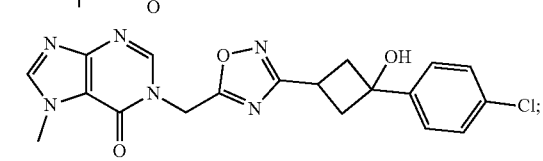
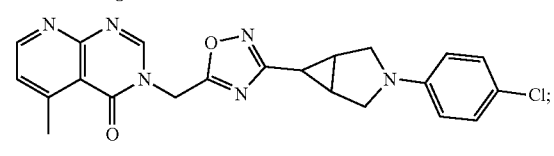
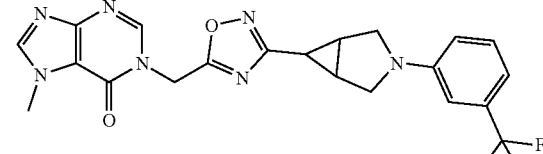
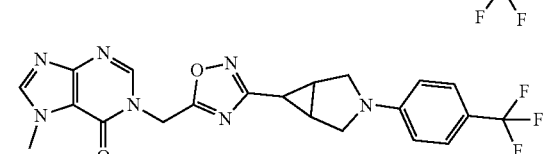
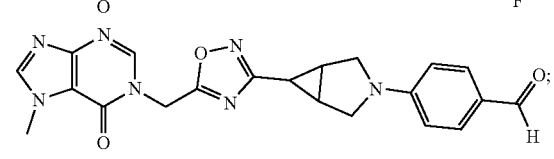

-continued
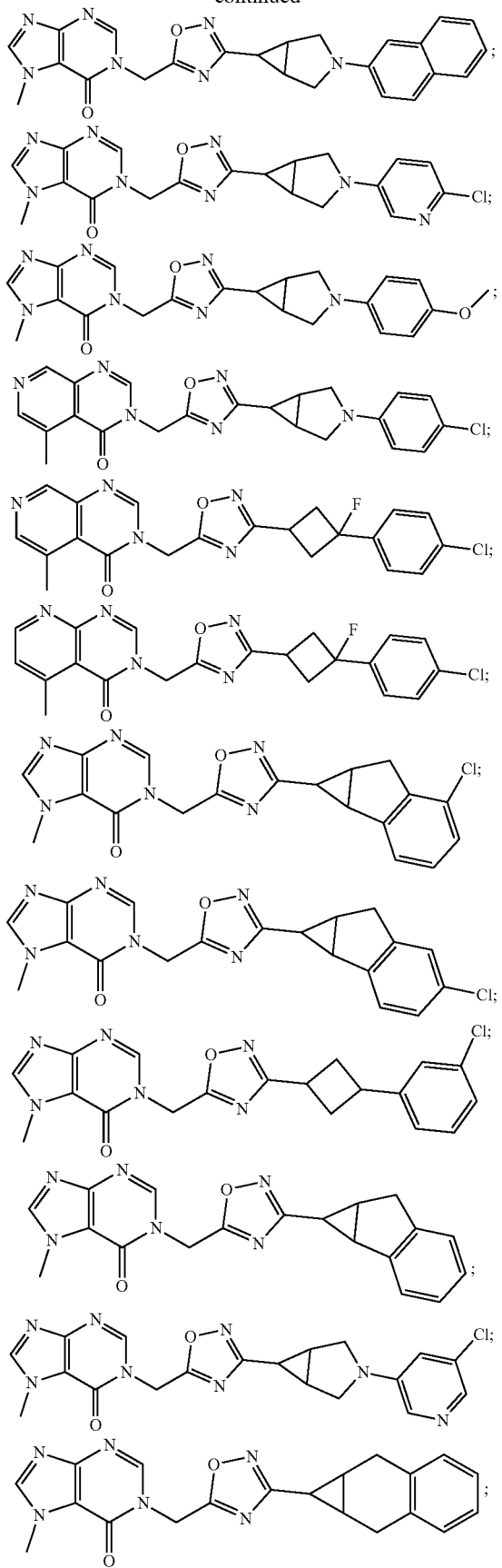
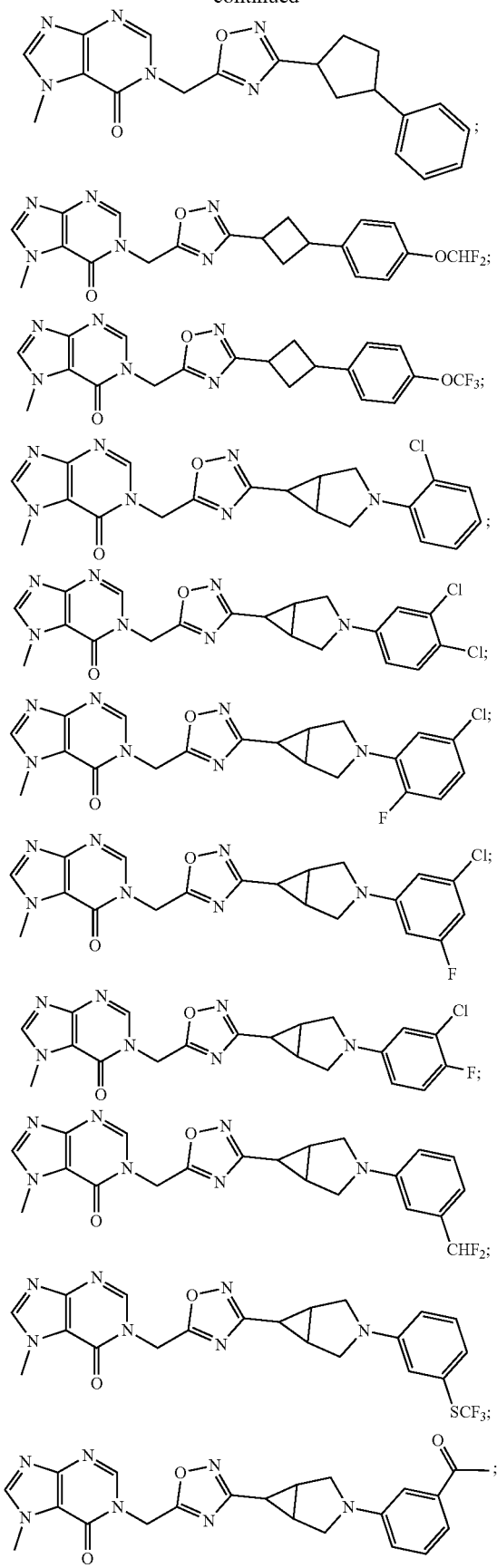

7
-continued
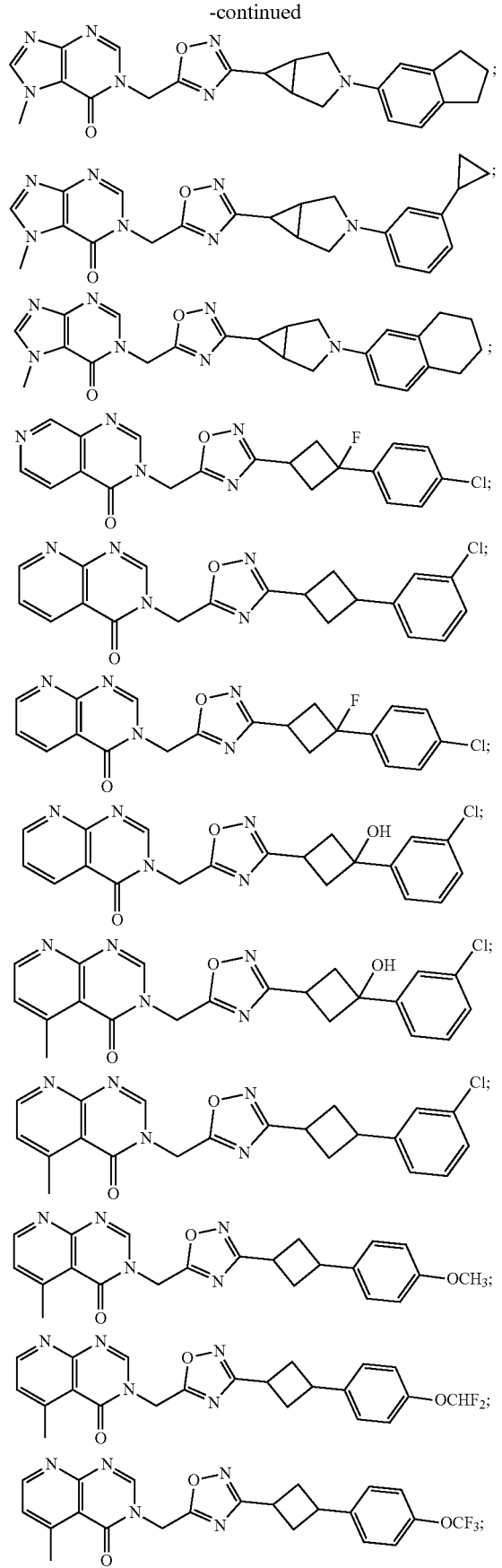
8
-continued
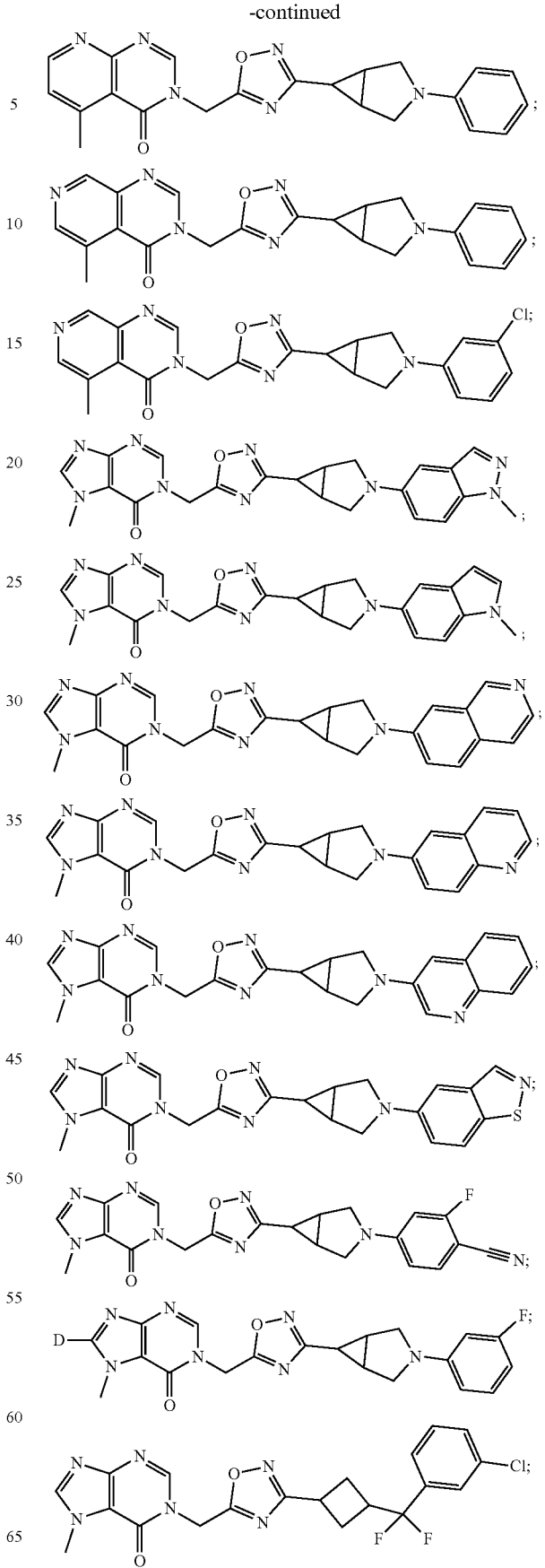

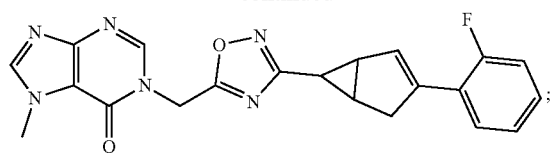;
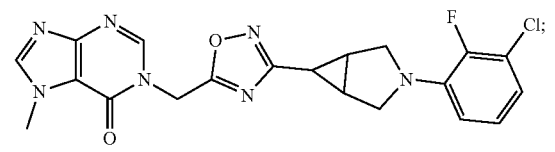;
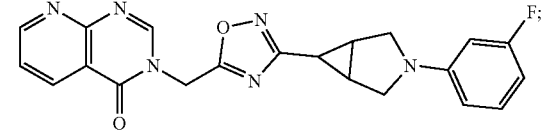;
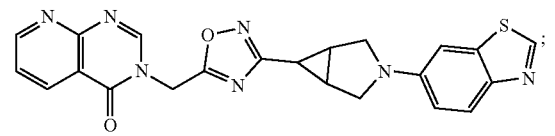;
;
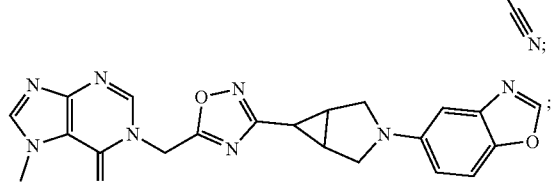;
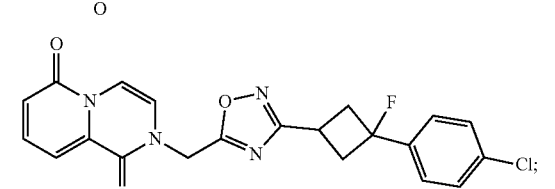;
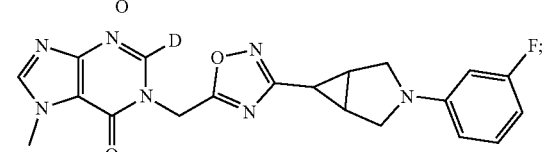;
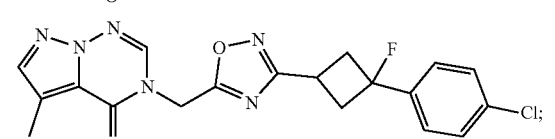;
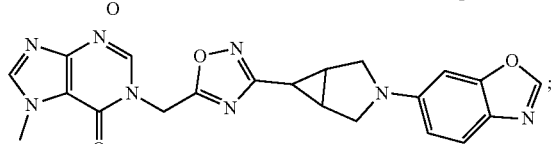;
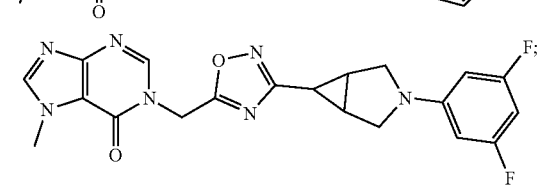
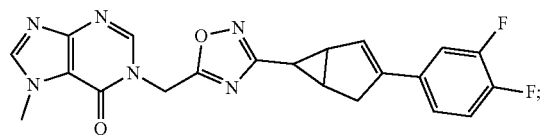;
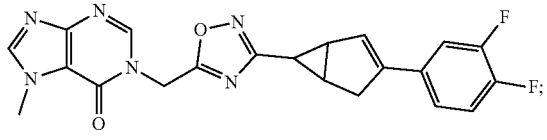;
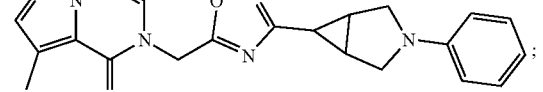;
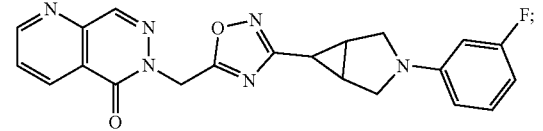;
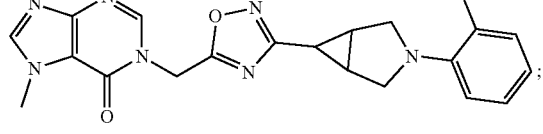;
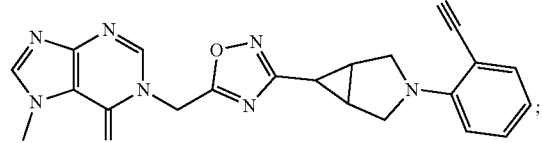;
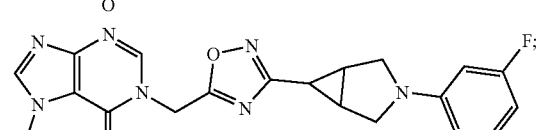;
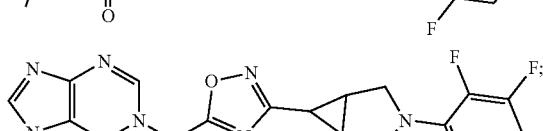;
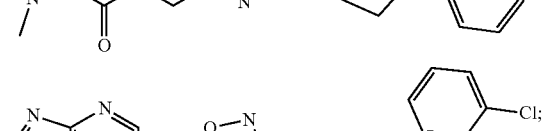;
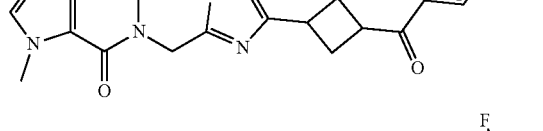;
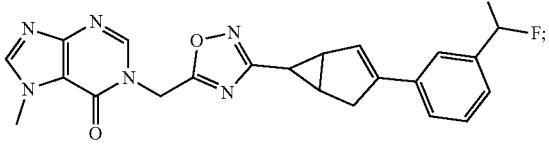;
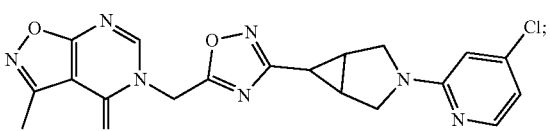;
;

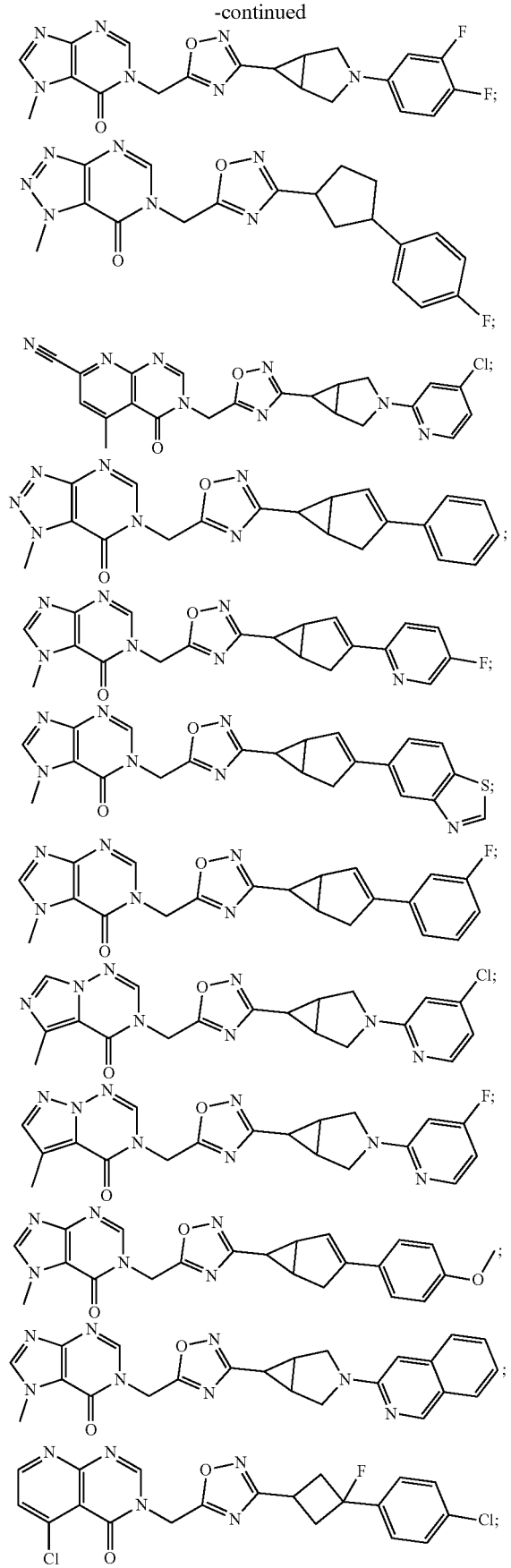
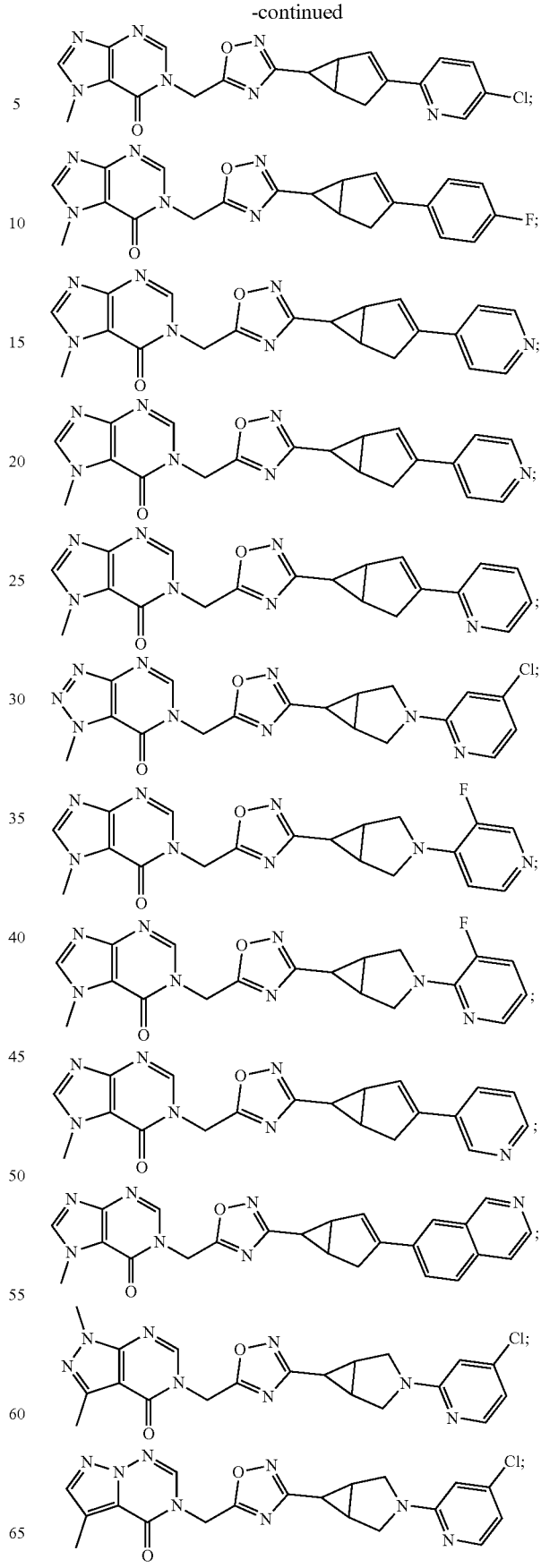

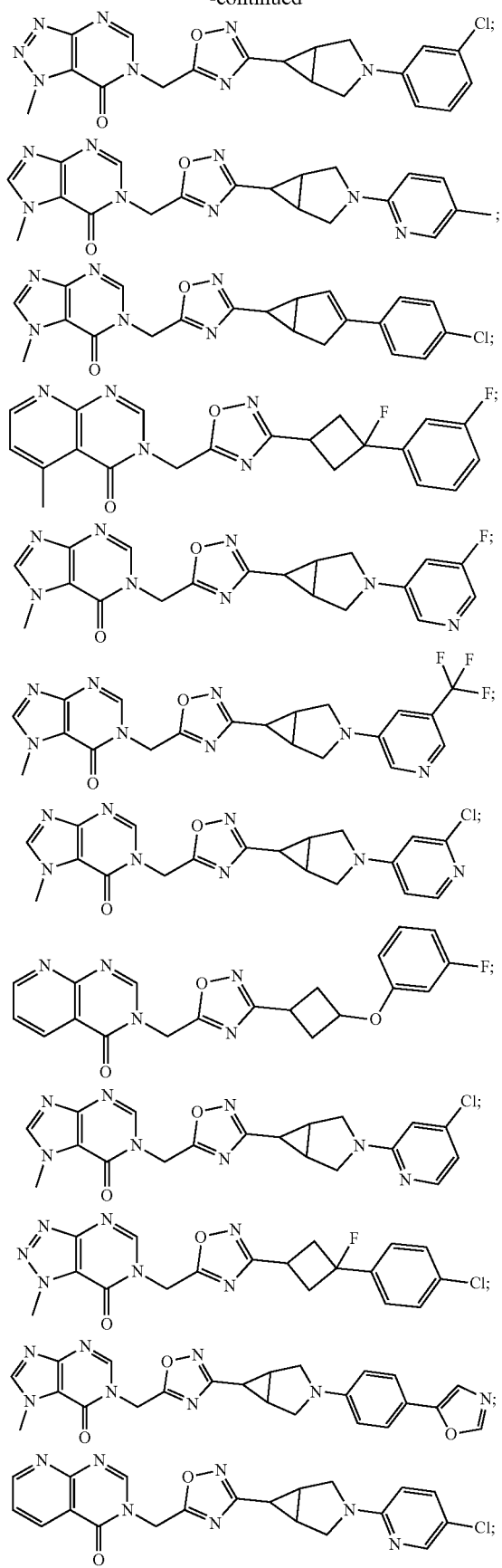
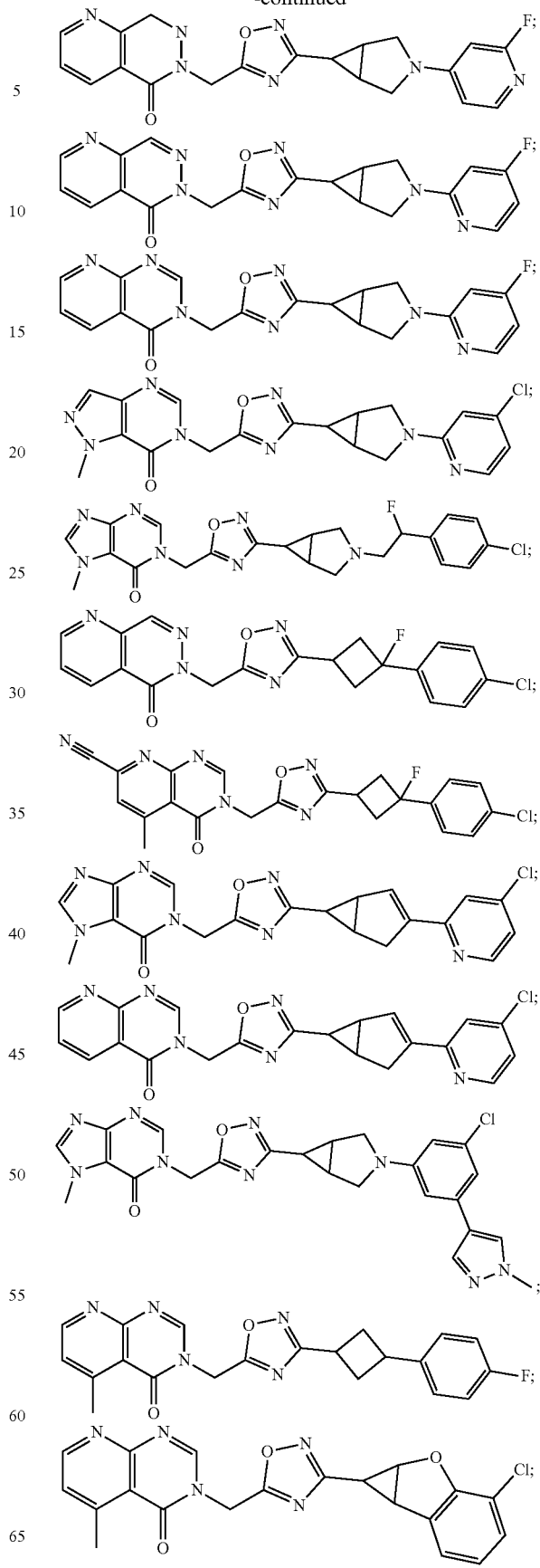

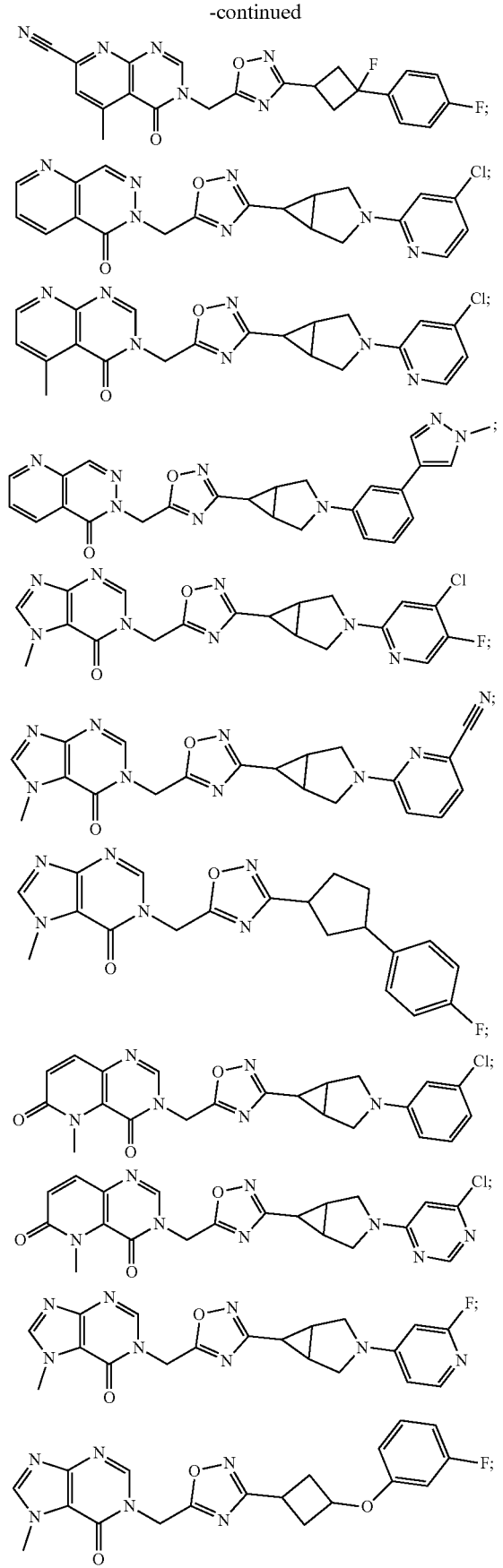
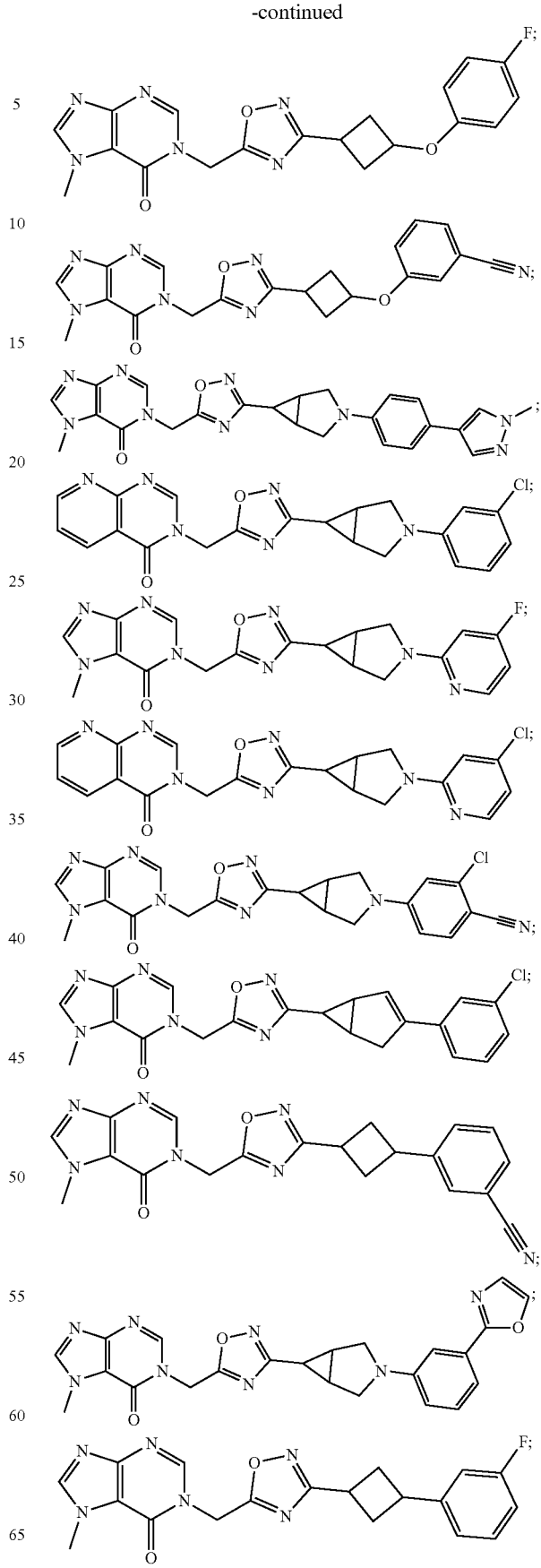

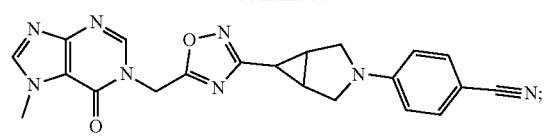
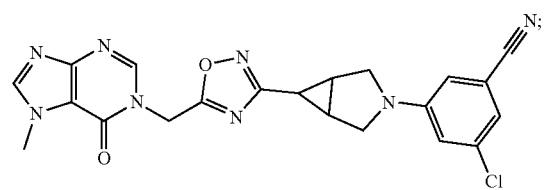
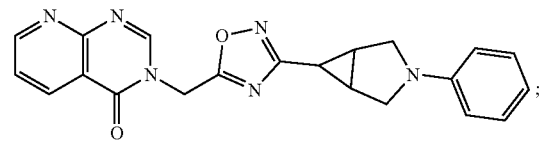
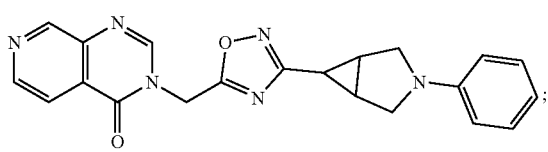
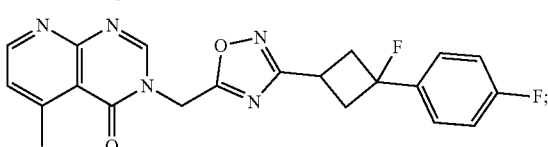
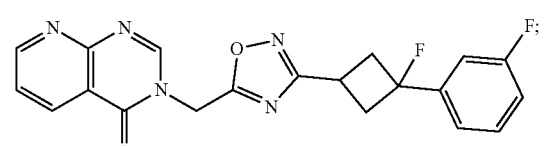
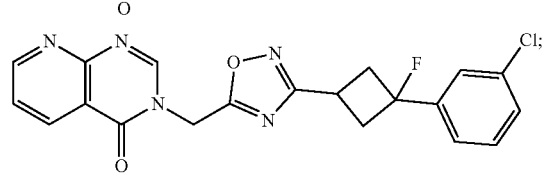
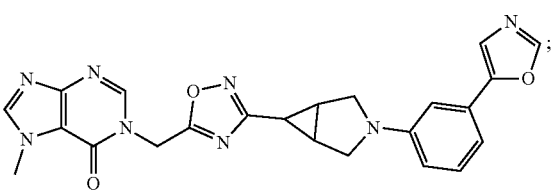
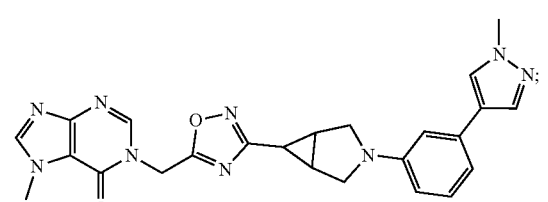
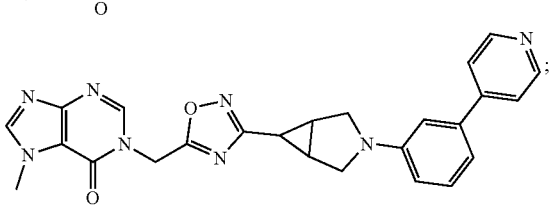
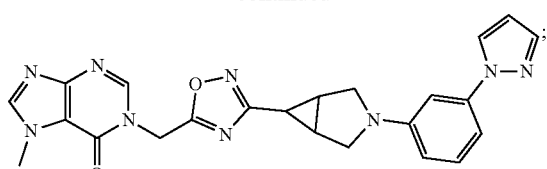
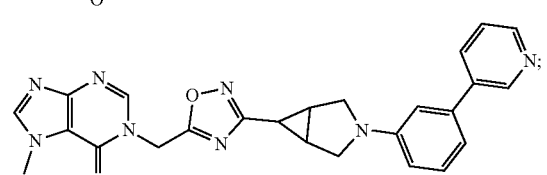
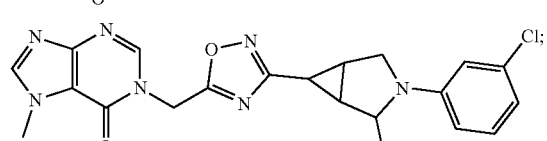
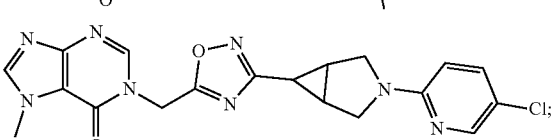
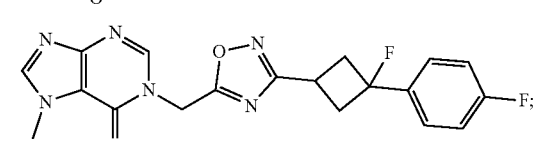
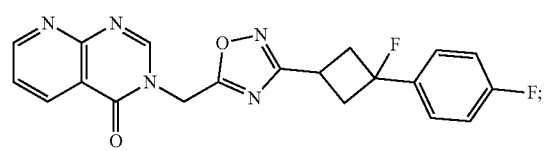
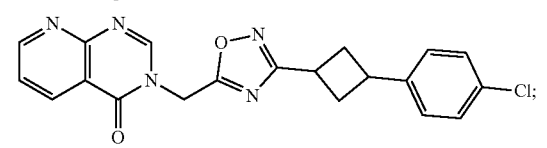
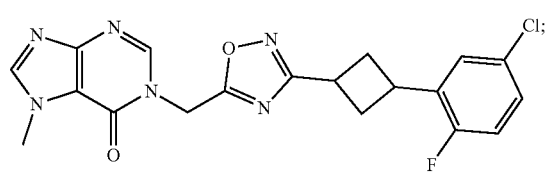
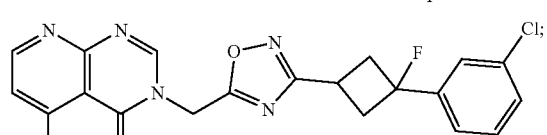
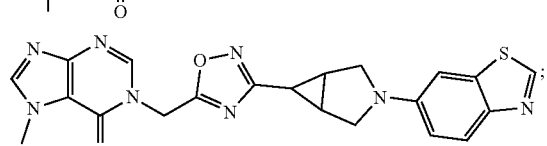
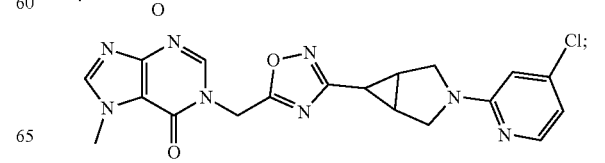

-continued
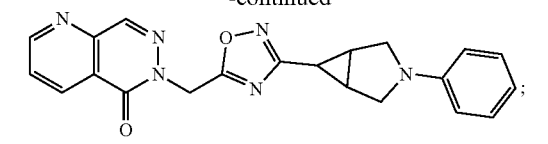
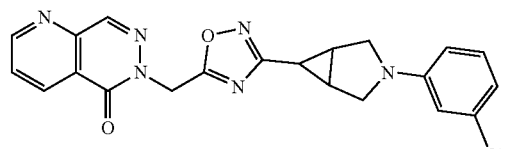
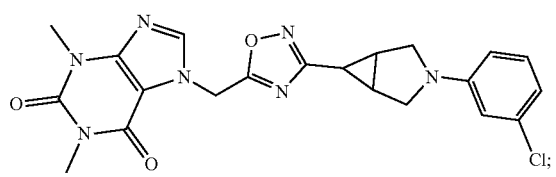
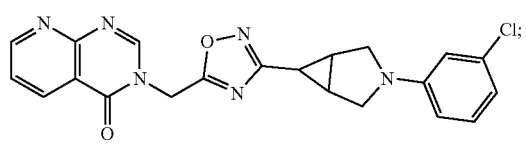
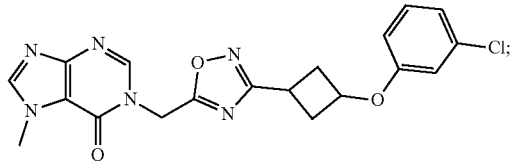
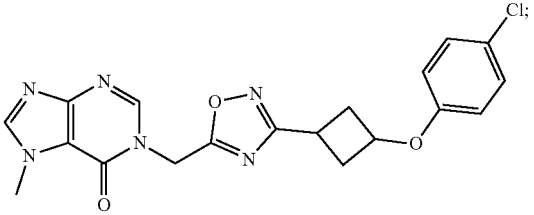
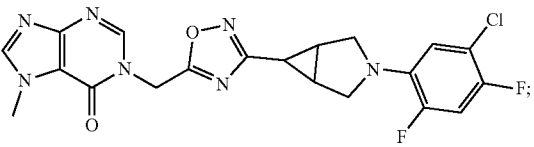
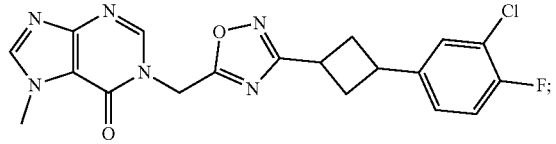
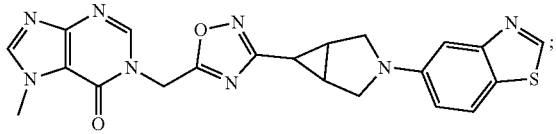
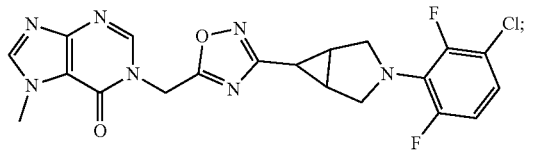
-continued
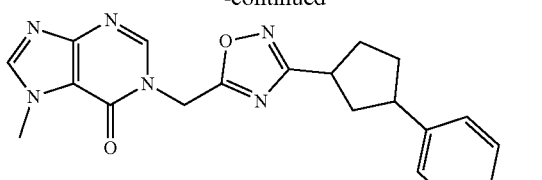
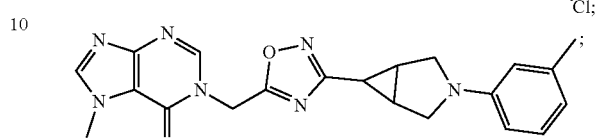
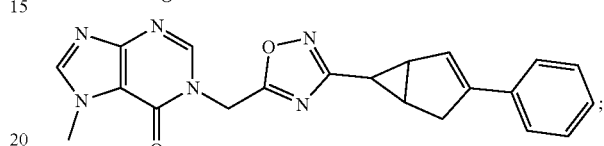
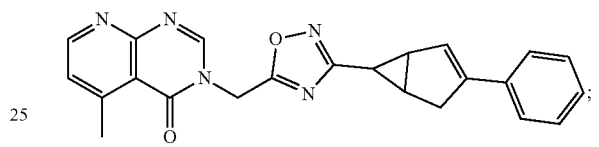
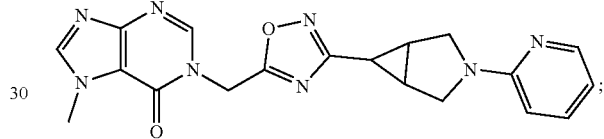
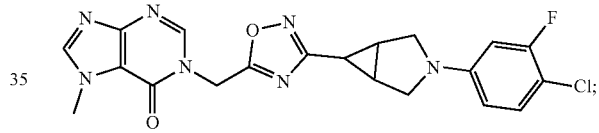
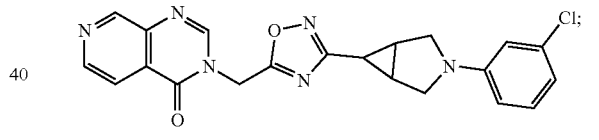

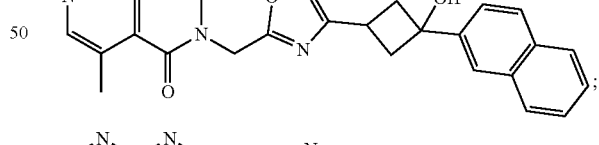
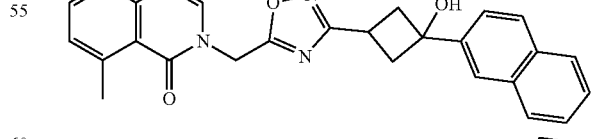

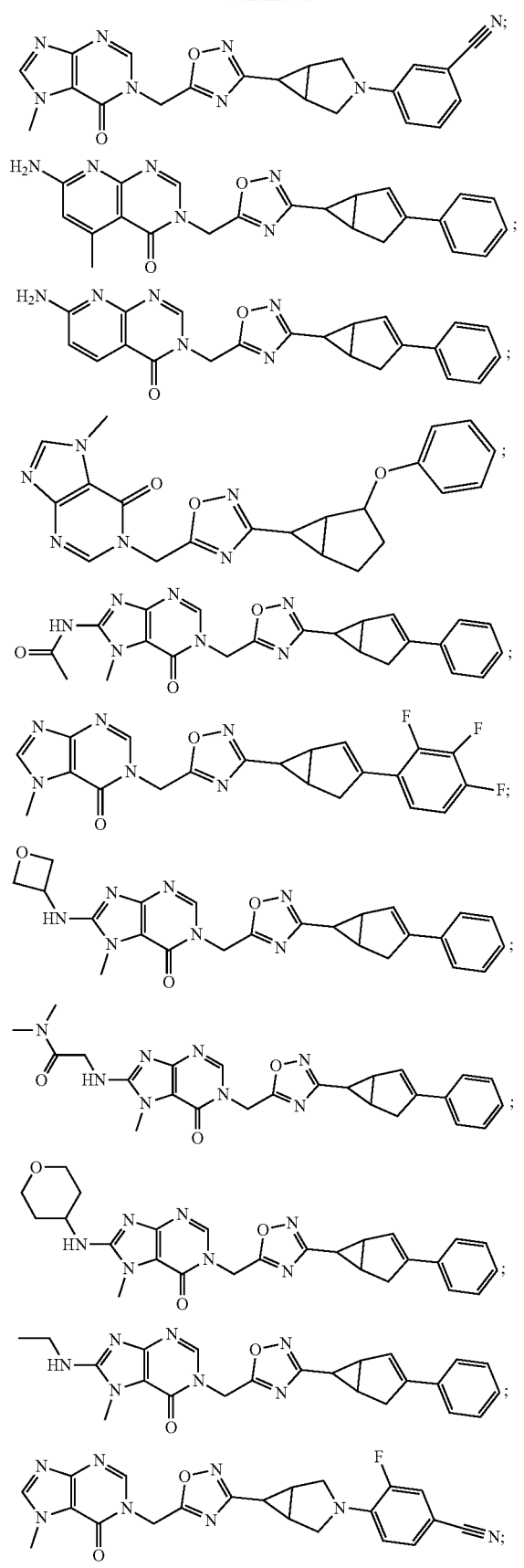
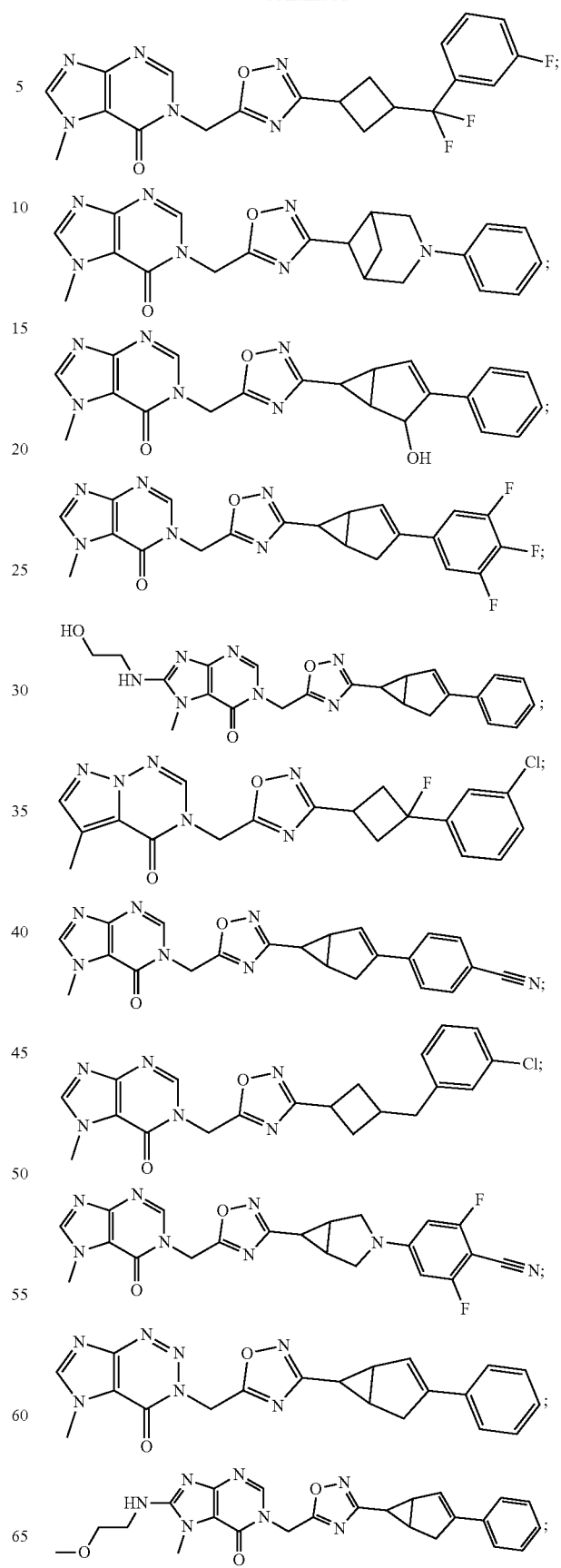

23
-continued
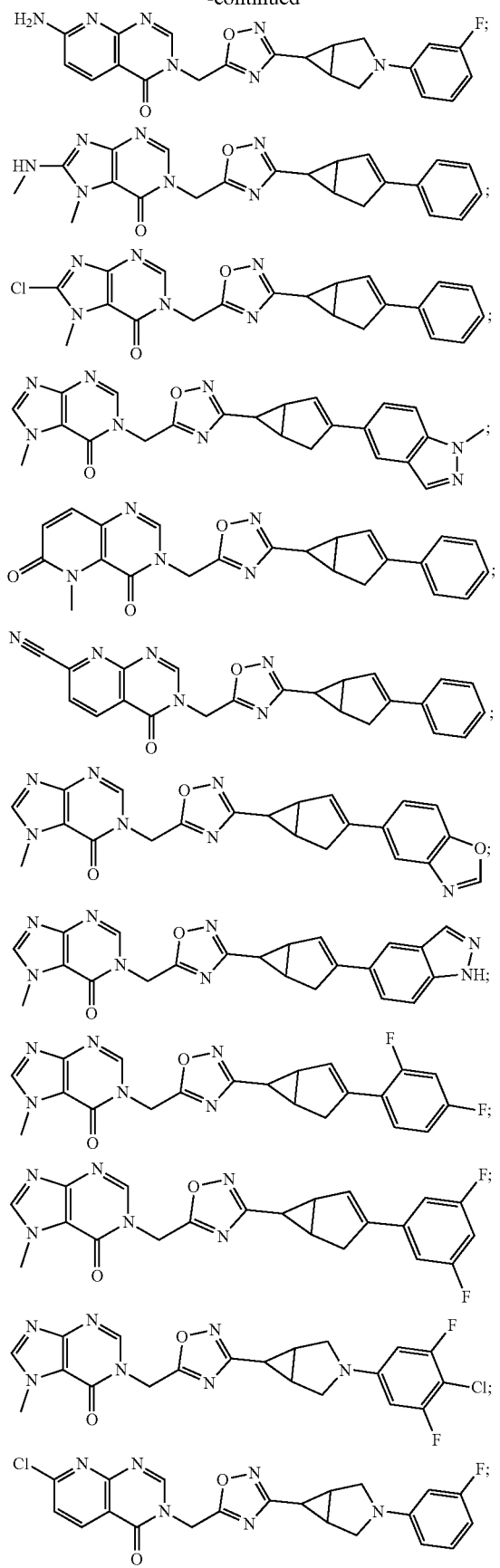
24
-continued
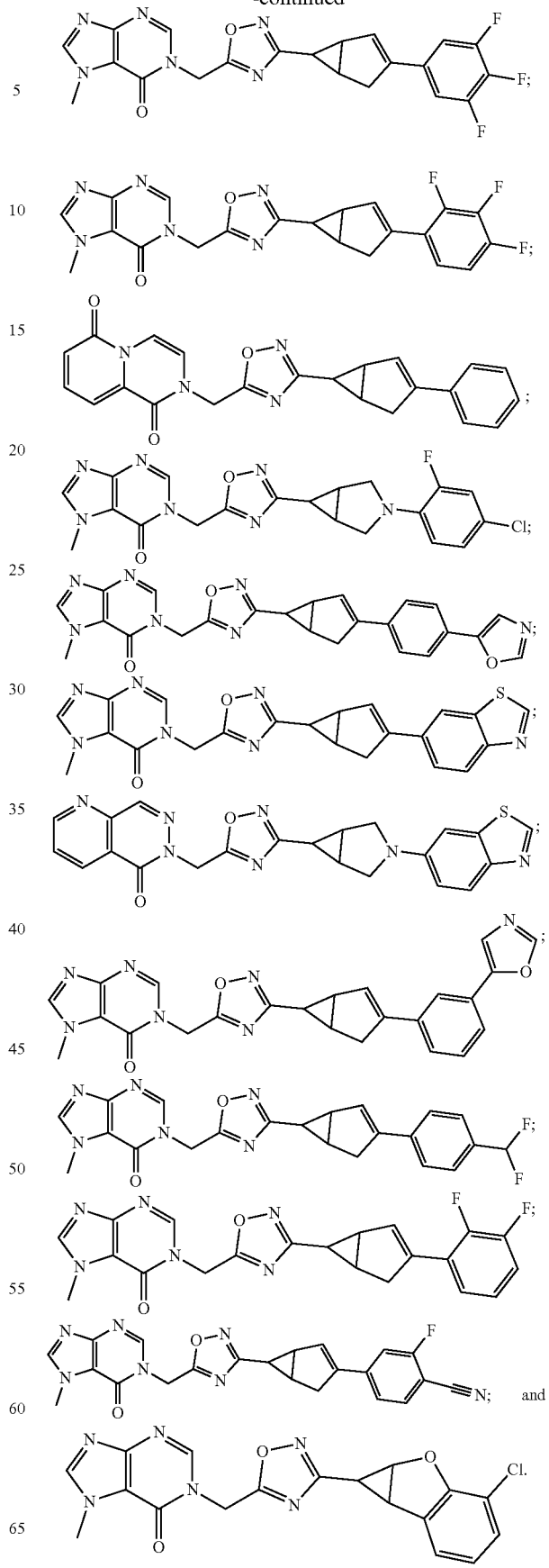

In other embodiments, the following stereoisomer compounds or pharmaceutically acceptable salts thereof are provided:
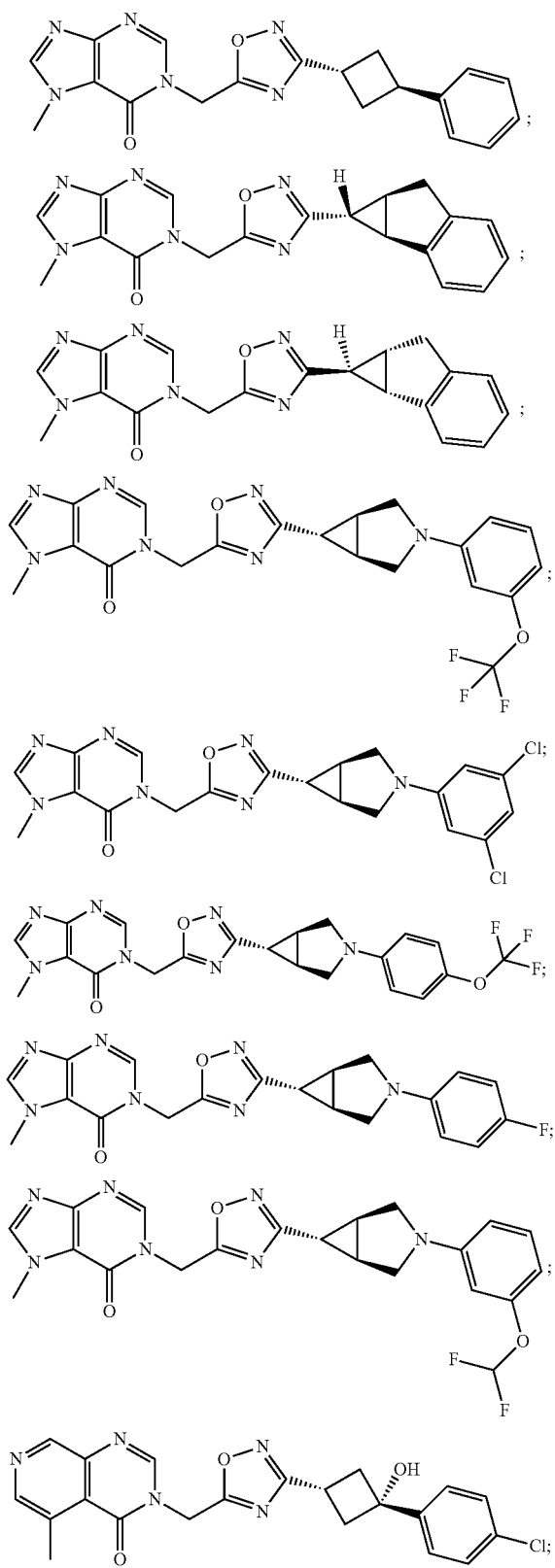
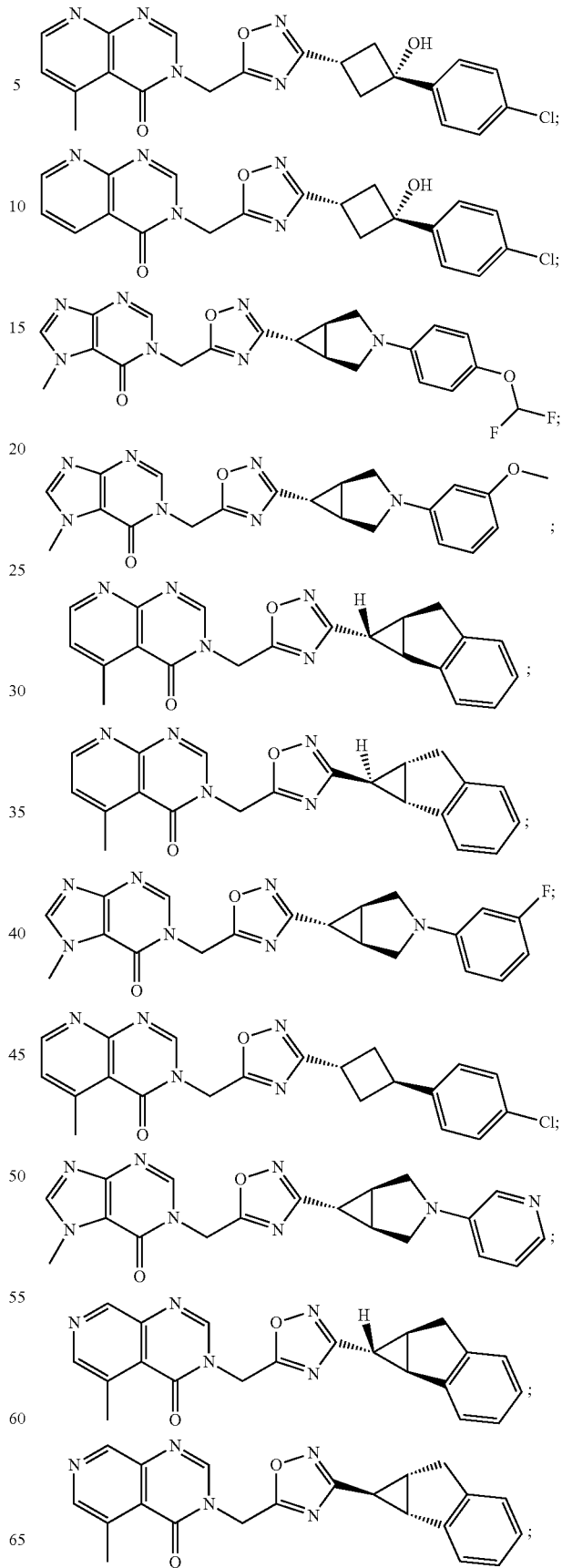

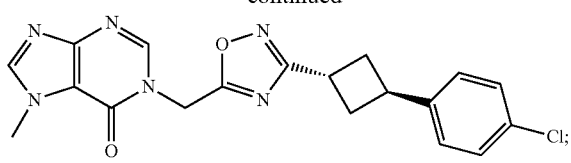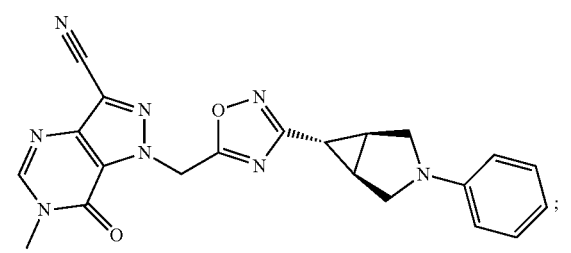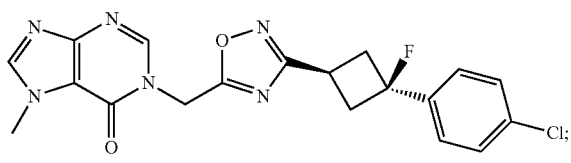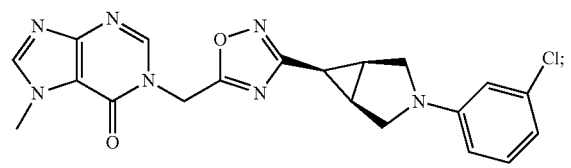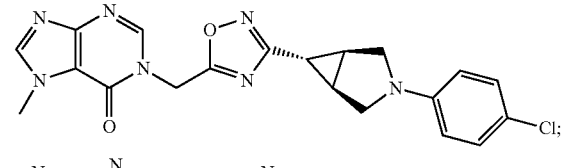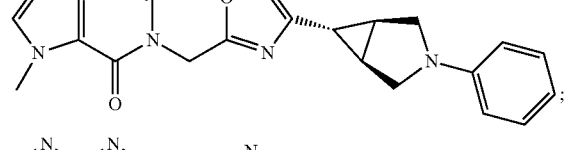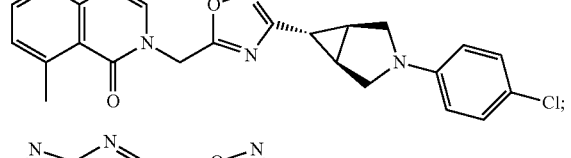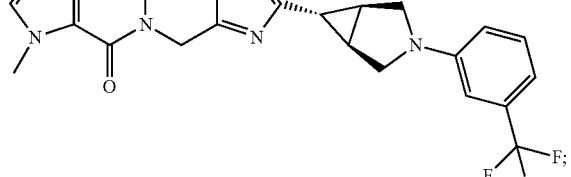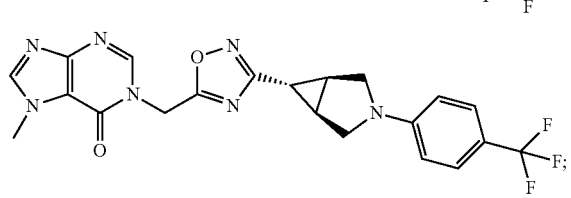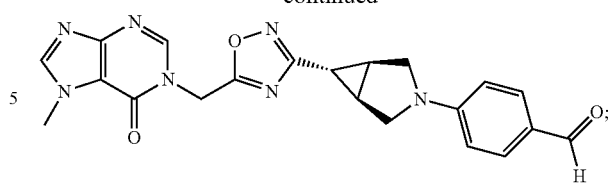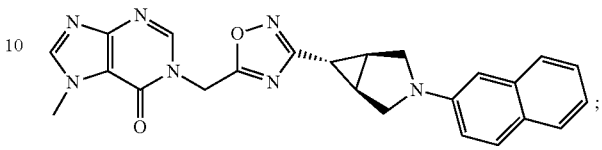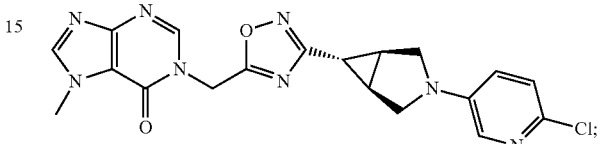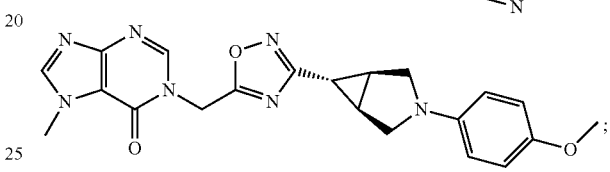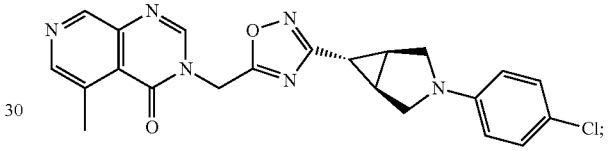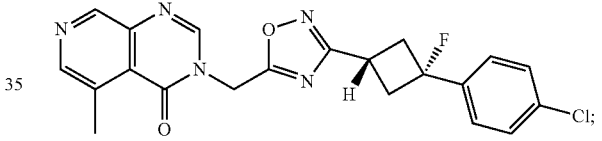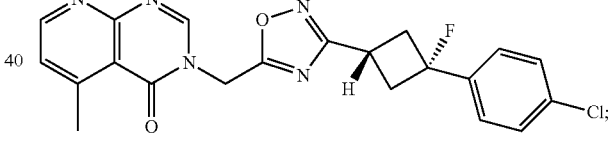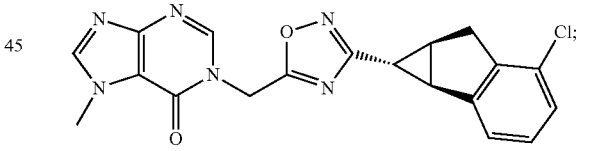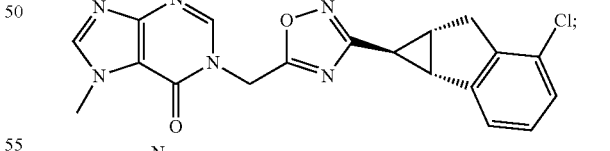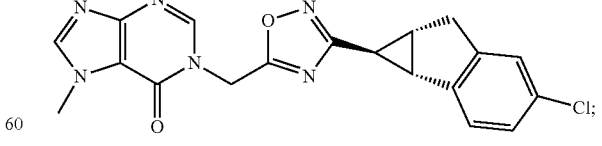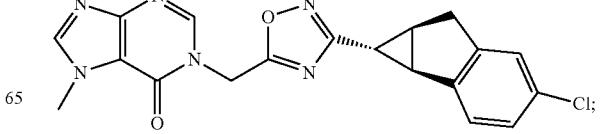

-continued
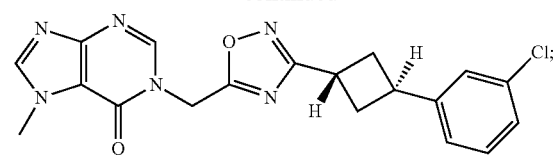
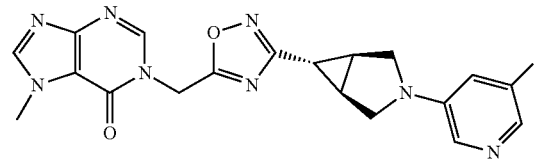
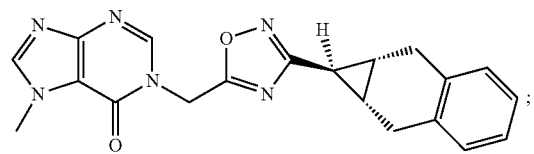
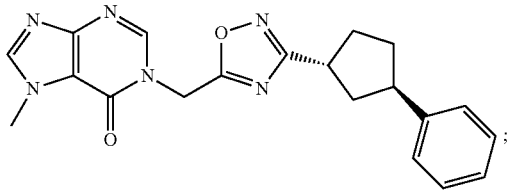
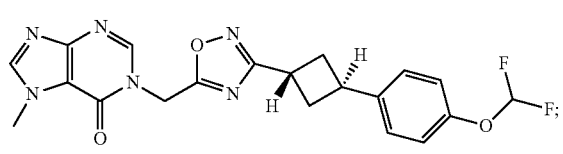
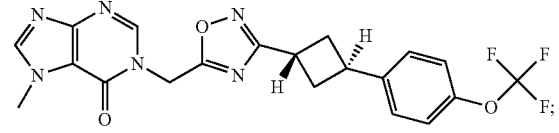
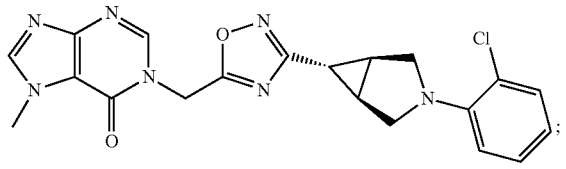
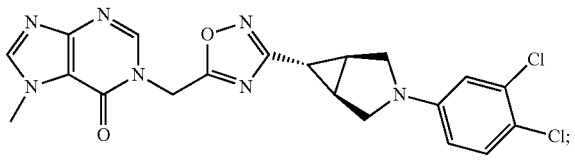
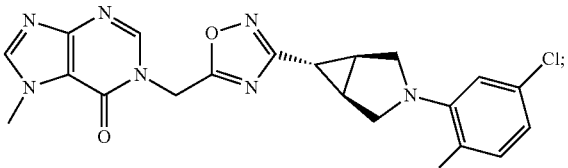
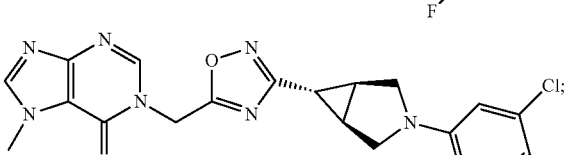
-continued
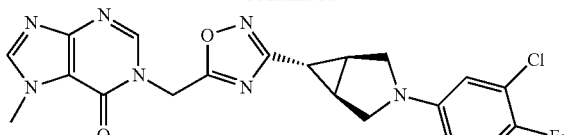
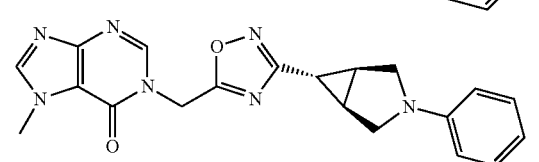
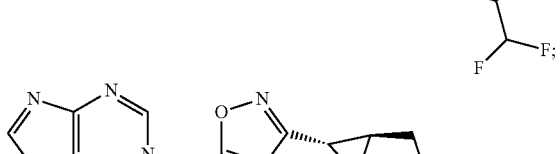
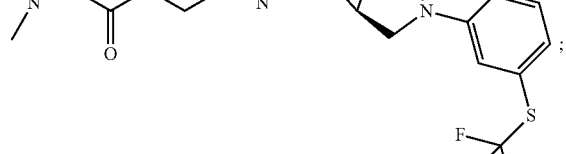
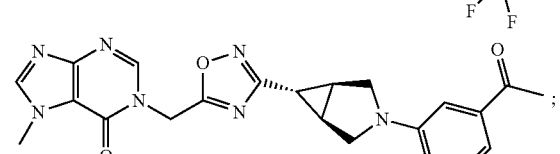
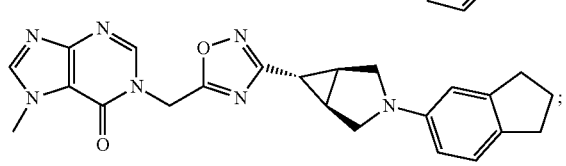
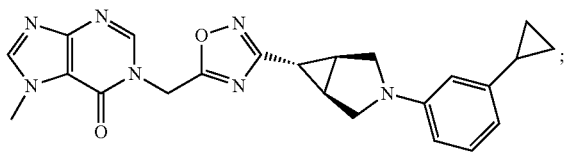
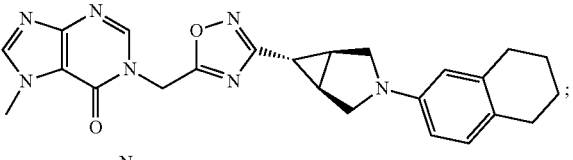
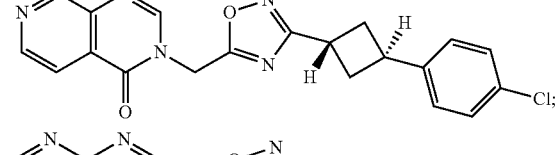
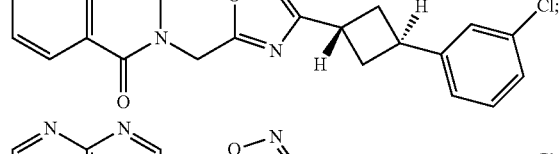

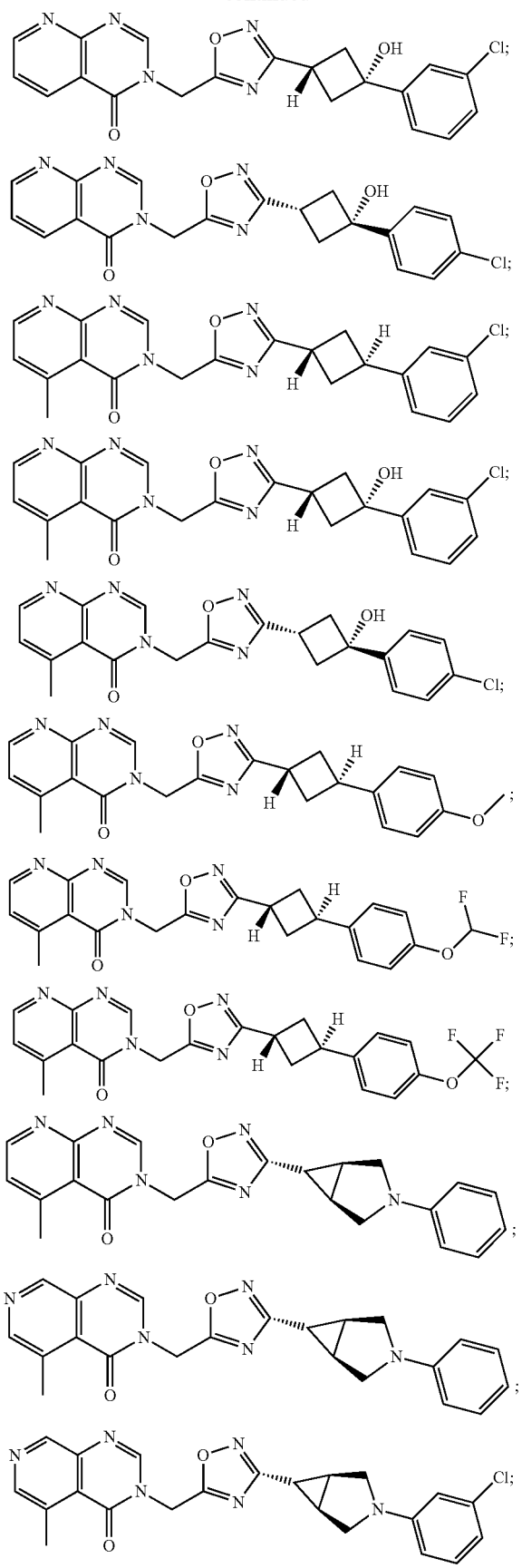
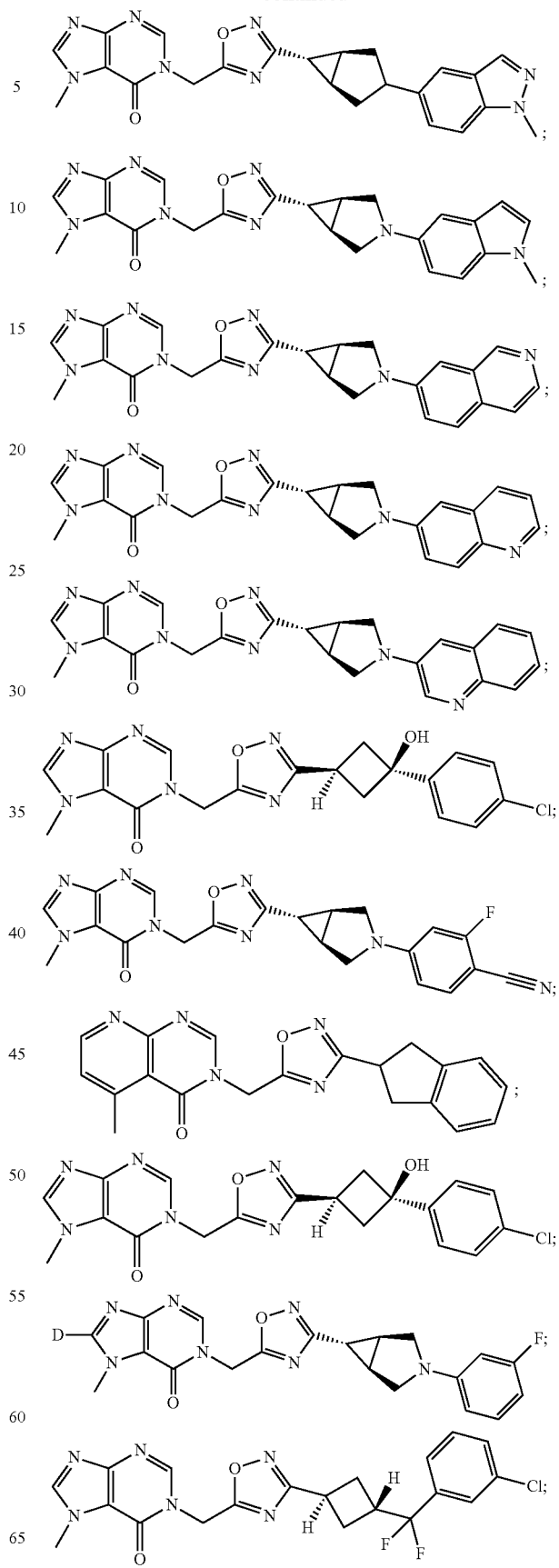

-continued
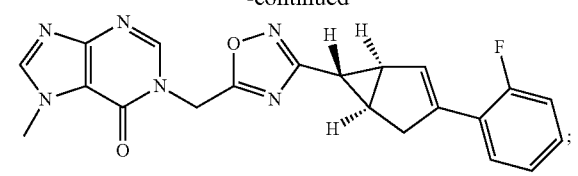
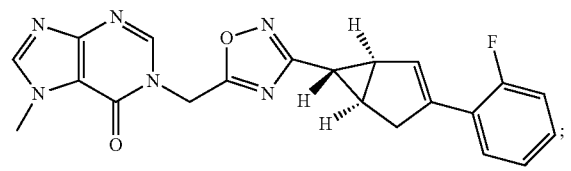
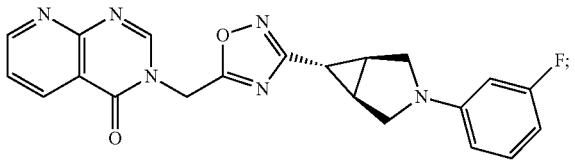
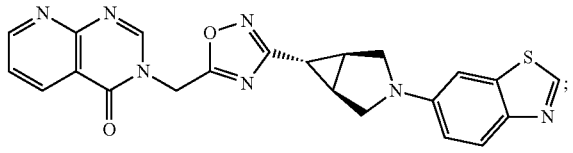
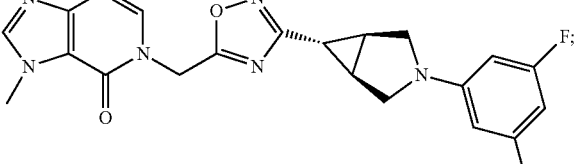

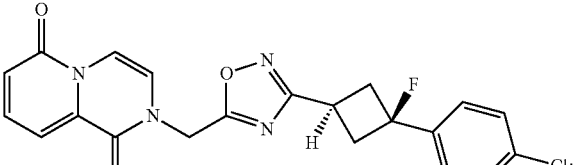

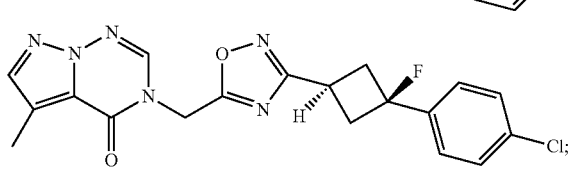
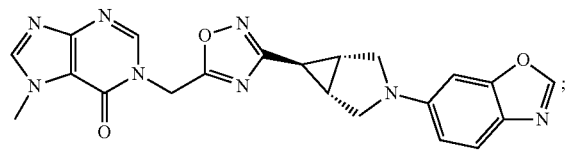
-continued
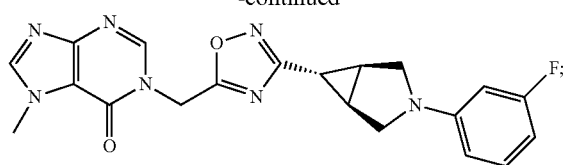
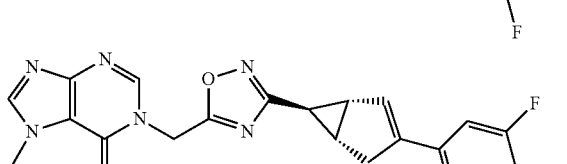
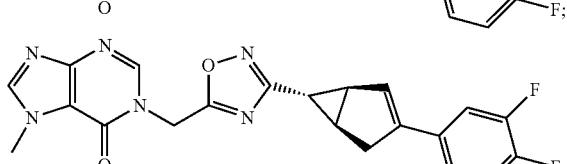
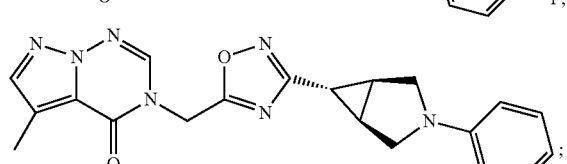
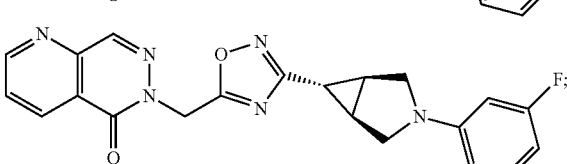
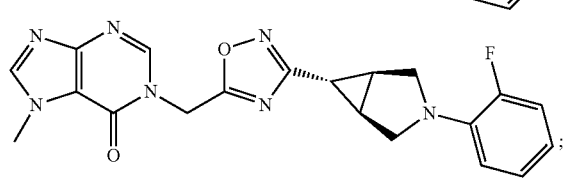
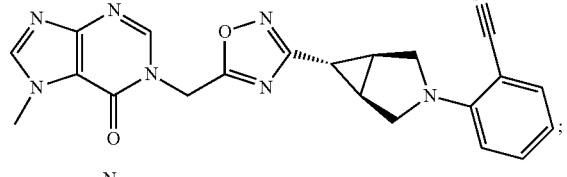
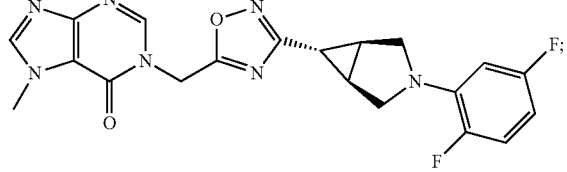
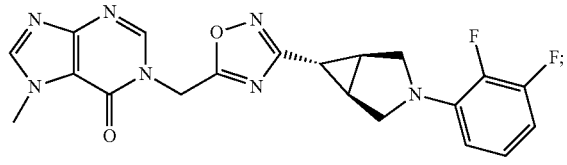
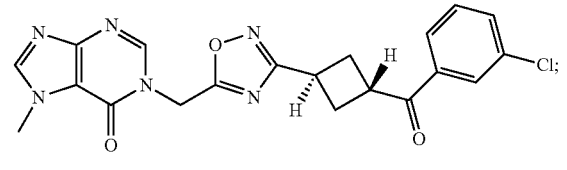

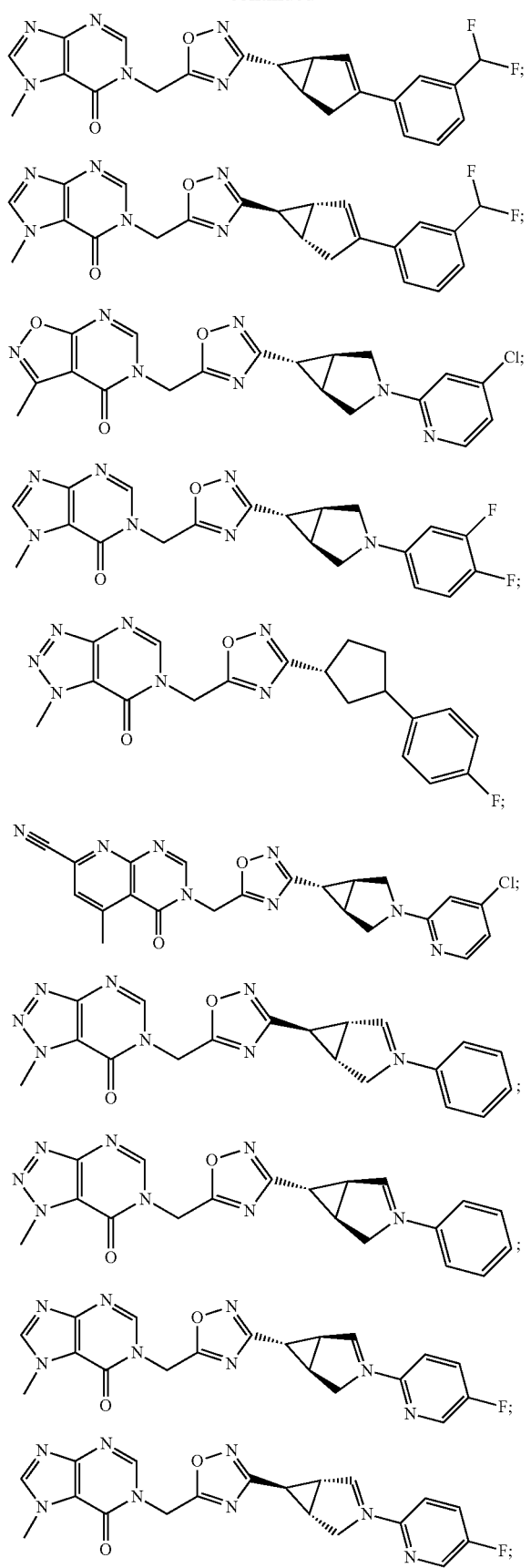
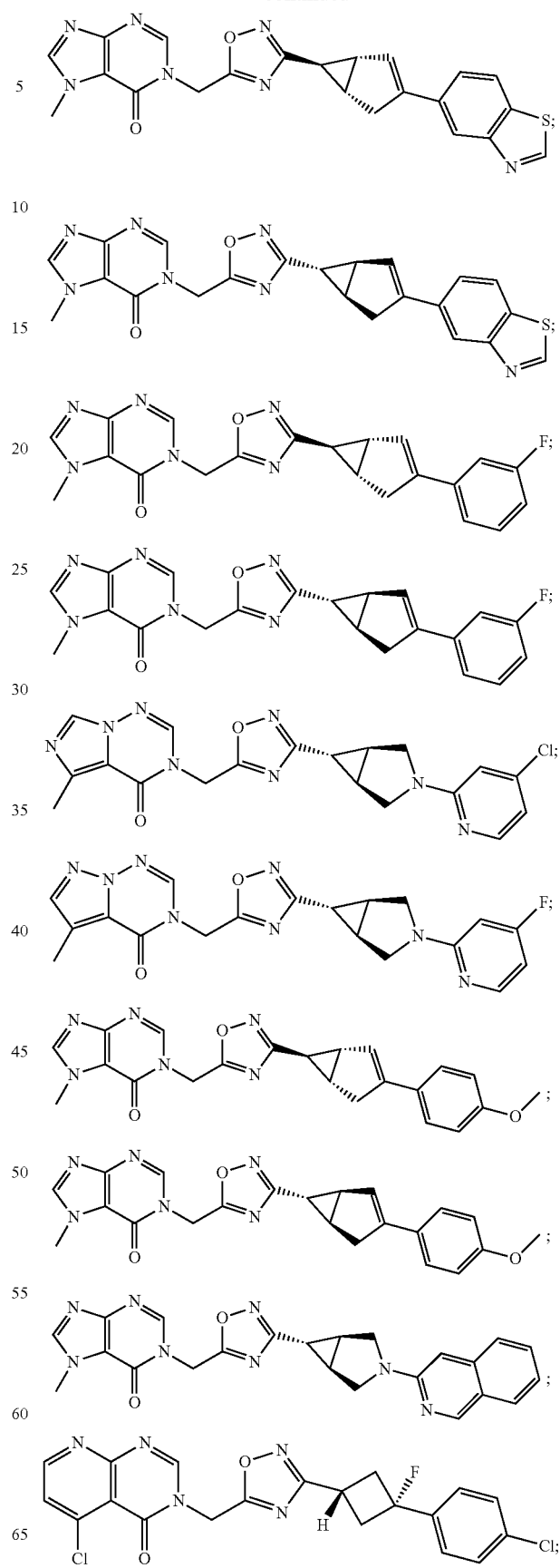

-continued
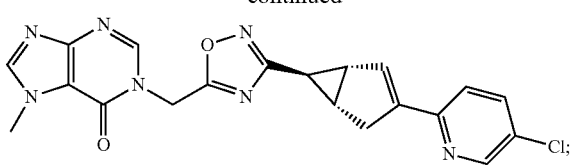
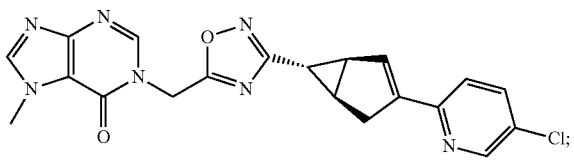
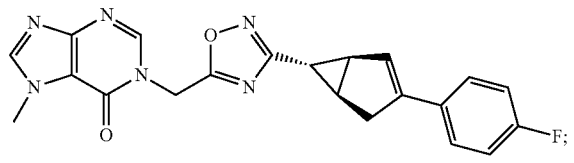
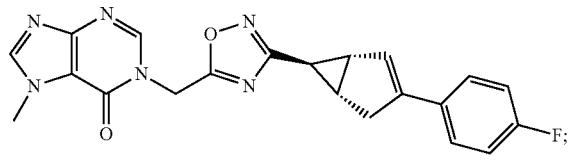
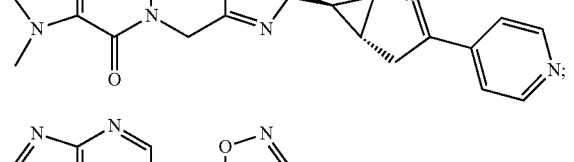
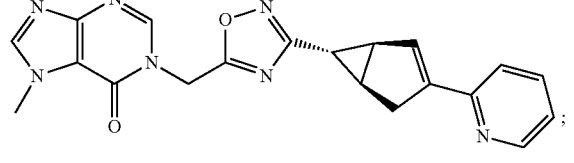
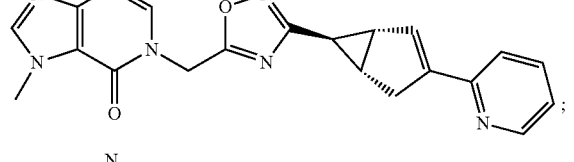
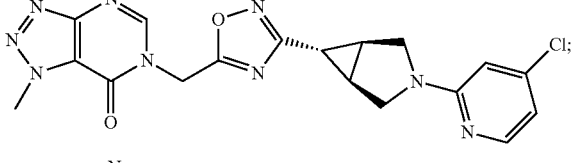
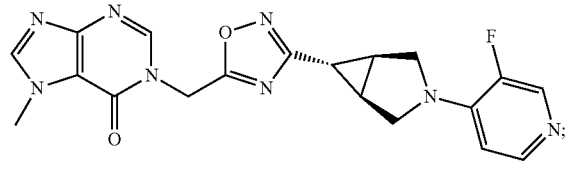
-continued
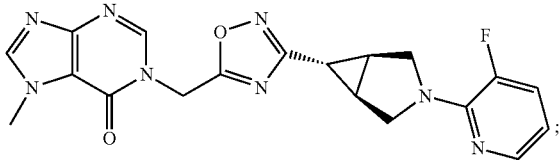
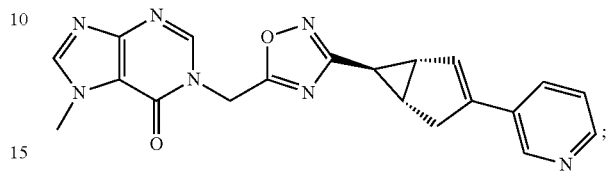
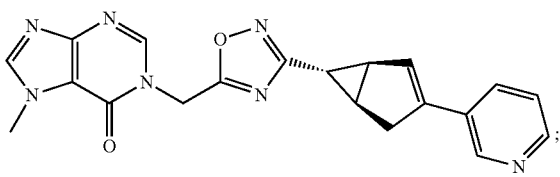
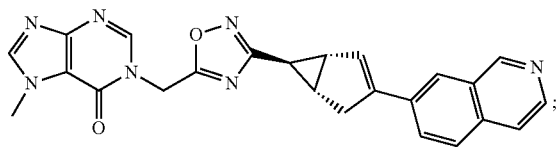
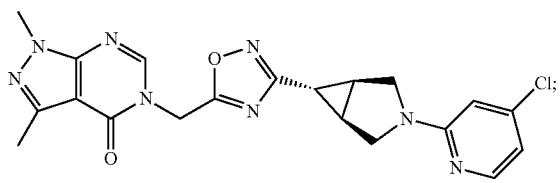
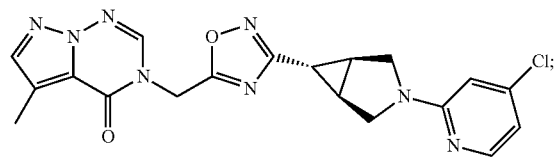
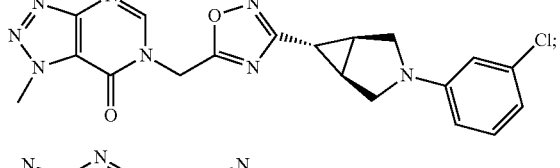
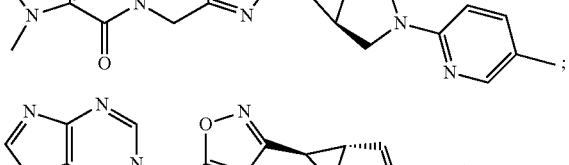
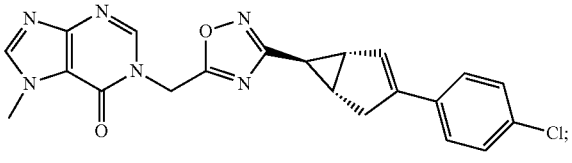

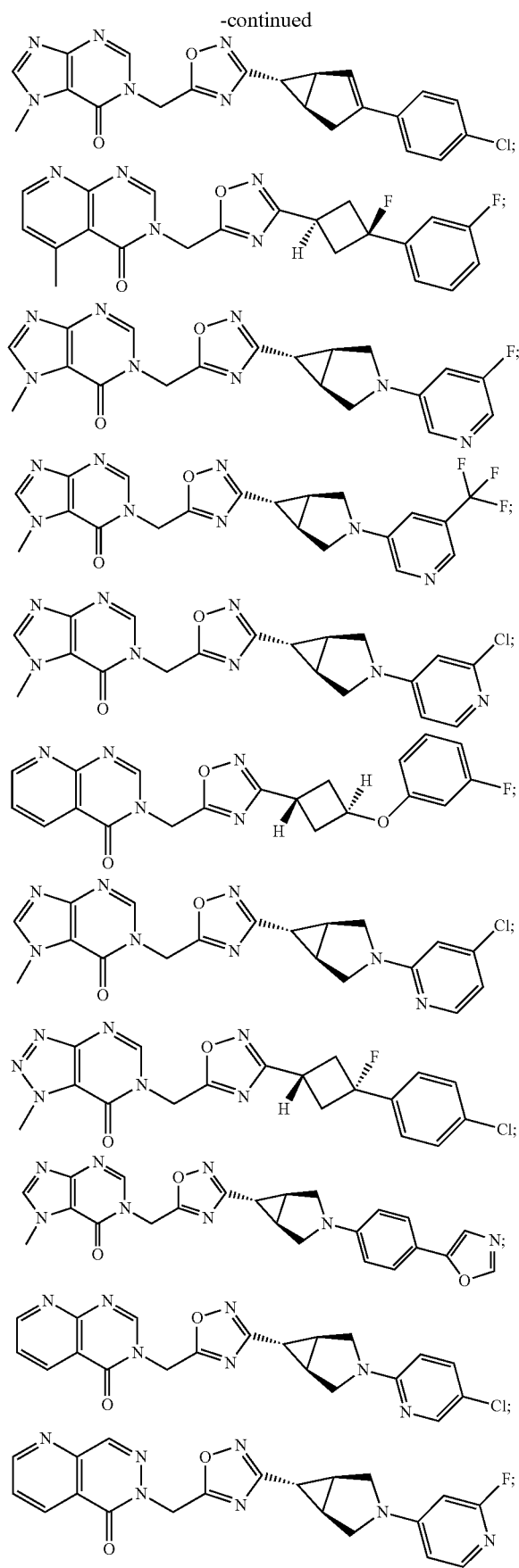

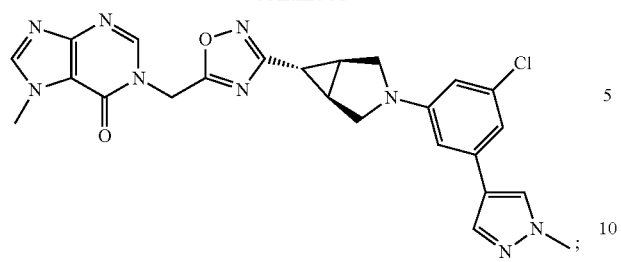
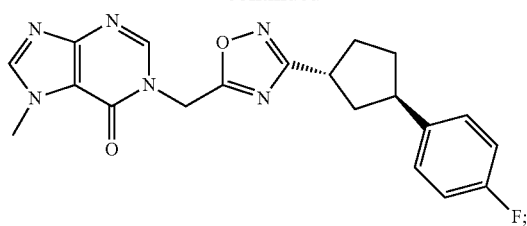
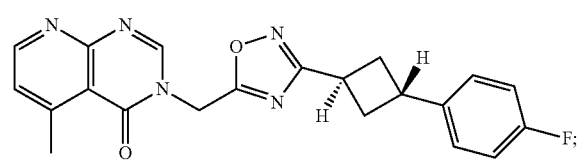
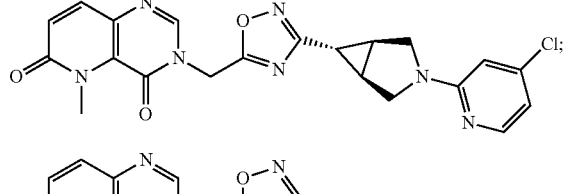
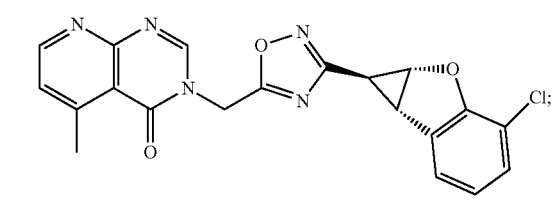
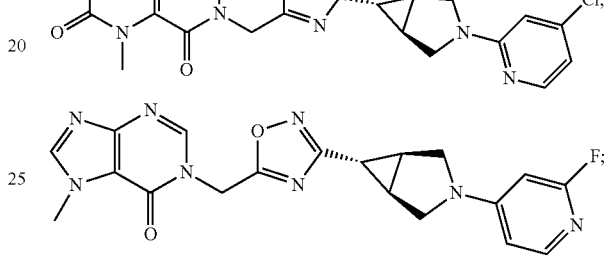
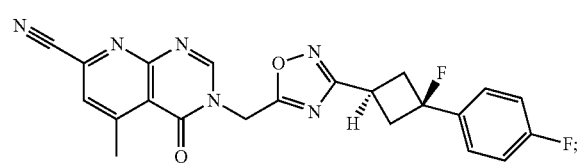
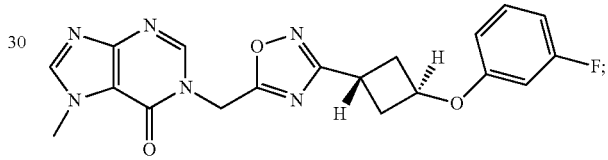
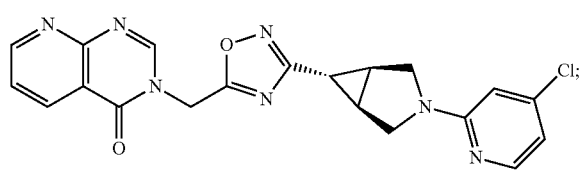
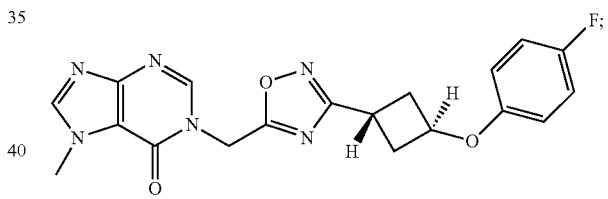
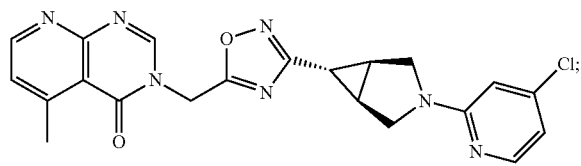
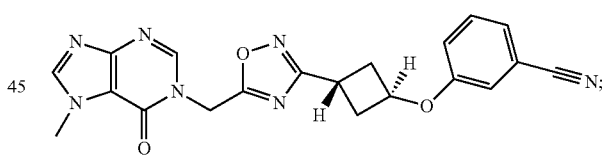
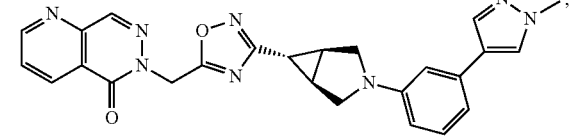
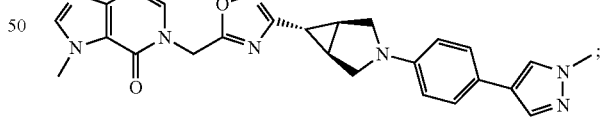
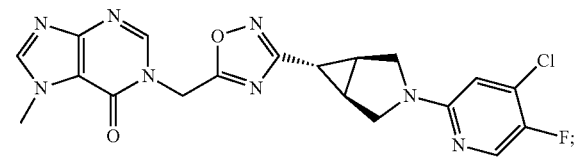
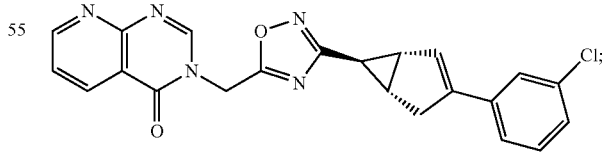
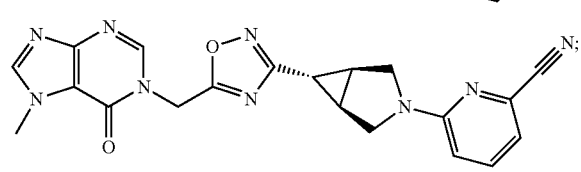
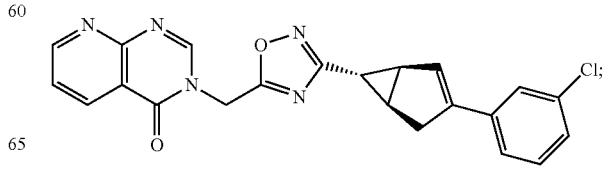

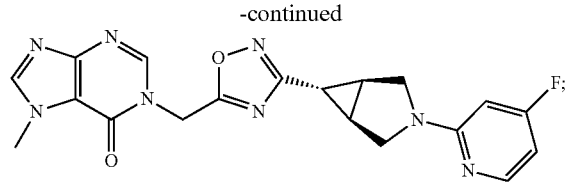

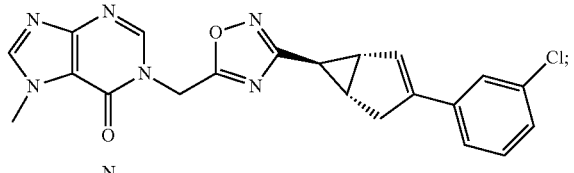
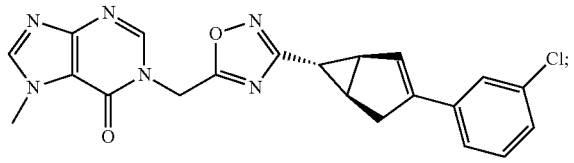
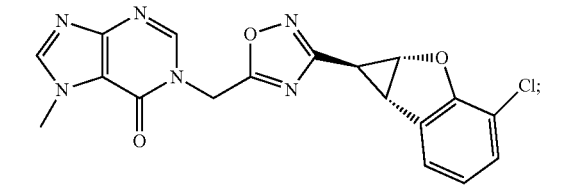
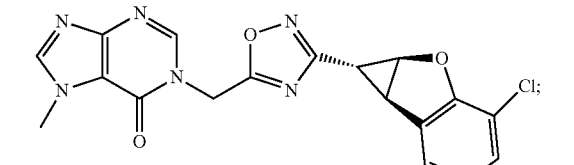
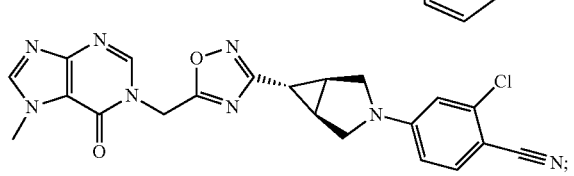
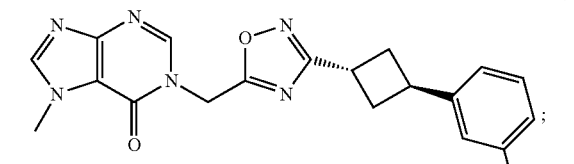
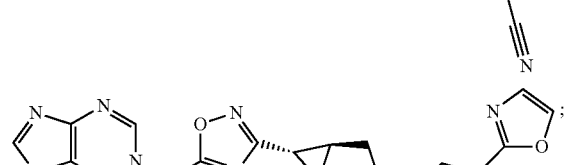
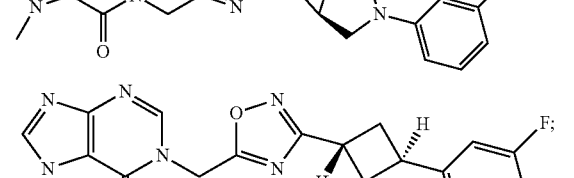
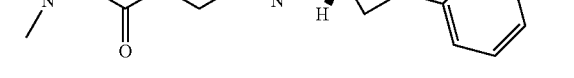
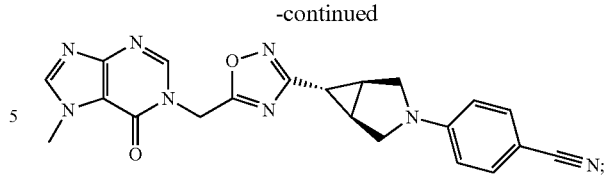
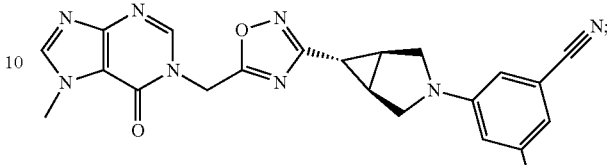
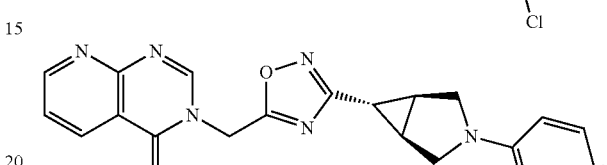
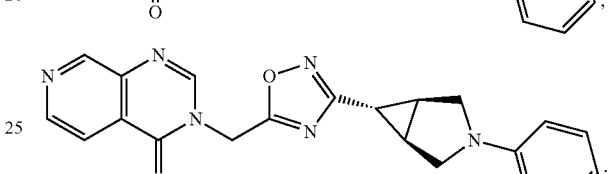
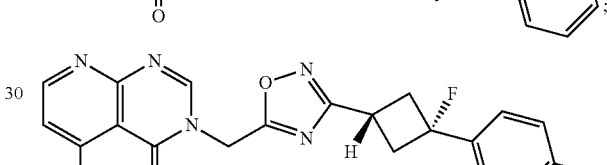
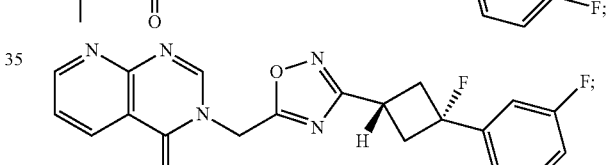
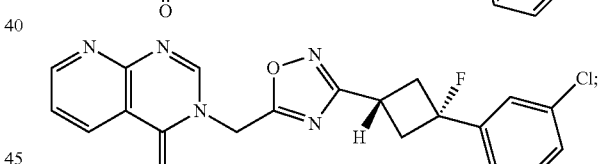
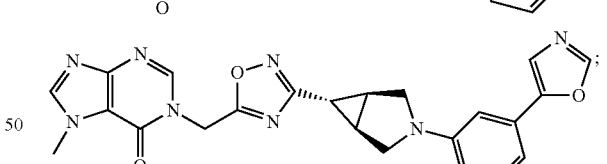
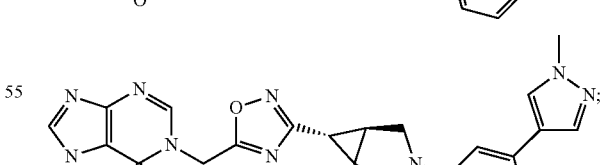
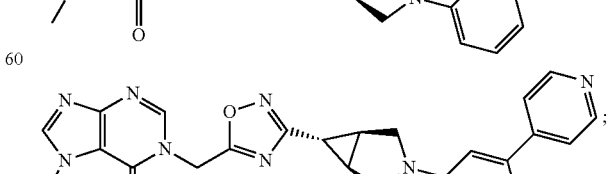

-continued
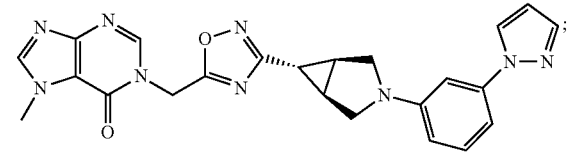
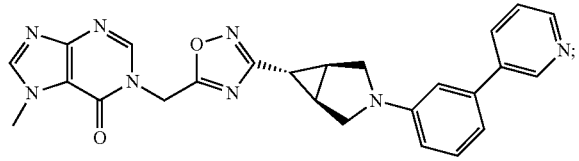
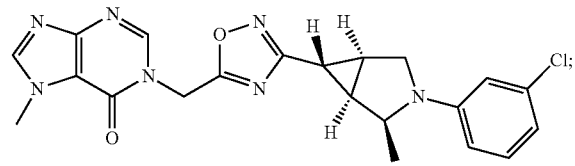
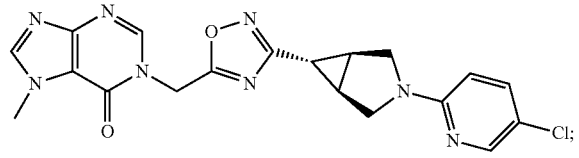
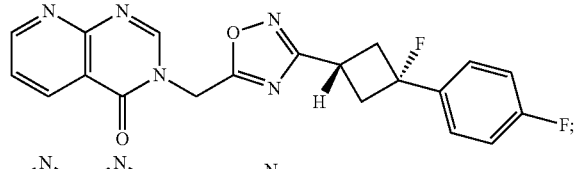
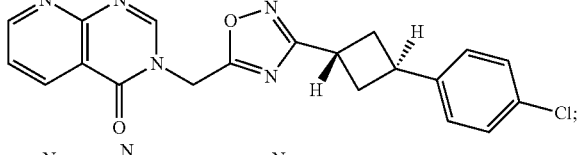
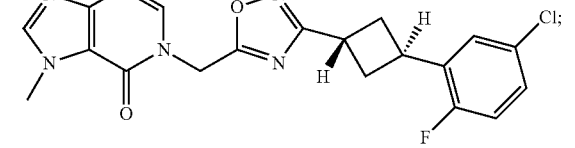
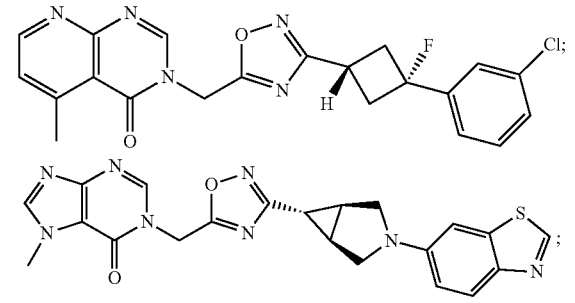
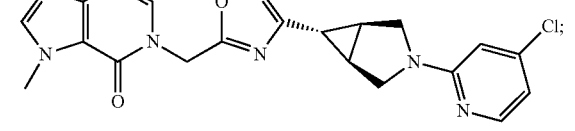
-continued

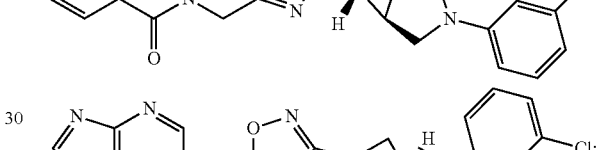
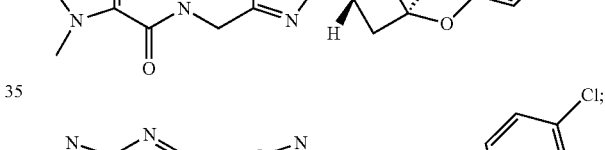
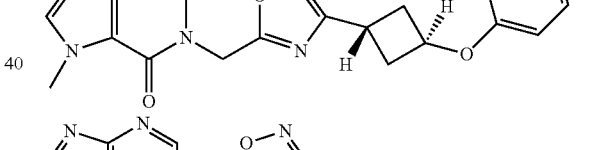
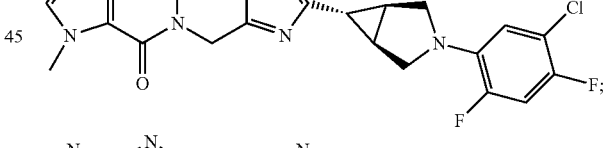
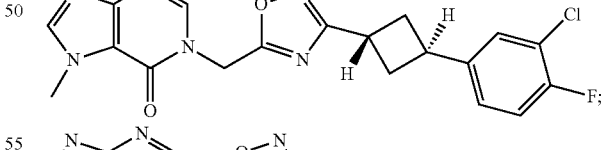
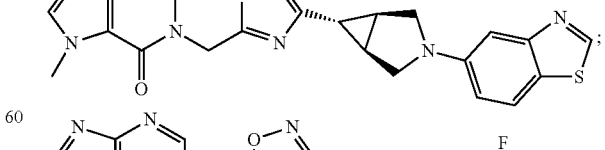
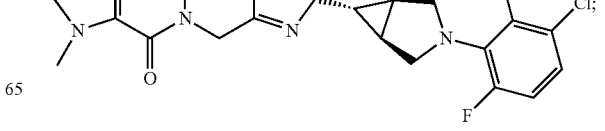

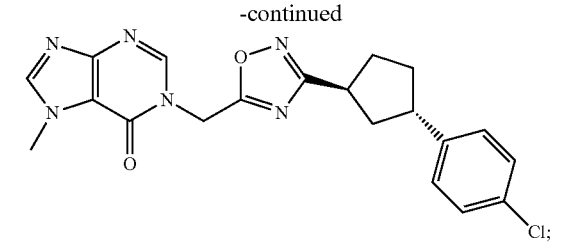
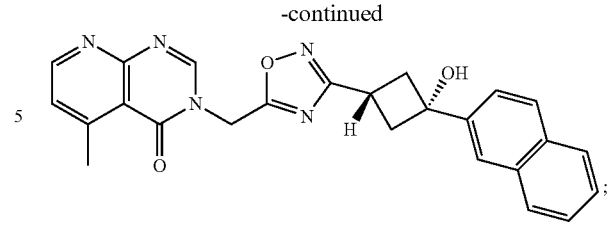
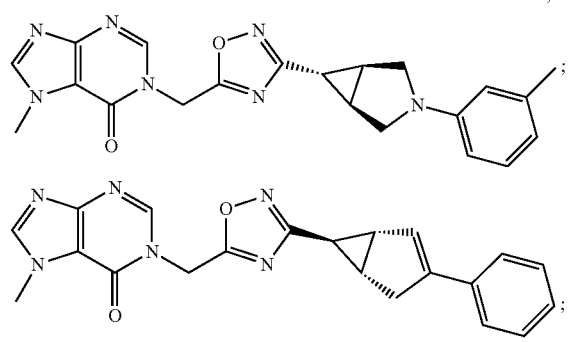
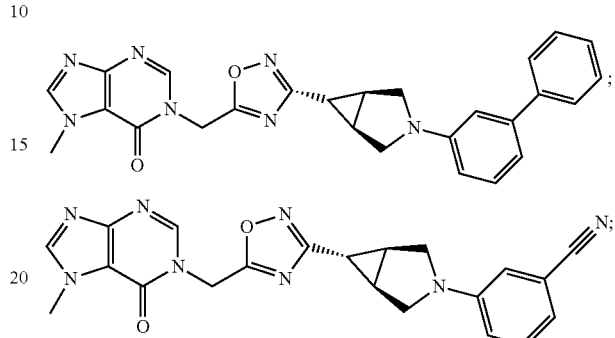
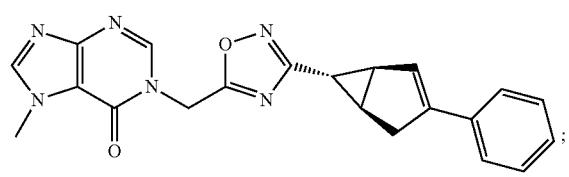
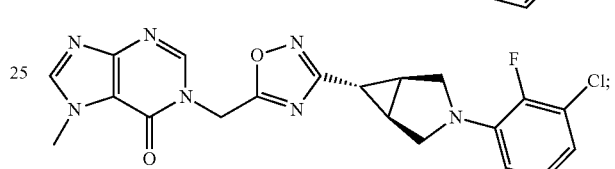
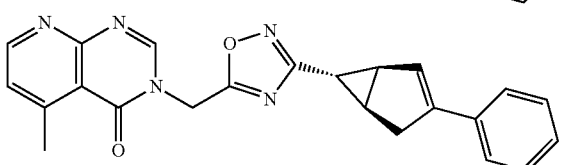
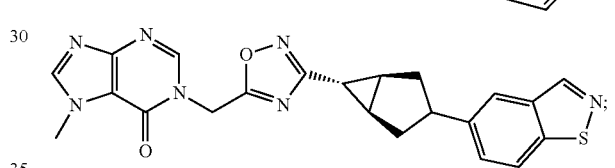
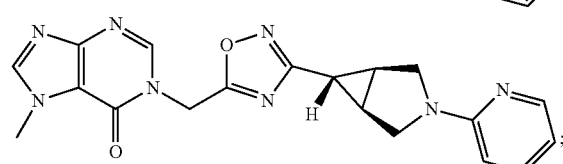
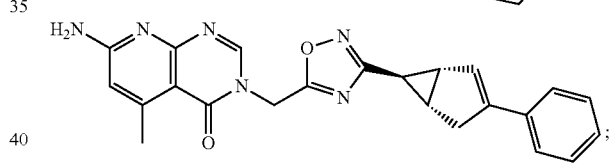
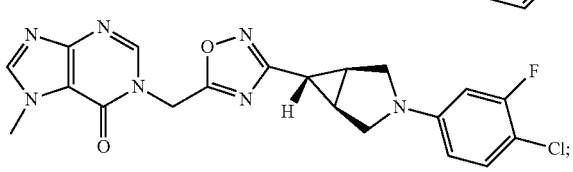
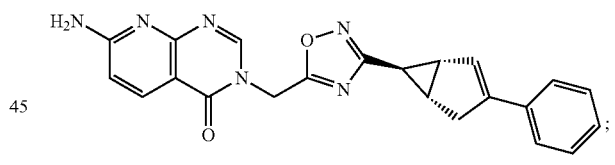
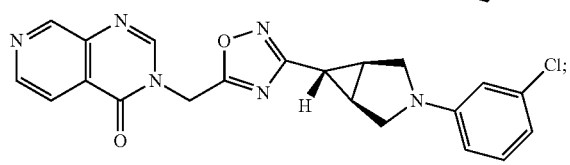
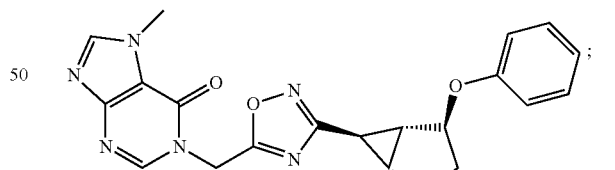
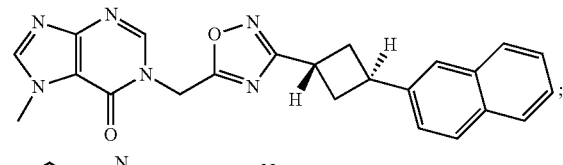
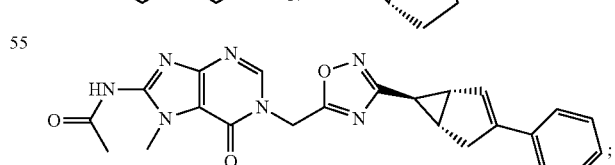
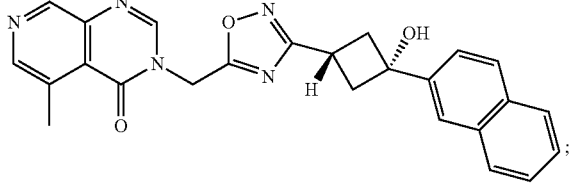
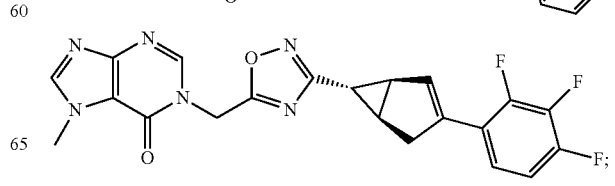

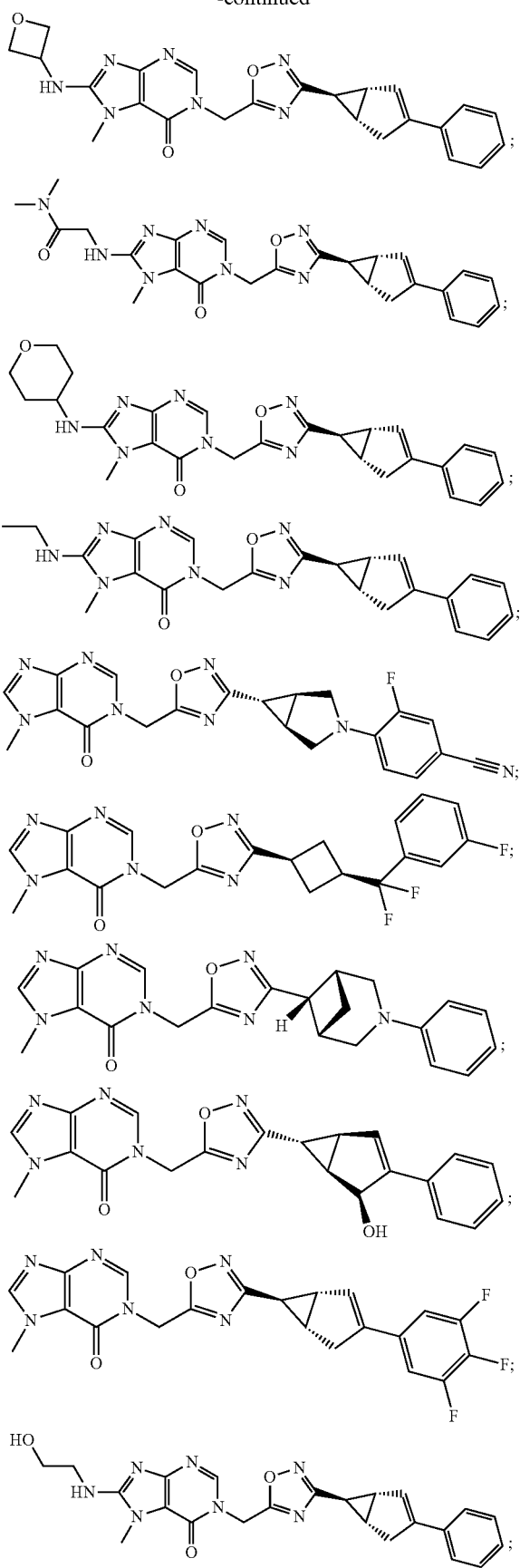
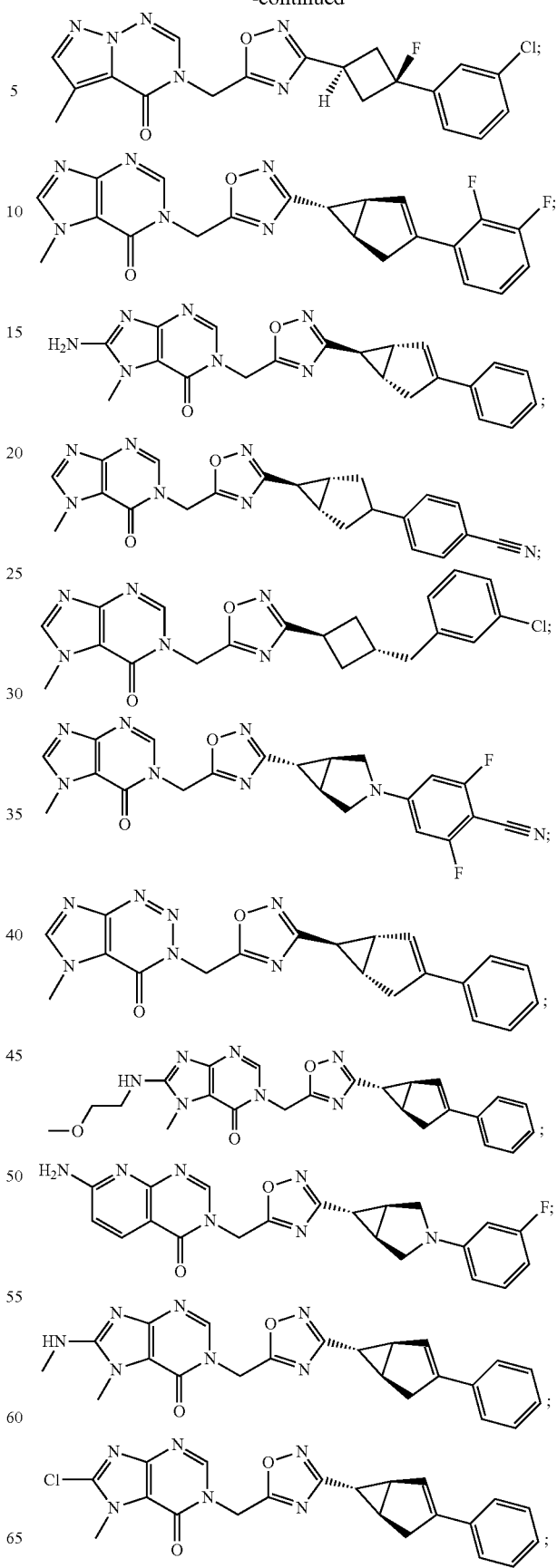

-continued
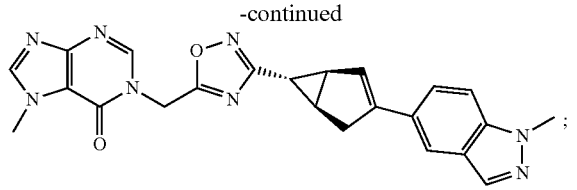
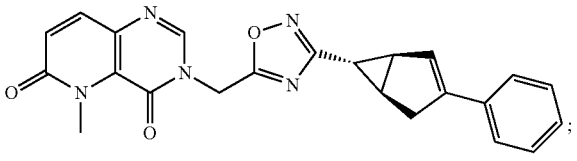
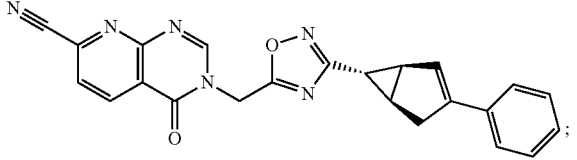
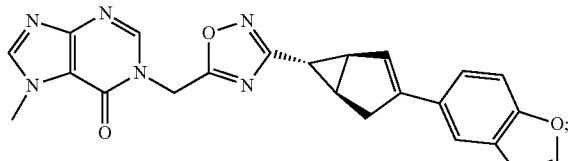
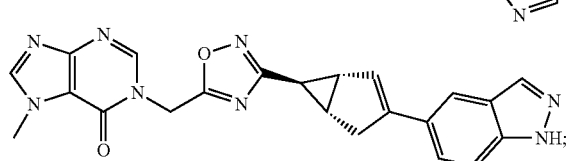
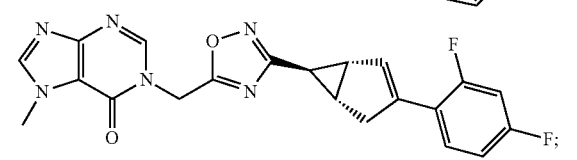
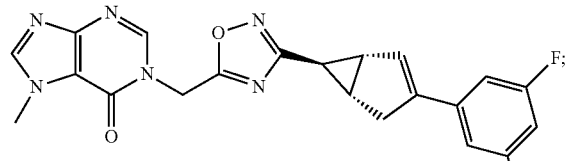
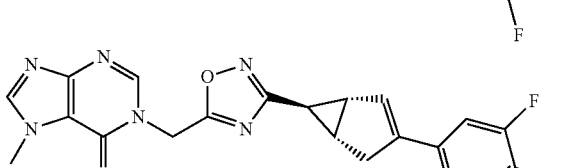
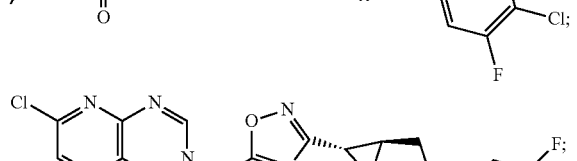
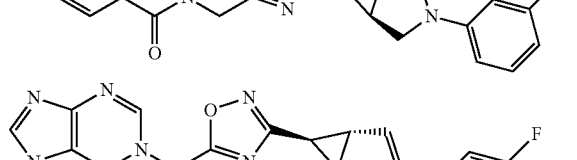
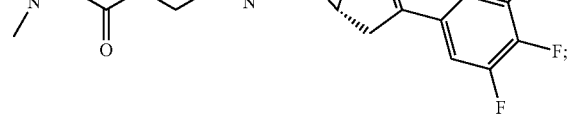
-continued
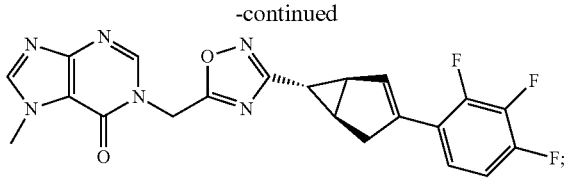
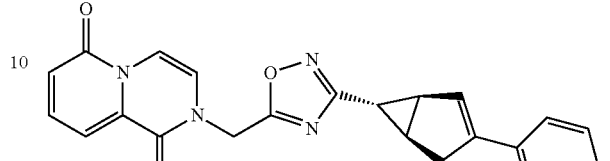
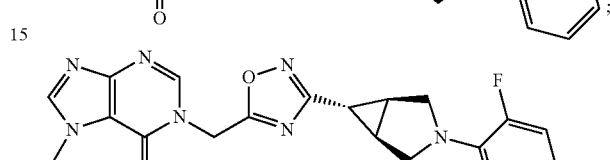
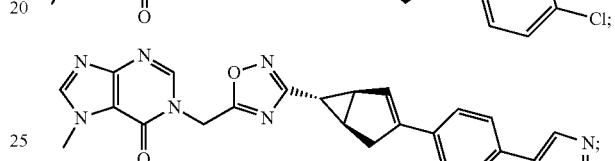
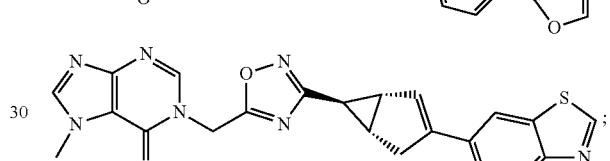
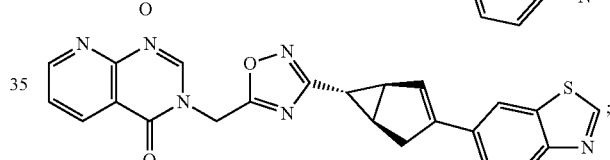
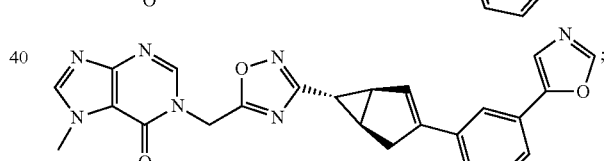
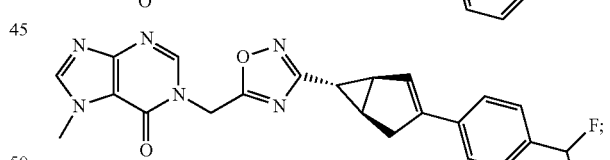
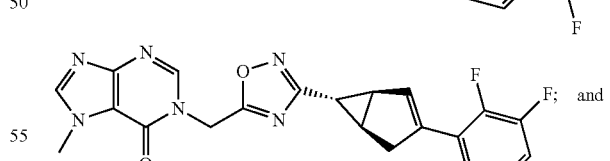
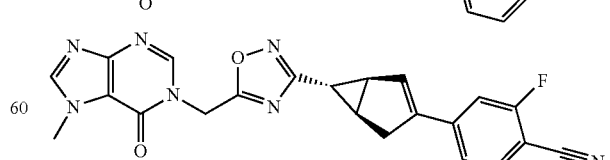; and
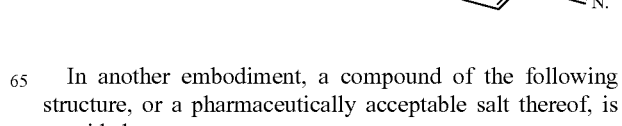.
In another embodiment, a compound of the following structure, or a pharmaceutically acceptable salt thereof, is provided:

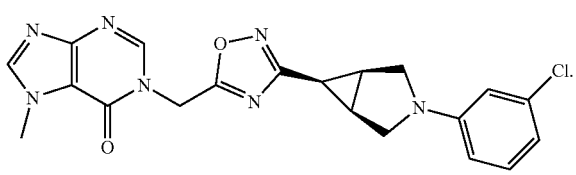 [SMILES: Cn1cnc2ncn(Cc3nc([C@@H]4[C@@H]5CN(c6cccc(Cl)c6)C[C@@H]54)no3)c(=O)c21]

In another embodiment, a compound of the following structure, or a pharmaceutically acceptable salt thereof, is provided:

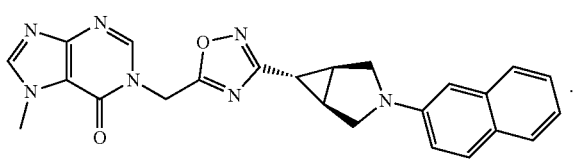 [SMILES: Cn1cnc2ncn(Cc3nc([C@H]4[C@@H]5CN(c6ccc7ccccc7c6)C[C@@H]54)no3)c(=O)c21]

In another embodiment, a compound of the following structure, or a pharmaceutically acceptable salt thereof, is provided:

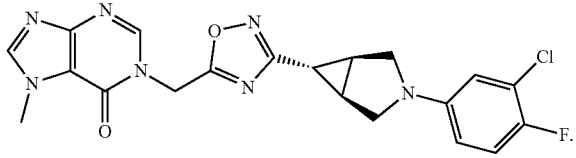 [SMILES: Cn1cnc2ncn(Cc3nc([C@H]4[C@@H]5CN(c6ccc(F)c(Cl)c6)C[C@@H]54)no3)c(=O)c21]

In another embodiment, a compound of the following structure, or a pharmaceutically acceptable salt thereof, is provided:

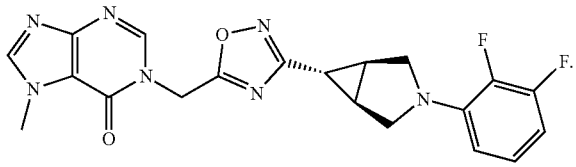 [SMILES: Cn1cnc2ncn(Cc3nc([C@H]4[C@@H]5CN(c6cccc(F)c6F)C[C@@H]54)no3)c(=O)c21]

In another embodiment, a compound of the following structure, or a pharmaceutically acceptable salt thereof, is provided:

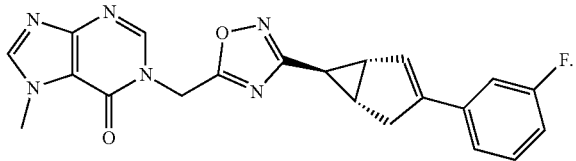 [SMILES: Cn1cnc2ncn(Cc3nc([C@H]4[C@@H]5C=C(c6cccc(F)c6)C[C@@H]54)no3)c(=O)c21]

In another embodiment, a compound of the following structure, or a pharmaceutically acceptable salt thereof, is provided:

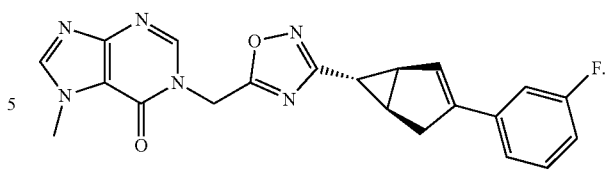

In another embodiment, a compound of the following structure, or a pharmaceutically acceptable salt thereof, is provided:

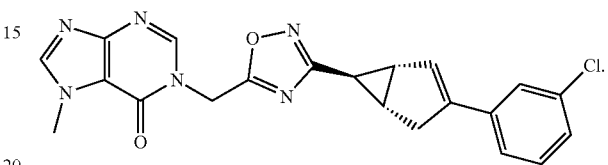

In another embodiment, a compound of the following structure, or a pharmaceutically acceptable salt thereof, is provided:

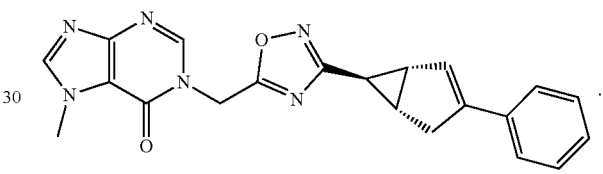

In another embodiment, a compound of the following structure, or a pharmaceutically acceptable salt thereof, is provided:

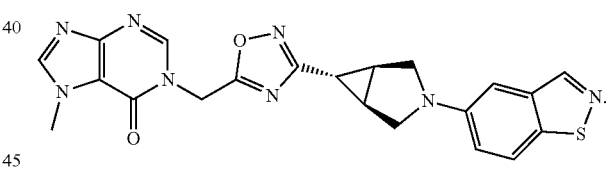

Some other embodiments provide pharmaceutical compositions comprising a compound described above, or a pharmaceutically acceptable salt thereof, and a pharmaceutically acceptable carrier, diluent or excipient.

Some other embodiments provide a compound as described above, or a pharmaceutically acceptable salt thereof, for use in medical therapy.

Some other embodiments provide a compound as described above, or a pharmaceutically acceptable salt thereof, for the treatment or prophylaxis of a respiratory disorder.

Some other embodiments provide a compound as described above, or a pharmaceutically acceptable salt thereof, for the preparation of a medicament for the treatment or prophylaxis of a respiratory disorder.

Some other embodiments provide a method for treating a respiratory disorder in a mammal comprising, administering a therapeutically effective amount of a compound as described above, or a pharmaceutically acceptable salt thereof, to the mammal.

Some other embodiments provide a compound as described above, or a pharmaceutically acceptable salt thereof, for modulating TRPA1 activity.

Some other embodiments provide a compound as described above, or a pharmaceutically acceptable salt thereof, for the treatment or prophylaxis of a disease or condition mediated by TRPA1 activity.

Some other embodiments provide a use of a compound as described above, or a pharmaceutically acceptable salt thereof, for the preparation of a medicament for the treatment or prophylaxis of a disease or condition that is mediated by TRPA1 activity.

Some other embodiments provide a method for modulating TRPA1 activity, comprising contacting TRPA1 with a compound as described above, or a pharmaceutically acceptable salt thereof.

Some other embodiments provide a method for treating a disease or condition mediated by TRPA1 activity in a mammal, comprising administering a therapeutically effective amount of a compound as described above, or a pharmaceutically acceptable salt thereof, to the mammal.

DETAILED DESCRIPTION OF THE INVENTION

Definitions

Unless otherwise indicated, the following specific terms and phrases used in the description and claims are defined as follows:

The terms "moiety" and "substituent" refer to an atom or group of chemically bonded atoms that is attached to another atom or molecule by one or more chemical bonds thereby forming part of a molecule.

The term "substituted" refers to the replacement of at least one of hydrogen atom of a compound or moiety with another substituent or moiety. Examples of such substituents include, without limitation, halogen, —OH, —CN, oxo, alkoxy, alkyl, alkylene, aryl, heteroaryl, haloalkyl, haloalkoxy, cycloalkyl and heterocycle. For example, the term "alkyl substituted by halogen" refers to the fact that one or more hydrogen atoms of a alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms. Alkyl groups may be optionally substituted independently with one or more substituents described herein.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenylene" refers to linear or branched-chain divalent hydrocarbon radical of two to eight carbon atoms ($C_2$-8) with at least one site of unsaturation, i.e., a carbon-carbon double bond, wherein the alkenylene radical may be optionally substituted. Examples include, but are not limited to, ethylenylene or vinylene (—CH═CH—), allyl (—CH$_2$CH═CH—), and the like.

The term "alkoxy" denotes a group of the formula —O—R', wherein R' is an alkyl group. Alkoxy groups may be optionally substituted independently with one or more substituents described herein. Examples of alkoxy moieties include methoxy, ethoxy, isopropoxy, and tert-butoxy.

"Aryl" means a cyclic aromatic hydrocarbon moiety having a mono-, bi- or tricyclic aromatic ring of 5 to 16 carbon ring atoms. Bicyclic aryl ring systems include fused bicyclics having two fused five-membered aryl rings (denoted as 5-5), having a five-membered aryl ring and a fused six-membered aryl ring (denoted as 5-6 and as 6-5), and having two fused six-membered aryl rings (denoted as 6-6). The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted.

The term "heteroaryl" denotes an aromatic heterocyclic mono-, bi- or tricyclic ring system of 5 to 16 ring atoms, comprising 1, 2, 3 or 4 heteroatoms selected from N, O and S, the remaining ring atoms being carbon. In some aspects, monocyclic heteroaryl rings may be 5-6 membered. Bicyclic heteroaryl ring systems include fused bicyclics having two fused five-membered heteroaryl rings (denoted as 5-5), having a five-membered heteroaryl ring and a fused six-membered heteroaryl ring (denoted as 5-6 and 6-5), and having two fused six-membered heteroaryl rings (denoted as 6-6). The heteroaryl group can be optionally substituted as defined herein. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl or trifluoromethyl.

The term "heteroalkyl" refers to a straight- or branched-chain alkyl as defined herein having from 2 to 14 carbons, from 2 to 10 carbons, or from 2 to 6 carbons in the chain, one or more of which has been replaced by a heteroatom selected from S, O, P and N. Non-limiting examples of heteroalkyls include alkyl ethers, secondary and tertiary alkyl amines, amides, and alkyl sulfides.

"Cycloalkyl" means a saturated or partially unsaturated carbocyclic moiety having mono-, bi- (including bridged bicyclic) or tricyclic rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_8$) cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl), bicyclo[3.1.0]hexanyl, bicyclo[3.1.0]hexenyl, bicyclo[3.1.1]heptanyl, and bicyclo[3.1.1]heptenyl. The cycloalkyl moiety can be attached in a "spirocycloakyl" fashion such as "spirocyclopropyl":

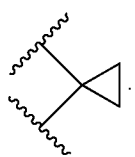 [SMILES: *C1(*)CC1]

"Heterocycle" or "heterocyclyl" refers to a 4, 5, 6 and 7-membered monocyclic, 7, 8, 9 and 10-membered bicyclic (including bridged bicyclic) or 10, 11, 12, 13, 14 and 15-membered bicyclic heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In some aspects, the heterocycle is a heterocycloalkyl. In particular embodiments heterocycle or heterocyclyl refers to a 4, 5, 6 or 7-membered heterocycle. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure. Any of the heterocycle ring atoms can be optionally substituted with one or more substituents described herein. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, azabicyclo[2.2.1]heptanyl, azabicyclo[3.1.0]hexanyl, azabicyclo[3.1.1]heptanyl, octahydroindolyl, or tetrahydroquinolinyl.

The term "fused bicyclic" denotes a ring system including two fused rings, including bridged cycloalkyl and bridged heterocycloalkyl as defined elsewhere herein. The rings are each independently, aryl, heteroaryl, cycloalkyl, and heterocycle. In some aspects, the rings are each independently, $C_{5-6}$ aryl, 5-6 membered heteroaryl, $C_{3-6}$ cycloalkyl, and 4-6 membered heterocycle. Non-limiting examples of fused bicyclic ring systems include $C_{5-6}$ aryl-$C_{5-6}$ aryl, $C_{5-6}$ aryl-4-6 membered heteroaryl, and $C_{5-6}$ aryl-$C_{5-6}$ cycloalkyl.

The term "fused tricyclic" denotes a ring system including three fused rings. The rings are each independently, aryl, heteroaryl, cycloalkyl, and heterocycle. In some aspects, the rings are each independently, $C_{5-6}$ aryl, 5-6 membered heteroaryl, $C_{3-6}$ cycloalkyl, and 4-6 membered heterocycle. An non-limiting example of a fused tricyclic ring system is $C_{3-6}$ cycloakyl-$C_{3-6}$ cycloalkyl-$C_{5-6}$ aryl, for instance, $C_3$ cycloalkyl-$C_5$ cycloalkyl-$C_6$ aryl.

Unless otherwise indicated, the term "hydrogen" or "hydro" refers to the moiety of a hydrogen atom (—H) and not $H_2$.

In the description herein, if there is a discrepancy between a depicted structure and a name given to that structure, then the depicted structure controls. Additionally, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. As used herein, "pharmaceutically acceptable" refers to a carrier, diluent or excipient that is compatible with the other ingredients of the formulation and not deleterious to the recipient thereof. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in compounds (l), (m) and (n) for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, a therapeutically effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

One embodiment of the present invention provides for compounds of formula I, stereoisomers thereof, tautomers thereof, and salts thereof:

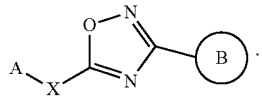
(I)

A is selected from substituted and unsubstituted 6-6 fused bicyclic heteroaryl, substituted and unsubstituted 5-6 fused bicyclic heteroaryl, and substituted and unsubstituted 6-5 fused bicyclic heteroaryl.

In some aspects, A is selected from:

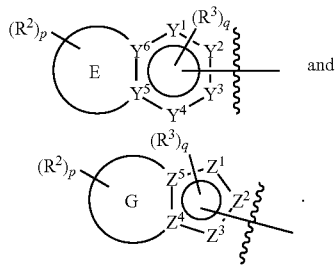

E is a five membered or a six membered heteroaryl ring wherein one ring carbon atom is optionally substituted with oxo. G is a six membered heteroaryl ring having one ring carbon atom substituted with oxo. One of $Y^1$, $Y^2$, $Y^3$ and $Y^4$ is —C(O)—, one to three of $Y^1$, $Y^2$, $Y^3$, $Y^4$, $Y^5$ and $Y^6$ are nitrogen, and the other of $Y^1$, $Y^2$, $Y^3$, $Y^4$, $Y^5$ and $Y^6$ are carbon. One or two of $Z^1$, $Z^2$, $Z^3$, $Z^4$ and $Z^5$ are nitrogen and the other of $Z^1$, $Z^2$, $Z^3$, $Z^4$ and $Z^5$ are carbon. Each $R^2$ is independently selected from H, deuterium, —$C_{1-4}$ alkyl, —$C_{1-4}$ haloalkyl, —CN, halo, haloalkoxy, $C_{1-4}$ alkoxy, —OH, —$SO_2$—$C_{1-4}$alkyl, —$C_{1-4}$CN, $C_{1-4}$ aldehyde, $C_{1-4}$ ketone, and $NR^{14}R^{15}$. $R^{14}$ and $R^{15}$ are independently selected from H, substituted and unsubstituted —$C_{1-4}$ alkyl, substituted and unsubstituted —C(O)—$C_{1-4}$ alkyl, substituted and unsubstituted $C_{3-6}$ cycloalkyl, substituted and unsubstituted 3- to 6-membered heterocycloalkyl, substituted and unsubstituted —$C_{1-4}$ heteroalkyl, and substituted and unsubstituted —$C_{1-4}$ alkyl-C(O)$NR^{16}R^{17}$, wherein $R^{16}$ and $R^{17}$ are independently selected from H and $C_{1-4}$ alkyl. p is 0, 1 or 2. $R^3$ is selected from H, —$C_{1-4}$ alkyl, —$C_{1-4}$ haloalkyl, —CN, and halo. q is 0 or 1.

In some aspects, A is a fused heteroaryl moiety selected from:

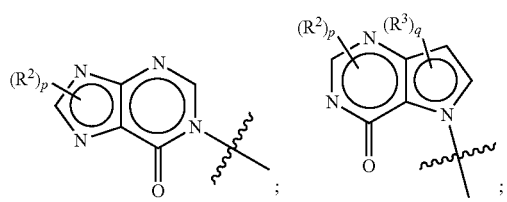

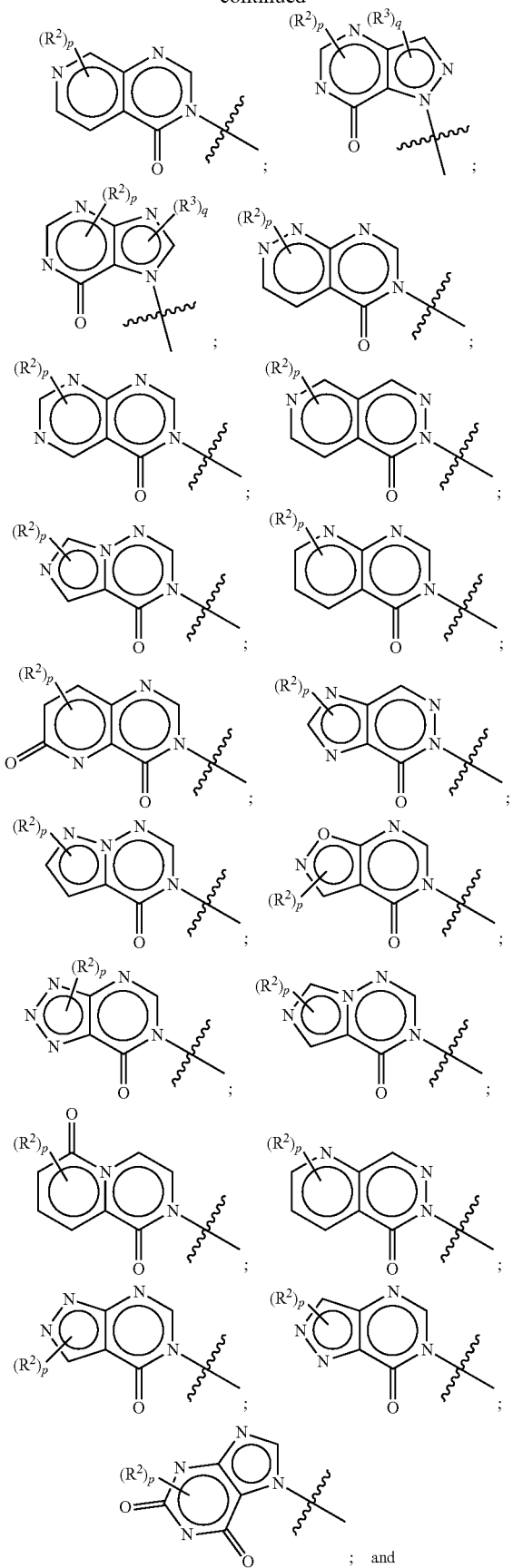

-continued

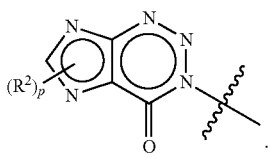

In some aspects, each $R^2$ is independently selected from H, -D, —$C_{1-4}$ alkyl, —$C_{1-4}$ haloalkyl, —CN, halo, —C(O)CH$_3$, —NH$_2$, NHC$_{1-4}$ alkyl wherein the $C_{1-4}$ alkyl optionally comprises an oxygen heteroatom or an —OH substitutent, —NHC(O)—$C_{1-4}$ alkyl, —NHCH$_2$C(O)N($C_{1-4}$ alkyl)$_2$, and —NH—$C_{4-6}$ heterocyclo comprising an oxygen heteroatom. In some aspects, each $R^2$ is independently selected from H, D, —CH$_3$, —CN, -halo, —NH$_2$, —NHCH$_3$, NHCH$_2$CH$_3$, —NHCH$_2$CH$_2$CH$_2$OH, —NHCH$_2$CH$_2$OCH$_3$, —NHC(O)CH$_3$, —NHCH$_2$C(O)N(CH$_3$)$_2$,

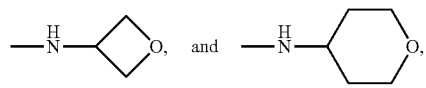

and p is 0 or 1. $R^3$ is selected from H, -D, —$C_{1-4}$ alkyl, —$C_{1-4}$ haloalkyl, —CN and halo. In some aspects, $R^3$ is selected from H, -D and —CN.

In some aspects, A is selected from:

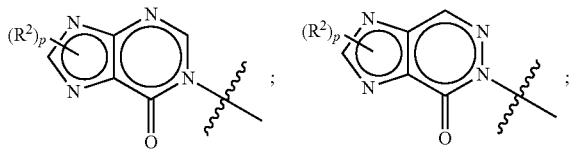

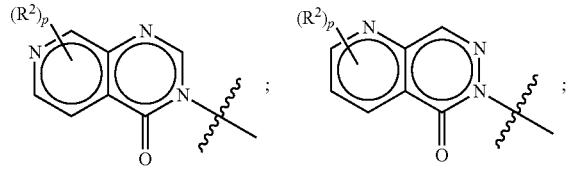

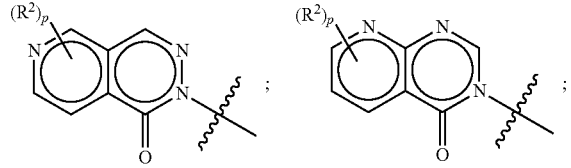

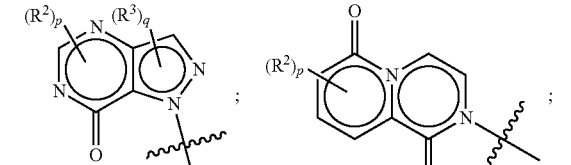

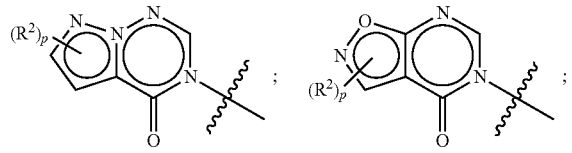

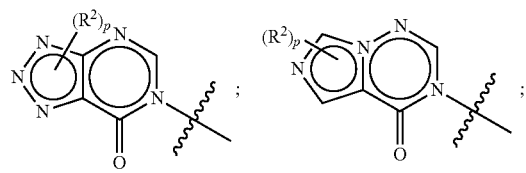

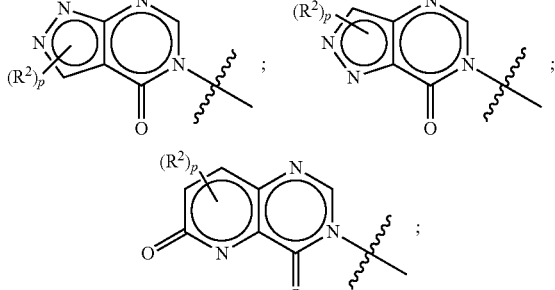

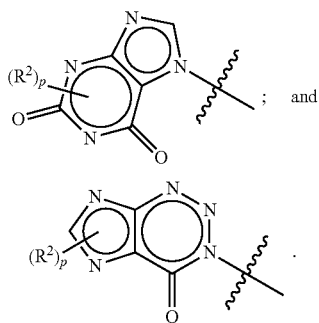

wherein $R^2$, $R^3$, p and q are as defined elsewhere herein.

In some aspects, A is selected from:

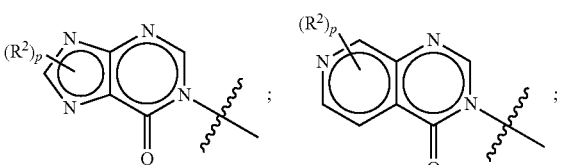

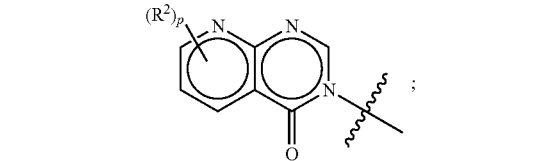

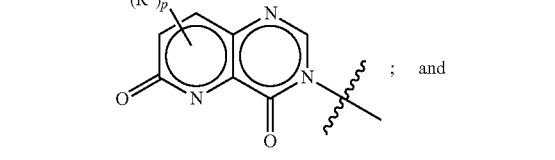

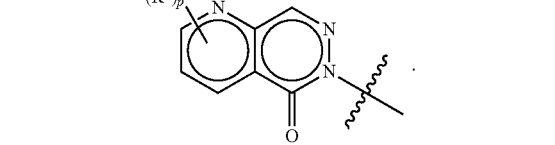

wherein $R^2$, $R^3$, p and q are as defined elsewhere herein.

In some aspects, A is selected from:
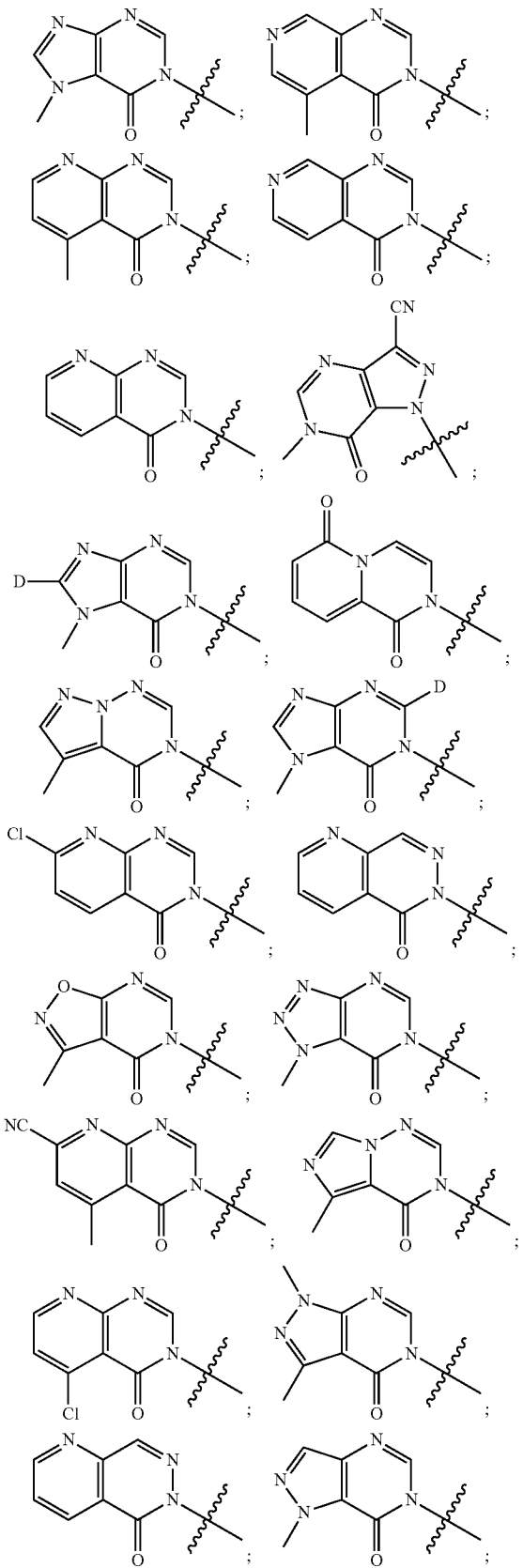
-continued
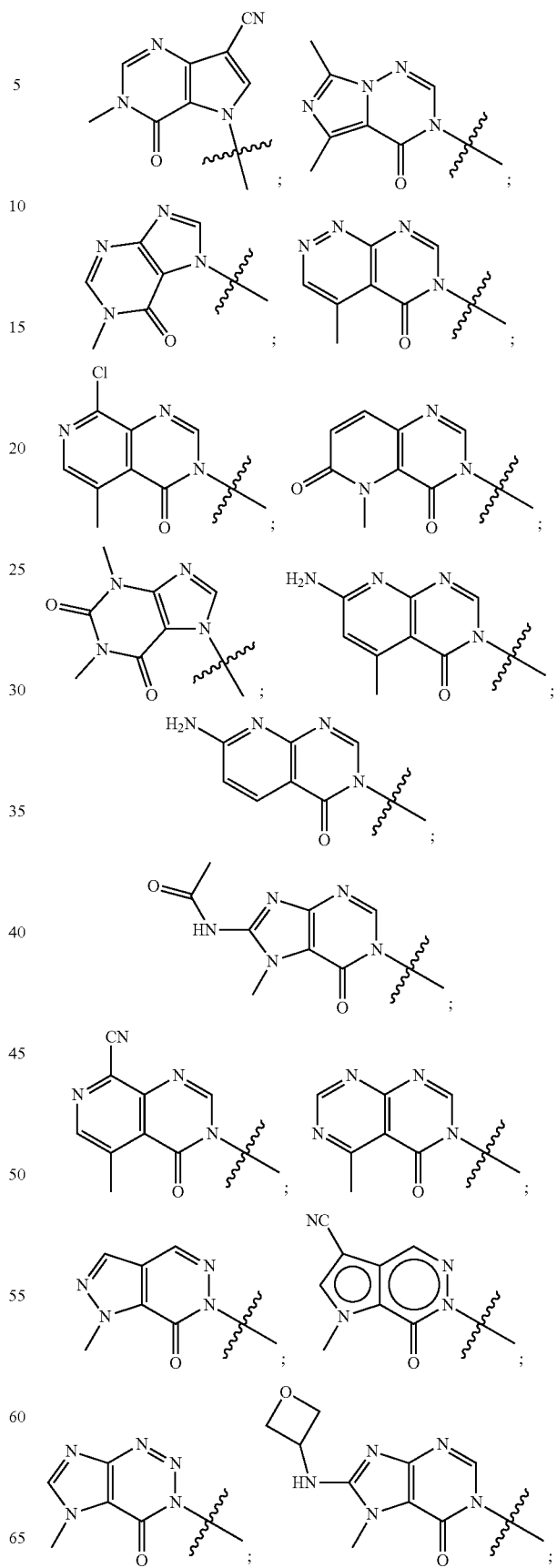

-continued
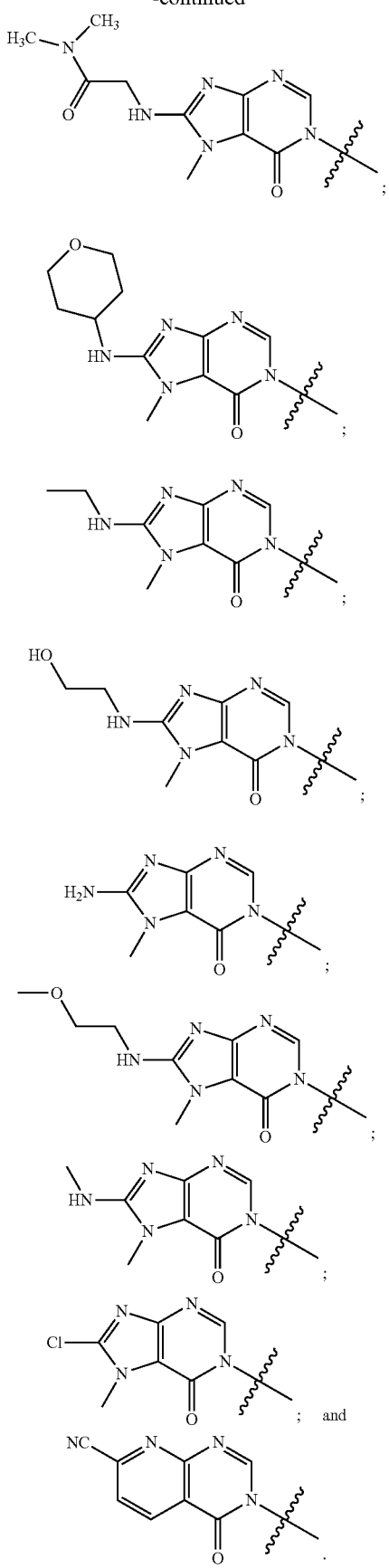
In some aspects, A is selected from:
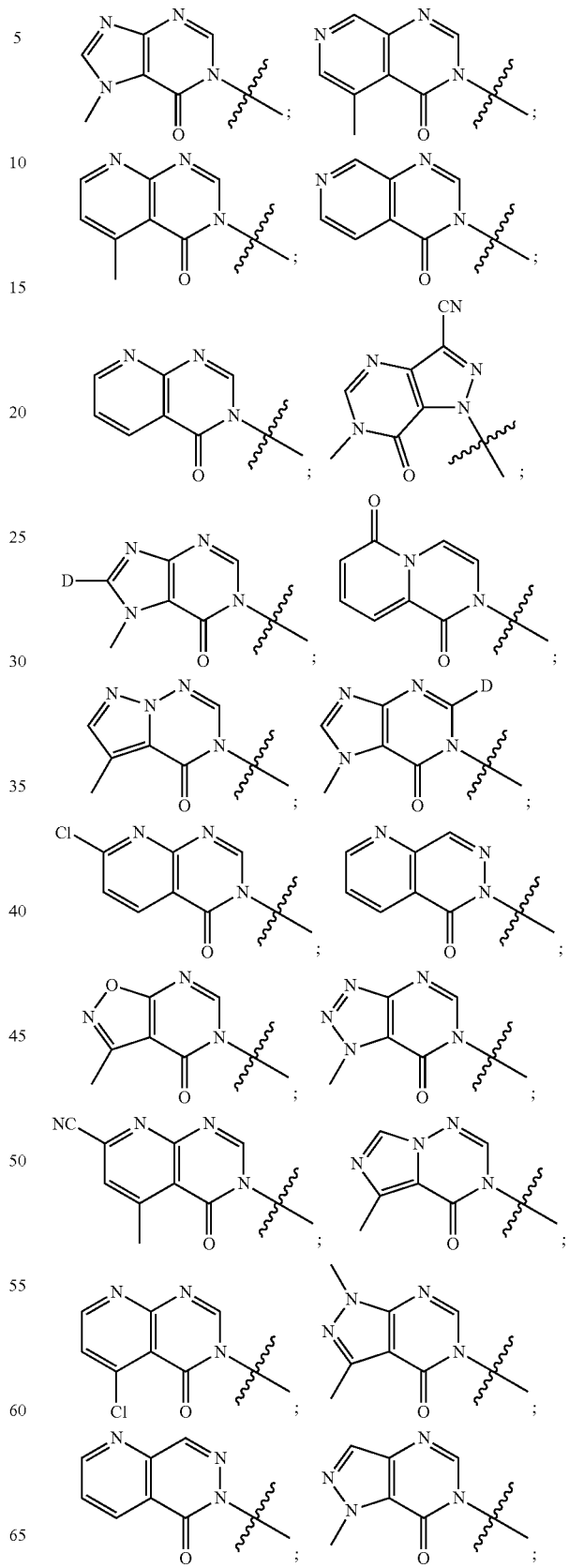

-continued

[chemical structures]

In some aspects, A is selected from:

[chemical structures]

In some aspects, A is:

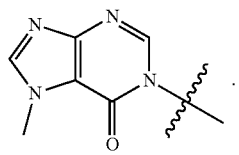 [SMILES: *n1cnc2ncn(C)c2c1=O]

X is selected from a bond, $C_{1-4}$ alkylene, —O—, —S—, —SO$_2$—, and —N(R$^1$)—, wherein R$^1$ is selected from H and $C_{1-6}$ alkyl. In some aspects, X is methylene.

B is selected from (a) substituted and unsubstituted $C_{4-6}$ cycloalkyl wherein, when substituted, the bond to the oxadiazole moiety and the bond to the substituent are on other than adjacent ring carbon atoms; (b) substituted and unsubstituted fused bicyclic bound to the oxadiazole moiety by a carbon-carbon bond; and (c) substituted and unsubstituted fused tricyclic.

In some aspects, B is a substituted or unsubstituted $C_{4-6}$ cycloalkyl of the formula:

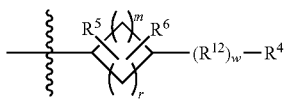

wherein:
R$^4$ is selected from substituted or unsubstituted aryl, substituted or unsubstituted heteroaryl, and substituted or unsubstituted naphthyl; R$^5$ and R$^6$ are independently selected from H, —C$_{1-4}$ alkyl, halogen and —OH; R$^{12}$ is selected from substituted and unsubstituted C$_{1-4}$ alkylene and —O—; m is 1 or 2; r is 1 or 2; and w is 0 or 1.

In some aspects, B is a substituted or unsubstituted $C_{4-6}$ cycloalkyl of the formula, or a stereoisomer thereof:

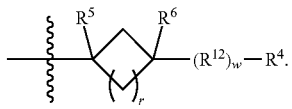

R$^4$, R$^5$, R$^6$, R$^{12}$, r and w are as defined herein.

In some aspects, R$^5$ and R$^6$ are independently selected from H, —OH, and F.

In some aspects, R$^4$ is:

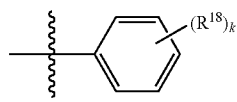

wherein each R$^{18}$ is independently selected from H, halogen, —OH, —C$_{1-4}$ alkyl, —C$_{1-4}$ haloalkyl, —CN, halo, C$_{1-4}$ haloalkoxy, C$_{1-4}$ alkoxy, —SO$_2$—C$_{1-4}$alkyl, —C$_{1-4}$CN, C$_{1-4}$ aldehyde, C$_{1-4}$ ketone, and fused aryl; and k is from 0 to 2. In some aspects, each R$^{18}$ is independently selected from H, Cl, —OCHF$_2$, —OCF$_3$, —OCH$_3$, and —CN.

In some aspects, when w is 1, R$^{12}$ is selected from C$_{1-4}$ haloalkylene and C$_{1-4}$ alkylene-one. In some aspects, R$^{12}$ is selected from difluoromethylene, methylene-one, and —O—.

In some aspects, B is a substituted or unsubstituted moiety of the formula, or a stereoisomer thereof:

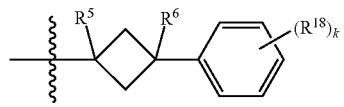

wherein:
each R$^{18}$ is independently selected from H, halogen, —OH, —C$_{1-4}$ alkyl, —C$_{1-4}$ haloalkyl, —CN, halo, C$_{1-4}$ haloalkoxy, C$_{1-4}$ alkoxy, —SO$_2$—C$_{1-4}$alkyl, —C$_{1-4}$CN, C$_{1-4}$ aldehyde, C$_{1-4}$ ketone, and fused aryl; and k is from 0 to 2. In some aspects, each R$^{18}$ is independently selected from H, Cl, —OCHF$_2$, —OCF$_3$, —OCH$_3$, and —CN.

In some such aspects, B is selected from the following, and stereoisomers thereof:

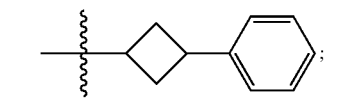

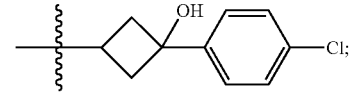

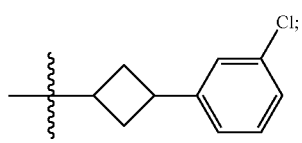

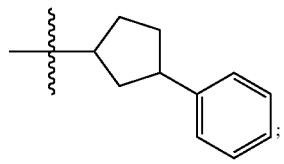

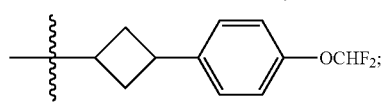

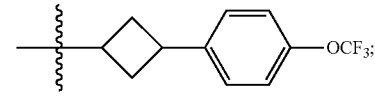

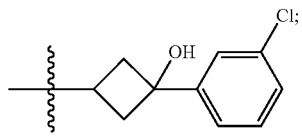

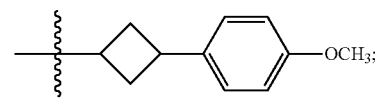

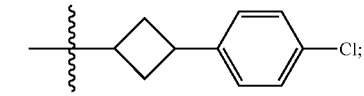

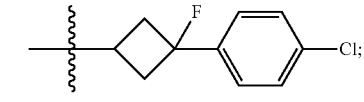

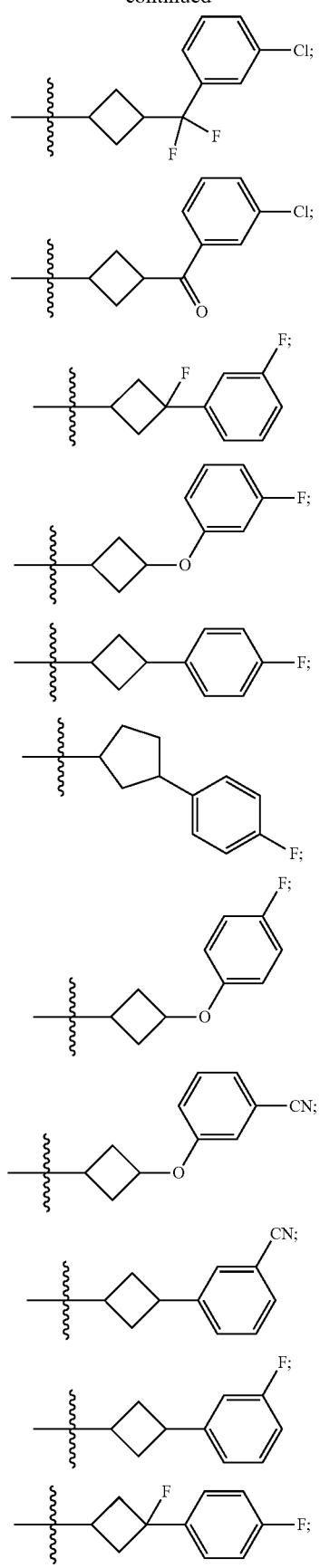
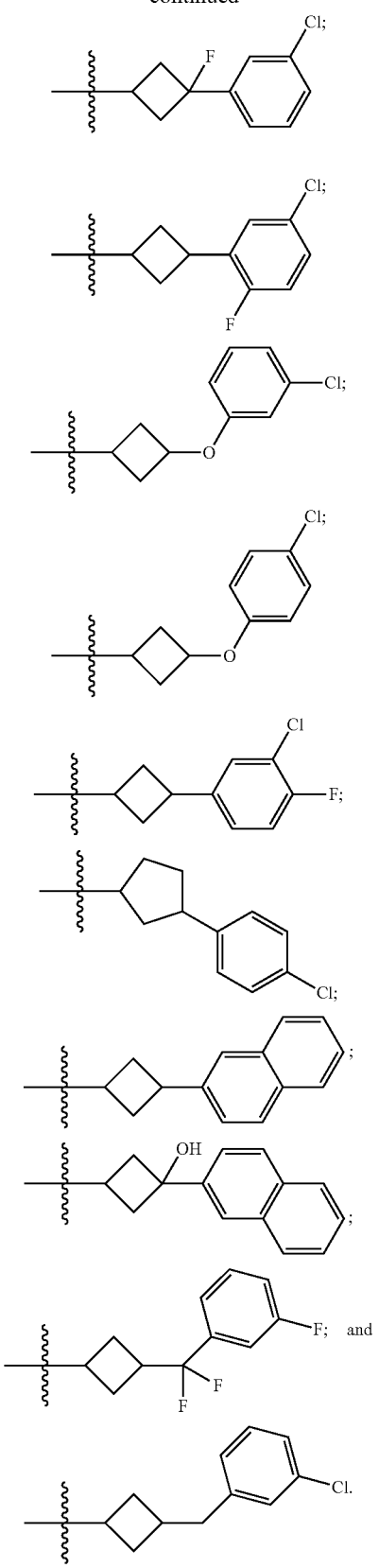
In some aspects, B is selected from, and stereoisomers thereof:

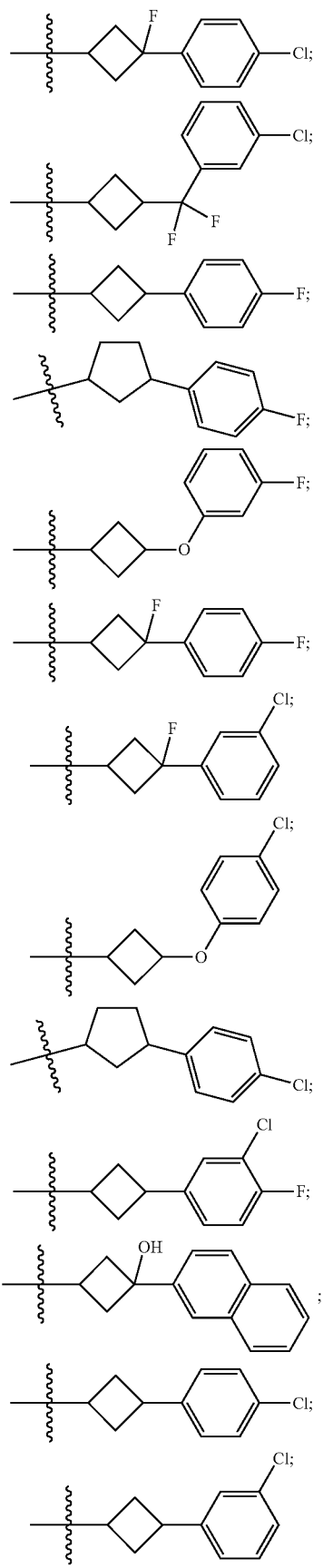

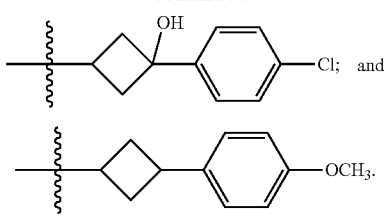

In some aspects, B is a substituted or unsubstituted fused tricyclic $C_{3-6}$ cycloalkyl-$C_{3-6}$ cycloalkyl-$C_{5-6}$ aryl. In some aspects, B is a substituted or unsubstituted $C_3$ cycloalkyl-$C_5$ cycloalkyl-$C_6$ aryl.

In some aspects, B is of the following formula or a stereoisomer thereof:

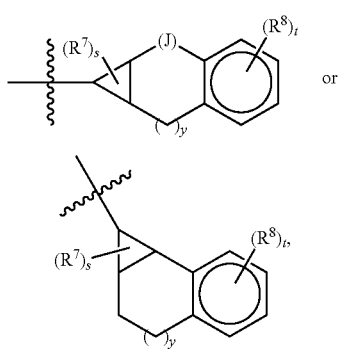

and
wherein $R^7$ is selected from H, —$C_{1-4}$ alkyl, halogen and —OH; J is —$CH_2$— or —O—; s is 0 or 1; y is 0 or 1; each $R^8$ is independently selected from —H, —OH, —$C_{1-4}$ alkyl, —$C_{1-4}$ haloalkyl, —CN, halo, $C_{1-4}$ haloalkoxy, $C_{1-4}$ alkoxy, —$SO_2$—$C_{1-4}$alkyl, —$C_{1-4}$CN, $C_{1-4}$ aldehyde, $C_{1-4}$ ketone; and t is 0, 1 or 2. In some aspects, $R^7$ is H. In some aspects, $R^8$ is selected from H and Cl. In some aspects, J is —$CH_2$— and y is 1, or J is —O— and y is 0 or 1.

In some aspects, B is of the formula or a stereoisomer thereof:

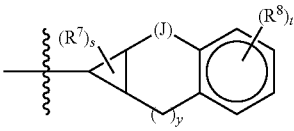

wherein $R^7$, $R^8$, J, y, s and t are as defined herein.

In some aspects, B is selected from, and stereoisomers thereof:

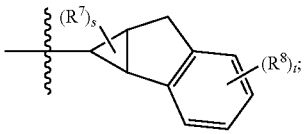

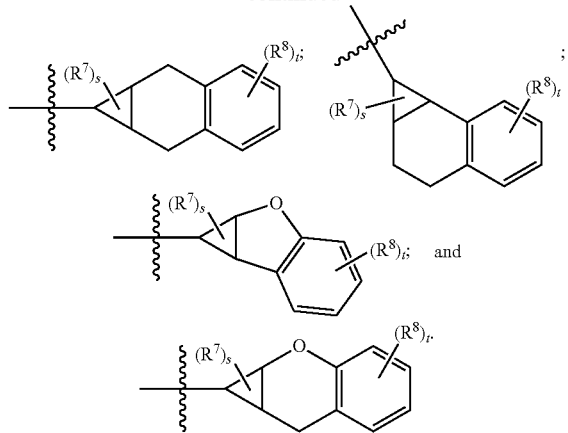

In certain aspects, $R^7$ is selected from H, halogen and —OH, s is 0 or 1; y is 0 or 1; each $R^8$ is independently selected from H and halogen; and t is 0, 1 or 2.

In some aspects, B is selected from, and stereoisomers thereof:

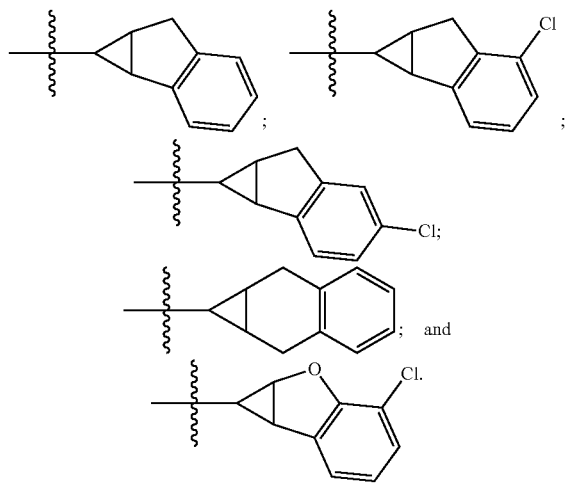

In some aspects, B is a substituted or unsubstituted fused bicyclic such as ($C_{3-6}$ cycloalkyl)-(4-6 membered heterocycloalkyl), or a stereoisomer thereof, bound to the oxadiazole moiety by a carbon-carbon bond.

In some such aspects, B is a fused bicyclic of the formula, or a stereoisomer thereof selected from:

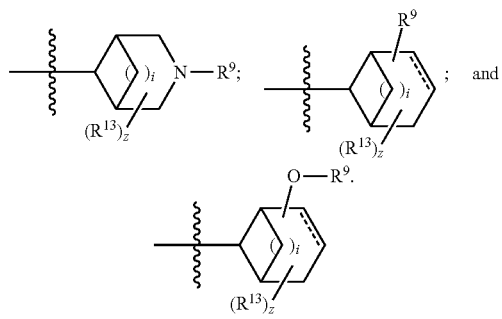

In such aspects, $R^9$ is selected from substituted or unsubstituted aryl, substituted or unsubstituted heteroaryl, substituted or unsubstituted fused bicyclic aryl, substituted or unsubstituted fused bicyclic heteroaryl, substituted or unsubstituted fused bicyclic aryl-heteroaryl, substituted or unsubstituted fused bicyclic aryl-cycloalkyl, substituted or unsubstituted fused bicyclic aryl-heterocycle, unsubstituted fused bicyclic heteroaryl-cycloalkyl, and substituted or unsubstituted fused bicyclic heteroaryl-heterocycle. $R^{13}$ is selected from $C_{1-4}$ alkyl and —OH. In some aspects, $R^{13}$ is —$CH_3$. z is 0 or 1. z is 0 or 1. The dashed line represents an optional bond thereby resulting in a double bond at that position.

In some aspects, B is a fused bicyclic of the formula, or a stereoisomer thereof selected from:

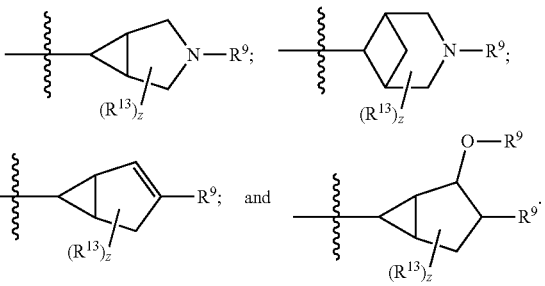

wherein $R^9$, $R^{13}$ and z are as defined elsewhere herein.

In some aspects, $R^9$ is selected from:

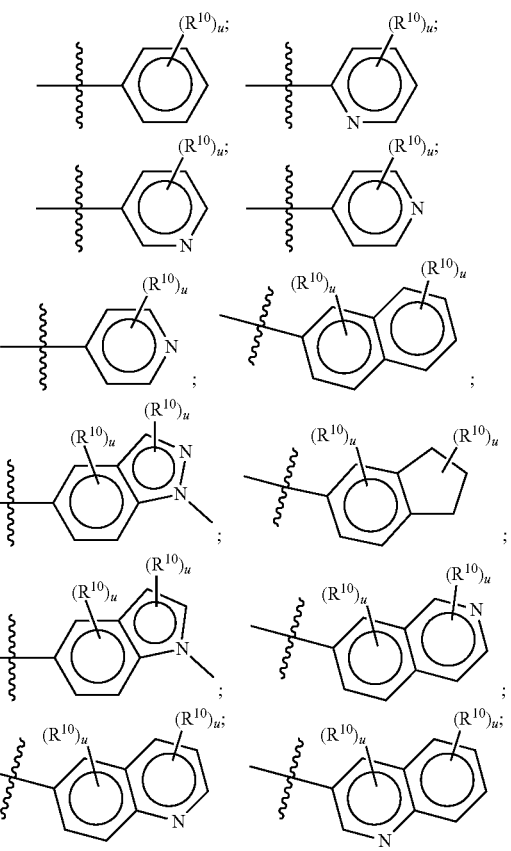

-continued

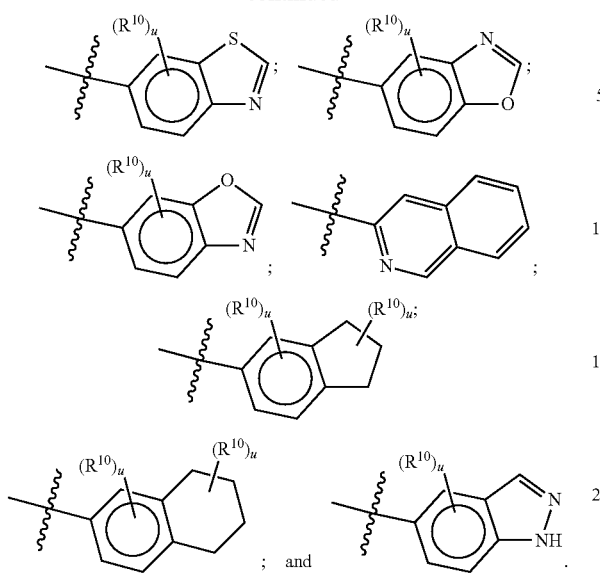

In such aspects, each $R^{10}$ is independently selected from H, halogen, —CN, —OH, $C_{1-4}$ alkyl, $C_{1-6}$ cycloalkyl, $C_{1-4}$ haloalkyl, $C_{1-4}$ haloalkoxy, $C_{1-4}$ alkoxy, —SO$_2$—$C_{1-4}$ alkyl, $C_{1-4}$ CN, $C_{1-4}$ aldehyde, $C_{1-4}$ ketone, —S—$C_{1-4}$ haloalkyl, substituted or unsubstituted 5- to 6-membered heteroaryl, substituted or unsubstituted 4- to 6-membered hetercycloalkyl, and substituted or unsubstituted $C_{5-6}$ aryl. Each u is independently selected from 0, 1, 2 and 3. In some aspects, each $R^{10}$ is independently selected from halogen, $C_1$ haloalkoxy, and $C_1$ alkoxy.

In some aspects, $R^9$ is selected from:

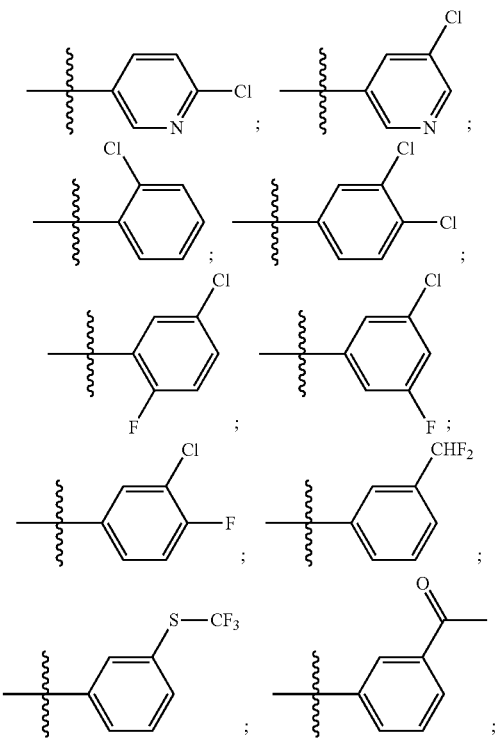

-continued

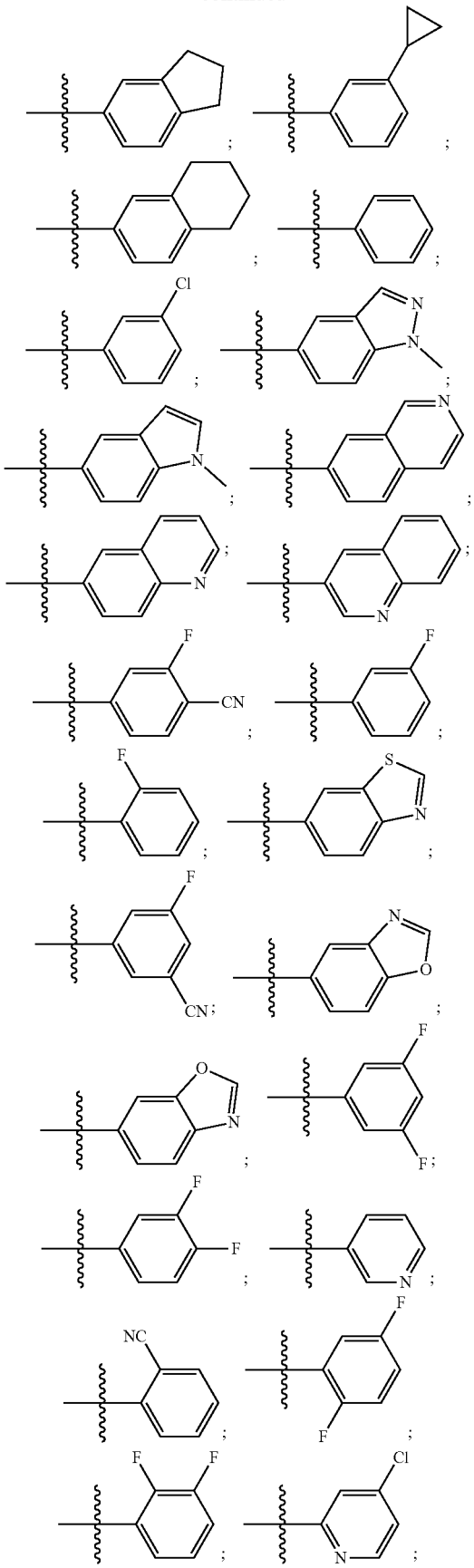

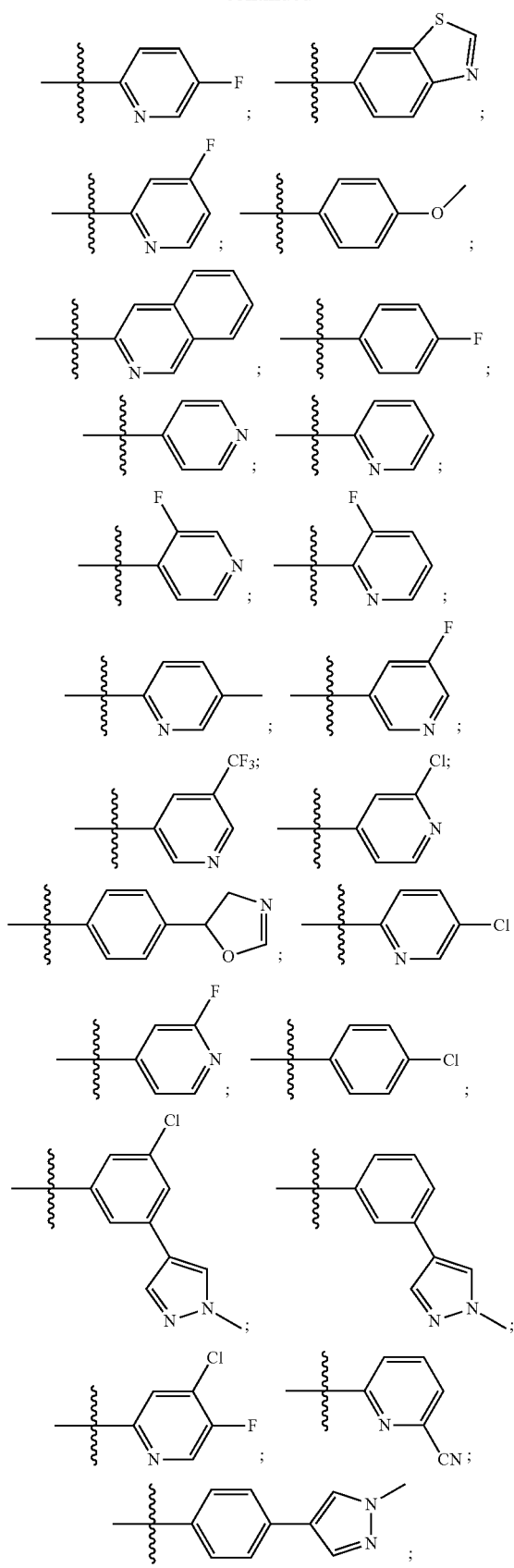
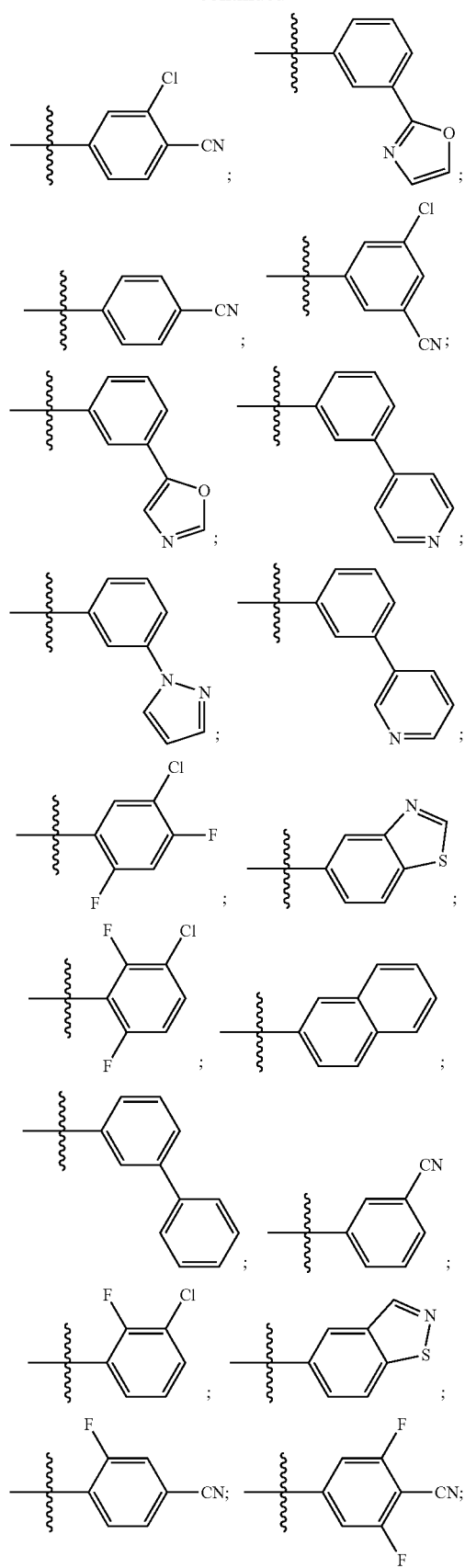

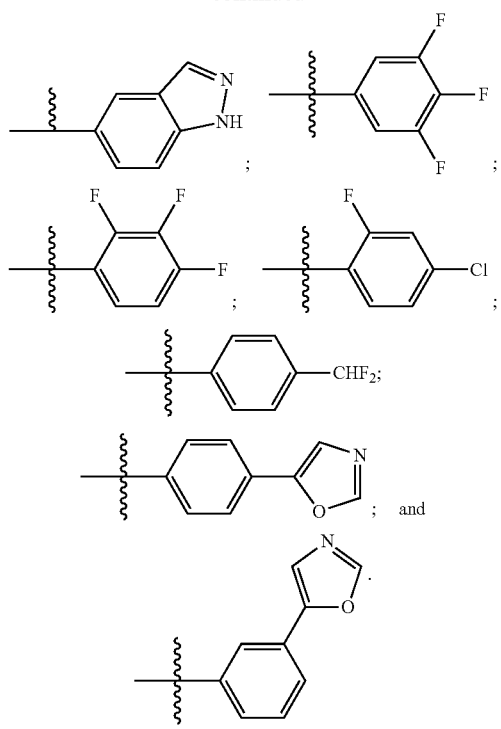
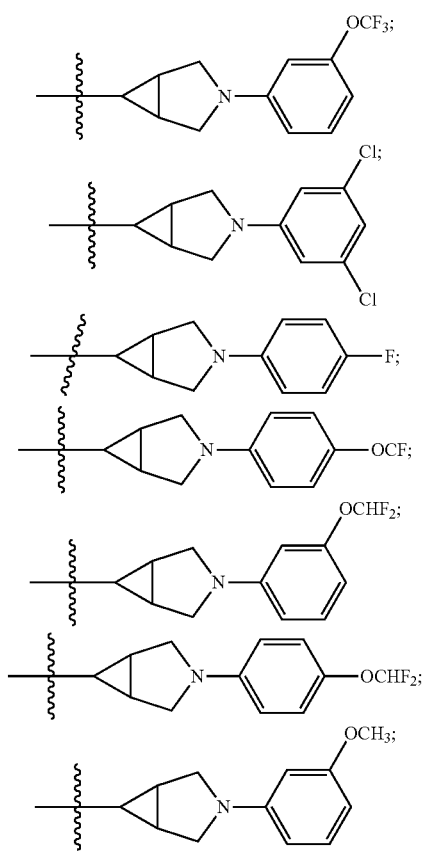
In some fused bicyclic aspects, B is selected from, and stereoisomers thereof:
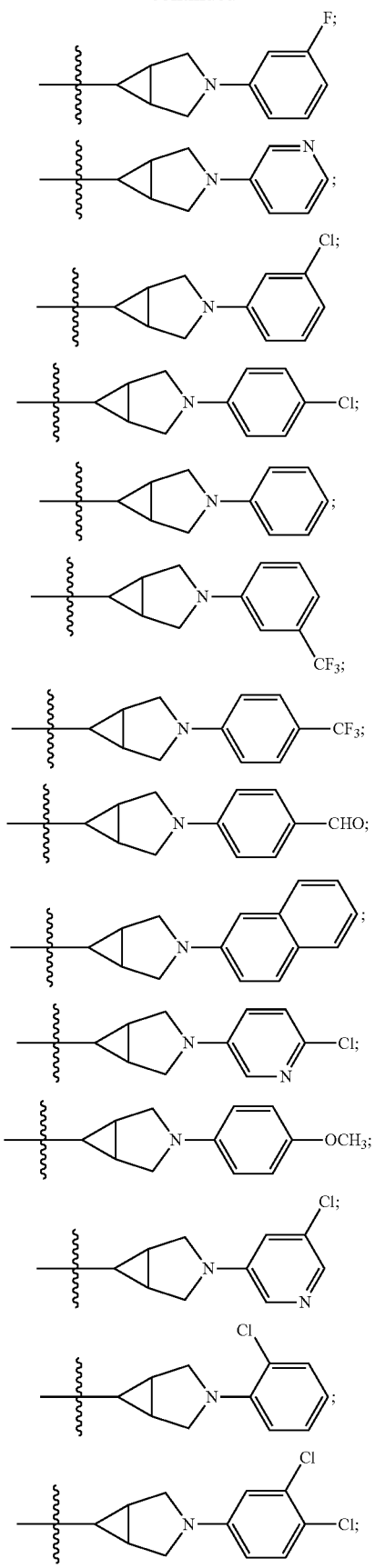

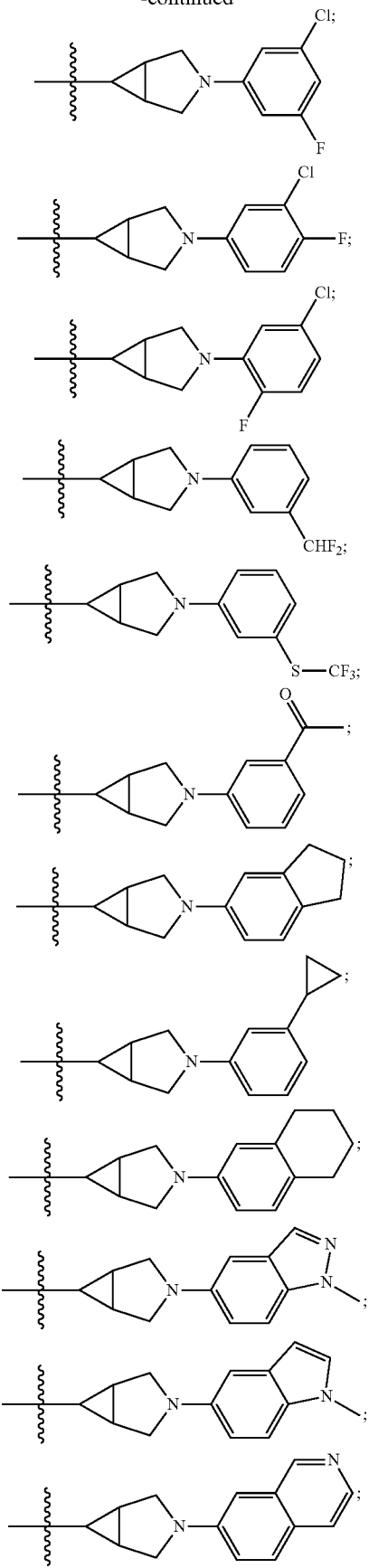
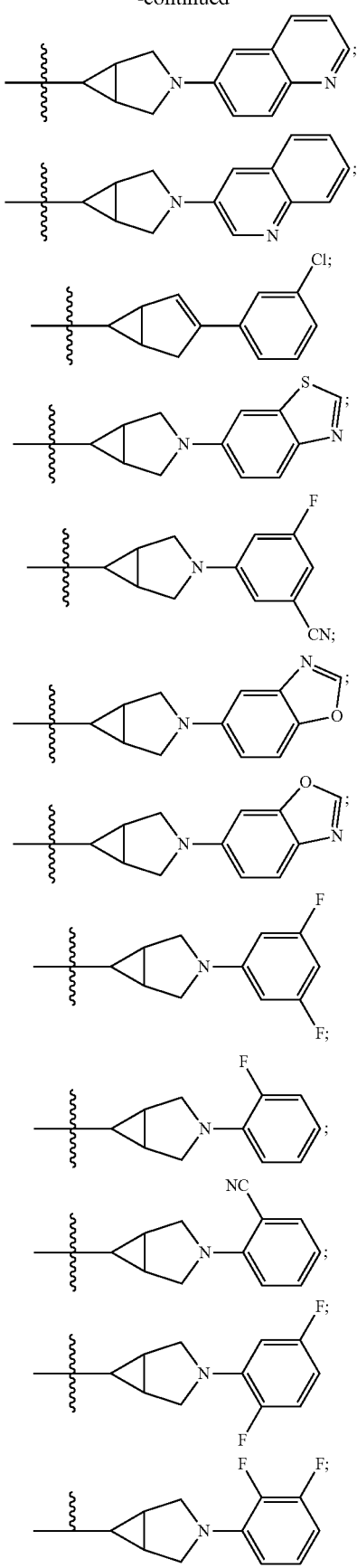

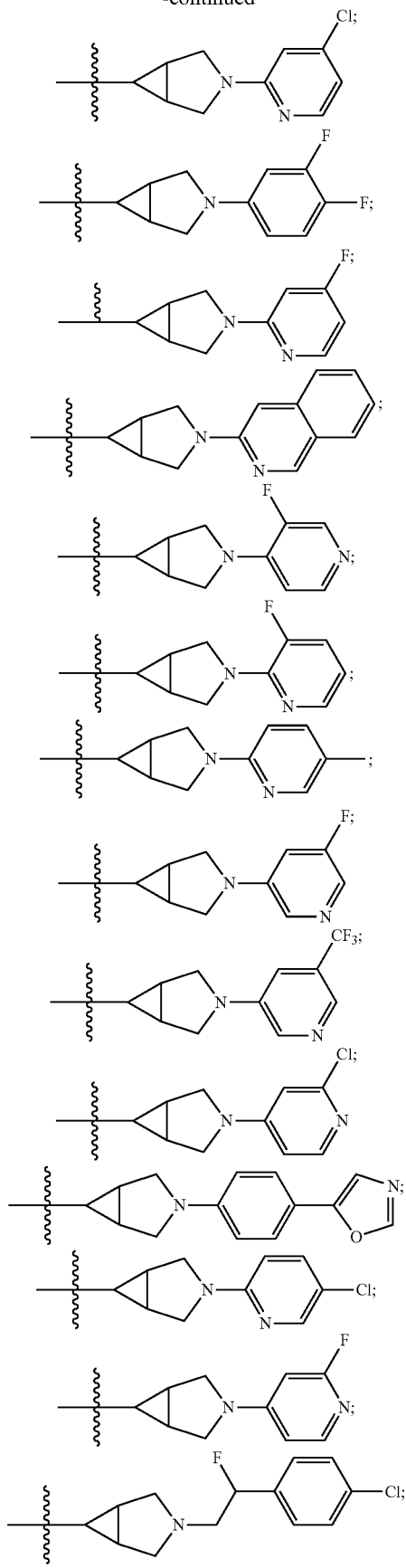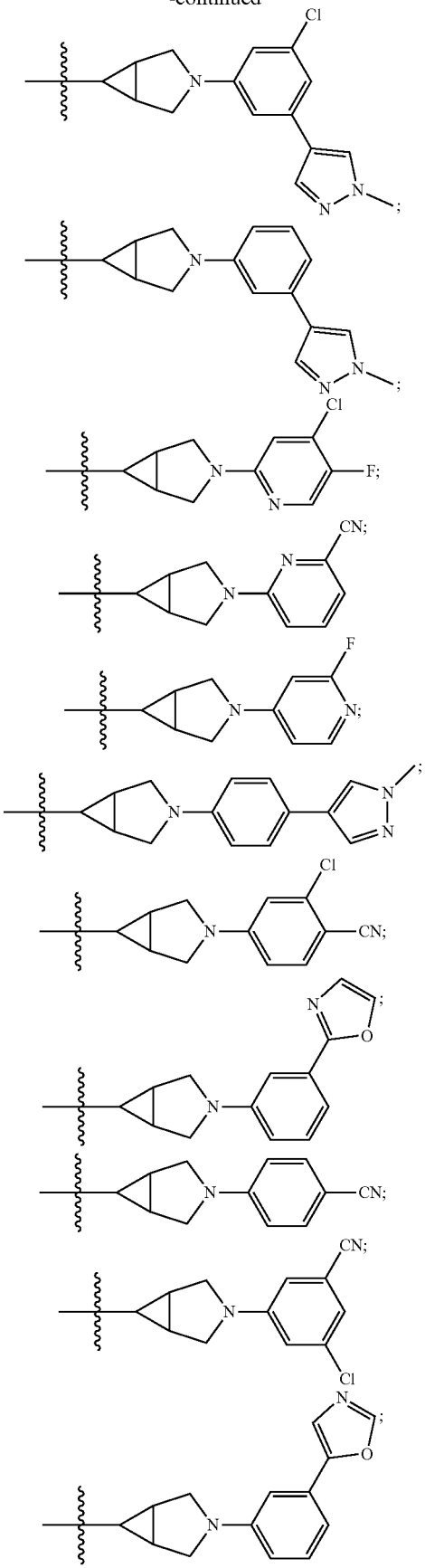

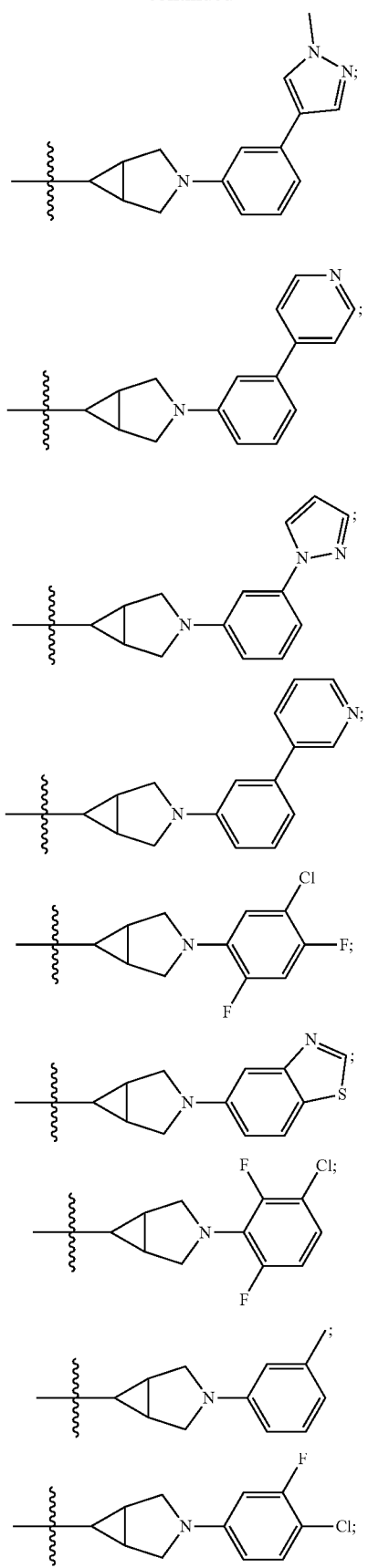
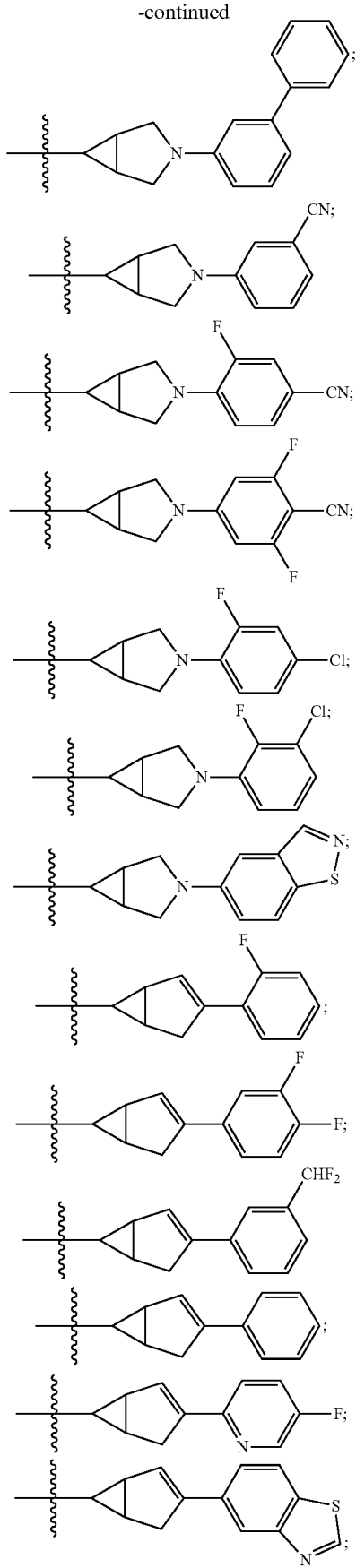

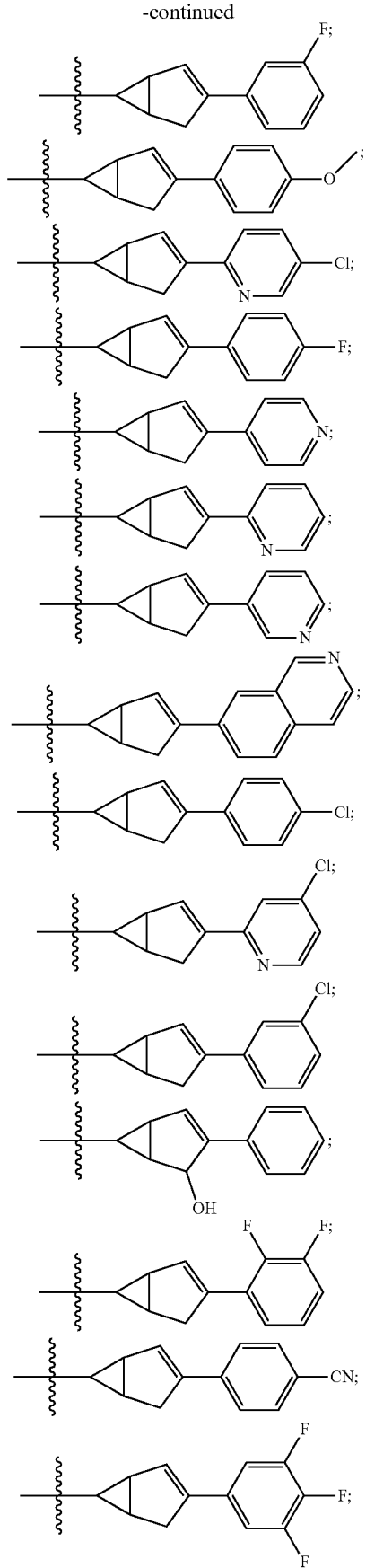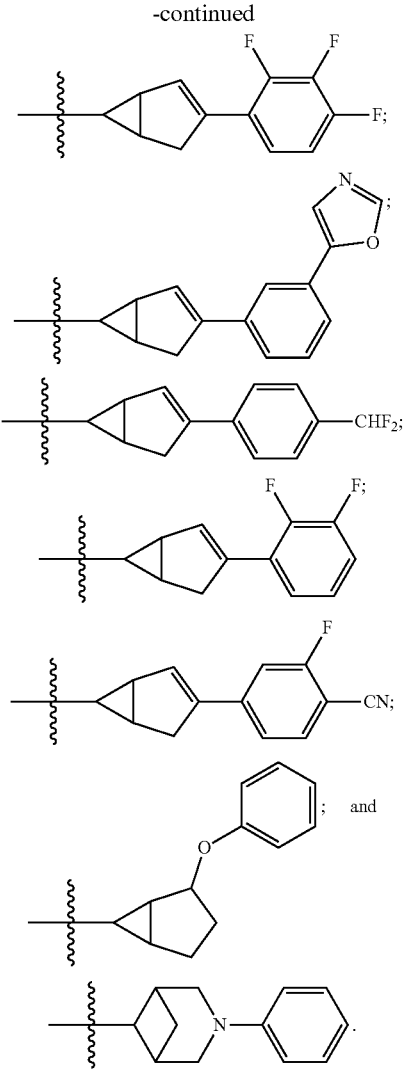
In some aspects, B is selected from the following, and stereoisomers thereof:
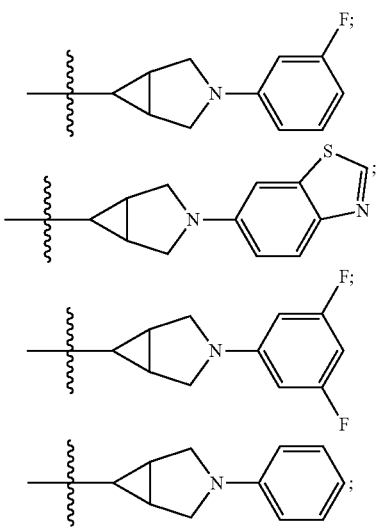

-continued
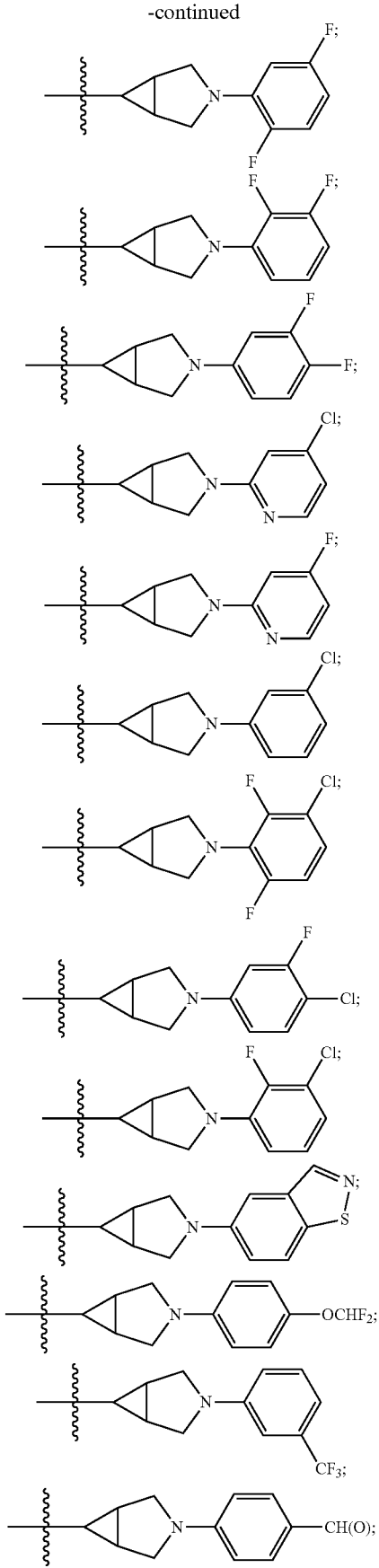
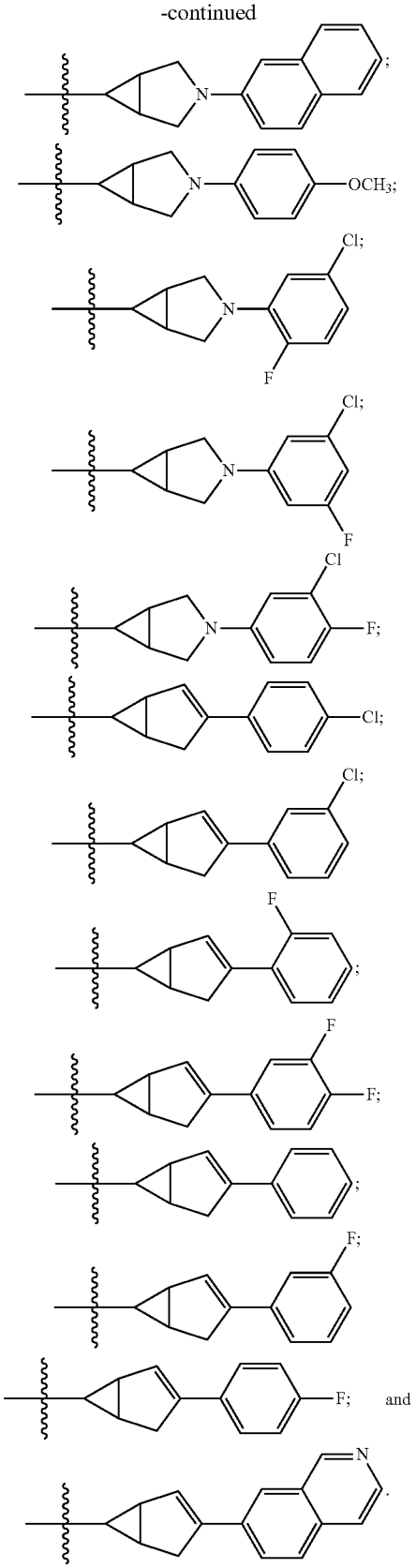
In some aspects, B is selected from, and stereoisomers thereof:

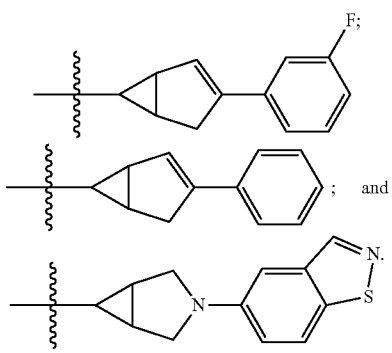

In some fused bicyclic aspects, B is:

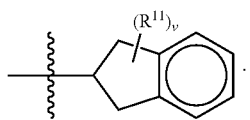

Each R[11] is independently selected from H, halogen, —OH, —$C_{1-4}$ alkyl, —$C_{1-4}$ haloalkyl, and —CN. v is 0, 1 or 2. In some aspects, B is selected from H, halogen, —OH, methyl, $C_1$ haloalkyl, and —CN. In some such aspects, B is:

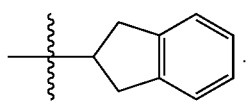 [SMILES: *C1Cc2ccccc2C1]

In some aspects, the compound of formula (I), or pharmaceutically acceptable salts and stereoisomers thereof, is selected from the following:

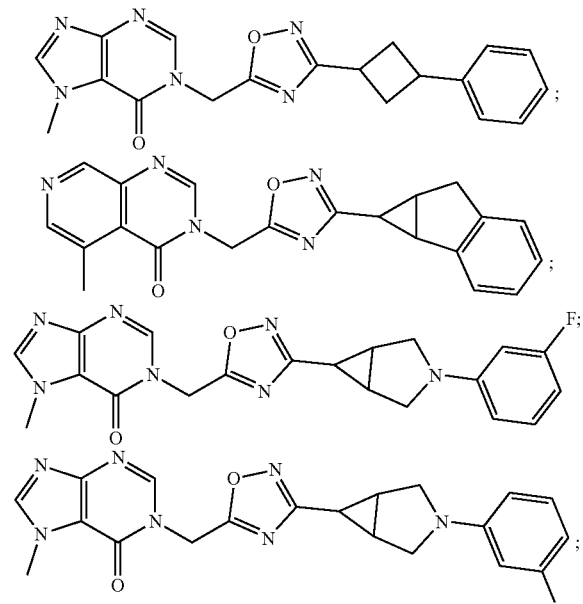

-continued

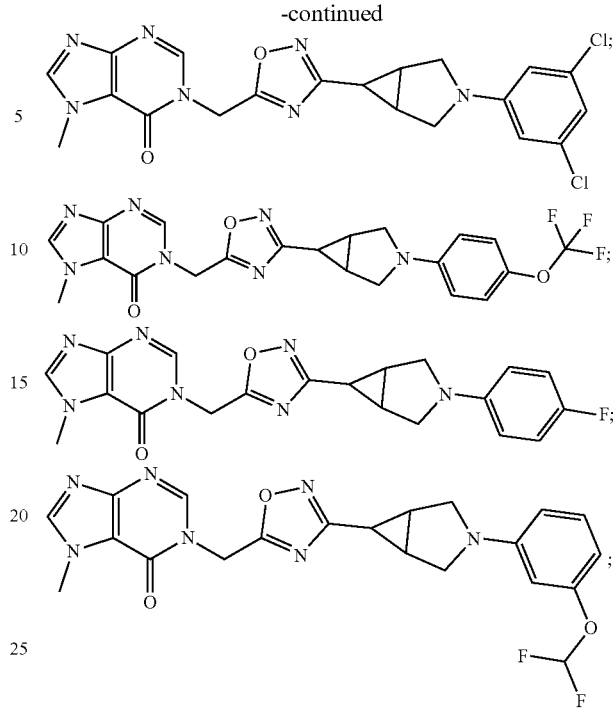

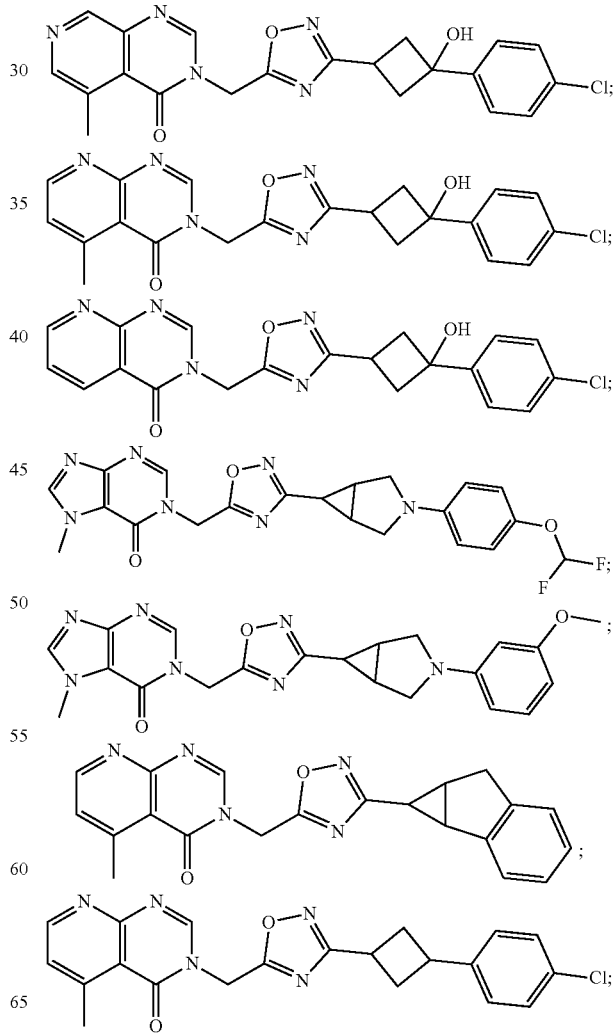

97
-continued
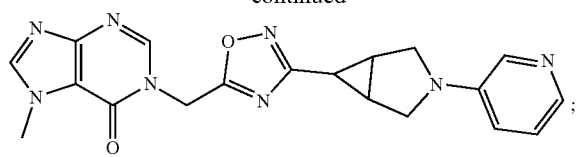
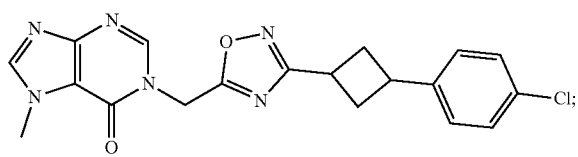
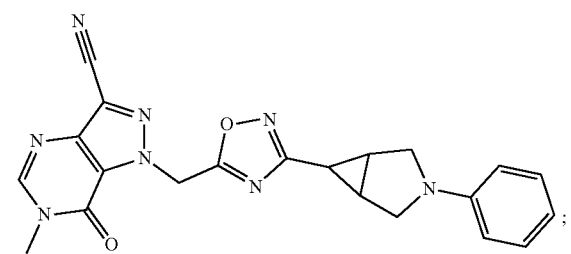
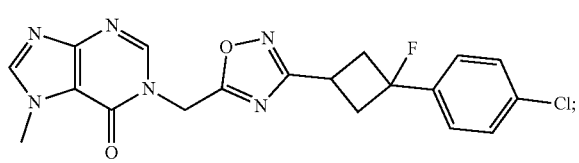
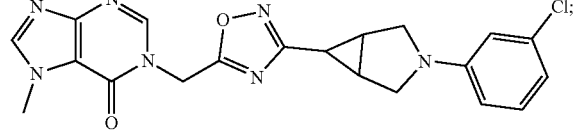
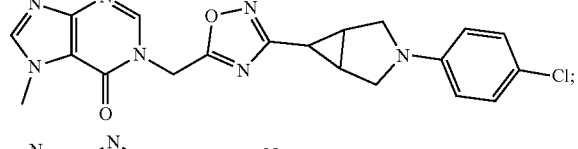
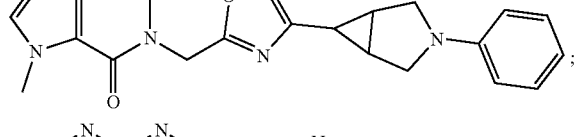
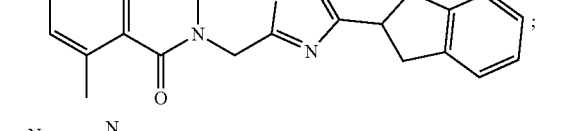
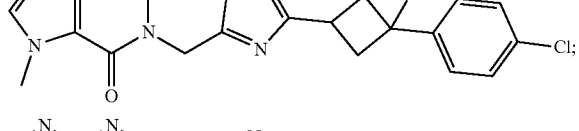
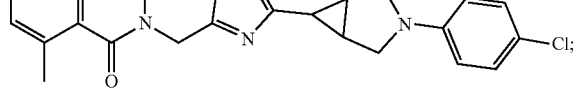
98
-continued
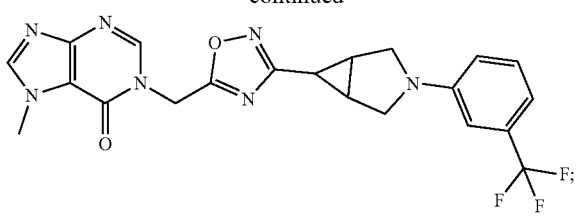
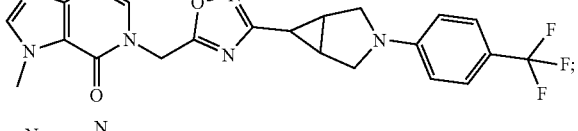
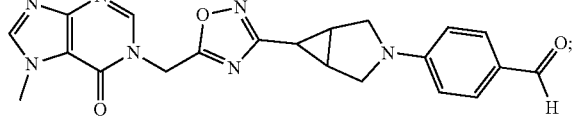
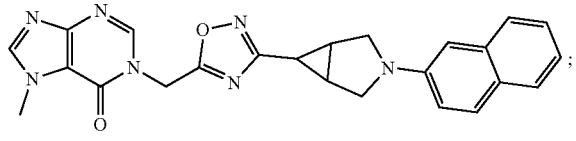
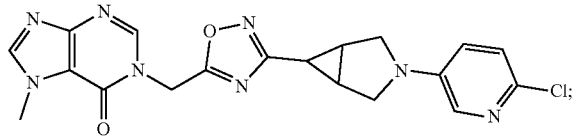
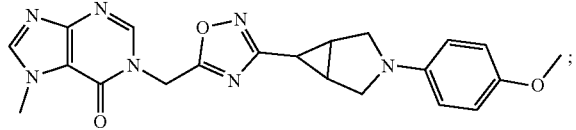
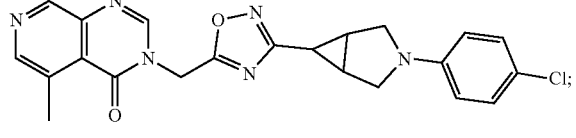
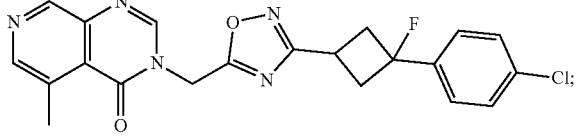
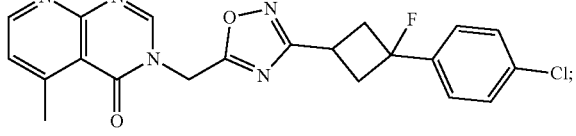
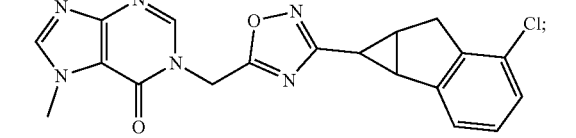
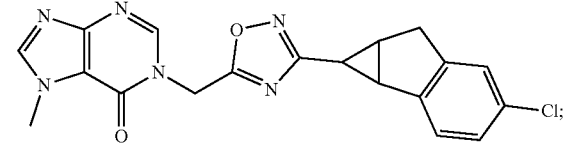

99
-continued
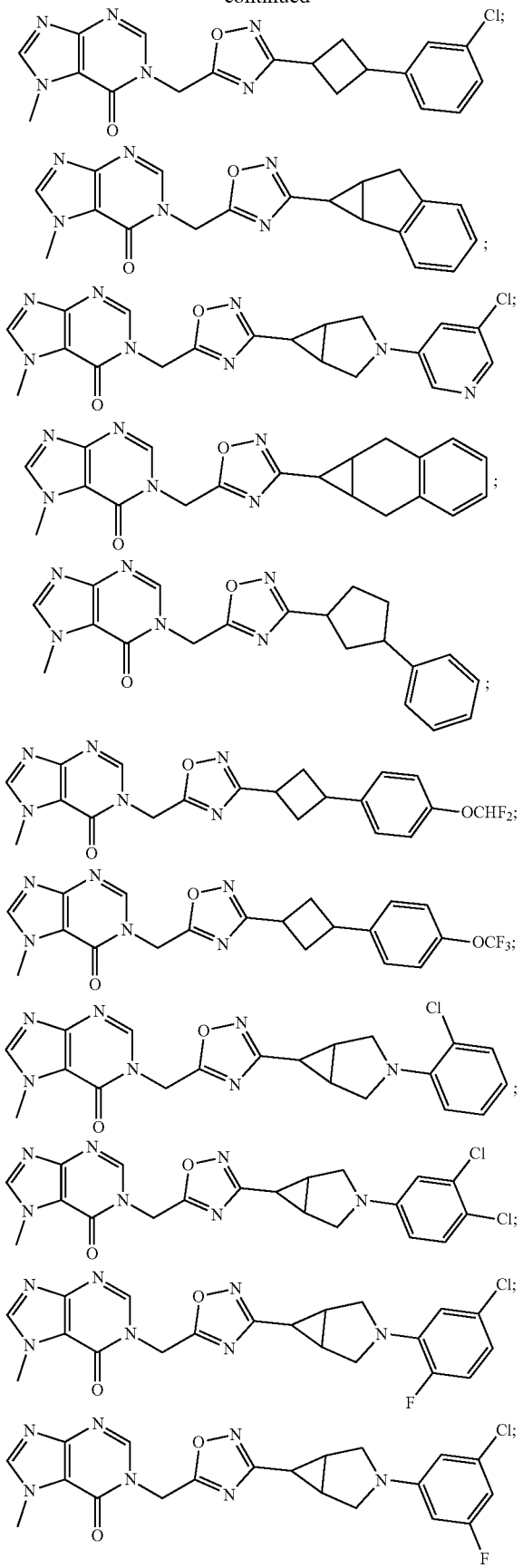
100
-continued
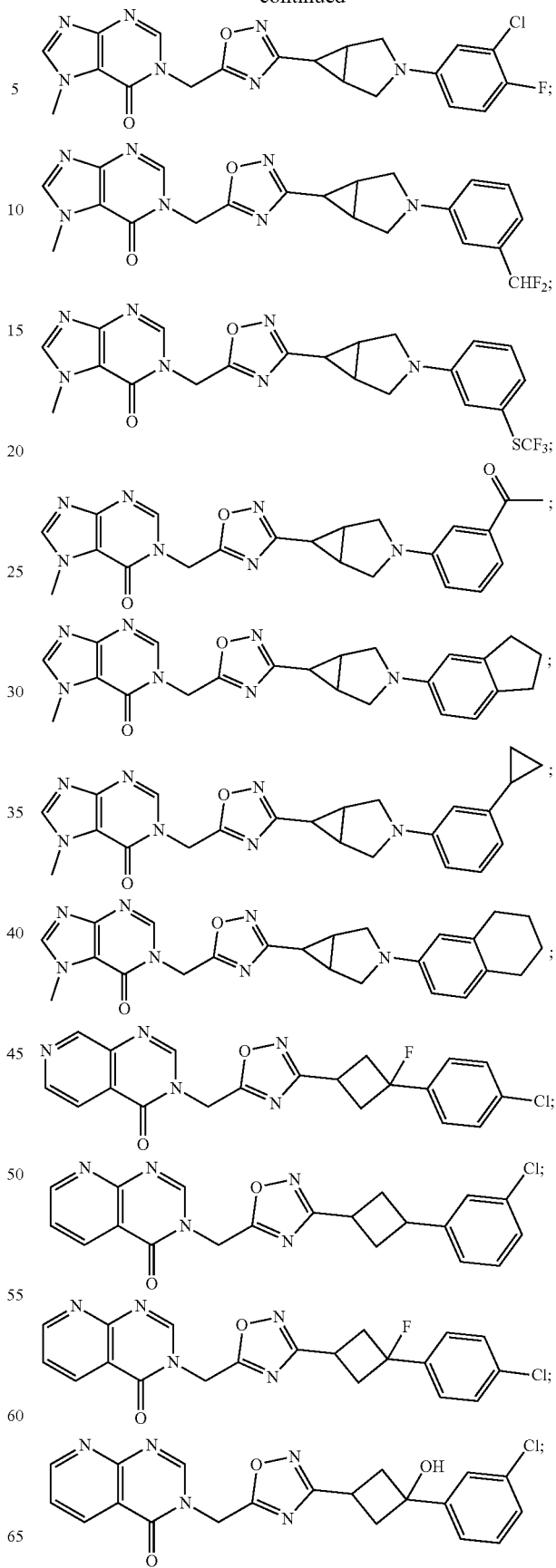

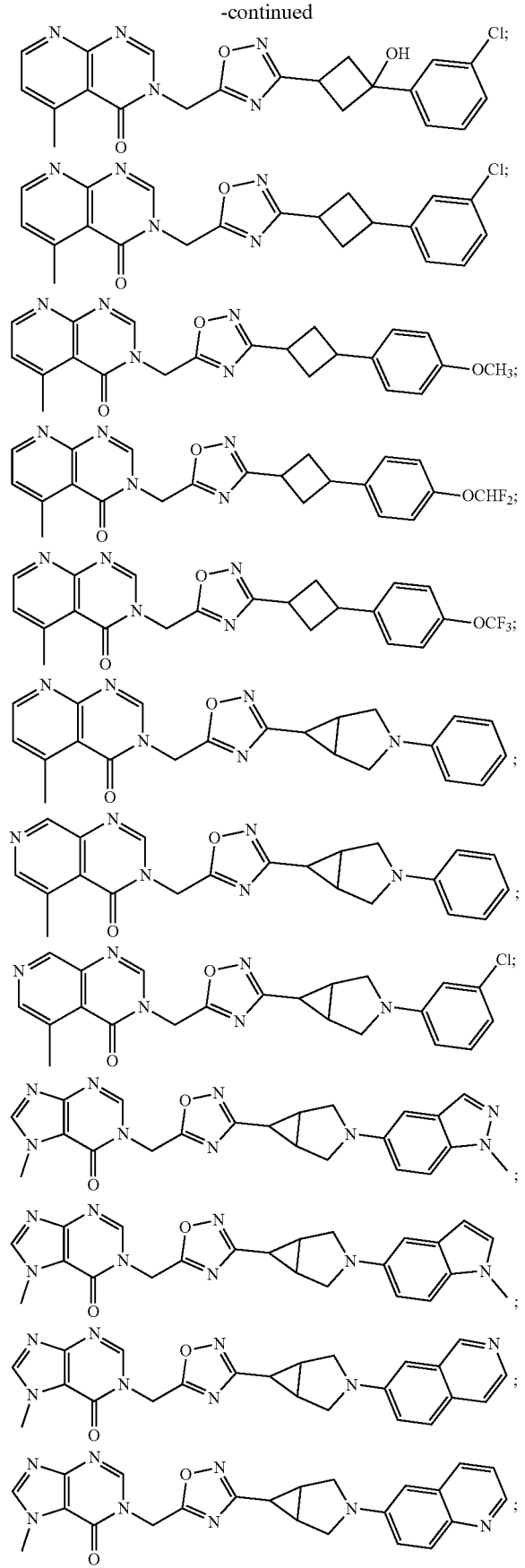
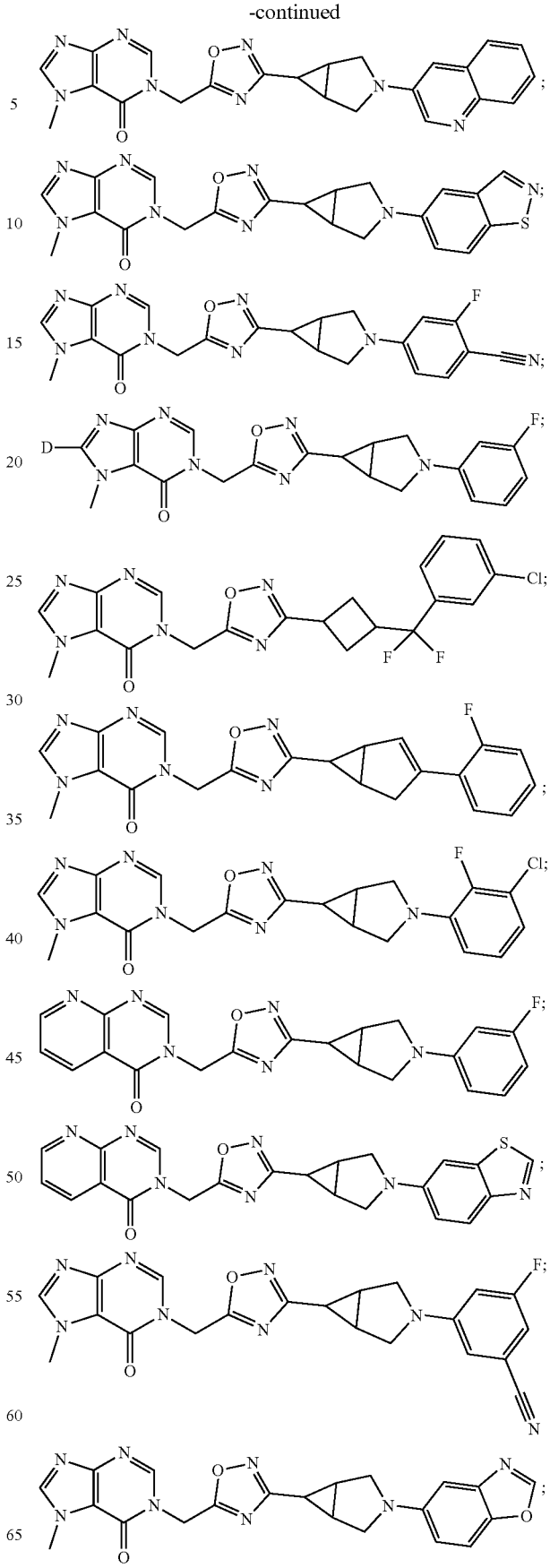

103
-continued
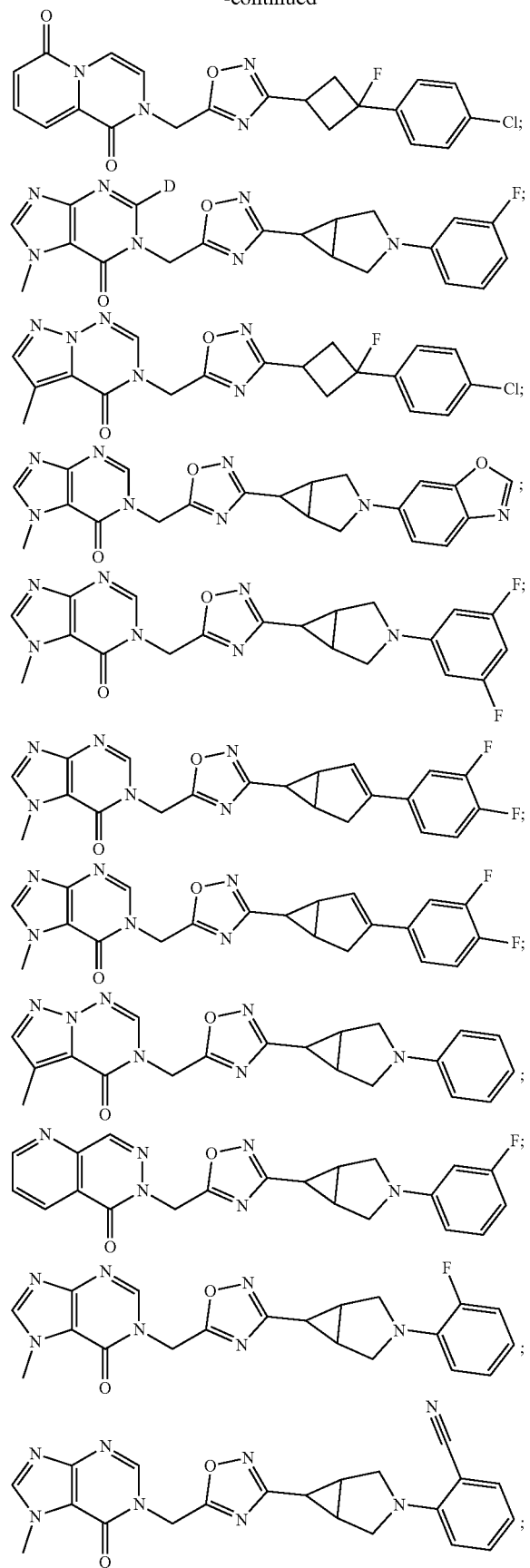
104
-continued
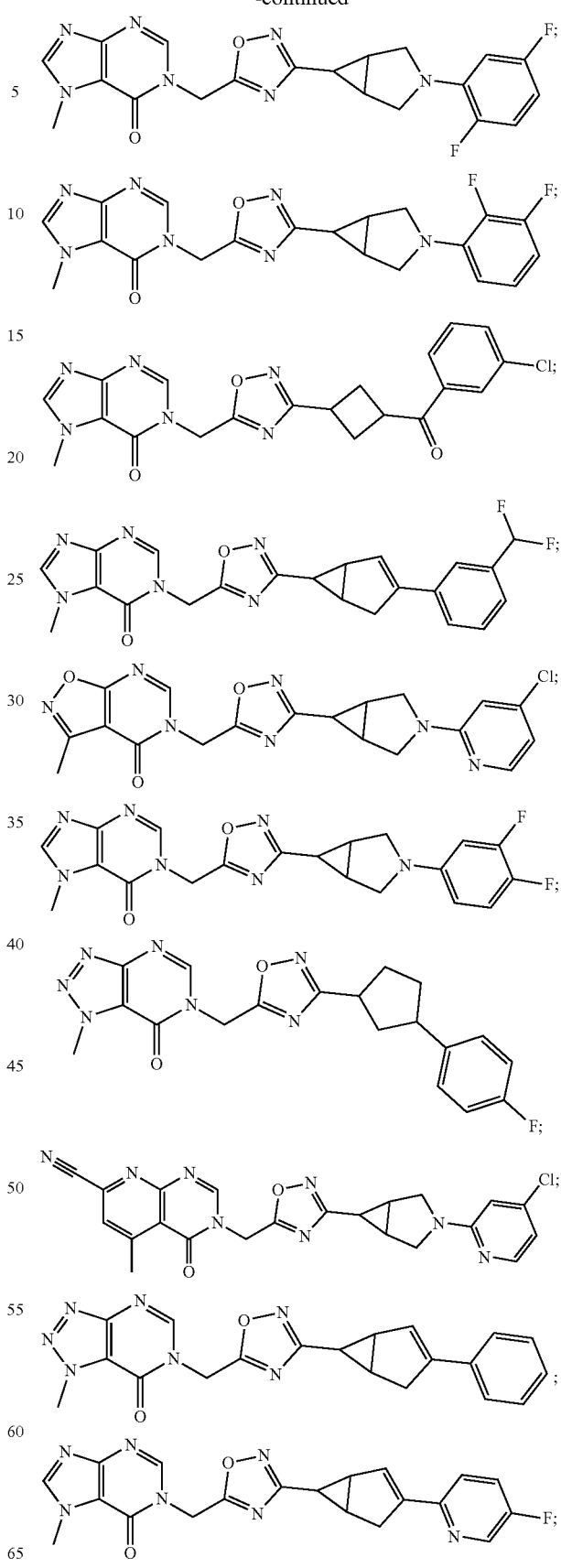

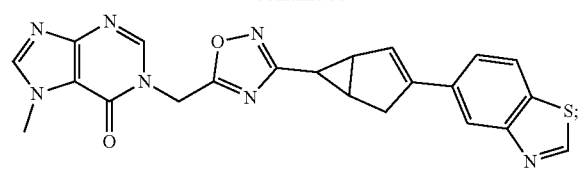
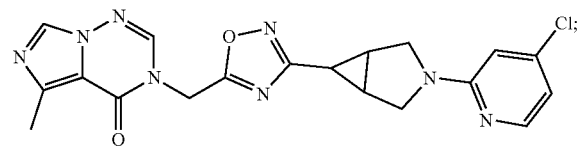
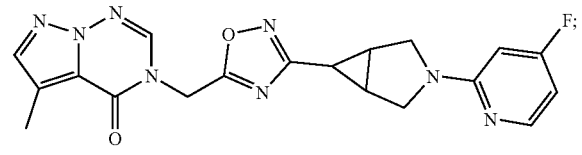
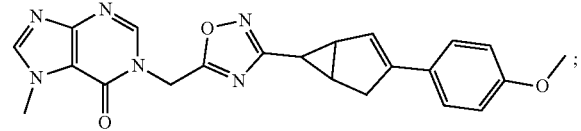
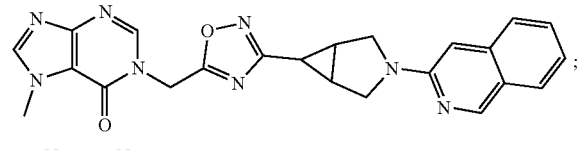
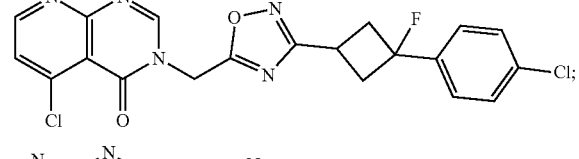
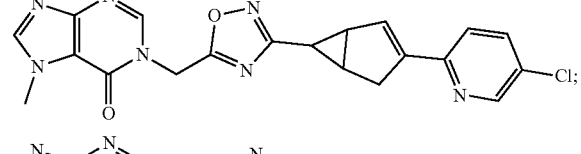
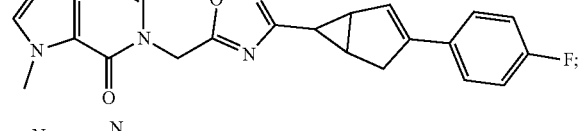
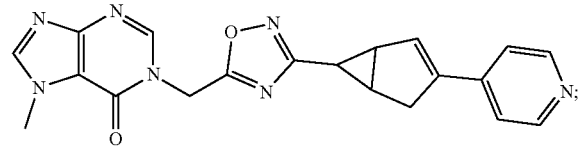
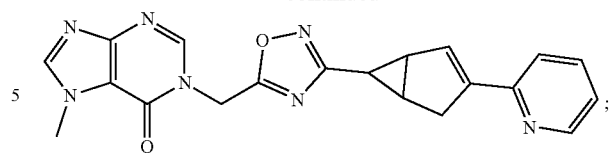
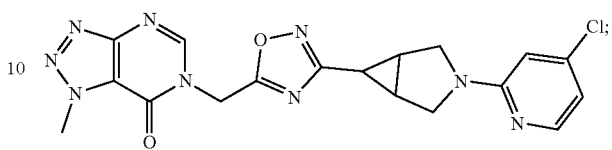
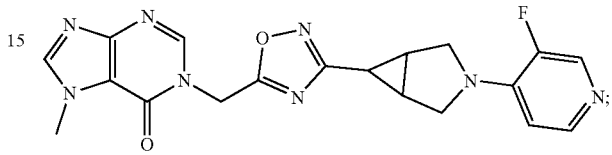
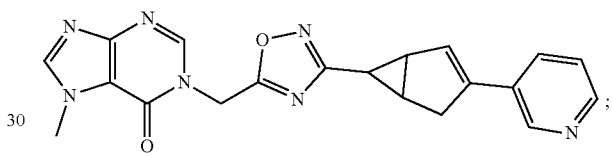
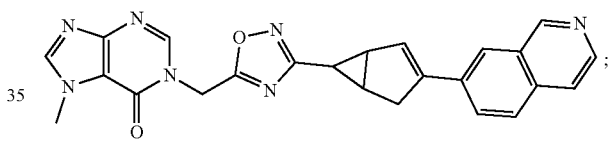
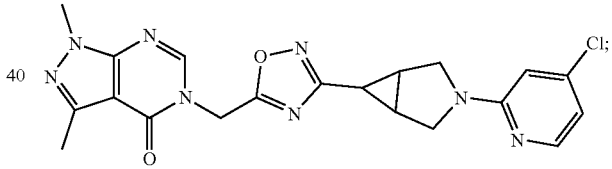

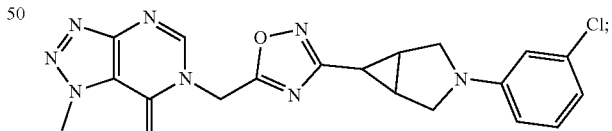
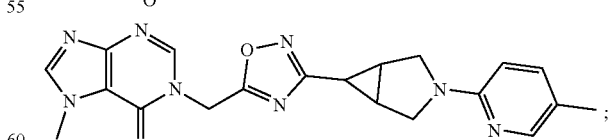

107
-continued
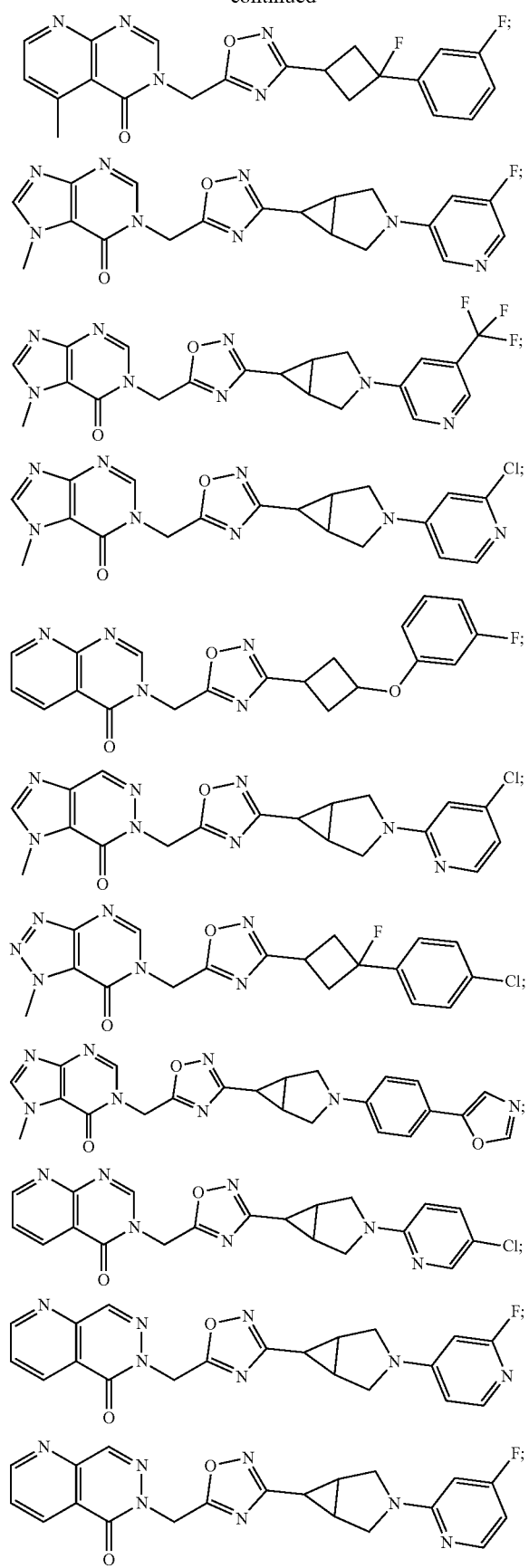
108
-continued
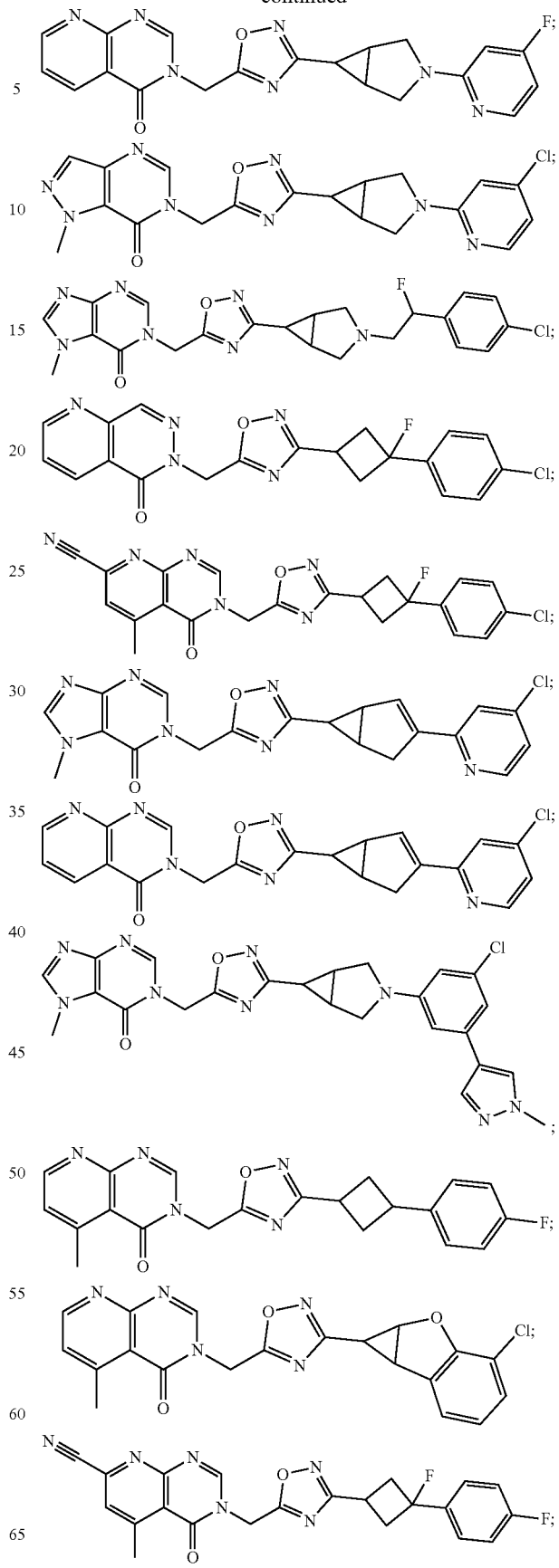

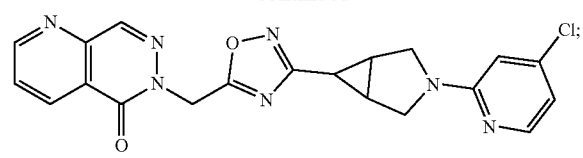
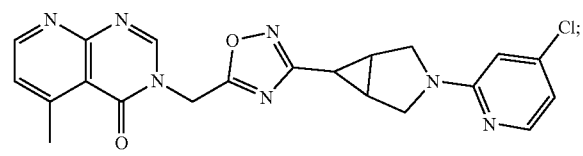
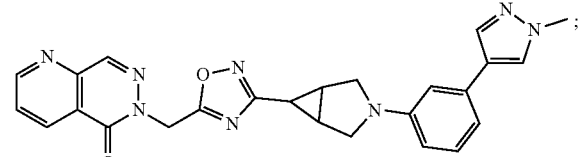
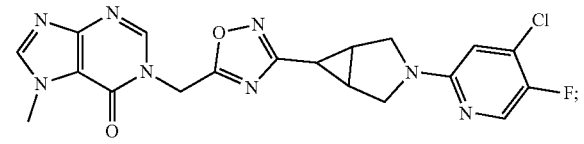
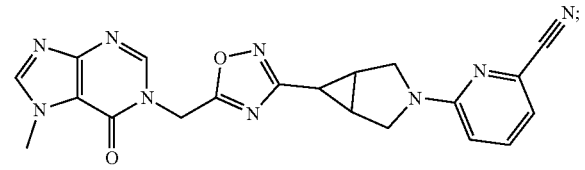
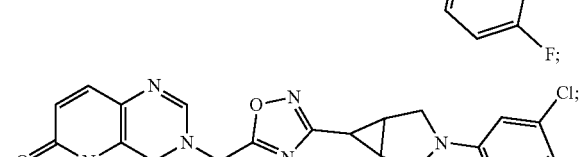
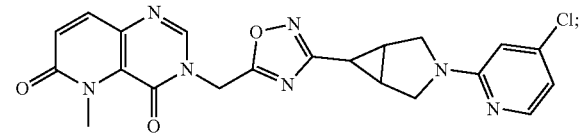
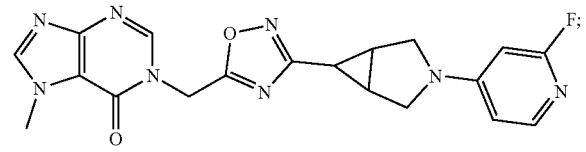
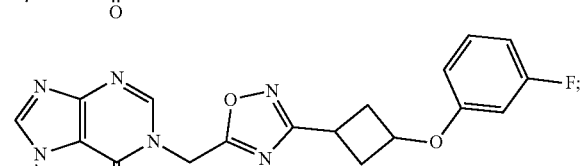
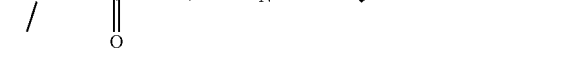
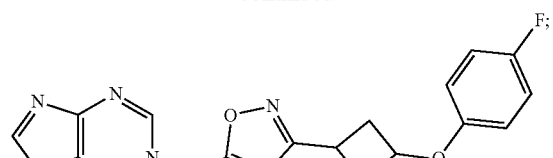
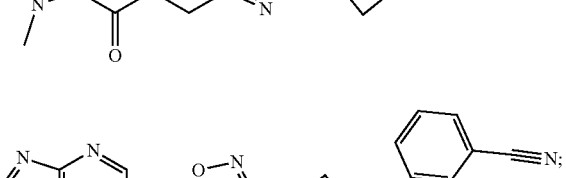
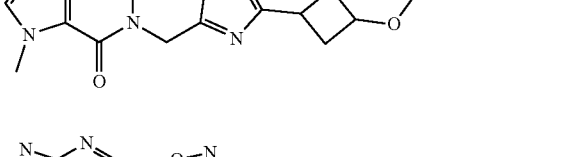
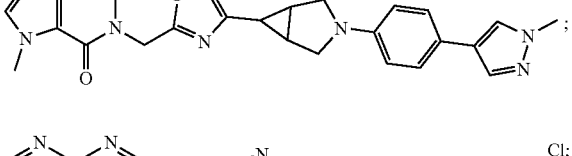
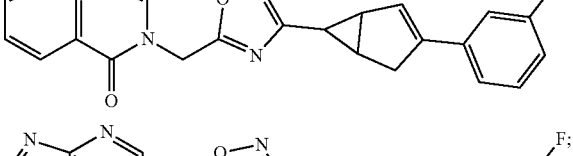
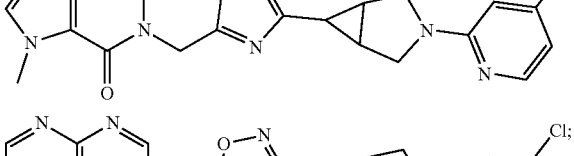
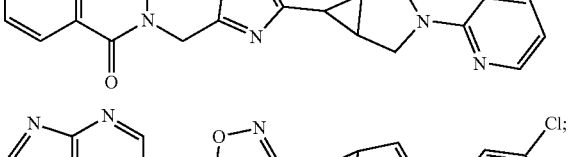
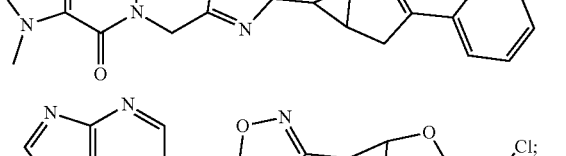
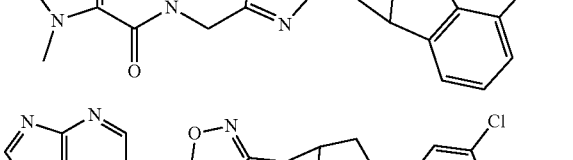
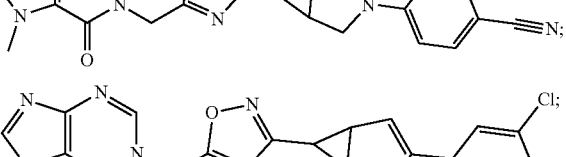

111
-continued
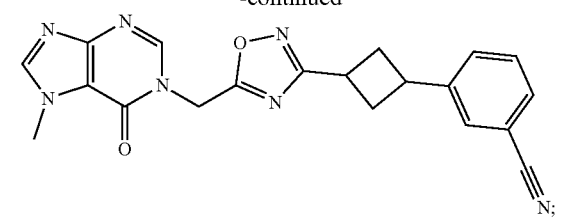
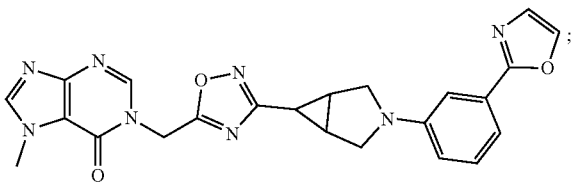
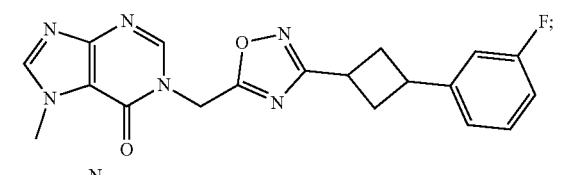
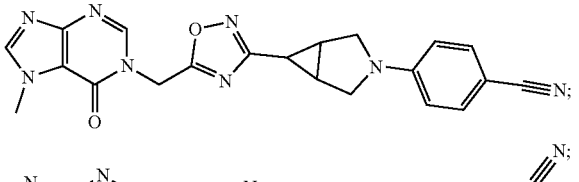
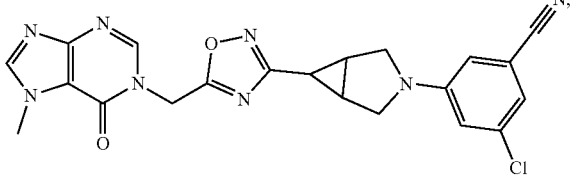
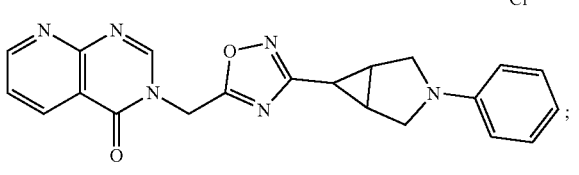
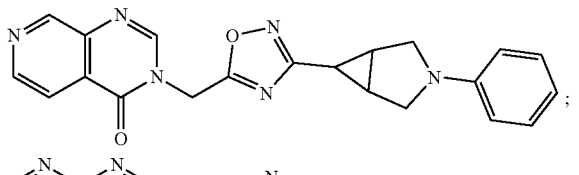
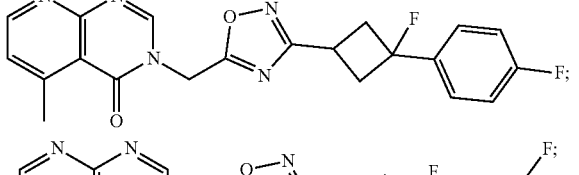
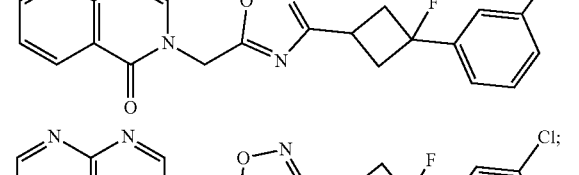
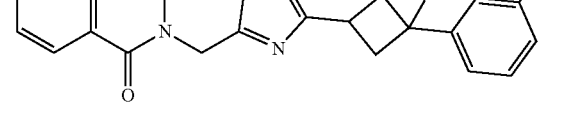
112
-continued
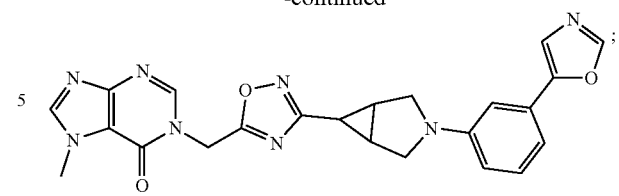
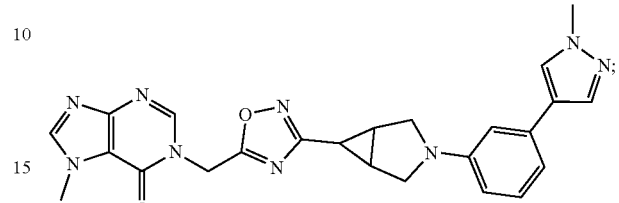
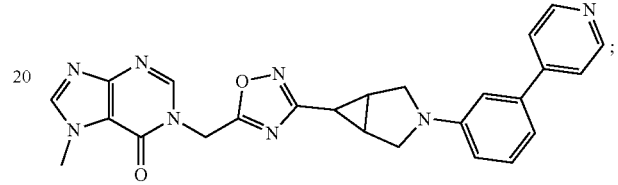
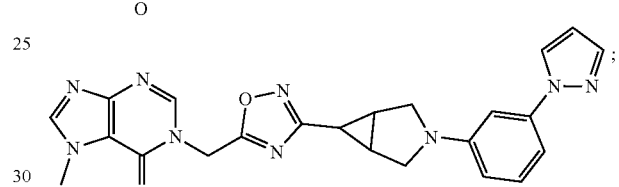
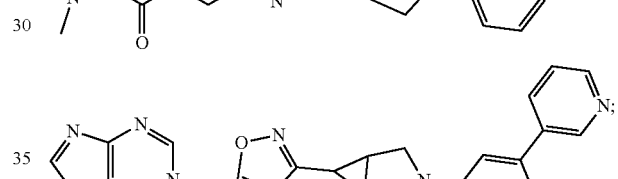
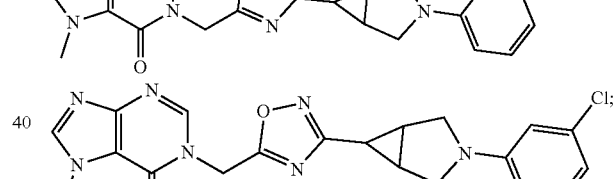
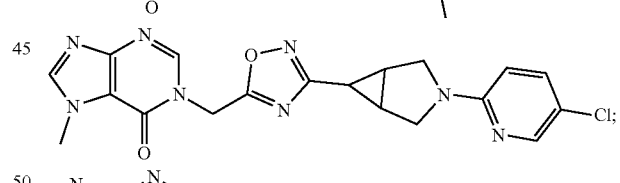
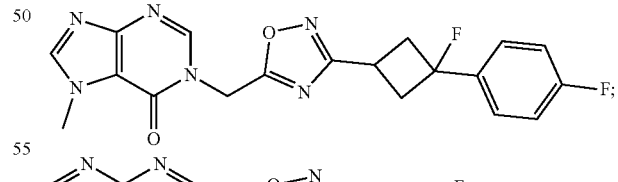
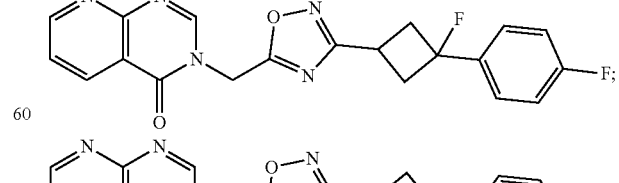
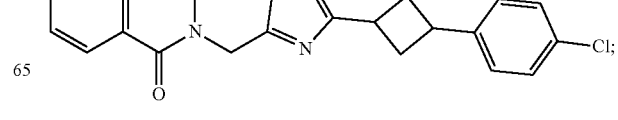

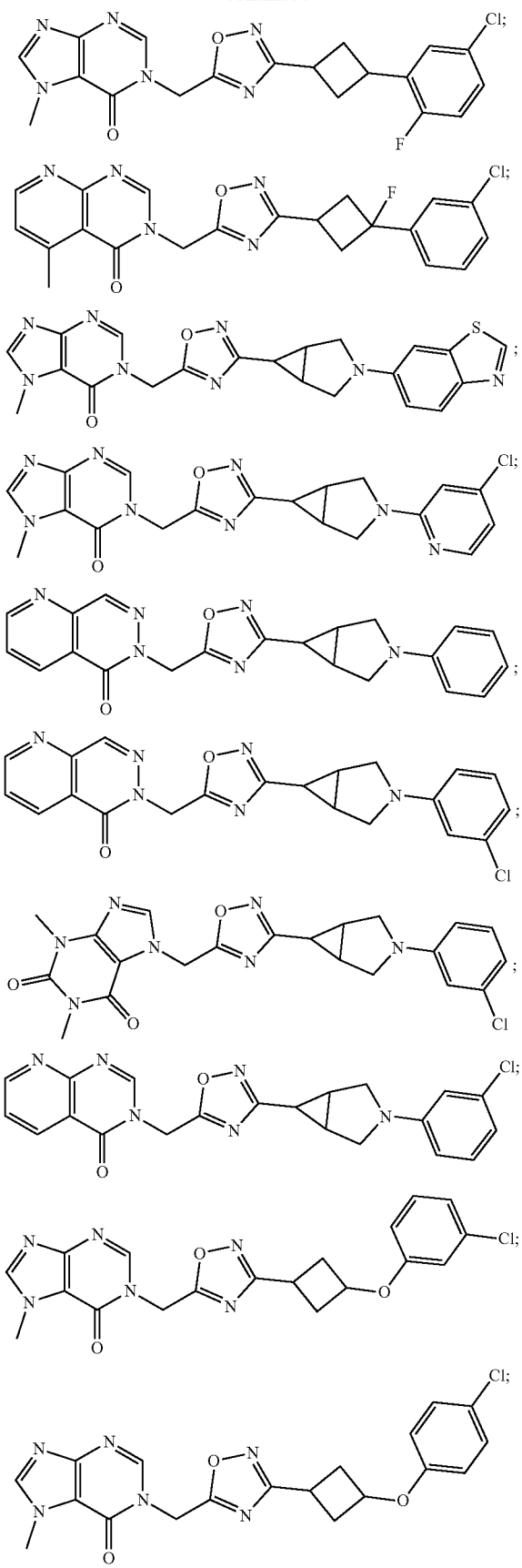
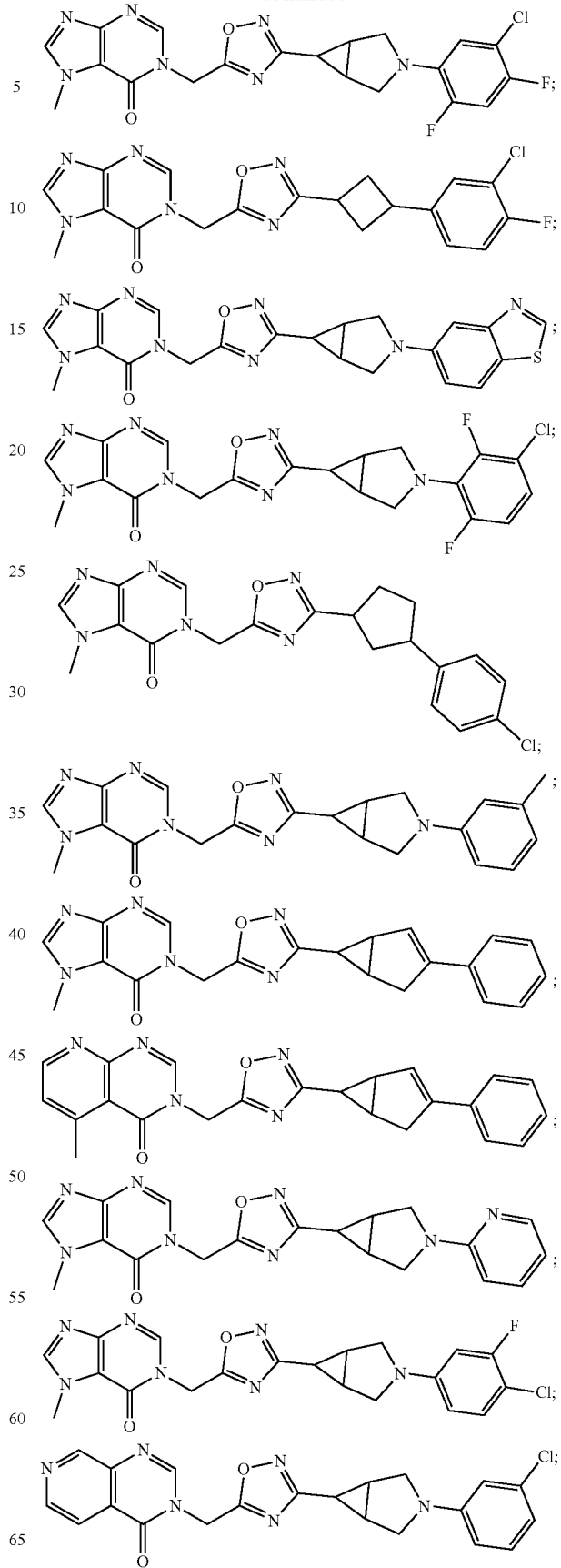

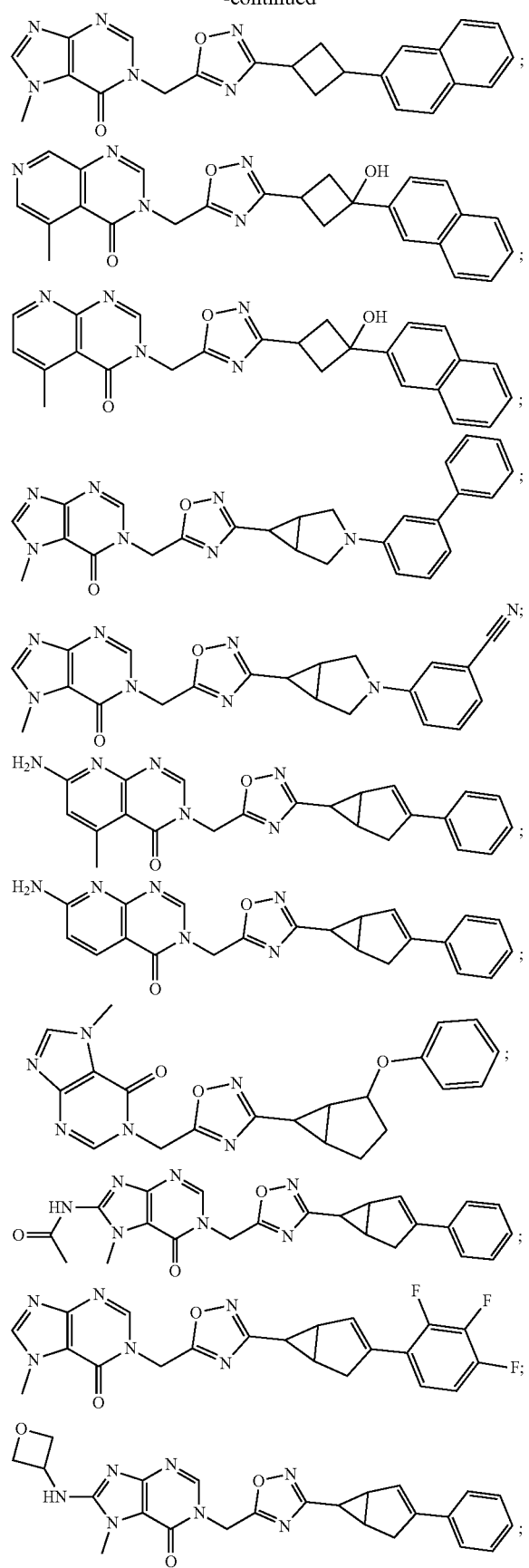
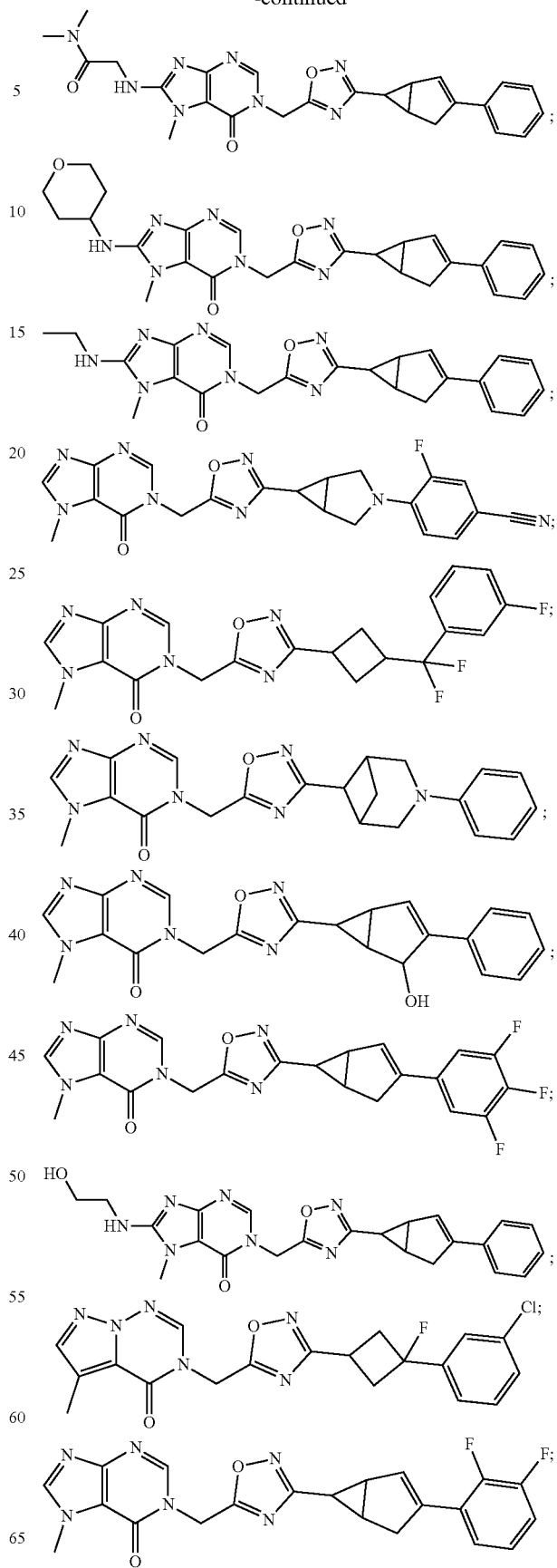

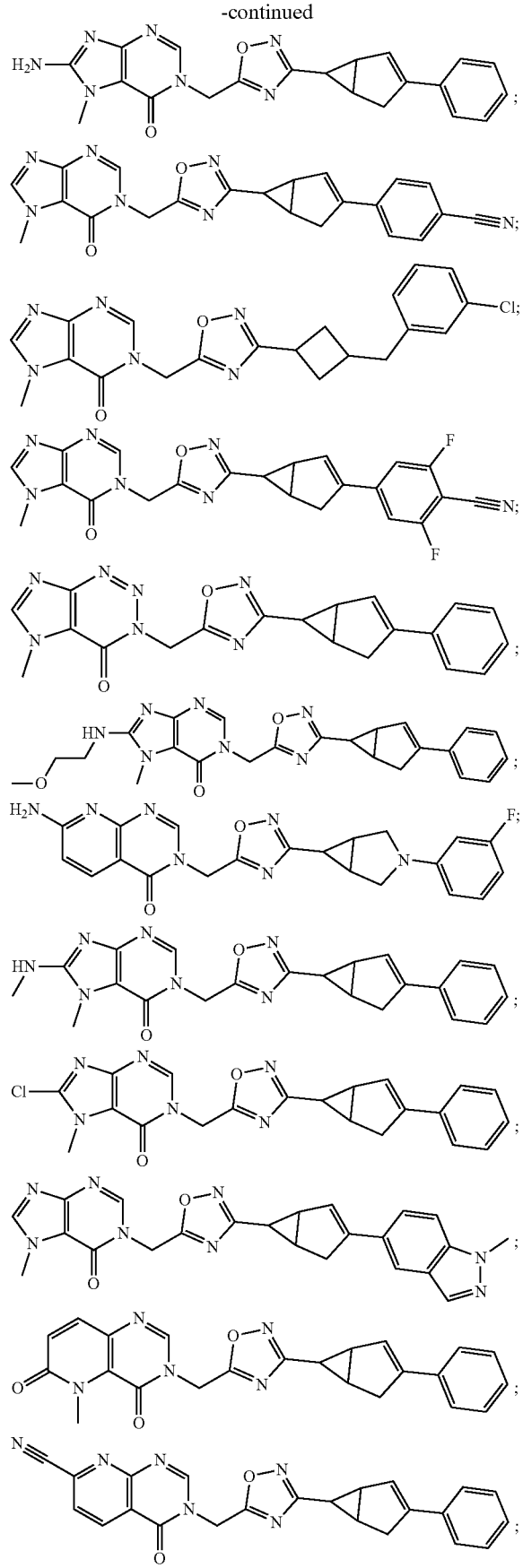
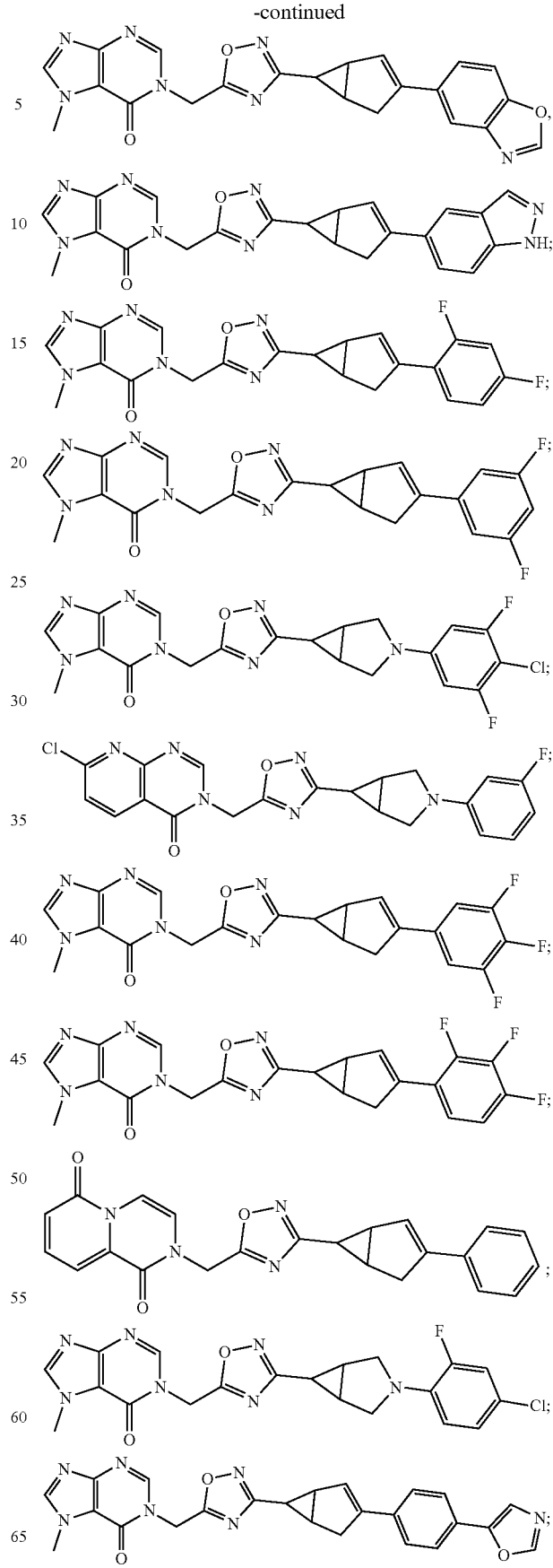

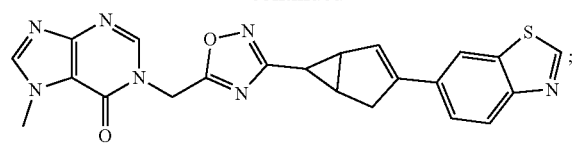
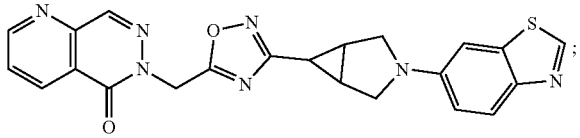
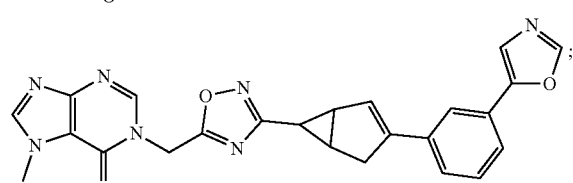
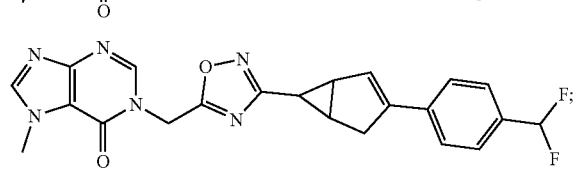
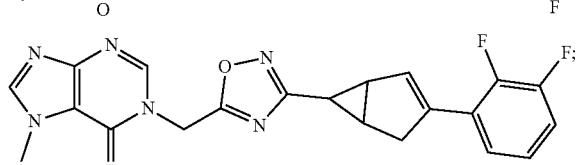
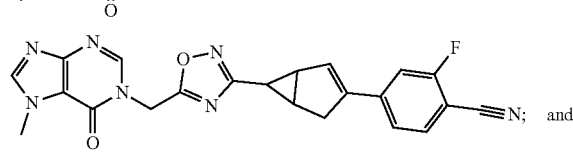
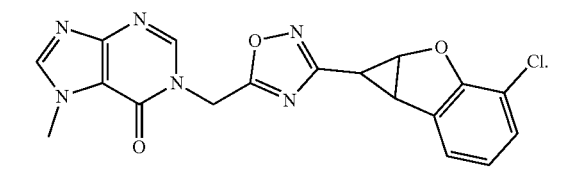
In some aspects, the compound of formula (I), or a pharmaceutically acceptable salt thereof, is a stereoisomer selected from the following:
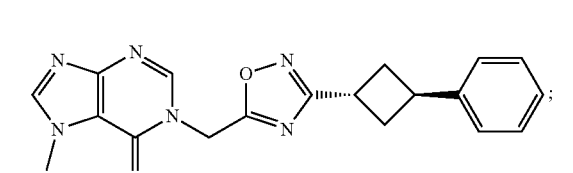

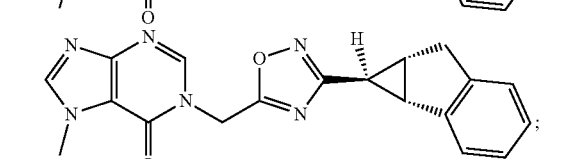
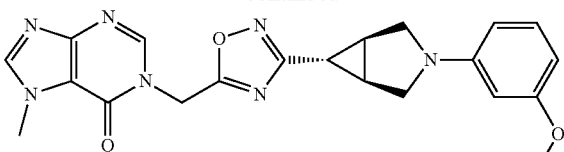
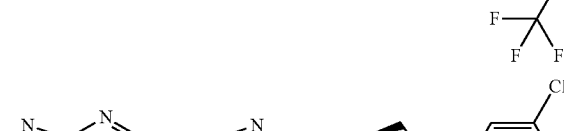
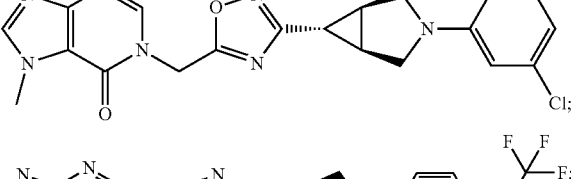
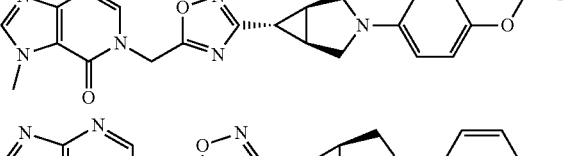
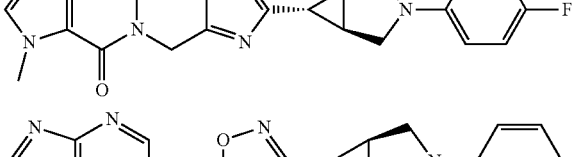
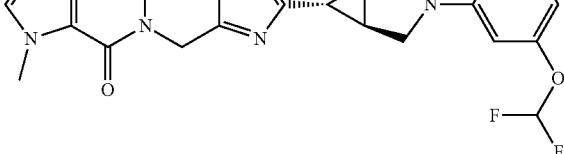
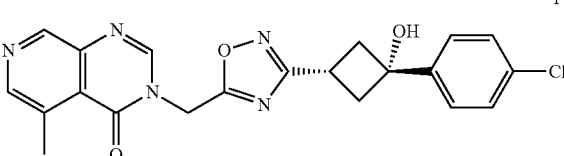
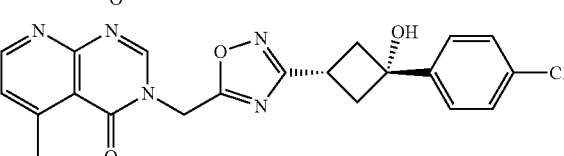
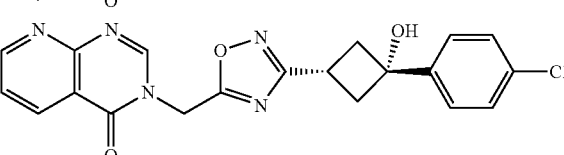
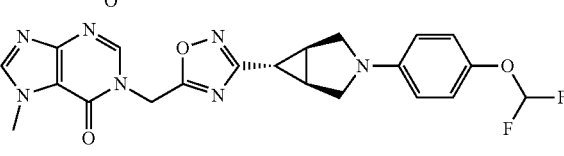
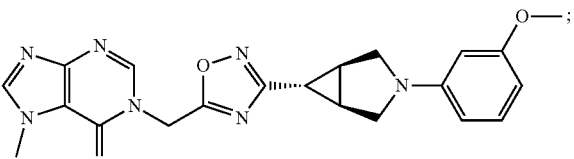

121
-continued
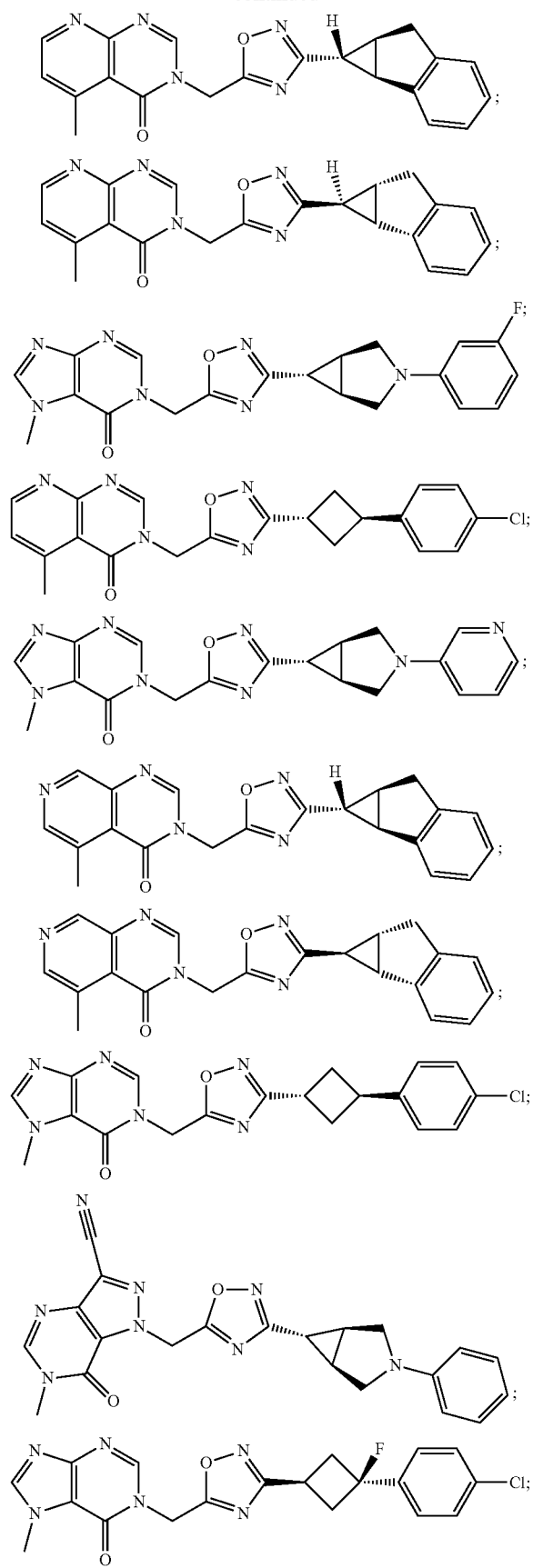
122
-continued
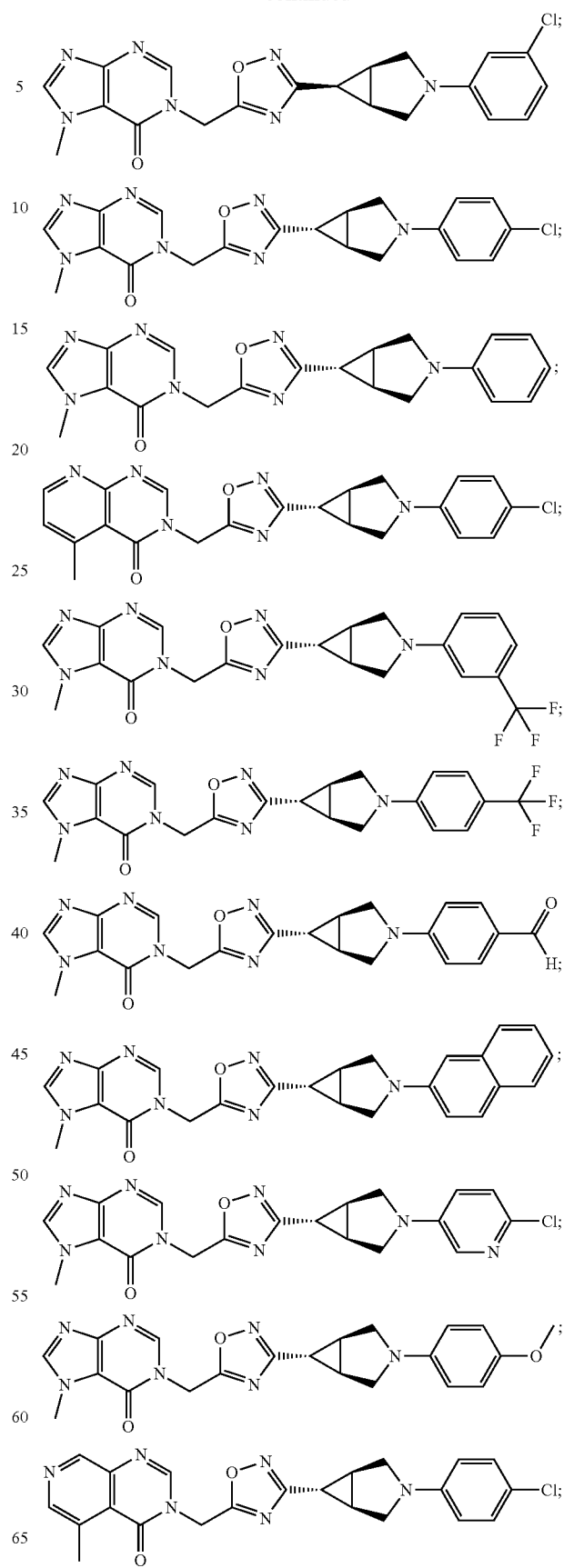

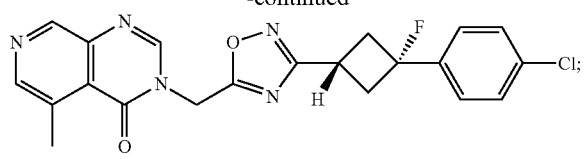
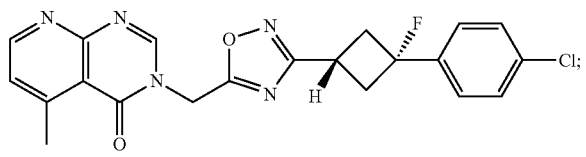
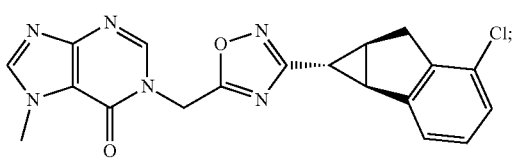
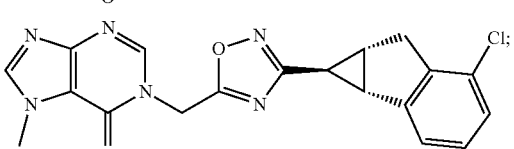
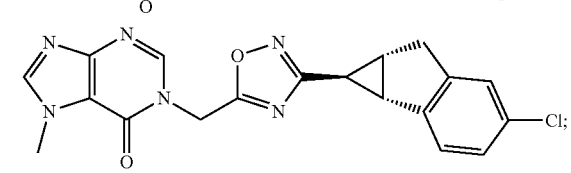
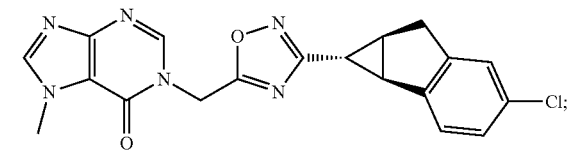
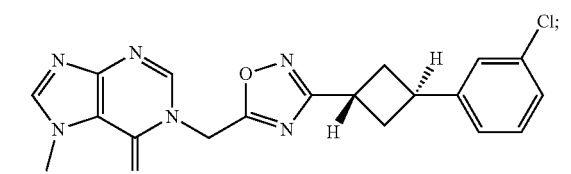
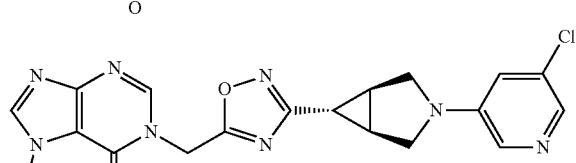
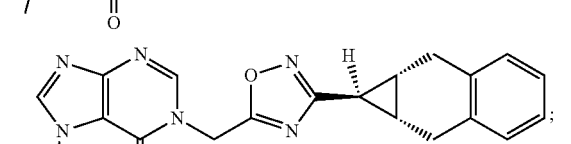
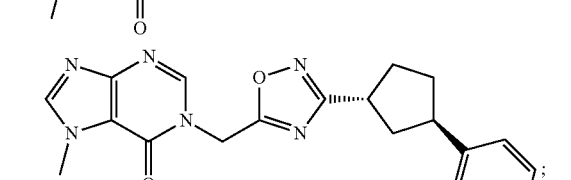
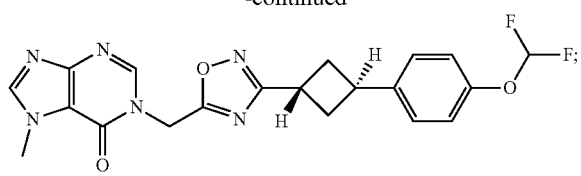
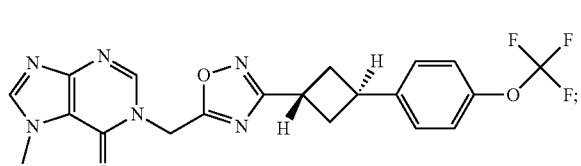
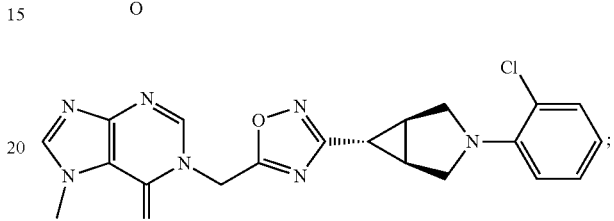
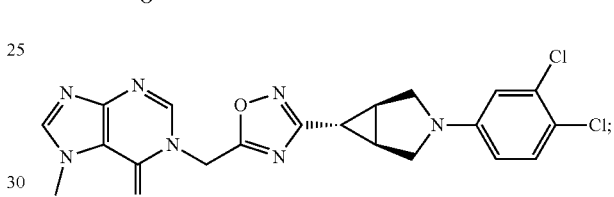
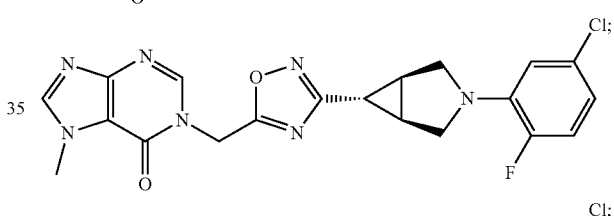
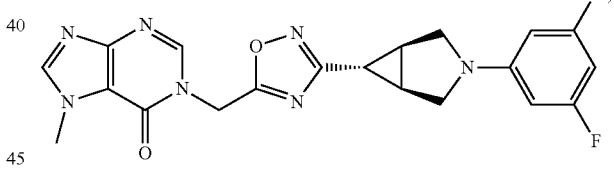
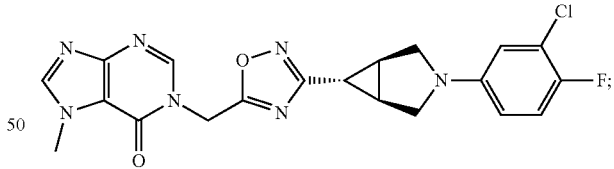
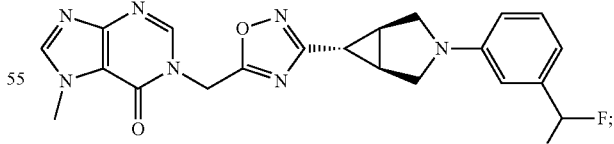
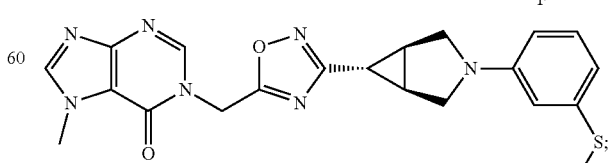

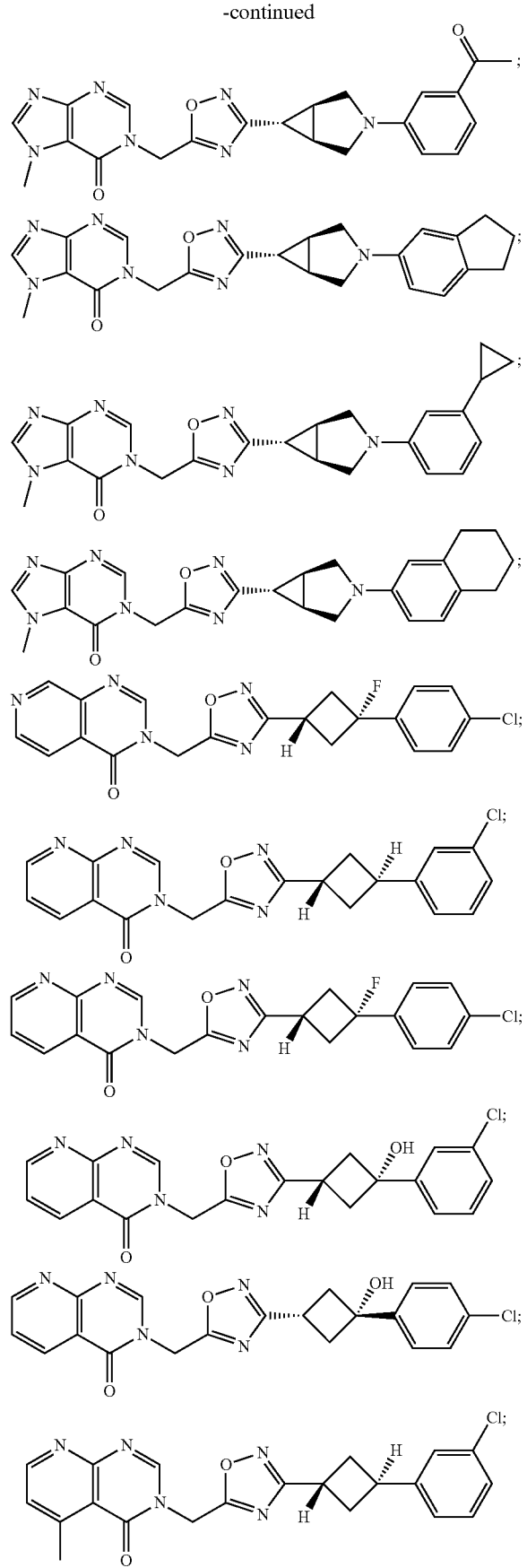
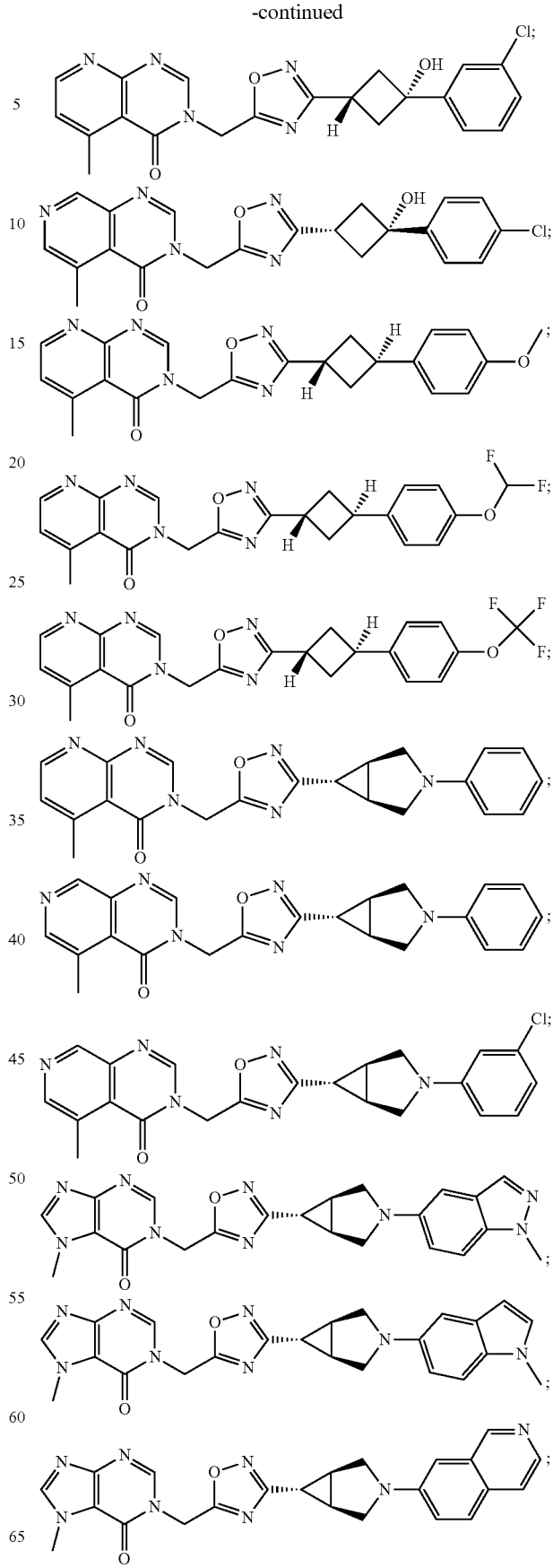

-continued
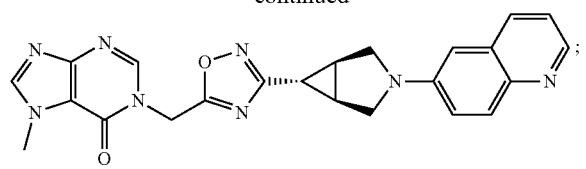
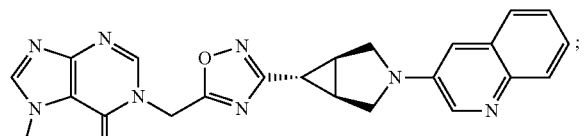
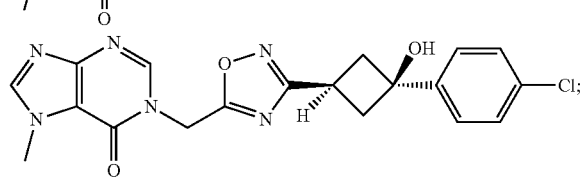
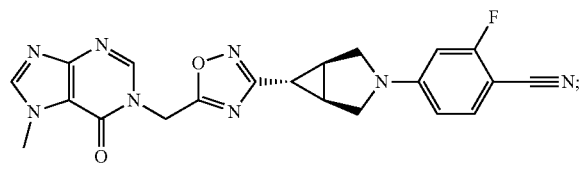
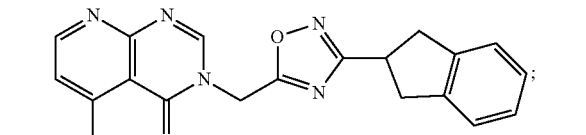
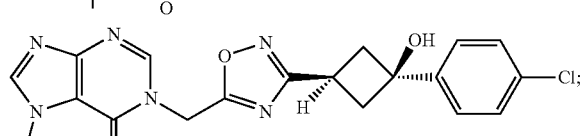
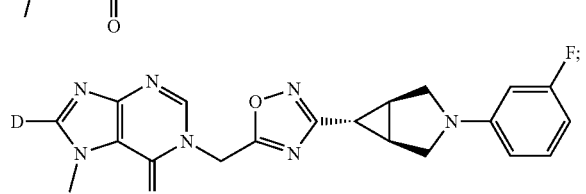
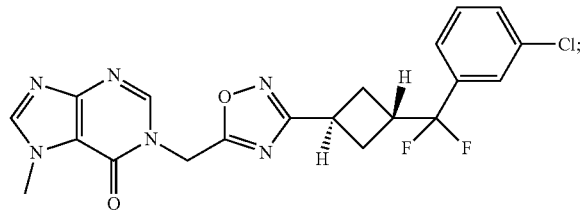
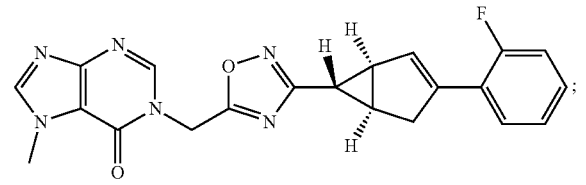
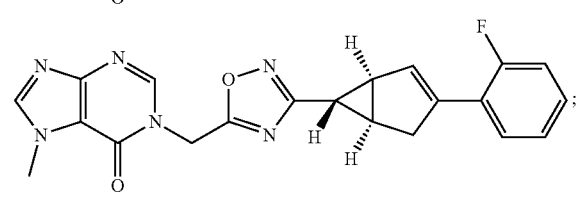
-continued
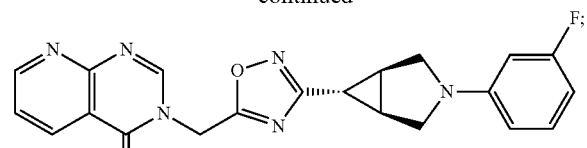
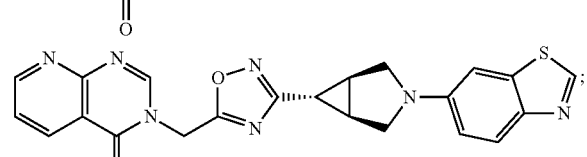
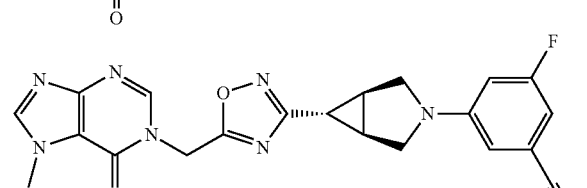
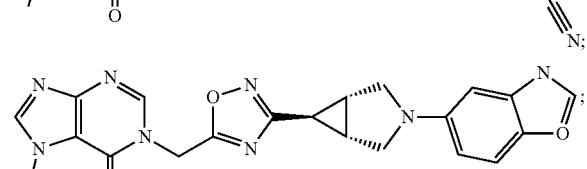
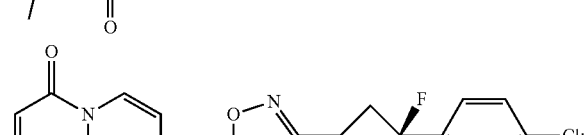
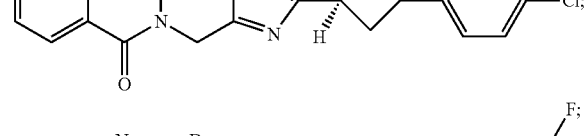
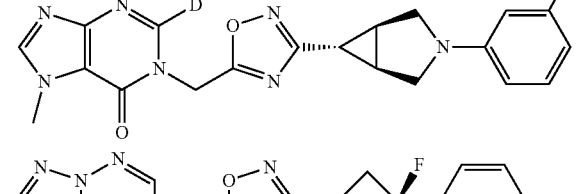
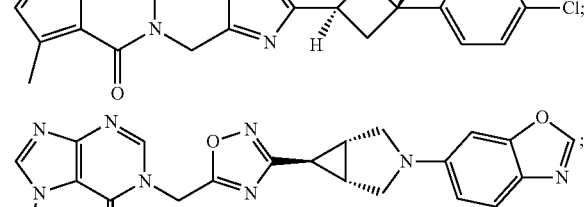
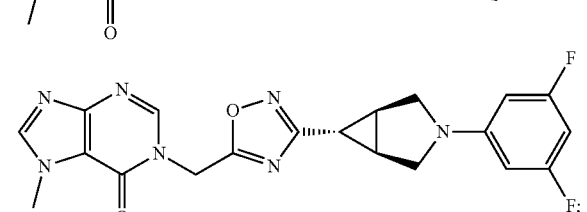
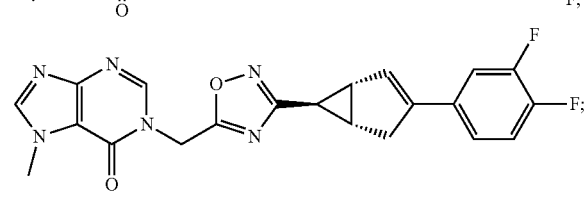

129
-continued
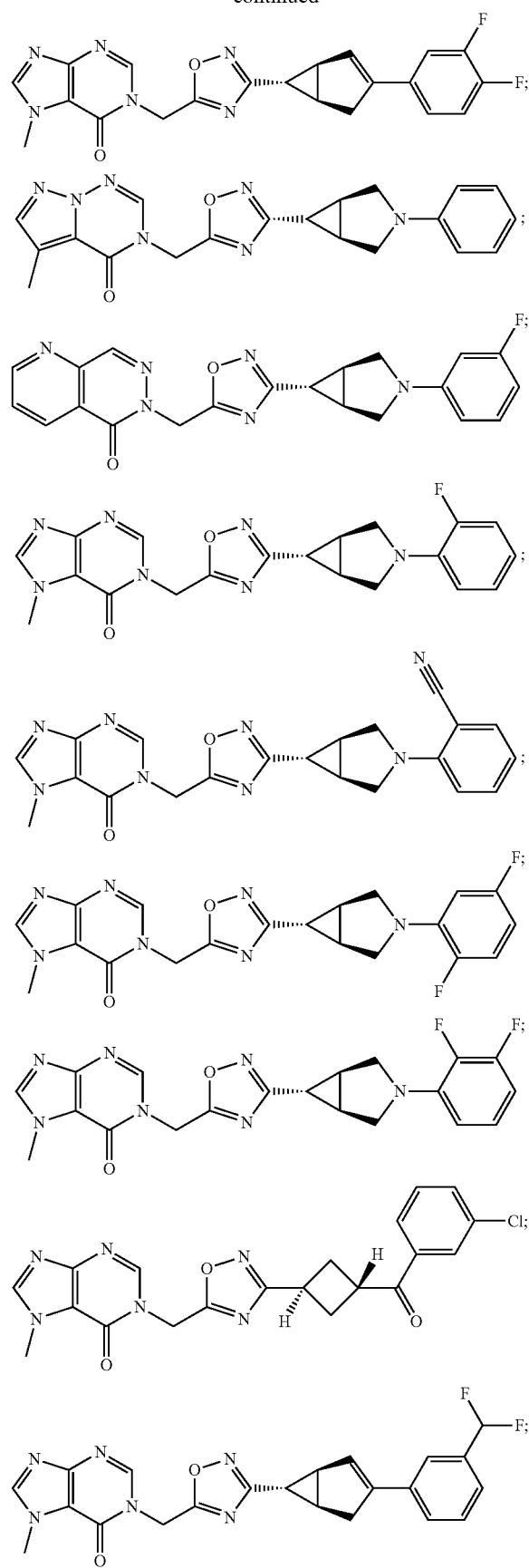
130
-continued
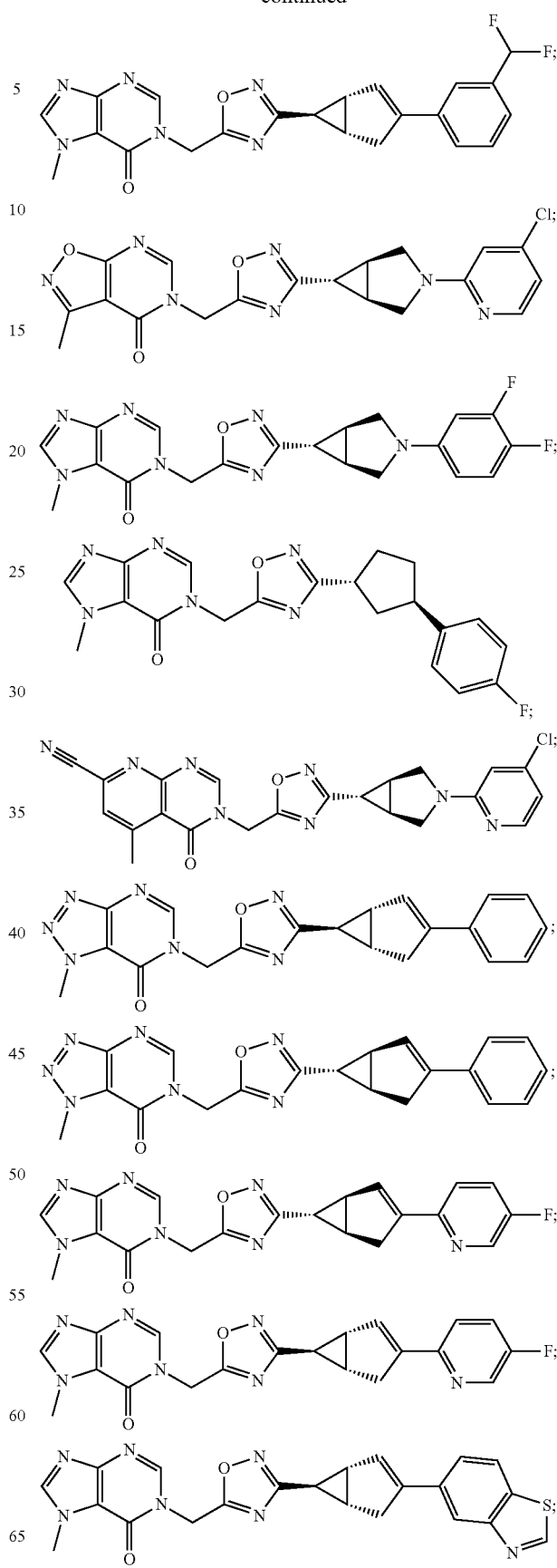

131
-continued
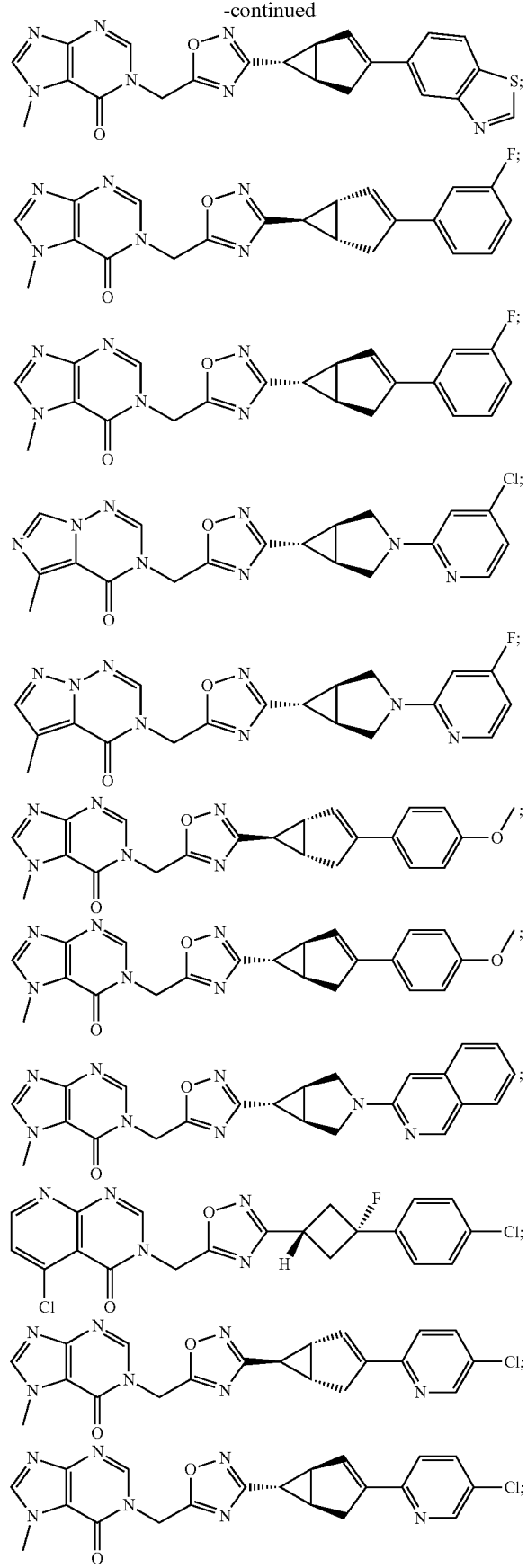
132
-continued
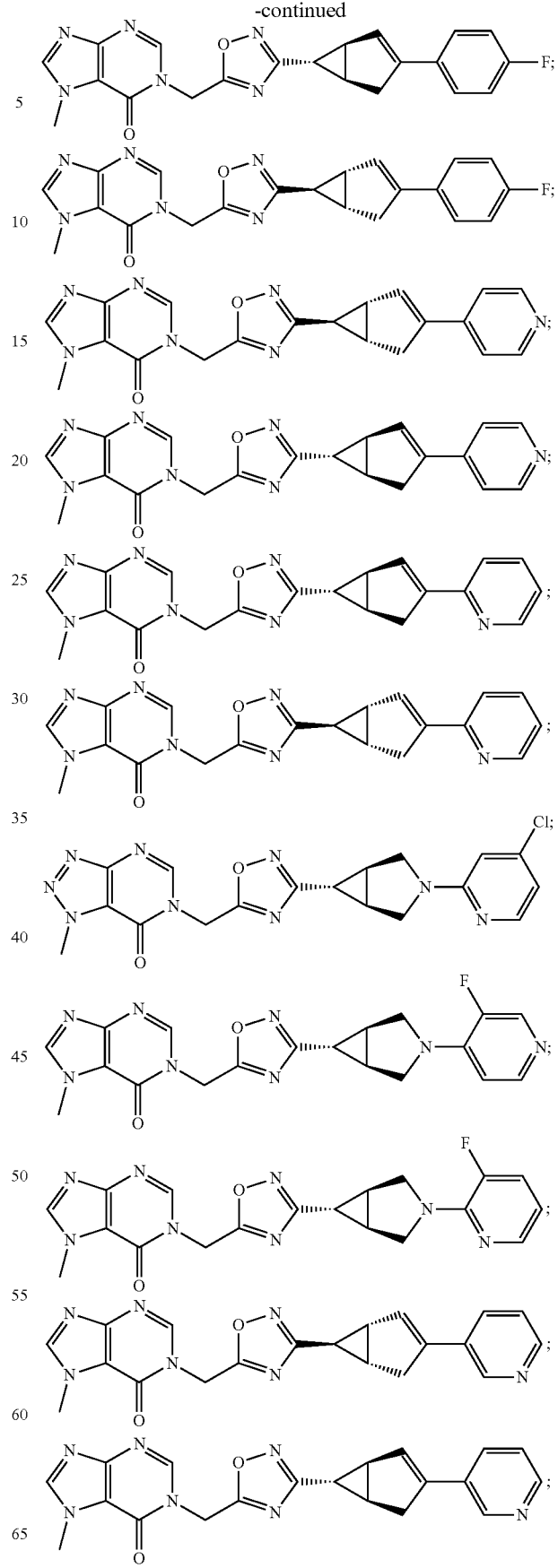

133
-continued
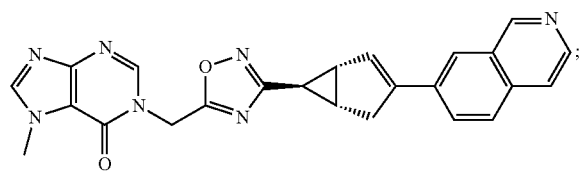;
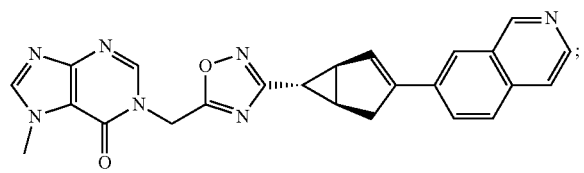;
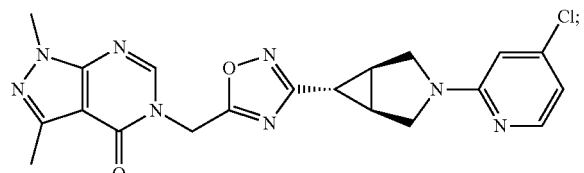;
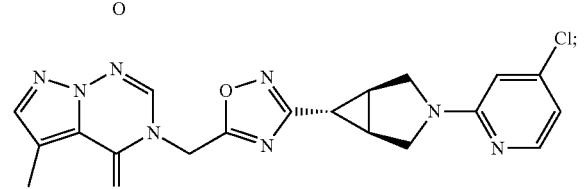;
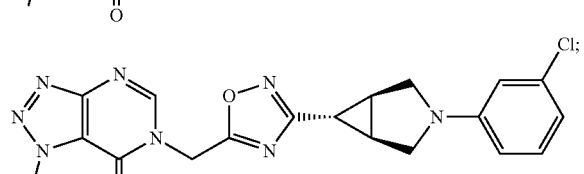;
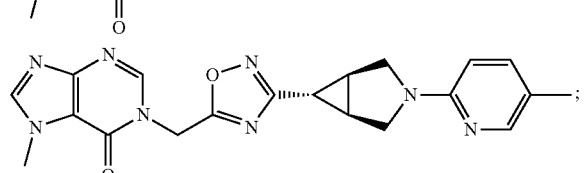;
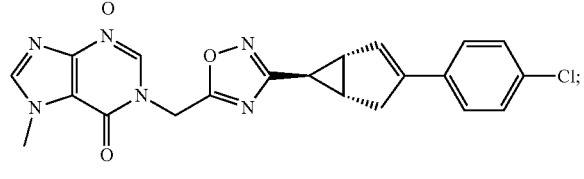;
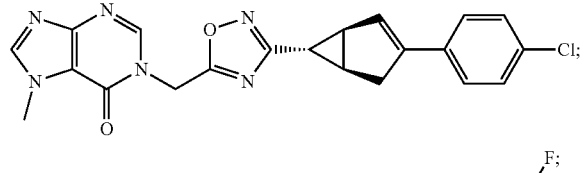;
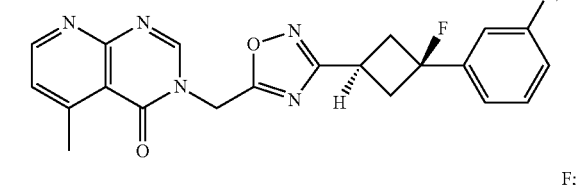;
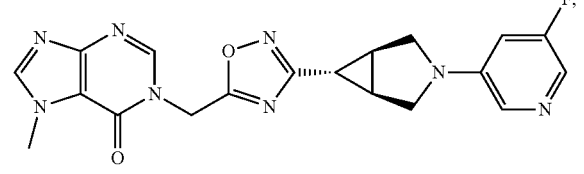;
134
-continued
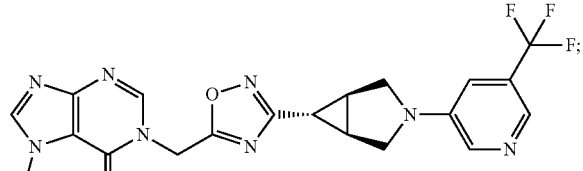;
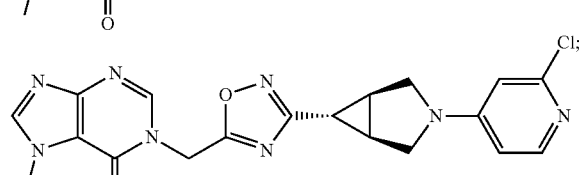;
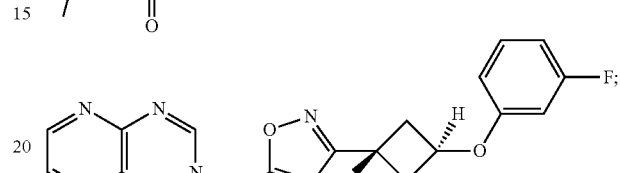;
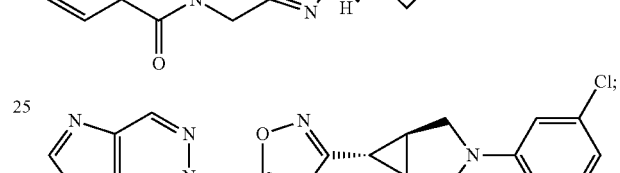;
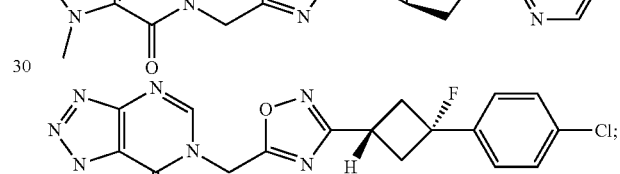;
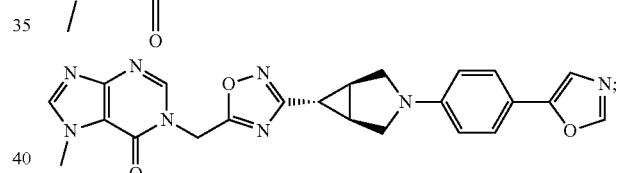;
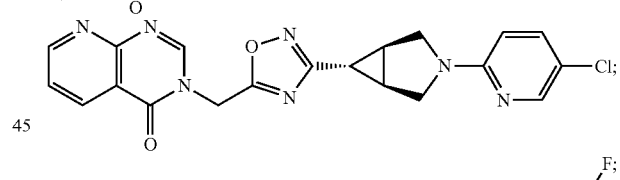;
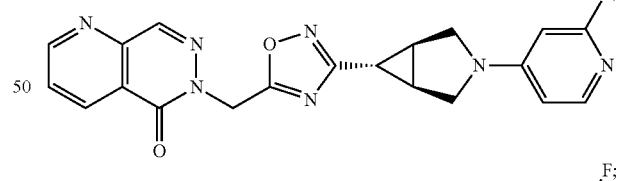;
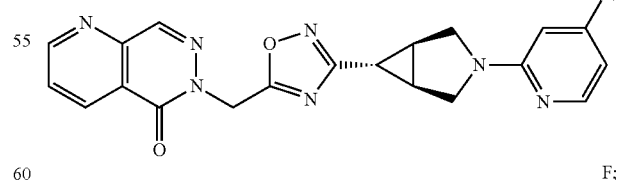;
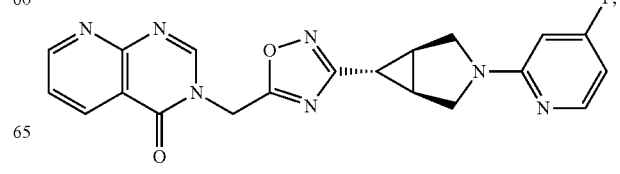;

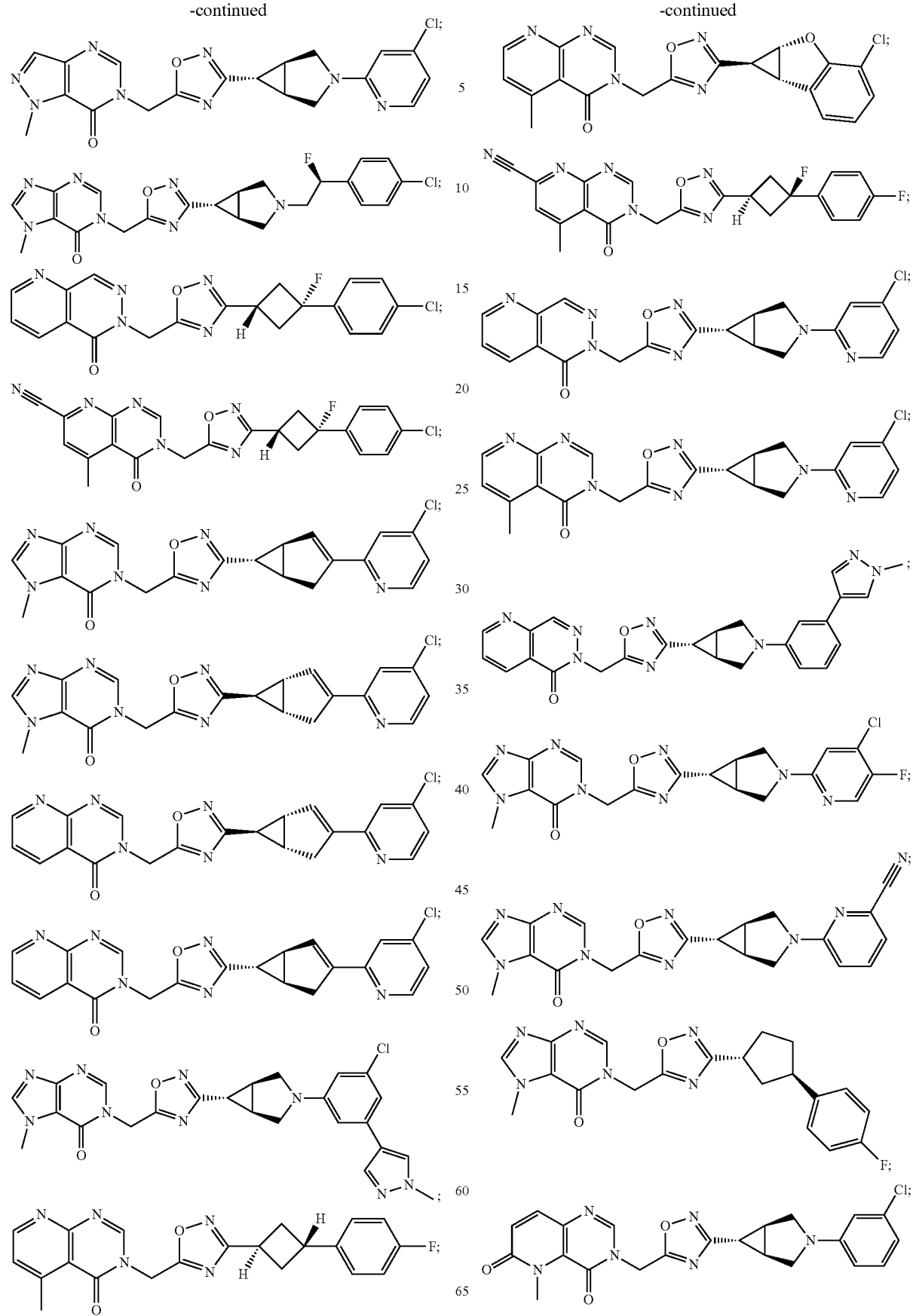

137
-continued
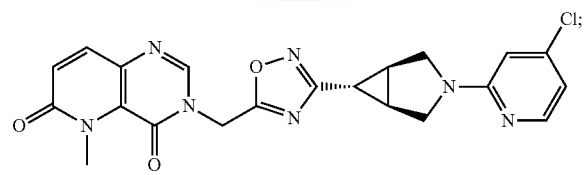
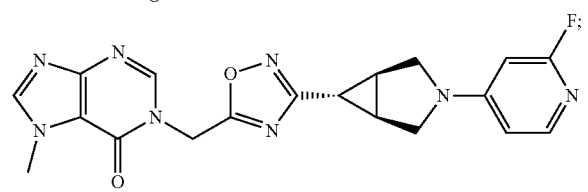
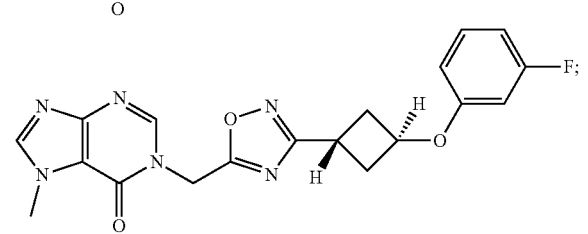
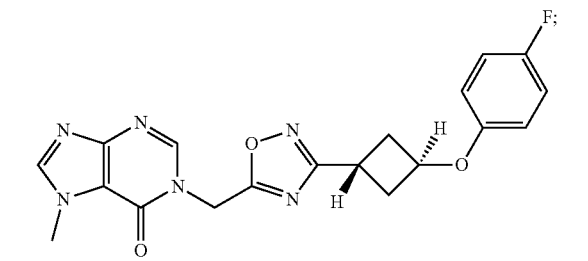
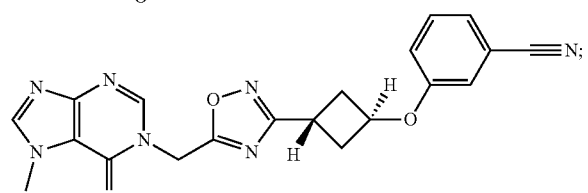
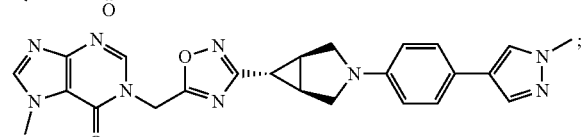
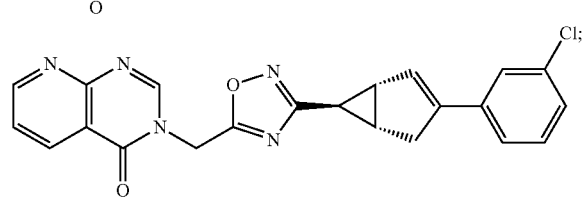
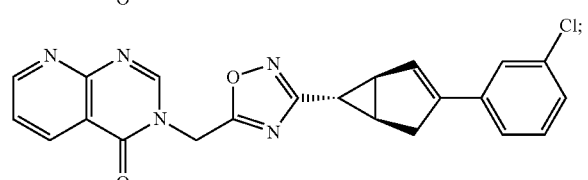
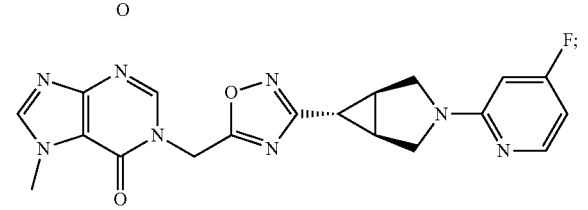
138
-continued
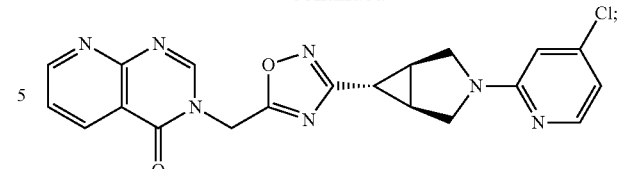
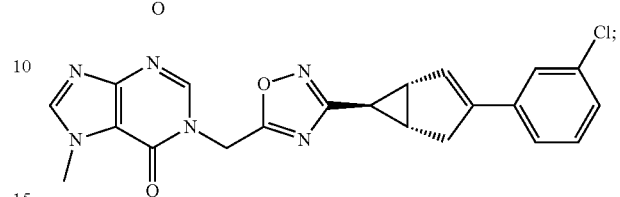
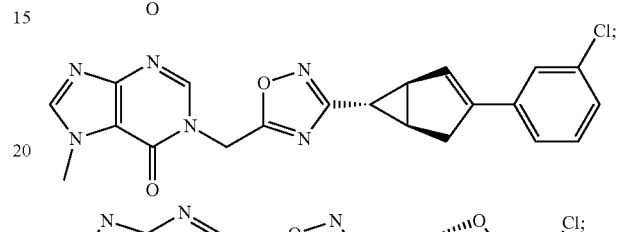
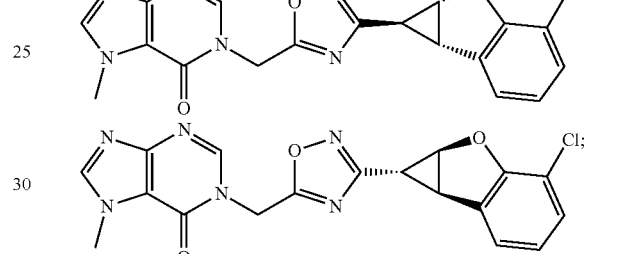
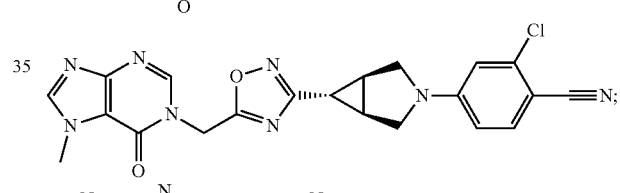
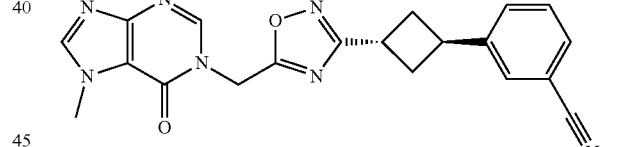
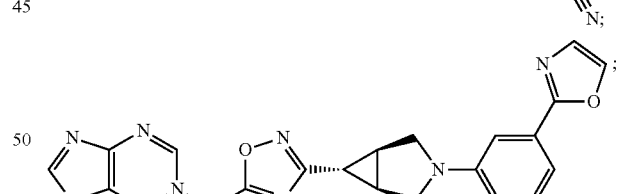
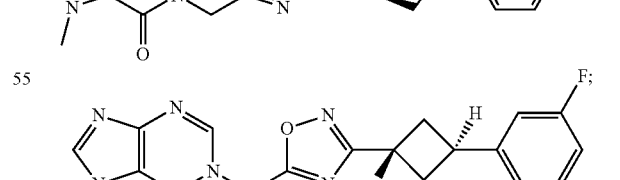
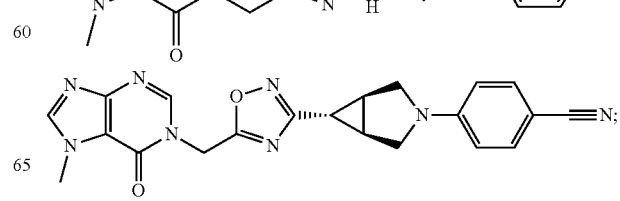

-continued
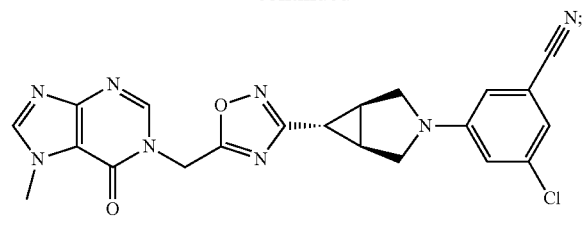
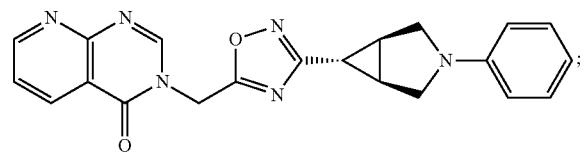
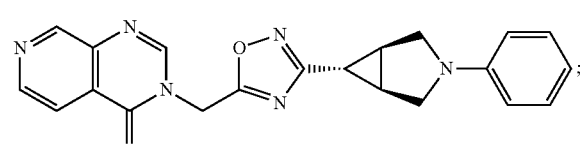
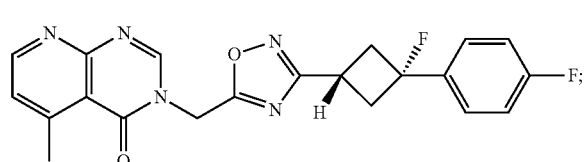
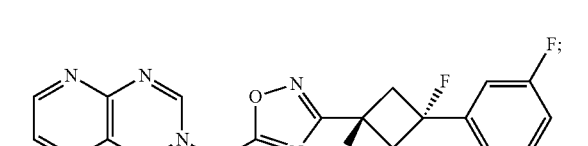
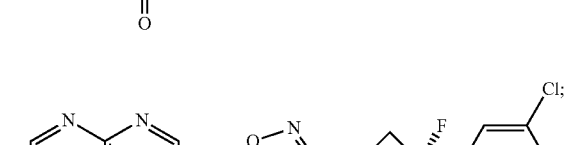
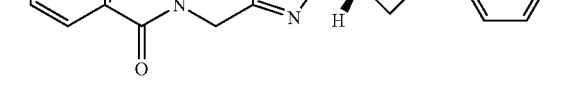
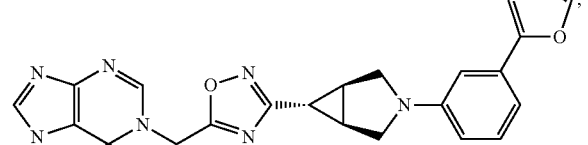
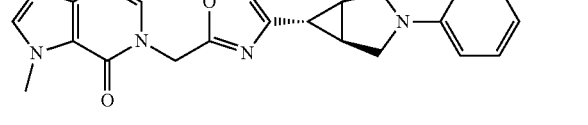
-continued
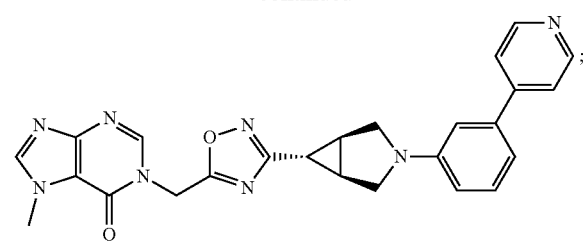
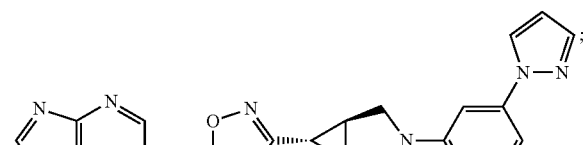
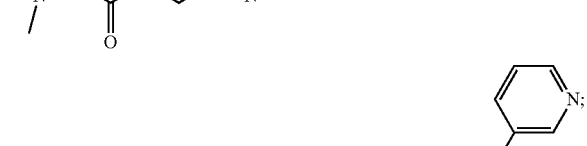
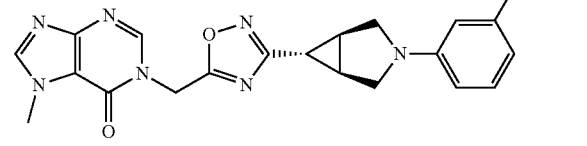
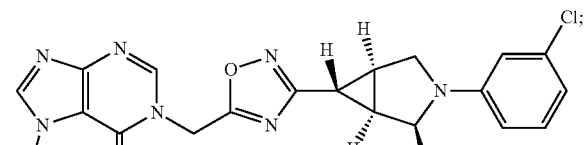
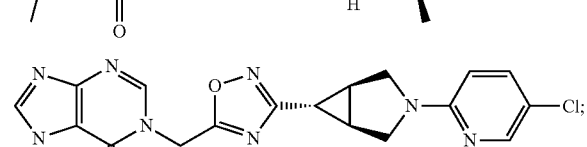
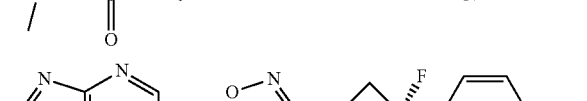
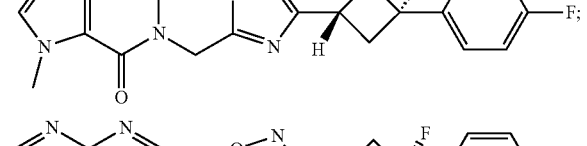
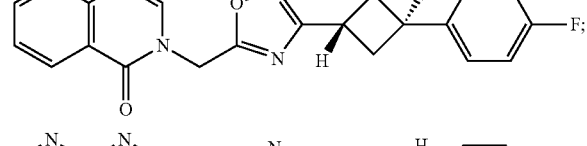
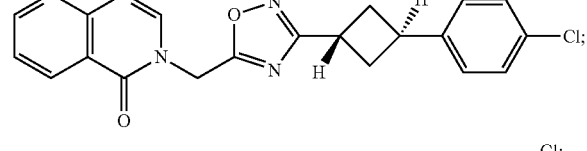
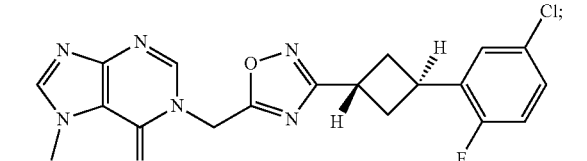

141
-continued
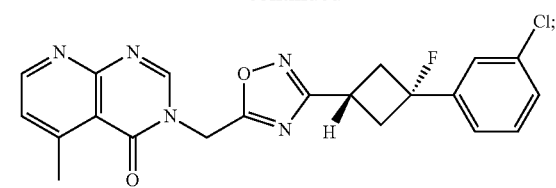
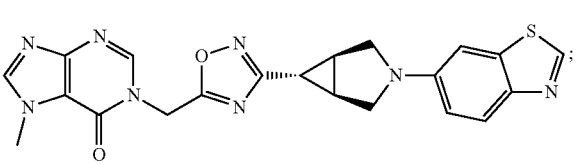
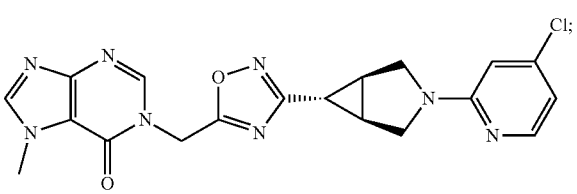
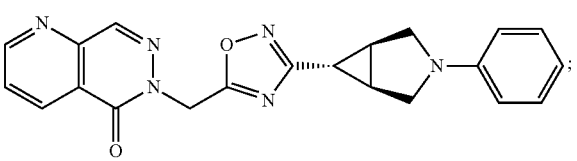
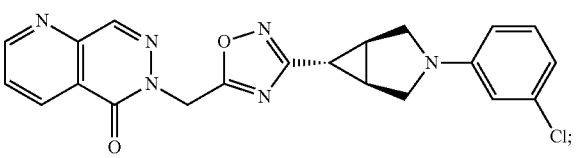
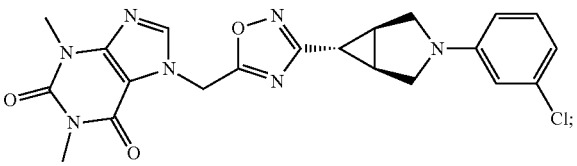
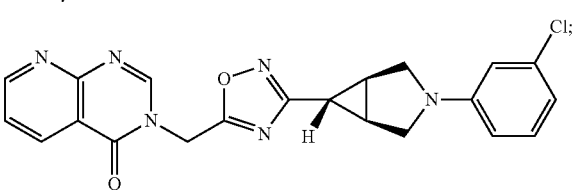
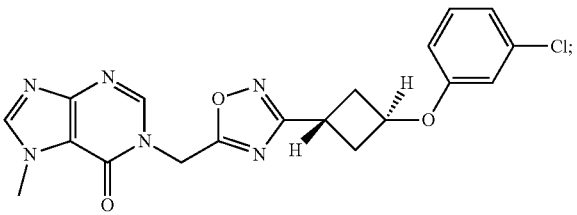
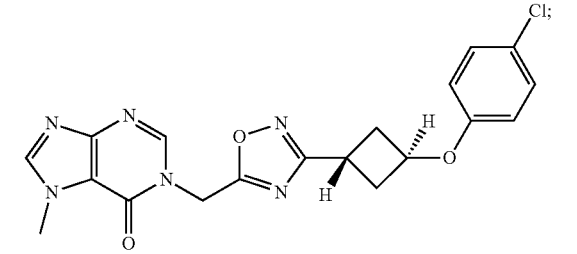
142
-continued
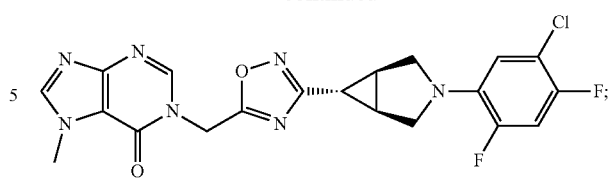
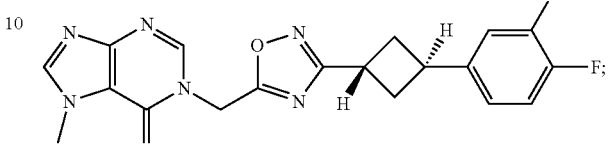
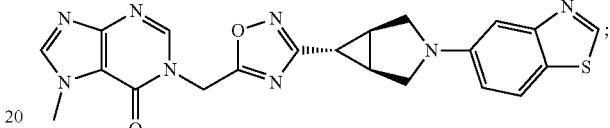
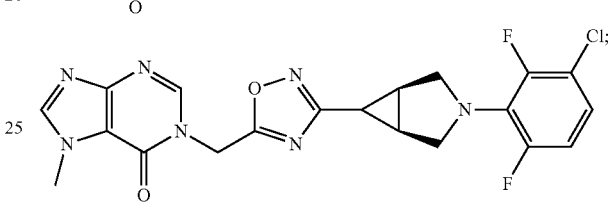
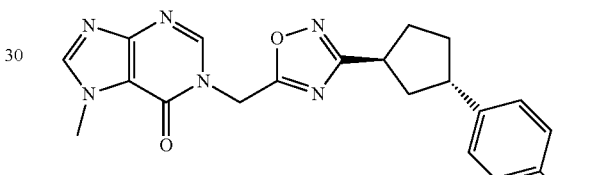
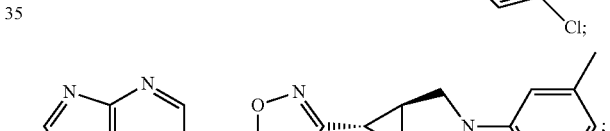
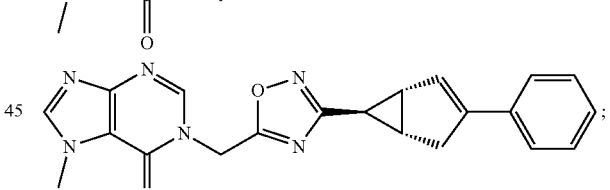
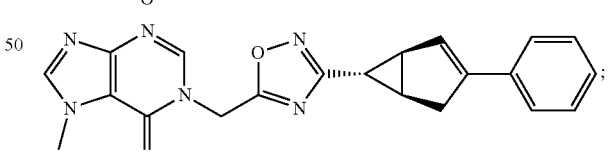
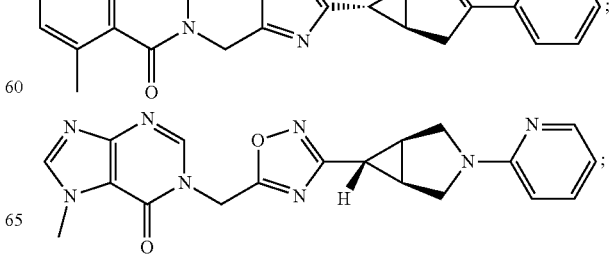

-continued
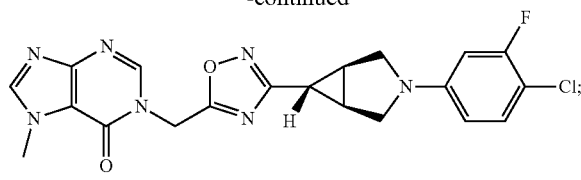
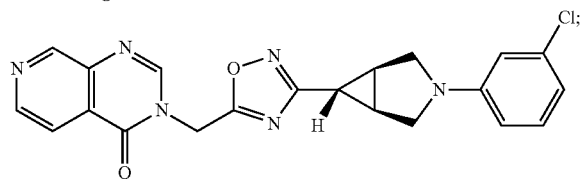
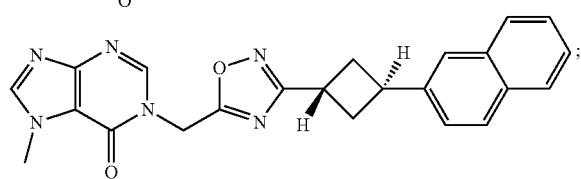
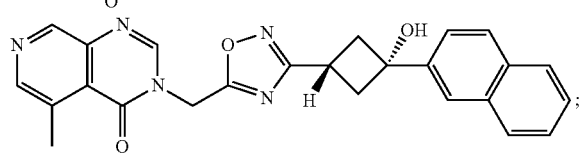
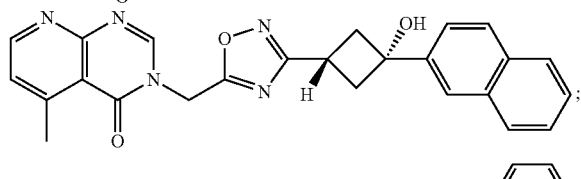
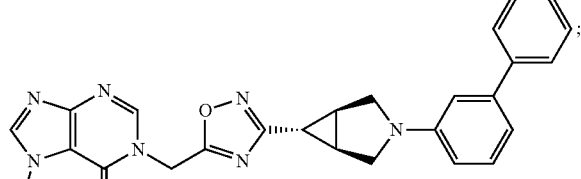
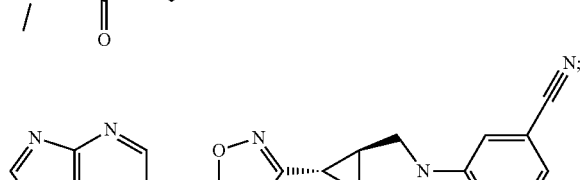
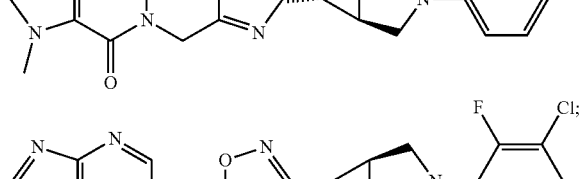
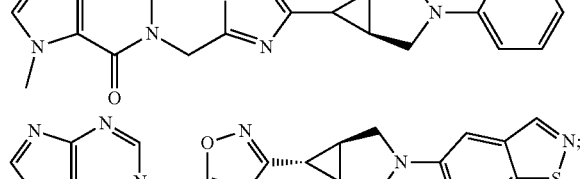
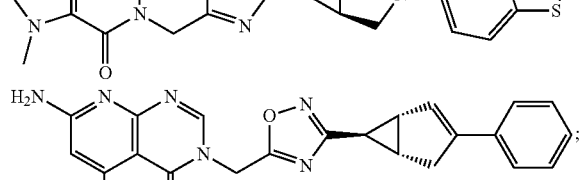
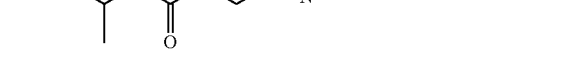
-continued
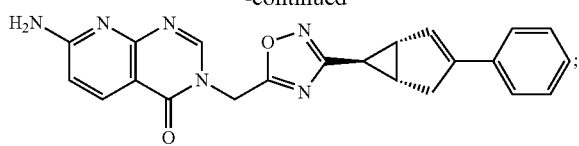
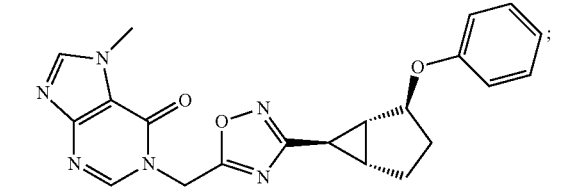
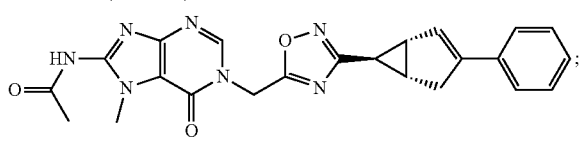
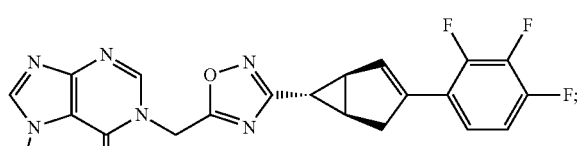
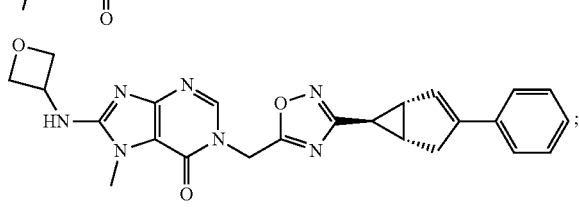
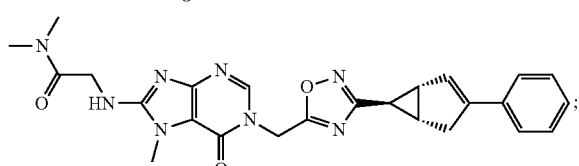
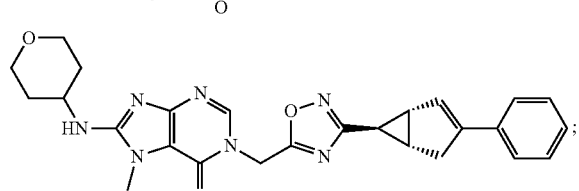
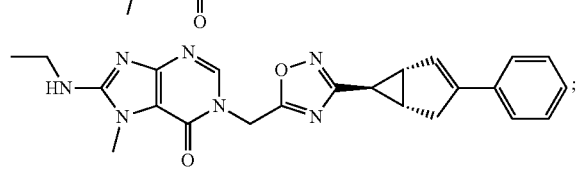
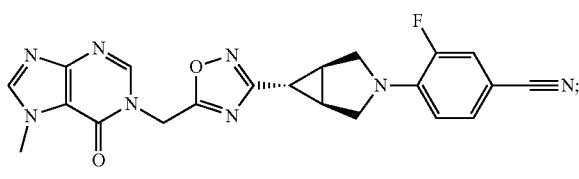
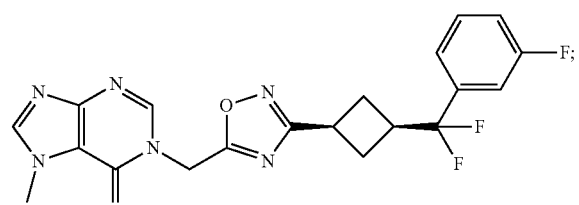

145
-continued
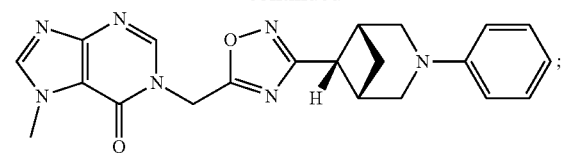
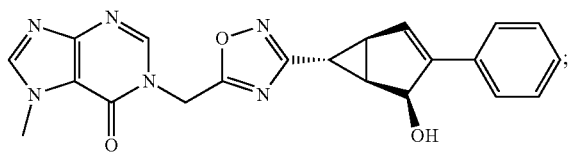
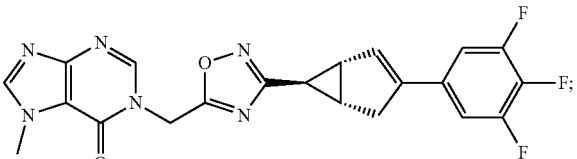
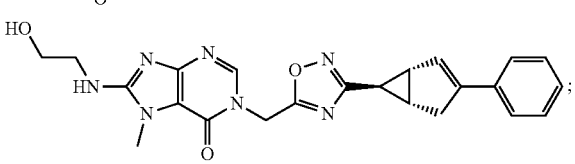
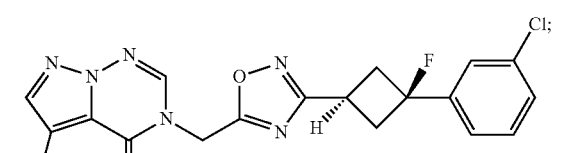
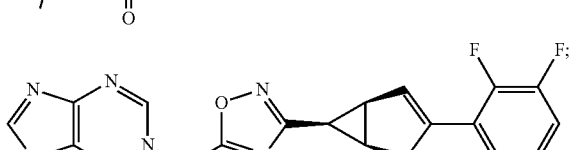
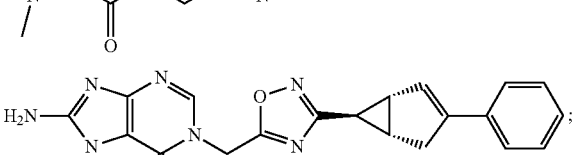
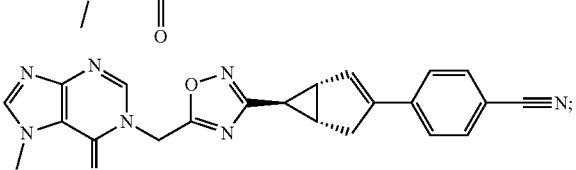
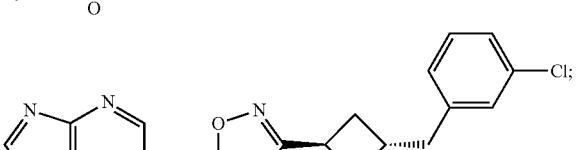
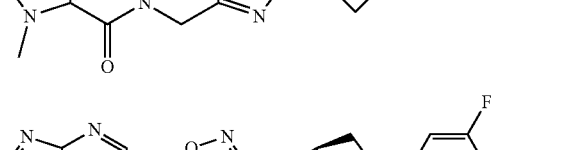
146
-continued
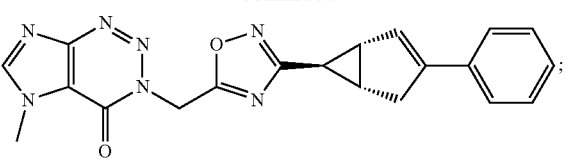
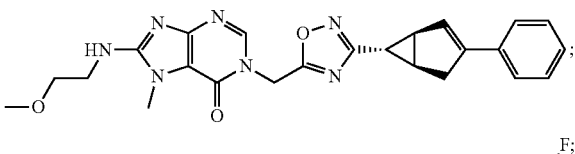
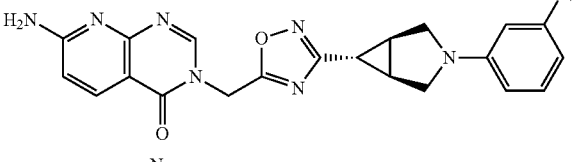
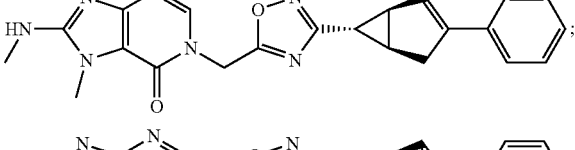
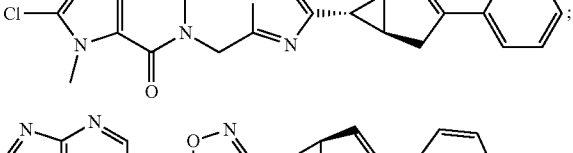
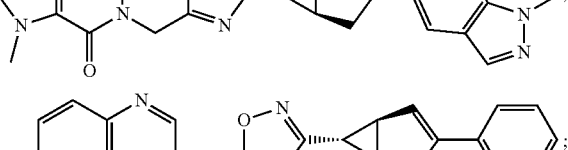
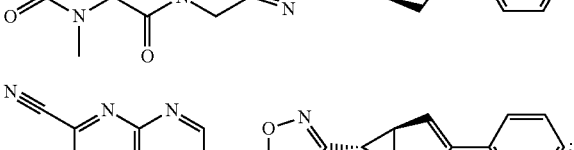
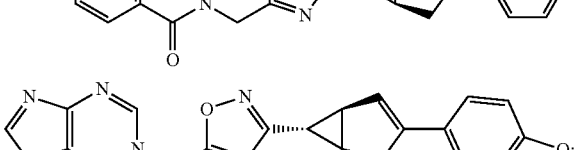
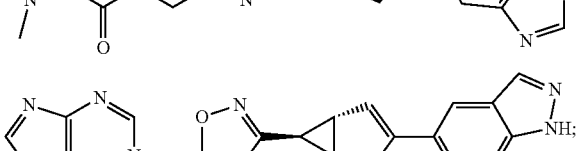
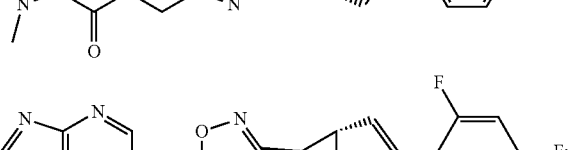
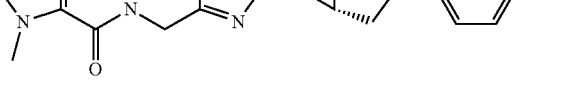

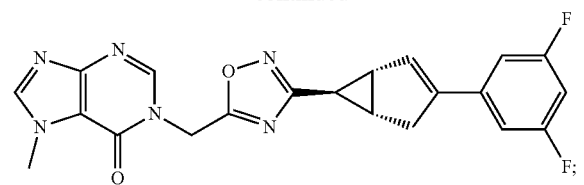
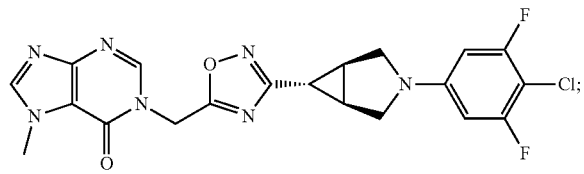
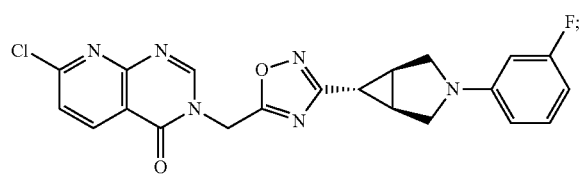
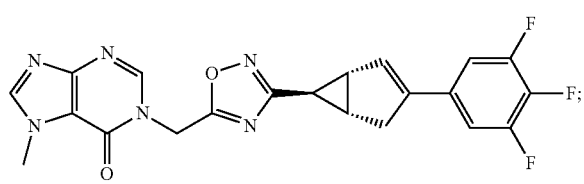
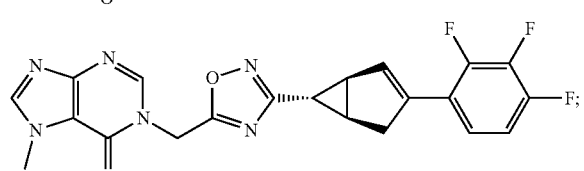
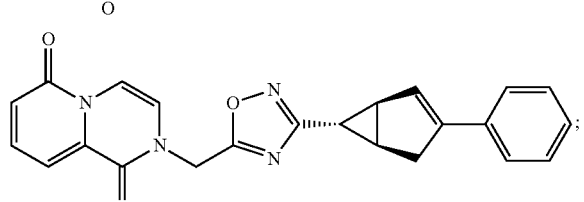
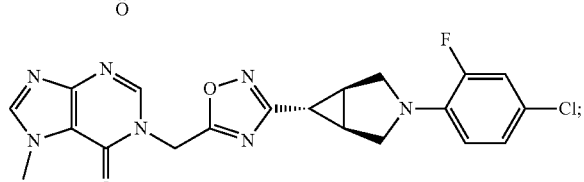
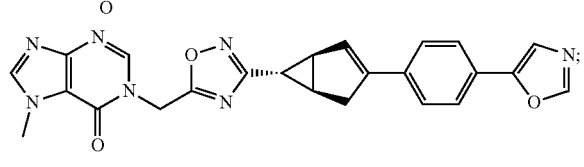
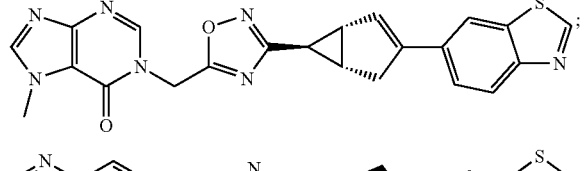
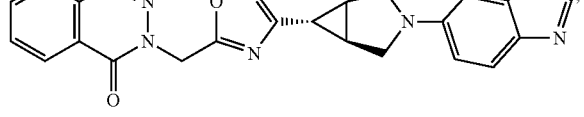
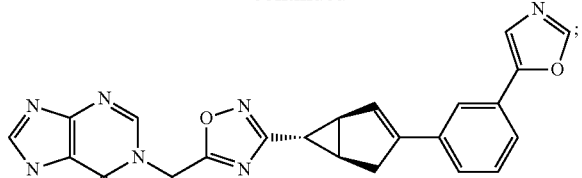
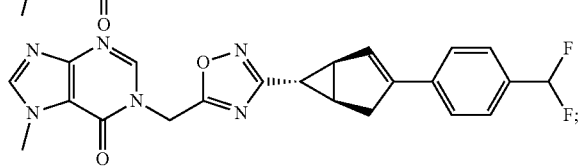
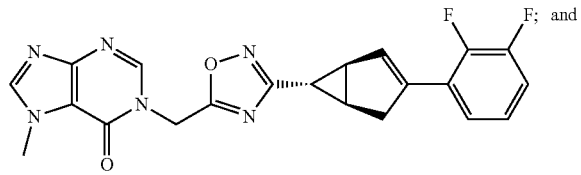
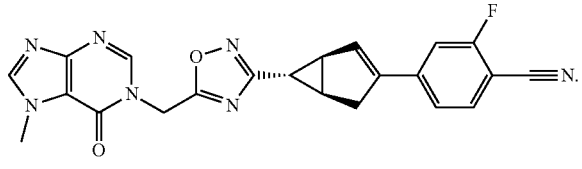
In some aspects, the compound of formula (I), or a pharmaceutically acceptable salt thereof, is a stereoisomer selected from the following:
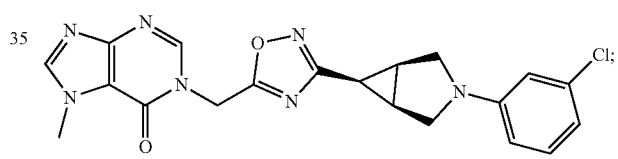
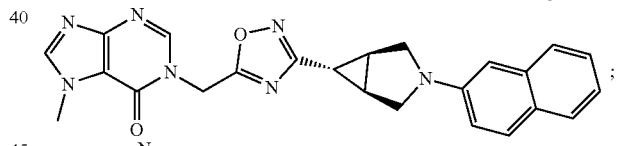
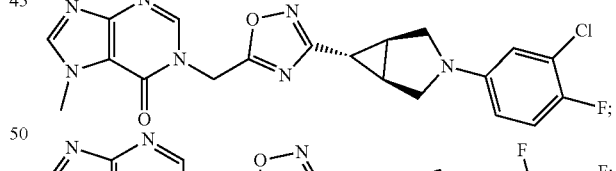
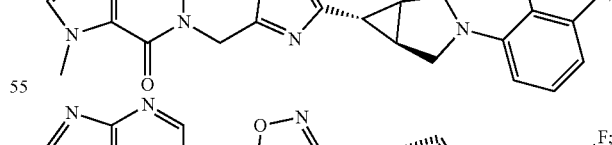
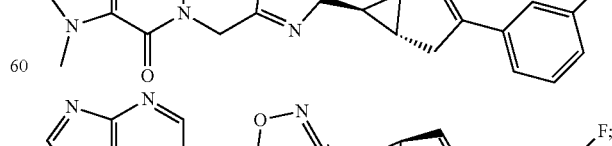
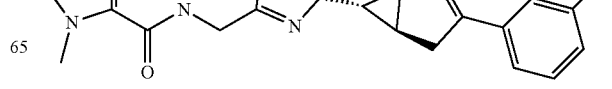

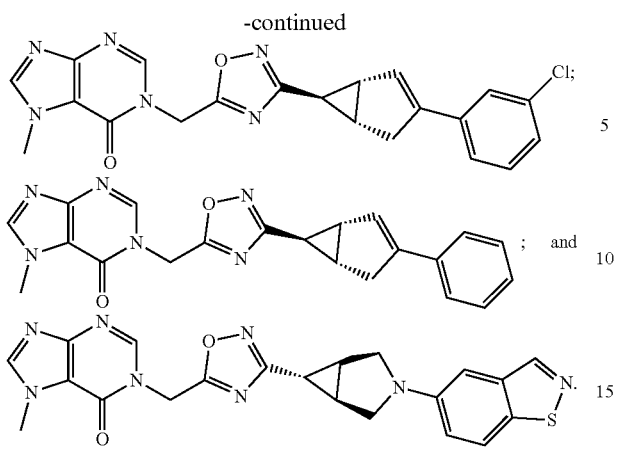

In another embodiment of the invention, the compounds of formula I are isotopically-labeled by having one or more atoms therein replaced by an atom having a different atomic mass or mass number. Such isotopically-labeled (i.e., radio-labeled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I and a pharmaceutically acceptable carrier, diluent and/or excipient.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention may include phosphates, phosphate esters, alkyl phosphates, alkyl phosphate esters, acyl ethers, or other prodrug moieties as discussed below. In some embodiments, the prodrug moiety is:

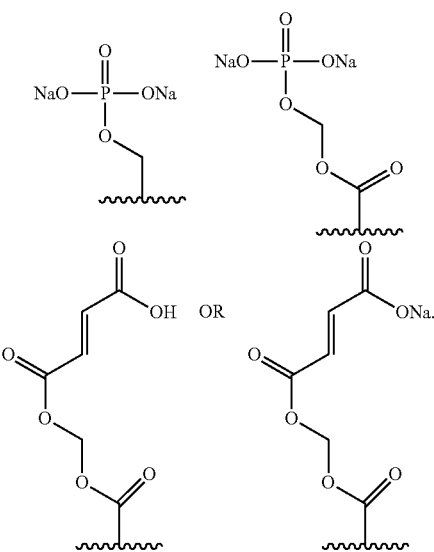

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxyl groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$) alkanoyloxy)ethyl, $(C_{1-6})$alkoxycarbonyloxymethyl, N—($C_{1-6}$)alkoxycarbonylaminomethyl, succinoyl, $(C_{1-6})$alkanoyl, alpha-amino($C_{1-4}$) alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition" as used herein, is intended to encompass a product comprising the specified ingredients in the specified amounts, as well as any product which results, directly or indirectly, from combination of the specified ingredients in the specified amounts.

In one embodiment, the invention provides for pharmaceutical compositions or medicaments comprising a compound of formula I or an embodiment thereof, and its stereoisomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21st Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. Exp. Mol. Pathol. 2006, 81(2), 166-170), fibromyalgia, migraine and headache (e.g. cluster headache, sinus headache, or tension headache; see, Goadsby Curr. Pain Headache Reports 2004, 8, 393), sinusitis, oral mucositis, toothache, dental trauma, dental extractions, dental infections, burn (Bolcskei et al., Pain 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., Lancet, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., J Pharmacal Exp Ther., 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. J. Pharmacal. Exp. Ther. 2003, 306, 387; Walker, K. M. et al., J. Pharmacal. Exp. Ther. 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005, 117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., Br. J. Pharmacal. 2004, 141, 1313-20; Yiangou, Y. et al., Lancet2001, 357, 1338-39; Kimball, E. S. et al., Neurogastroenterol. Motif., 2004, 16, 811), osteoarthritis (Szabo, A. et al., J. Pharmacal. Exp. Ther. 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

For example, compounds of the invention can be administered to treat tracheobronchial and diaphragmatic dysfunctions including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacal. 2003, 192, 21-35), cough (e.g., acute or chronic cough, or cough caused by irritation from gastroesophageal reflux disease; see, Lalloo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., J Neurosci., 2004, 24, 11253-11263), interstitial cystitis (Sculptoreanu, A. et al., Neurosci Lett., 2005, 381, 42-46), inflammatory prostate disease, prostatitis (Sanchez, M. et al., Eur J Pharmacal., 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound as described herein to a subject in need thereof.

In another embodiment, the invention provides for a compound as described herein or a pharmaceutically acceptable salt thereof for modulating TRPA1 activity.

In another embodiment, the invention provides for a compound as described herein or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound as described herein to a subject in need thereof.

In another embodiment, the invention provides for a compound as described herein or a pharmaceutically acceptable salt thereof for the treatment or prophylaxis of a respiratory disorder.

In another embodiment, the invention provides for the use of a compound as described herein or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound as described herein or a pharmaceutically acceptable salt thereof to the mammal.

In another embodiment, the invention provides for a method for modulating TRPA1 activity, comprising contacting TRPA1 with a compound as described herein or a pharmaceutically acceptable salt thereof.

In another embodiment, the invention provides for a compound as described herein or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound as described herein or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound as described herein or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder. In some embodiments, the disease or condition is asthma.

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to the following.

Opiate analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine.

Non-opiate analgesics, e.g., acetomeniphen, and salicylates (e.g., aspirin).

Nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac.

Anticonvulsants, e.g., carbamazepine, oxcarbazepine, lamotrigine, valproate, topiramate, gabapentin and pregabalin.

Antidepressants such as tricyclic antidepressants, e.g., amitriptyline, clomipramine, despramine, imipramine and nortriptyline.

COX-2 selective inhibitors, e.g., celecoxib, rofecoxib, parecoxib, valdecoxib, deracoxib, etoricoxib, and lumiracoxib.

Alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline.

Barbiturate sedatives, e.g., amobarbital, aprobarbital, butabarbital, butabital, mephobarbital, metharbital, methohexital, pentobarbital, phenobartital, secobarbital, talbutal, theamylal and thiopental.

Tachykinin (NK) antagonist, particularly an NK-3, NK-2 or NK-1 antagonist, e.g., (aR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S).

Coal-tar analgesics, e.g., paracetamol.

Serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine.

Noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics.

Dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine.

Acetylcholinesterase inhibitors, e.g., donepezil.

5-HT3 antagonists, e.g., ondansetron.

Metabotropic glutamate receptor (mGluR) antagonists.

Local anaesthetics, e.g., mexiletine and lidocaine.

Corticosteroids, e.g., dexamethasone.

Antiarrhythimics, e.g., mexiletine and phenytoin.

Muscarinic antagonists, e.g., tolterodine, propiverine, tropsium chloride, darifenacin, solifenacin, temiverine and ipratropium.

Cannabinoids.

Vanilloid receptor agonists (e.g., resinferatoxin) or antagonists (e.g., capsazepine).

Sedatives, e.g., glutethimide, meprobamate, methaqualone, and dichloralphenazone.

Anxiolytics, e.g., benzodiazepines.

Antidepressants, e.g., mirtazapine.

Topical agents, e.g., lidocaine, capsacin and resiniferotoxin.

Muscle relaxants, e.g., benzodiazepines, baclofen, carisoprodol, chlorzoxazone, cyclobenzaprine, methocarbamol and orphrenadine.

Anti-histamines or H1 antagonists.

NMDA receptor antagonists.

5-HT receptor agonists/antagonists.

PDEV inhibitors.

Tramadol®.

Cholinergic (nicotinic) analgesics.

Alpha-2-delta ligands.

Prostaglandin E2 subtype antagonists.

Leukotriene B4 antagonists.

5-lipoxygenase inhibitors.

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Although certain exemplary embodiments are depicted and described herein, the compounds of the present invention can be prepared using appropriate starting materials according to the methods described generally herein and/or by methods available to one of ordinary skill in the art.

Intermediates and final compounds may be purified by either flash chromatography, and/or by reverse-phase preparative HPLC (high performance liquid chromatography), and/or by supercritical fluid chromatography. Unless otherwise noted, flash chromatography may be carried out using prepacked silica gel cartridges from either ISCO or Sili-Cycle on an ISCO CombiFlash® chromatography instrument (from Teledyne Isco, Inc.). Reverse-phase preparative HPLC may be performed using a (1) Polaris C-18 5 µM column (50×21 mm), or (2) XBridge Prep C-18 OBD 5 µM column (19×150 mm). Supercritical fluid chromatography may be carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 µM, (2) 4.6 cm×5 cm, 5 µM, or (3) 15 cm×21.2 mm, M.

Mass spectrometry (MS) may be performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) may be performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Example 1: Preparation of 7-methyl-1-((3-((trans)-3-phenylcyclobutyl)-1,2,4-oxadiazol-5-yl)methyl)-1H-purin-6(7H)-one (Example Compound 1)

The overall Example 1 reaction scheme is as follows:

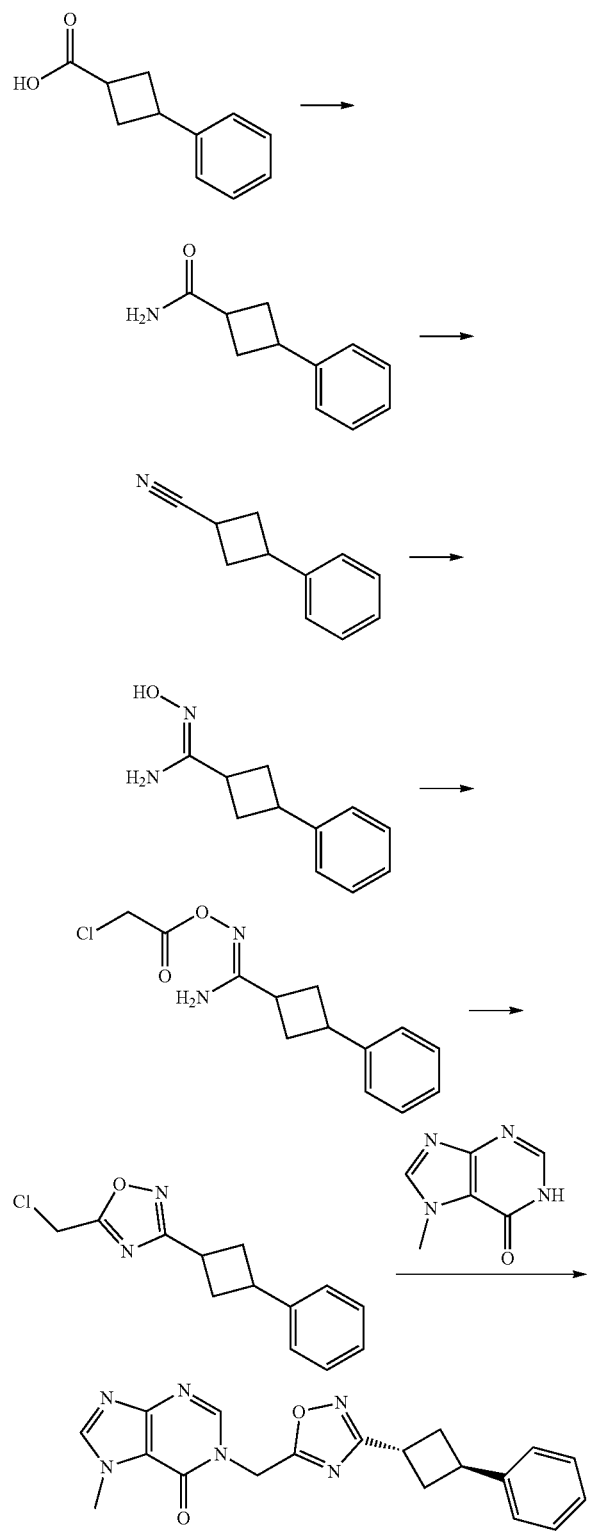

Step 1: Preparation of 3-phenylcyclobutanecarboxamide

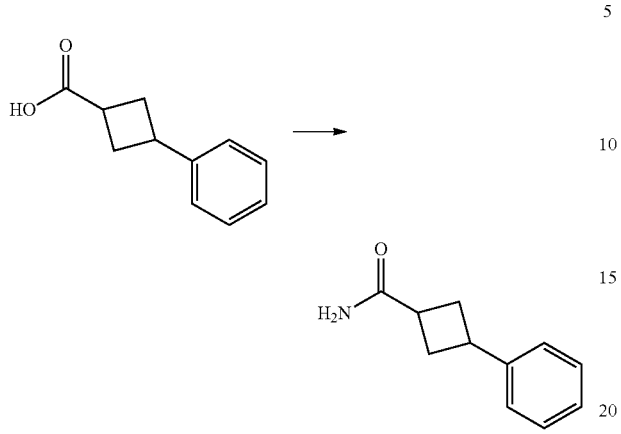

HATU (1.43 g, 3.65 mmol) and DIPEA (797 µL, 4.56 mmol) were added to a solution of 3-phenylcyclobutanecarboxylic acid (536 mg, 3.04 mmol) in DCM (15 mL) at 0° C. The mixture was stirred for 30 min followed by the addition of ammonia (7 M in MeOH) (869 µL, 6.08 mmol). The reaction was then stirred at room temperature overnight. The reaction mixture was concentrated on the rotavap, adsorbed onto silica and purified by flash column chromatography with 30-80% (3:1 iPrOAc/MeOH)/heptane to afford the title compound (602 mg, 113% yield) as a white solid.

Step 2: Preparation of 3-phenylcyclobutanecarbonitrile

Phosphoryl chloride (340 µL, 3.62 mmol) was added to a solution of 3-phenylcyclobutanecarboxamide (575.8 mg, 3.29 mmol) and triethylamine (925 µL, 6.57 mmol) in DCM (11 mL) at 0° C. The reaction was then stirred at room temperature for 4 h. The reaction was diluted with DCM and washed sequentially with saturated NaHCO$_3$, 1N HCl and water. The DCM layer was dried with MgSO$_4$, filtered and concentrated. The residue was adsorbed onto silica and purified by flash column chromatography with 0-50% iPrOAc/Heptane to afford the titled compound (354 mg, 68% yield) as a clear oil.

Step 3: Preparation of N'-hydroxy-3-phenylcyclobutanecarboximidamide

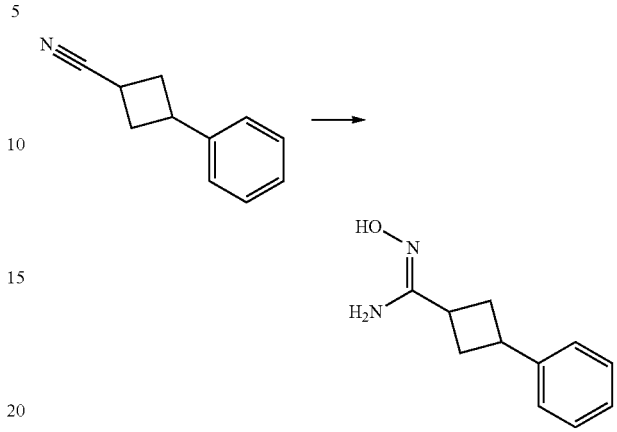

A mixture of 3-phenylcyclobutanecarbonitrile (354 mg, 2.25 mmol) and hydroxylamine (50 mass % in water) (1.38 mL, 22.50 mmol) in EtOH (5.6 mL) was stirred at 80° C. for 3 h. The reaction mixture was concentrated on the rotavap and taken up in iPrOAc. The organic layer was washed with water and brine, dried with MgSO$_4$, filtered and concentrated to provide the title compound white solid (415 mg, 97% yield).

Step 4: Preparation of N'-(2-chloroacetoxy)-3-phenylcyclobutanecarboximidamide

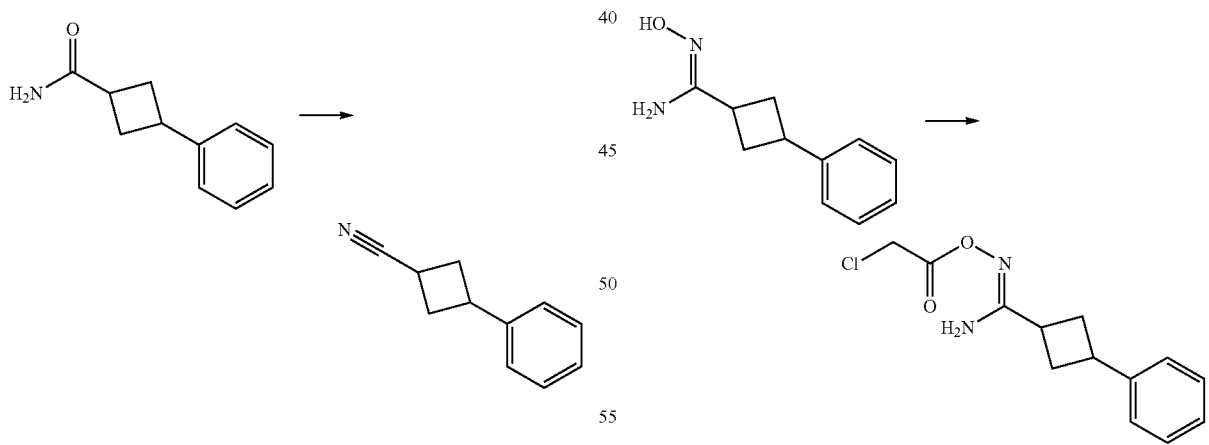

Chloroacetyl chloride (225 µL, 2.83 mmol) was added to a solution of N'-hydroxy-3-phenyl-cyclobutanecarboxamidine (415 mg, 2.18 mmol) in acetone (15 mL). The reaction was stirred at room temperature overnight. The reaction mixture was concentrated on the rotavap. The residue was then partitioned between DCM and saturated NaHCO$_3$. The organic layer was washed with brine, dried with MgSO$_4$, filtered and concentrated to afford the title compound as a crude white solid (517 mg, 89% yield).

Step 5: Preparation of 5-(chloromethyl)-3-(3-phenylcyclobutyl)-1,2,4-oxadiazole

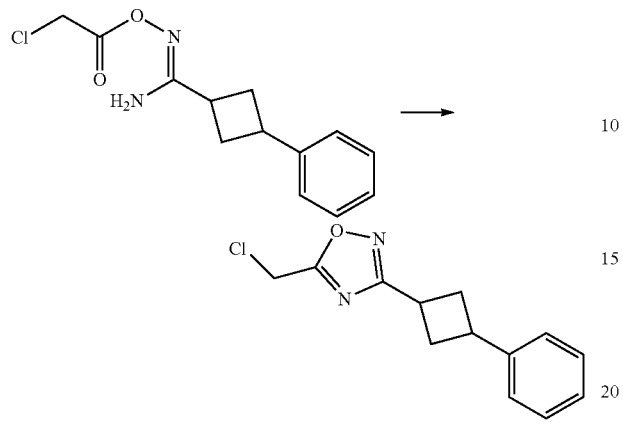

A mixture of N'-(2-chloroacetoxy)-3-phenylcyclobutanecarboximidamide (517 mg, 1.94 mmol) and 4 Å molecular sieves in toluene (13 mL) was stirred at 120° C. in a sealed tube overnight. The reaction mixture was filtered through celite and concentrated on the rotavap. The residue was adsorbed onto silica and purified by flash column chromatography with 0-50% iPOAc/heptane to afford the title compound (330 mg, 68% yield) as a clear oil.

Step 6: Preparation of 7-methyl-1-((3-((trans)-3-phenylcyclobutyl)-1,2,4-oxadiazol-5-yl)methyl)-1H-purin-6(7H)-one

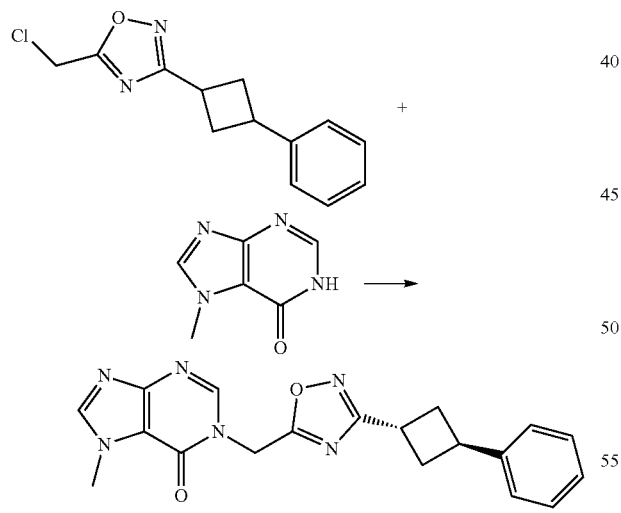

A mixture of 7-methyl-1H-purin-6(7H)-one (76.9 mg, 0.49 mmol), 5-(chloromethyl)-3-(3-phenylcyclobutyl)-1,2,4-oxadiazole (110 mg, 0.44 mmol), $Cs_2CO_3$ (289.0 mg, 0.88 mmol) and TBAI (16.7 mg, 0.04 mmol) in DMF (1.5 mL) was stirred at 70° C. for 2.5 h. The reaction mixture was diluted with iPrOAc, filtered through celite and concentrated on the rotavap. The residue was adsorbed onto silica and purified by flash column chromatography with 0-10% MeOH/DCM. The product was further purified by SFC using a Cellulose-3 column with 40% of 0.1% ammonium hydroxide in methanol in $CO_2$ to provide the title compound (35.5 mg, 20% yield) as a white solid. LCMS [M+H$^+$]: 363.1. 1H NMR (400 MHz, DMSO-d6) δ 8.47 (s, 1H), 8.26-8.20 (m, 1H), 7.37-7.27 (m, 4H), 7.27-7.15 (m, 1H), 5.58 (s, 2H), 3.96 (s, 3H), 3.80-3.58 (m, 2H), 2.65-2.51 (m, 4H).

Examples 2 and 3: Preparation of 7-methyl-1-[[3-[rac-(1R,1aR,6aS)-1,1a,6,6a-tetrahydrocyclopropa[a]inden-1-yl]-1,2,4-oxadiazol-5-yl]methyl]purin-6-one and 7-methyl-1-[[3-[rac-(1S,1aS,6aR)-1,1a,6,6a-tetrahydrocyclopropa[a]inden-1-yl]-1,2,4-oxadiazol-5-yl]methyl]purin-6-one (Example Compounds 2 and 3)

The overall Example 2 and 3 reaction scheme is as follows:

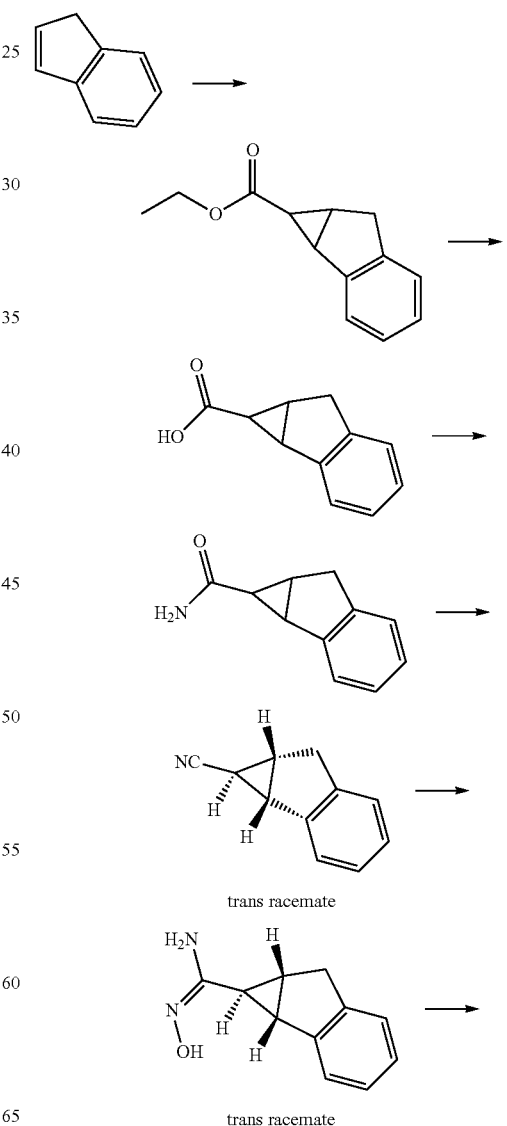

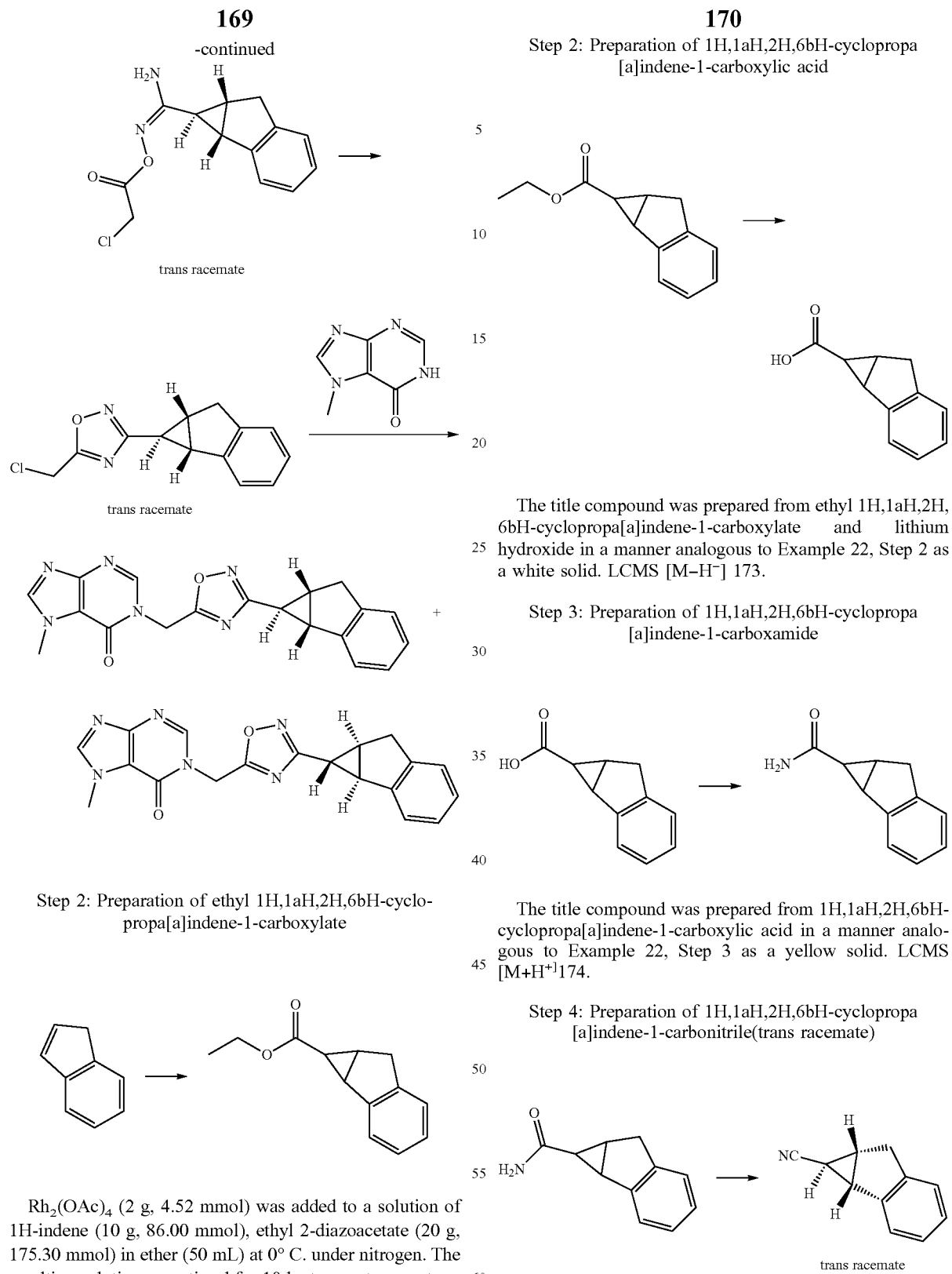

Step 2: Preparation of 1H,1aH,2H,6bH-cyclopropa[a]indene-1-carboxylic acid

The title compound was prepared from ethyl 1H,1aH,2H,6bH-cyclopropa[a]indene-1-carboxylate and lithium hydroxide in a manner analogous to Example 22, Step 2 as a white solid. LCMS [M−H⁻] 173.

Step 3: Preparation of 1H,1aH,2H,6bH-cyclopropa[a]indene-1-carboxamide

The title compound was prepared from 1H,1aH,2H,6bH-cyclopropa[a]indene-1-carboxylic acid in a manner analogous to Example 22, Step 3 as a yellow solid. LCMS [M+H⁺] 174.

Step 4: Preparation of 1H,1aH,2H,6bH-cyclopropa[a]indene-1-carbonitrile(trans racemate)

The cis/trans mixture was prepared from 1H,1aH,2H,6bH-cyclopropa[a]indene-1-carboxamide and TFAA in a manner analogous to Example 22, Step 4. The cis/trans mixture was then separated by a silica gel column eluting with ethyl acetate/petroleum ether (1/10) to give the trans mixture as a white solid. GCMS m/z 155.

Step 2: Preparation of ethyl 1H,1aH,2H,6bH-cyclopropa[a]indene-1-carboxylate Rh₂(OAc)₄ (2 g, 4.52 mmol) was added to a solution of 1H-indene (10 g, 86.00 mmol), ethyl 2-diazoacetate (20 g, 175.30 mmol) in ether (50 mL) at 0° C. under nitrogen. The resulting solution was stirred for 10 h at room temperature, quenched with water, extracted with ethyl acetate, washed with brine, dried over anhydrous sodium sulfate, and concentrated under vacuum. The residue was purified by a silica gel column eluting with ethyl acetate/petroleum ether (1:50) to afford the title compound (2.23 g, 13%) as a yellow solid. GCMS m/z=202

Step 5: Preparation of (E)-N'-hydroxy-1H,1aH,2H, 6bH-cyclopropa[a]indene-1-carboximidamide(trans racemate)

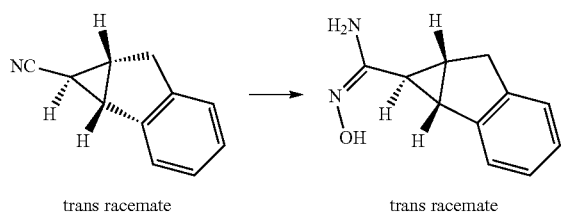

trans racemate       trans racemate

The title compound was prepared from 1H,1aH,2H,6bH-cyclopropa[a]indene-1-carbonitrile(trans racemate) and NH$_2$OH H$_2$O in a manner analogous to Example 22, Step 5 as a white solid. LCMS [M+H$^+$] 189.

Step 6: Preparation of (E)-[1H,1aH,2H,6bH-cyclopropa[a]inden-1-yl(amino)methylidene]amino 2-chloroacetate(trans racemate)

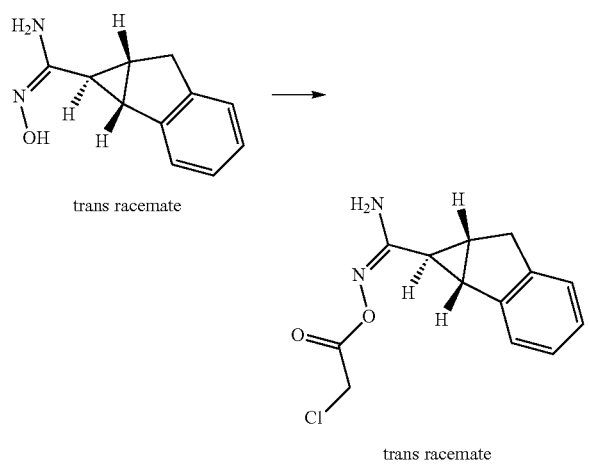

trans racemate trans racemate

The title compound was prepared from (E)-N_ydroxy-1H,1aH,2H,6bH-cyclopropa[a]indene-1-carboximidamide (trans racemate) and 2-chloroacetyl chloride in a manner analogous to Example 22, Step 6 as yellow oil. LCMS [M+H$^+$] 265.

Step 7: Preparation of 3-[1H,1aH,2H,6bH-cyclopropa[a]inden-1-yl]-5-(chloromethyl)-1,2,4-oxadiazole(trans racemate)

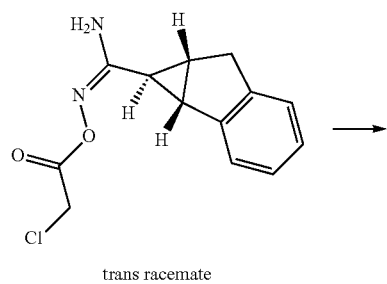

trans racemate

-continued

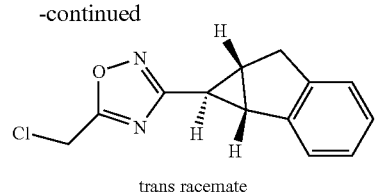

trans racemate

The title compound was prepared from (E)-[1H,1aH,2H, 6bH-cyclopropa[a]inden-1-yl(amino)methylidene]amino 2-chloroacetate (trans racemate) in a manner analogous to Example 22, Step 7 as oil. LCMS [M+H$^+$] 247.

Step 8: Preparation of 7-methyl-1-[[3-[rac-(1S,1aS, 6aR)-1,1a,6,6a-tetrahydrocyclopropa[a]inden-1-yl]-1,2,4-oxadiazol-5-yl]methyl]purin-6-one and 7-methyl-1-[[3-[rac-(1R,1aR,6aS)-1,1a,6,6a-tetrahydrocyclopropa[a]inden-1-yl]-1,2,4-oxadiazol-5-yl]methyl]purin-6-one

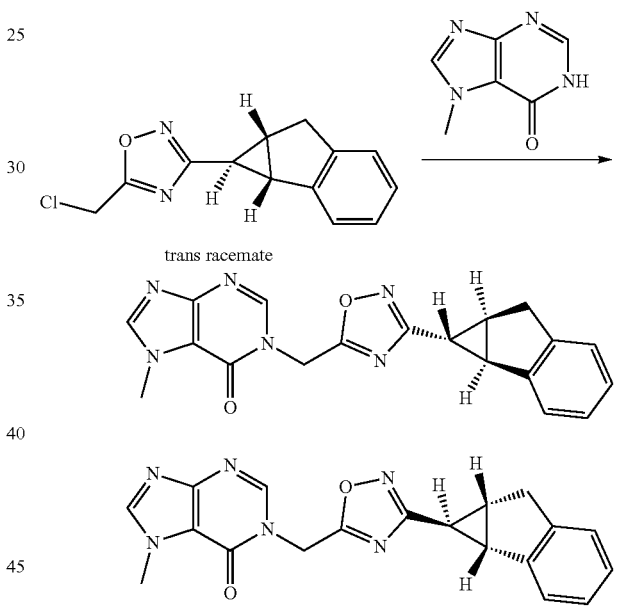

A mixture of 3-[1H,1aH,2H,6bH-cyclopropa[a]inden-1-yl]-5-(chloromethyl)-1,2,4-oxadiazole(trans racemate) (100 mg, 0.40 mmol), N,N-dimethylformamide (5 mL), TBAI (20 mg, 0.05 mmol), potassium carbonate (180 mg, 1.30 mmol), and 7-methyl-6,7-dihydro-1H-purin-6-one (61.5 mg, 0.40 mmol) was stirred for 2 h at room temperature. The solids were then filtered off. The filtrate was purified on a C18 silica gel column eluting with CH$_3$CN/H$_2$O (10 mmol/L NH$_4$HCO$_3$) increasing from 5% to 95% over 30 min. This resulted in 110 mg of a racemic mixture. The racemic mixture was then separated by Chiral-Prep-HPLC with the following conditions: Column: CHIRAL ART Cellulose-SB2*25 cm; mobile phase, MTBE and ethanol (0% to 50.0% ethanol for 28 min); Detector, UV 220/254 nm. The stereo chemistry for the final products were arbitrarily assigned.

Example 2, enantiomer 2 (44.2 mg): white solid; Rt=7.19 min (CHIRALART Cellulose SB Size, 0.46*15 cm; 3 um; mobile phase, MtBE (0.1% DEA):EtOH=70:30, 1.0 ml/min); LCMS [M+H+] 361; ¹H NMR (300 MHz, CD₃OD) δ 8.38 (s, 1H), 8.13 (s, 1H), 7.32-7.29 (m, 1H), 7.19-7.09 (m, 3H), 5.51 (s, 2H), 4.06 (s, 3H), 3.29-3.25 (m, 1H), 3.13-3.07 (m, 1H), 2.91-2.89 (m, 1H), 2.42-2.37 (m, 1H), 1.53 (t, J 3.6 Hz, 1H).

Example 3, enantiomer 1 (42.1 mg): white solid; Rt=5.36 min (CHIRALART Cellulose SB Size, 0.46*15 cm; 3 um; mobile phase, MtBE (0.1% DEA):EtOH=70:30, 1.0 ml/min); LCMS [M+H+] 361; ¹H NMR (300 MHz, CD₃OD) δ 8.38 (s, 1H), 8.13 (s, 1H), 7.32-7.27 (m, 1H), 7.19-7.09 (m, 3H), 5.51 (s, 2H), 4.05 (s, 3H), 3.29-3.24 (m, 1H), 3.12-3.06 (m, 1H), 2.90-2.88 (m, 1H), 2.42-2.37 (m, 1H), 1.52 (t, J 4.0 Hz, 1H).

Example 4: Preparation of 7-methyl-1-[[3-[(1R,5S, 6r)-3-(3-trifluoromethoxy)phenyl-3-azabicyclo [3.1.0]hexan-6-yl]-1,2,4-oxadiazol-5-yl]methyl]purin-6-one (Example Compound 4)

The overall Example 4 reaction scheme is as follows:

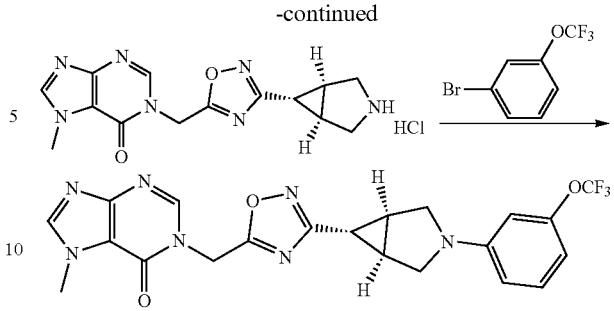

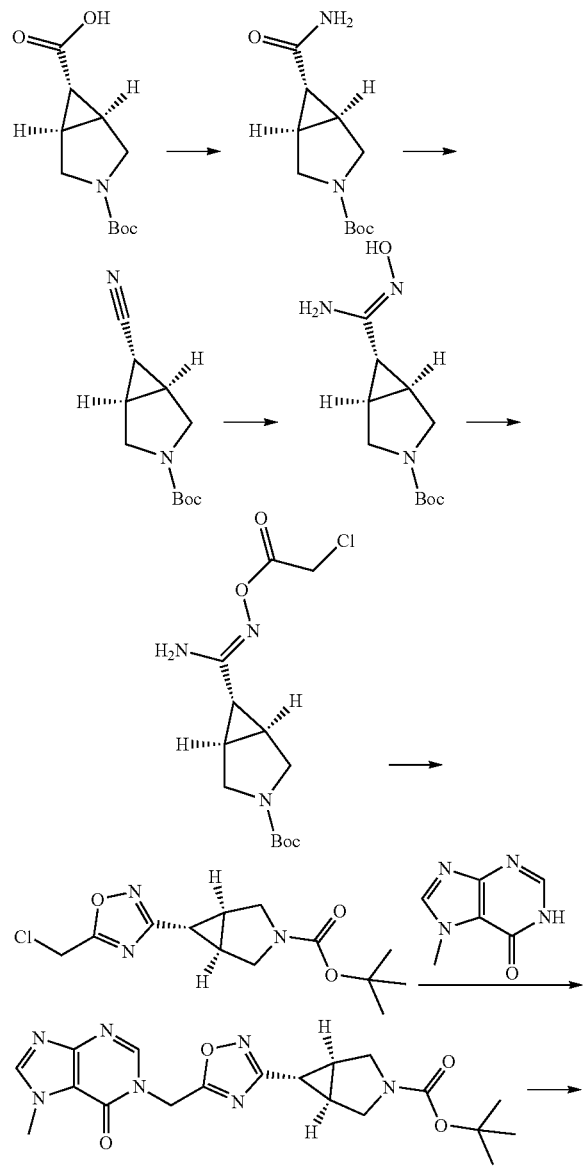

Step 1: Synthesis of tert-butyl (1R,5S,6r)-6-carbamoyl-3-azabicyclo[3.1.0]hexane-3-carboxylate

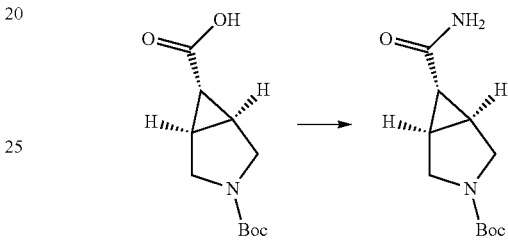

To a 100-mL round-bottom flask was added (1S,5R)-3-tert-butoxycarbonyl-3-azabicyclo [3.1.0]hexane-6-carboxylic acid (2.00 g, 8.80 mmol, 1 equiv), 1-(3-dimethylaminopropyl)-3-ethylcarbodiimide hydrochloride (2.04 g, 10.6 mmol, 1.2 equiv), and 1-hydroxybenzotriazole (1.43 g, 10.6 mmol, 1.2 equiv) in DCM (24 mL). N,N-diisopropylethylamine (1.86 mL, 10.6 mmol, 1.2 equiv) was added dropwise and then the reaction was cooled to 0° C. Then a 2.0 M solution of NH₃ in MeOH (19.9 mL, 39.8 mmol) was added dropwise to the solution and the reaction was stirred for 4 hours at room temperature. After 4 hours, the reaction was diluted with DCM, washed with brine, extracted 3 times with DCM, dried over Na₂SO₄, and concentrated under vacuum. The crude product was purified by column chromatography (10% MeOH in DCM) to afford tert-butyl (1S,5R)-6-carbamoyl-3-azabicyclo[3.1.0]hexane-3-carboxylate as a white crystalline solid (1.561 g, 78% yield).

Step 2: Synthesis of tert-butyl (1R,5S,6r)-6-cyano-3-azabicyclo[3.1.0]hexane-3-carboxylate

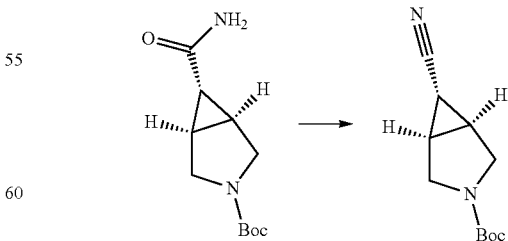

To a 50-mL round-bottom flask was added tert-butyl (1S,5R)-6-carbamoyl-3-azabicyclo[3.1.0]hexane-3-carboxylate (1.00 g, 4.42 mmol, 1 equiv) and cyanuric acid (815 mg, 4.42 mmol, 1 equiv) in DMF (17 mL). The reaction was stirred for 2 hours at room temperature. After 2 hours, the reaction was diluted with water and extracted 3 times with i-PrOAc. The organic layer was then washed 2 times with water and then brine, dried over $Na_2SO_4$, and concentrated under vacuum to afford tert-butyl (1S,5R)-6-cyano-3-azabicyclo [3.1.0]hexane-3-carboxylate as a clear yellow oil which crystallized over time (879 mg, 96% yield).

Step 3: Synthesis of tert-butyl (1R,5S,6r)-6-((Z)—N'-hydroxycarbamimidoyl)-3-azabicyclo[3.1.0]hexane-3-carboxylate

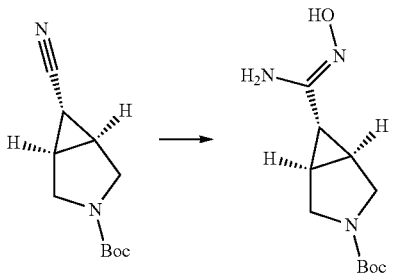 [SMILES: CC(C)(C)OC(=O)N1C[C@@H]2[C@@H](C#N)[C@@H]2C1 ; CC(C)(C)OC(=O)N1C[C@@H]2[C@H](C1)[C@H]2/C(N)=N/O]

To a solution of tert-butyl 6-cyano-3-azabicyclo[3.1.0]hexane-3-carboxylate (500 mg, 2.4 mmol, 1 eq.) in MeOH (10 mL) was added hydroxylamine hydrochloride (250.2 mg, 3.6 mmol, 1.5 eq.) followed by $NaHCO_3$ (1.0 g, 12.0 mmol, 5 eq.) and the reaction mixture was heated to reflux overnight. The reaction mixture was cooled to room temp, filtered and the filter cake was further washed with DCM. The filtrate was then concentrated in vacuo and the residue was taken up in DCM and washed with water, brine, dried over sodium sulfate, filtered and concentrated in vacuo to yield the crude title compound (558.5 mg, 96%).

Step 4: Synthesis of tert-butyl (1R,5S,6r)-6-((Z)—N'-(2-chloroacetoxy)carbamimidoyl)-3-azabicyclo [3.1.0]hexane-3-carboxylate

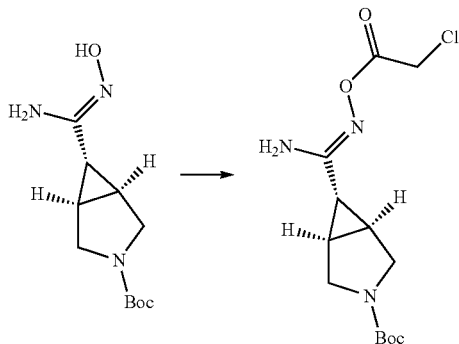 [SMILES: CC(C)(C)OC(=O)N1C[C@@H]2[C@H](C1)[C@H]2/C(N)=N/O ; CC(C)(C)OC(=O)N1C[C@@H]2[C@H](C1)[C@H]2/C(N)=N/OC(=O)CCl]

To a solution of tert-butyl 6-[(Z)—N'-hydroxycarbamimidoyl]-3-azabicyclo[3.1.0]hexane-3-carboxylate (558.5 mg, 2.3 mmol, 1 eq.) in acetone (15 mL) was added chloroacetyl chloride (0.19 mL, 2.4 mmol, 1.05 eq.), slowly, dropwise. The reaction mixture was stirred at room temperature for 30 mins. The reaction mixture was then concentrated in vacuo, and the residue was taken up in DCM and washed with saturated aqueous sodium bicarbonate and water, dried over sodium sulfate, filtered and concentrated in vacuo. The product was obtained a white foam (468.3 mg, 64%).

Step 5: Synthesis of tert-butyl (1R,5S,6r)-6-(5-(chloromethyl)-1,2,4-oxadiazol-3-yl)-3-azabicyclo [3.1.0]hexane-3-carboxylate

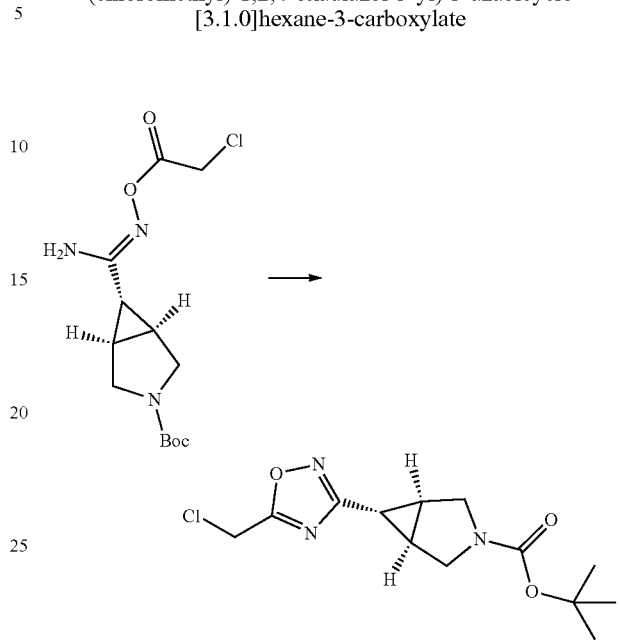

To a round-bottom flask was added tert-butyl 6-[(Z)—N'-(2-chloroacetyl)oxycarbamimidoyl]-3-azabicyclo[3.1.0]hexane-3-carboxylate (468.3 mg, 1.5 mmol, 1 eq.) followed by toluene (20 mL), a dean-stark apparatus was attached and the mixture was heated to 125° C. for 3 h. then cooled to room temp. The reaction mixture was concentrated in vacuo. The residue was adsorbed onto silica and purified by flash column chromatography with 0-100% EtOAc in Heptane to afford the desired compound as a light yellow oil that solidified over time (376.4 mg, 85%). 1H NMR (400 MHz, Chloroform-d) δ 4.61 (s, 2H), 3.79 (d, J=11.2 Hz, 1H), 3.70 (d, J=11.1 Hz, 1H), 3.53-3.43 (m, 2H), 2.20-2.08 (m, 2H), 1.97 (t, J=3.4 Hz, 1H), 1.46 (s, 9H).

Step 6: Preparation of tert-butyl (1R,5S,6r)-6-(5-((7-methyl-6-oxo-6,7-dihydro-1H-purin-1-yl)methyl)-1,2,4-oxadiazol-3-yl)-3-azabicyclo[3.1.0]hexane-3-carboxylate

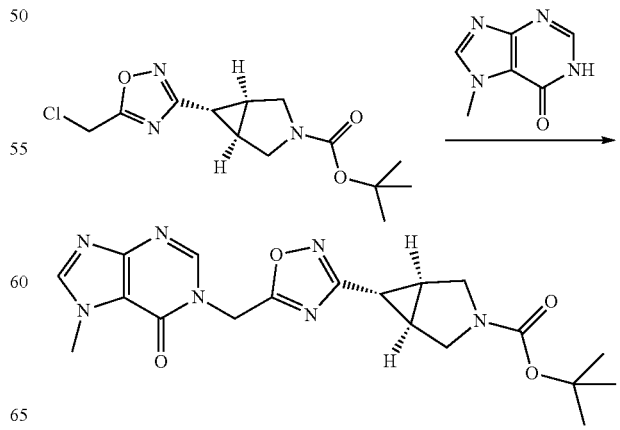

A mixture of 7-methyl-1H-purin-6-one (640 mg, 4.26 mmol), tert-butyl (1R,5S,6r)-6-(5-(chloromethyl)-1,2,4-oxadiazol-3-yl)-3-azabicyclo[3.1.0]hexane-3-carboxylate (1.41 g, 4.69 mmol), cesium carbonate (4.17 g, 12.8 mmol), tetrabutylammonium iodide (157 mg, 0.426 mmol) and N,N-dimethylformamide (43 mL) was stirred for 30 minutes at 60° C. The resulting mixture was cooled to room temperature, diluted with water, and extracted 3 times with i-PrOAc. The combined organic layers were washed with brine, dried over Na$_2$SO$_4$, filtered, and concentrated in vacuo. The residue was purified on a C18 silica gel column eluting with 3:1 MeOH:i-PrOAc in Heptane (10% to 80% over 30 min) to afford the title compound (1.43 g, 81%) as a light yellow solid.

Step 7: Preparation of 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride

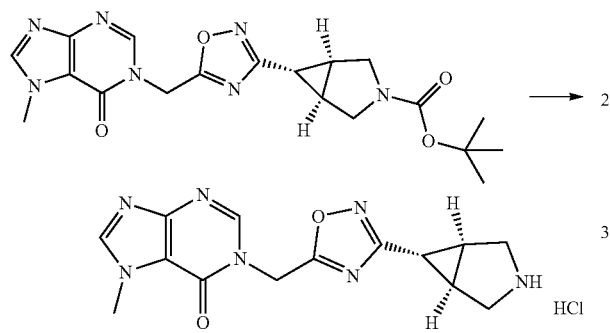

A mixture of tert-butyl (1R,5S,6r)-6-(5-((7-methyl-6-oxo-6,7-dihydro-1H-purin-1-yl)methyl)-1,2,4-oxadiazol-3-yl)-3-azabicyclo[3.1.0]hexane-3-carboxylate (1.43 g, 3.45 mmol) in DCM (24 mL) and 4.0 M hydrochloric acid in 1,4-dioxane (6 mL) was stirred for 16 hours at room temperature. The resulting mixture was concentrated under vacuum to afford the title compound (1.15 g, 96%) as a white crystalline solid.

Step 8: Preparation of 7-methyl-1-[[3-[(1R,5S,6r)-3-(3-trifluoromethoxy)phenyl-3-azabicyclo[3.1.0]hexan-6-yl]-1,2,4-oxadiazol-5-yl]methyl]purin-6-one

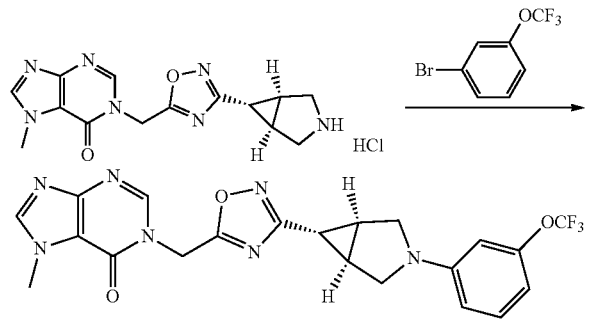

To a sealed tube containing 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) was added 1-bromo-3-(trifluoromethoxy)benzene (92.6 mg, 0.384 mmol), cesium carbonate (313 mg, 0.961 mmol), chloro-(2-dicyclohexylphosphino-2',6'-diisopropoxy-1,1'-biphenyl)[2-(2-aminoethyl)phenyl]palladium (II)-methyl-t-butyl ether adduct (26.7 mg, 0.0320 mmol), and 1,4-dioxane (1.2 mL). The headspace of the reaction vial was flushed with N$_2$ for 10 seconds and sealed and then the solution was stirred at 110° C. for 16 hours. The resulting mixture was diluted with MeOH and filtered through a plug of silica and concentrated in vacuo. The residue was purified by HPLC using a Gemini-NX C18 column with 30% of 0.1% ammonium hydroxide in water in acetonitrile to afford the titled compound as a white crystalline solid (28.4 mg, 19% yield). LCMS [M+H$^+$] 474.1. $^1$H NMR (400 MHz, DMSO) δ 8.43 (s, 1H), 8.23 (s, 1H), 7.24 (t, J=8.2 Hz, 1H), 6.57 (dd, J=8.3, 2.1 Hz, 2H), 6.44 (s, 1H), 5.52 (s, 2H), 3.95 (s, 3H), 3.68 (d, J=9.8 Hz, 2H), 3.30-3.26 (m, 2H), 2.27-2.13 (m, 2H), 2.03 (t, J=3.2 Hz, 1H).

Example 5: Preparation of 7-methyl-1-[[3-[(1R,5S,6r)-3-(3,5-dichlorophenyl)-3-azabicyclo[3.1.0]hexan-6-yl]-1,2,4-oxadiazol-5-yl]methyl]purin-6-one (Example Compound 5)

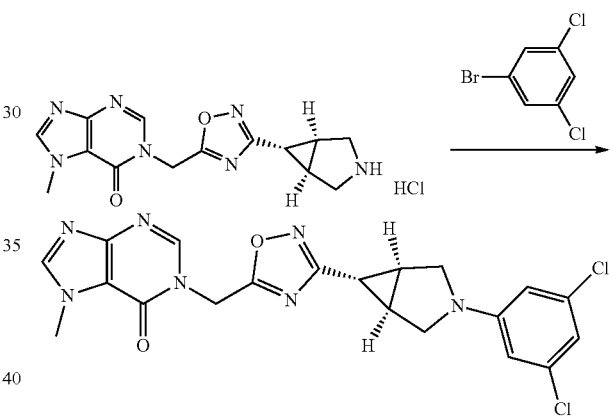

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-3,5-dichlorobenzene (86.8 mg, 0.384 mmol) as a white crystalline solid (19.0 mg, 13% yield), in a manner analogous to Example 4, Step 8. LCMS [M+H$^+$] 458.1. $^1$H NMR (400 MHz, DMSO) δ 8.43 (s, 1H), 8.23 (s, 1H), 6.73 (t, J=1.7 Hz, 1H), 6.55 (d, J=1.8 Hz, 2H), 5.52 (s, 2H), 3.95 (s, 3H), 3.68 (d, J=10.1 Hz, 2H), 3.36-3.31 (m, 2H), 2.25-2.15 (m, 2H), 1.99 (t, J=3.3 Hz, 1H).

Example 6: Preparation of 7-methyl-1-[[3-[(1R,5S,6r)-3-[4-(trifluoromethoxy)phenyl]-3-azabicyclo[3.1.0]hexan-6-yl]-1,2,4-oxadiazol-5-yl]methyl]purin-6-one (Example Compound 6)

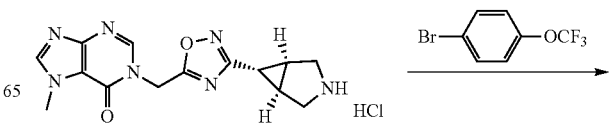

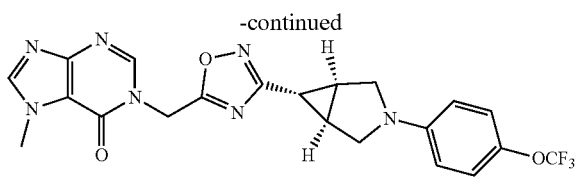
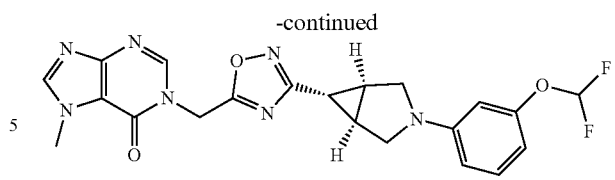

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-3-(trifluoromethoxy)benzene (92.6 mg, 0.384 mmol) as a white crystalline solid (27.4 mg, 18% yield), in a manner analogous to Example 4, Step 8. LCMS [M+H⁺] 474.1 ¹H NMR (400 MHz, DMSO) δ 8.43 (s, 1H), 8.23 (s, 1H), 7.14 (d, J=8.4 Hz, 2H), 6.65-6.53 (m, 2H), 5.52 (s, 2H), 3.95 (s, 3H), 3.67 (d, J=9.7 Hz, 2H), 3.30-3.25 (m, 2H), 2.28-2.14 (m, 2H), 2.03 (t, J=3.2 Hz, 1H).

Example 7: Preparation of 7-methyl-1-[[3-[(1R,5S,6r)-3-(4-fluorophenyl)-3-azabicyclo[3.1.0]hexan-6-yl]-1,2,4-oxadiazol-5-yl]methyl]purin-6-one (Example Compound 7)

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-3-(difluoromethoxy)benzene (85.7 mg, 0.384 mmol) as a white crystalline solid (35.5 mg, 24% yield), in a manner analogous to Example 4, Step 8. LCMS [M+H⁺] 456.1. ¹H NMR (400 MHz, DMSO) δ 8.43 (s, 1H), 8.23 (s, 1H), 7.38-6.96 (m, 2H), 6.43 (ddd, J=7.3, 4.7, 2.1 Hz, 2H), 6.31 (t, J=2.1 Hz, 1H), 5.52 (s, 2H), 3.95 (s, 3H), 3.67 (d, J=9.8 Hz, 2H), 3.28 (d, J=9.0 Hz, 2H), 2.24-2.16 (m, 2H), 2.01 (t, J=3.2 Hz, 1H).

Example 9: Preparation of 3-((3-((1s,3s)-3-(4-chlorophenyl)-3-hydroxycyclobutyl)-1,2,4-oxadiazol-5-yl)methyl)-5-methylpyrido[3,4-d]pyrimidin-4(3H)-one (Example Compound 9)

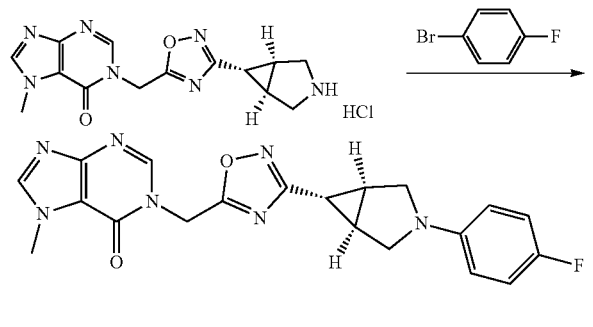
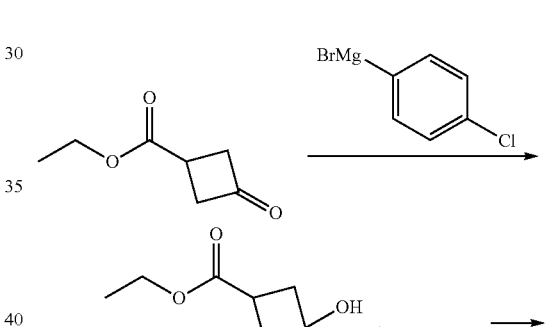

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-4-fluorobenzene (67.2 mg, 0.384 mmol) as a white crystalline solid (5.8 mg, 5% yield), in a manner analogous to Example 4, Step 8. LCMS [M+H⁺] 408.1. ¹H NMR (400 MHz, DMSO) δ 8.43 (s, 1H), 8.27-8.19 (m, 1H), 7.08-6.92 (m, 2H), 6.63-6.48 (m, 2H), 5.52 (s, 2H), 3.95 (s, 3H), 3.66 (d, J=9.5 Hz, 2H), 3.22-3.17 (m, 2H), 2.19 (t, J=2.1 Hz, 2H), 2.05 (t, J=3.2 Hz, 1H).

Example 8: Preparation of 7-methyl-1-[[3-[(1R,5S,6r)-3-[3-(difluoromethoxy)phenyl]-3-azabicyclo[3.1.0]hexan-6-yl]-1,2,4-oxadiazol-5-yl]methyl]purin-6-one (Example Compound 8)

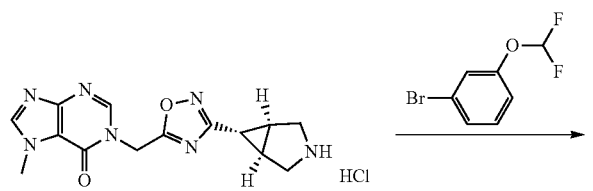
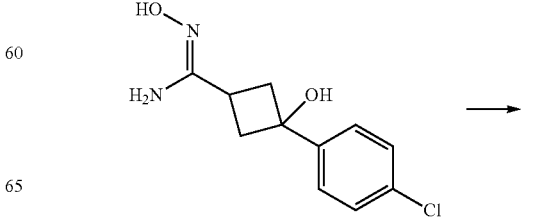

181

-continued

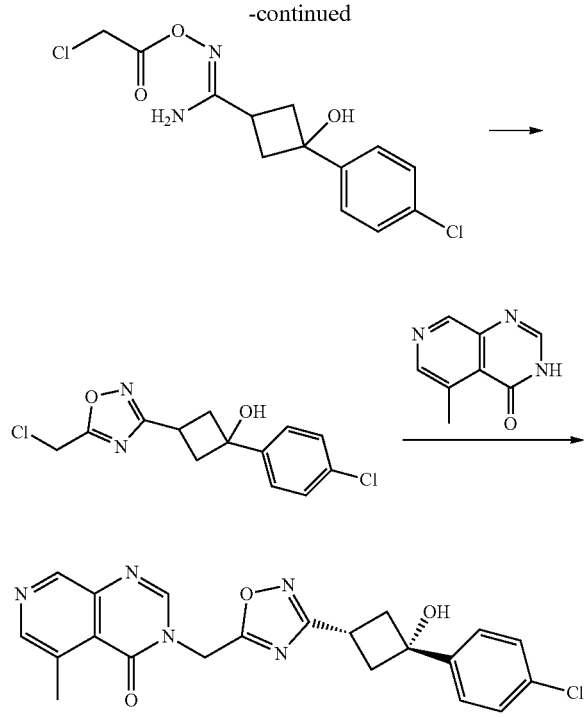

Step 1: Preparation of ethyl 3-(4-chlorophenyl)-3-hydroxycyclobutanecarboxylate

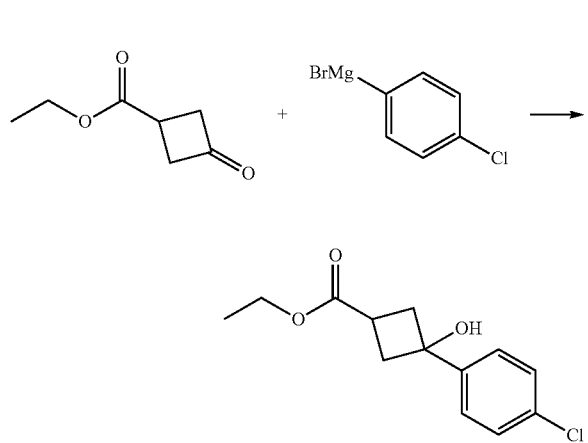

(4-chlorophenyl)magnesium bromide (1M in 2-Me-THF) (14.4 mL, 14.35 mmol) was added dropwise to a solution of ethyl 3-oxocyclobutanecarboxylate (2.00 g, 14.07 mmol) in THF (18 mL) at −78° C. under N₂. The reaction was stirred at −78° C. for 1.5 h. The reaction was quenched with saturated NH₄Cl. The reaction mixture was partitioned in water/iPrOAc and extracted with iPrOAc (3×). The combined organic extracts were washed with water and brine and they were dried over MgSO₄, filtered and concentrated. The crude mixture was adsorbed onto silica and purified by flash column chromatography with 0-50% iPrOAc/heptane to afford the titled compound (1.95 g, 54% yield) as a clear oil.

182

Step 2: Preparation of 3-(4-chlorophenyl)-3-hydroxycyclobutanecarboxamide

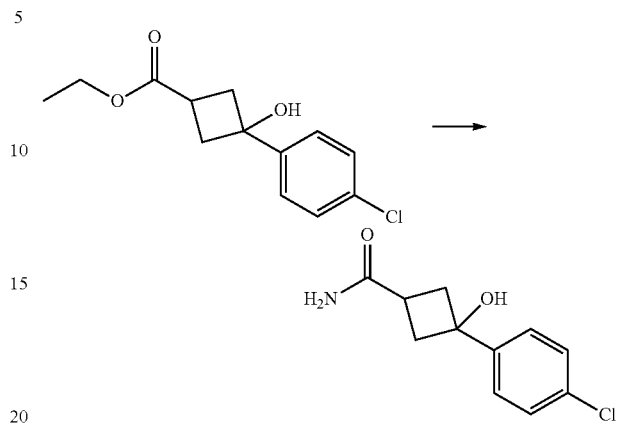

A mixture of ethyl 3-(4-chlorophenyl)-3-hydroxy-cyclobutanecarboxylate (551 mg, 2.16 mmol) in ammonia (7 M) in MeOH (5.4 mL, 37.86 mmol) was stirred at 50° C. overnight. The reaction mixture was concentrated to dryness to afford the title compound (469.4 mg, 96% yield) as a crude white solid.

Step 3: Preparation of 3-(4-chlorophenyl)-3-hydroxycyclobutanecarbonitrile

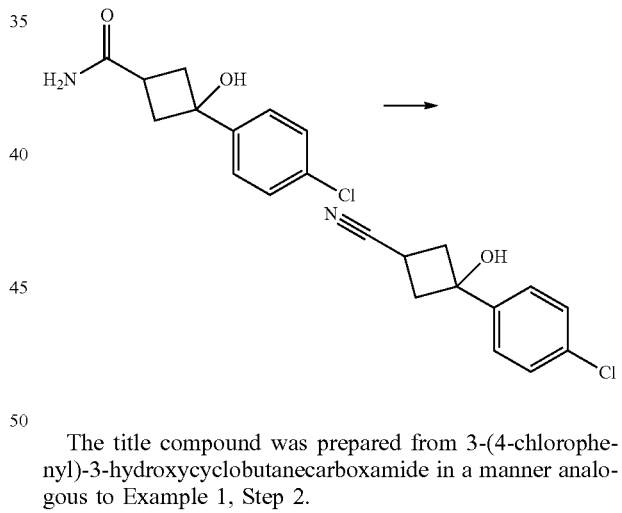

The title compound was prepared from 3-(4-chlorophenyl)-3-hydroxycyclobutanecarboxamide in a manner analogous to Example 1, Step 2.

Step 4: Preparation of 3-(4-chlorophenyl)-N',3-dihydroxycyclobutanecarboximidamide

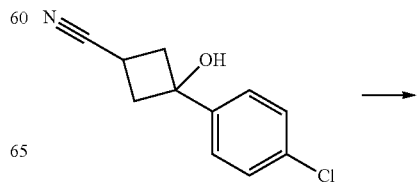

-continued

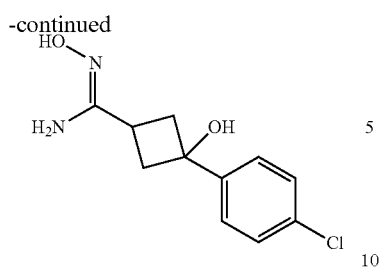

The title compound was prepared from 3-(4-chlorophenyl)-3-hydroxycyclobutanecarbonitrile in a manner analogous to Example 1, Step 3.

Step 5: Preparation of (N'-(2-chloroacetoxy)-3-(4-chlorophenyl)-3-hydroxycyclobutanecarboximidamide

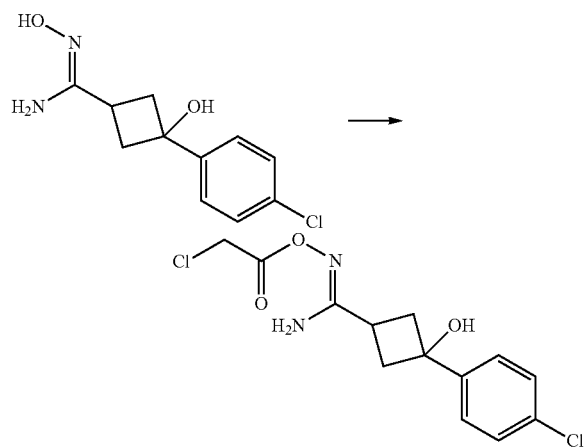

The title compound was prepared from 3-(4-chlorophenyl)-N',3-dihydroxycyclobutanecarboximidamide in a manner analogous to Example 1, Step 4.

Step 6: Preparation of 3-(5-(chloromethyl)-1,2,4-oxadiazol-3-yl)-1-(4-chlorophenyl)cyclobutanol

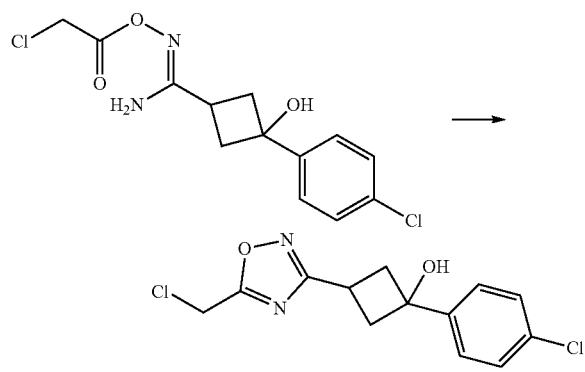

The title compound was prepared from (N'-(2-chloroacetoxy)-3-(4-chlorophenyl)-3-hydroxycyclobutanecarboximidamide in a manner analogous to Example 1, Step 5.

Step 7: Preparation of 3-((3-((1s,3s)-3-(4-chlorophenyl)-3-hydroxycyclobutyl)-1,2,4-oxadiazol-5-yl)methyl)-5-methylpyrido[3,4-d]pyrimidin-4(3H)-one

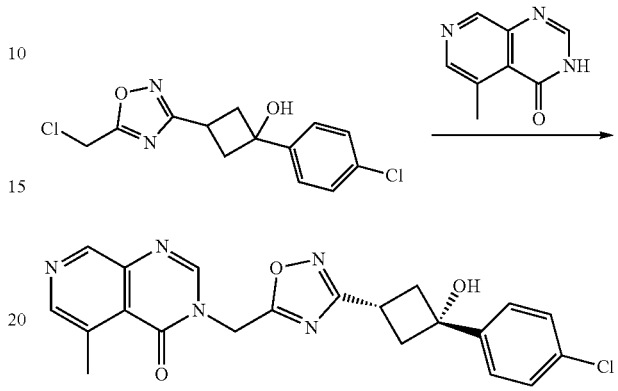

The title compound was prepared from 3-(5-(chloromethyl)-1,2,4-oxadiazol-3-yl)-1-(4-chlorophenyl)cyclobutanol and 5-methylpyrido[3,4-d]pyrimidin-4(3H)-one in a manner analogous to Example 1, Step 6. LCMS [M+H$^+$]: 424.1. 1H NMR (400 MHz, DMSO-d6) δ 8.93 (s, 1H), 8.64 (s, 1H), 8.53 (d, J=1.0 Hz, 1H), 7.62-7.54 (m, 2H), 7.44-7.37 (m, 2H), 5.89 (s, 1H), 5.53 (s, 2H), 3.28-3.18 (m, 1H), 2.84-2.73 (m, 2H), 2.70 (s, 3H), 2.59 (td, J=9.5, 2.6 Hz, 2H).

Example 10: Preparation of 3-((3-((1s,3s)-3-(4-chlorophenyl)-3-hydroxycyclobutyl)-1,2,4-oxadiazol-5-yl)methyl)-5-methylpyrido[2,3-d]pyrimidin-4(3H)-one (Example Compound 10)

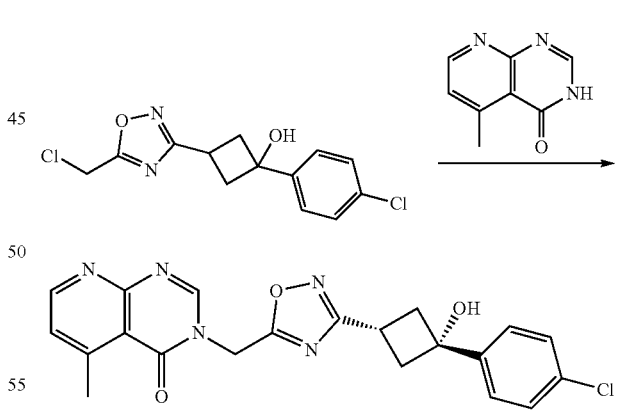

The title compound was prepared from 3-(5-(chloromethyl)-1,2,4-oxadiazol-3-yl)-1-(4-chlorophenyl)cyclobutanol and 5-methylpyrido[2,3-d]pyrimidin-4(3H)-one in a manner analogous to Example 1, Step 6. LCMS [M+H$^+$]: 424.1. 1H NMR (400 MHz, DMSO-d6) δ 8.79 (d, J=4.8 Hz, 1H), 8.72 (s, 1H), 7.62-7.52 (m, 2H), 7.44-7.36 (m, 3H), 5.89 (s, 1H), 5.52 (s, 2H), 3.41-3.17 (m, 1H), 2.84-2.71 (m, 5H), 2.65-2.52 (m, 2H).

Example 11: Preparation of 3-((3-((1s,3s)-3-(4-chlorophenyl)-3-hydroxycyclobutyl)-1,2,4-oxadiazol-5-yl)methyl)pyrido[2,3-d]pyrimidin-4(3H)-one (Example Compound 11)

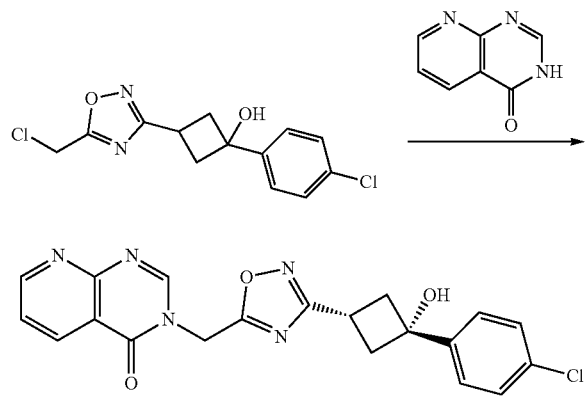

The title compound was prepared from 3-(5-(chloromethyl)-1,2,4-oxadiazol-3-yl)-1-(4-chlorophenyl)cyclobutanol and pyrido[2,3-d]pyrimidin-4(3H)-one in a manner analogous to Example 1, Step 6. LCMS [M+H⁺]: 410.1. 1H NMR (400 MHz, DMSO-d6) δ 9.03 (dd, J=4.6, 2.0 Hz, 1H), 8.78 (s, 1H), 8.57 (dd, J=7.9, 2.0 Hz, 1H), 7.63 (dd, J=7.9, 4.6 Hz, 1H), 7.61-7.54 (m, 2H), 7.43-7.36 (m, 2H), 5.89 (s, 1H), 5.58 (s, 2H), 3.30-3.17 (m, 1H), 2.84-2.71 (m, 2H), 2.64-2.53 (m, 2H).

Example 12: Preparation of 7-methyl-1-[[3-[(1R,5S,6 r)-3-[4-(difluoromethoxy)phenyl]-3-azabicyclo[3.1.0]hexan-6-yl]-1,2,4-oxadiazol-5-yl]methyl]purin-6-one (Example Compound 12)

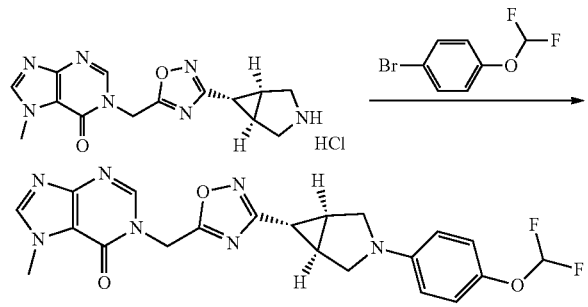

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-4-(difluoromethoxy)benzene (85.7 mg, 0.384 mmol) as a white crystalline solid (23.6 mg, 16% yield), in a manner analogous to Example 4, Step 8. LCMS [M+H⁺] 456.1. 1H NMR (400 MHz, DMSO) δ 8.43 (s, 1H), 8.23 (s, 1H), 7.00 (d, J=8.9 Hz, 2H), 6.97 (t, J=75.1 Hz, 1H), 6.58 (d, J=9.1 Hz, 2H), 5.52 (s, 2H), 3.95 (s, 3H), 3.66 (d, J=9.6 Hz, 2H), 3.26-3.19 (m, 2H), 2.20 (s, 2H), 2.03 (t, J=3.2 Hz, 1H).

Example 13: Preparation of 7-methyl-1-[[3-[(1R,5S,6 r)-3-(3-methoxyphenyl)-3-azabicyclo[3.1.0]hexan-6-yl]-1,2,4-oxadiazol-5-yl]methyl]purin-6-one (Example Compound 13)

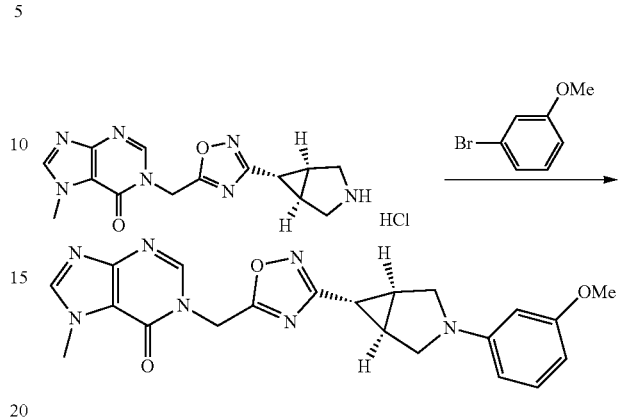

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (84.0 mg, 0.240 mmol) and 3-bromoanisole (53.9 mg, 0.288 mmol) as a white crystalline solid (11.8 mg, 12% yield), in a manner analogous to Example 4, Step 8. LCMS [M+H⁺] 420.1. 1H NMR (400 MHz, DMSO) δ 8.43 (s, 1H), 8.23 (s, 1H), 7.04 (t, J=8.1 Hz, 1H), 6.24 (dd, J=8.1, 2.1 Hz, 1H), 6.17 (dd, J=8.2, 1.8 Hz, 1H), 6.09 (t, J=2.2 Hz, 1H), 5.52 (s, 2H), 3.95 (s, 3H), 3.69 (s, 3H), 3.66 (d, J=9.7 Hz, 2H), 3.26-3.21 (m, 2H), 2.19 (s, 2H), 2.00 (t, J=3.2 Hz, 1H).

Examples 14 and 15: Preparation of 5-methyl-3-[[3-[rac-(1S,1aS,6aR)-1,1a,6,6a-tetrahydrocyclopropa[a]inden-1-yl]-1,2,4-oxadiazol-5-yl]methyl]pyrido[2,3-d]pyrimidin-4-one and 5-methyl-3-[[3-[rac-(1R,1 aR,6aS)-1,1a,6,6a-tetrahydrocyclopropa[a]inden-1-yl]-1,2,4-oxadiazol-5-yl]methyl]pyrido[2,3-d]pyrimidin-4-one (Example Compounds 14 and 15)

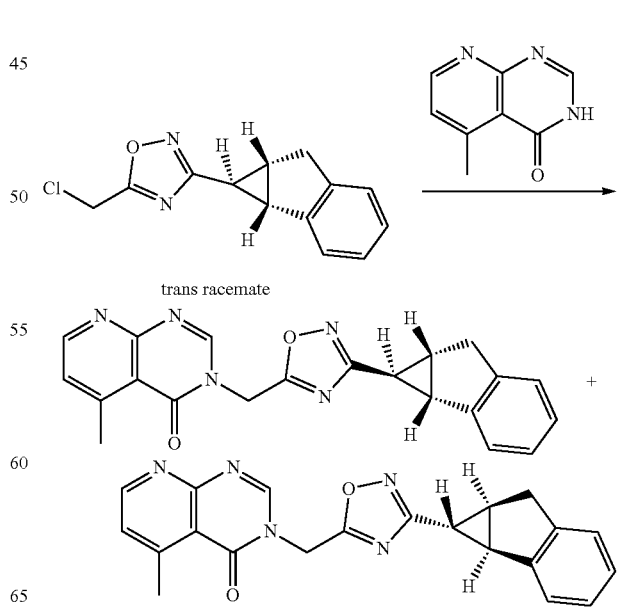

The title compounds were prepared from 3-[1H,1aH,2H, 6bH-cyclopropa[a]inden-1-yl]-5-(chloromethyl)-1,2,4-oxadiazole and 5-methyl-3H,4H-pyrido[2,3-d]pyrimidin-4-one (trans racemate) in a manner analogous to Examples 2 and 3, Step 8. The stereochemistry for the final products was arbitrarily assigned.

Example 14, enantiomer 2: white solid; Rt=6.12 min, (CHIRALPAK IG-3 Size: 0.46*10 cm; 3 μm, mobile phase: MtBE (0.1% DEA):EtOH=70:30, 1.0 ml/min); LCMS [M+H+]372; $^1$H NMR (400 MHz, DMSO-$d_6$) δ 8.79 (d, J 4.8 Hz, 1H), 8.70 (s, 1H), 7.41 (d, J 5.2 Hz, 1H), 7.39-7.37 (m, 1H), 7.23-7.21 (m, 1H), 7.16-7.12 (m, 2H), 5.49 (s, 2H), 3.27-3.23 (m, 1H), 3.12-3.08 (m, 1H), 2.90-2.88 (m, 1H), 2.77 (s, 3H), 2.40-2.36 (m, 1H), 1.60 (t, J 2.8 Hz, 1H).

Example 15, enantiomer 1: white solid; Rt=3.34 min (CHIRALPAK IG-3 Size: 0.46*10 cm; 3 μm, Mobile phase: MtBE (0.1% DEA):EtOH=70:30, 1.0 ml/min); LCMS [M+H+]372; $^1$H NMR (400 MHz, DMSO-$d_6$) δ 8.79 (d, J 4.8 Hz, 1H), 8.70 (s, 1H), 7.41 (d, J 5.2 Hz, 1H), 7.39-7.37 (m, 1H), 7.23-7.21 (m, 1H), 7.14-7.12 (m, 2H), 5.49 (s, 2H), 3.27-3.23 (m, 1H), 3.12-3.08 (m, 1H), 2.90-2.89 (m, 1H), 2.77 (s, 3H), 2.40-2.36 (m, 1H), 1.60 (t, J 3.2 Hz, 1H).

Example 16: Preparation of 7-methyl-1-[[3-[(1R, 5S,6 r)-3-(3-fluorophenyl)-3-azabicyclo[3.1.0] hexan-6-yl]-1,2,4-oxadiazol-5-yl]methyl]purin-6-one (Example Compound 16)

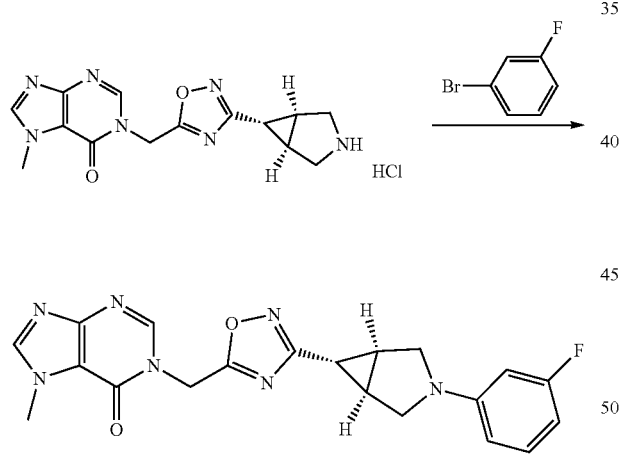

The title compound was prepared from 1-((3-((1R,5S,6r)-3-azabicyclo[3.1.0]hexan-6-yl)-1,2,4-oxadiazol-5-yl) methyl)-7-methyl-1,7-dihydro-6H-purin-6-one hydrochloride (112 mg, 0.320 mmol) and 1-bromo-3-fluorobenzene (67.2 mg, 0.384 mmol) as a white crystalline solid (27.7 mg, 21% yield), in a manner analogous to Example 4, Step 8. LCMS [M+H+] 408.1. $^1$H NMR (400 MHz, DMSO) δ 8.43 (s, 1H), 8.23 (s, 1H), 7.15 (q, J=7.9 Hz, 1H), 6.46-6.30 (m, 3H), 5.52 (s, 2H), 3.95 (s, 3H), 3.66 (d, J=9.8 Hz, 2H), 3.29 (d, J=3.2 Hz, 2H), 2.20 (s, 2H), 2.01 (t, J=3.2 Hz, 1H).

Example 17: Preparation of 3-((3-((trans)-3-(4-chlorophenyl)cyclobutyl)-1,2,4-oxadiazol-5-yl)methyl)-5-methylpyrido[2,3-d]pyrimidin-4(3H)-one (Example Compound 17)

The overall Example 17 reaction scheme is as follows:

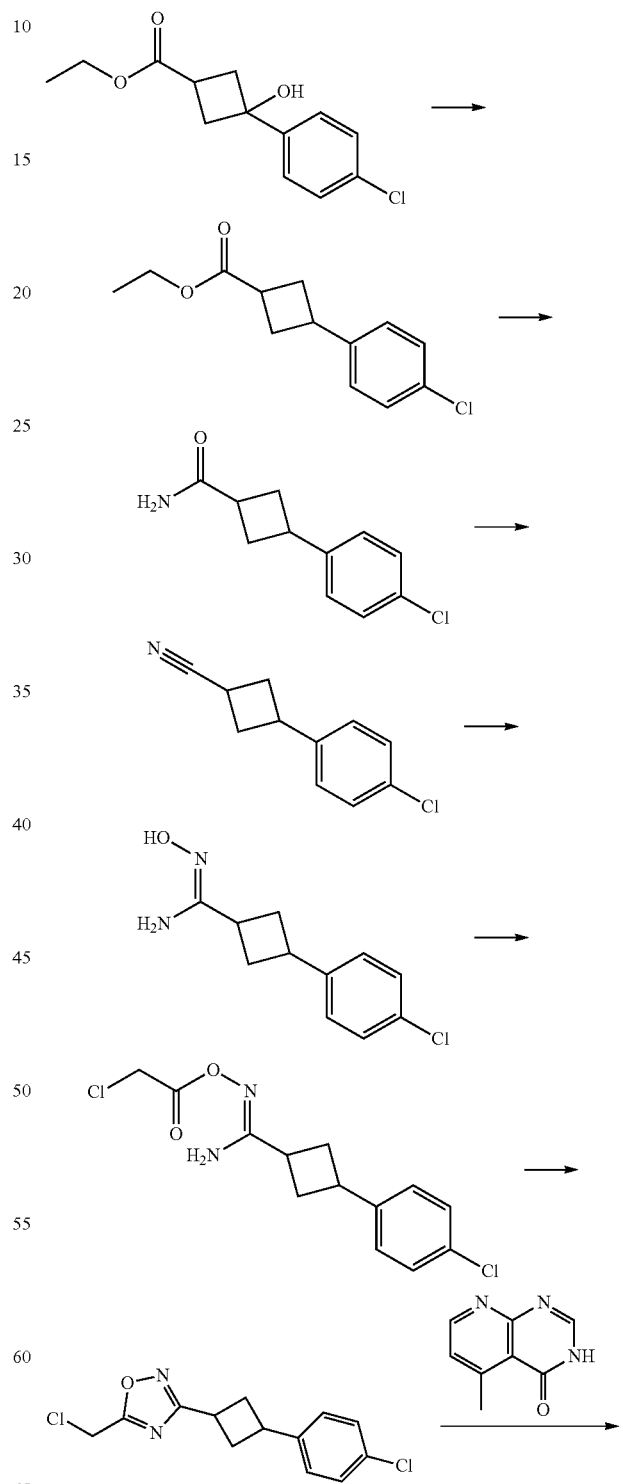

-continued

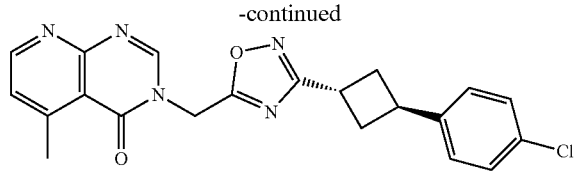

Step 1: Preparation of ethyl 3-(4-chlorophenyl)cyclobutanecarboxylate

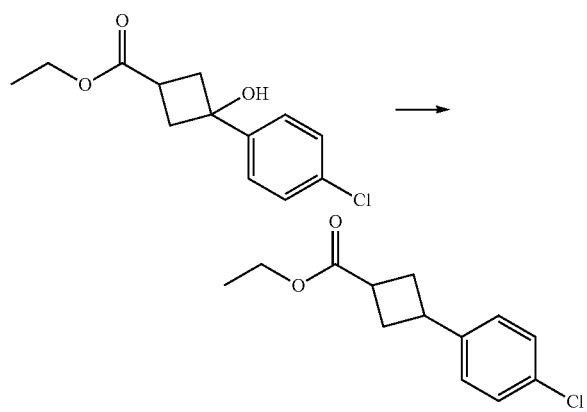

Triethylsilane (4.6 mL, 28.00 mmol) was added to a solution of ethyl 3-(4-chlorophenyl)-3-hydroxy-cyclobutanecarboxylate (1.20 g, 4.7 mmol) in TFA (6.7 mL) at 0° C. The reaction was stirred at room temperature overnight. The reaction was concentrated on the rotavap and the residue was taken up in iPrOAc/sat. NaHCO$_3$. The aqueous layer was extracted with iPrOAc (3×). The organics were washed with brine, dried with MgSO$_4$, filtered and concentrated. The crude mixture was adsorbed onto silica and purified by flash column chromatography with 0-40% iPrOAc/Heptane to afford the titled compound (1.03 g, 92% Yield) as a clear oil.

Step 2: Preparation of 3-(4-chlorophenyl)cyclobutanecarboxamide

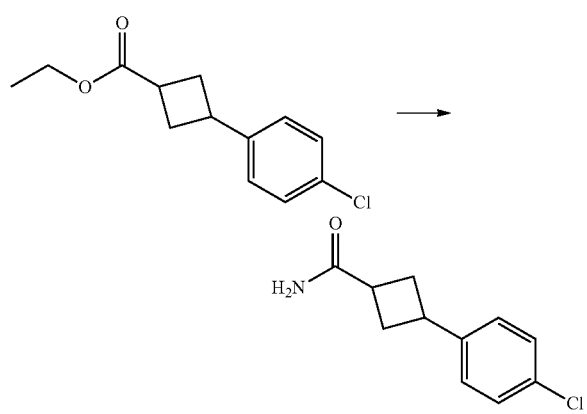

The title compound was prepared from ethyl 3-(4-chlorophenyl)cyclobutanecarboxylate in a manner analogous to Example 9, Step 2.

Step 3: Preparation of 3-(4-chlorophenyl)cyclobutanecarbonitrile

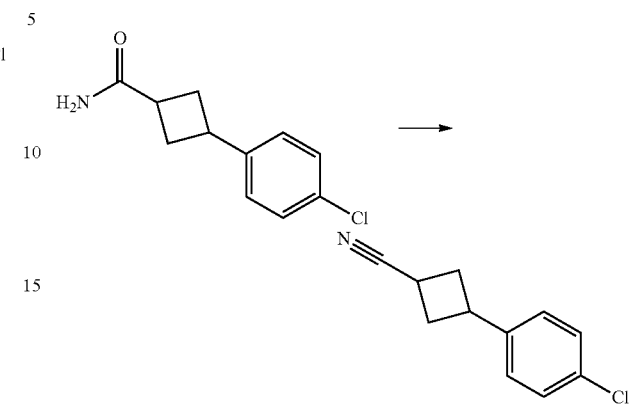

The title compound was prepared from 3-(4-chlorophenyl)cyclobutanecarboxamide in a manner analogous to Example 1, Step 2.

Step 4: Preparation of 3-(4-chlorophenyl)-N'-hydroxycyclobutanecarboximidamide

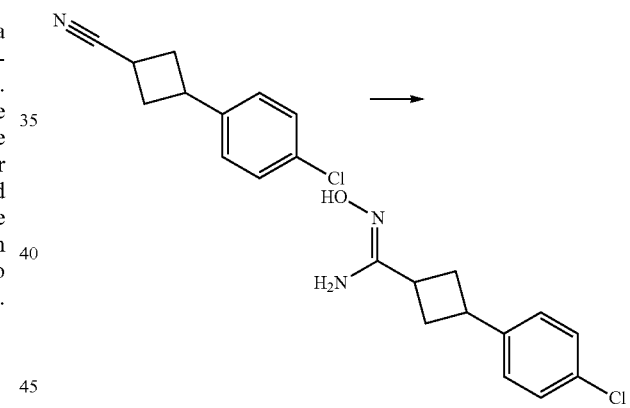

The title compound was prepared from 3-(4-chlorophenyl)cyclobutanecarbonitrile in a manner analogous to Example 1, Step 3.

Step 5: Preparation of N'-(2-chloroacetoxy)-3-(4-chlorophenyl)cyclobutanecarboximidamide

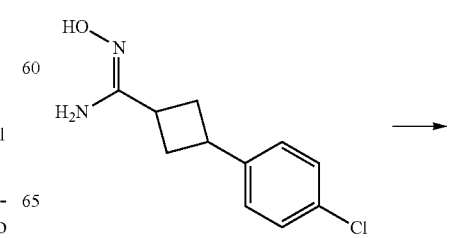

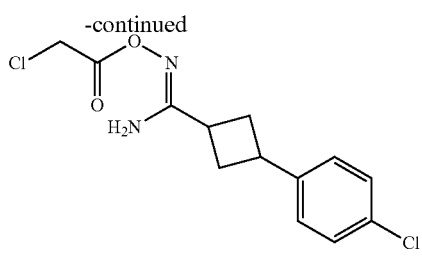

The title compound was prepared from 3-(4-chlorophenyl)-N'-hydroxycyclobutanecarboximidamide in a manner analogous to Example 1, Step 4.

Step 6: Preparation of 5-(chloromethyl)-3-(3-(4-chlorophenyl)cyclobutyl)-1,2,4-oxadiazole

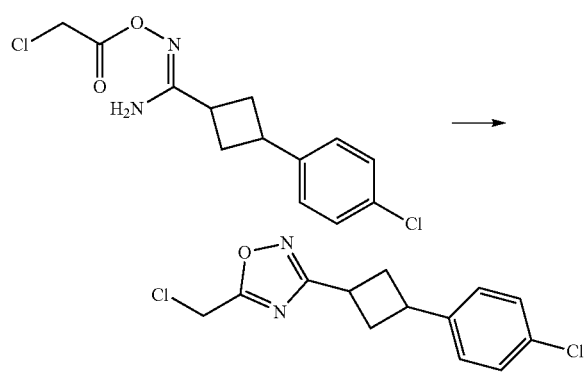

The title compound was prepared from N'-(2-chloroacetoxy)-3-(4-chlorophenyl)cyclobutanecarboximidamide in a manner analogous to Example 1, Step 5.

Step 7: Preparation of 3-((3-((trans)-3-(4-chlorophenyl)cyclobutyl)-1,2,4-oxadiazol-5-yl)methyl)-5-methylpyrido[2,3-d]pyrimidin-4(3H)-one

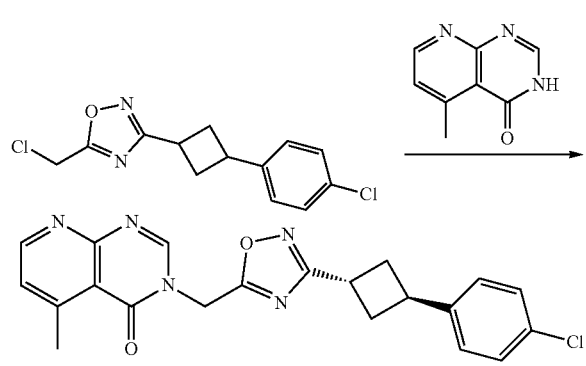

The title compound was prepared from 5-(chloromethyl)-3-(3-(4-chlorophenyl)cyclobutyl)-1,2,4-oxadiazole and 5-methylpyrido[2,3-d]pyrimidin-4(3H)-one in a manner analogous to Example 1, Step 6. LCMS [M+H⁺]: 408.1. 1H NMR (400 MHz, DMSO-d6) δ 8.79 (d, J=4.8 Hz, 1H), 8.73 (s, 1H), 7.41 (d, J=4.7 Hz, 1H), 7.39-7.31 (m, 4H), 5.55 (s, 2H), 3.73 (p, J=8.7 Hz, 1H), 3.68-3.59 (m, 1H), 2.77 (s, 3H), 2.64-2.50 (m, 4H).

Example 18: Preparation of 7-methyl-1-[[3-[(1R,5S,6r)-3-(3-pyridyl)-3-azabicyclo[3.1.0]hexan-6-yl]-1,2,4-oxadiazol-5-yl]methyl]purin-6-one (Example Compound 18)

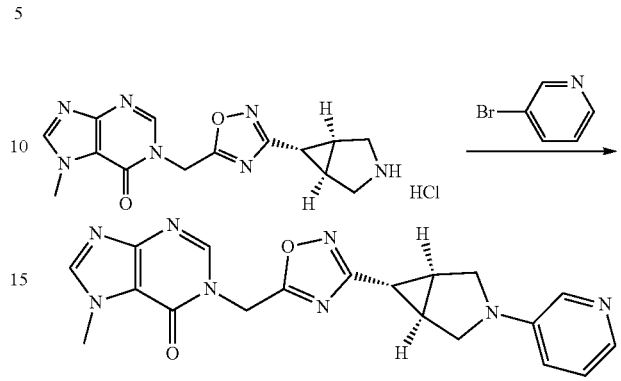

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (84.0 mg, 0.240 mmol) and 3-bromopyridine (45.5 mg, 0.288 mmol) as a white crystalline solid (33.0 mg, 35% yield), in a manner analogous to Example 4, Step 8. LCMS [M+H⁺] 391.1. ¹H NMR (400 MHz, DMSO) δ 8.43 (s, 1H), 8.27-8.19 (m, 1H), 7.95 (d, J=2.8 Hz, 1H), 7.88 (dd, J=4.6, 1.2 Hz, 1H), 7.15 (dd, J=8.3, 4.5 Hz, 1H), 6.93 (ddd, J=8.5, 2.9, 1.3 Hz, 1H), 5.52 (s, 2H), 3.95 (s, 3H), 3.72 (d, J=9.7 Hz, 2H), 3.31-3.24 (m, 2H), 2.27-2.18 (m, 2H), 2.04 (t, J=3.3 Hz, 1H).

Examples 19 and 20: Preparation of 5-methyl-3-[[3-[rac-(1R,1aR,6aS)-1,1a,6,6a-tetrahydrocyclopropa[a]inden-1-yl]-1,2,4-oxadiazol-5-yl]methyl]pyrido[3,4-d]pyrimidin-4-one and 5-methyl-3-[[3-[rac-(1S,1aS,6aR)-1,1a,6,6a-tetrahydrocyclopropa[a]inden-1-yl]-1,2,4-oxadiazol-5-yl]methyl]pyrido[3,4-d]pyrimidin-4-one (Example Compounds 19 and 20)

The overall reaction scheme is as follows:

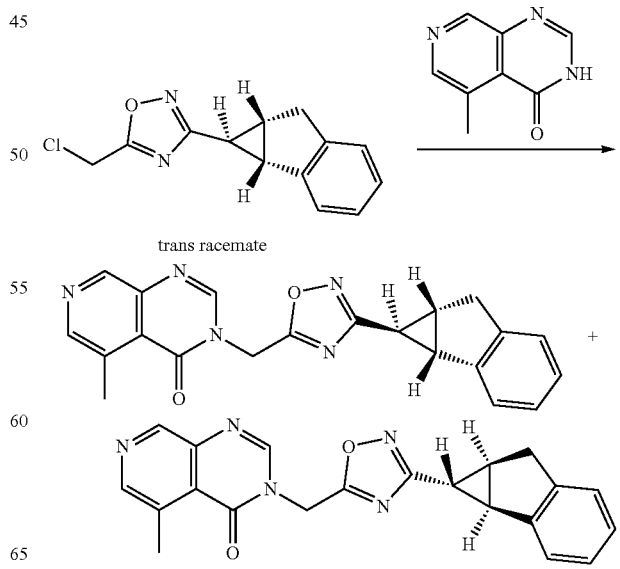

The title compounds were prepared from 3-1H,1aH,2H,6bH-cyclopropa[a]inden-1-yl-5-(chloromethyl)-1,2,4-oxadiazole (trans racemate) and 5-methylpyrido[3,4-d]pyrimidin-4(3H)-one in a manner analogous to Examples 2 and 3, Step 8. The stereochemistry for the final products was arbitrarily assigned.

Example 19, enantiomer 1: white solid; Rt=3.34 min (CHIRALPAK IG-3, Size: 0.46*10 cm; 3 μm, mobile phase: MtBE (0.1% DEA):EtOH=70:30, 1.0 ml/min); LCMS [M+H$^+$]372; $^1$H NMR (300 MHz, DMSO-d$_6$) δ 8.92 (s, 1H), 8.61 (s, 1H), 8.52 (s, 1H), 7.39-7.36 (m, 1H), 7.21-7.20 (m, 1H), 7.14-7.12 (m, 2H), 5.50 (s, 2H), 3.28-3.22 (m, 1H), 3.12-3.07 (m, 1H), 2.90-2.88 (m, 1H), 2.70 (s, 3H), 2.40-2.37 (m, 1H), 1.59 (s, 1H).

Example 20, enantiomer 2: white solid; Rt=4.71 min (CHIRALPAK IG-3, Size: 0.46*10 cm; 3 μm, mobile phase: MtBE (0.1% DEA):EtOH=70:30, 1.0 ml/min); LCMS [M+H$^+$]372; $^1$H NMR (300 MHz, DMSO-d$_6$) δ 8.92 (s, 1H), 8.61 (s, 1H), 8.52 (s, 1H), 7.39-7.36 (m, 1H), 7.23-7.20 (m, 1H), 7.16-7.11 (m, 2H), 5.50 (s, 2H), 3.28-3.22 (m, 1H), 3.12-3.06 (m, 1H), 2.90-2.88 (m, 1H), 2.70 (s, 3H), 2.40-2.36 (m, 1H), 1.59 (t, J=3.0 Hz, 1H).

Example 21: Preparation of 1-((3-((trans)-3-(4-chlorophenyl)cyclobutyl)-1,2,4-oxadiazol-5-yl)methyl)-7-methyl-1H-purin-6(7H)-one (Example Compound 21)

The overall Example 21 reaction scheme is as follows:

Step 1: Preparation of 1-((3-((trans)-3-(4-chlorophenyl)cyclobutyl)-1,2,4-oxadiazol-5-yl)methyl)-7-methyl-1H-purin-6(7H)-one The title compound was prepared from 5-(chloromethyl)-3-(3-(4-chlorophenyl)cyclobutyl)-1,2,4-oxadiazole and 7-methyl-1H-purin-6(7H)-one in a manner analogous to Example 1, Step 6. LCMS [M+H$^+$]: 397.1. 1H NMR (400 MHz, DMSO-d6) δ 8.47 (s, 1H), 8.24 (s, 1H), 7.41-7.30 (m, 4H), 5.58 (s, 2H), 3.96 (s, 3H), 3.73 (p, J=8.8 Hz, 1H), 3.68-3.58 (m, 1H), 2.64-2.50 (m, 4H).

Example 22: Preparation of 6-methyl-7-oxo-1-[[3-[(1R,5S,6s)-3-phenyl-3-azabicyclo[3.1.0]hexan-6-yl]-1,2,4-oxadiazol-5-yl]methyl]pyrazolo[4,3-d]pyrimidine-3-carbonitrile (Example Compound 22)

The overall Example 22 reaction scheme is as follows:

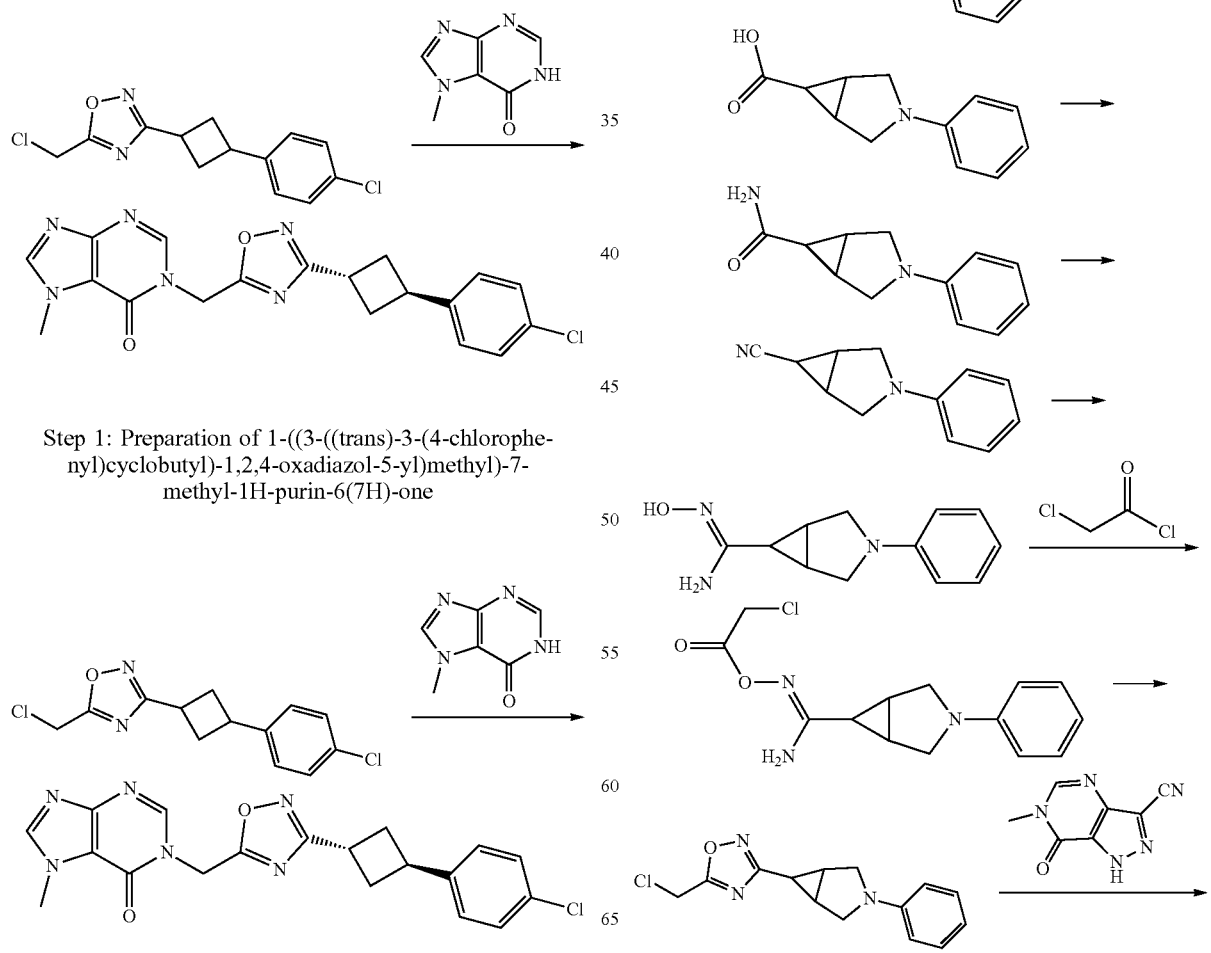

-continued

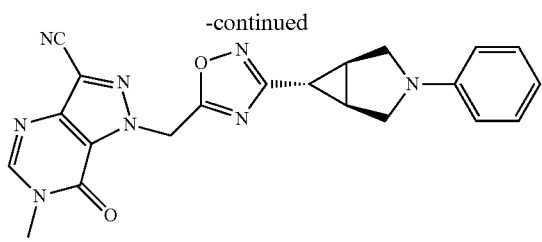

Step 1: Preparation of (1R,5S,6r)-ethyl 3-phenyl-3-aza-bicyclo[3.1.0]hexane-6-carboxylate

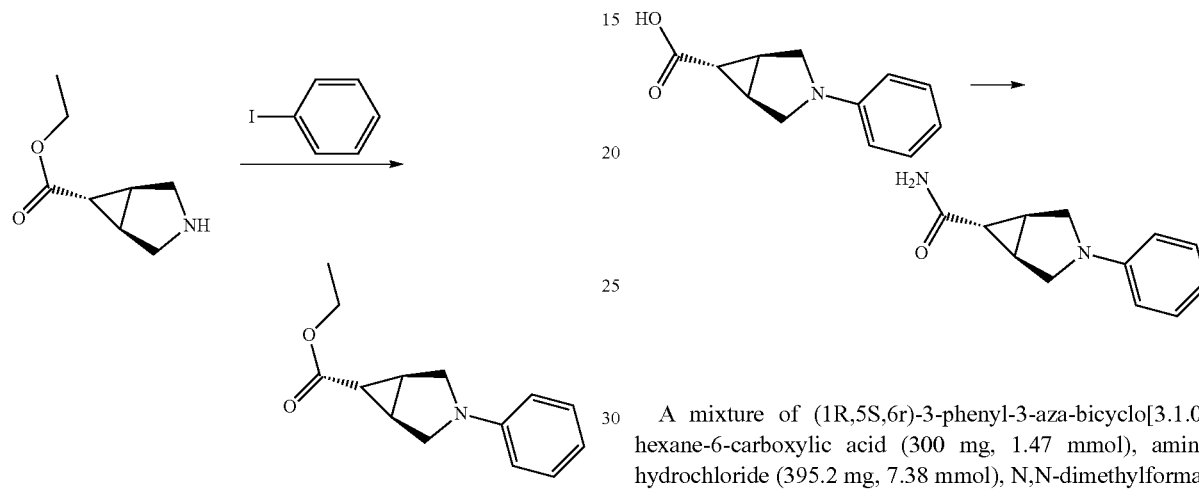

A mixture of (1R,5S,6r)-ethyl 3-aza-bicyclo[3.1.0]hexane-6-carboxylate (1 g, 5.21 mmol), iodobenzene (1.1 g, 5.39 mmol), Cs$_2$CO$_3$ (5 g, 15.34 mmol), Pd$_2$(dba)$_3$ (500 mg, 0.54 mmol), Sphos (650 mg, 1.58 mmol), and toluene (10 mL) was stirred for 2 h at 100° C. under nitrogen. The solids were filtered out. The resulting solution was purified on a C18 silica gel column eluting with CH$_3$CN/H$_2$O (10 mmol/L NH$_4$HCO$_3$, 5% to 95%, over 30 min). This resulted in the title compound (1.2 g, 99%) as a brown solid. LCMS [M+H$^+$] 232.

Step 2: Preparation of (1R,5S,6r)-3-phenyl-3-aza-bicyclo[3.1.0]hexane-6-carboxylic Acid

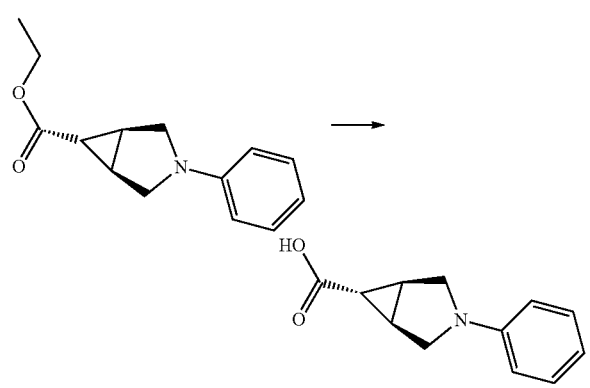

A mixture of (1R,5S,6r)-ethyl 3-phenyl-3-aza-bicyclo[3.1.0]hexane-6-carboxylate (1.2 g, 5.18 mmol), methanol (20 mL), water (4 mL), and lithium hydroxide (248.5 mg, 10.37 mmol) was stirred for 3 h at room temperature. The pH value of the solution was adjusted to 4 with diluted aqueous HCl. The resulting mixture was extracted with ethyl acetate and concentrated under vacuum. This resulted in the title compound (310 mg, 29%) as a brown solid. LCMS [M+H$^+$] 204.

Step 3: Preparation of (1R,5S,6r)-3-phenyl-3-aza-bicyclo[3.1.0]hexane-6-carboxamide

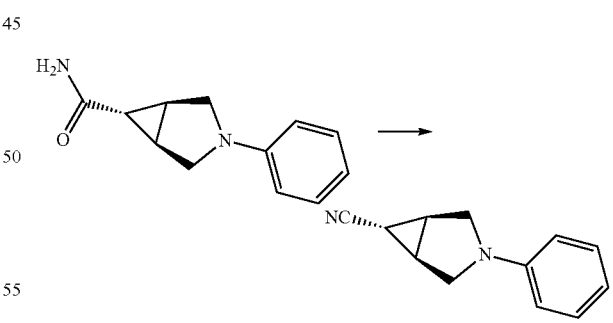

A mixture of (1R,5S,6r)-3-phenyl-3-aza-bicyclo[3.1.0]hexane-6-carboxylic acid (300 mg, 1.47 mmol), amine hydrochloride (395.2 mg, 7.38 mmol), N,N-dimethylformamide (5 mL), HATU (844.1 mg, 2.22 mmol), and DIEA (1.3 g, 10.05 mmol) was stirred for 3 h at room temperature. The resulting solution was purified on a C18 silica gel column eluting with CH$_3$CN/H$_2$O (10 mmol/L NH$_4$HCO$_3$, 5% to 95%, over 30 min). This resulted in the title compound (300 mg, crude) as a brown solid. LCMS [M+H$^+$] 203.

Step 4: Preparation of (1R,5S,6r)-3-phenyl-3-aza-bicyclo[3.1.0]hexane-6-carboxamide TFAA (625.8 mg, 2.98 mmol) was added dropwise to a solution of (1R,5S,6r)-3-phenyl-3-aza-bicyclo[3.1.0]hexane-6-carboxamide (300 mg, 1.48 mmol), dichloromethane (15 mL), and triethylamine (600 mg, 5.92 mmol) at 0° C. The resulting solution was stirred for 3 h at room temperature, quenched with water, extracted with dichloromethane, and concentrated under vacuum. This resulted in the title compound (280 mg, crude) as a brown solid. LCMS [M+H$^+$] 185.

Step 5: Preparation of (1R,5S,6r,Z)—N'-hydroxy-3-phenyl-3-aza-bicyclo[3.1.0]hexane-6-carboximidamide

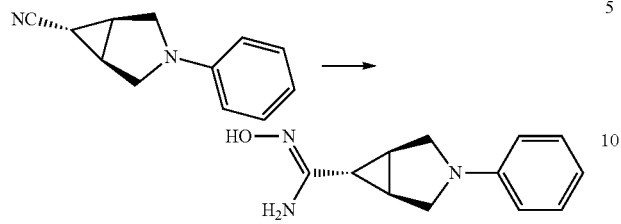

A mixture of (1R,5S,6r)-3-phenyl-3-aza-bicyclo[3.1.0]hexane-6-carboxamide (100 mg, 0.54 mmol), methanol (3 mL), sodium bicarbonate (228.3 mg, 2.71 mmol), and NH$_2$OH.HCl (112.6 mg, 1.62 mmol) was stirred for 3 h at 60° C. The resulting mixture was diluted with water, extracted with ethyl acetate, and concentrated under vacuum. This resulted in the title compound (140 mg, crude) as a light yellow solid. LCMS [M+H$^+$] 218.

Step 6: Preparation of (1R,5S,6r,Z)—N'-(2-chloroacetoxy)-3-phenyl-3-aza-bicyclo[3.1.0]hexane-6-carboximidamide

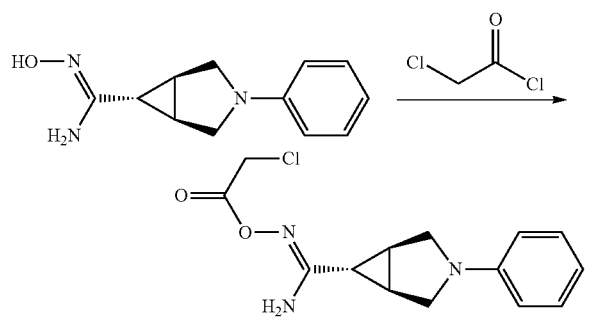

2-Chloroacetyl chloride (80.5 mg, 0.71 mmol) was added dropwise to a solution of (1R,5S,6r,Z)—N'-hydroxy-3-phenyl-3-aza-bicyclo[3.1.0]hexane-6-carboximidamide (130 mg, 0.59 mmol) in acetone (5 mL) at 0° C. The resulting solution was stirred for 3 h at room temperature and concentrated under vacuum. This resulted in the title compound (150 mg, 85%) as brown oil. LCMS [M+H$^+$] 294.

Step 7: Preparation of 5-(chloromethyl)-3-((1R,5S,6r)-3-phenyl-3-aza-bicyclo[3.1.0]hexan-6-yl)-1,2,4-oxadiazole

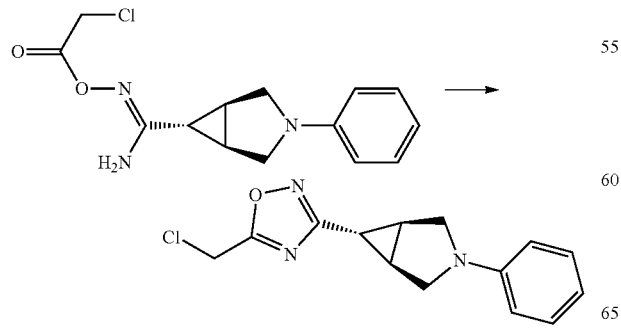

A solution of (1R,5S,6r,Z)—N'-(2-chloroacetoxy)-3-phenyl-3-aza-bicyclo[3.1.0]hexane-6-carboximidamide (150 mg, 0.51 mmol) in toluene (10 mL) was stirred for 2 h at 120° C. in an oil bath. The resulting mixture was concentrated under vacuum. This resulted in the title compound (150 mg, crude) as brown oil. LCMS [M+H$^+$] 276.

Step 8: Preparation of 6-methyl-7-oxo-1-[[3-[(1R,5S,6s)-3-phenyl-3-azabicyclo[3.1.0]hexan-6-yl]-1,2,4-oxadiazol-5-yl]methyl]pyrazolo[4,3-d]pyrimidine-3-carbonitrile

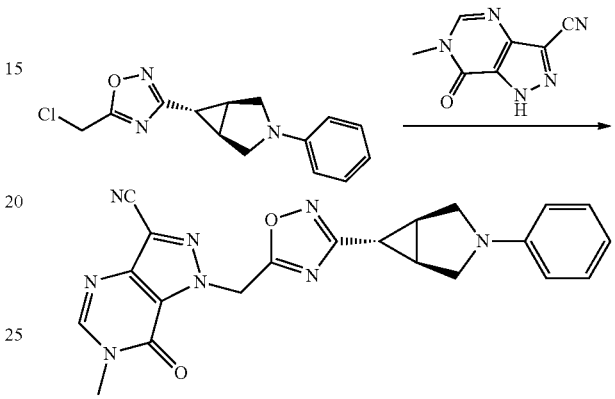

A mixture of 5-(chloromethyl)-3-((1R,5S,6r)-3-phenyl-3-aza-bicyclo[3.1.0]hexan-6-yl)-1,2,4-oxadiazole (114.5 mg, 0.65 mmol), TBAI (20.11 mg, 0.05 mmol), potassium carbonate (227.3 mg, 1.64 mmol), and N,N-dimethylformamide (2 mL) was stirred for 5 h at room temperature. The solids were filtered out. The resulting solution was purified on a C18 silica gel column eluting with CH$_3$CN/H$_2$O (10 mmol/L NH$_4$HCO$_3$, 5% to 95%, over 30 min). This resulted in the title compound (45.1 mg, 20%) as a yellow solid. LCMS [M+H$^+$] 415; $^1$H NMR (300 MHz, CDCl$_3$) δ 8.03 (s, 1H), 7.25-7.20 (m, 2H), 6.73 (t, J=7.2 Hz, 1H), 6.60 (d, J=7.8 Hz, 2H), 6.08 (s, 2H), 3.73 (d, J=9.3 Hz, 2H), 3.64 (s, 3H), 3.34-3.31 (m, 2H), 2.24-2.23 (m, 2H), 2.16-2.14 (m, 1H).

Example 23: Preparation of 1-((3-(((1s,3s)-3-(4-chlorophenyl)-3-fluorocyclobutyl)-1,2,4-oxadiazol-5-yl)methyl)-7-methyl-1H-purin-6(7H)-one (Example Compound 23)

The overall Example 23 reaction scheme is as follows:

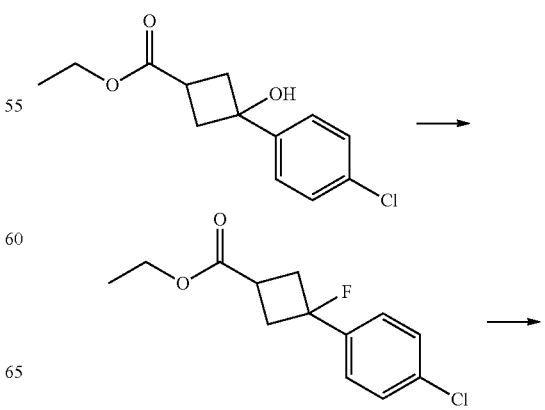

-continued

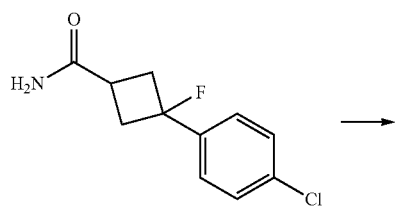

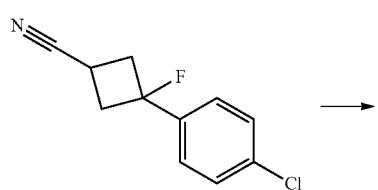

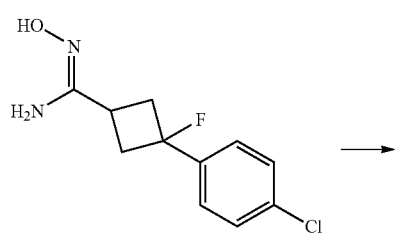

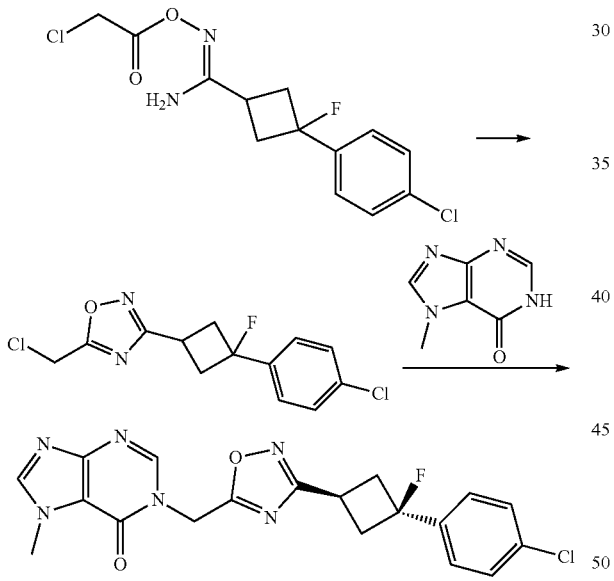

Step 1: Preparation of ethyl
3-(4-chlorophenyl)-3-fluorocyclobutanecarboxylate

-continued

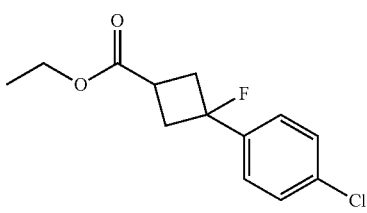

Deoxo-Fluor (830 µL, 4.27 mmol) was added to a solution of ethyl 3-(4-chlorophenyl)-3-hydroxy-cyclobutanecarboxylate (989 mg, 3.883 mmol) in DCM (39 mL) at 0° C. under $N_2$. The reaction was allowed to warm-up to room temperature over 3 h. The reaction mixture was partitioned in saturated $NaHCO_3$/DCM and extracted with DCM (3×). The combined organic extracts were washed with brine, dried over $MgSO_4$, filtered and concentrated. The crude mixture was adsorbed onto silica and purified by flash column chromatography with 0-30% iPrOAc/Heptane to afford the titled compound (919.4 mg, 92% yield) as a clear residue.

Step 2: Preparation of
3-(4-chlorophenyl)-3-fluorocyclobutanecarboxamide

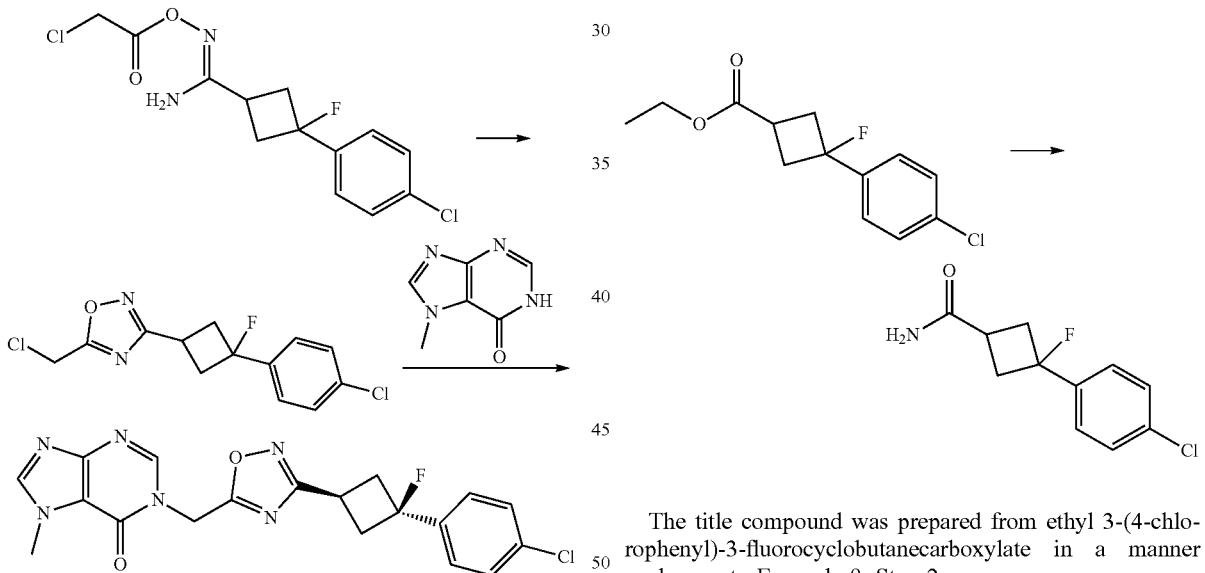

The title compound was prepared from ethyl 3-(4-chlorophenyl)-3-fluorocyclobutanecarboxylate in a manner analogous to Example 9, Step 2.

Step 3: Preparation of
3-(4-chlorophenyl)-3-fluorocyclobutanecarbonitrile

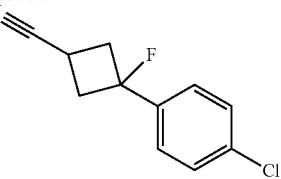

The title compound was prepared from 3-(4-chlorophenyl)-3-fluorocyclobutanecarboxamide in a manner analogous to Example 1, Step 2.

Step 4: Preparation of 3-(4-chlorophenyl)-3-fluoro-N'-hydroxycyclobutanecarboximidamide

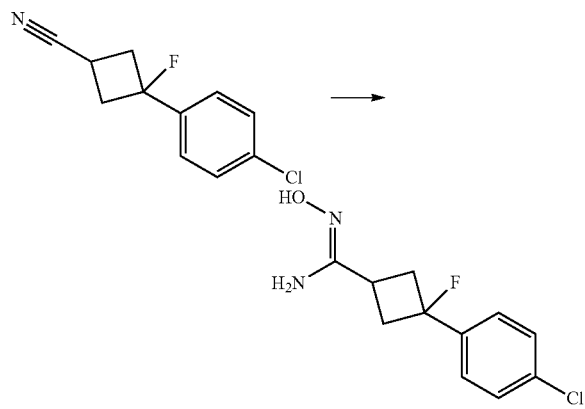

The title compound was prepared from 3-(4-chlorophenyl)-3-fluorocyclobutanecarbonitrile in a manner analogous to Example 1, Step 3.

Step 5: Preparation of N'-(2-chloroacetoxy)-3-(4-chlorophenyl)-3-fluorocyclobutanecarboximidamide

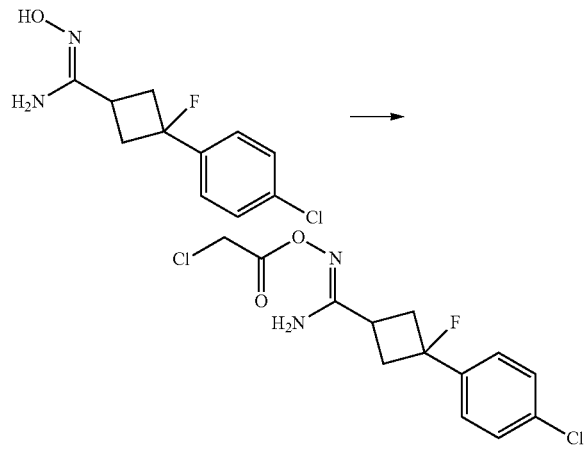

The title compound was prepared from 3-(4-chlorophenyl)-3-fluoro-N'-hydroxycyclobutanecarboximidamide in a manner analogous to Example 1, Step 4.

Step 6: Preparation of 5-(chloromethyl)-3-(3-(4-chlorophenyl)-3-fluorocyclobutyl)-1,2,4-oxadiazole

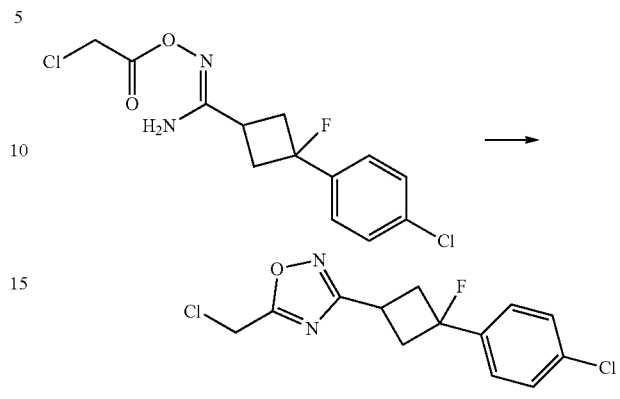

The title compound was prepared from N'-(2-chloroacetoxy)-3-(4-chlorophenyl)-3-fluorocyclobutanecarboximidamide in a manner analogous to Example 1, Step 5.

Step 7: Preparation of 1-((3-((1s,3s)-3-(4-chlorophenyl)-3-fluorocyclobutyl)-1,2,4-oxadiazol-5-yl)methyl)-7-methyl-1H-purin-6(7H)-one

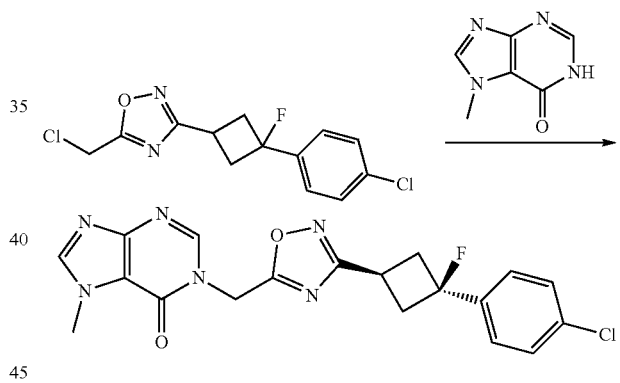

The title compound was prepared from 5-(chloromethyl)-3-(3-(4-chlorophenyl)-3-fluorocyclobutyl)-1,2,4-oxadiazole and 7-methyl-1H-purin-6(7H)-one in a manner analogous to Example 1, Step 6. LCMS [M+H⁺]: 415.0. 1H NMR (400 MHz, DMSO-d6) δ 8.46 (s, 1H), 8.24 (s, 1H), 7.65-7.56 (m, 2H), 7.58-7.47 (m, 2H), 5.58 (s, 2H), 3.95 (s, 3H), 3.49-3.37 (m, 1H), 3.11-2.97 (m, 2H), 2.93-2.75 (m, 2H).

Example 24: 7-methyl-1-[[3-[(1R,5S,6 r)-3-(3-chlorophenyl)-3-azabicyclo[3.1.0]hexan-6-yl]-1,2,4-oxadiazol-5-yl]methyl]purin-6-one (Example Compound 24)

The overall Example 24 reaction scheme is as follows:

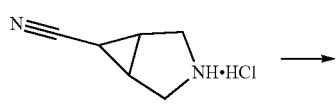

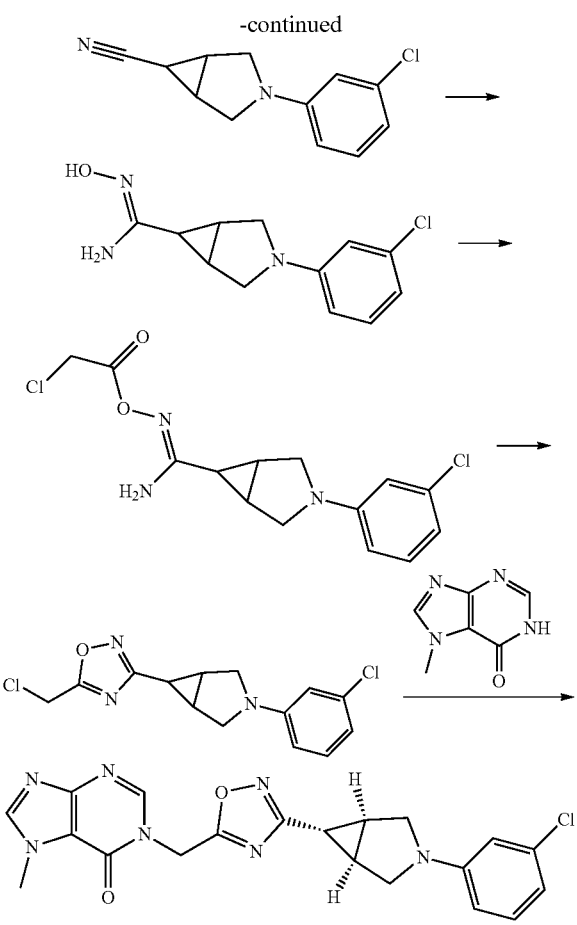

Step 1: Preparation of 3-(3-chlorophenyl)-3-azabicyclo[3.1.0]hexane-6-carbonitrile

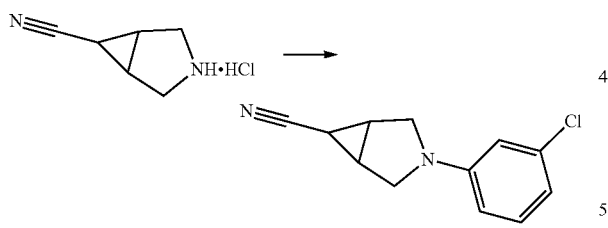

To a vial was added (1R,5S)-3-azabicyclo[3.1.0]hexane-6-carbonitrile; hydrochloride (203 mg, 1.40 mmol), chloro[9,9-dimethyl-4,5-bis(diphenylphosphino)xanthene] [2'-amino-1,1'-biphenyl]palladium(II) (127 mg, 0.14 mmol) and potassium phosphate tribasic (1.08 g, 4.91 mmol). The vial was then purged evacuated and backfilled with nitrogen. 1,4-Dioxane (3.0 mL) was then added followed by 3-bromochlorobenzene (0.18 mL, 1.54 mmol) and the reaction mixture was stirred at 110° C. for 16 h. The reaction mixture was diluted with dichloromethane, filtered through celite, eluting with dichloromethane and the filtrate was concentrated in vacuo. The residue was adsorbed onto silica and purified by flash column chromatography with 0-100% iPrOAc in heptane to afford the desired compound as an orange solid (197.8 mg, 64%). $^1$H NMR (400 MHz, CDCl$_3$-d) δ 7.12 (t, J=8.1 Hz, 1H), 6.73 (ddd, J=8.0, 1.8, 0.8 Hz, 1H), 6.53 (t, J=2.2 Hz, 1H), 6.42 (ddd, J=8.4, 2.3, 0.8 Hz, 1H), 3.65 (d, J=9.7 Hz, 2H), 3.41-3.23 (m, 2H), 2.40-2.30 (m, 2H), 1.45 (t, J=3.4 Hz, 1H).

Step 2: Preparation of (Z)-3-(3-chlorophenyl)-N-hydroxy-3-azabicyclo[3.1.0]hexane-6-carboximidamide

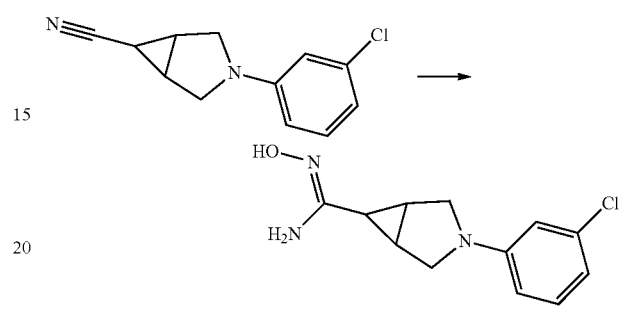

To a solution of 3-(3-chlorophenyl)-3-azabicyclo[3.1.0]hexane-6-carbonitrile (197 mg, 0.90 mmol) in methanol (10 mL) was added hydroxylamine hydrochloride (94 mg, 1.35 mmol) followed by sodium bicarbonate (378 mg, 4.50 mmol) and the reaction mixture was heated to reflux overnight. The reaction mixture was cooled to room temp, filtered and the filter cake was washed with DCM. The filtrate was concentrated in vacuo and the residue was taken up in DCM and washed with water, brine, dried over sodium sulfate, filtered and concentrated in vacuo to yield the crude title compound (210.0 mg, 93%) which was used directly in the next step.

Step 3: Preparation of (Z)—N-(2-chloroacetoxy)-3-(3-chlorophenyl)-3-azabicyclo[3.1.0]hexane-6-carboximidamide 3-(3-chlorophenyl)-N-hydroxy-3-azabicyclo[3.1.0]hexane-6-carboxamidine (210 mg, 0.83 mmol) in acetone (15 mL) was added chloroacetyl chloride (0.069 mL, 0.88 mmol) dropwise. The reaction mixture was stirred at room temperature for 30 mins. The reaction mixture was concentrated in vacuo, and the residue was taken up in DCM and washed with saturated aqueous sodium bicarbonate and water, dried over sodium sulfate, filtered and concentrated in vacuo to give the crude title compound as a white solid (223 mg, 81%) which was used directly in the next step.

Step 4: Preparation of 5-(chloromethyl)-3-(3-(3-chlorophenyl)-3-azabicyclo[3.1.0]hexan-6-yl)-1,2,4-oxadiazole

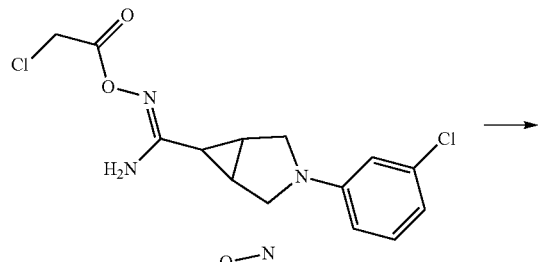

To a round-bottom flask was added (Z)—N-(2-chloroacetoxy)-3-(3-chlorophenyl)-3-azabicyclo[3.1.0]hexane-6-carboximidamide (223 mg, 0.68 mmol) followed by toluene (10 mL), a dean-stark apparatus was attached and the mixture was heated to 125° C. for 3 h then cooled to room temperature. The reaction mixture was concentrated in vacuo, the residue was adsorbed onto silica and purified by flash column chromatography with 0-100% iPrOAc in Heptane to afford the desired compound as a light yellow oil that solidified over time (92 mg, 33%). LCMS [M+H]$^+$ 311.1.

Step 5: Preparation of 7-methyl-1-[[3-[(1R,5S,6 r)-3-(3-chlorophenyl)-3-azabicyclo[3.1.0]hexan-6-yl]-1,2,4-oxadiazol-5-yl]methyl]purin-6-one

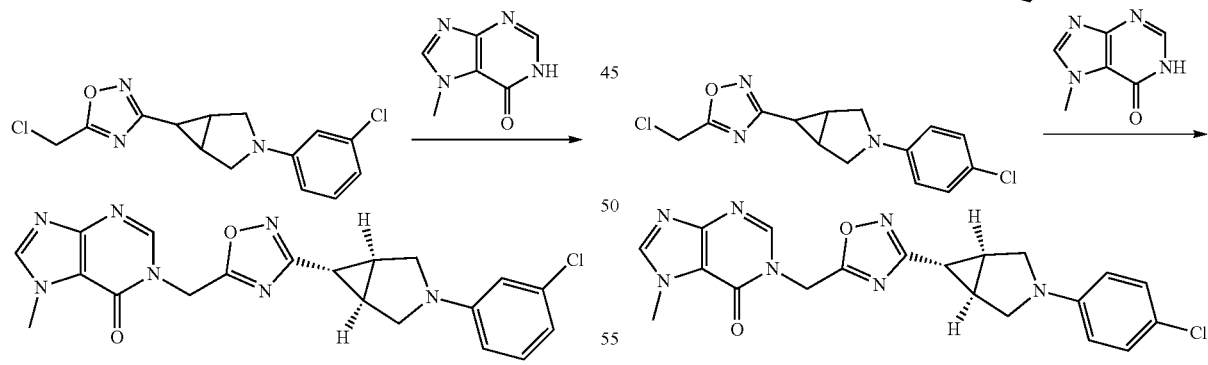

A mixture of 7-methyl-1H-purin-6(7H)-one (44 mg, 0.28 mmol), 5-(chloromethyl)-3-[3-(3-chlorophenyl)-3-azabicyclo[3.1.0]hexan-6-yl]-1,2,4-oxadiazole (91 mg, 0.29 mmol), cesium carbonate (272 mg, 0.84 mmol) and tetrabutylammonium iodide (10 mg, 0.028 mmol) in N,N-dimethylformamide (2.0 mL) were heated to 60° C. for 2 h. The reaction was cooled to room temperature, diluted with water and extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH: iPrOAc in Heptane to afford the desired compound as a brown oil. The residue was further purified by RP-HPLC to yield the title compound (25.9 mg, 22%) as a white solid. LCMS [M+H]$^+$ 424; $^1$H NMR (400 MHz, DMSO-d$_6$) δ 8.43 (s, 1H), 8.23 (s, 1H), 7.15 (t, J=8.1 Hz, 1H), 6.65 (dd, J=7.5, 1.9 Hz, 1H), 6.56 (t, J=2.2 Hz, 1H), 6.54-6.49 (m, 1H), 5.52 (s, 2H), 3.95 (s, 3H), 3.67 (d, J=9.9 Hz, 2H), 3.30-3.25 (m, 2H), 2.23-2.18 (m, 2H), 2.01 (t, J=3.3 Hz, 1H).

Example 25: 7-methyl-1-[[3-[(1R,5S,6 r)-3-(4-chlorophenyl)-3-azabicyclo[3.1.0]hexan-6-yl]-1,2,4-oxadiazol-5-yl]methyl]purin-6-one (Example Compound 25)

The overall Example 25 reaction scheme is as follows:

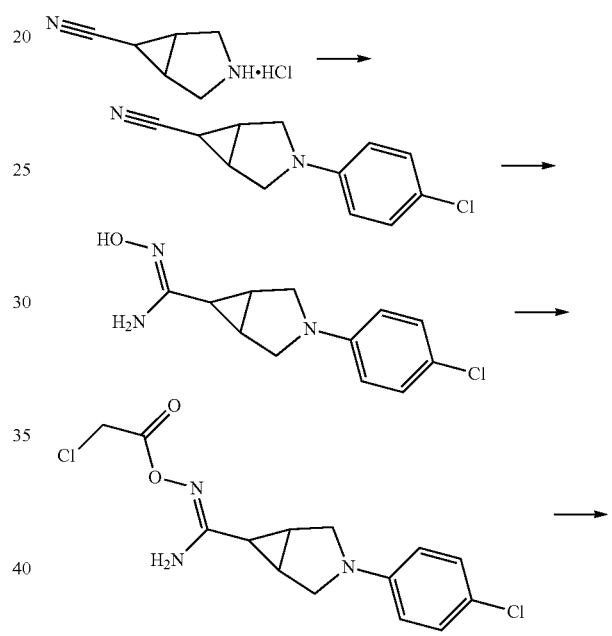

Step 1: Preparation of 3-(4-chlorophenyl)-3-azabicyclo[3.1.0]hexane-6-carbonitrile

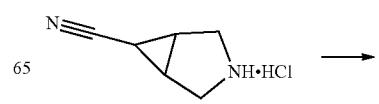

-continued

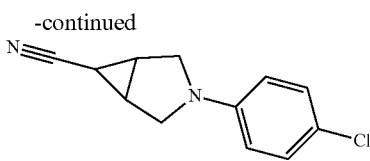

To a vial was added 3-azabicyclo[3.1.0]hexane-6-carbonitrile; hydrochloride (250 mg, 1.73 mmol), chloro[9,9-dimethyl-4,5-bis(diphenylphosphino)xanthene][2'-amino-1,1'-biphenyl]palladium(II) (157 mg, 0.17 mmol) and potassium phosphate tribasic (1.32 g, 6.05 mmol). The vial was then purged evacuated and backfilled with nitrogen. 1,4-Dioxane (3.5 mL) was then added followed by 4-bromochlorobenzene (0.23 mL, 1.90 mmol) and the reaction mixture was stirred at 110° C. for 16 h. The reaction mixture was diluted with dichloromethane, filtered through celite, eluting with dichloromethane and the filtrate was concentrated in vacuo. The residue was adsorbed onto silica and purified by flash column chromatography with 0-100% iPrOAc in heptane to afford the desired compound as an orange solid (217 mg, 57%). $^1$H NMR (400 MHz, CDCl$_3$-d) δ 7.21-7.12 (m, 2H), 6.52-6.43 (m, 2H), 3.65 (d, J=9.7 Hz, 2H), 3.31-3.19 (m, 2H), 2.40-2.30 (m, 2H), 1.48 (t, J=3.4 Hz, 1H).

Step 2: Preparation of (Z)-3-(4-chlorophenyl)-N-hydroxy-3-azabicyclo[3.1.0]hexane-6-carboximidamide

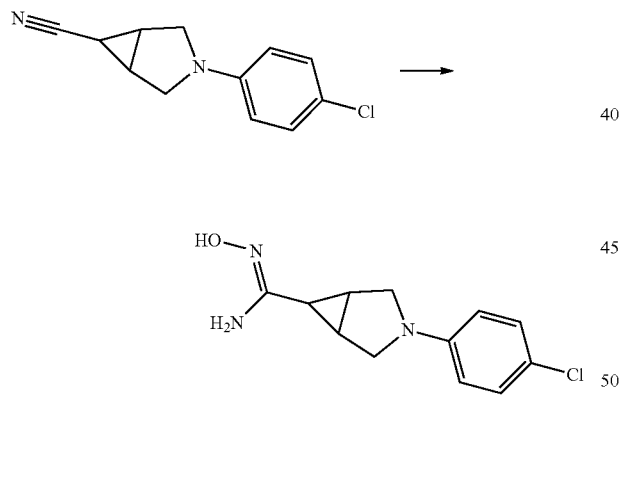

To a solution of 3-(4-chlorophenyl)-3-azabicyclo[3.1.0]hexane-6-carbonitrile (217 mg, 1.00 mmol) in methanol (10 mL) was added hydroxylamine hydrochloride (103 mg, 1.49 mmol) followed by sodium bicarbonate (416 mg, 4.96 mmol) and the reaction mixture was heated to reflux overnight. The reaction mixture was cooled to room temp, filtered and the filter cake was washed with DCM. The filtrate was concentrated in vacuo and the residue was taken up in DCM and washed with water, brine, dried over sodium sulfate, filtered and concentrated in vacuo to yield the crude title compound which was used directly in the next step (187 mg, 75%).

Step 3: Preparation of (Z)—N-(2-chloroacetoxy)-3-(4-chlorophenyl)-3-azabicyclo[3.1.0]hexane-6-carboximidamide

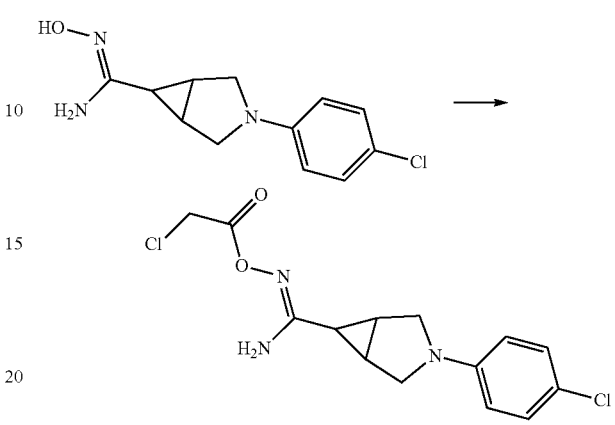

To a solution of (Z)-3-(4-chlorophenyl)-N-hydroxy-3-azabicyclo[3.1.0]hexane-6-carboximidamide (187 mg, 0.74 mmol) in acetone (15 mL) was added chloroacetyl chloride (0.062 mL, 0.78 mmol) dropwise. The reaction mixture was stirred at room temp for 30 mins. The reaction mixture was concentrated in vacuo, and the residue was taken up in DCM and washed with sat. aq. sodium bicarbonate and water, dried over sodium sulfate, filtered and concentrated in vacuo to yield a white solid which was used directly in the next step (221 mg, 91%).

Step 4: Preparation of 5-(chloromethyl)-3-(3-(4-chlorophenyl)-3-azabicyclo[3.1.0]hexan-6-yl)-1,2,4-oxadiazole

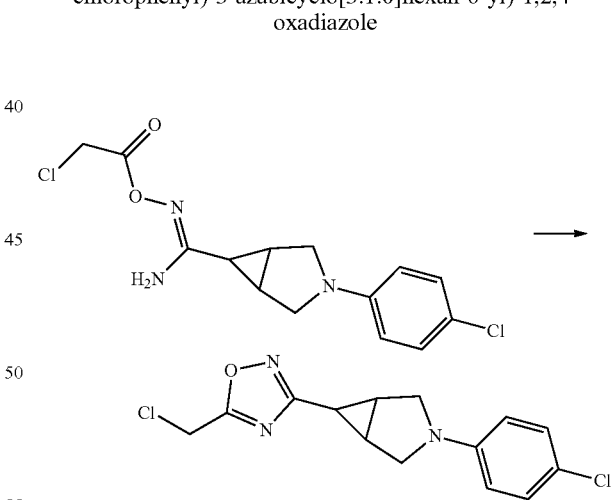

To a round-bottom flask was added (Z)—N-(2-chloroacetoxy)-3-(4-chlorophenyl)-3-azabicyclo[3.1.0]hexane-6-carboximidamide (221 mg, 0.67 mmol) followed by toluene (10 mL), a dean-stark apparatus was attached and the mixture was heated to 125° C. for 3 h. then cooled to room temperature. The reaction mixture was concentrated in vacuo, the residue was adsorbed onto silica and purified by flash column chromatography with 0-100% iPrOAc in Heptane to afford the desired compound as a light yellow oil that solidified over time (173 mg, 56%). LCMS [M+H$^+$] 311.1; $^1$H NMR (400 MHz, CDCl$_3$-d) δ 7.19-7.14 (m, 2H), 6.53-

6.45 (m, 2H), 4.63 (s, 2H), 3.70 (d, J=9.3 Hz, 2H), 3.39-3.31 (m, 2H), 2.38-2.27 (m, 2H), 2.17 (t, J=3.3 Hz, 1H).

Step 5: Preparation of 7-methyl-1-[[3-[(1R,5S,6 r)-3-(4-chlorophenyl)-3-azabicyclo[3.1.0]hexan-6-yl]-1,2,4-oxadiazol-5-yl]methyl]purin-6-one

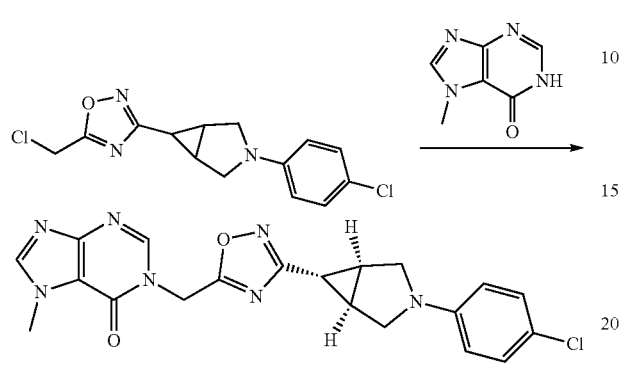

A mixture of 7-methyl-1H-purin-6(7H)-one (22 mg, 0.14 mmol), 5-(chloromethyl)-3-(3-(4-chlorophenyl)-3-azabicyclo[3.1.0]hexan-6-yl)-1,2,4-oxadiazole (48 mg, 0.15 mmol), cesium carbonate (136 mg, 0.42 mmol) and tetrabutylammonium iodide (5.1 mg, 0.014 mmol) in N,N-dimethylformamide (1.0 mL) were heated to 60° C. for 30 min. The reaction was cooled to room temperature, diluted with water and extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH: iPrOAc in Heptane to afford the desired compound as a brown oil. The residue was further purified by RP-HPLC to yield the title compound (2.1 mg, 3.6%) as a white solid. LCMS [M+H]⁺ 424; ¹H NMR (400 MHz, DMSO-d₆) δ 8.43 (s, 1H), 8.23 (s, 1H), 7.21-7.13 (m, 2H), 6.60-6.53 (m, 2H), 5.52 (s, 2H), 3.95 (s, 3H), 3.66 (d, J=9.7 Hz, 2H), 3.26-3.20 (m, 2H), 2.23-2.17 (m, 2H), 2.02 (t, J=3.2 Hz, 1H).

Example 26: 7-methyl-1-[[3-[(1R,5S,6 r)-3-phenyl-3-azabicyclo[3.1.0]hexan-6-yl]-1,2,4-oxadiazol-5-yl]methyl]purin-6-one (Example Compound 26)

The overall Example 26 reaction scheme is as follows:

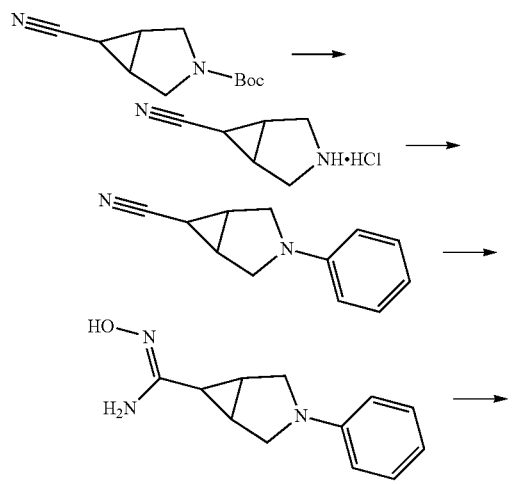

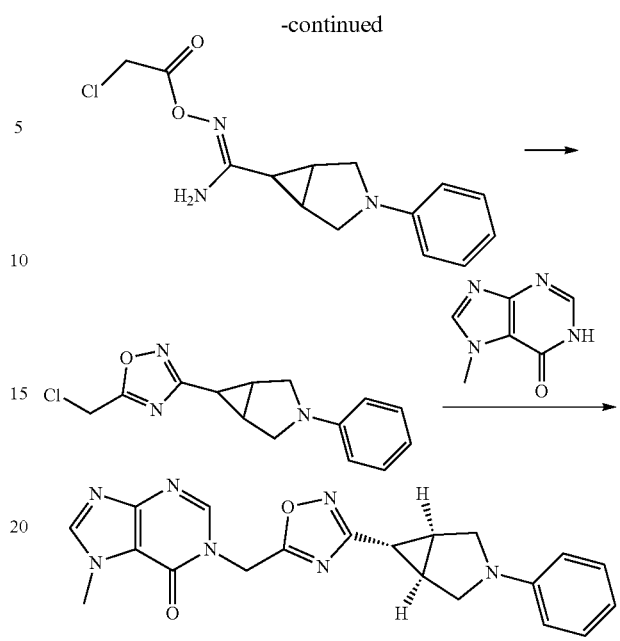

Step 1: Preparation of 3-azabicyclo[3.1.0]hexane-6-carbonitrile hydrochloride

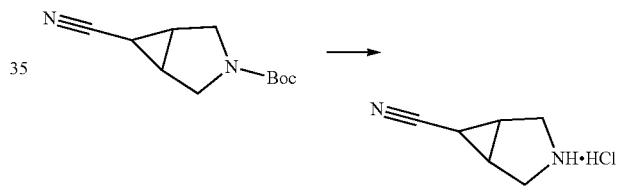

To a solution of tert-butyl 6-cyano-3-azabicyclo[3.1.0]hexane-3-carboxylate (400 mg, 1.9 mmol) in dichloromethane (12 mL) was added hydrochloric acid (4 mol/L) in 1,4-dioxane (5 mL, 20 mmol). The reaction mixture was stirred at room temperature overnight. The reaction mixture was concentrated in vacuo and the crude residue was used directly in the following step (277 mg, 99%).

Step 2: Preparation of 3-phenyl-3-azabicyclo[3.1.0]hexane-6-carbonitrile

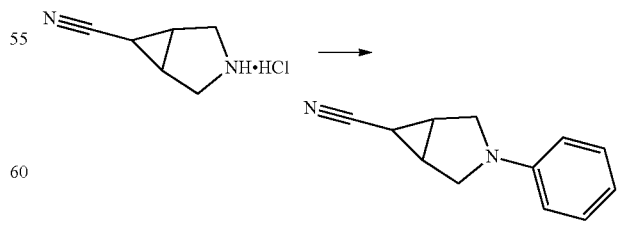

To a vial was added crude 3-azabicyclo[3.1.0]hexane-6-carbonitrile hydrochloride from step 1 (277 mg, 1.9 mmol), chloro[9,9-dimethyl-4,5-bis(diphenylphosphino)xanthene][2'-amino-1,1'-biphenyl]palladium(II) (174 mg, 0.19 mmol)

and potassium phosphate tribasic (1.47 g, 6.71 mmol). The vial was then purged evacuated and backfilled with nitrogen. 1,4-dioxane (3.5 mL) was then added followed by bromobenzene (0.22 mL, 2.11 mmol) and the reaction mixture was stirred at 110° C. for 16 h. The reaction mixture was diluted with dichloromethane, filtered through celite, eluting with dichloromethane and the filtrate was concentrated in vacuo. The residue was adsorbed onto silica and purified by flash column chromatography with 0-100% iPrOAc in heptane to afford the desired compound as an orange solid (194 mg, 55%). $^1$H NMR (400 MHz, CDCl$_3$-d) δ 7.27-7.17 (m, 2H), 6.81-6.71 (m, 1H), 6.61-6.52 (m, 2H), 3.69 (d, J=9.7 Hz, 2H), 3.32-3.20 (m, 2H), 2.38-2.28 (m, 2H), 1.48 (t, J=3.4 Hz, 1H).

Step 3: Preparation of (Z)—N-hydroxy-3-phenyl-3-azabicyclo[3.1.0]hexane-6-carboximidamide

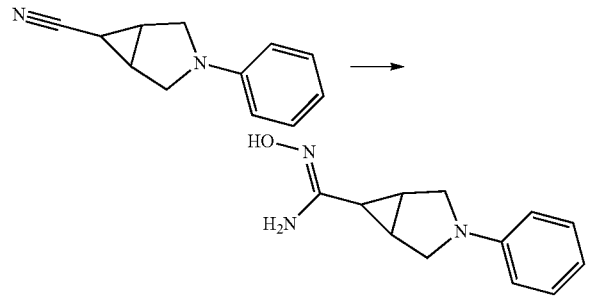

To a solution of 3-phenyl-3-azabicyclo[3.1.0]hexane-6-carbonitrile (194 mg, 1.06 mmol) in methanol (10 mL) was added hydroxylamine hydrochloride (110 mg, 1.58 mmol) followed by sodium bicarbonate (443 mg, 5.27 mmol) and the reaction mixture was heated to reflux overnight. The reaction mixture was cooled to room temperature, filtered and the filter cake was washed with DCM. The filtrate was concentrated in vacuo and the residue was taken up in DCM and washed with water, brine, dried over sodium sulfate, filtered and concentrated in vacuo to yield the crude title compound (196 mg, 86%).

Step 4: Preparation of (Z)—N-(2-chloroacetoxy)-3-phenyl-3-azabicyclo[3.1.0]hexane-6-carboximidamide

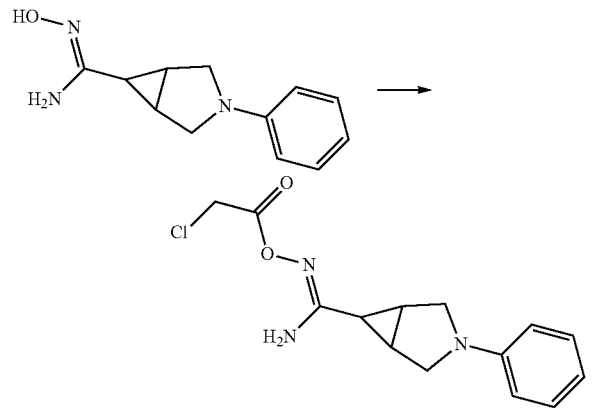

To a solution of N-hydroxy-3-phenyl-3-azabicyclo[3.1.0]hexane-6-carboxamidine (196 mg, 0.90 mmol) in acetone (15 mL) was added chloroacetyl chloride (0.075 mL, 0.95 mmol), slowly, dropwise. The reaction mixture was stirred at room temp for 30 mins. The reaction mixture was concentrated in vacuo, and the residue was taken up in DCM and washed with sat. aq. sodium bicarbonate and water, dried over sodium sulfate, filtered and concentrated in vacuo to yield a white solid which was used directly in the next step (264 mg, 99%).

Step 5: Preparation of 5-(chloromethyl)-3-(3-phenyl-3-azabicyclo[3.1.0]hexan-6-yl)-1,2,4-oxadiazole

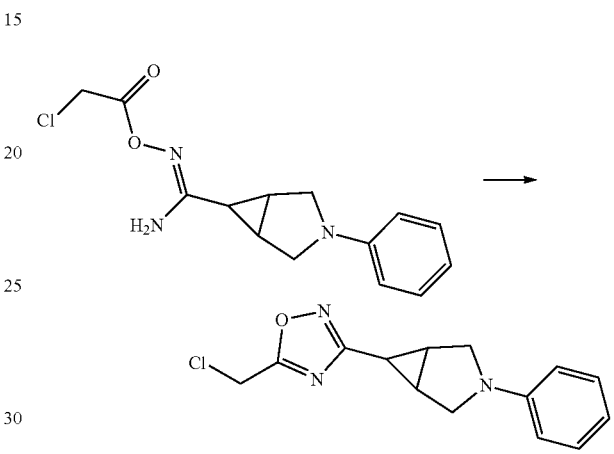

To a round-bottom flask was added [(Z)-[amino-(3-phenyl-3-azabicyclo[3.1.0]hexan-6-yl)methylene]amino] 2-chloroacetate (282 mg, 0.96 mmol) followed by toluene (15 mL), a dean-stark apparatus was attached and the mixture was heated to 125° C. for 3 h. then cooled to room temperature. The reaction mixture was concentrated in vacuo, the residue was adsorbed onto silica and purified by flash column chromatography with 0-100% iPrOAc in Heptane to afford the desired compound as a light yellow oil that solidified over time (173 mg, 66%). LCMS [M+H$^+$] 276.1.

Step 6: Preparation of 7-methyl-1-[[3-[(1R,5S,6r)-3-phenyl-3-azabicyclo[3.1.0]hexan-6-yl]-1,2,4-oxadiazol-5-yl]methyl]purin-6-one

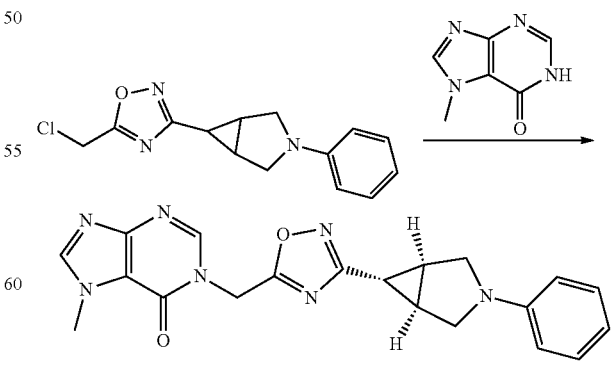

A mixture of 7-methyl-1H-purin-6(7H)-one (26 mg, 0.16 mmol), 5-(chloromethyl)-3-(-3-phenyl-3-azabicyclo[3.1.0] hexan-6-yl)-1,2,4-oxadiazole (50 mg, 0.18 mmol), cesium carbonate (161 mg, 0.49 mmol) and tetrabutylammonium iodide (6.1 mg, 0.016 mmol) in N,N-dimethylformamide (1.0 mL) were heated to 60° C. for 30 min. The reaction was cooled to room temperature, diluted with water and extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH: iPrOAc in Heptane to afford the desired compound as a brown oil. The residue was further purified by RP-HPLC to yield the title compound (32.3 mg, 50%) as a white solid. LCMS [M+H]+ 390; $^1$H NMR (400 MHz, DMSO-d$_6$) δ 8.43 (s, 1H), 8.23 (s, 1H), 7.20-7.11 (m, 2H), 6.68-6.59 (m, 1H), 6.64-6.52 (m, 2H), 5.52 (s, 2H), 3.95 (s, 3H), 3.67 (d, J=9.7 Hz, 2H), 3.26-3.21 (m, 2H), 2.22-2.17 (m, 2H), 2.03 (t, J=3.3 Hz, 1H).

Example 27: Preparation of 3-((3-(2,3-dihydro-1H-inden-2-yl)-1,2,4-oxadiazol-5-yl)methyl)-5-methyl-pyrido[2,3-d]pyrimidin-4(3H)-one (Example Compound 27)

The overall Example 27 reaction scheme is as follows:

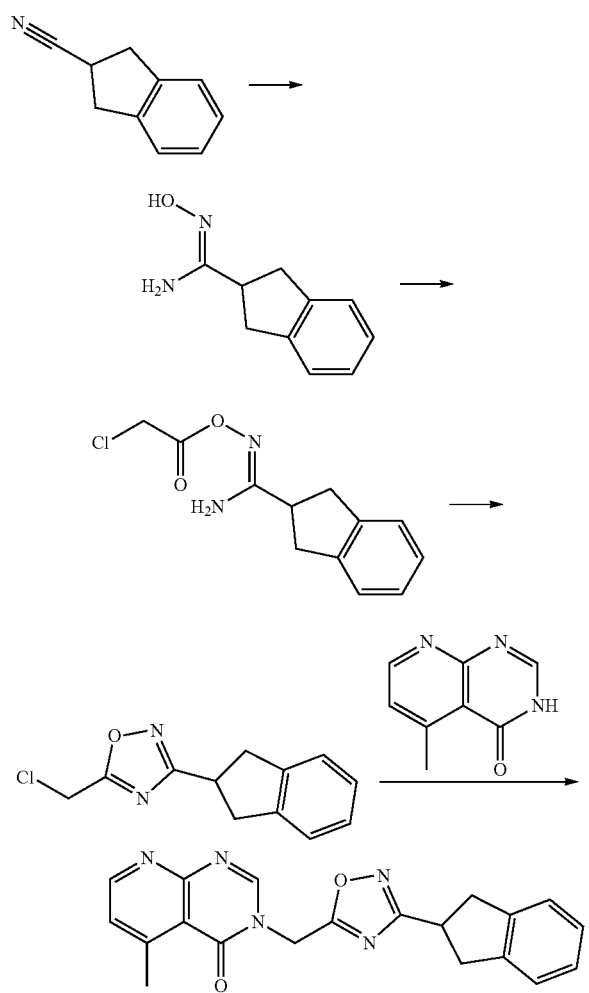

Step 1: Preparation of N'-hydroxy-2,3-dihydro-1H-indene-2-carboximidamide

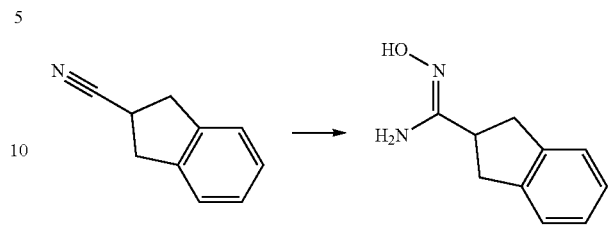

The title compound was prepared from 2,3-dihydro-1H-indene-2-carbonitrile in a manner analogous to Example 1, Step 3.

Step 2: Preparation of N'-(2-chloroacetoxy)-2,3-dihydro-1H-indene-2-carboximidamide

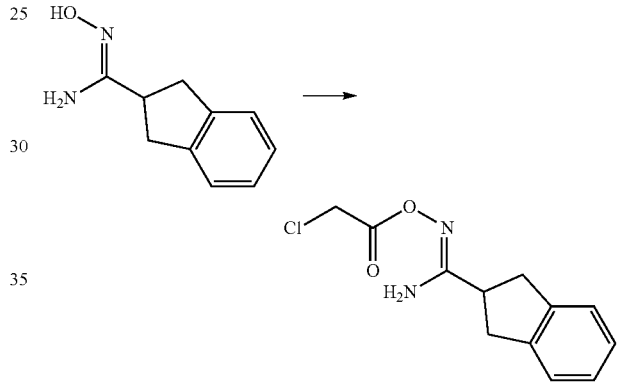

The title compound was prepared from N'-hydroxy-2,3-dihydro-1H-indene-2-carboximidamide in a manner analogous to Example 1, Step 4.

Step 3: Preparation of 5-(chloromethyl)-3-(2,3-dihydro-1H-inden-2-yl)-1,2,4-oxadiazole

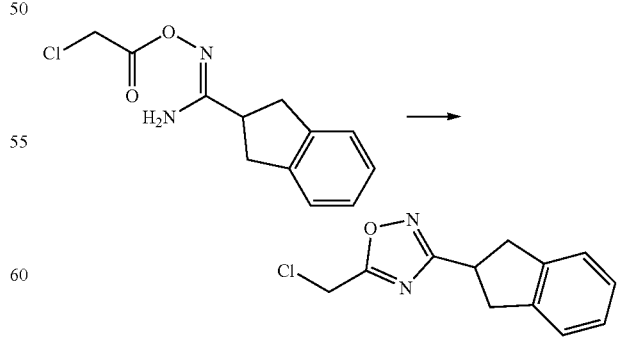

The title compound was prepared from N'-(2-chloroacetoxy)-2,3-dihydro-1H-indene-2-carboximidamide in a manner analogous to Example 1, Step 5.

Step 4: Preparation of 3-((3-(2,3-dihydro-1H-inden-2-yl)-1,2,4-oxadiazol-5-yl)methyl)-5-methylpyrido[2,3-d]pyrimidin-4(3H)-one

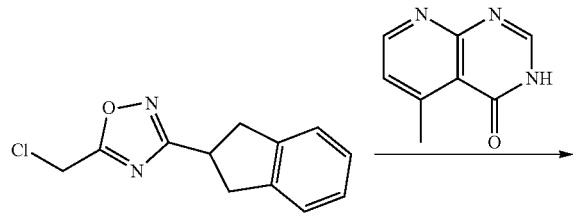

The title compound was prepared from 5-(chloromethyl)-3-(2,3-dihydro-1H-inden-2-yl)-1,2,4-oxadiazole and 5-methylpyrido[2,3-d]pyrimidin-4(3H)-one in a manner analogous to example 1. LCMS [M+H$^+$]: 360.1. 1H NMR (400 MHz, DMSO-d6) δ 8.78 (d, J=4.8 Hz, 1H), 8.70 (s, 1H), 7.40 (dd, J=4.8, 1.0 Hz, 1H), 7.28-7.18 (m, 2H), 7.22-7.10 (m, 2H), 5.51 (s, 2H), 3.88-3.71 (m, 1H), 3.33-3.20 (m, 2H), 3.13 (dd, J=15.7, 7.4 Hz, 2H), 2.76 (d, J=0.8 Hz, 3H).

Example 28: Preparation of 1-((3-((1s,3s)-3-(4-chlorophenyl)-3-hydroxycyclobutyl)-1,2,4-oxadiazol-5-yl)methyl)-7-methyl-1H-purin-6(7H)-one (Example Compound 28)

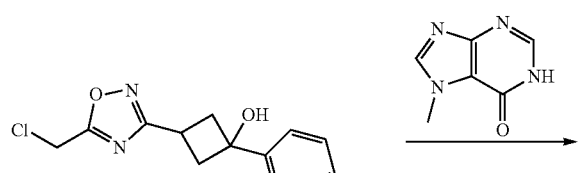

The title compound was prepared from 3-(5-(chloromethyl)-1,2,4-oxadiazol-3-yl)-1-(4-chlorophenyl)cyclobutanol and 7-methyl-1H-purin-6(7H)-one in a manner analogous to Example 1, Step 6. LCMS [M+H$^+$]: 413. $^1$H NMR (400 MHz, DMSO-d6) δ 8.46 (s, 1H), 8.24 (s, 1H), 7.61-7.56 (m, 2H), 7.43-7.37 (m, 2H), 5.91 (s, 1H), 5.56 (s, 2H), 3.95 (s, 3H), 3.29-3.20 (quin, J=9.0 Hz, 1H), 2.83-2.74 (m, 2H), 2.64-2.54 (m, 2H).

Example 29: Preparation of 5-methyl-3-[[3-[(1R,5S,6r)-3-(4-chlorophenyl)-3-azabicyclo[3.1.0]hexan-6-yl]-1,2,4-oxadiazol-5-yl]methyl]pyrido[2,3-d]pyrimidin-4-one (Example Compound 29)

The overall Example 29 reaction scheme is as follows:

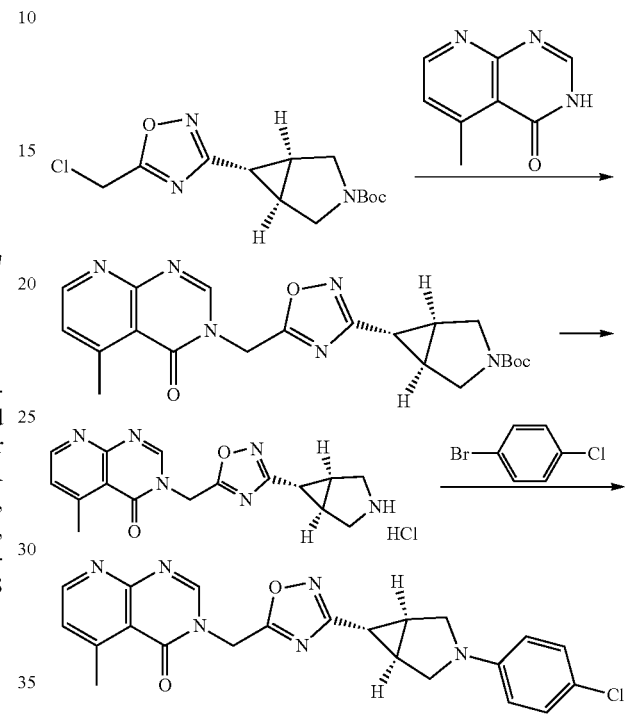

Step 1: Preparation of (1R,5S,6r)-tert-butyl 6-(5-((5-methyl-4-oxopyrido[2,3-d]pyrimidin-3(4H)-yl)methyl)-1,2,4-oxadiazol-3-yl)-3-azabicyclo[3.1.0]hexane-3-carboxylate The title compound was prepared from (1R,5S,6r)-tert-butyl 6-(5-(chloromethyl)-1,2,4-oxadiazol-3-yl)-3-azabicyclo[3.1.0]hexane-3-carboxylate and 5-methylpyrido[2,3-d]pyrimidin-4(3H)-one in a manner analogous to Example 4, Step 6.

Step 2: Preparation of 3-((3-((1R,5S,6r)-3-azabicyclo[3.1.0]hexan-6-yl)-1,2,4-oxadiazol-5-yl)methyl)-5-methylpyrido[2,3-d]pyrimidin-4(3H)-one

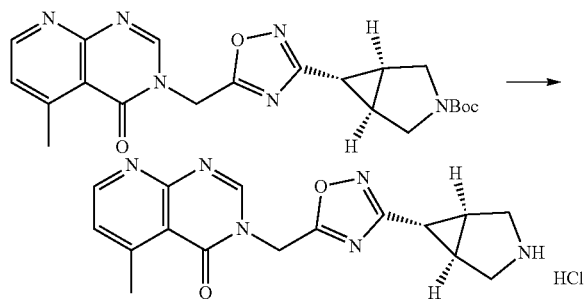

The title compound was prepared from (1R,5S,6r)-tert-butyl 6-(5-((5-methyl-4-oxopyrido[2,3-d]pyrimidin-3(4H)-yl)methyl)-1,2,4-oxadiazol-3-yl)-3-azabicyclo[3.1.0]hexane-3-carboxylate in a manner analogous to Example 4, Step 7.

Step 3: Preparation of 5-methyl-3-[[3-[(1R,5S,6r)-3-(4-chlorophenyl)-3-azabicyclo[3.1.0]hexan-6-yl]-1,2,4-oxadiazol-5-yl]methyl]pyrido[2,3-d]pyrimidin-4-one

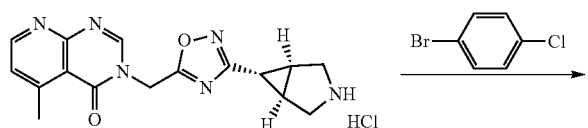

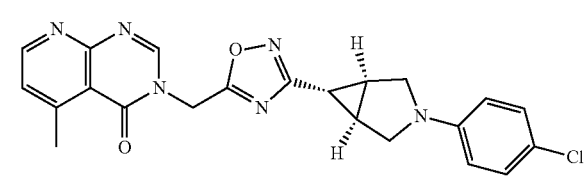

The title compound was prepared from 3-[[3-[(1R,5S)-3-azabicyclo[3.1.0]hexan-6-yl]-1,2,4-oxadiazol-5-yl]methyl]-5-methylpyrido[2,3-d]pyrimidin-4-one hydrochloride (115 mg, 0.320 mmol) and 1-bromo-4-chlorobenzene (73.5 mg, 0.384 mmol) as a white crystalline solid (4.0 mg, 3% yield), in a manner analogous to Example 4, Step 8. LCMS [M+H⁺] 435.1. ¹H NMR (400 MHz, DMSO) δ 8.79 (d, J=4.8 Hz, 1H), 8.69 (s, 1H), 7.40 (d, J=4.8 Hz, 1H), 7.17 (d, J=8.9 Hz, 2H), 6.56 (d, J=9.0 Hz, 2H), 5.48 (s, 2H), 3.65 (d, J=9.7 Hz, 2H), 3.26-3.21 (m, 2H), 2.77 (s, 3H), 2.20 (s, 2H), 2.03 (t, J=3.2 Hz, 1H).

Example 30: Preparation of 7-methyl-1-[[3-[(1R,5S,6r)-3-[3-(trifluoromethyl)phenyl]-3-azabicyclo[3.1.0]hexan-6-yl]-1,2,4-oxadiazol-5-yl]methyl]purin-6-one (Example Compound 30)

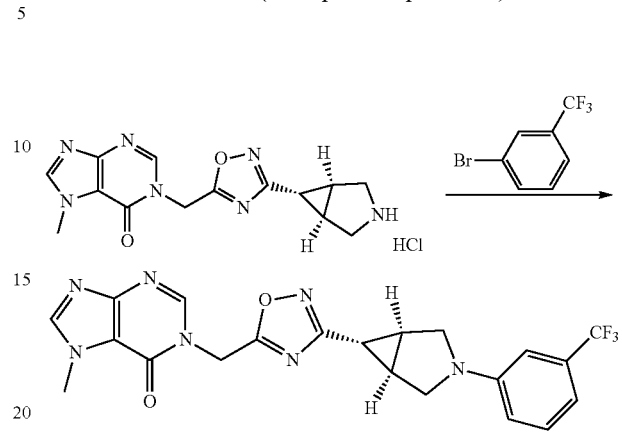

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 3-bromobenzotrifluoride (86.5 mg, 0.384 mmol) as a white crystalline solid (45.5 mg, 31% yield), in a manner analogous to Example 4, Step 8. LCMS [M+H⁺] 458.1. ¹H NMR (400 MHz, DMSO) δ 8.43 (s, 1H), 8.26-8.17 (m, 1H), 7.36 (t, J=7.9 Hz, 1H), 6.93 (d, J=7.6 Hz, 1H), 6.83 (d, J=8.4 Hz, 1H), 6.76 (s, 1H), 5.52 (s, 2H), 3.95 (s, 3H), 3.74 (d, J=9.8 Hz, 2H), 3.36-3.33 (m, 2H), 2.28-2.16 (m, 2H), 2.04 (t, J=3.2 Hz, 1H).

Example 31: Preparation of 7-methyl-1-[[3-[(1R,5S,6r)-3-[4-(trifluoromethyl)phenyl]-3-azabicyclo[3.1.0]hexan-6-yl]-1,2,4-oxadiazol-5-yl]methyl]purin-6-one (Example Compound 31)

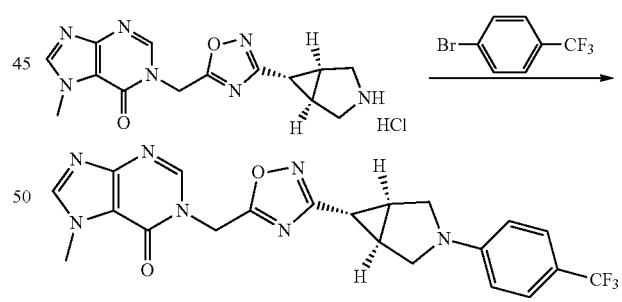

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 4-bromobenzotrifluoride (86.5 mg, 0.384 mmol) as a white crystalline solid (34.0 mg, 23% yield), in a manner analogous to Example 4, Step 8. LCMS [M+H⁺] 458.1. ¹H NMR (400 MHz, DMSO) δ 8.43 (s, 1H), 8.23 (s, 1H), 7.45 (d, J=8.7 Hz, 2H), 6.67 (d, J=8.7 Hz, 2H), 5.52 (s, 2H), 3.95 (s, 3H), 3.72 (d, J=10.0 Hz, 2H), 3.41-3.35 (m, 2H), 2.24 (s, 2H), 2.02 (t, J=3.3 Hz, 1H).

Example 32: Preparation of 4-[(1R,5S,6r)-6-[5-[(7-methyl-6-oxo-purin-1-yl)methyl]-1,2,4-oxadiazol-3-yl]-3-azabicyclo[3.1.0]hexan-3-yl]benzaldehyde (Example Compound 32)

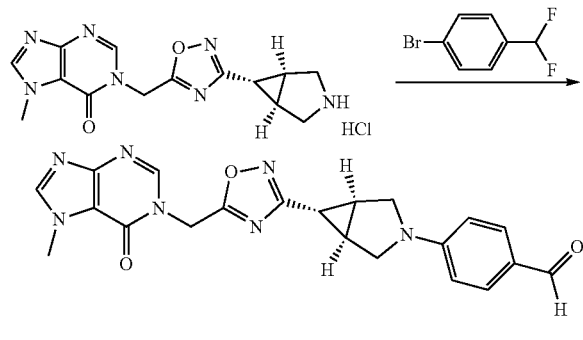

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 1-bromo-4-(difluoromethyl)benzene (79.5 mg, 0.384 mmol) as a white crystalline solid (26.4 mg, 20% yield), in a manner analogous to Example 4, Step 8. LCMS [M+H⁺] 418.1. ¹H NMR (400 MHz, DMSO) δ 9.68 (s, 1H), 8.43 (s, 1H), 8.27-8.19 (m, 1H), 7.68 (d, J=8.8 Hz, 2H), 6.67 (d, J=8.8 Hz, 2H), 5.52 (s, 2H), 3.95 (s, 3H), 3.77 (d, J=10.5 Hz, 2H), 3.54-3.42 (m, 2H), 2.26 (s, 2H), 2.02 (t, J=3.3 Hz, 1H).

Example 33: Preparation of 7-methyl-1-[[3-[(1R,5S,6r)-3-[2-naphthyl]-3-azabicyclo[3.1.0]hexan-6-yl]-1,2,4-oxadiazol-5-yl]methyl]purin-6-one (Example Compound 33)

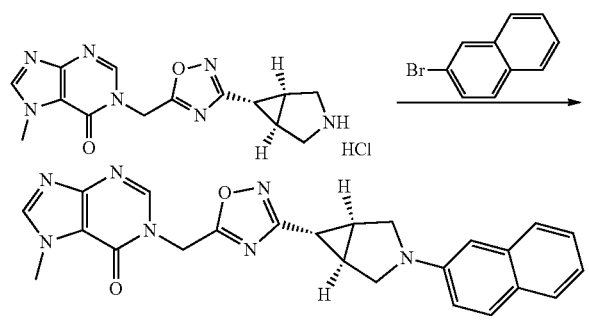

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 2-bromonaphthalene (79.6 mg, 0.384 mmol) as a white crystalline solid (42.1 mg, 30% yield), in a manner analogous to Example 4, Step 8. LCMS [M+H⁺] 440.1. ¹H NMR (400 MHz, DMSO) δ 8.44 (s, 1H), 8.24 (s, 1H), 7.71 (t, J=9.0 Hz, 2H), 7.63 (d, J=8.1 Hz, 1H), 7.33 (ddd, J=8.2, 6.8, 1.2 Hz, 1H), 7.15 (ddd, J=8.0, 6.9, 1.1 Hz, 1H), 7.06 (dd, J=9.0, 2.4 Hz, 1H), 6.81 (d, J=2.2 Hz, 1H), 5.53 (s, 2H), 3.96 (s, 3H), 3.82 (d, J=9.8 Hz, 2H), 3.43-3.35 (m, 2H), 2.30-2.18 (m, 2H), 2.12-2.04 (m, 1H).

Example 34: Preparation of 7-methyl-1-[[3-[(1R,5S,6r)-3-[6-chloro-3-pyridyl]-3-azabicyclo[3.1.0]hexan-6-yl]-1,2,4-oxadiazol-5-yl]methyl]purin-6-one (Example Compound 34)

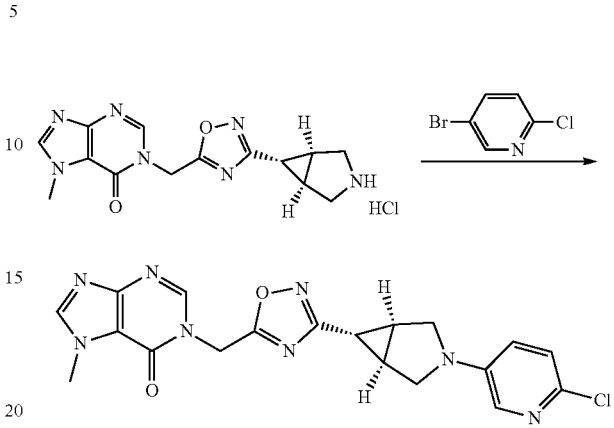

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 5-bromo-2-chloropyridine (73.9 mg, 0.384 mmol) as a white crystalline solid (9.2 mg, 7% yield), in a manner analogous to Example 4, Step 8. LCMS [M+H⁺] 425.1. ¹H NMR (400 MHz, DMSO) δ 8.43 (s, 1H), 8.23 (s, 1H), 7.71 (d, J=3.0 Hz, 1H), 7.24 (d, J=8.7 Hz, 1H), 7.03 (dd, J=8.8, 3.2 Hz, 1H), 5.52 (s, 2H), 3.95 (s, 3H), 3.70 (d, J=9.8 Hz, 2H), 3.33-3.25 (m, 2H), 2.22 (d, J=2.3 Hz, 2H), 2.03 (t, J=3.3 Hz, 1H).

Example 35: Preparation of 7-methyl-1-[[3-[(1R,5S,6r)-3-[4-methoxyphenyl]-3-azabicyclo[3.1.0]hexan-6-yl]-1,2,4-oxadiazol-5-yl]methyl]purin-6-one (Example Compound 35)

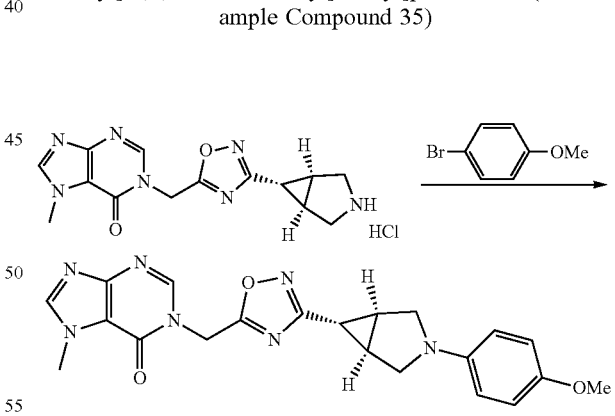

The title compound was prepared from 1-((3-((1R,5S,6r)-3-azabicyclo[3.1.0]hexan-6-yl)-1,2,4-oxadiazol-5-yl)methyl)-7-methyl-1,7-dihydro-6H-purin-6-one hydrochloride (112 mg, 0.320 mmol) and 4-bromoanisole (71.9 mg, 0.384 mmol) as a white crystalline solid (6.9 mg, 5% yield), in a manner analogous to Example 4, Step 8. LCMS [M+H⁺] 420.1. ¹H NMR (400 MHz, DMSO) δ 8.43 (s, 1H), 8.23 (s, 1H), 6.87-6.69 (m, 2H), 6.63-6.45 (m, 2H), 5.52 (s, 2H), 3.95 (s, 3H), 3.64 (d, J=8.0 Hz, 5H), 3.12 (d, J=9.0 Hz, 2H), 2.24-2.10 (m, 2H), 2.06 (t, J=3.2 Hz, 1H).

Example 36: Preparation of 5-methyl-3-[[3-[(1R,5S,6r)-3-(4-chlorophenyl)-3-azabicyclo[3.1.0]hexan-6-yl]-1,2,4-oxadiazol-5-yl]methyl]pyrido[3,4-d]pyrimidin-4-one (Example Compound 36)

The overall Example 36 reaction scheme is as follows:

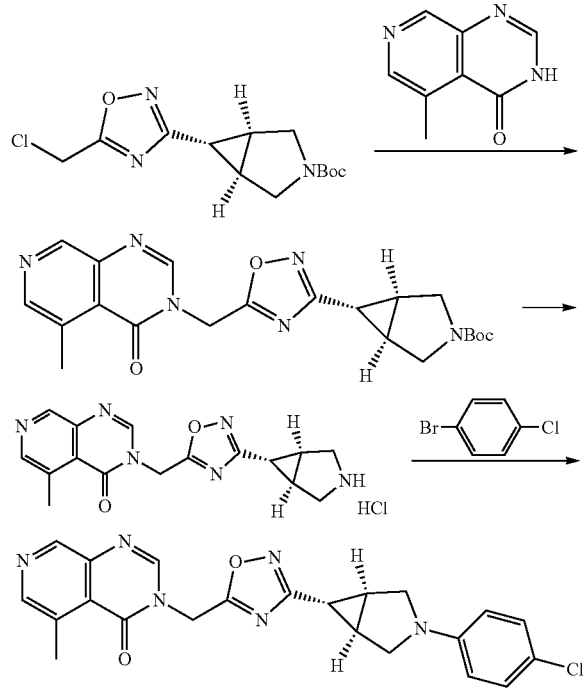

Step 1: Preparation of (1R,5S,6r)-tert-butyl 6-(5-((5-methyl-4-oxopyrido[3,4-d]pyrimidin-3(4H)-yl)methyl)-1,2,4-oxadiazol-3-yl)-3-azabicyclo [3.1.0] hexane-3-carboxylate

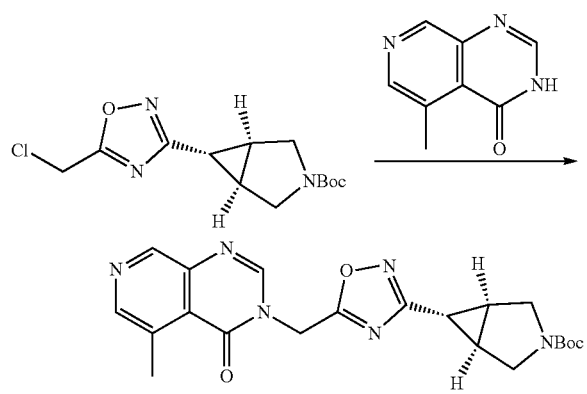

The title compound was prepared from (1R,5S,6r)-tert-butyl 6-(5-(chloromethyl)-1,2,4-oxadiazol-3-yl)-3-azabicyclo[3.1.0]hexane-3-carboxylate and 5-methylpyrido[3,4-d]pyrimidin-4(3H)-one in a manner analogous to Example 4, Step 6.

Step 2: Preparation of 3-((3-((1R,5S,6r)-3-azabicyclo[3.1.0]hexan-6-yl)-1,2,4-oxadiazol-5-yl)methyl)-5-methylpyrido[34-d]pyrimidin-4(3H)-one hydrochloride

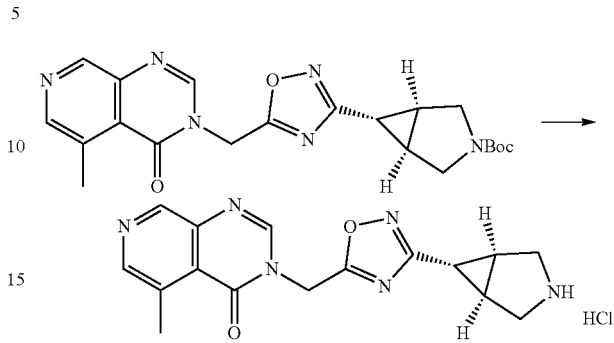

The title compound was prepared from (1R,5S,6r)-tert-butyl 6-(5-((5-methyl-4-oxopyrido[3,4-d]pyrimidin-3(4H)-yl)methyl)-1,2,4-oxadiazol-3-yl)-3-azabicyclo[3.1.0]hexane-3-carboxylate in a manner analogous to Example 4, Step 7.

Step 3: Preparation of 5-methyl-3-[[3-[(1R,5S,6r)-3-(4-chlorophenyl)-3,2,4-oxadiazol-5-yl)methyl)-5-yl]methyl]pyrido[3,4-d]pyrimidin-4-one

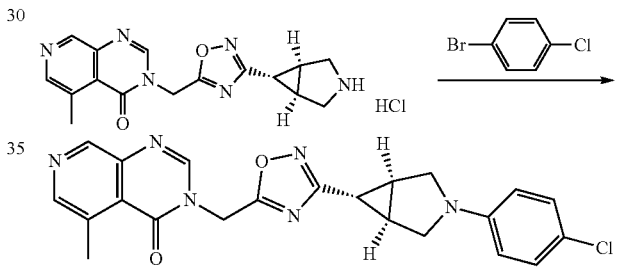

The title compound was prepared from 3-((3-((1R,5S,6r)-3-azabicyclo[3.1.0]hexan-6-yl)-1,2,4-oxadiazol-5-yl)methyl)-5-methylpyrido[3,4-d]pyrimidin-4(3H)-one hydrochloride (115 mg, 0.320 mmol) and 1-bromo-4-chlorobenzene (73.5 mg, 0.384 mmol) as a white crystalline solid (9.2 mg, 7% yield), in a manner analogous to Example 4, Step 8. LCMS [M+H$^+$] 435.1. $^1$H NMR (400 MHz, DMSO) δ 8.95-8.89 (m, 1H), 8.61 (s, 1H), 8.55-8.49 (m, 1H), 7.21-7.13 (m, 2H), 6.60-6.52 (m, 2H), 5.49 (s, 2H), 3.65 (d, J=9.7 Hz, 2H), 3.26-3.21 (m, 2H), 2.70 (s, 3H), 2.24-2.16 (m, 2H), 2.03 (t, J=3.2 Hz, 1H).

Example 37: Preparation of 3-((3-((1s,3s)-3-(4-chlorophenyl)-3-fluorocyclobutyl)-1,2,4-oxadiazol-5-yl)methyl)-5-methylpyrido[3,4-d]pyrimidin-4(3H)-one (Example Compound 37)

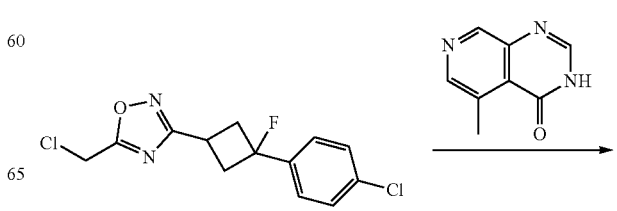

223
-continued

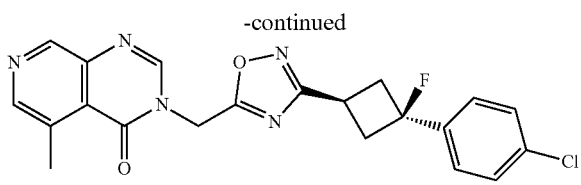

The title compound was prepared from 5-(chloromethyl)-3-(3-(4-chlorophenyl)-3-fluorocyclobutyl)-1,2,4-oxadiazole and 5-methylpyrido[3,4-d]pyrimidin-4(3H)-one in a manner analogous to Example 1, Step 6. LCMS [M+H+]: 426.2. $^1$H NMR (300 MHz, DMSO-$d_6$) δ 8.95 (s, 1H), 8.66 (s, 1H), 8.54 (s, 1H), 7.62 (d, J 8.1 Hz, 2H), 7.52 (d, J 8.4 Hz, 2H), 5.57 (s, 2H), 3.51-3.38 (m, 1H), 3.13-2.98 (m, 2H), 2.95-2.78 (m, 2H), 2.71 (s, 3H).

Example 38: Preparation of 3-((3-((1s,3s)-3-(4-chlorophenyl)-3-fluorocyclobutyl)-1,2,4-oxadiazol-5-yl)methyl)-5-methylpyrido[2,3-d]pyrimidin-4(3H)-one (Example Compound 38)

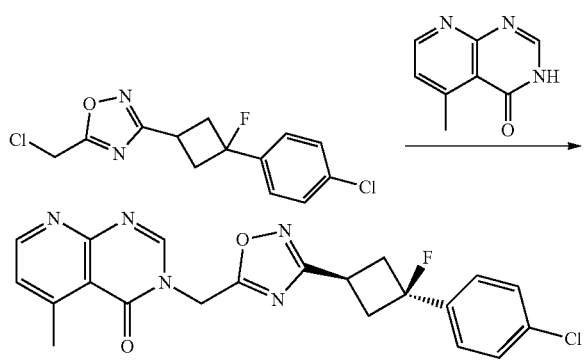

The title compound was prepared from 5-(chloromethyl)-3-(3-(4-chlorophenyl)-3-fluorocyclobutyl)-1,2,4-oxadiazole and 5-methylpyrido[2,3-d]pyrimidin-4(3H)-one in a manner analogous to Example 1, Step 6. LCMS [M+H+]: 426.2. $^1$H NMR (300 MHz, DMSO-$d_6$) δ 8.81 (d, J 4.8 Hz, 1H), 8.74 (s, 1H), 7.62 (d, J 8.5 Hz, 2H), 7.52 (d, J 8.3 Hz, 2H), 7.42 (d, J 5.1 Hz, 1H), 5.56 (s, 2H), 3.43 (m, 1H), 3.05 (m, 2H), 2.96-2.80 (m, 2H), 2.78 (s, 3H).

Example 39: Preparation of 1-((3-((1R,5S,6r)-3-(3-fluorophenyl)-3-azabicyclo[3.1.0]hexan-6-yl)-1,2,4-oxadiazol-5-yl)methyl)-7-methyl-1,7-dihydro-6H-purin-6-one-8-d (Example Compound 80

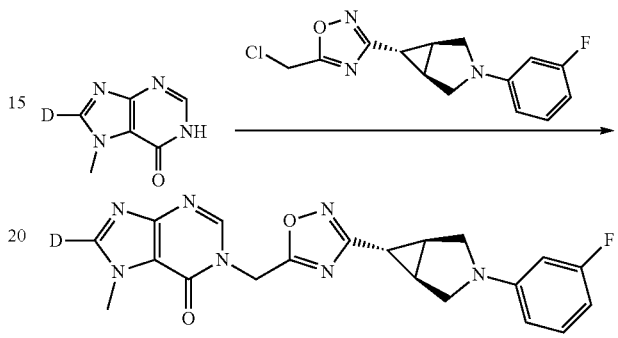

A mixture of 8-deuterio-7-methyl-1H-purin-6-one (30 mg, 0.20 mmol), 5-(chloromethyl)-3-[(1R,5S)-3-(3-fluorophenyl)-3-azabicyclo[3.1.0]hexan-6-yl]-1,2,4-oxadiazole (58 mg, 0.20 mmol), $K_2CO_3$ (54 mg, 0.40 mmol), and TBAI (3 mg, 0.01 mmol) in N,N-dimethylformamide (2 mL) was stirred at room temperature for 2 hours. The resulting solution was purified by reversed-phase HPLC to yield the title compound (28 mg, 35% yield)) as a white solid. LCMS [M+H+]: 409.2. $^1$H NMR (400 MHz, DMSO-$d_6$) δ 8.44 (s, 1H), 7.16-7.12 (m, 1H), 6.44-6.36 (m, 3H), 5.52 (s, 2H), 3.95 (s, 3H), 3.68 (d, J=10.0 Hz, 2H), 3.31-3.26 (m, 2H), 2.20 (m, 2H), 2.01 (t, J=3.2 Hz, 1H).

Example 40: Preparation of 1-((3-((1r,3r)-3-((3-chlorophenyl)difluoromethyl) cyclobutyl)-1,2,4-oxadiazol-5-yl)methyl)-7-methyl-1,7-dihydro-6H-purin-6-one (Example compound 81

The overall Example 40 reaction scheme is as follows:

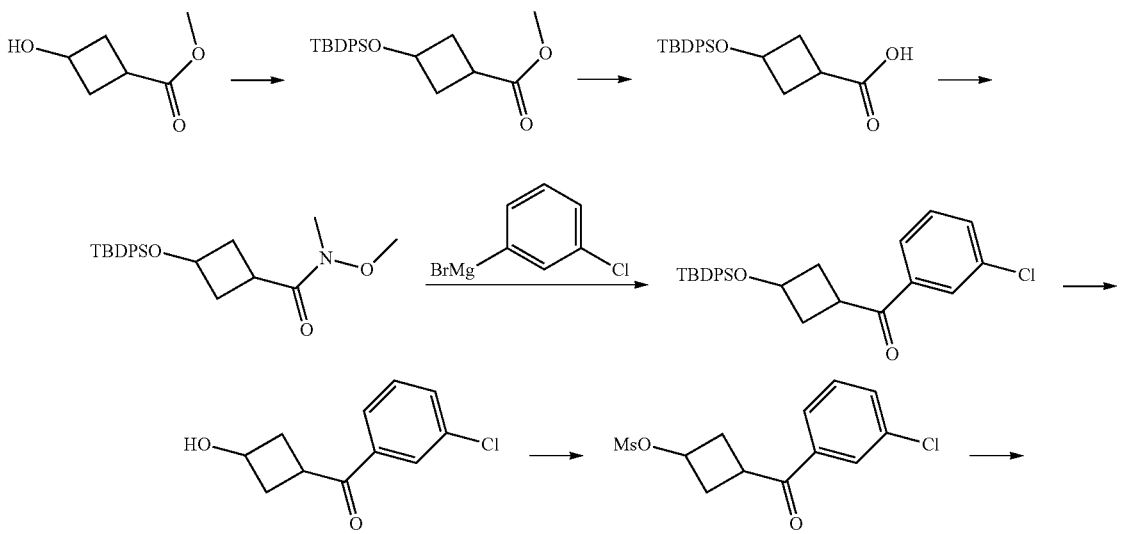

Step 1: Preparation of methyl 3-((tert-butyldiphenylsilyl)oxy)cyclobutane-1-carboxylate TBDPSCl (12.63 g, 46.10 mmol) was added to a solution of methyl-3-hydroxycyclobutanecarboxylate (5.0 g, 38.42 mmol) and imidazole (5.23 g, 76.84 mmol) in dichloromethane (40 mL) at room temperature, the solution was stirred at room temperature for 3 hours. The reaction was diluted with DCM, washed with water and brine, dried over Na$_2$SO$_4$, and concentrated under vacuum to afford the title compound (14 g, 98% yield) as colorless oil.

Step 2: Preparation of 3-((tert-butyldiphenylsilyl)oxy)cyclobutane-1-carboxylic Acid A solution of methyl 3-[tert-butyl(diphenyl)silyl]oxycyclobutanecarboxylate (13.0 g, 35.27 mmol) and NaOH (5M) (14.11 mL, 70.55 mmol) in ethanol (50 mL) was stirred at room temperature for 4 hours. The pH value of the solution was adjusted to 7 with HCl (1M). The reaction solution was extracted with ethyl acetate, washed with water and brine, dried over Na$_2$SO$_4$, and concentrated under vacuum to afford the title compound (10 g, 80% yield) as colorless oil.

Step 3: Preparation of 3-((tert-butyldiphenylsilyl)oxy)-N-methoxy-N-methylcyclobutane-1-carboxamide A solution of 3-[tert-butyl(diphenyl)silyl]oxycyclobutanecarboxylic acid (11.0 g, 31.03 mmol) and N,O-dimethylhydroxylamine hydrochloride (6.05 g, 62.06 mmol), DIEA (20.01 g, 155.14 mmol) in N,N-dimethylformamide (400 mL) was stirred at 25° C. for 5 min. Then HATU (17.7 g, 46.54 mmol) was added in portions and stirred at 25° C. for 2 hours. The reaction was diluted with water, extracted with ethyl acetate, washed with water and brine, dried over Na₂SO₄, and concentrated under vacuum. The crude product was adsorbed onto silica gel and purified by flash column chromatography eluted with DCM/PE (4:1) to afford the title compound (11 g, 89% yield).

Step 4: Preparation of (3-((tert-butyldiphenylsilyl)oxy)cyclobutyl) (3-chlorophenyl) methanone

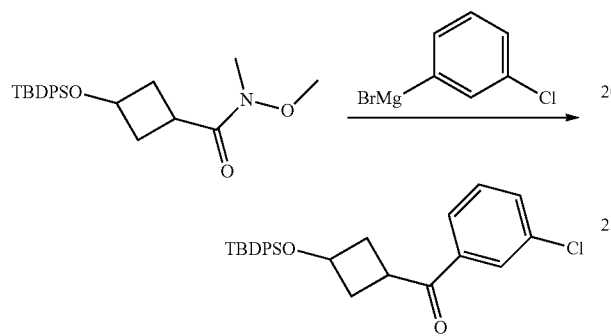

3-chlorophenylmagnesiumbromide (110.67 mL, 55.33 mmol) was added dropwise to a solution of 3-[tert-butyl(diphenyl)silyl]oxy-N-methoxy-N-methyl-cyclobutanecarboxamide (11.0 g, 27.67 mmol) in tetrahydrofuran (200 mL) at 0° C. and the resulting mixture was stirred at room temperature for 2 hours. The reaction was quenched with water, extracted with ethyl acetate, washed with water and brine, and concentrated under vacuum. The crude product was adsorbed onto silica gel and purified by flash column chromatography eluted with PE/DCM (1:1) to afford the title compound (10.8 g, 86% yield) as greenish oil.

Step 5: Preparation of (3-chlorophenyl)(3-hydroxycyclobutyl)methanone

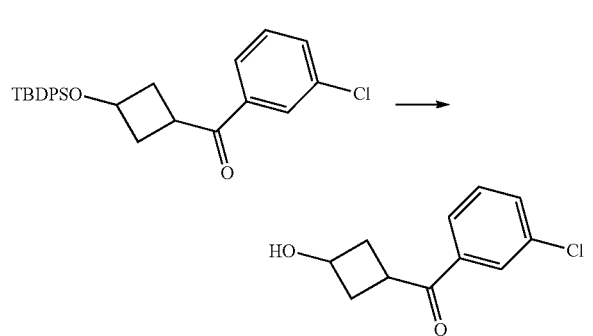

A solution of [3-[tert-butyl(diphenyl)silyl]oxycyclobutyl]-(3-chlorophenyl) methanone (10.8 g, 24.05 mmol) and TBAF.3H₂O (9.85 g, 31.27 mmol) in tetrahydrofuran (150 mL) was stirred at room temperature for 2 hours. The solvent was removed under vacuum. The crude product was adsorbed onto silica gel and purified by flash column chromatography eluted with ethyl acetate/petroleum ether (1:1) to afford the title compound (4.5 g, 88% yield) as light yellow oil.

Step 6: Preparation of 3-(3-chlorobenzoyl)cyclobutyl methanesulfonate

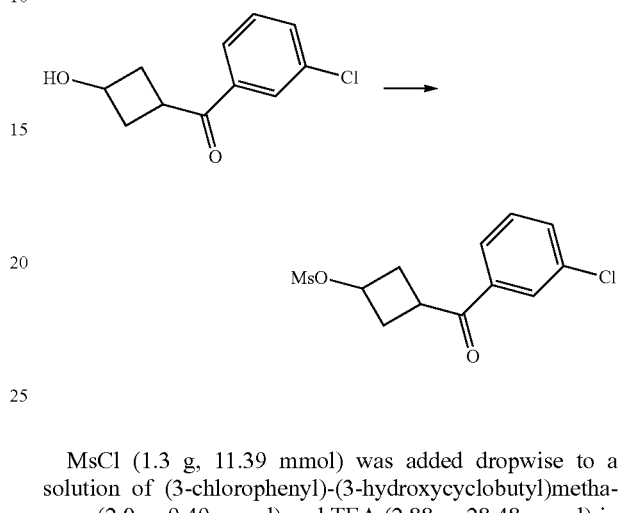

MsCl (1.3 g, 11.39 mmol) was added dropwise to a solution of (3-chlorophenyl)-(3-hydroxycyclobutyl)methanone (2.0 g, 9.49 mmol) and TEA (2.88 g, 28.48 mmol) in dichloromethane (60 mL) at room temperature and the resulting mixture was stirred for 1 hour. The reaction was concentrated under vacuum, diluted with ethyl acetate, washed with water, dried by Na₂SO₄, and concentrated under vacuum to afford the title compound (2.7 g, 98% yield) as colorless oil.

Step 7: Preparation of 3-(3-chlorobenzoyl)cyclobutane-1-carbonitrile

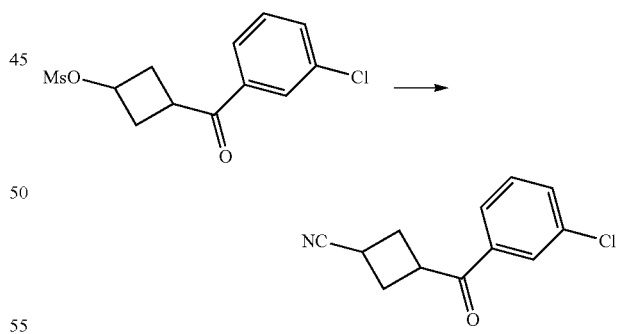

A solution of [3-(3-chlorobenzoyl)cyclobutyl] methanesulfonate (2.7 g, 9.35 mmol) and NaCN (0.69 g, 14.03 mmol) in dimethyl sulfoxide (20 mL) was stirred at 130° C. for 12 hours. The solution was diluted with H₂O, extracted with ethyl acetate, washed with water and brine, dried with Na₂SO₄, and concentrated under vacuum. The crude product was adsorbed onto silica gel and purified by flash column chromatography eluted with ethyl acetate/petroleum ether (1:4) to afford the title compound (1.57 g, 76% yield) as light brown oil.

Step 8: Preparation of (Z)-3-(3-chlorobenzoyl)-N'-hydroxycyclobutane-1-carboximidamide

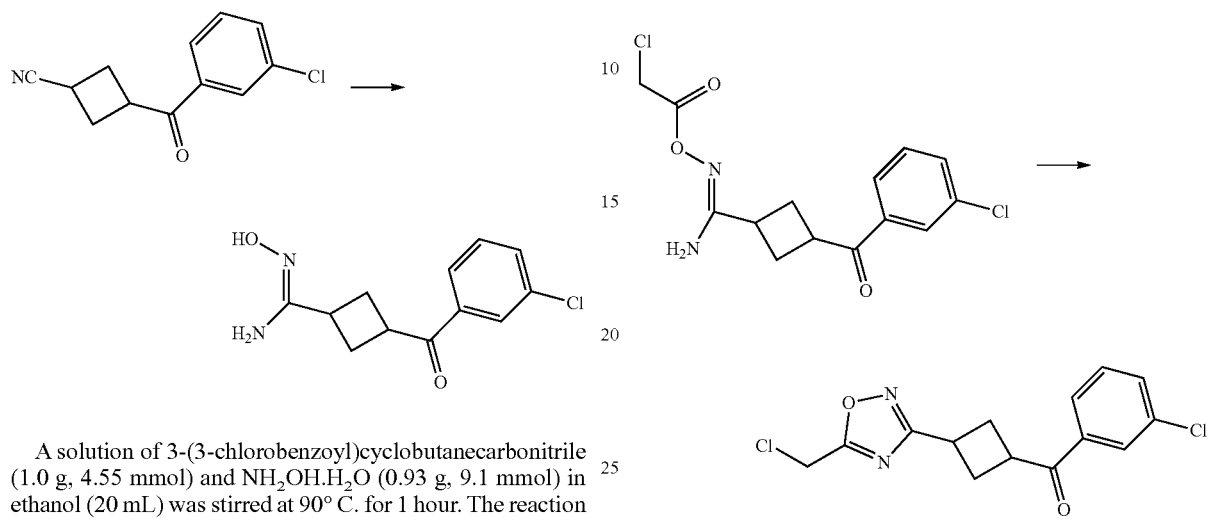

A solution of 3-(3-chlorobenzoyl)cyclobutanecarbonitrile (1.0 g, 4.55 mmol) and NH$_2$OH.H$_2$O (0.93 g, 9.1 mmol) in ethanol (20 mL) was stirred at 90° C. for 1 hour. The reaction mixture was concentrated under vacuum to afford the title compound (1.16 g, 100% yield) as a white solid.

Step 9: Preparation of (Z)—N'-(2-chloroacetoxy)-3-(3-chlorobenzoyl) cyclobutane-1-carboximidamide 2-chloroacetyl chloride (0.57 g, 5.05 mmol) was added dropwise to a solution of 3-(3-chlorobenzoyl)-N-hydroxycyclobutanecarboxamidine (1.16 g, 4.59 mmol) and TEA (0.51 g, 5.05 mmol) in acetone (20 mL) at 0° C. and the resulting mixture was stirred at room temperature for 1 hours. The reaction mixture was concentrated under vacuum, diluted with ethyl acetate, washed with water, dried with Na$_2$SO$_4$, and concentrated under vacuum to afford the title compound (1.5 g, 99% yield) as crude greenish oil.

Step 10: Preparation of (3-(5-(chloromethyl)-1,2,4-oxadiazol-3-yl)cyclobutyl) (3-chlorophenyl)methanone

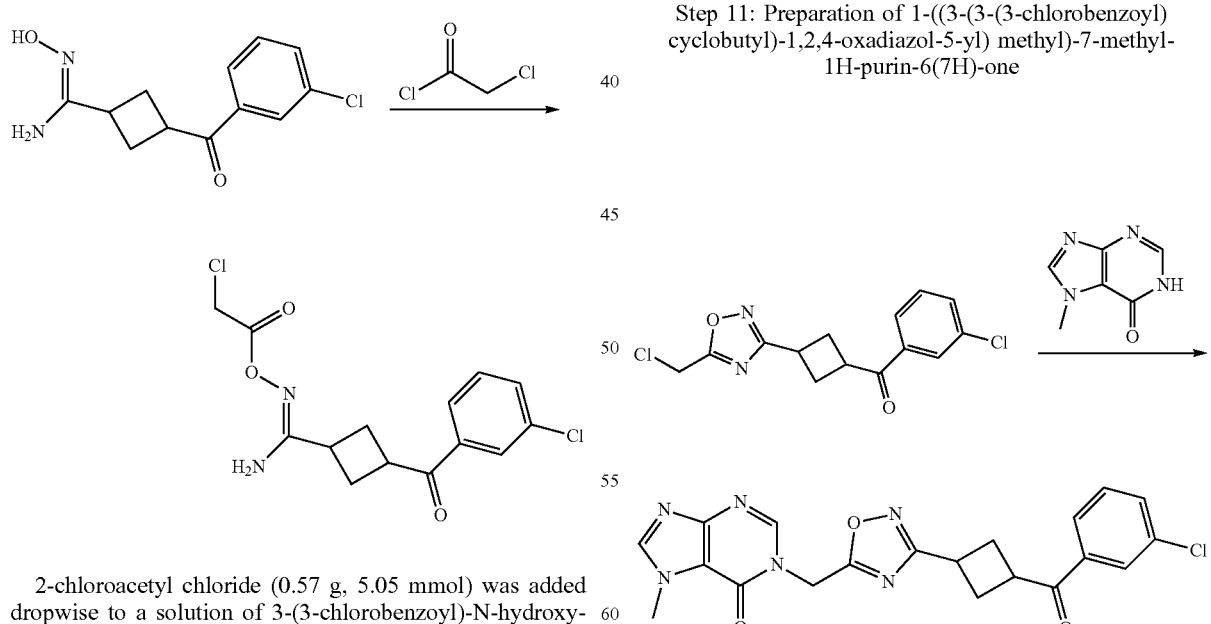

A solution of [amino-[3-(3-chlorobenzoyl)cyclobutyl]methylene]amino 2-chloroacetate (600 mg, 1.82 mmol) in toluene (10 mL) was stirred at 80° C. for 12 hours. The reaction mixture was concentrated under vacuum. The crude product was adsorbed onto silica gel and purified by flash column chromatography eluted with ethyl acetate/petroleum ether (1:5) to afford the title compound (350 mg, 61% yield) as greenish oil.

Step 11: Preparation of 1-((3-(3-(3-chlorobenzoyl)cyclobutyl)-1,2,4-oxadiazol-5-yl) methyl)-7-methyl-1H-purin-6(7H)-one The title compound was prepared from (3-(5-(chloromethyl)-1,2,4-oxadiazol-3-yl)cyclobutyl)(3-chlorophenyl)methanone (60 mg, 0.19 mmol) and 7-methyl-1H-purin-6(7H)-one (28.95 mg, 0.19 mmol) in a manner analogous to Example 1, Step 6.

Step 12: Preparation of 1-[[3-[3-[2-(3-chlorophenyl)-1,3-dithian-2-yl] cyclobutyl]-1,2,4-oxadiazol-5-yl]methyl]-7-methyl-purin-6-one HPLC to yield the title compound (5 mg, 6% yield) as a white solid. LCMS [M+H⁺]: 447.1. ¹H NMR (400 MHz, DMSO-$d_6$) δ 8.44 (s, 1H), 8.24 (s, 1H), 7.59 (s, 2H),

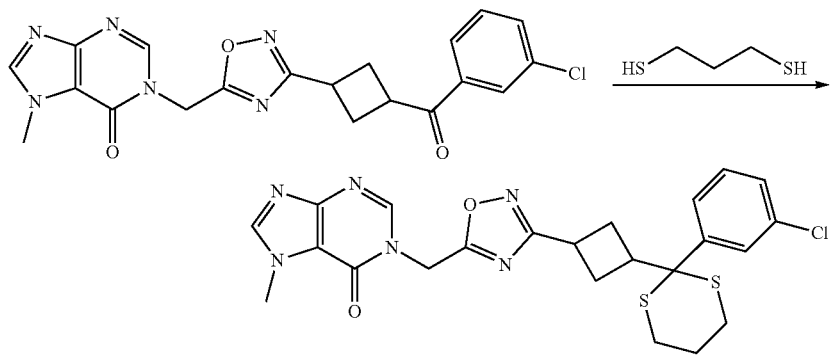

Boron trifluoride etherate (640 mg, 4.51 mmol) was added dropwise to a solution of 1-[[3-[3-(3-chlorobenzoyl)cyclobutyl]-1,2,4-oxadiazol-5-yl]methyl]-7-methyl-purin-6-one (200 mg, 0.47 mmol) and 1,3-propanedithiol (80 mg, 0.74 mmol) in DCM (1 mL). The resulting mixture was stirred for four days at room temperature, diluted with saturated aqueous NaHCO₃, extracted with ethyl acetate, washed with brine, and concentrated under vacuum. The residue was purified by reversed phase HPLC to yield the title compound (150 mg, 62% yield) as a white solid.

Step 13: Preparation of 1-((3-((1r,3r)-3-((3-chlorophenyl)difluoromethyl)cyclobutyl)-1,2,4-oxadiazol-5-yl)methyl)-7-methyl-1,7-dihydro-6H-purin-6-one 7.55-7.51 (d, J=7.1 Hz, 2H), 5.55 (s, 2H), 3.94 (s, 3H), 3.59 (s, 1H), 3.33-3.32 (m, 1H), 2.57-2.53 (m, 2H), 2.31-2.27 (m, 2H).

Examples 41 and 42: Preparation of 7-methyl-1-[[3-[(1R,5R,6S)-3-(2-fluorophenyl)-6-bicyclo[3.1.0]hex-2-enyl]-1,2,4-oxadiazol-5-yl]methyl]purin-6-one (Example Compound 83) and 7-methyl-1-[[3-[(1S,5S,6R)-3-(2-fluorophenyl)-6-bicyclo[3.1.0]hex-2-enyl]-1,2,4-oxadiazol-5-yl]methyl]purin-6-one (Example Compound 82)

The overall Examples 41 and 42 reaction scheme is as follows:

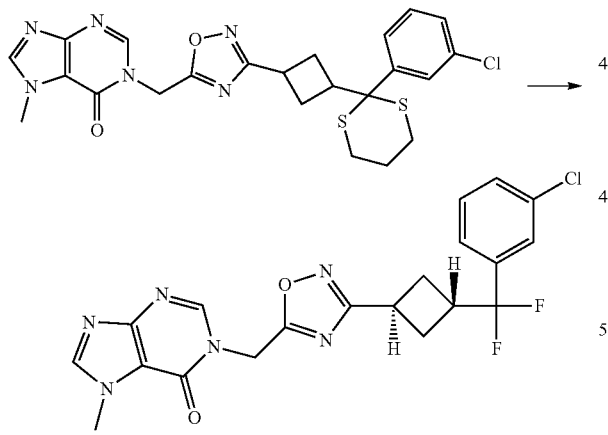

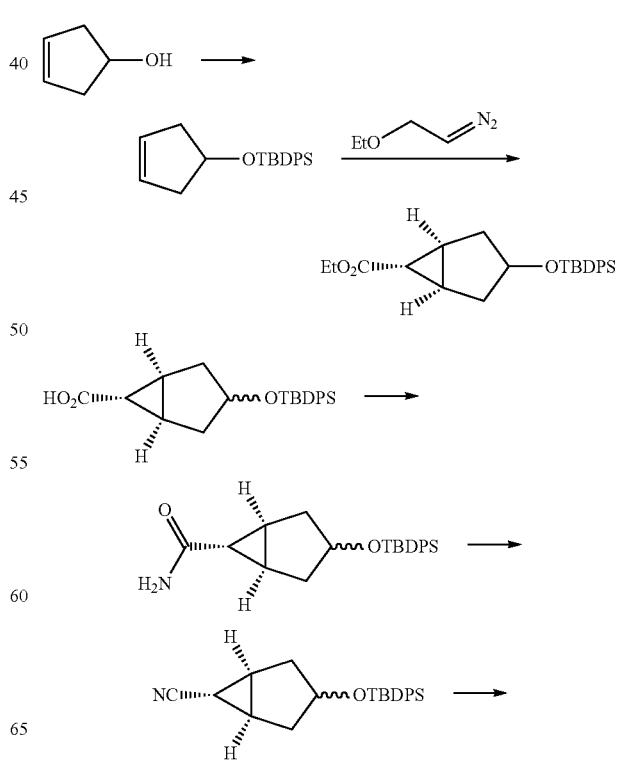

Pyridine hydrofluoride (80%) (0.25 mL, 2.78 mmol) was added dropwise into a solution of DBH (280 mg, 0.98 mmol) in DCM (15 mL) at −78° C. under nitrogen. The resulting solution was stirred over 20 min below −70° C. and then a solution of 1-[[3-[3-[2-(3-chlorophenyl)-1,3-dithian-2-yl] cyclobutyl]-1,2,4-oxadiazol-5-yl]methyl]-7-methyl-purin-6-one (100 mg, 0.19 mmol) in DCM (5 mL) was added dropwise at −78° C. The resulting solution was stirred for 2 hours at room temperature, quenched by aqueous solution of Na₂S₂O₃, adjusted to pH 7 with saturated NaHCO₃, extracted with ethyl acetate, washed with brine, concentrated under vacuum, and then purified by reversed phase

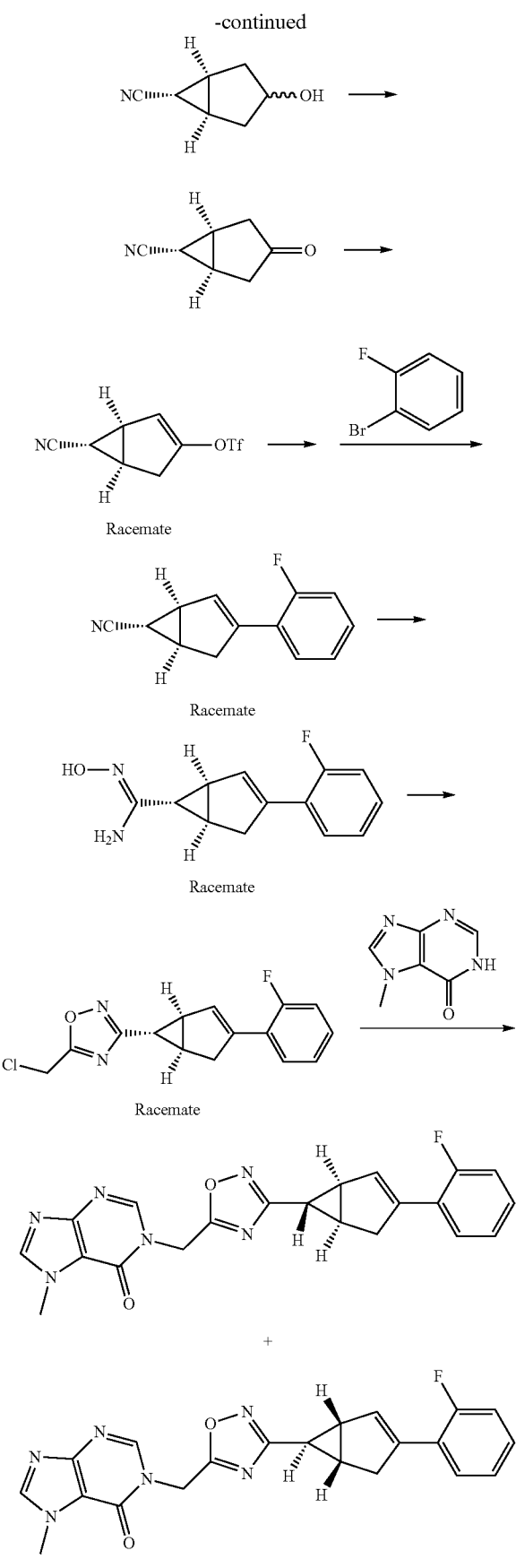

Racemate

Racemate

Racemate

Racemate

+

Step 1: Preparation of tert-butyl(cyclopent-3-en-1-yloxy)diphenylsilane

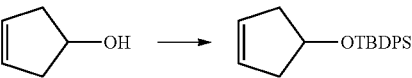

Into a 2000-mL 3-necked round-bottom flask purged and maintained with an inert atmosphere of nitrogen, was placed cyclopent-3-en-1-ol (100 g, 1.17 mol, 1.00 equiv, 98%), N,N-dimethylformamide (1000 mL), Imidazole (198 g, 2.50 equiv, 98%). This was followed by the addition of TBDPSCl (376 g, 0.98 equiv, 98%) dropwise with stirring at 0-5° C. in 1 hr. The resulting solution was stirred for 15 h at 25° C. in a water bath. The reaction was repeated for 1 time. The reaction was then quenched by the addition of 10 L of water, extracted with 3×1000 mL of ethyl acetate and the organic layers combined. The resulting mixture was washed with 1×500 mL of brine. The residue was applied onto a silica gel column with ethyl acetate/petroleum ether (0:100). This resulted in 690 g (90%) of tert-butyl(cyclopent-3-en-1-yloxy)diphenylsilane as a colorless oil.

Step 2: Preparation of ethyl (1R,5S,6R)-3-[(tert-butyldiphenylsilyl)oxy]bicyclo[3.1.0]hexane-6-carboxylate

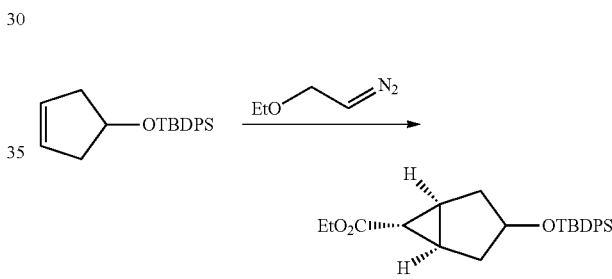

Into a 3000-mL 3-necked round-bottom flask purged and maintained with an inert atmosphere of nitrogen, was placed dichloromethane (1.5 L), tert-butyl(cyclopent-3-en-1-yloxy) diphenylsilane (172.5 g, 534.86 mmol, 1.00 equiv), tris (acetyloxy)dirhodium-1-yl acetate (2.83 g, 6.34 mmol, 0.01 equiv). This was followed by the addition of a solution of ethyl 2-diazoacetate (134.35 g, 1.18 mol, 2.20 equiv) in dichloromethane (1.5 L) dropwise with stirring at 25° C. in 8 hr. The resulting solution was stirred for overnight at 25° C. in a water bath. The reaction was repeated for 3 times. The resulting mixture was concentrated under vacuum. This resulted in 864 g (crude) of ethyl (1R,5S,6R)-3-[(tert-butyldiphenylsilyl)oxy]bicyclo[3.1.0]hexane-6-carboxylate as yellow oil.

Step 3: Preparation of (1R,5S,6R)-3-[(tert-butyldiphenylsilyl)oxy]bicyclo[3.1.0]hexane-6-carboxylic Acid

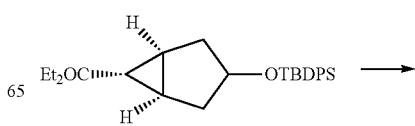

-continued

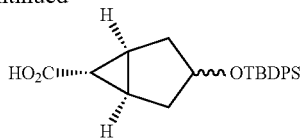

Into a 10000-mL 4-necked round-bottom flask purged and maintained with an inert atmosphere of nitrogen, was placed ethyl (1R,5S,6R)-3-[(tert-butyldiphenylsilyl)oxy]bicyclo[3.1.0]hexane-6-carboxylate (860 g, 2.10 mol, 1.00 equiv), ethanol (3000 ml). This was followed by the addition of sodium hydroxide (583 g, 8.13 equiv, 5N) dropwise with stirring at 15° C. in 2 hr. The resulting solution was stirred for 24 h at 25° C. in a water bath. The resulting mixture was concentrated under vacuum. The pH value of the solution was adjusted to 3-4 with HCl (4 N). The solid was collected by filtration and dried in an oven under reduced pressure. This resulted in 400 g (50%) of (1R,5S,6R)-3-[(tert-butyldiphenylsilyl)oxy]bicyclo[3.1.0]hexane-6-carboxylic acid as off-white solid.

Step 4: Preparation of (1R,5S,6S)-3-[(tert-butyldiphenylsilyl)oxy]bicyclo[3.1.0]hexane-6-carboxamide

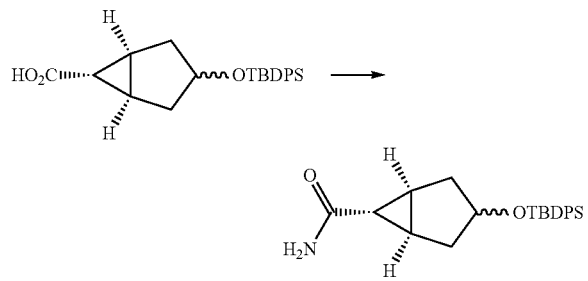

Into a 10000-mL 4-necked round-bottom flask purged and maintained with an inert atmosphere of nitrogen, was placed (1R,5S,6S)-3-[(tert-butyldiphenylsilyl)oxy]bicyclo[3.1.0]hexane-6-carboxylic acid (400.0 g, 1.05 mol, 1.00 equiv), N,N-dimethylformamide (4000 mL). This was followed by the addition of HATU (599.52 g, 1.58 mol, 1.50 equiv) at 10° C. To this was added DIEA (407.6 g, 3.15 mol, 3.00 equiv) at 15° C. and stirred for 30 min at 25° C. in a water bath. To the mixture was added NH₄Cl (168.9 g, 3.16 mol, 3.00 equiv) portionwise with stirring at 15° C. The resulting solution was stirred for 3 h at 25° C. in a water bath. The resulting solution was diluted with 8000 mL of water. The solids were collected by filtration. The solid was dried in an oven under reduced pressure. This resulted in 370 g (92.7%) of (1R,5S,6S)-3-[(tert-butyldiphenylsilyl)oxy]bicyclo[3.1.0]hexane-6-carboxamide as a white solid.

Step 5: Preparation of (1R,5S,6S)-3-[(tert-butyldiphenylsilyl)oxy]bicyclo[3.1.0]hexane-6-carbonitrile Into a 5000-mL 4-necked round-bottom flask purged and maintained with an inert atmosphere of nitrogen, was placed Dioxane (3500 mL), (1R,5S,6S)-3-[(tert-butyldiphenylsilyl)oxy]bicyclo[3.1.0]hexane-6-carboxamide (370.0 g, 974.79 mmol, 1.00 equiv), Pyridine (200 g, 2.53 mol, 2.60 equiv). This was followed by the addition of TFAA (266.1 g, 1.27 mol, 1.30 equiv) dropwise with stirring at 15° C. in 1 hr. The resulting solution was stirred for 4 h at 25° C. in a water bath. The resulting solution was diluted with 2500 mL of NaHCO₃ (aq.) and 2500 mL of H₂O. The resulting solution was extracted with 3×1 L of dichloromethane and the organic layers combined and concentrated under vacuum. The residue was applied onto a silica gel column with EA:PE (1:4). This resulted in 300 g (85%) of (1R,5S,6S)-3-[(tert-butyldiphenylsilyl)oxy]bicyclo[3.1.0]hexane-6-carbonitrile as a white solid.

Step 6: Preparation of (1R,5S,6S)-3-hydroxybicyclo[3.1.0]hexane-6-carbonitrile

Into a 5000-mL 4-necked round-bottom flask purged and maintained with an inert atmosphere of nitrogen, was placed tetrahydrofuran (3000 mL), (1R,5S,6S)-3-[(tert-butyldiphenylsilyl)oxy]bicyclo[3.1.0]hexane-6-carbonitrile (300 g, 829.76 mmol, 1.00 equiv). This was followed by the addition of TBAF (1246 mL, 1.50 equiv, 1 mol/L) dropwise with stirring at 15° C. in 2 hr. The resulting solution was stirred for 14 h at 25° C. in a water bath. The reaction was then quenched by the addition of 3000 mL of saturated NH₄Cl (aq.) and 2000 mL of H₂O. The resulting solution was extracted with 3×1 L of ethyl acetate and the organic layers combined and concentrated under vacuum. The residue was applied onto a silica gel column with EA:PE (2:3). This resulted in 86 g (84.3%) of (1R,5S,6S)-3-hydroxybicyclo[3.1.0]hexane-6-carbonitrile as yellow oil.

Step 7: Preparation of (1R,5S,6S)-3-oxobicyclo[3.1.0]hexane-6-carbonitrile

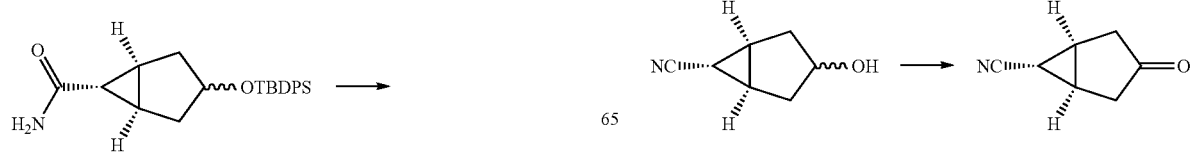

Into a 10000-mL 4-necked round-bottom flask purged and maintained with an inert atmosphere of nitrogen, was placed (1R,5S,6S)-3-hydroxybicyclo[3.1.0]hexane-6-carbonitrile (86 g, 698.32 mmol, 1.00 equiv), dichloromethane (6000 mL). This was followed by the addition of DMP (370 g, 872.35 mmol, 1.25 equiv), in portions at 0-5° C. in 2 hr. The resulting solution was stirred for 2 h at 0-5° C. in a water/ice bath. The resulting solution was allowed to react, with stirring, for an additional 12 h while the temperature was maintained at 25° C. in a water bath. The reaction was then quenched by the addition of 1 L of saturated NaSO₃. The resulting solution was diluted with 1 L of water. The pH value of the solution was adjusted to 7 with saturated sodium bicarbonate. The resulting solution was extracted with 3×1 L of dichloromethane and the organic layers combined and concentrated under vacuum. The residue was applied onto a silica gel column with ethyl acetate/petroleum ether (1:2). This resulted in 55 g (65%) of (1R,5S,6S)-3-oxobicyclo [3.1.0]hexane-6-carbonitrile as off-white solid.

Step 8: Preparation of rac-(1S,5R,6S)-6-cyanobicyclo[3.1.0]hex-2-en-3-yl trifluoromethanesulfonate

A solution of (trans)-3-oxobicyclo[3.1.0]hexane-6-carbonitrile (7.50 g, 61.9 mmol) and 2,6-di-tert-butyl-4-methylpyridine (50.9 g, 248 mmol) in DCE (280 mL) was stirred in a 75° C. oil bath in a 1 L RBF mounted with a condenser. Trifluoromethanesulfonic anhydride (41.7 mL, 248 mmol) was added over 15 min. The reaction mixture was heated for an additional 1 h50. Heat was removed and the mixture was cooled with an ice bath for 1 hour. The reaction was slowly quenched by the addition of silica gel over 2 min. and the mixture was allowed to stir at room temperature for 15 min. The slurry was directly filtered on a silica gel pad (2 L fritted funnel with 1000 mL of silica gel), eluting with a solution of ethyl acetate in hexanes (5 to 25% gradient) to afford rac-(1 S,5R,6S)-6-cyanobicyclo[3.1.0]hex-2-en-3-yl trifluoromethanesulfonate (12.7 g, 50.1 mmol, 81% yield) as a pale orange solid. ¹H NMR (500 MHz, CDCl₃) δ 5.88 (q, J=1.8 Hz, 1H), 3.05 (ddd, J=18.3, 7.2, 1.7 Hz, 1H), 2.75 (dt, J=18.3, 2.0 Hz, 1H), 2.56-2.51 (m, 1H), 2.25 (td, J=7.1, 3.7 Hz, 1H), 1.10 (t, J=3.4 Hz, 1H).

Step 9: Preparation of rac-(1R,5R,6S)-3-(2-fluorophenyl)bicyclo[3.1.0]hex-3-ene-6-carbonitrile

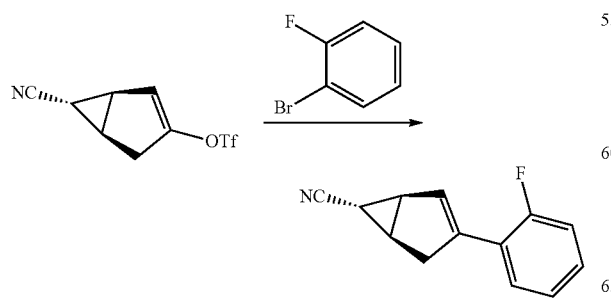

Degassed 1,4-Dioxane (11 mL) was added to a nitrogen purged and caped microwave vial containing rac-(1 S,5R,6S)-6-cyanobicyclo[3.1.0]hex-2-en-3-yl trifluoromethanesulfonate (850 mg, 3.36 mmol), dppf (186 mg, 0.340 mmol), Pd(dppf)Cl₂ (246 mg, 0.340 mmol), Bis(pinacolato)diborane (1.28 g, 5.04 mmol) and potassium acetate (999 mg, 10.1 mmol). The reaction mixture was heated at 70° C. for 1.5 hours. To the reaction mixture at 20° C. were added a 5M solution of potassium phosphate in water (3.4 mL, 16.8 mmol) and a solution of 1-bromo-2-fluorobenzene (1.1 mL, 10.1 mmol) in dioxane (1 mL). The reaction mixture was heated at 110° C. for 2 hours and allowed to stand overnight at 20° C. The obtained residue was purified by flash column chromatography (40 g column) on silica gel using a solution of EtOAc in hexanes (0 to 5% gradient) to afford rac-(1R, 5R,6S)-3-(2-fluorophenyl)bicyclo[3.1.0]hex-3-ene-6-carbonitrile (535 mg, 2.69 mmol, 80% yield) as a yellow oil.

Step 10: Preparation of rac-(1R,5R,6S)-3-(2-fluorophenyl)-N-hydroxy-bicyclo[3.1.0]hex-3-ene-6-carboxamidine

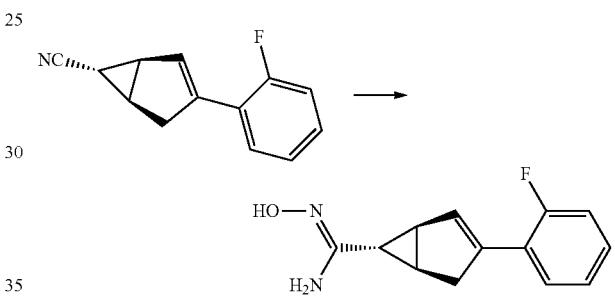

Hydroxylamine (50% in water, 1.1 mL, 18.2 mmol) was added to a solution of rac-(1R,5R,6S)-3-(2-fluorophenyl) bicyclo[3.1.0]hex-3-ene-6-carbonitrile (726 mg, 3.65 mmol) in EtOH (18 mL). The reaction mixture was stirred in an oil bath at 80° C. for 2 hours. The reaction mixture was concentrated under vacuum and it was co-evaporated with EtOH and DCM to afford rac-(1R,5R,6S)-3-(2-fluorophenyl)-N-hydroxy-bicyclo[3.1.0]hex-3-ene-6-carboxamidine (799 mg, 3.44 mmol, 94% yield) as a white solid. LCMS [M+H⁺] 233.4. The obtained material was used directly in the next reaction.

Step 11: Preparation of 5-(chloromethyl)-3-[rac-(1R,5R,6S)-3-(2-fluorophenyl)-6-bicyclo[3.1.0]hex-3-enyl]-1,2,4-oxadiazole

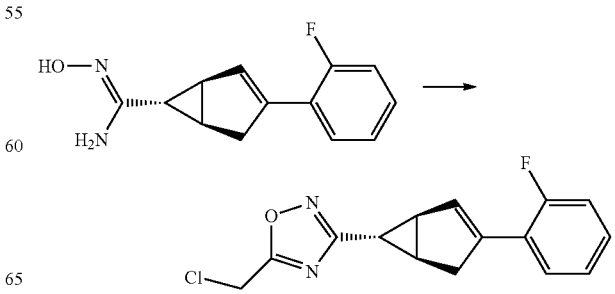

To a 100 mL RBF mounted with a condenser were added rac-(1R,5R,6S)-3-(2-fluorophenyl)-N-hydroxy-bicyclo[3.1.0]hex-3-ene-6-carboxamidine (799. mg, 3.44 mmol), DCE (34 mL) and chloroacetic anhydride (941 mg, 5.50 mmol). The reaction mixture was stirred 5 min. at 20° C. followed by the addition of pivalic acid (3.51 g, 34.4 mmol). The reaction mixture was stirred 1 h30 in a 90° C. oil bath and it was diluted with EtOAc and an aqueous solution of saturated NaHCO$_3$. The resulting mixture was transferred in a separatory funnel and the layers were separated. The organic layer was washed with an aqueous solution of saturated NaHCO$_3$ (3×) and brine, dried over anhydrous sodium sulfate, filtered and concentrated under vacuum. The obtained residue was purified by flash column chromatography (40 g column) on silica gel using a solution of EtOAc in hexanes (0 to 5% gradient) to afford 5-(chloromethyl)-3-[rac-(1R,5R,6S)-3-(2-fluorophenyl)-6-bicyclo[3.1.0]hex-3-enyl]-1,2,4-oxadiazole (768 mg, 2.64 mmol, 77% yield) as a yellow oil. LCMS [M+H$^+$] 291.3; $^1$H NMR (400 MHz, CDCl$_3$) δ 7.30-7.24 (m, 1H), 7.23-7.17 (m, 1H), 7.13-7.01 (m, 2H), 6.63-6.58 (m, 1H), 4.63 (s, 2H), 3.28-3.20 (m, 1H), 3.03-2.94 (m, 1H), 2.66-2.59 (m, 1H), 2.42-2.34 (m, 1H), 1.78-1.71 (m, 1H).

Step 12: Preparation of 7-methyl-1-[[3-[(1R,5R,6S)-3-(2-fluorophenyl)-6-bicyclo[3.1.0]hex-2-enyl]-1,2,4-oxadiazol-5-yl]methyl]purin-6-one (Example Compound 83) and 7-methyl-1-[[3-[(1S,5S,6R)-3-(2-fluorophenyl)-6-bicyclo[3.1.0]hex-2-enyl]-1,2,4-oxadiazol-5-yl]methyl]purin-6-one (Example Compound 82)

In a 50 mL RBF were charged 7-methyl-1H-purin-6-one (252 mg, 1.68 mmol), 5-(chloromethyl)-3-[rac-(1R,5R,6S)-3-(2-fluorophenyl)-6-bicyclo[3.1.0]hex-3-enyl]-1,2,4-oxadiazole (325 mg, 1.12 mmol), tetrabutylammonium iodide (41 mg, 0.11 mmol), potassium carbonate (464 mg, 3.35 mmol) and DMF (11 mL). The reaction mixture was stirred at 20° C. for 2 hours and it was diluted with water. The formed solid was collected by filtration to afford a racemic mixture of the desired product (416 mg, 1.03 mmol, 92% yield) as a light pink solid. The racemic material was separated by SFC with the following conditions: Column: ChiralCel OJ 10×250 mm, 5 μm, Isocratic 45% MeOH+10 mM Ammonium Formate, 10 mL/min, 100 Bar, 35° C., Run time: 14 min.

Example 42, enantiomer 1, (Example Compound 83): white solid, Rt=3.30 min (ChiralCel OJ, 4.6×150 mm, 5 to 55% MeOH+10 mM AmFor—5 mL/min); LCMS [M+H$^+$] 405.1; $^1$H NMR (400 MHz, DMSO-d6) δ 8.44 (s, 1H), 8.24 (s, 1H), 7.41-7.34 (m, 1H), 7.32-7.25 (m, 1H), 7.23-7.13 (m, 2H), 6.56 (s, 1H), 5.51 (s, 2H), 3.95 (s, 3H), 3.19-3.09 (m, 1H), 3.02-2.92 (m, 1H), 2.53-2.47 (m, 1H), 2.31-2.20 (m, 1H), 1.70-1.64 (m, 1H).

Example 41, enantiomer 2, (Example Compound 82): white solid, Rt=3.45 min (ChiralCel OJ, 4.6×150 mm, 5 to 55% MeOH+10 mM AmFor—5 mL/min); LCMS [M+H$^+$] 405.1; $^1$H NMR (400 MHz, DMSO-d6) δ 8.44 (s, 1H), 8.24 (s, 1H), 7.43-7.34 (m, 1H), 7.33-7.24 (m, 1H), 7.23-7.12 (m, 2H), 6.56 (s, 1H), 5.52 (s, 2H), 3.95 (s, 3H), 3.20-3.09 (m, 1H), 3.02-2.90 (m, 1H), 2.54-2.46 (m, 1H), 2.31-2.16 (m, 1H), 1.70-1.64 (m, 1H).

Example 43: Preparation of 1-((3-((1R,5S,6r)-3-(3-fluorophenyl)-3-azabicyclo[3.1.0]hexan-6-yl)-1,2,4-oxadiazol-5-yl)methyl)-7-methyl-1,7-dihydro-6H-purin-6-one-2-d (Example Compound 89)

The overall Example 43 reaction scheme is as follows:

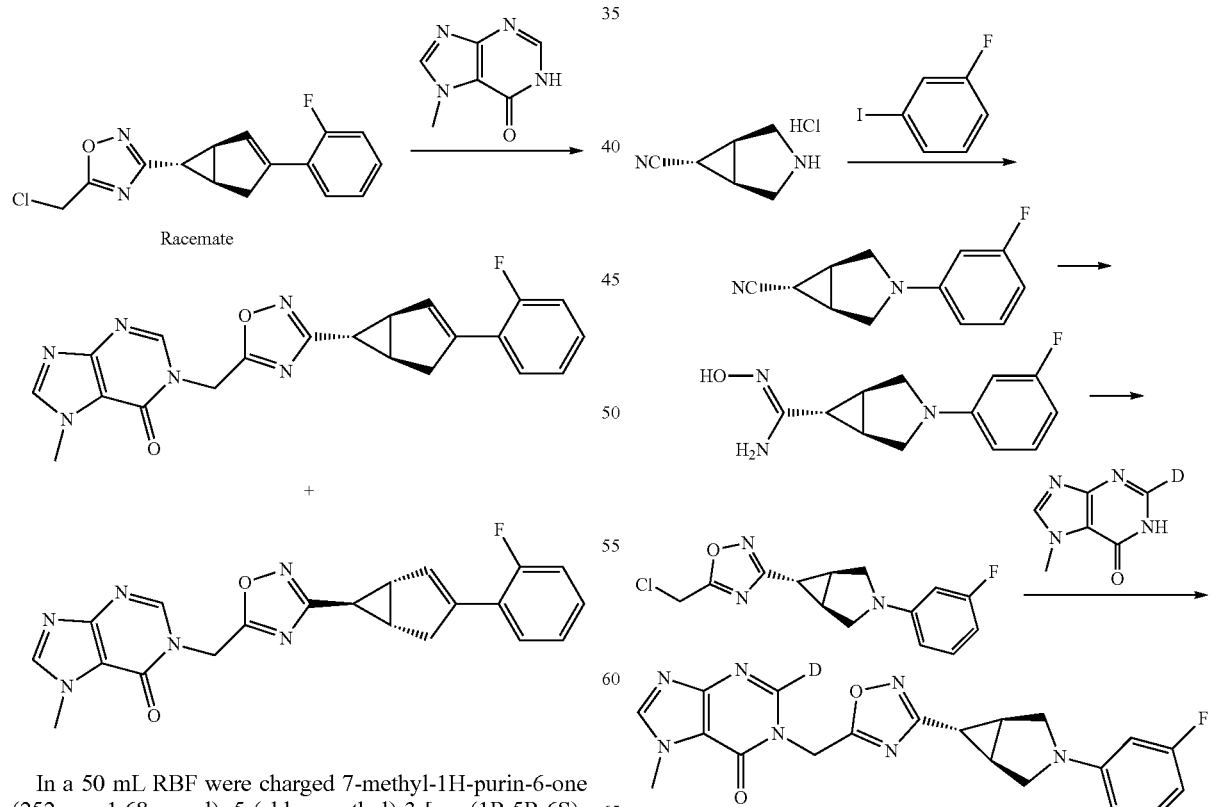

Step 1: Preparation of 3-(3-fluorophenyl)-3-azabi-cyclo[3.1.0]hexane-6-carbonitrile

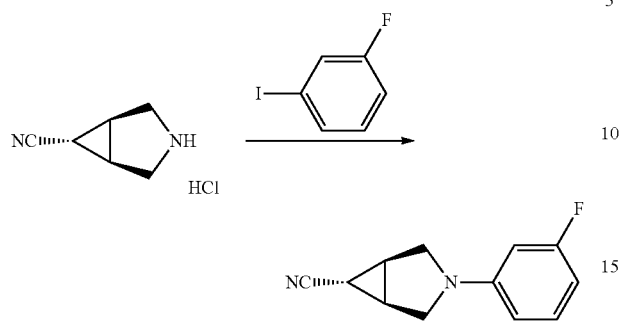

A mixture of 3-fluoroiodobenzene (1.02 g, 4.62 mmol), 3-azabicyclo[3.1.0]hexane-6-carbonitrile (500 mg, 4.62 mmol), Pd$_2$(dba)$_3$·CHCl$_3$ (423 mg, 0.46 mmol), SPhos (569 mg, 1.39 mmol), and Cs$_2$CO$_3$ (4519 mg, 13.87 mmol) in 1,4-dioxane (5 mL) was stirred for 2 hours at 100° C. under nitrogen. The solid was filtered out and the filtrate was concentrated under reduced pressure. The residue was adsorbed onto silica gel and purified by flash column chromatography eluted with ethyl acetate/petroleum ether (10/1). This resulted in the title compound (300 mg, 32% yield) as a yellow solid.

Step 2: Preparation of 3-(3-fluorophenyl)-N'-hydroxy-3-azabicyclo[3.1.0] hexane-6-carboxamidine

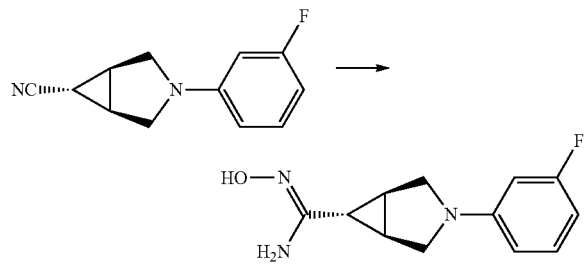

The title compound was prepared from (1R,5S,6r)-3-(3-fluorophenyl)-3-aza-bicyclo[3.1.0]hexane-6-carbonitrile in a manner analogous to Example 64, Step 4.

Step 3: Preparation of 5-(chloromethyl)-3-[3-(3-fluorophenyl)-3-azabicyclo hexan-6-yl]-1,2,4-oxadiazole

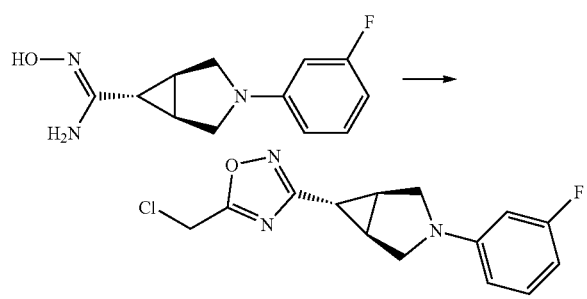

A solution of [3-(3-fluorophenyl)-N'-hydroxy-3-azabicyclo[3.1.0]hexane-6-carboxamidine (650 mg, 2.76 mmol)], pivalic acid (2.82 g, 27.63 mmol), and chloroaceticanhydride (755 mg, 4.42 mmol) in 1,2-dichloroethane was stirred at 90° C. for 3 hours. The reaction was quenched with saturated aqueous NaHCO$_3$, extracted with ethyl acetate, dried over anhydrous sodium sulfate, and concentrated under vacuum. The residue was adsorbed onto silica gel and purified by flash column chromatography eluted with ethyl acetate/petroleum ether (1:2). This resulted in the title compound (400 mg, 49% yield) as a light yellow solid.

Step 4: Preparation of 1-((3-((1R,5S,6r)-3-(3-fluorophenyl)-3-azabicyclo[3.1.0]hexan-6-yl)-1,2,4-oxadiazol-5-yl)methyl)-7-methyl-1,7-dihydro-6H-purin-6-one-2-d

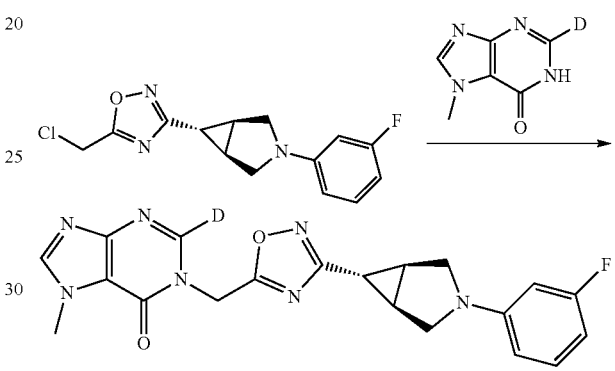

The title compound was prepared from [5-(chloromethyl)-3-[(1R,5S)-3-(3-fluorophenyl)-3-azabicyclo[3.1.0] hexan-6-yl]-1,2,4-oxadiazole (50 mg, 0.17 mmol) and 2-deuterio-7-methyl-1H-purin-6-one (25 mg, 0.17 mmol) as a white solid (25 mg, 36% yield), in a manner analogous to Example 39. LCMS [M+H$^+$]:409. $^1$H NMR (400 MHz, DMSO-d6) δ 8.24 (s, 1H), 7.21-7.10 (m, 1H), 6.49-6.27 (m, 3H), 5.52 (s, 2H), 3.95 (s, 3H), 3.66 (d, J=9.8 Hz, 2H), 3.30-3.25 (m, 2H), 2.20 (d, J=3.1 Hz, 2H), 2.01 (t, J=3.3 Hz, 1H).

Example 44: Preparation of 3-((3-((1s,3s)-3-(4-chlorophenyl)-3-fluorocyclobutyl)-1,2,4-oxadiazol-5-yl)methyl)-5-methylpyrazolo[5,1-f][1,2,4]triazin-4(3H)-one (Example compound 90)

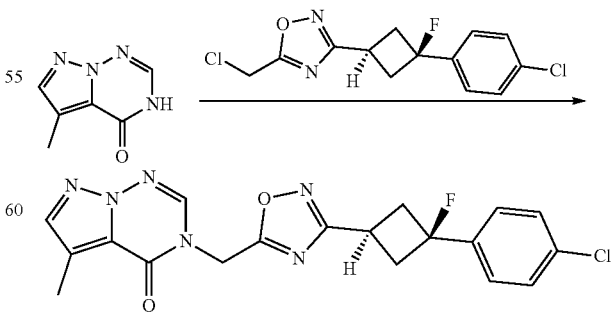

The title compound was prepared from 5-methyl-3H-pyrazolo[5,1-f][1,2,4] triazin-4-one (30 mg, 0.20 mmol) and 5-(chloromethyl)-3-[3-(4-chlorophenyl)-3-fluoro-cyclobutyl]-1,2,4-oxadiazole (60 mg, 0.20 mmol) as a white solid (21 mg, 25.3% yield), in a manner analogous to Example 39. LCMS [M+H$^+$] 415. $^1$H NMR (400 MHz, DMSO-d$_6$) δ 8.43 (s, 1H), 7.77 (s, 1H), 7.61 (d, J=8.4 Hz, 2H), 7.51 (d, J=8.4 Hz, 2H), 5.50 (s, 2H), 3.46-3.39 (m, 1H), 3.09-3.00 (m, 2H), 2.91-2.77 (m, 2H), 2.36 (s, 3H).

Example 45: Preparation of 1-((3-((1R,5S,6r)-3-(benzo[d]oxazol-6-yl)-3-azabicyclo[3.1.0]hexan-6-yl)-1,2,4-oxadiazol-5-yl)methyl)-7-methyl-1,7-dihydro-6H-purin-6-one (Example Compound 91)

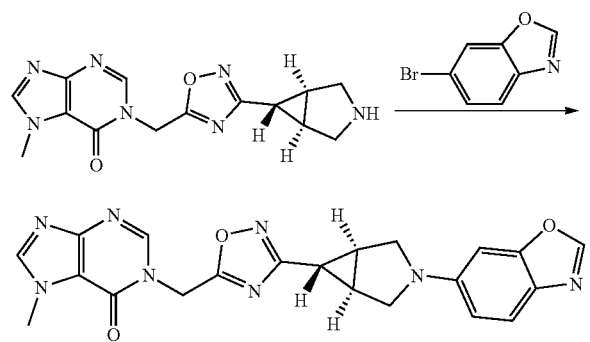

The title compound was prepared from 1-[[3-[(1S,5R)-3-azabicyclo[3.1.0] hexan-6-yl]-1,2,4-oxadiazol-5-yl]methyl]-7-methyl-purin-6-one (104 mg, 0.33 mmol) and 6-bromobenzo[d]oxazole (86.5 mg, 0.384 mmol) in a manner analogous to Example 75 as a white solid (6 mg, 4% yield). LCMS [M+H$^+$]: 413.0. $^1$H NMR (300 MHz, DMSO-d$_6$) δ 8.43 (s, 2H), 8.23 (s, 1H), 7.55 (s, 1H), 6.86 (s, 1H), 6.69-6.67 (m, 1H), 5.53 (s, 2H), 4.05-3.95 (m, 6H), 2.34-2.06 (m, 4H).

Example 46: Preparation of 1-((3-((1R,5S,6r)-3-(3,5-difluorophenyl)-3-azabicyclo[3.1.0]hexan-6-yl)-1,2,4-oxadiazol-5-yl)methyl)-7-methyl-1,7-dihydro-6H-purin-6-one (Example Compound 92)

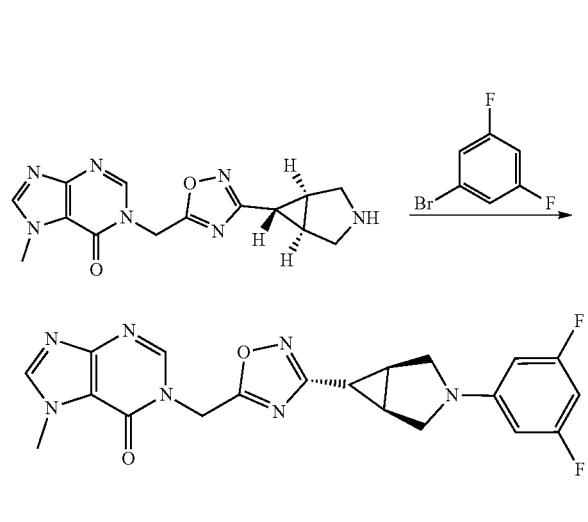

The title compound was prepared from 1-[[3-[(1R,5S)-3-azabicyclo[3.1.0] hexan-6-yl]-1,2,4-oxadiazol-5-yl]methyl]-7-methyl-purin-6-one (100 mg, 0.32 mmol) and 1-bromo-3,5-difluorobenzene (61 mg, 0.32 mmol) as a white solid (17 mg, 13% yield), in a manner analogous to Example 4, Step 8. LCMS [M+H$^+$] 426. $^1$H NMR (400 MHz, DMSO-d$_6$) δ 8.43 (s, 1H), 8.24 (s, 1H), 6.37-6.21 (m, 1H), 6.29-6.18 (m, 2H), 5.52 (s, 2H), 3.95 (s, 3H), 3.65 (d, J=10.0 Hz, 2H), 3.30 (d, J=2.5 Hz, 2H), 2.21 (s, 2H), 1.99 (t, J=3.3 Hz, 1H).

Examples 47 and 48: Preparation of 1-((3-((1R,5R,6S)-3-(3,4-difluorophenyl)bicyclo[3.1.0]hex-2-en-6-yl)-1,2,4-oxadiazol-5-yl)methyl)-7-methyl-1,7-dihydro-6H-purin-6-one (Example Compound 94) and 1-((3-((1S,5S,6R)-3-(3,4-difluorophenyl)bicyclo[3.1.0]hex-2-en-6-yl)-1,2,4-oxadiazol-5-yl)methyl)-7-methyl-1,7-dihydro-6H-purin-6-one (Example Compound 93)

The overall Examples 47 and 48 reaction scheme is as follows:

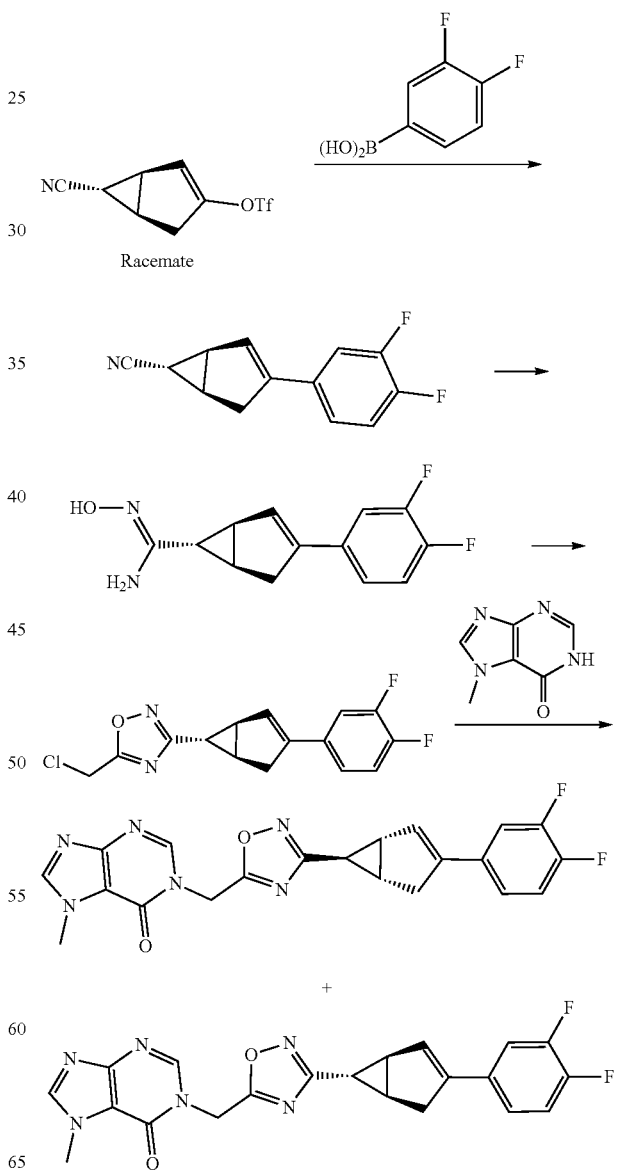

Step 1: Preparation of rac-(1R,5R,6S)-3-(3,4-difluorophenyl)bicyclo[3.1.0]hex-3-ene-6-carbonitrile

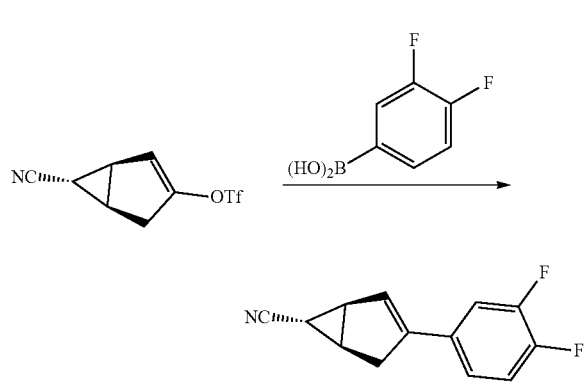

A 100 mL pressure vessel was charged with 3,4-difluorophenylboronic acid (1.10 g, 6.95 mmol), cesium carbonate (2.05 g, 6.32 mmol) and dichloro[1,1'-bis(di-t-butylphosphino)ferrocene]palladium(II) (115 mg, 0.170 mmol). The flask was evacuated and backfilled with nitrogen (3×). To this mixture was added a degassed solution of rac-(1 S,5R,6S)-6-cyanobicyclo[3.1.0]hex-2-en-3-yl trifluoromethanesulfonate (800 mg, 3.16 mmol) in 1,4-Dioxane (29 mL) and Water (2.9 mL). The flask was sealed and the reaction mixture was stirred at 120° C. for 1 h30. The reaction mixture was diluted with EtOAc and washed with water and brine. The organic layer was dried over anhydrous $MgSO_4$, filtered and concentrated under reduced pressure. The obtained residue was purified by flash column chromatography on silica gel eluting with EtOAc and hexanes (0 to 20% gradient) to afford rac-(1R,5R,6S)-3-(3,4-difluorophenyl)bicyclo[3.1.0]hex-3-ene-6-carbonitrile (577 mg, 2.66 mmol, 84% yield) as a beige solid.

Step 2: Preparation of rac-(1R,5R,6S,Z)-3-(3,4-difluorophenyl)-N'-hydroxybicyclo[3.1.0]hex-2-ene-6-carboximidamide

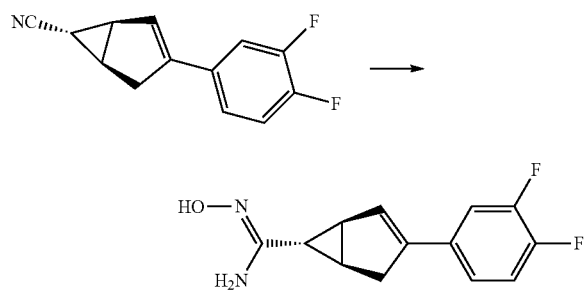 [SMILES: N#C[C@@H]1[C@H]2C=C(c3ccc(F)cc3)C[C@@H]12 ; N/C(=N\O)[C@@H]1[C@H]2C=C(c3ccc(F)cc3)C[C@H]21]

The title compound was prepared from rac-(1R,5R,6S)-3-(3,4-difluorophenyl)bicyclo[3.1.0]hex-3-ene-6-carbonitrile as a white solid in a manner analogous to Examples 41 and 42, Step 10.

Step 3: Preparation of rac-5-(chloromethyl)-3-((1R,5R,6S)-3-(3,4-difluorophenyl)bicycle[3.1.0]hex-2-en-6-yl)-1,2,4-oxadiazole

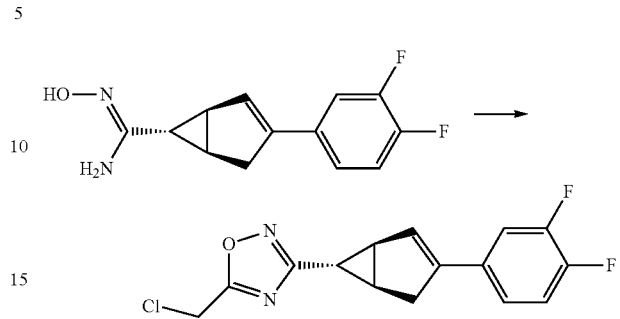

Using AcOH as solvent, the title compound was prepared from rac-(1R,5R,6S,Z)—N'-hydroxy-3-phenylbicyclo[3.1.0]hex-2-ene-6-carboximidamide as a white solid in a manner analogous to Examples 41 and 42, Step 11.

Step 4: Preparation of 1-((3-((1R,5R,6S)-3-(3,4-difluorophenyl)bicyclo[3.1.0]hex-2-en-6-yl)-1,2,4-oxadiazol-5-yl)methyl)-7-methyl-1,7-dihydro-6H-purin-6-one (Example Compound 94) and 1-((3-((1S,5S,6R)-3-(3,4-difluorophenyl)bicyclo[3.1.0]hex-2-en-6-yl)-1,2,4-oxadiazol-5-yl)methyl)-7-methyl-1,7-dihydro-6H-purin-6-one (Example Compound 93)

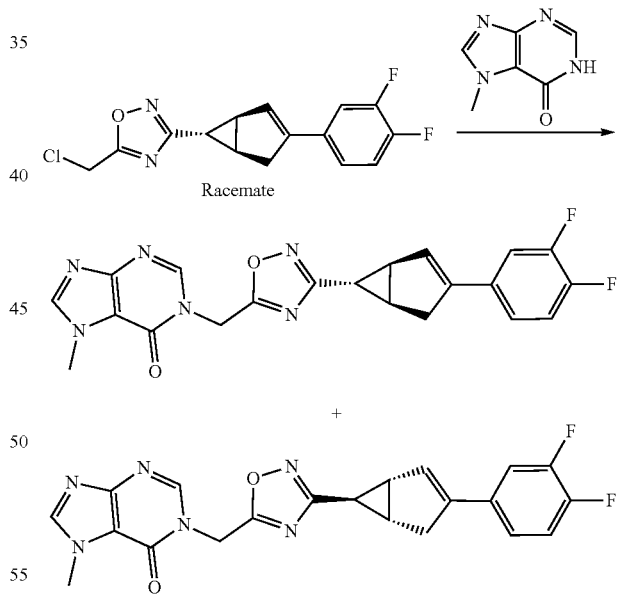

The title compounds were prepared from rac-5-(chloromethyl)-3-((1R,5R,6S)-3-(3,4-difluorophenyl)bicyclo[3.1.0]hex-2-en-6-yl)-1,2,4-oxadiazole and 7-methyl-1H-purin-6-one in a manner analogous to Examples 41 and 42, Step 12. The racemic mixture was separated by SFC with the following conditions: Conditions: ChiralCel OJ 10×250 mm, 5 μm Isocratic 40% IPA, 10 mL/min, 100 Bar Column temp: 35° C., Run Time: 17 min.

Example 48, enantiomer 1, (Example Compound 94): white solid, Rt=12.4 min (ChiralCel OJ 4.6×150 mm, 20%

IPA, 5 mL/min); LCMS [M+H⁺] 423.1; ¹H NMR (400 MHz, DMSO-d6) 8.42 (s, 1H), 8.22 (s, 1H), 7.50 (ddd, J=12.3, 7.9, 2.0 Hz, 1H), 7.36 (dt, J=10.6, 8.6 Hz, 1H), 7.23 (s, 1H), 6.58 (d, J=1.6 Hz, 1H), 5.49 (s, 2H), 3.93 (s, 3H), 3.04 (dd, J=17.9, 5.9 Hz, 1H), 2.88 (d, J=17.7 Hz, 1H), 2.43 (dd, J=6.3, 2.4 Hz, 1H), 2.24 (td, J=6.5, 3.5 Hz, 1H), 1.63 (dd, J=7.6, 4.6 Hz, 1H).

Example 47, enantiomer 2, (Example Compound 93): white solid, Rt=14.2 min (ChiralCel OJ 4.6×150 mm, 20% IPA, 5 mL/min); LCMS [M+H⁺] 423.1; ¹H NMR (400 MHz, DMSO-d6) 8.42 (s, 1H), 8.22 (s, 1H), 7.50 (ddd, J=12.3, 7.8, 2.0 Hz, 1H), 7.40-7.30 (m, 1H), 7.23 (s, 1H), 6.59 (d, J=1.7 Hz, 1H), 5.49 (s, 2H), 3.93 (s, 3H), 3.04 (dd, J=18.0, 5.9 Hz, 1H), 2.88 (d, J=17.6 Hz, 1H), 2.43 (dd, J=6.3, 2.4 Hz, 1H), 2.24 (dt, J=9.9, 5.2 Hz, 1H), 1.65-1.61 (m, 1H).

Example 49 Preparation of 1-((3-((1R,5S,6r)-3-(2,3-difluorophenyl)-3-azabicyclo[3.1.0]hexan-6-yl)-1,2,4-oxadiazol-5-yl)methyl)-7-methyl-1,7-dihydro-6H-purin-6-one (Example Compound 100)

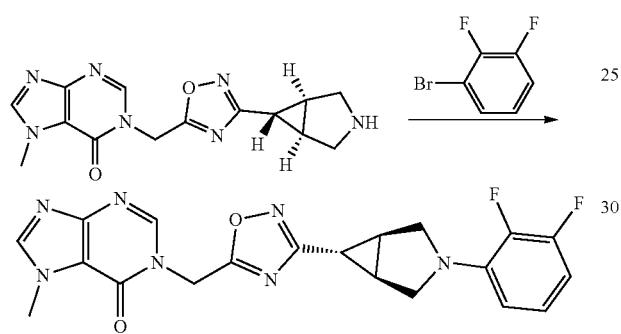

The title compound was prepared from 1-[[3-[(1R,5S)-3-azabicyclo[3.1.0] hexan-6-yl]-1,2,4-oxadiazol-5-yl]methyl]-7-methyl-purin-6-one (100 mg, 0.32 mmol) and 1-bromo-2,3-difluorobenzene (61 mg, 0.32 mmol) as a white solid (26 mg, 19.6% yield), in a manner analogous to Example 4, Step 8, LCMS [M+H⁺] 426. ¹H NMR (400 MHz, DMSO-d₆) δ 8.44 (s, 1H), 8.24 (s, 1H), 7.03-6.94 (m, 1H), 6.74-6.65 (m, 1H), 6.56 (t, J=8.3 Hz, 1H), 5.52 (s, 2H), 3.95 (s, 3H), 3.81-3.77 (m, 2H), 3.41-3.31 (m, 2H), 2.17 (d, J=2.8 Hz, 2H), 2.12-2.11 (m, 1H).

Example 50: Preparation of 1-((3-((1R,5S,6r)-3-(3,4-difluorophenyl)-3-azabicyclo[3.1.0]hexan-6-yl)-1,2,4-oxadiazol-5-yl)methyl)-7-methyl-1,7-dihydro-6H-purin-6-one (Example Compound 105)

The overall Example 50 reaction scheme is as follows:

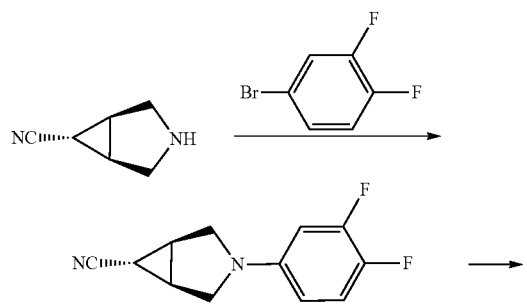

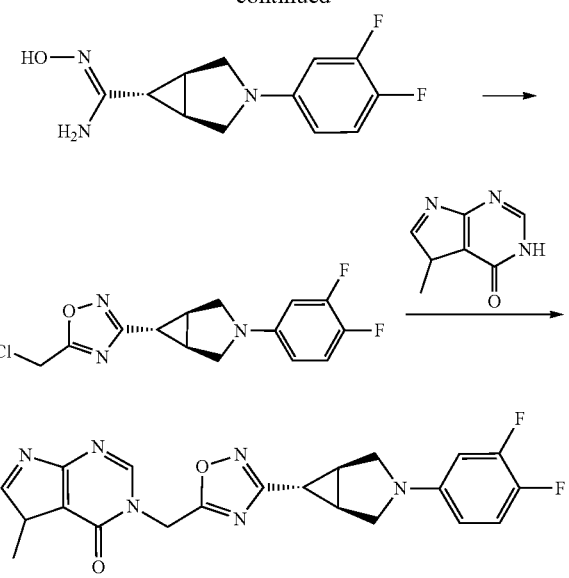

Step 1: Preparation of (1R,5S,6r)-3-(3,4-difluorophenyl)-3-azabicyclo[3.1.0]hexane-6-carbonitrile

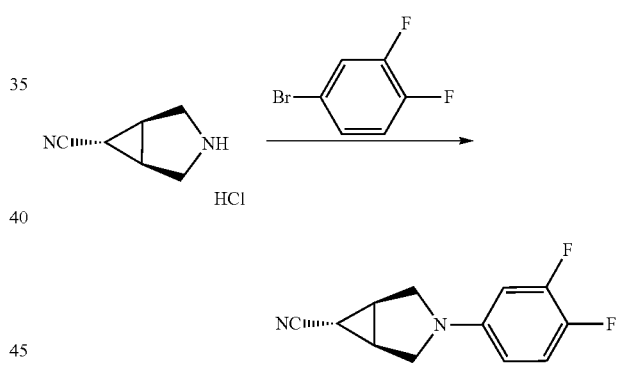

To a vial was added 3-azabicyclo[3.1.0]hexane-6-carbonitrile hydrochloride (200 mg, 1.38 mmol), chloro[9,9-dimethyl-4,5-bis(diphenylphosphino)xanthene] [2'-amino-1,1'-biphenyl]palladium(II) (125 mg, 0.138 mmol) and potassium phosphate tribasic (1.06 g, 4.84 mmol). 1,4-Dioxane (7.0 mL) was then added followed by 1-bromo-3,4-difluorobenzene (293 mg, 1.52 mmol). The headspace was flushed with nitrogen for 10 seconds, the vial was sealed, and the reaction mixture was stirred at 110° C. for 16 h. The reaction mixture was washed with water, extracted 3 times with iPrOAc, dried over sodium sulfate, filtered, and concentrated in vacuo. The residue was adsorbed onto silica and purified by flash column chromatography with 0-100% iPrOAc in heptane to afford the desired compound as a white solid (126 mg, 41%). ¹H NMR (400 MHz, CDCl₃-d) δ 7.19 (dt, J=10.7, 9.3 Hz, 1H), 6.58 (ddd, J=14.0, 6.9, 2.9 Hz, 1H), 6.35-6.29 (m, 1H), 3.59 (d, J=9.9 Hz, 2H), 3.16 (d, J=9.6 Hz, 2H), 2.48-2.42 (m, 2H), 1.69 (t, J=3.4 Hz, 1H).

Step 2: Preparation of (1R,5S,6r,Z)—N-hydroxy-3-(3,4-difluorophenyl)-3-azabicyclo[3.1.0]hexane-6-carboximidamide

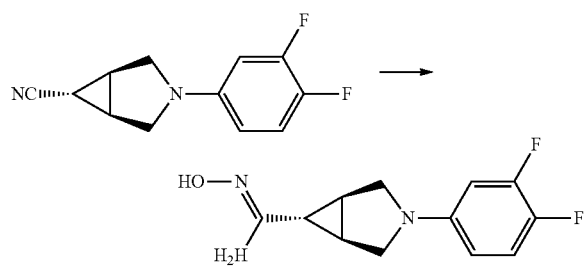

The title compound was prepared from (1R,5S,6r)-3-(3,4-difluorophenyl)-3-azabicyclo[3.1.0]hexane-6-carbonitrile (126 mg, 0.572 mmol) in a manner analogous to Examples 41 and 42, Step 10.

Step 3: Preparation of 5-(chloromethyl)-3-((1R,5S,6r)-3-(3,4-difluorophenyl)-3-azabicyclo[3.1.0]hexan-6-yl)-1,2,4-oxadiazole

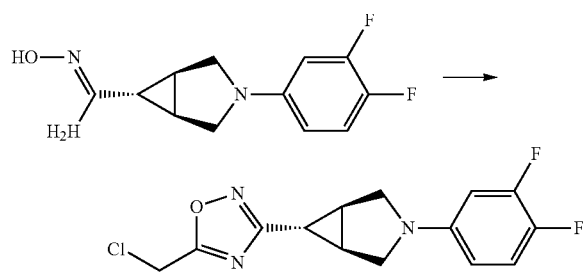

The title compound was prepared from (1R,5S,6r,Z)—N-hydroxy-3-(3,4-difluorophenyl)-3-azabicyclo[3.1.0]hexane-6-carboximidamide (145 mg, 0.572 mmol) as a yellow oil (135 mg, 76%) in a manner analogous to Example 41 and 42, Step 11. $^1$H NMR (400 MHz, CDCl$_3$-d) δ 7.21 (dt, J:=10.7, 9.3 Hz, 1H), 6.60 (ddd, J:=14.0, 6.9, 2.9-Hz, 1H), 6.38-6.32 (n, 1H), 5.05 (s, 2H), 3.68 (d, J=9.7 Hz, 2H), 3.27 (d, J=9.7 Hz, 2H), 2.29-2.25 (nm, 2H), 2.08 (t, J=3.2 Hz, 1H).

Step 4: Preparation of 1-((3-((1R,5S,6r)-3-(3,4-difluorophenyl)-3-azabicyclo[3.1.0]hexan-6-yl)-1,2,4-oxadiazol-5-yl)methyl)-7-methyl-1,7-dihydro-6H-purin-6-one (Example Compound 105)

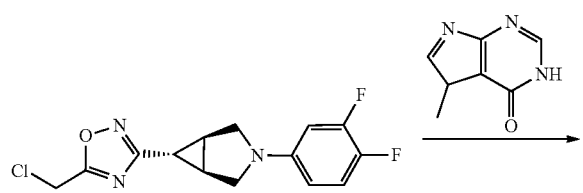

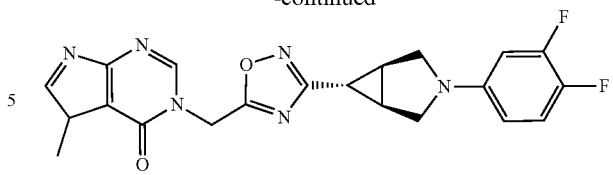

The title compound was prepared from 5-(chloromethyl)-3-((1R,5S,6r)-3-(3,4-difluorophenyl)-3-azabicyclo[3.1.0]hexan-6-yl)-1,2,4-oxadiazole (135 mg, 0.433 mmol) and 7-methyl-1,7-dihydro-6H-purin-6-one (71.5 mg, 0.476 mmol) as a white solid (74.5 mg, 40% yield), in a manner analogous to Example 25, Step 5. LCMS [M+H$^+$] 426.2. $^1$H NMR (400 MHz, DMSO) δ 8.43 (s, 1H), 8.23 (s, 1H), 7.19 (dt, J=10.8, 9.2 Hz, 1H), 6.63-6.50 (m, 1H), 6.37-6.28 (m, 1H), 5.52 (s, 2H), 3.95 (s, 3H), 3.64 (d, J=9.8 Hz, 2H), 3.27-3.19 (m, 2H), 2.23-2.15 (m, 2H), 2.02 (t, J=3.3 Hz, 1H).

Example 51: Preparation of 3-((3-((1R,5S,6r)-3-(4-chloropyridin-2-yl)-3-azabicyclo[3.1.0]hexan-6-yl)-1,2,4-oxadiazol-5-yl)methyl)-5-methyl-4-oxo-3,4-dihydropyrido[2,3-d]pyrimidine-7-carbonitrile (Example Compound 107)

The overall Example 51 reaction scheme is as follows:

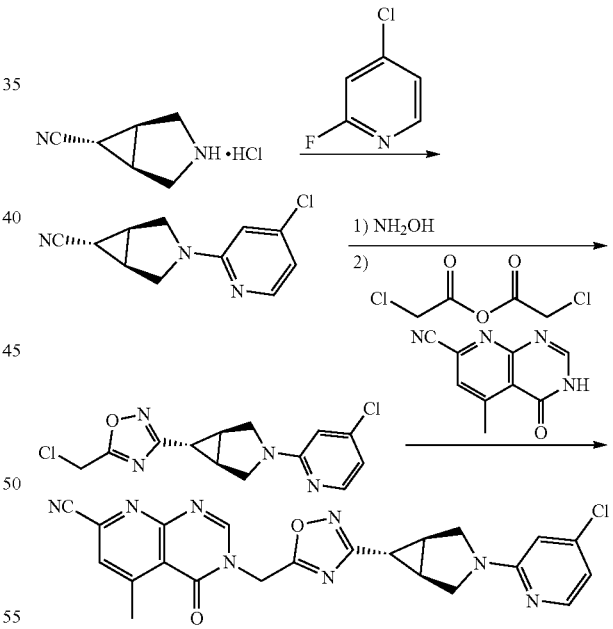

Step 1: Preparation of (1R,5S)-3-(4-chloropyridin-2-yl)-3-azabicyclo[3.1.0]hexane-6-carbonitrile

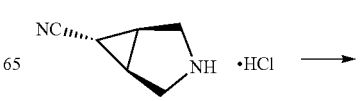

-continued

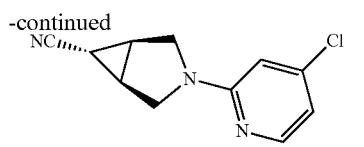

To a sealed tube was added (1R,5S)-3-azabicyclo[3.1.0]hexane-6-carbonitrile; hydrochloride (as prepared in Example 21, Step 6) (203 mg, 1.40 mmol), 1,8-diazabicyclo[5.4.0]undec-7-ene (1.05 mL, 7.02 mmol), 4-chloro-2-fluoropyridine (0.42 mL, 4.21 mmol) and pyridine (5.0 mL, 62 mmol) and the reaction mixture was stirred at 110° C. for 18 h. The reaction mixture was diluted with water and extracted with EtOAc (3×). The combined organic layers were washed with brine, dried over sodium sulfate, filtered and concentrated in vacuo. The residue was adsorbed onto silica and purified by flash column chromatography with 0-100% iPrOAc in heptane to afford the desired compound as a beige solid (246 mg, 80%). LCMS [M+H$^+$]: 220.1.

Step 2: Preparation of 5-(chloromethyl)-3-((1R,5S,6r)-3-(4-chloropyridin-2-yl)-3-azabicyclo[3.1.0]hexan-6-yl)-1,2,4-oxadiazole

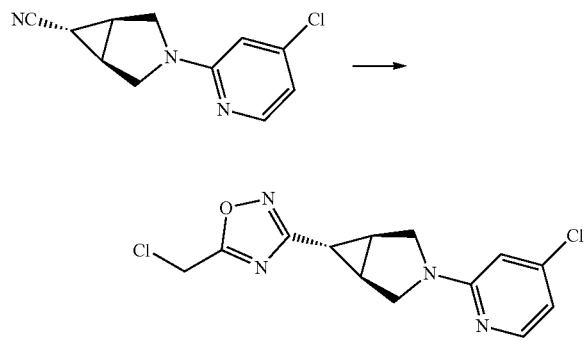

To a solution of 3-(4-chloro-2-pyridyl)-3-azabicyclo[3.1.0]hexane-6-carbonitrile (246 mg, 1.12 mmol) in ethanol (7.5 mL) was added hydroxylamine (50 mass %) in H$_2$O (0.34 mL, 5.60 mmol) and the reaction mixture was heated to 80° C. for 2 hours. The reaction mixture was concentrated in vacuo, the residue was redissolved in ethanol (10 mL) and concentrated in vacuo again. The residue was taken up in 1,2-dichloroethane (5.6 mL) and pivalic acid (1.16 g, 11.2 mmol) and chloroacetic anhydride (309 mg, 1.79 mmol) were added and the mixture was heated to 90° C. for 40 min. The reaction mixture was diluted in EtOAc and sat. aq. sodium bicarbonate, partitioned the aqueous layer was extracted with EtOAc (3×), dried over sodium sulfate and concentrated in vacuo to give the title compound as an orange oil that solidified over time (400 mg, 99%). LCMS [M+H$^+$]: 311.0. 1H NMR (400 MHz, CDCl$_3$) δ 8.04 (d, J=5.3 Hz, 1H), 6.60 (dd, J=5.3, 1.7 Hz, 1H), 6.37 (d, J=1.7 Hz, 1H), 4.63 (s, 2H), 3.89 (d, J=10.4 Hz, 2H), 3.62-3.53 (m, 2H), 2.36-2.29 (m, 2H), 2.08 (t, J=3.3 Hz, 1H).

Step 3: Preparation of 3-((3-((1R,5S,6r)-3-(4-chloropyridin-2-yl)-3-azabicyclo[3.1.0]hexan-6-yl)-1,2,4-oxadiazol-5-yl)methyl)-5-methyl-4-oxo-3,4-dihydropyrido[2,3-d]pyrimidine-7-carbonitrile (Example Compound 107)

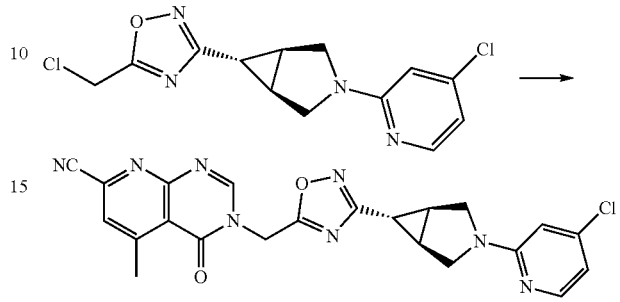

A mixture of 5-methyl-4-oxo-3H-pyrido[2,3-d]pyrimidine-7-carbonitrile (43 mg, 0.23 mmol), 5-(chloromethyl)-3-[3-(4-chloro-2-pyridyl)-3-azabicyclo[3.1.0]hexan-6-yl]-1,2,4-oxadiazole (65 mg, 0.21 mmol), potassium carbonate (87 mg, 0.63 mmol) and sodium iodide (1.6 mg, 0.010 mmol) in acetone (1.5 mL) were stirred at room temperature for 15 h. The reaction mixture was diluted with acetone, filtered through a fritted funnel, eluting with acetone and the filtrate was concentrated in vacuo. The residue was adsorbed onto silica and purified by flash column chromatography with 10-80% 3:1 MeOH:iPrOAc in heptane to afford the partially purified desired compound as a white solid. The residue was further purified by achiral SFC to yield the title compound (7.9 mg, 8.2%) as a white solid. LCMS [M+H$^+$]: 461.1. 1H NMR (400 MHz, DMSO-d6) δ 8.80 (s, 1H), 8.06-8.04 (m, 1H), 8.02 (d, J=5.5 Hz, 1H), 6.66 (dd, J=5.5, 1.7 Hz, 1H), 6.54 (d, J=1.8 Hz, 1H), 5.50 (s, 2H), 3.81 (d, J=10.9 Hz, 2H), 3.48-3.43 (m, 2H), 2.81 (s, 3H), 2.22-2.18 (m, 2H), 1.98 (t, J=3.3 Hz, 1H).

Examples 52 and 53: Preparation of 1-methyl-6-((3-((1R,5R,6S)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one (Example Compound 109) and 1-methyl-6-((3-((1 S,5 S,6R)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one (Example Compound 108)

The overall Examples 52 and 53 reaction scheme is as follows:

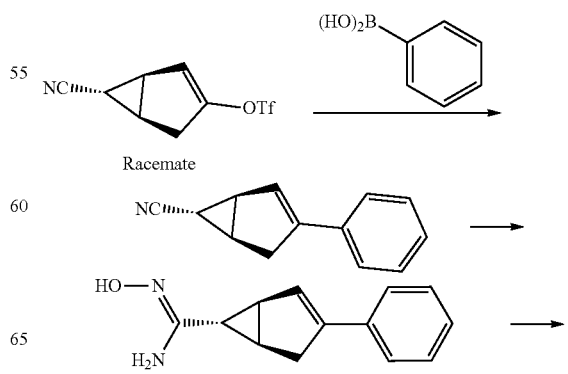

253
-continued

Step 1: Preparation of rac-(1R,5R,6S)-3-phenylbicyclo[3.1.0]hex-2-ene-6-carbonitrile

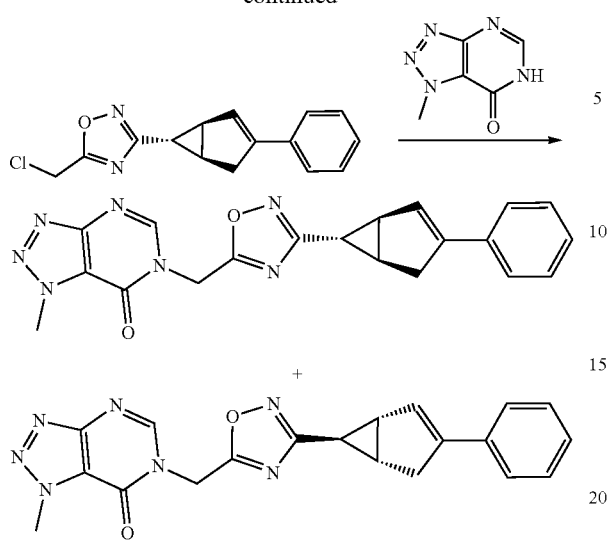

A 50 mL RBF was charged with rac-(1S,5R,6S)-6-cyanobicyclo[3.1.0]hex-2-en-3-yl trifluoromethanesulfonate (600 mg, 2.37 mmol), THF (10 mL) and Water (1 mL). The reaction mixture was bubbled with nitrogen for 10 min. before adding successively phenylboronic acid (636 mg, 5.21 mmol), potassium fluoride (344 mg, 5.92 mmol) and Pd(dppf)Cl$_2$.DCM (116 mg, 0.140 mmol). The mixture was stirred in a 65° C. oil bath for 30 min. and the heat was removed. The mixture was transferred in a separatory funnel and a saturated aqueous solution of NaHCO$_3$ was added. The mixture was extracted with DCM (3×50 mL). The combined organic layers were dried over anhydrous Na$_2$SO$_4$, filtered and concentrated under reduced pressure. The obtained residue was purified on a SiO$_2$ gel pad eluting with EtOAc and hexanes (0 to 10% gradient) to afford the title rac-(1R, 5R,6S)-3-phenylbicyclo[3.1.0]hex-2-ene-6-carbonitrile (310 mg, 1.71 mmol, 72% yield) as a white solid. $^1$H NMR (500 MHz, CDCl$_3$) 7.36-7.29 (m, 4H), 7.28-7.24 (m, 1H), 6.30 (q, J=1.8 Hz, 1H), 3.16 (ddd, J=17.8, 6.9, 1.8 Hz, 1H), 2.89 (dt, J=4.3, 2.4 Hz, 1H), 2.71-2.60 (m, 1H), 2.39 (td, J=6.6, 3.7 Hz, 1H), 0.94 (t, J=3.0 Hz, 1H).

254

Step 2: Preparation of rac-(1R,5R,6S,Z)—N'-hydroxy-3-phenylbicyclo[3.1.0]hex-2-ene-6-carboximidamide

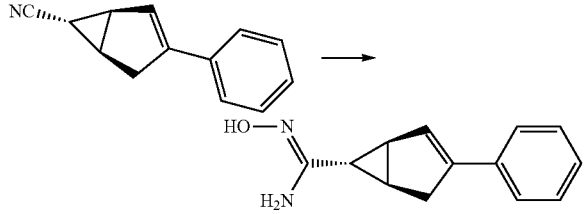

The title compound was prepared from rac-(1R,5R,6S)-3-phenylbicyclo[3.1.0]hex-2-ene-6-carbonitrile as a white solid in a manner analogous to Examples 41 and 42, Step 10. LCMS [M+H$^+$] 215.0.

Step 3: Preparation of 5-(chloromethyl)-3-(rac-(1R, 5R,6S)-3-phenylbicyclo[3.1.0]hex-2-en-6-yl)-1,2,4-oxadiazole

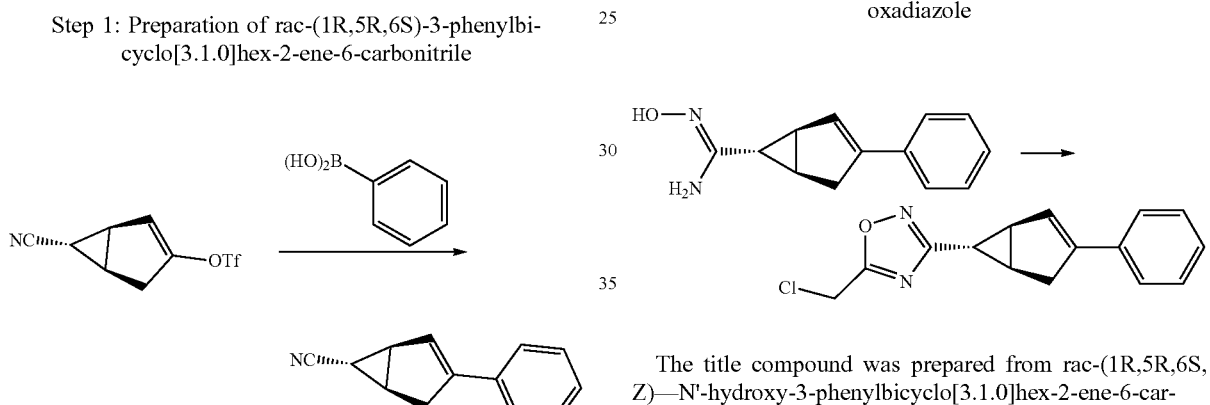

The title compound was prepared from rac-(1R,5R,6S, Z)—N'-hydroxy-3-phenylbicyclo[3.1.0]hex-2-ene-6-carboximidamide as a white solid in a manner analogous to Examples 41 and 42, Step 11. LCMS [M+H$^+$] 273.3; $^1$H NMR (500 MHz, CDCl$_3$) δ 7.40-7.37 (m, 2H), 7.33-7.29 (m, 2H), 7.26-7.22 (m, 1H), 6.42 (q, J=1.9 Hz, 1H), 4.63 (s, 2H), 3.20 (ddd, J=17.6, 6.9, 1.8 Hz, 1H), 2.95 (dt, J=17.6, 2.2 Hz, 1H), 2.59 (dq, J=6.8, 2.3 Hz, 1H), 2.39 (td, J=6.7, 3.5 Hz, 1H), 1.74 (dd, J=3.4, 2.5 Hz, 1H).

Step 4: Preparation of 1-methyl-6-((3-((1R,5R,6S)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one (Example Compound 109) and 1-methyl-6-((3-((1S,5S,6R)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one (Example Compound 108)

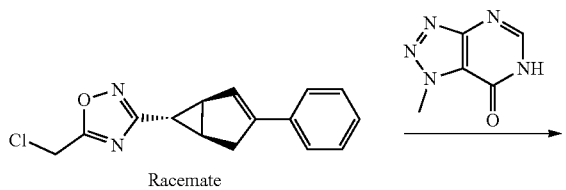

Racemate

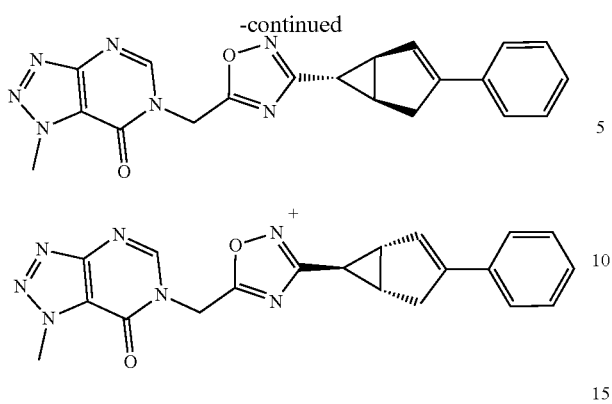

The title compounds were prepared from 5-(chloromethyl)-3-(rac-(1R,5R,6S)-3-phenylbicyclo[3.1.0]hex-2-en-6-yl)-1,2,4-oxadiazole and 1-methyl-1H-[1,2,3]triazolo[4,5-d]pyrimidin-7(6H)-one in a manner analogous to Examples 41 and 42, Step 12. The racemic mixture was separated by SFC with the following conditions: Column: Lux Cellulose-3, 10×250 mm 5 μm, 45% isopropanol, 10 mL/min, 150 bar, Column Temp: 40° C., Run time: 18 min.

Example 53, enantiomer 1, (Example Compound 109): white solid, Rt=12.8 min (Lux Cellulose-3, 10×250 mm 5 μm, 45% isopropanol, 10 mL/min); LCMS [M+H$^+$] 388.1; $^1$H NMR (400 MHz, CDCl$_3$) δ 8.10 (s, 1H), 7.39-7.14 (m, 5H), 6.34 (s, 1H), 5.34 (s, 2H), 4.43 (s, 3H), 3.12 (dd, J=17.7, 6.7 Hz, 1H), 2.87 (d, J=17.7 Hz, 1H), 2.53-2.45 (m, 1H), 2.34-2.24 (m, 1H), 1.68-1.61 (m, 1H).

Example 52, enantiomer 2, (Example Compound 108): white solid, Rt=15.8 min (Lux Cellulose-3, 10×250 mm 5 μm, 45% isopropanol, 10 mL/min); LCMS [M+H$^+$] 388.1; $^1$H NMR (400 MHz, CDCl$_3$) δ 8.06 (s, 1H), 7.35-7.11 (m, 5H), 6.30 (s, 1H), 5.30 (s, 2H), 4.39 (s, 3H), 3.08 (dd, J=17.6, 6.5 Hz, 1H), 2.83 (d, J=17.6 Hz, 1H), 2.49-2.39 (m, 1H), 2.29-2.19 (m, 1H), 1.65-1.56 (m, 1H).

Examples 54 and 55: Preparation of 1-((3-((1R,5R,6S)-3-(3-fluorophenyl)bicyclo[3.1.0]hex-2-en-6-yl)-1,2,4-oxadiazol-5-yl)methyl)-7-methyl-1,7-dihydro-6H-purin-6-one (Example Compound 115) and 1-((3-((1S,5S,6R)-3-(3-fluorophenyl)bicyclo[3.1.0]hex-2-en-6-yl)-1,2,4-oxadiazol-5-yl)methyl)-7-methyl-1,7-dihydro-6H-purin-6-one (Example Compound 114)

The overall Examples 54 and 55 reaction scheme is as follows:

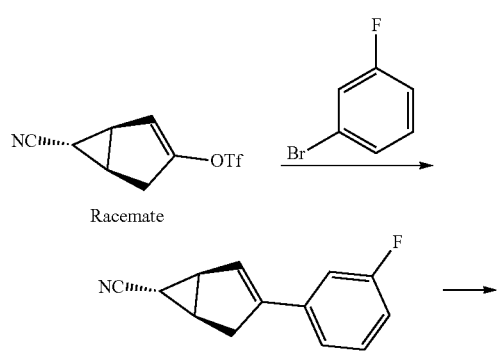

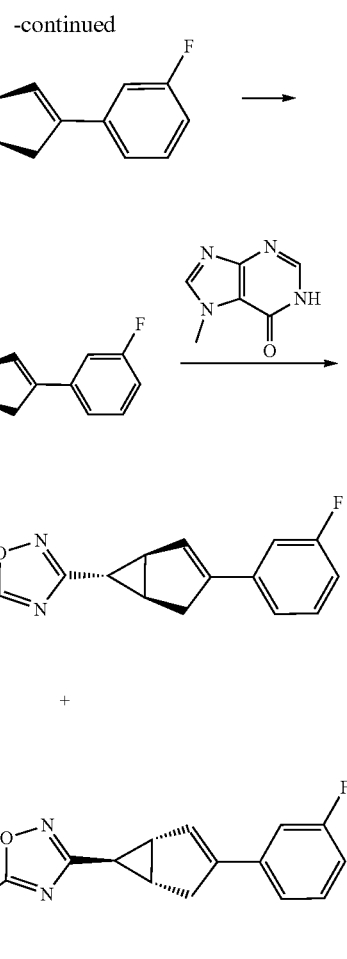

Step 1: Preparation of rac-(1R,5R,6S)-3-(3-fluorophenyl)bicyclo[3.1.0]hex-2-ene-6-carbonitrile

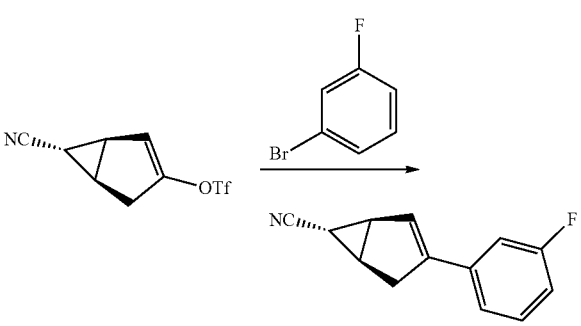

The title compound was prepared from rac-(1S,5R,6S)-6-cyanobicyclo[3.1.0]hex-2-en-3-yl trifluoromethanesulfonate and 1-bromo-3-fluorobenzene as a white solid in a manner analogous to Examples 41 and 42, Step 9. $^1$H NMR (500 MHz, CDCl$_3$) δ 7.30-7.25 (m, 1H), 7.12-7.09 (m, 1H), 7.03-7.00 (m, 1H), 6.98-6.93 (m, 1H), 6.34-6.31 (m, 1H), 3.14 (ddd, J=17.9, 6.8, 1.9 Hz, 1H), 2.90-2.83 (m, 1H), 2.68 (dq, J=6.3, 2.4 Hz, 1H), 2.42-2.37 (m, 1H), 0.96-0.94 (m, 1H).

Step 2: Preparation of rac-(1R,5R,6S,Z)-3-(3-fluorophenyl)-N'-hydroxybicyclo[3.1.0]hex-2-ene-6-carboximidamide

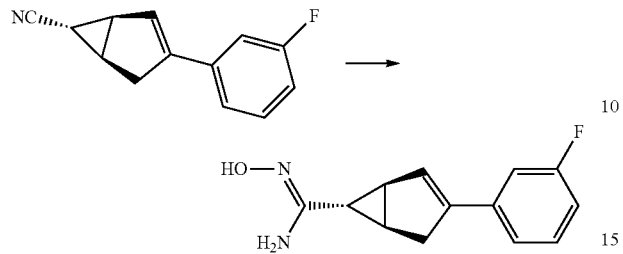

The title compound was prepared from rac-(1R,5R,6S)-3-(3-fluorophenyl)bicyclo[3.1.0]hex-2-ene-6-carbonitrile as beige solid in a manner analogous to Examples 41 and 42, Step 10. LCMS [M+H⁺] 233.4.

Step 3: Preparation of 5-(chloromethyl)-3-(rac-(1R,5R,6S)-3-(3-fluorophenyl)bicyclo[3.1.0]hex-2-en-6-yl)-1,2,4-oxadiazole

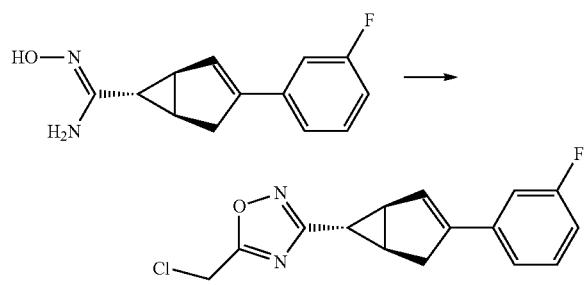

The title compound was prepared from rac-(1R,5R,6S,Z)-3-(3-fluorophenyl)-N'-hydroxybicyclo[3.1.0]hex-2-ene-6-carboximidamide as a white solid in a manner analogous to Examples 41 and 42, Step 11. $^1$H NMR (400 MHz, CDCl$_3$) δ 7.30-7.24 (m, 1H), 7.17-7.13 (m, 1H), 7.08-7.04 (m, 1H), 6.93 (td, J=8.3, 2.2 Hz, 1H), 6.46-6.43 (m, 1H), 4.63 (s, 2H), 3.17 (dd, J=17.7, 6.9 Hz, 1H), 2.96-2.88 (m, 1H), 2.62-2.57 (m, 1H), 2.40 (td, J=6.6, 3.5 Hz, 1H), 1.76-1.73 (m, 1H).

Step 4: Preparation of 1-((3-((1R,5R,6S)-3-(3-fluorophenyl)bicyclo[3.1.0]hex-2-en-6-yl)-1,2,4-oxadiazol-5-yl)methyl)-7-methyl-1,7-dihydro-6H-purin-6-one (Example Compound 115) and 1-((3-((1S,5S,6R)-3-(3-fluorophenyl)bicyclo[3.1.0]hex-2-en-6-yl)-1,2,4-oxadiazol-5-yl)methyl)-7-methyl-1,7-dihydro-6H-purin-6-one (Example Compound 114)

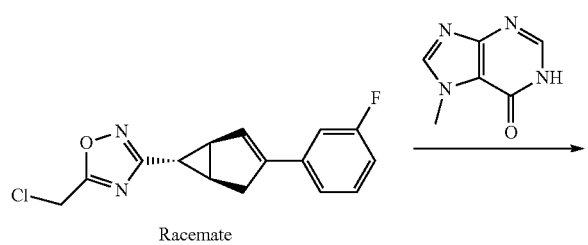

Racemate

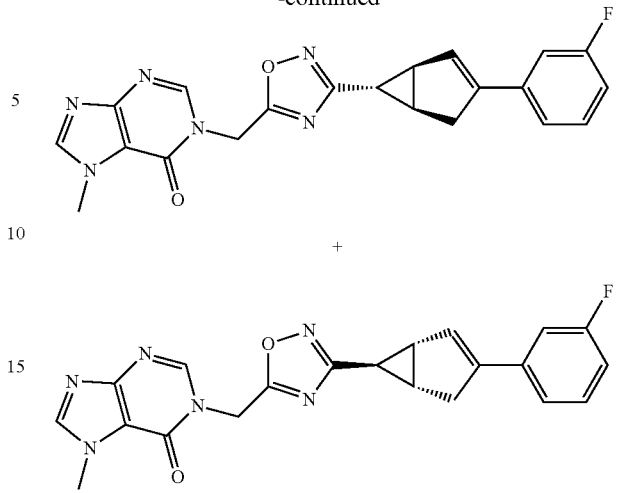

The title compounds were prepared from 5-(chloromethyl)-3-(rac-(1R,5R,6S)-3-(3-fluorophenyl)bicyclo[3.1.0]hex-2-en-6-yl)-1,2,4-oxadiazole and 7-methyl-1H-purin-6-one in a manner analogous to Examples 41 and 42, Step 12. The racemic mixture was separated by SFC with the following conditions: ChiralCel OJ, 10×250 mm, 5 μm Isocratic 30% MeOH+10 mM Ammonium Formate, 10 mL/min 100 Bar, Column temperature: 35° C., Run Time: 25 min.

Example 55, enantiomer (Example Compound 115): white solid, Rt=16.5 min (ChiralCel OJ, 10×250 mm, 5 μm Isocratic 30% MeOH+10 mM Ammonium Formate, 10 mL/min 100 Bar, Column temp: 35° C., Run Time: 25 min.); LCMS [M+H⁺] 405.3; $^1$H NMR (400 MHz, DMSO-d6) δ 8.44 (s, 1H), 8.24 (s, 1H), 7.39-7.31 (m, 1H), 7.29-7.23 (m, 2H), 7.11-7.03 (m, 1H), 6.66-6.62 (m, 1H), 5.51 (s, 2H), 3.95 (s, 3H), 3.08 (dd, J=18.5, 6.5 Hz, 1H), 2.95-2.87 (m, 1H), 2.48-2.43 (m, 1H), 2.26 (td, J=6.4, 3.4 Hz, 1H), 1.67-1.64 (m, 1H).

Example 54, enantiomer (Example Compound 114): white solid, Rt=18.5 min (ChiralCel OJ, 10×250 mm, 5 μm Isocratic 30% MeOH+10 mM Ammonium Formate, 10 mL/min 100 Bar, Column temp: 35° C., Run Time: 25 min.); LCMS [M+H⁺] 405.1; $^1$H NMR (400 MHz, DMSO-d6) δ 8.44 (s, 1H), 8.24 (s, 1H), 7.39-7.31 (m, 1H), 7.29-7.23 (m, 2H), 7.11-7.03 (m, 1H), 6.66-6.62 (m, 1H), 5.51 (s, 2H), 3.95 (s, 3H), 3.08 (dd, J=18.5, 6.5 Hz, 1H), 2.95-2.87 (m, 1H), 2.48-2.43 (m, 1H), 2.26 (td, J=6.4, 3.4 Hz, 1H), 1.67-1.64 (m, 1H).

Examples 56 and 57: Preparation of 1-((3-((1R,5R,6S)-3-(4-fluorophenyl)bicyclo[3.1.0]hex-2-en-6-yl)-1,2,4-oxadiazol-5-yl)methyl)-7-methyl-1,7-dihydro-6H-purin-6-one (Example Compound 124) and 1-((3-((1S,5S,6R)-3-(4-fluorophenyl)bicyclo[3.1.0]hex-2-en-6-yl)-1,2,4-oxadiazol-5-yl)methyl)-7-methyl-1,7-dihydro-6H-purin-6-one (Example Compound 125)

The overall Examples 56 and 57 reaction scheme is as follows:

Step 1: Preparation of rac-(1R,5R,6S)-3-(4-fluorophenyl)bicyclo[3.1.0]hex-2-ene-6-carbonitrile

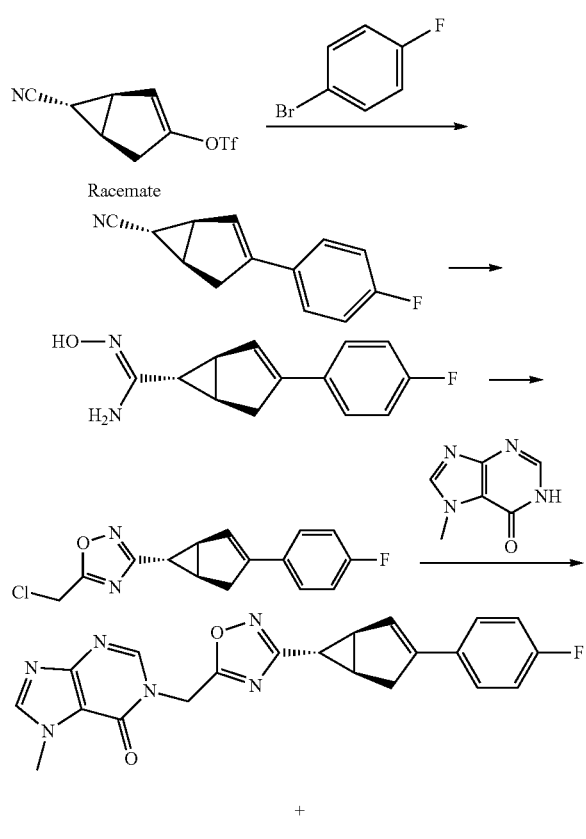

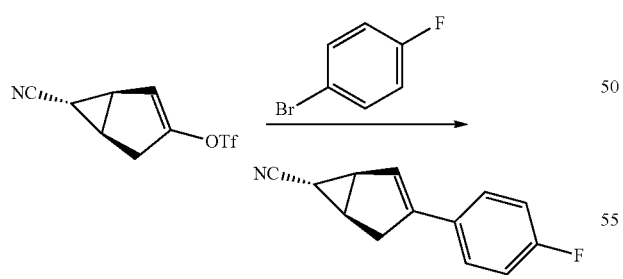

The title compound was prepared from rac-(1S,5R,6S)-6-cyanobicyclo[3.1.0]hex-2-en-3-yl trifluoromethanesulfonate and 1-bromo-4-fluorobenzene as a white solid in a manner analogous to Examples 41 and 42, Step 9. $^1$H NMR (400 MHz, CDCl$_3$) δ 7.34-7.27 (m, 2H), 7.04-6.96 (m, 2H), 6.22 (d, J=1.9 Hz, 1H), 3.13 (ddd, J=17.9, 6.8, 1.6 Hz, 1H), 2.90-2.80 (m, 1H), 2.69-2.61 (m, 1H), 2.42-2.35 (m, 1H), 0.96-0.91 (m, 1H).

Step 2: Preparation of rac-(1R,5R,6S)-3-(4-fluorophenyl)-N'-hydroxybicyclo[3.1.0]hex-2-ene-6-carboximidamide

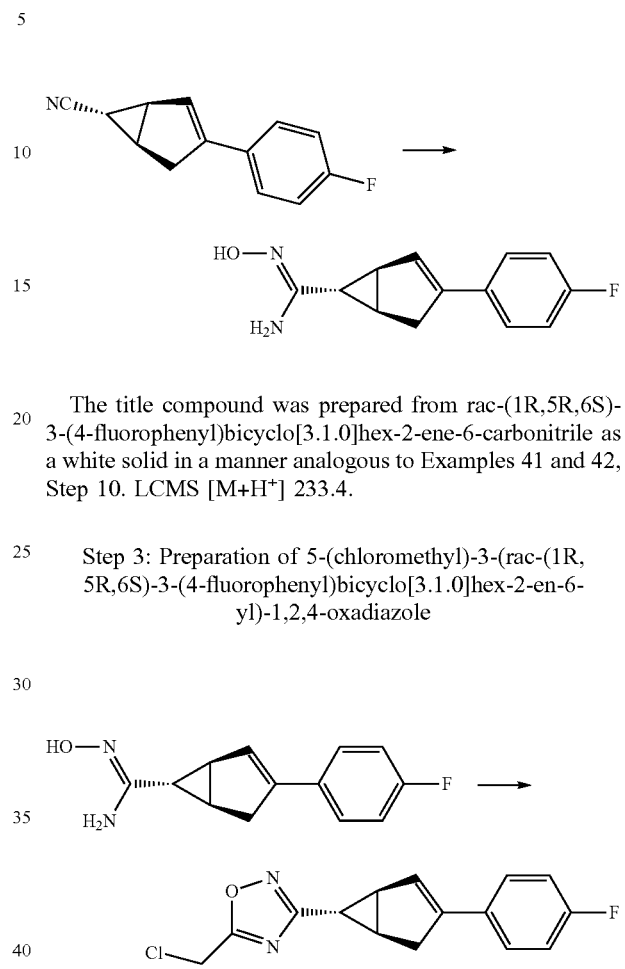

The title compound was prepared from rac-(1R,5R,6S)-3-(4-fluorophenyl)bicyclo[3.1.0]hex-2-ene-6-carbonitrile as a white solid in a manner analogous to Examples 41 and 42, Step 10. LCMS [M+H$^+$] 233.4.

Step 3: Preparation of 5-(chloromethyl)-3-(rac-(1R,5R,6S)-3-(4-fluorophenyl)bicyclo[3.1.0]hex-2-en-6-yl)-1,2,4-oxadiazole The title compound was prepared from rac-(1R,5R,6S)-3-(4-fluorophenyl)-N'-hydroxybicyclo[3.1.0]hex-2-ene-6-carboximidamide as a white solid in a manner analogous to Examples 41 and 42, Step 11.

Step 4: Preparation of 1-((3-((1R,5R,6S)-3-(4-fluorophenyl)bicyclo[3.1.0]hex-2-en-6-yl)-1,2,4-oxadiazol-5-yl)methyl)-7-methyl-1,7-dihydro-6H-purin-6-one (Example Compound 124) and 1-((3-((1S,5S,6R)-3-(4-fluorophenyl)bicyclo[3.1.0]hex-2-en-6-yl)-1,2,4-oxadiazol-5-yl)methyl)-7-methyl-1,7-dihydro-6H-purin-6-one (Example Compound 125)

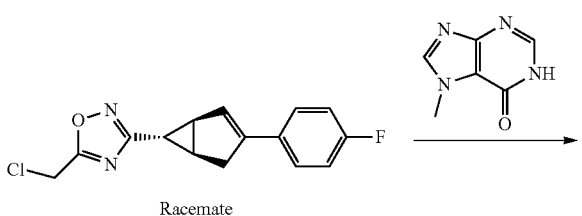

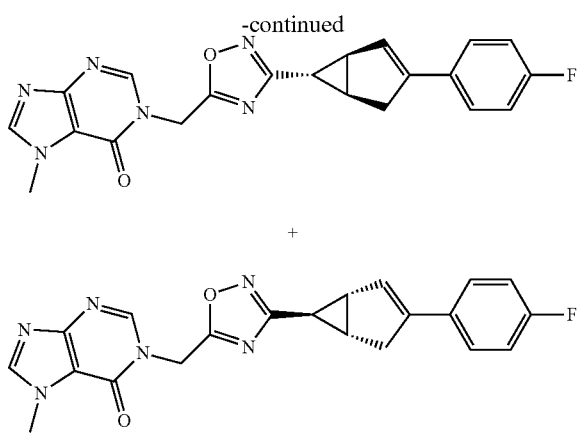

The title compounds were prepared from 5-(chloromethyl)-3-(rac-(1R,5R,6S)-3-(4-fluorophenyl)bicyclo[3.1.0]hex-2-en-6-yl)-1,2,4-oxadiazole and 7-methyl-1H-purin-6-one in a manner analogous to Examples 41 and 42, Step 12. The racemic mixture was separated by SFC with the following conditions: ChiralCel OJ 10×250 mm, 5 µm, Isocratic 45% MeOH+10 mM Ammonium Formate, 10 mL/min, 100 Bar, Column temperature: 35° C. Run Time: 18 min.

Example 56, enantiomer 1, (Example Compound 124): white solid, Rt=3.84 min (ChiralCel OJ, 4.6×150 mm, 5 to 55% MeOH+10 mM AmFor—5 mL/min); LCMS [M+H$^+$] 405.2; $^1$H NMR (400 MHz, DMSO-D6) δ 8.43 (s, 1H), 8.26-8.22 (m, 1H), 7.51-7.41 (m, 2H), 7.18-7.10 (m, 2H), 6.50 (d, J=1.7 Hz, 1H), 5.51 (s, 2H), 3.95 (s, 3H), 3.08 (dd, J=19.0, 6.9 Hz, 1H), 2.90 (d, J=17.6 Hz, 1H), 2.47-2.41 (m, 1H), 2.25 (td, J=6.5, 3.4 Hz, 1H), 1.66-1.61 (m, 1H).

Example 57, enantiomer 2, (Example Compound 125): white solid, Rt=3.98 min (ChiralCel OJ, 4.6×150 mm, 5 to 55% MeOH+10 mM AmFor—5 mL/min); LCMS [M+H$^+$] 405.3; $^1$H NMR (400 MHz, DMSO-D6) δ 8.44 (s, 1H), 8.27-8.22 (m, 1H), 7.50-7.41 (m, 2H), 7.19-7.10 (m, 2H), 6.50 (d, J=1.7 Hz, 1H), 5.51 (s, 2H), 3.95 (s, 3H), 3.07 (dd, J=18.2, 6.0 Hz, 1H), 2.90 (d, J=17.7 Hz, 1H), 2.47-2.41 (m, 1H), 2.25 (td, J=6.5, 3.4 Hz, 1H), 1.67-1.62 (m, 1H).

Examples 58 and 59: Preparation of 1-((3-((1R,5R,6S)-3-(isoquinolin-7-yl)bicyclo[3.1.0]hex-2-en-6-yl)-1,2,4-oxadiazol-5-yl)methyl)-7-methyl-1,7-dihydro-6H-purin-6-one (Example Compound 136) and 1-((3-((1S,5S,6R)-3-(isoquinolin-7-yl)bicyclo[3.1.0]hex-2-en-6-yl)-1,2,4-oxadiazol-5-yl)methyl)-7-methyl-1,7-dihydro-6H-purin-6-one (Example compound 135)

The overall Examples 58 and 59 reaction scheme is as follows:

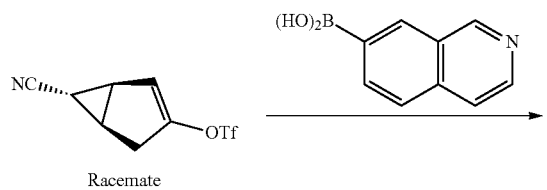
Racemate

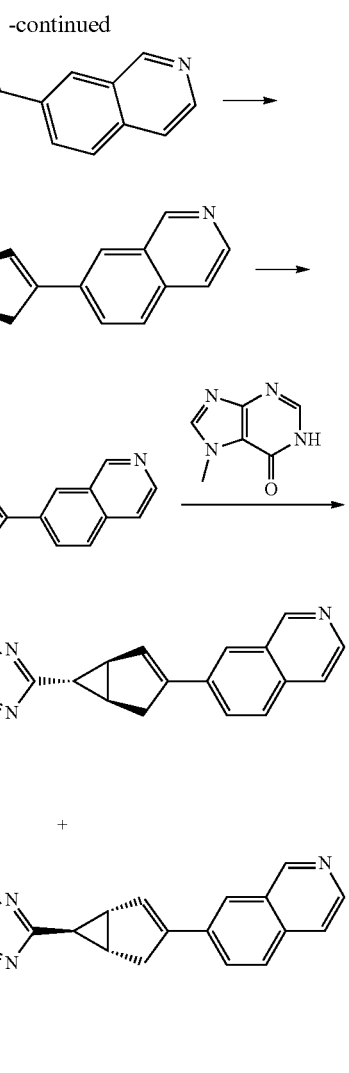

Step 1: Preparation of rac-(1R,5R,6S)-3-(7-isoquinolyl)bicyclo[3.1.0]hex-3-ene-6-carbonitrile

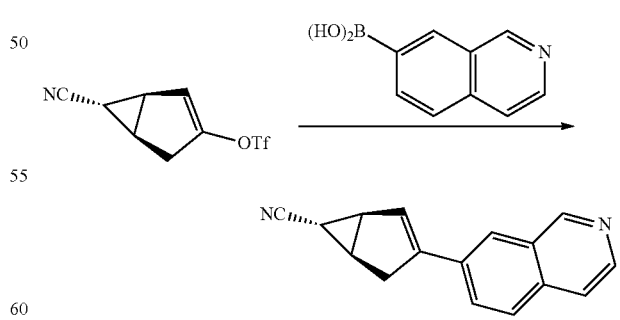

Using cesium carbonate as a base, the title compound was prepared from rac-(1S,5R,6S)-6-cyanobicyclo[3.1.0]hex-2-en-3-yl trifluoromethanesulfonate and isoquinolin-7-ylboronic acid as a beige solid in a manner analogous to Examples 52 and 53, Step 1. LCMS [M+H$^+$] 233.3.

Step 2: Preparation of rac-(1R,5R,6S,Z)—N'-hydroxy-3-(isoquinolin-7-yl)bicyclo[3.1.0]hex-2-ene-6-carboximidamid

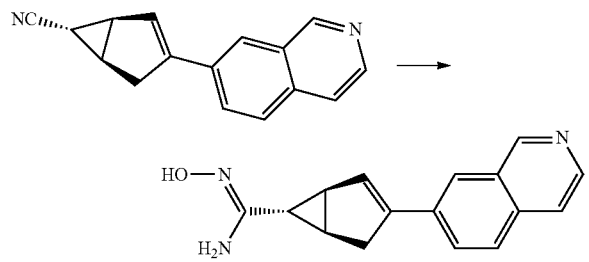

The title compound was prepared from rac-(1R,5R,6S)-3-(7-isoquinolyl)bicyclo[3.1.0]hex-3-ene-6-carbonitrile as a beige solid in a manner analogous to Examples 41 and 42, Step 10. LCMS [M+H$^+$] 266.2.

Step 3: Preparation of 5-(chloromethyl)-3-[rac-(1R, 5R,6S)-3-(7-isoquinolyl)-6-bicyclo[3.1.0]hex-3-enyl]-1,2,4-oxadiazole

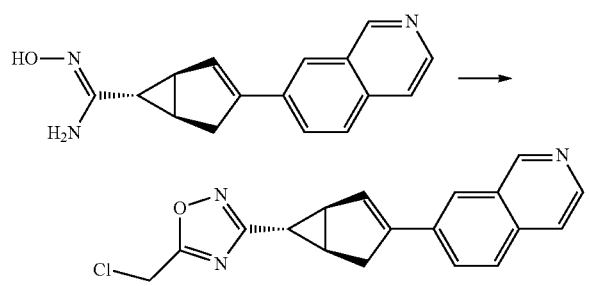

The title compound was prepared from rac-(1R,5R,6S, Z)—N'-hydroxy-3-(isoquinolin-7-yl)bicyclo[3.1.0]hex-2-ene-6-carboximidamide as a yellow oil in a manner analogous to Examples 41 and 42, Step 11. LCMS [M+H$^+$] 266.2.

Step 4: Preparation of 1-((3-((1R,5R,6S)-3-(isoquinolin-7-yl)bicyclo[3.1.0]hex-2-en-6-yl)-1,2,4-oxadiazol-5-yl)methyl)-7-methyl-1,7-dihydro-6H-purin-6-one (Example Compound 136) and 1-((3-((1S,5S, 6R)-3-(isoquinolin-7-yl)bicyclo[3.1.0]hex-2-en-6-yl)-1,2,4-oxadiazol-5-yl)methyl)-7-methyl-1,7-dihydro-6H-purin-6-one (Example Compound 135)

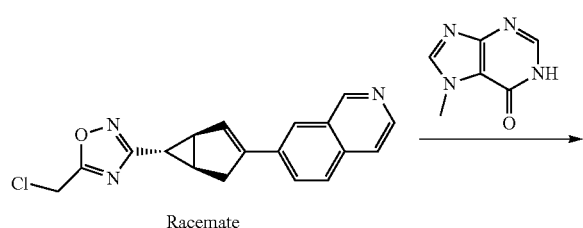

Racemate

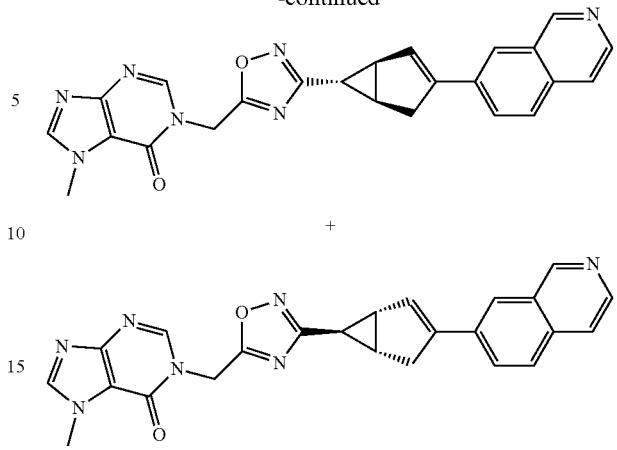

The title compounds were prepared from 5-(chloromethyl)-3-[rac-(1R,5R,6S)-3-(7-isoquinolyl)-6-bicyclo[3.1.0] hex-3-enyl]-1,2,4-oxadiazole and 7-methyl-1H-purin-6-one in a manner analogous to Examples 41 and 42, Step 12. The racemic mixture was separated by SFC with the following conditions: Column: ChiralPack IA 10×250 mm, 5 μm, Isocratic 55% ACN+EtOH 1:1, 10 mL/min, 100 Bar, Column temperature: 35° C., Run Time: 53 min.

Example 59, enantiomer 1, (Example Compound 136): white solid, Rt=22.8 min (ChiralPack IA 10×250 mm, 5 μm, Isocratic 55% ACN+EtOH 1:1, 10 mL/min); LCMS [M+H$^+$] 438.0; $^1$H NMR (400 MHz, DMSO-d6) δ 9.27 (s, 1H), 8.48-8.41 (m, 2H), 8.24 (s, 1H), 8.04-7.95 (m, 2H), 7.92-7.85 (m, 1H), 7.78 (d, J=5.5 Hz, 1H), 6.81-6.76 (m, 1H), 5.52 (s, 2H), 3.96 (s, 3H), 3.28-3.16 (m, 1H), 3.13-3.02 (m, 1H), 2.57-2.49 (m, 1H), 2.38-2.29 (m, 1H), 1.74 (t, J=2.9 Hz, 1H).

Example 58, enantiomer 2, (Example Compound 135): white solid, Rt=35.1 min (ChiralPack IA 10×250 mm, 5 μm, Isocratic 55% ACN+EtOH 1:1, 10 mL/min); LCMS [M+H$^+$] 438.0; $^1$H NMR (400 MHz, DMSO-d6) δ 9.27 (s, 1H), 8.48-8.41 (m, 2H), 8.24 (s, 1H), 8.03-7.94 (m, 2H), 7.92-7.85 (m, 1H), 7.77 (d, J=5.4 Hz, 1H), 6.81-6.76 (m, 1H), 5.52 (s, 2H), 3.96 (s, 3H), 3.28-3.16 (m, 1H), 3.13-3.02 (m, 1H), 2.57-2.49 (m, 1H), 2.38-2.29 (m, 1H), 1.76-1.70 (m, 1H).

Example 60: Preparation of 6-((3-((1R,5S,6r)-3-(3-chlorophenyl)-3-azabicyclo[3.1.0]hexan-6-yl)-1,2,4-oxadiazol-5-yl)methyl)-1-methyl-1,6-dihydro-7H-[1, 2,3]triazolo[4,5-d]pyrimidin-7-one (Example Compound 139)

The overall Example 60 reaction scheme is as follows:

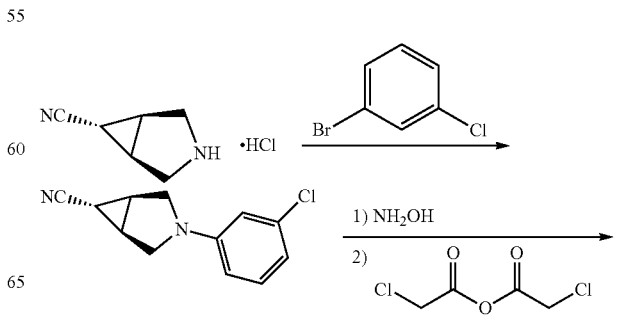

265
-continued

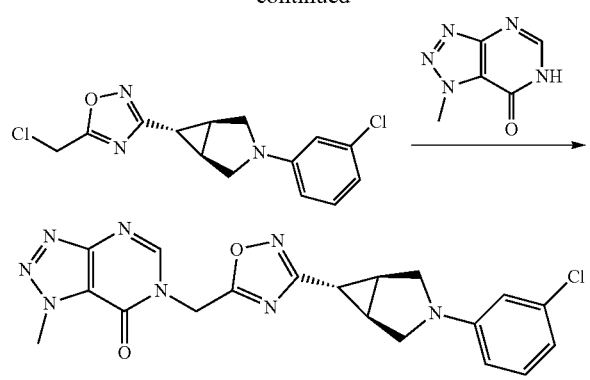

Step 1: Preparation of (1R,5S,6r)-3-(3-chlorophenyl)-3-azabicyclo[3.1.0]hexane-6-carbonitrile

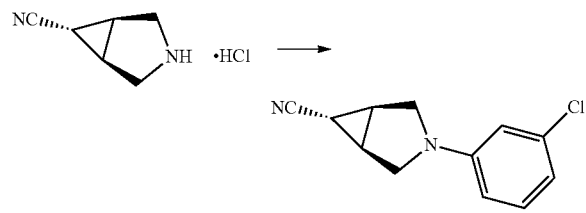

To a vial was added (1R,5S)-3-azabicyclo[3.1.0]hexane-6-carbonitrile; hydrochloride (as prepared in Example 21, Step 6) (2.41 g, 16.7 mmol), chloro[9,9-dimethyl-4,5-bis(diphenylphosphino)xanthene][2'-amino-1,1'-biphenyl]palladium(II) (1.51 g, 1.67 mmol) and potassium phosphate tribasic (12.8 g, 58.3 mmol). The vial was then purged evacuated and backfilled with nitrogen. 1,4-dioxane (29 mL) was then added followed by 3-bromochlorobenzene (2.15 mL, 18.3 mmol) and the reaction mixture was stirred at 110° C. for 16 h. The reaction mixture was diluted with dichloromethane, filtered through celite, eluting with dichloromethane and the filtrate was concentrated in vacuo. The residue was adsorbed onto silica and purified by flash column chromatography with 0-100% iPrOAc in heptane to afford the desired compound as an orange solid (1.35 g, 37%). 1H NMR (400 MHz, Chloroform-d) δ 7.12 (t, J=8.1 Hz, 1H), 6.73 (ddd, J=8.0, 1.8, 0.8 Hz, 1H), 6.53 (t, J=2.2 Hz, 1H), 6.42 (ddd, J=8.4, 2.3, 0.8 Hz, 1H), 3.65 (d, J=9.7 Hz, 2H), 3.41-3.23 (m, 2H), 2.40-2.30 (m, 2H), 1.45 (t, J=3.4 Hz, 1H).

Step 2: Preparation of 5-(chloromethyl)-3-((1R,5S,6r)-3-(3-chlorophenyl)-3-azabicyclo[3.1.0]hexan-6-yl)-1,2,4-oxadiazole

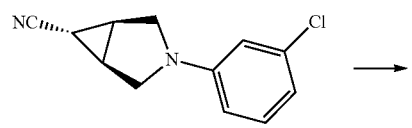

266
-continued

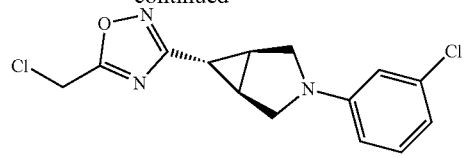

To a solution of 3-(3-chlorophenyl)-3-azabicyclo[3.1.0]hexane-6-carbonitrile (1.35 g, 6.17 mmol) in methanol (60 mL) was added hydroxylamine hydrochloride (643 mg, 9.25 mmol) followed by sodium bicarbonate (2.59 g, 30.8 mmol) and the reaction mixture was heated to reflux overnight. The reaction mixture was cooled to room temperature, filtered and the filter cake was washed with MeOH. The filtrate was concentrated in vacuo and the residue was taken up in DCM and washed with water, brine, dried over sodium sulfate, filtered and concentrated in vacuo. The residue was dissolved in dichloromethane (30 mL), triethylamine (0.46 mL, 3.33 mmol) was added, the mixture was cooled to 0° C. and chloroacetyl chloride (0.26 mL, 3.33 mmol) was added, dropwise. The reaction mixture was stirred at 0° C. for 10 mins. The reaction mixture was concentrated in vacuo and the residue was taken up in DCM and washed with sat. aq. sodium bicarbonate and water, dried over sodium sulfate, filtered and concentrated in vacuo. The residue was dissolved in toluene (45 mL), a dean-stark apparatus was attached and the mixture was heated to 125° C. for 3 h. then cooled to room temperature and the reaction mixture was concentrated in vacuo. The residue was adsorbed onto silica and purified by flash column chromatography with 0-100% EtOAc in heptane to afford the desired compound as a light yellow oil that solidified over time (672 mg, 35% over 3 steps). 1H NMR (400 MHz, Chloroform-d) δ 7.12 (t, J=8.1 Hz, 1H), 6.73-6.66 (m, 1H), 6.55 (t, J=2.2 Hz, 1H), 6.49-6.41 (m, 1H), 4.63 (s, 2H), 3.70 (d, J=9.4 Hz, 2H), 3.44-3.33 (m, 2H), 2.38-2.26 (m, 2H), 2.15 (t, J=3.3 Hz, 1H).

Step 3: Preparation of 6-((3-((1R,5S,6r)-3-(3-chlorophenyl)-3-azabicyclo[3.1.0]hexan-6-yl)-1,2,4-oxadiazol-5-yl)methyl)-1-methyl-1,6-dihydro-7H-[1,2,3]triazolo[4,5-d]pyrimidin-7-one (Example Compound 139)

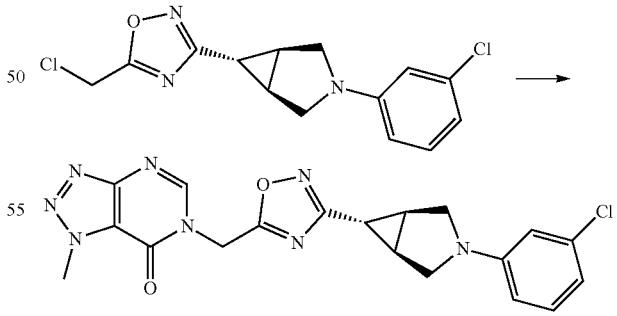

A mixture of 1-methyl-6H-triazolo[4,5-d]pyrimidin-7-one (40 mg, 0.27 mmol), 5-(chloromethyl)-3-[3-(3-chlorophenyl)-3-azabicyclo[3.1.0]hexan-6-yl]-1,2,4-oxadiazole (75 mg, 0.24 mmol), potassium carbonate (100 mg, 0.73 mmol) and sodium iodide (1.8 mg, 0.012 mmol) in acetone (2 mL) were stirred at room temperature for 2 h. The reaction mixture was diluted with acetone, filtered through a fritted funnel, eluting with acetone and the filtrate was concentrated in vacuo. The residue was adsorbed onto silica and purified by flash column chromatography with 10-80% 3:1 MeOH: iPrOAc in Heptane to afford the partially purified desired compound as a white solid. The residue was further purified by achiral SFC to yield the title compound (15.3 mg, 15%) as a white solid. LCMS [M+H$^+$]: 425.1. 1H NMR (400 MHz, DMSO-d6) δ 8.57 (s, 1H), 7.15 (t, J=8.1 Hz, 1H), 6.65 (dd, J=7.6, 1.9 Hz, 1H), 6.57-6.55 (m, 1H), 6.53-6.49 (m, 1H), 5.57 (s, 2H), 4.36 (s, 3H), 3.67 (d, J=9.9 Hz, 2H), 3.30-3.25 (m, 2H), 2.22-2.19 (m, 2H), 2.01 (t, J=3.3 Hz, 1H).

Example 61: Preparation of 7-methyl-1-((3-((1R,5S,6r)-3-(5-methylpyridin-2-yl)-3-azabicyclo[3.1.0]hexan-6-yl)-1,2,4-oxadiazol-5-yl)methyl)-1,7-dihydro-6H-purin-6-one (Example Compound 140)

The overall Example 61 reaction scheme is as follows:

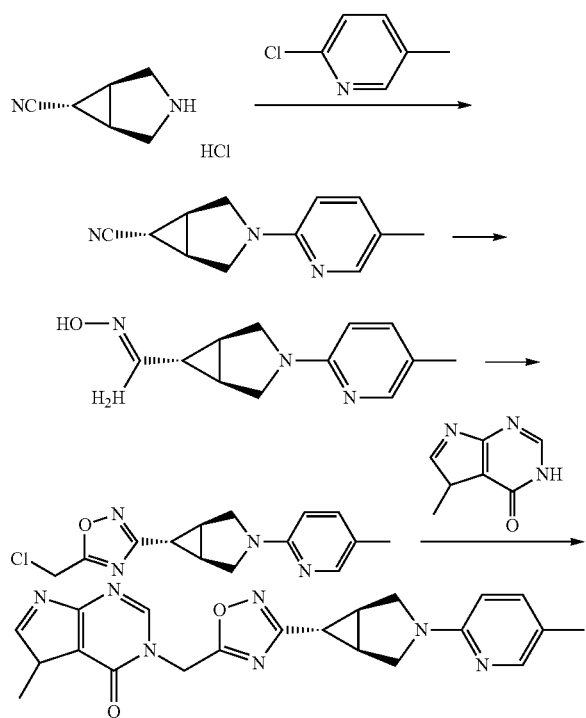

Step 1: Preparation of (1R,5S,6r)-3-(5-methylpyridin-2-yl)-3-azabicyclo[3.1.0]hexane-6-carbonitrile

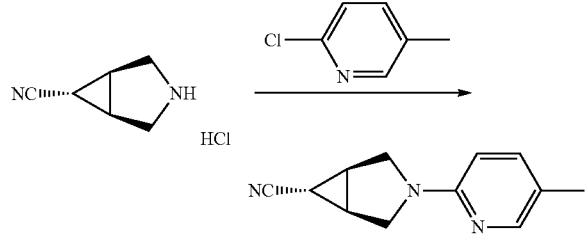

To a vial was added 3-azabicyclo[3.1.0]hexane-6-carbonitrile hydrochloride (300 mg, 2.07 mmol), chloro[2-dicyclohexylphosphino-2',6'-diisopropoxy-1,1'-biphenyl][2'-amino-, 1'-biphenyl]palladium(II) (164 mg, 0.207 mmol) and cesium carbonate (2.37 g, 7.26 mmol). 1,4-Dioxane (9.0 mL) was then added followed by 2-chloro-5-methylpyridine (249 μL, 2.28 mmol). The headspace was flushed with nitrogen for 10 seconds, the vial was sealed, and the reaction mixture was stirred at 110° C. for 16 h. The reaction mixture was washed with water, extracted 3 times with iPrOAc, dried over sodium sulfate, filtered, and concentrated in vacuo. The residue was adsorbed onto silica and purified by flash column chromatography with 0-100% iPrOAc in heptane to afford the desired compound as a white solid (293 mg, 71%). $^1$H NMR (400 MHz, CDCl$_3$-d) δ 7.89 (s, 1H), 7.33 (dd, J=8.5, 2.4 Hz, 1H), 6.40 (d, J=8.7 Hz, 1H), 3.73 (d, J=10.7 Hz, 2H), 3.29-3.26 (m, 2H), 2.43-2.40 (m, 2H), 2.12 (s, 3H), 1.65 (t, J=3.3 Hz, 1H).

Step 2: Preparation of (1R,5S,6r,Z)—N-hydroxy-3-(5-methylpyridin-2-yl)-3-azabicyclo[3.1.0]hexane-6-carboximidamide

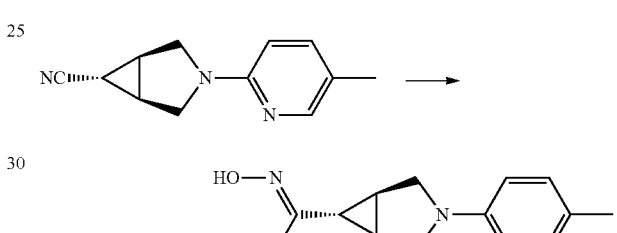

The title compound was prepared from (1R,5S,6r)-3-(5-methylpyridin-2-yl)-3-azabicyclo[3.1.0]hexane-6-carbonitrile (293 mg, 1.47 mmol) in a manner analogous to Example 50, Step 2.

Step 3: Preparation of 5-(chloromethyl)-3-((1R,5S,6r)-3-(5-methylpyridin-2-yl)-3-azabicyclo[3.1.0]hexan-6-yl)-1,2,4-oxadiazole

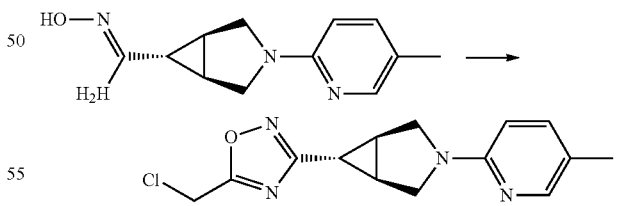

The title compound was prepared from (1R,5S,6r,Z)—N-hydroxy-3-(5-methylpyridin-2-yl)-3-azabicyclo[3.1.0]hexane-6-carboximidamide (342 mg, 1.47 mmol) as a yellow oil (224 mg, 52% yield) in a manner analogous to Example 50, Step 3. $^1$H NMR (400 MHz, CDCl$_3$-d) δ 7.91 (dd, J=1.6, 0.8 Hz, 1H), 7.34 (dd, J=8.5, 2.4 Hz, 1H), 6.43 (d, J=8.6 Hz, 1H), 5.05 (s, 2H), 3.81 (d, J=10.5 Hz, 21-1H), 3.41 (d, J:=9.4 Hz, 21-), 2.27-2.23 (m, 2H), 2.13 (s, 3H), 2.03 (t, J=: 3.3 Hz, 11H).

Step 4: Preparation of 7-methyl-1-((3-((1R,5S,6r)-3-(5-methylpyridin-2-yl)-3-azabicyclo[3.1.0]hexan-6-yl)-1,2,4-oxadiazol-5-yl)methyl)-1,7-dihydro-6H-purin-6-one (Example Compound 140)

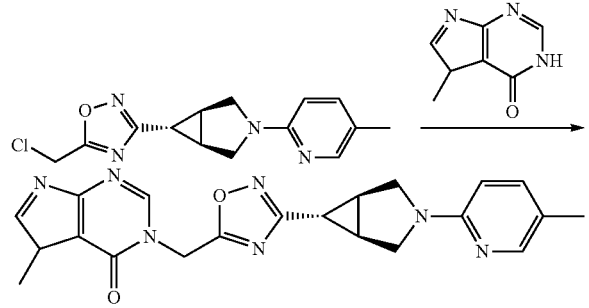

The title compound was prepared from 5-(chloromethyl)-3-((1R,5S,6r)-3-(5-methylpyridin-2-yl)-3-azabicyclo[3.1.0]hexan-6-yl)-1,2,4-oxadiazole (224 mg, 0.770 mmol) and 7-methyl-1,7-dihydro-6H-purin-6-one (127 mg, 0.847 mmol) as a white solid (24.5 mg, 8% yield), in a manner analogous to Example 25, Step 5. LCMS [M+H⁺] 405.2. ¹H NMR (400 MHz, DMSO) δ 8.43 (s, 1H), 8.23 (s, 1H), 7.92-7.85 (m, 1H), 7.33 (dd, J=8.6, 2.2 Hz, 1H), 6.40 (d, J=8.5 Hz, 1H), 5.51 (s, 2H), 3.95 (s, 3H), 3.78 (d, J=10.5 Hz, 2H), 3.40-3.34 (m, 2H), 2.17 (d, J=2.3 Hz, 2H), 2.12 (s, 3H), 1.97 (t, J=3.2 Hz, 1H).

Examples 62 and 63: Preparation of 1-((3-((1R,5R,6S)-3-(4-chlorophenyl)bicyclo[3.1.0]hex-2-en-6-yl)-1,2,4-oxadiazol-5-yl)methyl)-7-methyl-1,7-dihydro-6H-purin-6-one (Example Compound 142) and 1-((3-((1S,5S,6R)-3-(4-chlorophenyl)bicyclo[3.1.0]hex-2-en-6-yl)-1,2,4-oxadiazol-5-yl)methyl)-7-methyl-1,7-dihydro-6H-purin-6-one (Example Compound 141)

The overall Examples 62 and 63 reaction scheme is as follows:

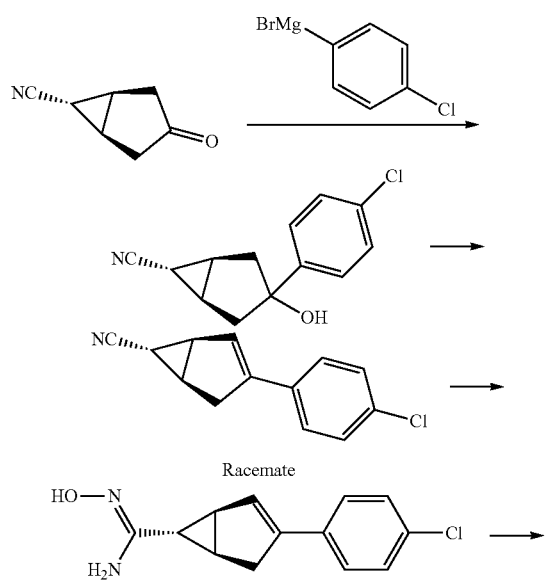

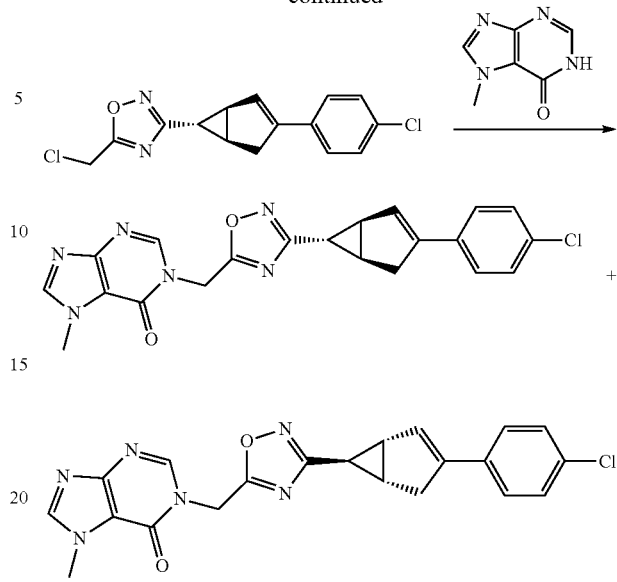

Step 1: Preparation of (1S,5R)-3-(4-chlorophenyl)-3-hydroxy-bicyclo[3.1.0]hexane-6-carbonitrile

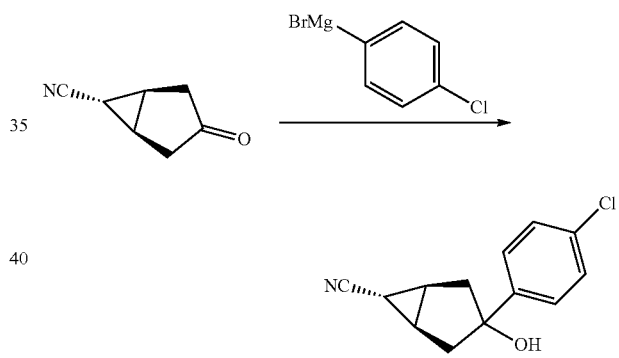

Anhydrous CeCl₃ (839 mg, 3.41 mmol) was charged in a 100 mL round bottom flask under nitrogen and followed by the addition of THF (14 mL). The mixture was stirred at 20° C. overnight. The white suspension was cooled to −78° C. and 4-chlorophenylmagnesium bromide (3.1 mL, 3.1 mmol) was added dropwise. The solution was stirred at −78° C. for 1.5 hour followed by the dropwise addition of a solution of (trans)-3-oxobicyclo[3.1.0]hexane-6-carbonitrile (125 mg, 1.03 mmol) in THF (5 mL). The temperature was kept at −78° C. for 2 h and the reaction mixture was quenched by the slow addition of a saturated aqueous solution of NaHCO₃. The mixture was allowed to warm at room temperature and it was diluted with water. The resulting mixture was extracted with ethyl ether (3×). The combined organic layers were washed with brine, dried over anhydrous MgSO₄, filtered and concentrated under reduced pressure to give crude (1S,5R)-3-(4-chlorophenyl)-3-hydroxy-bicyclo[3.1.0]hexane-6-carbonitrile (241 mg, 100% yield). The crude material was used directly in the next reaction.

Step 2: Preparation of rac-(1R,5R,6S)-3-(4-chlorophenyl)bicyclo[3.1.0]hex-3-ene-6-carbonitrile

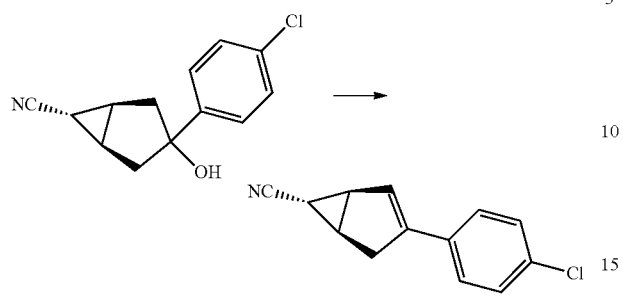

To a solution of crude (1S,5R)-3-(4-chlorophenyl)-3-hydroxy-bicyclo[3.1.0]hexane-6-carbonitrile (241 mg, 1.03 mmol) in DCM (5 mL) was added trifluoroacetic acid (0.79 mL, 10 mmol). The reaction mixture was stirred at 20° C. for 20 min. and the reaction mixture was concentrated under reduced pressure. The obtained residue was purified by flash column chromatography (24 g column) on silica gel using a solution of EtOAc in hexanes (0 to 5% gradient) to afford rac-(1R,5R,6S)-3-(4-chlorophenyl)bicyclo[3.1.0]hex-3-ene-6-carbonitrile (160 mg, 72% yield) as a white solid. $^1$H NMR (500 MHz, CDCl$_3$) δ 7.34-7.24 (m, 4H), 6.32-6.30 (m, 1H), 3.16 (ddd, J=17.9, 6.8, 1.9 Hz, 1H), 2.92-2.84 (m, 1H), 2.72-2.67 (m, 1H), 2.45-2.39 (m, 1H), 0.98-0.95 (m, 1H).

Step 3: Preparation of rac-(1R,5R,6S,Z)-3-(4-chlorophenyl)-N'-hydroxybicyclo[3.1.0]hex-2-ene-6-carboximidamide

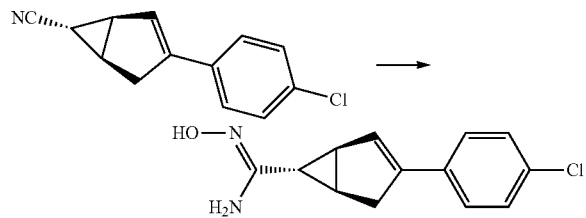

The title compound was prepared from rac-(1R,5R,6S)-3-(4-chlorophenyl)bicyclo[3.1.0]hex-3-ene-6-carbonitrile as a white solid in a manner analogous to Examples 41 and 42, Step 10. LCMS [M+H$^+$] 249.2.

Step 4: Preparation of 5-(chloromethyl)-3-[rac-(1R,5R,6S)-3-(4-chlorophenyl)-6-bicyclo[3.1.0]hex-3-enyl]-1,2,4-oxadiazole

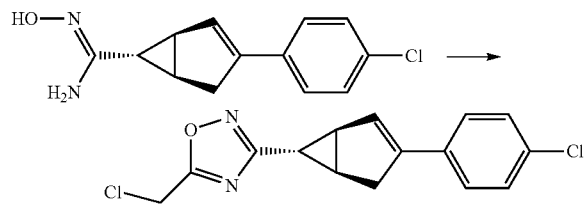

The title compound was prepared from rac-(1R,5R,6S,Z)-3-(4-chlorophenyl)-N'-hydroxybicyclo[3.1.0]hex-2-ene-6-carboximidamide as a white solid in a manner analogous to Examples 41 and 42, Step 11. LCMS [M+H$^+$] 249.2. $^1$H NMR (500 MHz, CDCl$_3$) δ 7.33-7.26 (m, 4H), 6.42-6.40 (m, 1H), 4.63 (s, 2H), 3.17 (dd, J=17.8, 7.0 Hz, 1H), 2.94-2.88 (m, 1H), 2.61-2.54 (m, 1H), 2.42-2.37 (m, 1H), 1.77-1.72 (m, 1H).

Step 5: Preparation of 1-((3-((1R,5R,6S)-3-(4-chlorophenyl)bicyclo[3.1.0]hex-2-en-6-yl)-1,2,4-oxadiazol-5-yl)methyl)-7-methyl-1,7-dihydro-6H-purin-6-one (Example Compound 142) and 1-((3-((1S,5S,6R)-3-(4-chlorophenyl)bicyclo[3.1.0]hex-2-en-6-yl)-1,2,4-oxadiazol-5-yl)methyl)-7-methyl-1,7-dihydro-6H-purin-6-one (Example Compound 141)

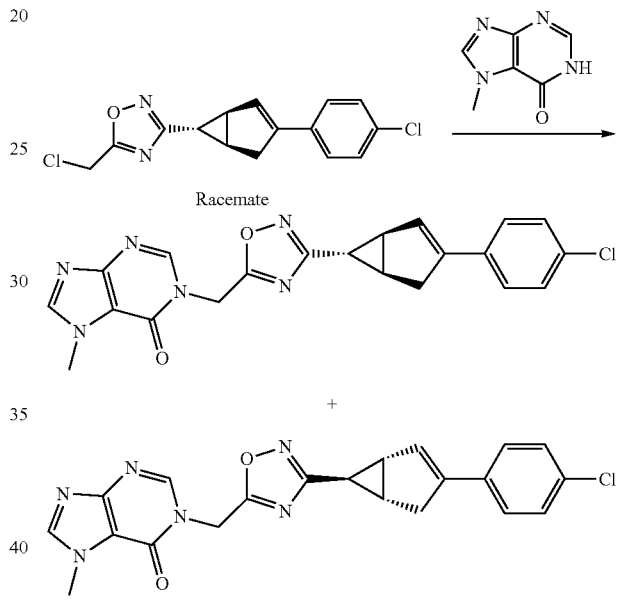

The title compounds were prepared from 5-(chloromethyl)-3-[rac-(1R,5R,6S)-3-(4-chlorophenyl)-6-bicyclo[3.1.0]hex-3-enyl]-1,2,4-oxadiazole and 7-methyl-1H-purin-6-one in a manner analogous to Examples 41 and 42, Step 12. The racemic mixture was separated by SFC with the following conditions: Column: Lux Cellulose-3, 10×250 mm, 5 μm, 40% isopropanol, 10 mL/min, 150 bar, Column Temperature: 40° C., Run time: 17 min.

Example 63, enantiomer 1, (Example Compound 142): white solid, Rt=13.6 min (Lux Cellulose-3, 10×250 mm 5 μm, 40% isopropanol, 10 mL/min); LCMS [M+H$^+$] 421.1; $^1$H NMR (400 MHz, DMSO-d6) δ 8.43 (s, 1H), 8.24 (s, 1H), 7.44 (d, J=8.6 Hz, 2H), 7.37 (d, J=8.6 Hz, 2H), 6.58 (s, 1H), 5.51 (s, 2H), 3.95 (s, 3H), 3.11-3.02 (m, 1H), 2.94-2.85 (m, 1H), 2.48-2.42 (m, 1H), 2.30-2.20 (m, 1H), 1.65 (t, J=2.9 Hz, 1H).

Example 62, enantiomer 2, (Example Compound 141): white solid, Rt=15.9 min (Lux Cellulose-3, 10×250 mm 5 μm, 40% isopropanol, 10 mL/min); LCMS [M+H$^+$] 421.2; $^1$H NMR (400 MHz, DMSO-d6) δ 8.43 (s, 1H), 8.24 (s, 1H), 7.44 (d, J=8.5 Hz, 2H), 7.37 (d, J=8.5 Hz, 2H), 6.58 (s, 1H), 5.51 (s, 2H), 3.95 (s, 3H), 3.12-3.02 (m, 1H), 2.95-2.86 (m, 1H), 2.48-2.42 (m, 1H), 2.29-2.22 (m, 1H), 1.68-1.64 (m, 1H)

Example 64: Preparation of 3-((3-((1s,3s)-3-fluoro-3-(3-fluorophenyl)cyclobutyl)-1,2,4-oxadiazol-5-yl)methyl)-5-methylpyrido[2,3-d]pyrimidin-4(3H)-one (Example Compound 143)

The overall Example 64 reaction scheme is as follows:

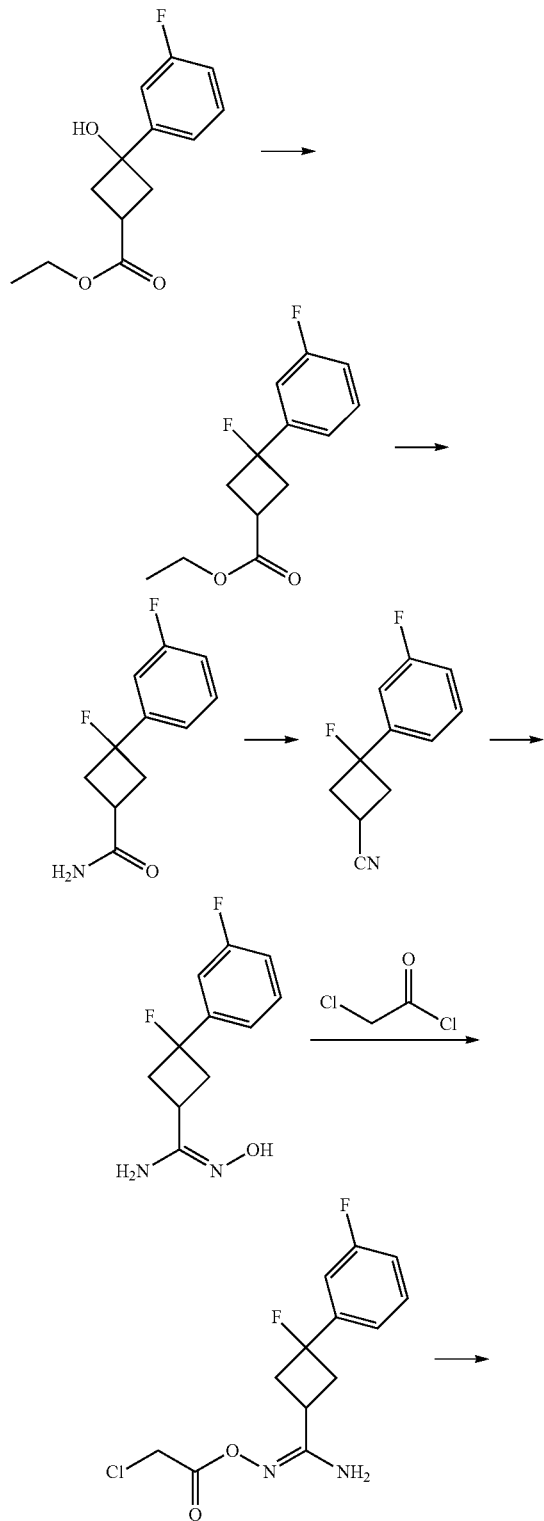

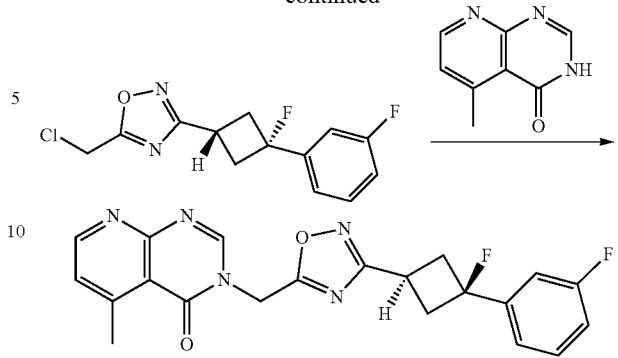

Step 1: Preparation of ethyl 3-fluoro-3-(3-fluorophenyl) cyclobutanecarboxylate

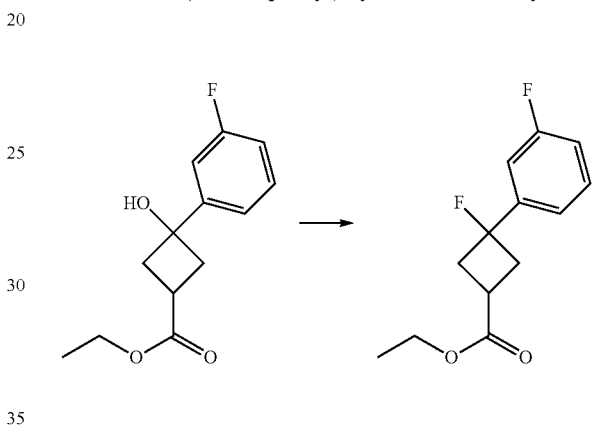

DAST (1.12 g, 6.93 mmol) was added dropwise to a solution of ethyl 3-(3-fluorophenyl)-3-hydroxy-cyclobutanecarboxylate (1.5 g, 6.3 mmol) in dichloromethane (15 mL) and the resulting mixture was stirred at 0° C. for 1 hour. The reaction was quenched with saturated aqueous NaHCO₃, extracted with DCM, dried over anhydrous sodium sulfate, and concentrated under vacuum. The residue was adsorbed onto silica gel and purified by flash column chromatography eluted with ethyl acetate/petroleum ether (1/4) to afford the title compound (1.23 g, 81% yield) as yellow oil.

Step 2: Preparation of 3-fluoro-3-(3-fluorophenyl)cyclobutanecarboxamide

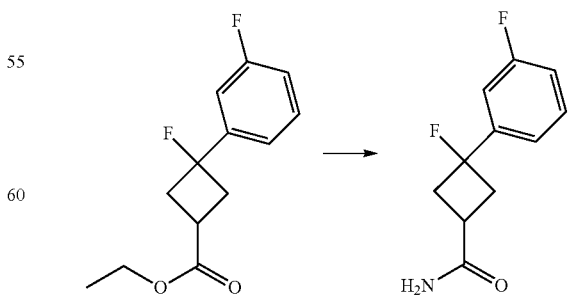

A solution of ethyl 3-fluoro-3-(3-fluorophenyl)cyclobutanecarboxylate (1.10 g, 4.58 mmol) in NH₃ (g)/MeOH (7

M) (10 mL, 4.58 mmol) was stirred at 60° C. for 12 hours. The solvent was removed under vacuum to afford the title compound (940 mg, 97% yield) as a yellow solid.

Step 3: Preparation of 3-fluoro-3-(3-fluorophenyl)cyclobutanecarbonitrile

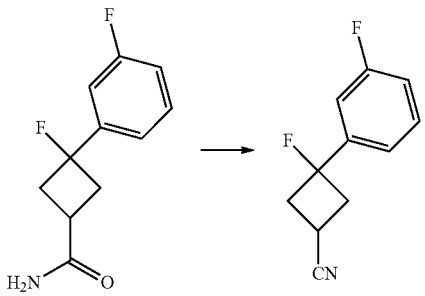 [SMILES: NC(=O)C1CC(F)(c2cccc(F)c2)C1 ; N#CC1CC(F)(c2cccc(F)c2)C1]

POCl₃ (811.78 mg, 5.34 mmol) was added dropwise to a solution of 3-fluoro-3-(3-fluorophenyl)cyclobutanecarboxamide (940 mg, 4.45 mmol) and Et₃N (1.35 g, 13.35 mmol) in dichloromethane (10 mL) at 0° C. and the resulting mixture was stirred at 0° C. for 2 hours. The reaction was quenched with saturated aqueous NaHCO₃, extracted with ethyl acetate, washed with brine, dried over anhydrous sodium sulfate, and concentrated under vacuum. The residue was adsorbed onto silica gel and purified by flash column chromatography eluted with ethyl acetate/petroleum ether (1/4). This resulted in the title compound (620 mg, 72.1% yield) as yellow oil.

Step 4: Preparation of 3-fluoro-3-(3-fluorophenyl)-N'-hydroxy-cyclobutanecarboxamidine

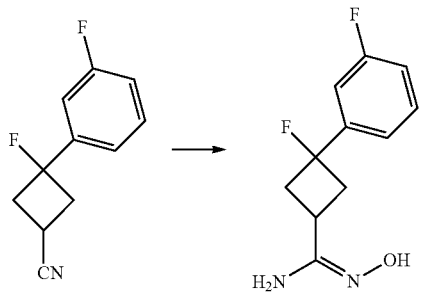 [SMILES: N#CC1CC(F)(c2cccc(F)c2)C1 ; N/C(=N/O)C1CC(F)(c2cccc(F)c2)C1]

A solution of 3-fluoro-3-(3-fluorophenyl)cyclobutanecarbonitrile (10 mg, 0.05 mmol) and NH₂OH (50% aq) (26 mg, 0.52 mmol) in ethanol (3 mL) was stirred at 80° C. for 2 hours. The solvent was removed under vacuum to afford the title compound (10 mg, 85% yield) as yellow oil.

Step 5: Preparation of (E)-[amino-[3-fluoro-3-(3-fluorophenyl)cyclobutyl]methylene]amino] 2-chloroacetate

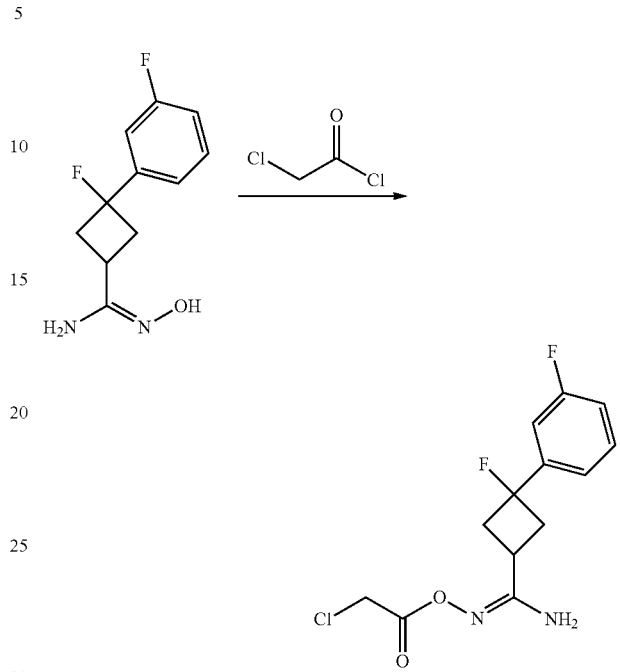

Chloroacethyl chloride (299 mg, 2.65 mmol) was added dropwise to a solution of [3-fluoro-3-(3-fluorophenyl)-N'-hydroxy-cyclobutanecarboxamidine (500 mg, 2.21 mmol) and Et₃N (223 mg, 2.21 mmol)] in acetone (20 mL) at 25° C. and the resulting mixture was stirred at 25° C. for 2 hours. The solids were filtered out. The filtrate was concentrated under reduced pressure to afford the title compound (600 mg, 89% yield) as yellow oil.

Step 6: Preparation of 5-(chloromethyl)-3-[3-fluoro-3-(3-fluorophenyl) cyclobutyl]-1,2,4-oxadiazole

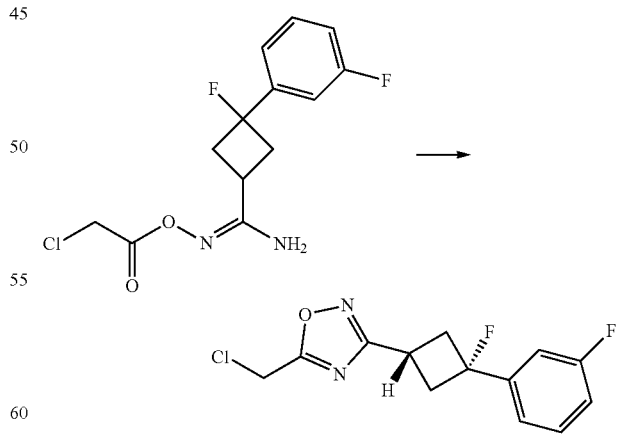

A solution of [amino-[3-fluoro-3-(3-fluorophenyl)cyclobutyl] methylene]amino-2-chloroacetate (600 mg, 1.98 mmol) in toluene (20 mL) was stirred at 100° C. for 2 hours. The solvent was removed under vacuum to afford the title compound (450 mg, 79% yield) as yellow oil.

Step 7: Preparation of 3-((3-((1s,3s)-3-fluoro-3-(3-fluorophenyl)cyclobutyl)-1,2,4-oxadiazol-5-yl)methyl)-5-methylpyrido[2,3-d]pyrimidin-4(3H)-one (Example Compound 143)

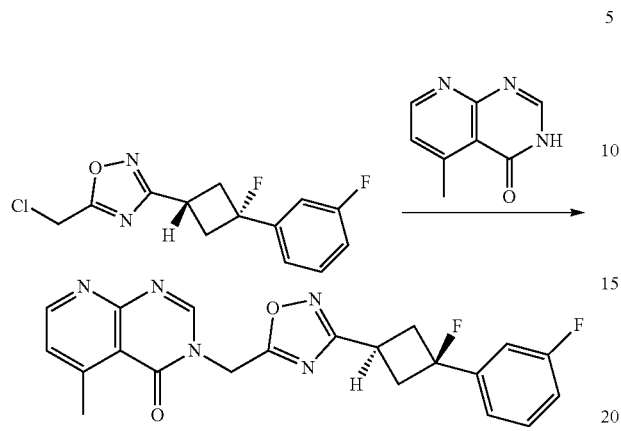

The title compound was prepared from 5-(chloromethyl)-3-[3-fluoro-3-(3-fluorophenyl)cyclobutyl]-1,2,4-oxadiazole and 5-methylpyrido[2,3-d]pyrimidin-4(3H)-one as a white solid (23 mg, 5.8% yield) in a manner analogous to Example 39. LCMS [M+H$^+$]: 410. $^1$H NMR (400 MHz, CDCl$_3$) δ 8.84 (d, J=4.9 Hz, 1H), 8.42 (s, 1H), 7.44-7.39 (m, 1H), 7.30-7.28 (m, 2H), 7.24-7.21 (m, 1H), 7.10-7.05 (m, 1H), 5.41 (s, 2H), 3.43-3.34 (m, 1H), 3.14-3.03 (m, 2H), 3.02-2.94 (m, 2H), 2.92 (s, 3H).

Example 65: Preparation of 3-((3-((1s,3s)-3-(4-chlorophenyl)-3-fluorocyclobutyl)-1,2,4-oxadiazol-5-yl)methyl)-5-methyl-4-oxo-3,4-dihydropyrido[2,3-d]pyrimidine-7-carbonitrile (Example Compound 158)

The overall Example 65 reaction scheme is as follows:

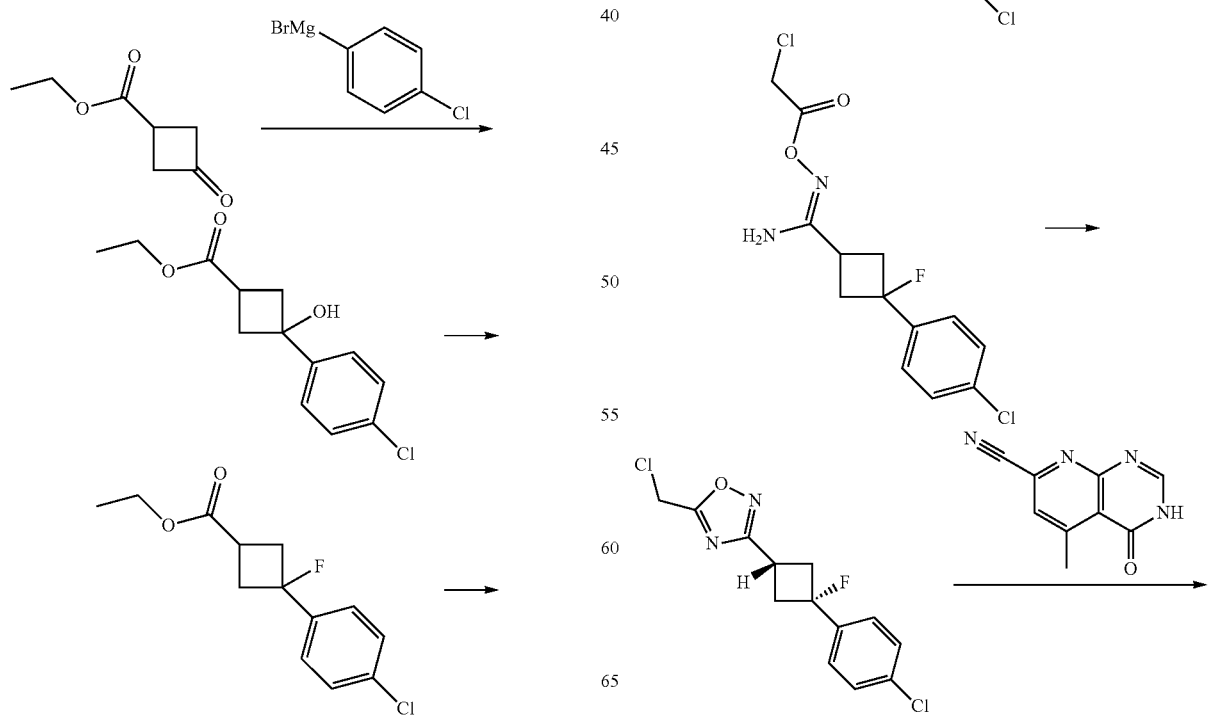

279

-continued

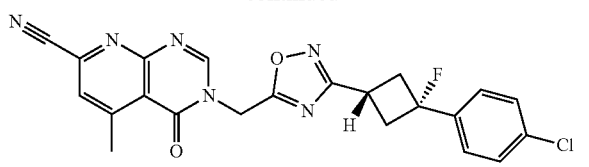

Step 1: Preparation of ethyl
3-(4-chlorophenyl)-3-hydroxycyclobutanecarboxylate

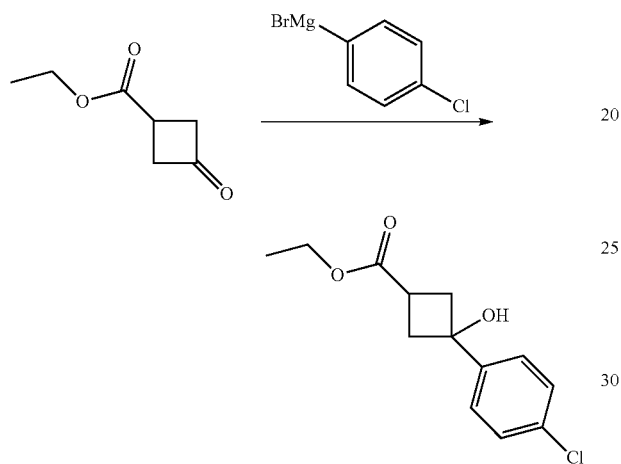

Bromo-(4-chlorophenyl)magnesium (1M in 2-Me-THF) (71.8 mL, 71.755 mmol) was added dropwise using an addition funnel over 30 min to a solution of ethyl 3-oxocyclobutanecarboxylate (1.00 g, 70.3 mmol) in THF (88 mL) at −78° C. under $N_2$. The reaction was stirred at −78° C. for 1 h. The reaction was quenched with saturated $NH_4Cl$. The reaction mixture was partitioned in water/iPrOAc and extracted with iPrOAc (3×). The combined organic extracts were washed with water and brine and they were dried over $MgSO_4$, filtered and concentrated. The crude mixture was adsorbed on silica and purified by silica gel column with 0-50% iPrOAc/heptane to afford the title compound (10.3 g, 58% Yield) as a clear oil.

Step 2: Preparation of ethyl
3-(4-chlorophenyl)-3-fluorocyclobutanecarboxylate

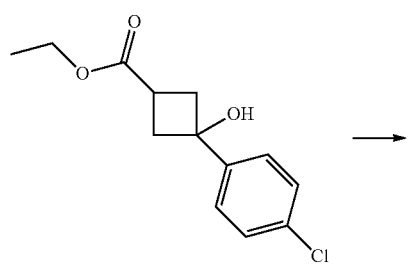

280

-continued

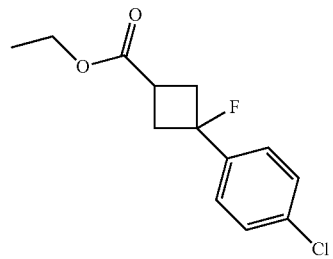

Deoxo-Fluor (8.7 mL, 44.9 mmol was added to a solution of ethyl 3-(4-chlorophenyl)-3-hydroxy-cyclobutanecarboxylate (10.4 mg, 40.8 mmol) in DCM (408 mL) at 0° C. under $N_2$. The reaction was stirred at room temperature for 3 h. The reaction mixture was partitioned in saturated $NaHCO_3$/DCM and extracted with DCM (3×). The combined organic extracts were dried over $MgSO_4$, filtered and concentrated. The crude mixture was adsorbed on silica gel and purified by silica gel column with 0-30% iPrOAc/Heptane to afford the title compound (9.25 g, 88% Yield) as a clear oil.

Step 3: Preparation of
3-(4-chlorophenyl)-3-fluorocyclobutanecarboxamide

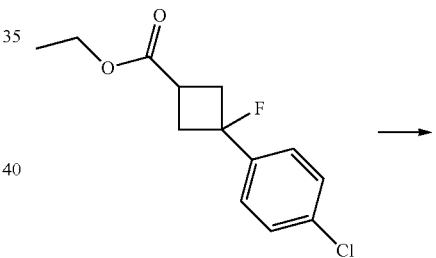

A mixture of ethyl 3-(4-chlorophenyl)-3-fluoro-cyclobutanecarboxylate (9.25 g, 36.0 mmol) in ammonia (7 mol/L) in MeOH (72 mL) was stirred at room temperature overnight. The reaction mixture was concentrated to dryness to afford the title compound as a crude white solid.

Step 4: Preparation of 3-(4-chlorophenyl)-3-fluorocyclobutanecarbonitrile

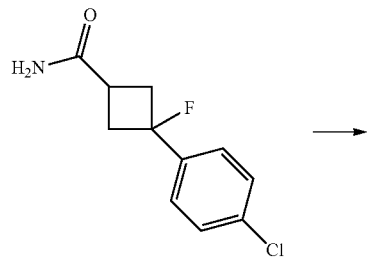

Phosphoryl chloride (3.9 mL, 41.8 mmol) was added to a solution of 3-(4-chlorophenyl)-3-fluoro-cyclobutanecarboxamide (7.32 g, 32.2 mmol) and TEA (9.1 mL, 64.3 mmol) in DCM (107 mL) at 0° C. The reaction was stirred at room temperature for 6 h. The reaction was partitioned in DCM/saturated NaHCO$_3$, extracted with DCM (2×) and washed with water and brine. The DCM layer was dried with MgSO$_4$, filtered and concentrated. The crude mixture was adsorbed on silica gel and purified by silica gel column with 0-30% iPrOAc/Heptane to afford the title compound (5.66 g, 84% Yield) as a white solid. The product was a 3:1 trans/cis mixture by NMR.

Step 5: Epimerization of 3-(4-chlorophenyl)-3-fluorocyclobutanecarbonitrile

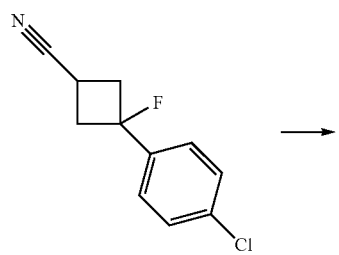

A mixture of 3-(4-chlorophenyl)-3-fluoro-cyclobutanecarbonitrile (5.66 g, 27.0 mmol) and KOtBu (9.57 g, 81.0 mmol) in MeOH (135 mL) was stirred at 60° C. overnight. The reaction mixture was partitioned in saturated NH$_4$Cl/iPrOAc and extracted with iPrOAc (3×). The combined organic extracts were washed with water and brine, dried over MgSO$_4$, filtered and concentrated. NMR showed 1.3:1 ratio of the two isomers in favor of the undesired trans isomer. The mixture was subjected again to the reaction conditions. The reaction mixture was partitioned in saturated NH$_4$Cl/iPrOAc and extracted with iPrOAc (3×). The combined organic extracts were washed with water and brine, dried over MgSO$_4$, filtered and concentrated. The crude mixture was adsorbed on silica gel and was purified by silica gel column with 0-30% iPrOAc/Heptane to afford the title compound (3.85 g, 68% Yield) as a white solid. The product was a 1.6:1 cis/trans mixture by NMR.

Step 6: Preparation of (Z)-3-(4-chlorophenyl)-3-fluoro-N'-hydroxycyclobutanecarboximidamide

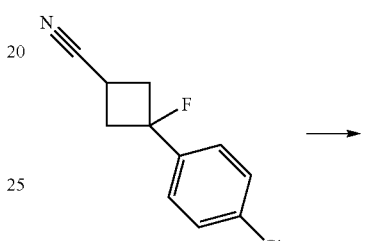

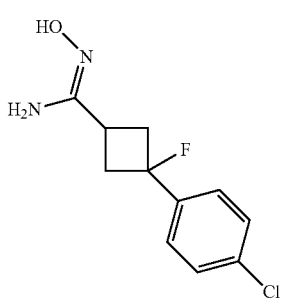

A mixture of 3-(4-chlorophenyl)-3-fluoro-cyclobutanecarbonitrile (3.85 g, 18.4 mmol) and hydroxylamine (50 mass %) in H$_2$O (11.3 mL, 184 mmol) in EtOH (46 mL) was stirred at 80° C. overnight. The reaction mixture was concentrated on the rotavap and taken up in iPrOAc/water. The aqueous layer was extracted with iPrOAc (3×). The combined organic layers were washed brine, dried with MgSO$_4$, filtered and concentrated to afford the title compound (4.71 g, 106% Yield) as a crude pale yellow solid.

Step 7: Preparation of (Z)—N'-(2-chloroacetoxy)-3-(4-chlorophenyl)-3-fluorocyclobutanecarboximidamide

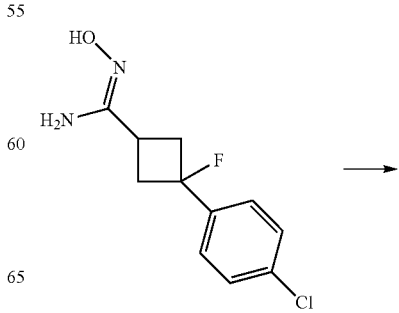

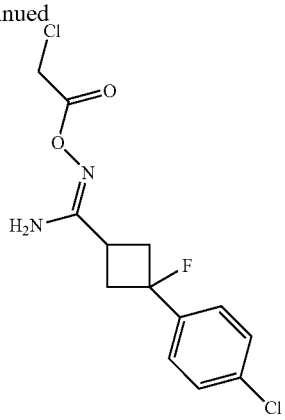

Chloroacetyl chloride (1.9 mL, 23.3 mmol) was added to a solution of 3-(4-chlorophenyl)-3-fluoro-N'-hydroxy-cyclobutanecarboxamidine (4.71 g, 19.4 mmol) in acetone (129 mL). The reaction was stirred at room temperature for 3 h. Chloroacetyl chloride (0.8 mL, 9.70 mmol) was added and the mixture was stirred for 2 h. The reaction mixture was concentrated on the rotavap. The residue was taken up in DCM/saturated NaHCO$_3$ and the aqueous layer was extracted with DCM (3×). The organic layer was washed with brine, dried with MgSO$_4$, filtered and concentrated to afford the title compound as a crude white solid.

Step 8: Preparation of 5-(chloromethyl)-3-((1s,3s)-3-(4-chlorophenyl)-3-fluorocyclobutyl)-1,2,4-oxadiazole

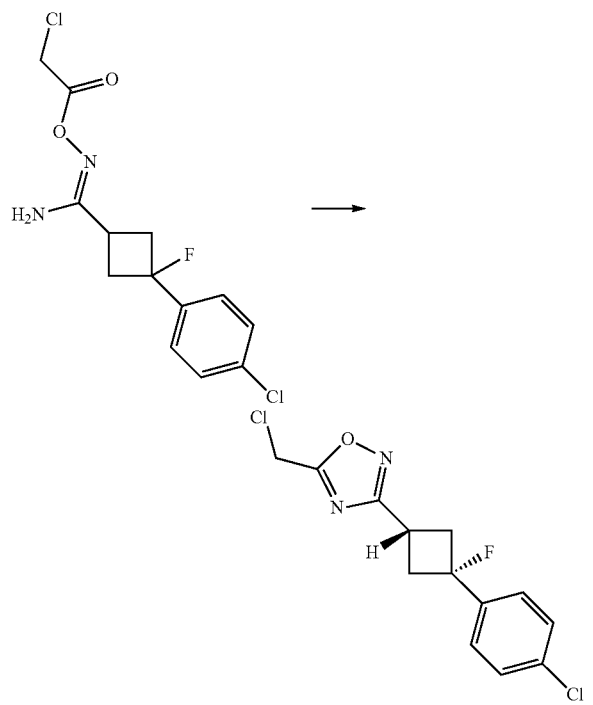

A mixture of [(Z)-[amino-[3-(4-chlorophenyl)-3-fluoro-cyclobutyl]methylene]amino]2-chloroacetate (6.20 g, 19.0 mmol) and MS 4 Å in toluene (190 mL) was stirred at 120° C. overnight. The reaction mixture was filtered and concentrated on the rotavap. The crude mixture was adsorbed on silica gel and purified by silica gel column with 0-40% iPOAc/heptane. The mixed fractions were pooled and repurified by silica gel column with 10% iPOAc/heptane to afford the title compound (2.26 g, 39% yield) as a white solid.

Step 9: Preparation of 3-((3-((1s,3s)-3-(4-chlorophenyl)-3-fluorocyclobutyl)-1,2,4-oxadiazol-5-yl)methyl)-5-methyl-4-oxo-3,4-dihydropyrido[2,3-d]pyrimidine-7-carbonitrile (Example Compound 158)

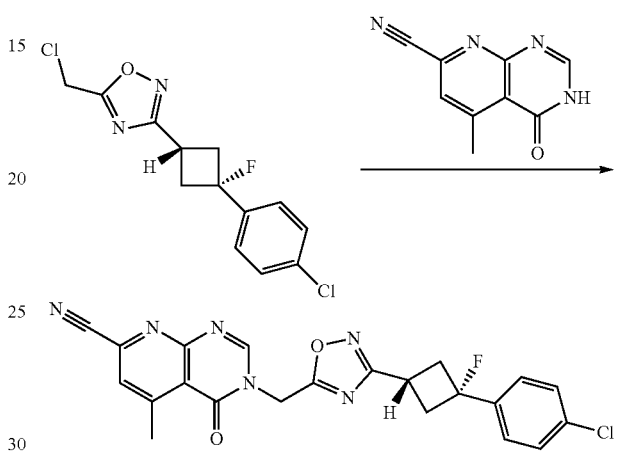

A mixture of 5-methyl-4-oxo-3H-pyrido[2,3-d]pyrimidine-7-carbonitrile (28.0 mg, 0.15 mmol), 5-(chloromethyl)-3-[3-(4-chlorophenyl)-3-fluoro-cyclobutyl]-1,2,4-oxadiazole (50.0 mg, 0.17 mmol), K$_2$CO$_3$ (42.0 mg, 0.30 mmol) and NaI (2.3 mg, 0.02 mmol) in acetone (0.8 mL) was stirred at room temperature for 5 h. The reaction mixture was filtered through diatomaceous earth. The filtrate was adsorbed on silica gel and purified by silica gel column with 20-80% (3:1 iPrOAc/MeOH)/Heptane. The product was further purified by preparative HPLC using a Chiralpak IA column with 30-70% of acetonitrile in 0.1% formic acid in water. This resulted in the titled compound (27.9 mg, 41% Yield) as a white solid. LCMS [M+H$^+$]: 451.1. 1H NMR (400 MHz, DMSO-d6) δ 8.84 (s, 1H), 8.04 (s, 1H), 7.64-7.57 (m, 2H), 7.51 (d, J=8.3 Hz, 2H), 5.57 (s, 2H), 3.50-3.36 (m, 1H), 3.04 (tdd, J=10.7, 8.5, 2.8 Hz, 2H), 2.91-2.77 (m, 5H).

Examples 66 and 67: Preparation of 1-((3-((1S,5S,6R)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one (Example Compound 160) and 1-((3-((1R,5R,6S)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one (Example compound 159)

The overall Examples 66 and 67 reaction scheme is as follows:

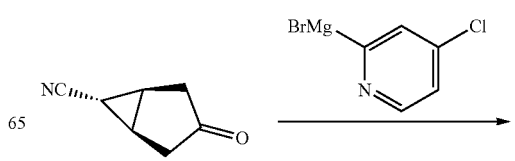

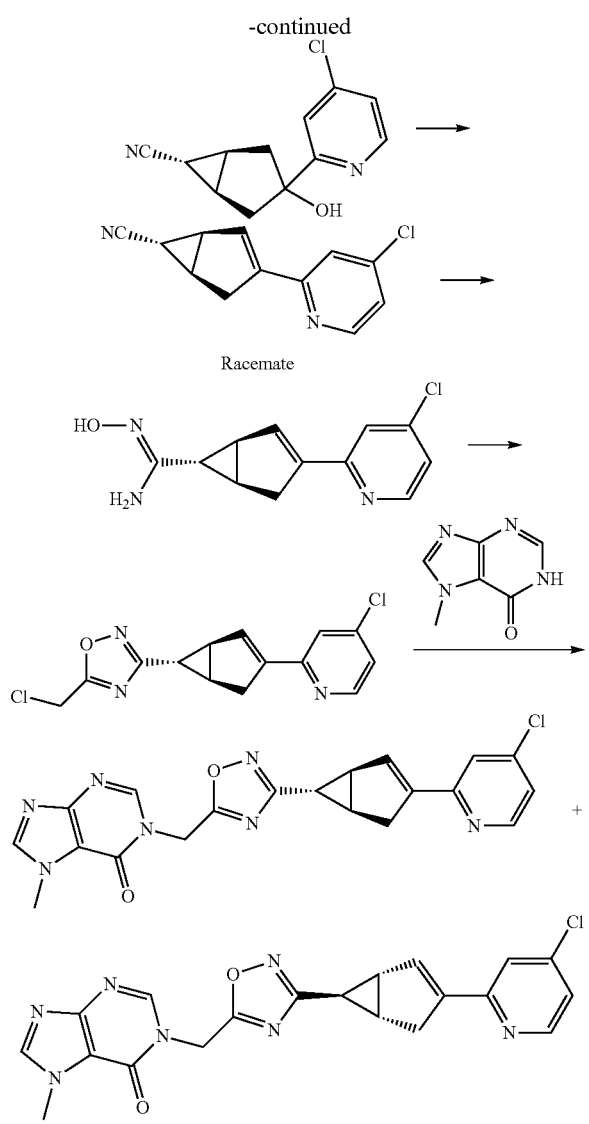

Step 1: Preparation of (1R,5S,6r)-3-(4-chloropyridin-2-yl)-3-hydroxybicyclo[3.1.0]hexane-6-carbonitrile

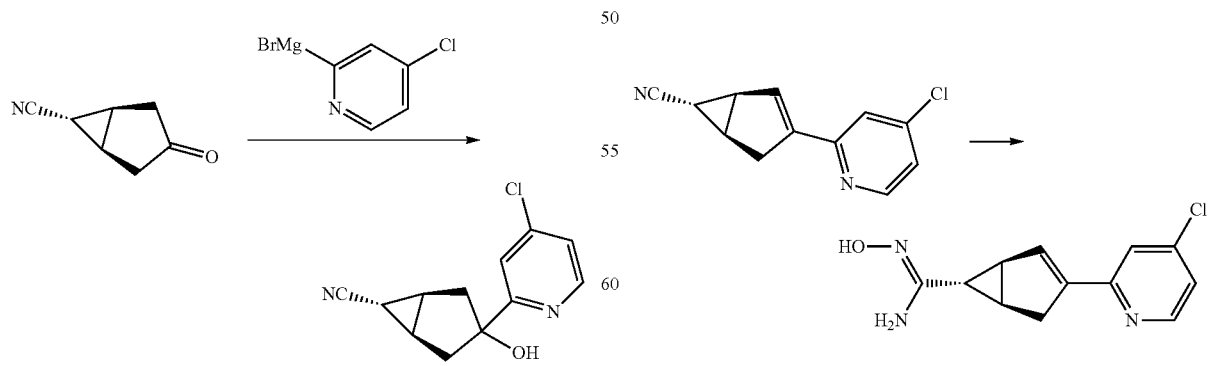

The title compound was prepared from (trans)-3-oxobicyclo[3.1.0]hexane-6-carbonitrile, CeCl₃ and (4-chloropyridin-2-yl)magnesium bromide as a white solid in a manner analogous to Examples 141 and 142, Step 1. LCMS [M+H⁺] 235.2. ¹H NMR (500 MHz, CDCl₃) δ 8.40 (dd, J=5.3, 0.6 Hz, 1H), 7.38 (dd, J=1.8, 0.6 Hz, 1H), 7.24 (dd, J=5.3, 1.9 Hz, 1H), 4.94 (s, 1H), 2.46-2.39 (m, 2H), 2.26 (t, J=3.4 Hz, 1H), 2.17 (d, J=14.5 Hz, 2H), 2.16-2.14 (m, 2H).

Step 2: Preparation of rac-(1R,5R,6S)-3-(4-chloropyridin-2-yl)bicyclo[3.1.0]hex-2-ene-6-carbonitrile

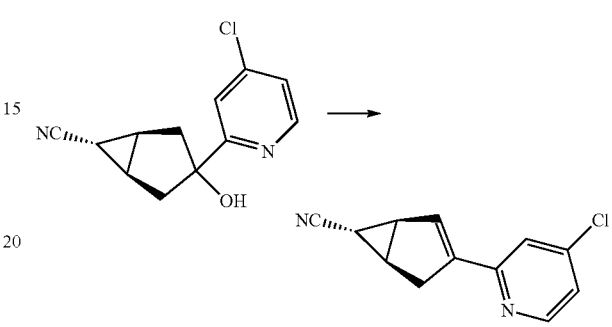

To a solution of (1R,5S,6r)-3-(4-chloropyridin-2-yl)-3-hydroxybicyclo[3.1.0]hexane-6-carbonitrile (160 mg, 0.680 mmol) in Toluene (4.1 mL) was added burgess reagent (447 mg, 1.87 mmol) under nitrogen. The flask was stirred in a 50° C. oil bath for 1 hour. The reaction mixture was cooled at 0° C. and a saturated aqueous solution of NaHCO₃ (15 mL) and water (10 mL) were added. The resulting mixture was extracted with EtOAc (3×30 mL). The combined organic layers were dried over anhydrous MgSO₄, filtered and concentrated under reduced pressure. The obtained residue was purified by flash column chromatography (24 g column) on silica gel eluting with a solution of EtOAc in hexanes (10 to 35% gradient) to afford rac-(1R,5R,6S)-3-(4-chloropyridin-2-yl)bicyclo[3.1.0]hex-2-ene-6-carbonitrile (111 mg, 0.512 mmol, 75% yield) as a white solid. LCMS [M+H⁺] 217.2; ¹H NMR (500 MHz, CDCl₃) δ 8.42 (dd, J=5.3, 0.3 Hz, 1H), 7.30 (dd, J=1.8, 0.3 Hz, 1H), 7.15 (dd, J=5.3, 1.9 Hz, 1H), 6.70 (q, J=2.0 Hz, 1H), 3.23-3.13 (m, 1H), 2.99 (dt, J=18.3, 2.3 Hz, 1H), 2.75-2.66 (m, 1H), 2.43 (td, J=6.6, 3.7 Hz, 1H), 0.98 (dd, J=3.5, 2.7 Hz, 1H).

Step 3: Preparation of rac-(1R,5R,6S,Z)-3-(4-chloropyridin-2-yl)-N'-hydroxybicyclo[3.1.0]hex-2-ene-6-carboximidamide The title compound was prepared from rac-(1R,5R,6S)-3-(4-chloropyridin-2-yl)bicyclo[3.1.0]hex-2-ene-6-carbonitrile as a white solid in a manner analogous to Examples 41 and 42, Step 10. LCMS [M+H⁺] 250.1.

Step 4: Preparation of 5-(chloromethyl)-3-(rac-(1R,5R,6S)-3-(4-chloropyridin-2-yl)bicyclo[3.1.0]hex-2-en-6-yl)-1,2,4-oxadiazole

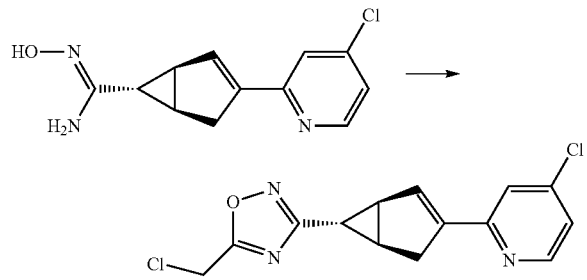

The title compound was prepared from rac-(1R,5R,6S,Z)-3-(4-chloropyridin-2-yl)-N'-hydroxybicyclo[3.1.0]hex-2-ene-6-carboximidamide as a white solid in a manner analogous to Examples 41 and 42, Step 11. LCMS [M+H⁺] 308.0.

Step 5: Preparation of 1-((3-((1S,5S,6R)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one (Example compound 160) and 1-((3-((1R,5R,6S)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one (Example Compound 159)

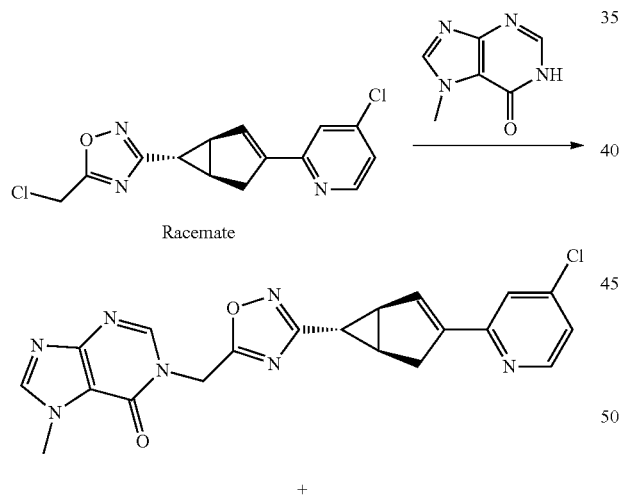

The title compounds were prepared from 5-(chloromethyl)-3-(rac-(1R,5R,6S)-3-(4-chloropyridin-2-yl)bicyclo[3.1.0]hex-2-en-6-yl)-1,2,4-oxadiazole and 7-methyl-1H-purin-6-one in a manner analogous to Examples 41 and 42, Step 5. The racemic mixture was separated by SFC with the following conditions: Column: ID 10×250 mm, 5 μm Isocratic 45% ACN+EtOH (1:1), 10 mL/min, 100 Bar, Column Temperature: 35° C., Run time: 30 min.

Example 67, enantiomer 1, (Example Compound 160): white solid, Rt=14.3 min (ID 10×250 mm, 5 μm Isocratic 45% ACN+EtOH (1:1), 10 mL/min, 100 Bar); LCMS [M+H⁺]422.0; ¹H NMR (500 MHz, DMSO-d6) δ 8.47 (dd, J=5.3, 0.3 Hz, 1H), 8.43 (s, 1H), 8.24-8.22 (m, 1H), 7.67 (d, J=1.6 Hz, 1H), 7.36 (dd, J=5.3, 2.0 Hz, 1H), 6.97 (q, J=1.8 Hz, 1H), 5.51 (s, 2H), 3.95 (s, 3H), 3.11 (ddd, J=17.9, 6.7, 1.5 Hz, 1H), 2.99 (d, J=18.2 Hz, 1H), 2.29 (td, J=6.4, 3.5 Hz, 1H), 1.70 (dd, J=3.3, 2.6 Hz, 1H). 1H hidden by DMSO signal.

Example 66, enantiomer 2, (Example Compound 159): white solid, Rt=17.5 min (ID 10×250 mm, 5 μm Isocratic 45% ACN+EtOH (1:1), 10 mL/min, 100 Bar); LCMS [M+H⁺]422.0; ¹H NMR (500 MHz, DMSO-d6) δ 8.47 (dd, J=5.4, 0.4 Hz, 1H), 8.43 (s, 1H), 8.23 (d, J=0.4 Hz, 1H), 7.67 (d, J=1.6 Hz, 1H), 7.36 (dd, J=5.3, 2.0 Hz, 1H), 6.97 (q, J=1.7 Hz, 1H), 5.51 (s, 2H), 3.95 (s, 3H), 3.11 (ddd, J=8.3, 6.5, 1.2 Hz, 1H), 2.99 (d, J=18.3 Hz, 1H), 2.29 (td, J=6.6, 3.7 Hz, 1H), 1.70 (dd, J=3.4, 2.6 Hz, 1H). 1H hidden by DMSO signal.

Example 68: Preparation of 6-((3-((1R,5S,6r)-3-(4-chloropyridin-2-yl)-3-azabicyclo[3.1.0]hexan-6-yl)-1,2,4-oxadiazol-5-yl)methyl)pyrido[2,3-d]pyridazin-5(6H)-one (Example Compound 167)

The overall Example 68 reaction scheme is as follows:

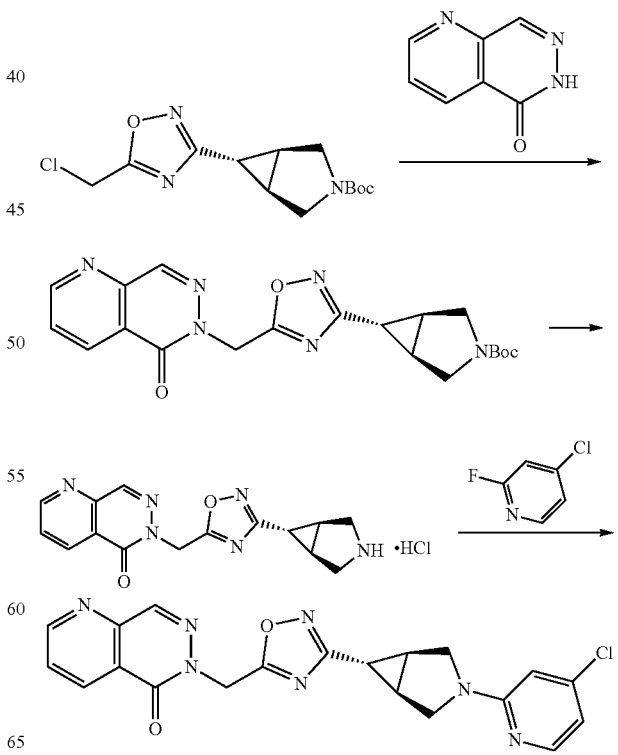

Step 1: Preparation of tert-butyl (1R,5S,6r)-6-(5-((5-oxopyrido[2,3-d]pyridazin-6(5H)-yl)methyl)-1,2,4-oxadiazol-3-yl)-3-azabicyclo[3.1.0]hexane-3-carboxylate

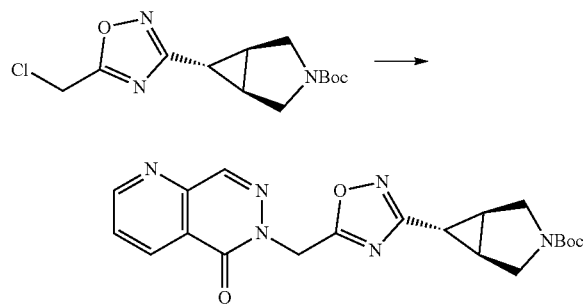

A mixture of pyrido[2,3-d]pyridazin-5(6h)-one (426 mg, 2.75 mmol), tert-butyl 6-[5-(chloromethyl)-1,2,4-oxadiazol-3-yl]-3-azabicyclo[3.1.0]hexane-3-carboxylate (as prepared in Example 4, Step 5) (750 mg, 2.50 mmol), cesium carbonate (2.45 g, 7.51 mmol) and tetrabutylammonium iodide (46 mg, 0.13 mmol) in N,N-dimethylformamide (25.0 mL) were stirred at room temperature for 3 h. The reaction mixture was extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH: iPrOAc in heptane to afford the desired compound as a beige solid (969 mg, 94%). LCMS [M+H$^+$]: 411.2.

Step 2: Preparation of 6-((3-((1R,5S,6r)-3-azabicyclo[3.1.0]hexan-6-yl)-1,2,4-oxadiazol-5-yl)methyl)pyrido[2,3-d]pyridazin-5(6H)-one hydrochloride

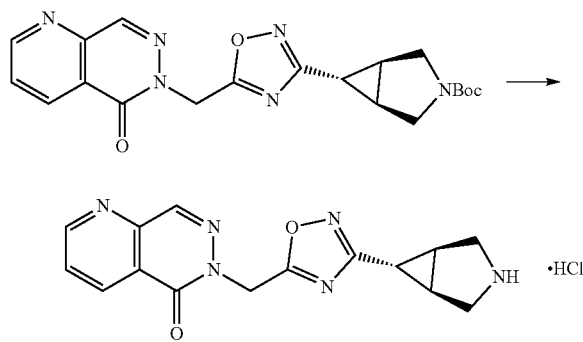

To a solution of tert-butyl (1R,5S)-6-[5-[(5-oxopyrido[2,3-d]pyridazin-6-yl)methyl]-1,2,4-oxadiazol-3-yl]-3-azabicyclo[3.1.0]hexane-3-carboxylate (969 mg, 2.36 mmol) in dichloromethane (10 mL) was added hydrochloric acid (4 mol/L) in 1,4-dioxane (5.9 mL, 24 mmol). The reaction mixture was stirred at room temperature for 4 h then concentrated in vacuo to give the crude title compound as a beige solid (818 mg, 99%) The residue was used as without further purification.

Step 3: Preparation of 6-((3-((1R,5S,6r)-3-(4-chloropyridin-2-yl)-3-azabicyclo[3.1.0]hexan-6-yl)-1,2,4-oxadiazol-5-yl)methyl)pyrido[2,3-d]pyridazin-5(6H)-one (Example Compound 167)

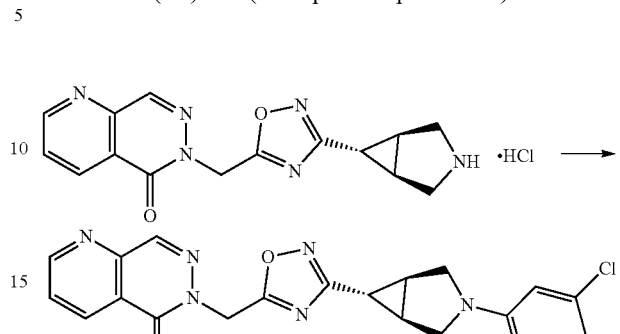

To a sealable tube was added 6-[[3-[(1R,5S)-3-azabicyclo[3.1.0]hexan-6-yl]-1,2,4-oxadiazol-5-yl]methyl]pyrido[2,3-d]pyridazin-5-one hydrochloride (200 mg, 0.58 mmol), potassium phosphate tribasic (625 mg, 2.88 mmol), 4-chloro-2-fluoropyridine (0.18 mL, 1.7 mmol) and 1,4-dioxane (2.5 mL). The reaction mixture was stirred at 110° C. for 18 h. The reaction mixture was diluted with dichloromethane, filtered through celite, eluting with dichloromethane and the filtrate was concentrated in vacuo. The residue was adsorbed onto silica and purified by flash column chromatography with 10-80% 3:1 MeOH: iPrOAc in heptane to afford the partially purified desired compound as an orange solid. The residue was further purified by achiral SFC to yield the title compound (81.1 mg, 33%) as a white solid. LCMS [M+H$^+$]: 422.1. 1H NMR (400 MHz, DMSO-d6) δ 9.21 (dd, J=4.6, 1.7 Hz, 1H), 8.65 (dd, J=8.5, 1.8 Hz, 1H), 8.60 (s, 1H), 8.03 (d, J=5.4 Hz, 1H), 7.93 (dd, J=8.1, 4.6 Hz, 1H), 6.67 (dd, J=5.5, 1.7 Hz, 1H), 6.55 (d, J=1.8 Hz, 1H), 5.67 (s, 2H), 3.82 (d, J=10.9 Hz, 2H), 3.47 (dt, J=11.0, 1.9 Hz, 2H), 2.23-2.19 (m, 2H), 1.99 (t, J=3.3 Hz, 1H).

Example 69: Preparation of 1-((3-((1r,3r)-3-(3-fluorophenoxy)cyclobutyl)-1,2,4-oxadiazol-5-yl)methyl)-7-methyl-1,7-dihydro-6H-purin-6-one (Example Compound 176)

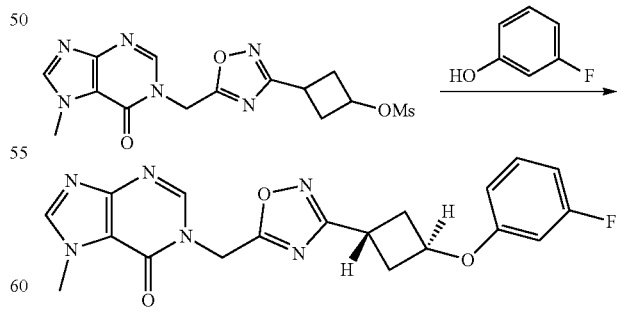

To a solution of [3-[5-[(7-methyl-6-oxo-purin-1-yl)methyl]-1,2,4-oxadiazol-3-yl]cyclobutyl] methanesulfonate (from Example 84, Step 10) (100 mg, 0.26 mmol) in dimethyl sulfoxide (1 mL) was added 3-fluorophenol (58 mg, 0.53 mmol) and Cs$_2$CO$_3$ (171 mg, 0.53 mmol). The resulting solution was stirred for 18 hours at 80° C. The resulting mixture was purified by reversed phase HPLC to yield the title compound (22 mg, 21% yield) as a white solid. LCMS [M+H$^+$]: 397.4. $^1$H NMR (300 MHz, DMSO-d$_6$) δ 8.46 (s, 1H), 8.24 (s, 1H), 7.34-7.26 (m, 1H), 6.79-6.73 (m, 1H), 6.68-6.65 (m, 2H), 5.59 (s, 2H), 4.93-4.87 (m, 1H), 3.97 (s, 3H), 3.74-3.68 (m, 1H), 2.72-2.66 (m, 2H), 2.59-2.54 (m, 2H).

Example 70: Preparation of 1-((3-((1R,5S,6r)-3-(4-fluoropyridin-2-yl)-3-azabicyclo[3.1.0]hexan-6-yl)-1,2,4-oxadiazol-5-yl)methyl)-7-methyl-1,7-dihydro-6H-purin-6-one (Example Compound 182)

The overall Example 70 reaction scheme is as follows:

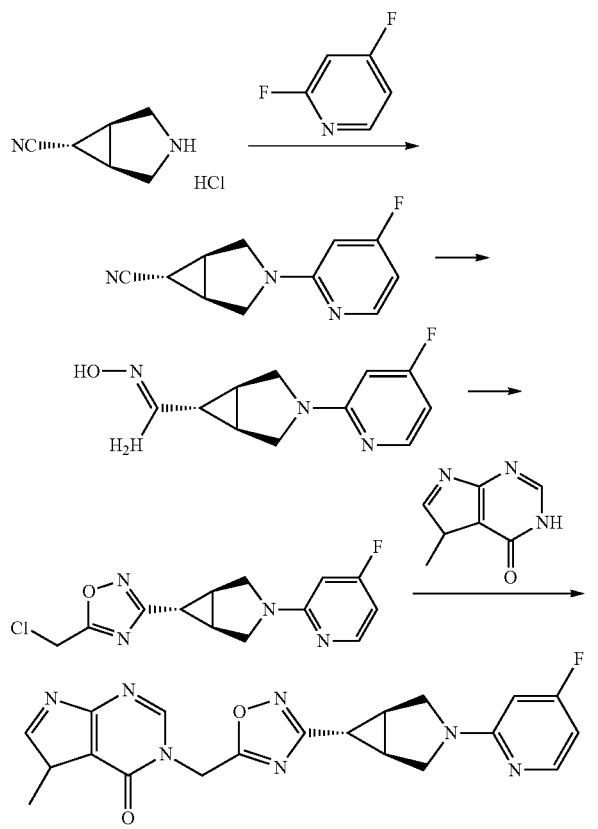

Step 1: Preparation of (1R,5S,6r)-3-(4-fluoropyridin-2-yl)-3-azabicyclo[3.1.0]hexane-6-carbonitrile

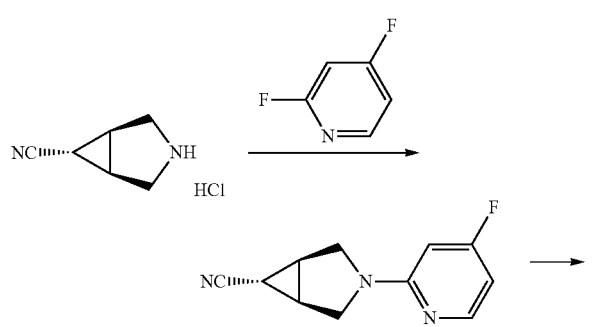

To a vial was added 3-azabicyclo[3.1.0]hexane-6-carbonitrile hydrochloride (500 mg, 3.46 mmol), 1,8-diazabicyclo[5.4.0]undec-7-ene (2.66 mL, 17.3 mmol), pyridine (14 mL) and 2,4-difluoropyridine (940 µL, 10.4 mmol). The reaction mixture was stirred at 110° C. for 16 h. The reaction mixture was washed with water, extracted 3 times with iPrOAc, dried over sodium sulfate, filtered, and concentrated in vacuo. The residue was adsorbed onto silica and purified by flash column chromatography with 0-100% iPrOAc in heptane to afford the desired compound as a yellow solid (128 mg, 18%). $^1$H NMR (400 MHz, CDCl$_3$-d) δ 8.06 (dd, J=9.7, 5.8 Hz, 1H), 6.50 (ddd, J=8.0, 5.7, 2.2 Hz, 1H), 6.31 (dd, J=12.5, 2.1 Hz, 1H), 3.76 (d, J=11.0 Hz, 2H), 3.40-3.36 (m, 2H), 2.47-2.42 (m, 2H), 1.66 (t, J=3.4 Hz, 1H).

Step 2: Preparation of (1R,5S,6r,Z)-3-(4-fluoropyridin-2-yl)-N-hydroxy-3-azabicyclo[3.1.0]hexane-6-carboximidamide

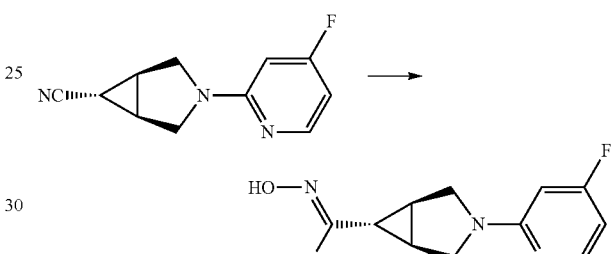

The title compound was prepared from (1R,5S,6r)-3-(4-fluoropyridin-2-yl)-3-azabicyclo[3.1.0]hexane-6-carbonitrile (128 mg, 0.630 mmol) in a manner analogous to Examples 41 and 42, Step 10.

Step 3: Preparation of 5-(chloromethyl)-3-((1R,5S,6r)-3-(4-fluoropyridin-2-yl)-3-azabicyclo[3.1.0]hexan-6-yl)-1,2,4-oxadiazole

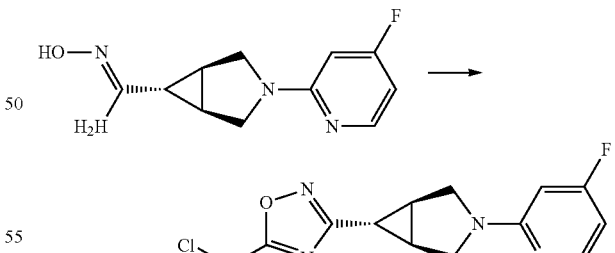

The title compound was prepared from (1R,5S,6r,Z)-3-(4-fluoropyridin-2-yl)-N-hydroxy-3-azabicyclo[3.1.0]hexane-6-carboximidamide (149 mg, 0.630 mmol) as a yellow oil (158 mg, 85% yield) in a manner analogous to Examples 41 and 42, Step 11. $^1$H NMR (400 MHz, CDCl$_3$-d) δ 8.08 (dd, J=9.7, 5.7 Hz, 1H), 6.55-6.46 (m, 1H), 6.33 (dd, J=12.5, 2.2 Hz, 1H), 5.06 (s, 2H), 3.84 (d, J=10.8 Hz, 2H), 3.49 (dd, J=8.8, 1.8 Hz, 2H), 2.29-2.25 (m, 2H), 2.03 (t, J=3.3 Hz, 1H).

Step 4: Preparation of 1-((3-((1R,5S,6r)-3-(4-fluoropyridin-2-yl)-3-azabicyclo[3.1.0]hexan-6-yl)-1,2,4-oxadiazol-5-yl)methyl)-7-methyl-1,7-dihydro-6H-purin-6-one (Example Compound 182)

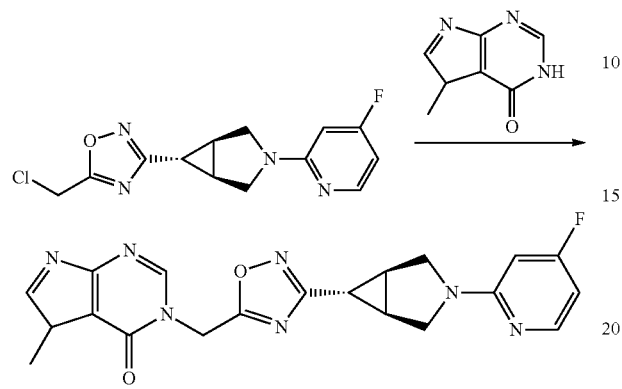

A mixture of 7-methyl-1H-purin-6(7H)-one (48.8 mg, 0.325 mmol), 5-(chloromethyl)-3-((1R,5S,6r)-3-(4-fluoropyridin-2-yl)-3-azabicyclo[3.1.0]hexan-6-yl)-1,2,4-oxadiazole (87.0 mg, 0.295 mmol), and cesium carbonate (289 mg, 0.886 mmol) in N,N-dimethylformamide (3.0 mL) were heated to 60° C. for 30 min. The reaction was cooled to room temperature, diluted with water and extracted with iPrOAc (3×). The combined organic layers were washed with brine, dried over sodium sulfate, filtered and concentrated in vacuo. The residue was adsorbed onto silica and purified by flash column chromatography with 0-80% MeOH in DCM to afford the desired compound as a brown oil. The residue was further purified by RP-HPLC to yield the title compound (67.8 mg, 56%) as a white solid. LCMS [M+H$^+$] 409.1. $^1$H NMR (400 MHz, DMSO) δ 8.43 (s, 1H), 8.23 (d, J=0.6 Hz, 1H), 8.06 (dd, J=9.7, 5.7 Hz, 1H), 6.49 (ddd, J=8.7, 5.7, 2.2 Hz, 1H), 6.30 (dd, J=12.5, 2.2 Hz, 1H), 5.52 (s, 2H), 3.98-3.93 (m, 3H), 3.80 (d, J=10.8 Hz, 2H), 3.45 (dt, J=10.9, 1.8 Hz, 2H), 2.24-2.14 (m, 2H), 1.97 (t, J=3.3 Hz, 1H).

Examples 71 and 72: Preparation of 1-((3-((1R,5R,6S)-3-(3-chlorophenyl) bicyclo[3.1.0]hex-2-en-6-yl)-1,2,4-oxadiazol-5-yl)methyl)-7-methyl-1,7-dihydro-6H-purin-6-one (Example Compound 185) and 1-((3-((1S,5S,6R)-3-(3-chlorophenyl)bicyclo[3.1.0]hex-2-en-6-yl)-1,2,4-oxadiazol-5-yl)methyl)-7-methyl-1,7-dihydro-6H-purin-6-one (Example Compound 184)

The overall Examples 71 and 72 reaction scheme is as follows:

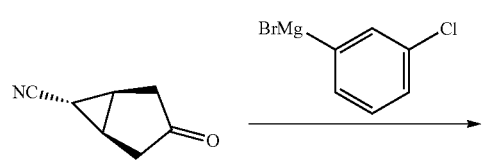

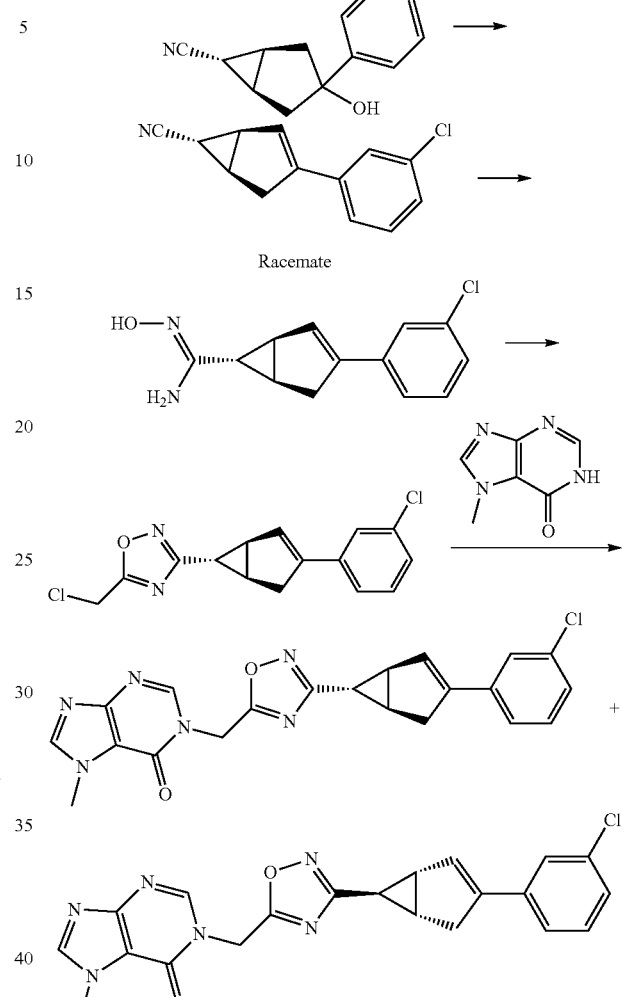

Step 1: Preparation of (1R,5S,6r)-3-(3-chlorophenyl)-3-hydroxybicyclo[3.1.0]hexane-6-carbonitrile

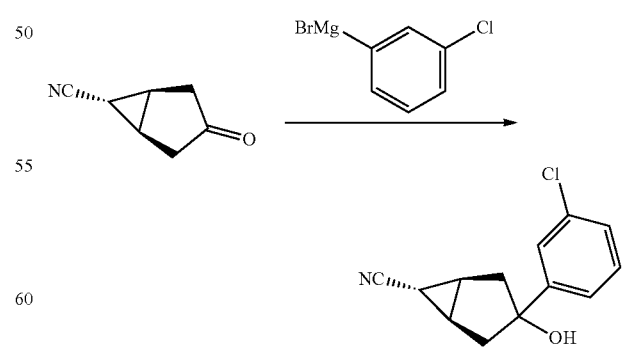

The title compound was prepared from (trans)-3-oxobicyclo[3.1.0]hexane-6-carbonitrile, CeCl$_3$ and 3-Chlorophenylmagnesium bromide as a colorless oil in a manner analogous to Examples 62 and 63, Step 1.

Step 2: Preparation of rac-(1R,5R,6S)-3-(3-chlorophenyl)bicyclo[3.1.0]hex-2-ene-6-carbonitrile

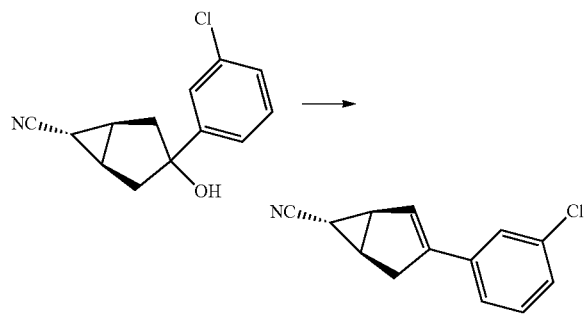

The title compound was prepared from (1R,5S,6r)-3-(3-chlorophenyl)-3-hydroxybicyclo[3.1.0]hexane-6-carbonitrile as a colorless oil in a manner analogous to Examples 62 and 63, Step 2. $^1$H NMR (500 MHz, CDCl$_3$) δ 7.32-7.29 (m, 1H), 7.25-7.19 (m, 3H), 6.33 (q, J=1.9 Hz, 1H), 3.13 (ddd, J=17.9, 6.8, 1.9 Hz, 1H), 2.86 (ddd, J=17.9, 2.5, 2.0 Hz, 1H), 2.68 (dq, J=6.7, 2.4 Hz, 1H), 2.40 (ddd, J=6.6, 6.6, 3.7 Hz, 1H), 0.96-0.92 (m, 1H).

Step 3: Preparation of rac-(1R,5R,6S,Z)-3-(3-chlorophenyl)-N'-hydroxybicyclo[3.1.0]hex-2-ene-6-carboximidamide The title compound was prepared from rac-(1R,5R,6S)-3-(3-chlorophenyl)bicyclo[3.1.0]hex-2-ene-6-carbonitrile as a white solid in a manner analogous to Examples 41 and 42, Step 10. LCMS [M+H$^+$] 249.1.

Step 4: Preparation of 5-(chloromethyl)-3-(rac-(1R,5R,6S)-3-(3-chlorophenyl)bicyclo[3.1.0]hex-2-en-6-yl)-1,2,4-oxadiazole To a 0° C. solution of rac-(1R,5R,6S,Z)-3-(3-chlorophenyl)-N'-hydroxybicyclo[3.1.0]hex-2-ene-6-carboximidamide (519. mg, 2.09 mmol) and triethylamine (0.32 mL, 2.3 mmol) in DCM (14 mL) was added chloroacetyl chloride (0.17 mL, 2.09 mmol) over 5 min. The mixture was allowed to stir at 0° C. for 30 min. and more triethylamine (0.12 mL, 0.83 mmol) and chloroacetyl chloride (0.07 mL, 0.83 mmol) were added. After 20 more min. at 0° C., water (100 mL) was added and the mixture was extracted with DCM (3×50 mL). The combined organic layers were washed with brine, dried over anhydrous MgSO$_4$, filtered and concentrated under reduced pressure. The obtained residue was then dissolved in toluene 35 mL. 4 Å molecular sieves were added and the resulting mixture was heated in a 105° C. oil bath for 1 h30. The solvent was evaporated and the crude material was purified by flash column chromatography (50 g column) on silica gel using a solution of EtOAc in hexanes (5 to 10% gradient) to afford 5-(chloromethyl)-3-(rac-(1R,5R,6S)-3-(3-chlorophenyl)bicyclo[3.1.0]hex-2-en-6-yl)-1,2,4-oxadiazole (501 mg, 1.63 mmol, 78% yield) as a white solid.

Step 5: Preparation of 1-((3-((1R,5R,6S)-3-(3-chlorophenyl)bicyclo[3.1.0]hex-2-en-6-yl)-1,2,4-oxadiazol-5-yl)methyl)-7-methyl-1,7-dihydro-6H-purin-6-one (Example Compound 185) and 1-((3-((1S,5S,6R)-3-(3-chlorophenyl)bicyclo[3.1.0]hex-2-en-6-yl)-1,2,4-oxadiazol-5-yl)methyl)-7-methyl-1,7-dihydro-6H-purin-6-one (Example Compound 184)

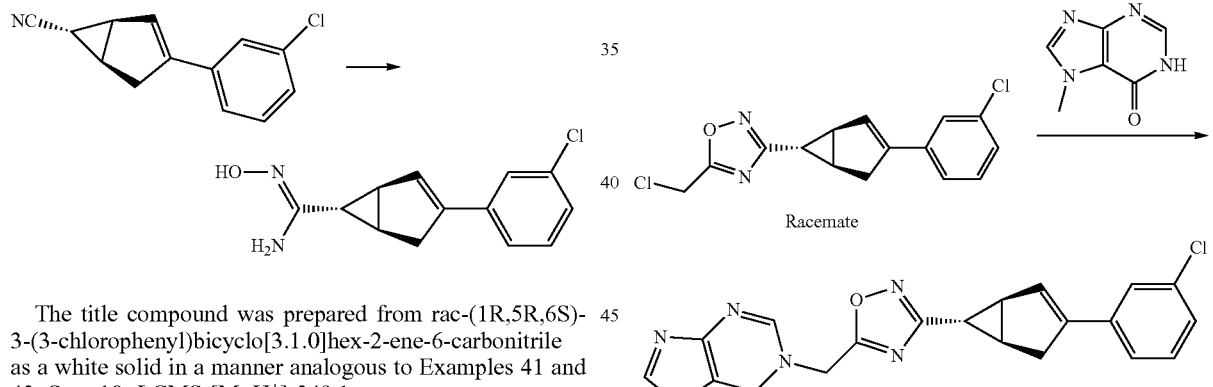

Racemate

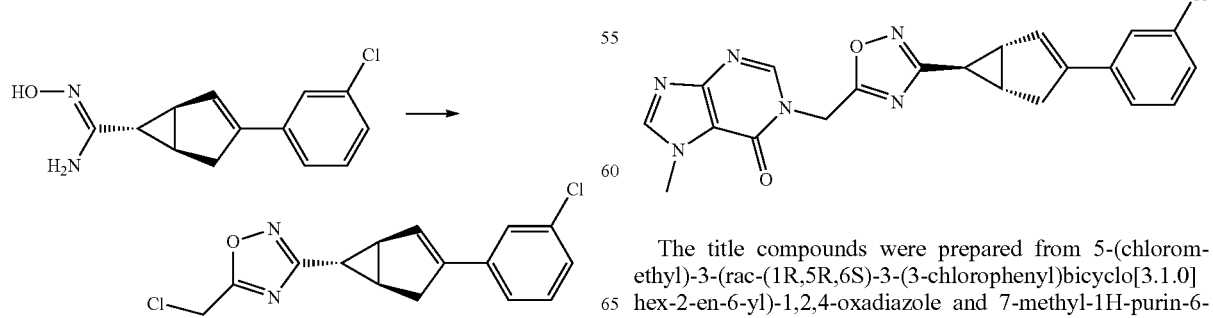

The title compounds were prepared from 5-(chloromethyl)-3-(rac-(1R,5R,6S)-3-(3-chlorophenyl)bicyclo[3.1.0]hex-2-en-6-yl)-1,2,4-oxadiazole and 7-methyl-1H-purin-6-one in a manner analogous to Examples 41 and 42, Step 12. The racemic mixture was separated by SFC with the following conditions: Column: Lux Cellulose-3, 10×250 mm 5 µm, Isocratic 30% IPA, Column Temperature: 35° C., Run time: 30 min.

Example 72, enantiomer 1, (Example Compound 185): off-white solid, Rt=22.8 min (Lux Cellulose-3, 10×250 mm 5 µm, Isocratic 30% IPA); LCMS [M+H$^+$] 421.0; $^1$H NMR (500 MHz, DMSO-d6) δ 8.43 (s, 1H), 8.23 (s, J=6.8 Hz, 1H), 7.47 (t, J=1.7 Hz, 1H), 7.39 (dt, J=7.7, 1.4 Hz, 1H), 7.34 (t, J=7.8 Hz, 1H), 7.31-7.27 (m, 1H), 6.65 (q, J=1.9 Hz, 1H), 5.51 (s, 2H), 3.95 (s, 3H), 3.12-3.03 (m, 1H), 2.92 (d, J=17.8 Hz, 1H), 2.46 (dq, J=4.8, 2.5 Hz, 1H), 2.26 (td, J=6.5, 3.4 Hz, 1H), 1.68-1.63 (m, 1H).

Example 71, enantiomer 2, (Example Compound 184): white solid, Rt=25.4 min (Lux Cellulose-3, 10×250 mm 5 µm, Isocratic 30% IPA); LCMS [M+H$^+$] 421.0; $^1$H NMR (500 MHz, DMSO-d6) δ 8.43 (s, 1H), 8.22 (s, 1H), 7.46 (t, J=1.7 Hz, 1H), 7.38 (dt, J=7.7, 1.4 Hz, 1H), 7.34 (t, J=7.7 Hz, 1H), 7.30-7.27 (m, 1H), 6.64 (q, J=1.8 Hz, 1H), 5.51 (s, 2H), 3.95 (s, 3H), 3.07 (ddd, J=17.5, 6.7, 1.3 Hz, 1H), 2.91 (d, J=17.8 Hz, 1H), 2.45 (dt, J=8.7, 2.4 Hz, 1H), 2.26 (td, J=6.5, 3.4 Hz, 1H), 1.65 (dd, J=3.2, 2.6 Hz, 1H).

Examples 73 and 74: Preparation of 1-((3-((1S,1aR,6bS)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one (Example Compound 186) and 1-((3-((1R,1aS,6bR)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one (Example Compound 187)

The overall Examples 73 and 74 reaction scheme is as follows:

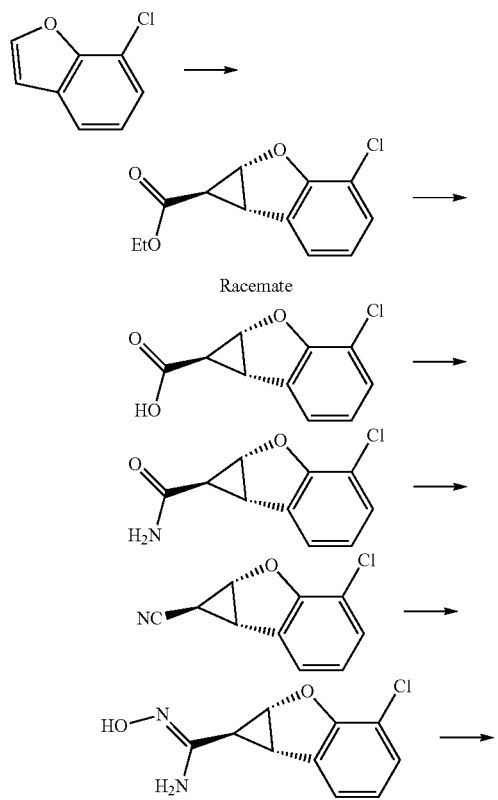

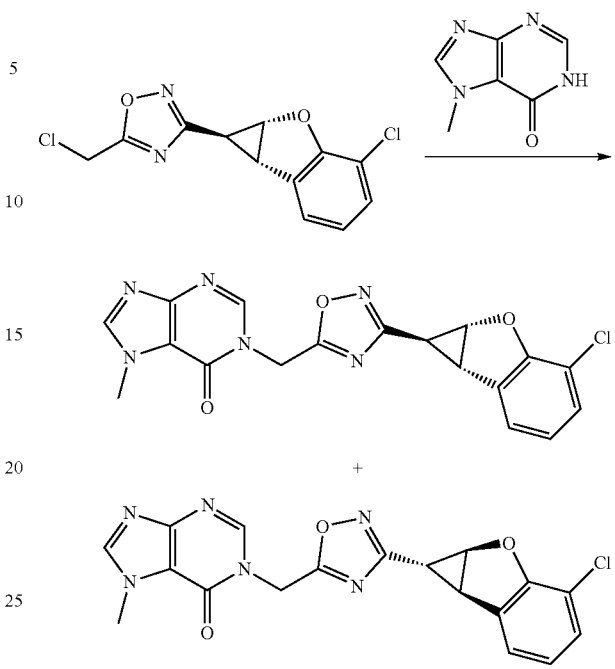

Step 1: Preparation of rac-(1R,1aR,6bS)-ethyl 3-chloro-1a,6b-dihydro-1H-cyclopropa[b]benzofuran-1-carboxylate

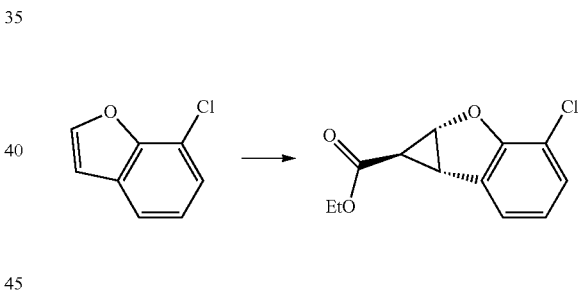

To a solution of 7-chlorobenzofuran (0.39 mL, 3.28 mmol) in 1,2-dichloroethane (5 mL) was added rhodium (II) acetate dimer (72 mg, 0.160 mmol) under nitrogen. The mixture was heated to 85° C. and a solution of ethyl diazoacetate (2.0 mL, 16.4 mmol) in 1,2-dichloroethane (5 mL) was added via a syringe pump over 3 hours. The reaction was stirred at 85° C. for 2 hours then overnight at 20° C. The mixture was concentrated, diluted with water and extracted with ethyl acetate. The organic layer was separated, dried over anhydrous magnesium sulfate, filtered, and concentrated. The residue was purified by flash column chromatography (0-100% DCM in hexanes, 50 g SiO$_2$ column) to give rac-(1R,1aR,6bS)-ethyl 3-chloro-1a,6b-dihydro-1H-cyclopropa[b]benzofuran-1-carboxylate (387 mg, 1.62 mmol, 49% yield). $^1$H NMR (500 MHz, CDCl$_3$) δ 7.28 (dd, J=7.4, 1.0 Hz, 1H), 7.17 (dd, J=8.1, 1.2 Hz, 1H), 6.90-6.86 (m, 1H), 5.16 (dd, J=5.4, 1.1 Hz, 1H), 4.21-4.12 (m, 2H), 3.31 (dd, J=5.4, 3.2 Hz, 1H), 1.35 (dd, J=3.2, 1.1 Hz, 1H), 1.30-1.26 (m, 3H).

Step 2: Preparation of rac-(1R,1 aR,6bS)-3-chloro-1a,6b-dihydro-1H-cyclopropa[b]benzofuran-1-carboxylic Acid

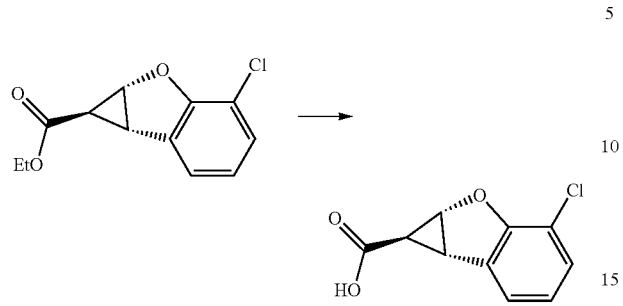

rac-(1R,1 aR,6bS)-ethyl 3-chloro-1a,6b-dihydro-1H-cyclopropa[b]benzofuran-1-carboxylate (637 mg, 2.67 mmol) was dissolved in THF (16 mL) and Methanol (8 mL) and lithium hydroxide (0.2 mL, 20.8 mmol) was added. The mixture was stirred at 20° C. for 16 hours. The reaction mixture was diluted with EtOAc, acidified with 1N HCl and extracted with EtOAc (3×). The combined organic layers were dried over anhydrous MgSO$_4$, filtered and concentrated under reduced pressure to afford rac-(1R,1aR,6bS)-3-chloro-1a,6b-dihydro-1H-cyclopropa[b]benzofuran-1-carboxylic acid (461 mg, 2.19 mmol, 82% yield). The crude material was used as is. $^1$H NMR (500 MHz, MeOD) δ 7.38 (dd, J=7.5, 1.1 Hz, 1H), 7.18 (dd, J=8.1, 1.2 Hz, 1H), 6.92 (dd, J=8.0, 7.5 Hz, 1H), 5.19 (dd, J=5.4, 1.1 Hz, 1H), 3.38-3.33 (m, 1H), 1.22-1.17 (m, 1H). Carboxylic acid OH in the solvent signal.

Step 3: Preparation of rac-(1R,1 aR,6bS)-3-chloro-1a,6b-dihydro-1H-cyclopropa[b]benzofuran-1-carboxamide

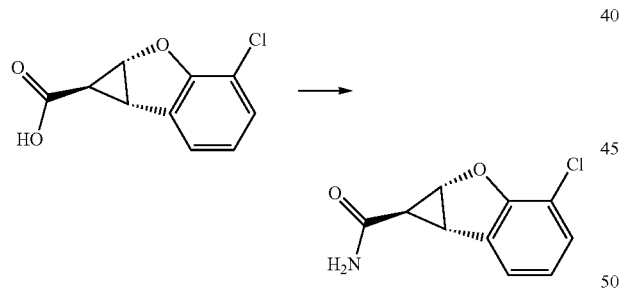

To a solution of crude rac-(1R,1aR,6bS)-3-chloro-1a,6b-dihydro-1H-cyclopropa[b]benzofuran-1-carboxylic acid (461 mg, 2.19 mmol) in DCM (8 mL) was added N,N-diisopropylethylamine (1.9 mL, 10.9 mmol) and HATU (1.25 g, 3.28 mmol). The mixture was stirred for 30 min. at 20° C. followed by the addition of ammonium chloride (176 mg, 3.28 mmol). After 20 min., the reaction was stopped by diluting with a saturated aqueous solution of NaHCO$_3$. The resulting mixture was extracted with EtOAc (3×50 mL). The combined organic layers were washed with brine, dried over anhydrous MgSO$_4$, filtered and concentrated under reduced pressure. Sonication of the crude material in EtOAc gave a white suspension that was filtered to give rac-(1R,1aR,6bS)-3-chloro-1a,6b-dihydro-1H-cyclopropa[b]benzofuran-1-carboxamide (350 mg, 1.67 mmol, 76% yield) as a white solid. LCMS [M+H$^+$] 210.1.

Step 4: Preparation of rac-(1S,1aR,6bS)-3-chloro-1a,6b-dihydro-1H-cyclopropa[b]benzofuran-1-carbonitrile

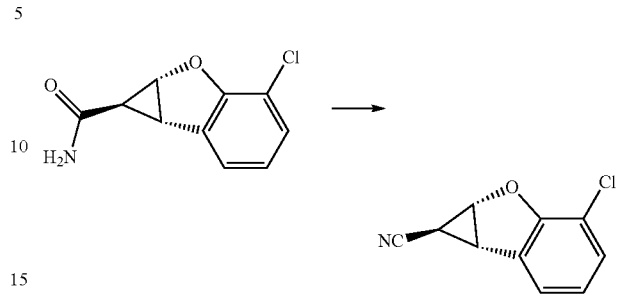

Trifluoroacetic anhydride (0.15 mL, 1.07 mmol) was added to a solution of rac-(1R,1aR,6bS)-3-chloro-1a,6b-dihydro-1H-cyclopropa[b]benzofuran-1-carboxamide (150 mg, 0.720 mmol) and pyridine (0.15 mL, 1.86 mmol) in 1,4-Dioxane (5 mL) under a nitrogen atmosphere at 0° C. The resulting mixture was stirred for 1 hour at 20° C. and it was diluted with EtOAc and a saturated aqueous solution of NaHCO$_3$. The layers were separated and the aqueous layer was extracted with EtOAc (2×). The combined organic layers were washed with brine, dried over anhydrous MgSO$_4$, filtered and concentrated under reduced pressure to afford rac-(1S,1aR,6bS)-3-chloro-1a,6b-dihydro-1H-cyclopropa[b]benzofuran-1-carbonitrile (140 mg, 0.731 mmol, 100% yield).

Step 5: Preparation of rac-(1S,1aR,6bS,Z)-3-chloro-N'-hydroxy-1a,6b-dihydro-1H-cyclopropa[b]benzofuran-1-carboximidamide

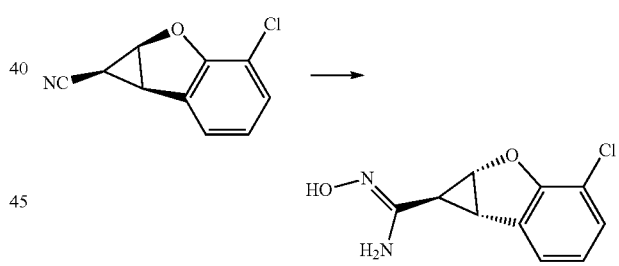

The title compound was prepared from rac-(1S,1aR,6bS)-3-chloro-1a,6b-dihydro-1H-cyclopropa[b]benzofuran-1-carbonitrile in a manner analogous to Examples 41 and 42, Step 10.

Step 6: Preparation of 3-(rac-(1S,1aR,6bS)-3-chloro-1a,6b-dihydro-1H-cyclopropa[b]benzofuran-1-yl)-5-(chloromethyl)-1,2,4-oxadiazole

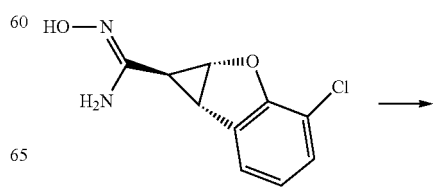

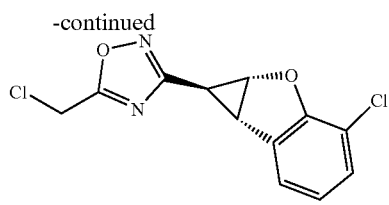

Using AcOH as solvent, the title compound was prepared from rac-(1S,1aR,6bS,Z)-3-chloro-N'-hydroxy-1a,6b-dihydro-1H-cyclopropa[b]benzofuran-1-carboximidamide in a manner analogous to Examples 41 and 42, Step 11.

Step 7: Preparation of 1-((3-((1S,1aR,6bS)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one (Example Compound 186) and 1-((3-((1R,1aS,6bR)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one (Example Compound 187)

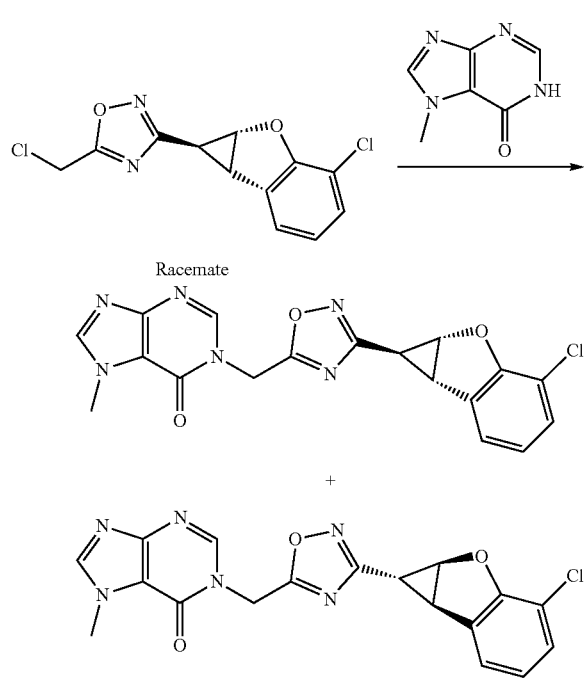

The title compounds were prepared from 3-(rac-(1S,1aR,6bS)-3-chloro-1a,6b-dihydro-1H-cyclopropa[b]benzofuran-1-yl)-5-(chloromethyl)-1,2,4-oxadiazole and 7-methyl-1H-purin-6-one in a manner analogous to Examples 41 and 42, Step 12. The racemic mixture was separated by SFC with the following conditions: Column: ChiralPak IA, 250 mm×4.6 mm ID, 5 μm, 10:30:60 MeOH:DCM:Hexane DEA, 0.8 mL/min, 49 Bar, 26° C., run time 16 min.

Example 73, enantiomer 1, (Example Compound 186): white solid, Rt=12.2 min (ChiralPack IA 250 mm×4.6 mm ID, 5 μm); LCMS [M+H⁺] 397.0; ¹H NMR (500 MHz, DMSO-d6) δ 8.44 (s, 1H), 8.24 (s, 1H), 7.46 (dd, J=7.5, 1.0 Hz, 1H), 7.28 (dd, J=8.1, 1.1 Hz, 1H), 7.00-6.92 (m, 1H), 5.55 (s, 2H), 5.39 (dd, J=5.4, 1.3 Hz, 1H), 3.95 (s, 3H), 3.43 (dd, J=5.4, 3.4 Hz, 1H), 2.05 (dd, J=3.4, 1.3 Hz, 1H).

Example 74, enantiomer 2, (Example Compound 187): white solid, Rt=14.2 min (ChiralPack IA 250 mm×4.6 mm ID, 5 μm); LCMS [M+H⁺] 397.0; ¹H NMR (500 MHz, DMSO-d6) δ 8.45 (s, 1H), 8.24 (s, 1H), 7.47 (dd, J=7.5, 1.0 Hz, 1H), 7.28 (dd, J=8.1, 1.1 Hz, 1H), 6.99-6.95 (m, 1H), 5.56 (s, 2H), 5.39 (dd, J=5.4, 1.3 Hz, 1H), 3.96 (s, 3H), 3.43 (dd, J=5.4, 3.4 Hz, 1H), 2.06 (dd, J=3.4, 1.3 Hz, 1H).

Example 75: Preparation of 2-chloro-4-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile (Example Compound 188)

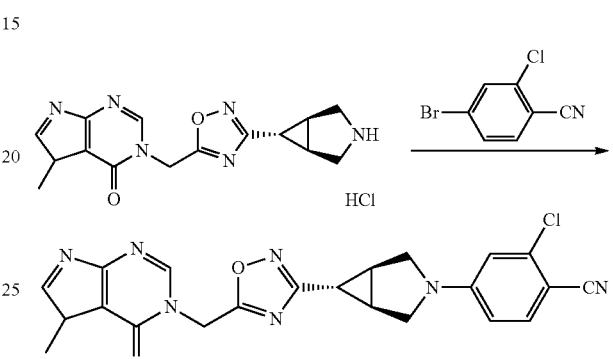

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 4-bromo-2-chlorobenzonitrile (83.2 mg, 0.384 mmol) as a white solid (1.8 mg, 1% yield), in a manner analogous to Example 4, Step 8. LCMS [M+H⁺] 449.1. ¹H NMR (400 MHz, DMSO) δ 8.43 (s, 1H), 8.23 (s, 1H), 7.61 (d, J=8.8 Hz, 1H), 6.76 (d, J=2.3 Hz, 1H), 6.60 (dd, J=8.9, 2.3 Hz, 1H), 5.52 (s, 2H), 3.95 (s, 3H), 3.74 (d, J=10.6 Hz, 2H), 3.47 (d, J=6.6 Hz, 2H), 2.26-2.24 (m, 2H), 2.01 (t, J=3.3 Hz, 1H).

Example 76: Preparation of 4-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile (Example compound 192)

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 4-bromobenzonitrile (69.9 mg, 0.384 mmol) as a white solid (38.8 mg, 29% yield), in a manner analogous to Example 4, Step 8. LCMS [M+H⁺] 415.1. ¹H NMR (400 MHz, DMSO) δ 8.43 (s, 1H), 8.23 (s, 1H), 7.58-7.49 (m, 2H), 6.68-6.59 (m, 2H), 5.52 (s, 2H), 3.95 (s, 3H), 3.72 (d, J=10.3 Hz, 2H), 3.42 (dt, J=10.4, 1.9 Hz, 2H), 2.29-2.20 (m, 2H), 2.01 (t, J=3.3 Hz, 1H).

Example 77: Preparation of 3-((3-((1R,5S,6r)-3-phenyl-3-azabicyclo[3.1.0]hexan-6-yl)-1,2,4-oxadiazol-5-yl)methyl)pyrido[2,3-d]pyrimidin-4(3H)-one (Example Compound 194)

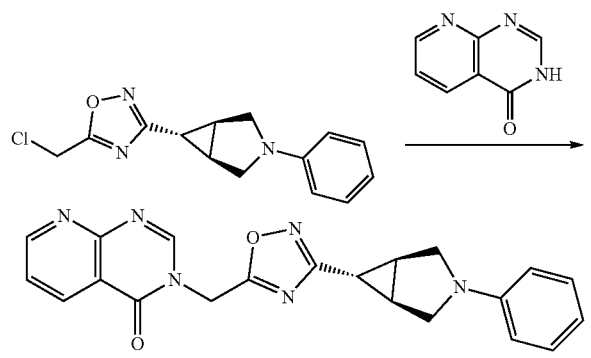

A mixture of pyrido[2,3-d]pyrimidin-4(3h)-one (28 mg, 0.18 mmol), 5-(chloromethyl)-3-(3-phenyl-3-azabicyclo[3.1.0]hexan-6-yl)-1,2,4-oxadiazole (as prepared in Example 4, Step 7) (45 mg, 0.16 mmol), potassium carbonate (68 mg, 0.49 mmol) and sodium iodide (1.2 mg, 0.0082 mmol) in acetone (1.5 mL) were stirred at room temperature for 16 h. The reaction mixture was diluted with acetone, filtered through a fritted funnel, eluting with acetone and the filtrate was concentrated in vacuo. The residue was adsorbed onto silica and purified by flash column chromatography with 10-80% 3:1 MeOH: iPrOAc in heptane to afford the partially purified desired compound as a white solid. The residue was further purified by achiral SFC to yield the title compound (14.3 mg, 23%) as a white solid. LCMS [M+H$^+$]: 387.2. 1H NMR (400 MHz, DMSO-d6) δ 9.03 (dd, J=4.6, 2.0 Hz, 1H), 8.75 (s, 1H), 8.57 (dd, J=7.9, 2.0 Hz, 1H), 7.63 (dd, J=8.0, 4.6 Hz, 1H), 7.19-7.10 (m, 2H), 6.68-6.57 (m, 1H), 6.60-6.52 (m, 2H), 5.54 (s, 2H), 3.67 (d, J=9.7 Hz, 2H), 3.24-3.19 (m, 2H), 2.22-2.16 (m, 2H), 2.03 (t, J=3.2 Hz, 1H).

Example 78: Preparation of 3-((3-((1s,3s)-3-fluoro-3-(4-fluorophenyl)cyclobutyl)-1,2,4-oxadiazol-5-yl)methyl)-5-methylpyrido[2,3-d]pyrimidin-4(3H)-one (Example Compound 196)

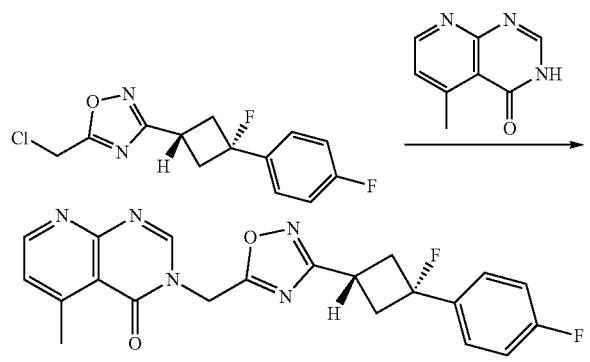

The title compound was prepared from 5-(chloromethyl)-3-((1s,3s)-3-fluoro-3-(4-fluorophenyl)cyclobutyl)-1,2,4-oxadiazole (200 mg, 0.70 mmol) and 5-methylpyrido[2,3-d]pyrimidin-4(3H)-one (113 mg, 0.70 mmol) in a manner analogous to Example 1, Step 6 as a white solid (44 mg, 15% yield). LCMS [M+H$^+$]: 410. $^1$H NMR (300 MHz, DMSO-d$_6$) δ 8.79 (d, J=4.8 Hz, 1H), 8.73 (s, 1H), 7.66-7.61 (m, 2H), 7.42 (dd, J=4.8, 1.0 Hz, 1H), 7.34-7.22 (m, 2H), 5.55 (s, 2H), 3.38-3.32 (m, 1H), 3.12-3.02 (m, 2H), 2.95-2.74 (m, 2H), 2.73 (s, 3H).

Example 79: Preparation of 1-((3-((1R,2S,5S,6R)-3-(3-chlorophenyl)-2-methyl-3-azabicyclo[3.1.0]hexan-6-yl)-1,2,4-oxadiazol-5-yl)methyl)-7-methyl-1,7-dihydro-6H-purin-6-one (Example Compound 204)

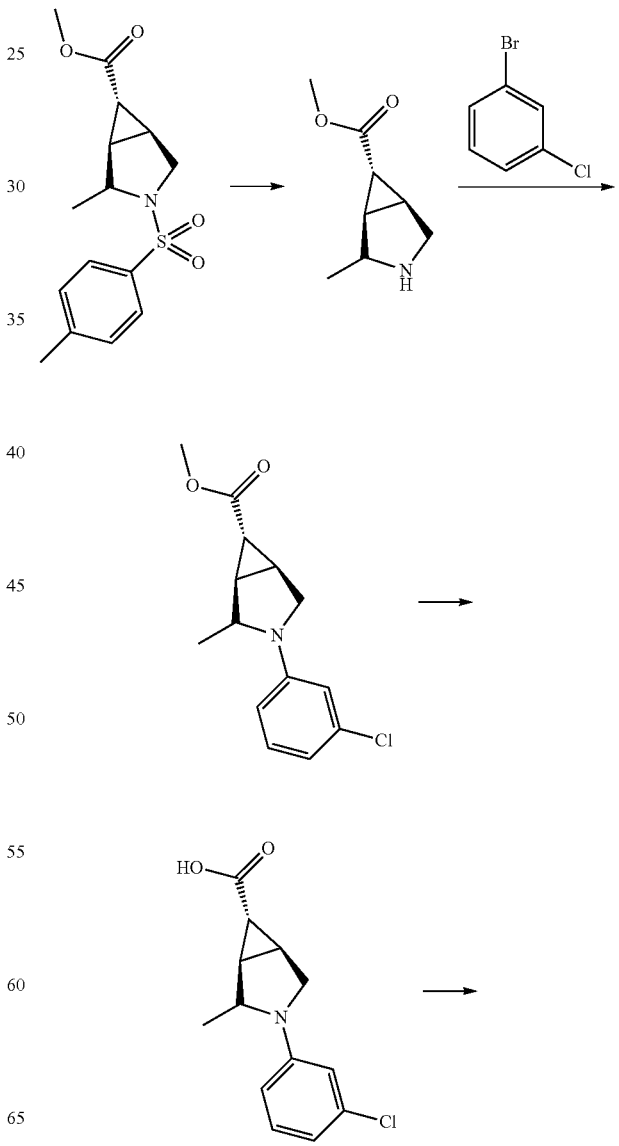

-continued

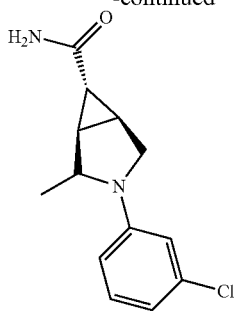 

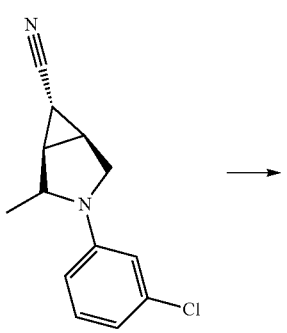 

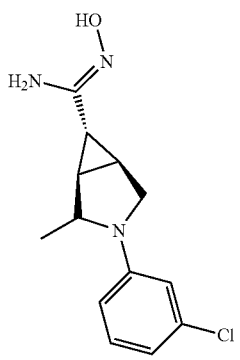 

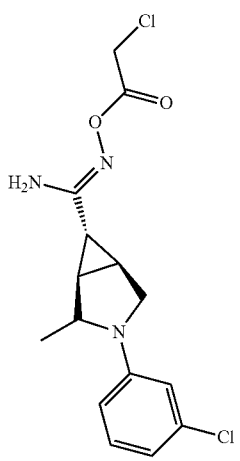 

-continued

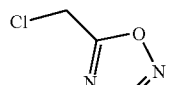

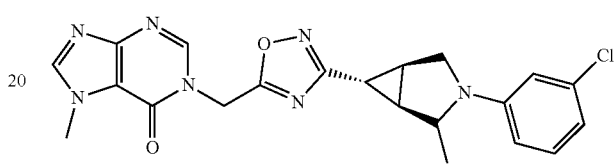

Step 1: Preparation of (1R,2R,5S,6R)-methyl 2-methyl-3-azabicyclo[3.1.0]hexane-6-carboxylate

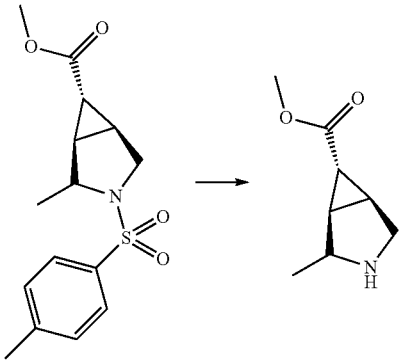

A mixture of (+/−)-methyl (1R,5S,6R)-2-methyl-3-(p-tolylsulfonyl)-3-azabicyclo[3.1.0]hexane-6-carboxylate (5.00 g, 16.2 mmol) and magnesium powder (7.87 g, 323 mmol) in MeOH (162 mL) was stirred at room temperature overnight. The vial was kept in a water bath. The reaction mixture was quenched with 200 mL of saturated NH₄Cl (pH~9-10) and stirred until everything went in solution (~30 min). The solution was concentrated to dryness, taken up in MeOH and the salts were filtered off using a diatomaceous earth plug. The filtrate was adsorbed on silica gel and purified by silica gel column with 5-10%, 10% MeOH/DCM+0.5% NH₄OH to afford the title compound (952 mg, 38% Yield) as a yellow thick oil.

Step 2: Preparation of (1R,2R,5S,6R)-methyl 3-(3-chlorophenyl)-2-methyl-3-azabicyclo[3.1.0]hexane-6-carboxylate

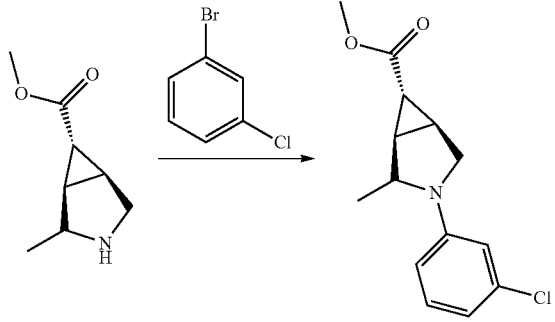

(+/−)-Methyl (1R,5S,6R)-2-methyl-3-azabicyclo[3.1.0]hexane-6-carboxylate (526 mg, 3.39 mmol) was added as a solution in degassed 1,4-dioxane (23 mL), followed by 1-bromo-3-chloro-benzene (779 mg, 4.07 mmol) to a mixture of RuPhos Pd G1 (283 mg, 0.34 mmol) and $Cs_2CO_3$ (3.32 mg, 10.2 mmol) under $N_2$. The vial was sealed and stirred at 110° C. overnight. The reaction mixture were filtered through diatomaceous earth and concentrated on the rotavap. The crude mixture was adsorbed on silica gel and purified by silica gel column with 0-50% EtOAc/Heptane to afford the title compound (653 mg, 73% Yield).

Step 3: Preparation of (1R,2R,5S,6R)-3-(3-chlorophenyl)-2-methyl-3-azabicyclo[3.1.0]hexane-6-carboxylic Acid

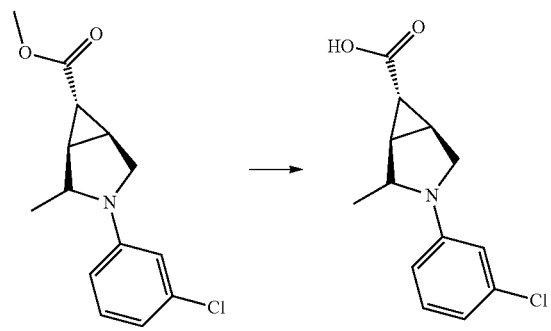

A mixture of (+/−)-methyl (1R,5S,6R)-3-(3-chlorophenyl)-2-methyl-3-azabicyclo[3.1.0]hexane-6-carboxylate (653 mg, 2.46 mmol) and LiOH 2M (4.9 mL mg, 9.83 mmol) in MeOH (76 mL)/THF (121 mL) was stirred at room temperature overnight. The reaction was quenched with 1M HCl and extracted with EtOAc (3×), dried over $MgSO_4$, filtered and concentrated to afford the title compound (622 mg, 100% Yield) as a crude orange foam.

Step 4: Preparation of (1R,2R,5S,6R)-3-(3-chlorophenyl)-2-methyl-3-azabicyclo[3.1.0]hexane-6-carboxamide

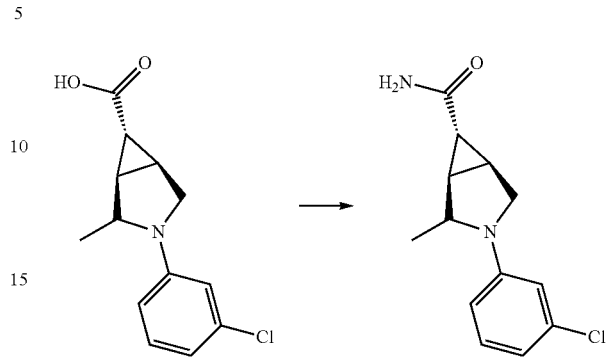

HATU (1.16 g, 2.96 mmol) and DIPEA (647 µL, 3.70 mmol) were added to a solution of (+/−)-(1R,5S,6R)-3-(3-chlorophenyl)-2-methyl-3-azabicyclo[3.1.0]hexane-6-carboxylic acid (621 mg, 2.47 mmol) in DCM (9.9 mL). The mixture was stirred for 5 min and then ammonia (7 mol/L) in MeOH (1.1 mL, 7.40 mmol) was added. The reaction was stirred at room temperature for 2 h. The reaction was partitioned in brine/DCM, extracted with DCM (3×), dried with $MgSO_4$, filtered and concentrated. The crude mixture was adsorbed on silica gel and purified by silica gel column with 0-10% MeOH/DCM to afford the title compound (1.35 g, 218% Yield) as a yellow wet solid.

Step 5: Preparation of (1R,2R,5S,6R)-3-(3-chlorophenyl)-2-methyl-3-azabicyclo[3.1.0]hexane-6-carbonitrile

Phosphoryl chloride (659 µL, 7.00 mmol) was added to a solution of (1R,5S,6R)-3-(3-chlorophenyl)-2-methyl-3-azabicyclo[3.1.0]hexane-6-carboxamide (1.35 g, 5.38 mmol) and TEA (1.5 mL mg, 10.8 mmol) in DCM (18 mL) at 0° C. The reaction was stirred at room temperature overnight. The reaction was diluted with DCM and washed with saturated $NaHCO_3$, water and brine. The DCM layer was dried with $MgSO_4$, filtered and concentrated. The crude mixture was adsorbed on silica gel and purified by silica gel column with 0-50% iPrOAc/Heptane to afford the title compound (423 mg, 34% Yield) as a yellow thick oil.

Step 6: Preparation of (1R,2R,5S,6R,Z)-3-(3-chlorophenyl)-N'-hydroxy-2-methyl-3-azabicyclo[3.1.0]hexane-6-carboximidamide

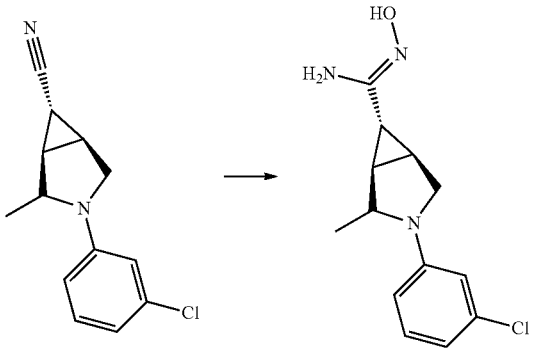

A mixture of (+/−)-(1R,5S,6R)-3-(3-chlorophenyl)-2-methyl-3-azabicyclo[3.1.0]hexane-6-carbonitrile (423 mg, 1.82 mmol) and hydroxylamine (50 mass %) in H₂O (1.1 mL, 18.2 mmol) in EtOH (4.5 mL) was stirred at 80° C. for 5 h. The reaction mixture was concentrated on the rotavap and taken up in iPrOAc. The organic layer was washed with water and brine, dried with MgSO₄, filtered and concentrated to afford the title compound (429 mg, 89% Yield) as a crude white foam.

Step 7: Preparation of (1R,2R,5S,6R,Z)—N'-(2-chloroacetoxy)-3-(3-chlorophenyl)-2-methyl-3-azabicyclo[3.1.0]hexane-6-carboximidamide

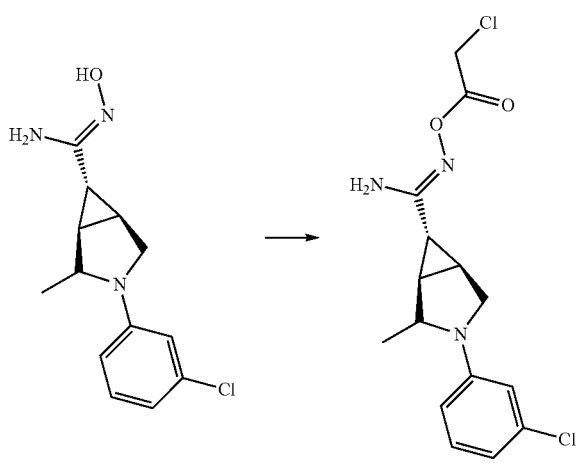

Chloroacetyl chloride (154 µL, 1.94 mmol) was added to a solution of (+/−)-(1R,5S,6R)-3-(3-chlorophenyl)-N'-hydroxy-2-methyl-3-azabicyclo[3.1.0]hexane-6-carboxamidine (429 mg, 1.61 mmol) in acetone (11 mL). The reaction was stirred at room temperature for 2 days. Chloroacetyl chloride (77 µL, 0.97 mmol) was added and the mixture was stirred at room temperature for 2 h. The reaction mixture was concentrated on the rotavap. The residue was taken up in DCM/sat NaHCO₃ and the aqueous layer was extracted with DCM (3×). The organic layer was washed with brine, dried with MgSO₄, filtered and concentrated to afford the title compound (498 mg, 90% Yield) as a crude grey foam.

Step 8: Preparation of 5-(chloromethyl)-3-((1R,2R,5S,6R)-3-(3-chlorophenyl)-2-methyl-3-azabicyclo[3.1.0]hexan-6-yl)-1,2,4-oxadiazole

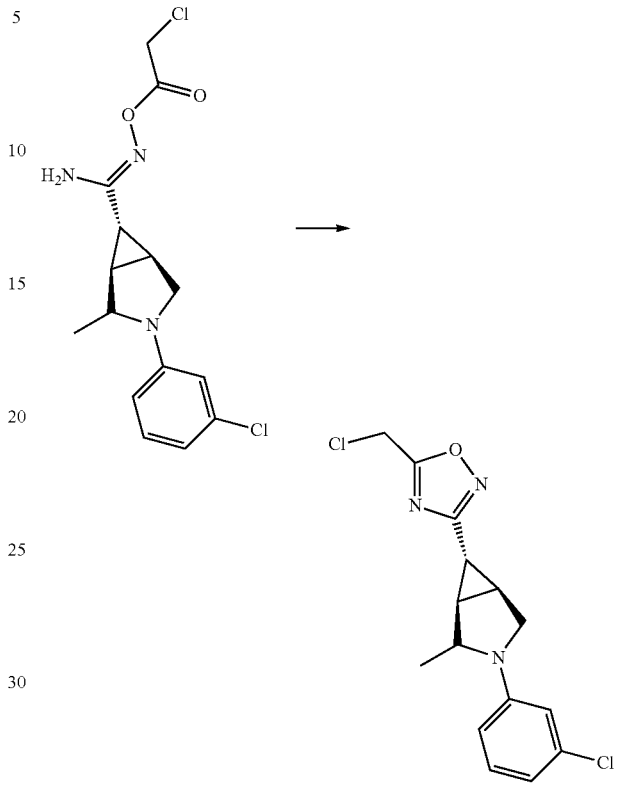

A mixture of (+/−)-[(Z)-[amino-[(1R,5 S,6R)-3-(3-chlorophenyl)-2-methyl-3-azabicyclo[3.1.0]hexan-6-yl]methylene]amino] 2-chloroacetate (498 mg, 1.46 mmol) and MS 4 Å in toluene (15 mL) was stirred at 120° C. overnight. The reaction mixture was filtered through diatomaceous earth and concentrated on the rotavap. The crude mixture was adsorbed on silica gel and purified by silica gel column with 0-50% iPOAc/heptane to afford the title compound (416 mg, 88% Yield) as a yellow thick oil.

Step 9: Preparation of 1-((3-((1R,2S,5S,6R)-3-(3-chlorophenyl)-2-methyl-3-azabicyclo[3.1.0]hexan-6-yl)-1,2,4-oxadiazol-5-yl)methyl)-7-methyl-1,7-dihydro-6H-purin-6-one (Example Compound 204)

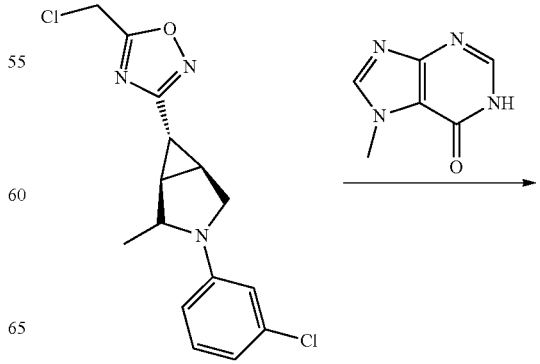

-continued

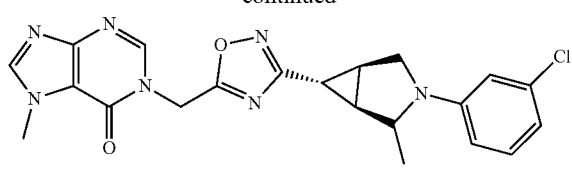

A mixture of 7-methyl-1H-purin-6(7H)-one (223 mg, 1.41 mmol), 5-(chloromethyl)-3-[(1R,5S,6R)-3-(3-chlorophenyl)-2-methyl-3-azabicyclo[3.1.0]hexan-6-yl]-1,2,4-oxadiazole (416 mg, 1.28 mmol), Cs$_2$CO$_3$ (836 mg, 2.56 mmol) and TBAI (48.3 mg, 0.13 mmol) in DMF (4 mL) was stirred at 60° C. overnight. The reaction mixture was diluted with iPrOAc, filtered through diatomaceous earth and concentrated on the rotavap. The crude mixture was adsorbed on silica gel and purified by silica gel column with 50-80% (3:1 iPrOAc/MeOH)/heptane. The compound was further purified by chiral SFC using a Chiralpak ID column with 40% of 0.1% ammonium hydroxide in methanol in CO$_2$. This resulted in the titled compound (51.2 mg, 9% Yield) as a white solid. LCMS [M+H$^+$]: 438.1. 1H NMR (400 MHz, DMSO-d6) δ 8.43 (s, 1H), 8.23 (s, 1H), 7.13 (t, J=8.0 Hz, 1H), 6.60 (dd, J=7.6, 1.9 Hz, 1H), 6.56-6.49 (m, 2H), 5.51 (s, 2H), 4.21 (q, J=6.1 Hz, 1H), 3.95 (s, 3H), 3.53 (d, J=10.0 Hz, 1H), 3.38-3.34 (m, 1H), 2.15 (dt, J=7.0, 3.5 Hz, 1H), 1.97 (dd, J=7.3, 3.3 Hz, 1H), 1.93 (t, J=3.2 Hz, 1H), 1.07 (d, J=6.1 Hz, 3H).

Example 80: Preparation of 1-((3-((1R,5S,6r)-3-(benzo[d]thiazol-6-yl)-3-azabicyclo[3.1.0]hexan-6-yl)-1,2,4-oxadiazol-5-yl)methyl)-7-methyl-1,7-dihydro-6H-purin-6-one (Example Compound 211)

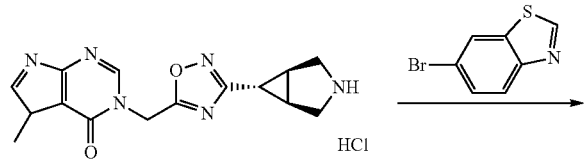

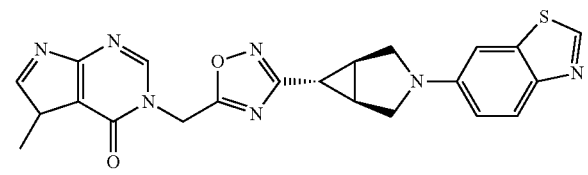

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 6-bromobenzothiazole (82.3 mg, 0.384 mmol) as a white solid (11.4 mg, 8% yield), in a manner analogous to Example 4, Step 8. LCMS [M+H$^+$] 447.1. $^1$H NMR (400 MHz, DMSO) δ 8.96 (s, 1H), 8.44 (s, 1H), 8.23 (d, J=0.7 Hz, 1H), 7.85 (d, J=8.9 Hz, 1H), 7.21 (d, J=2.4 Hz, 1H), 6.86 (dd, J=9.0, 2.5 Hz, 1H), 5.53 (s, 2H), 3.98-3.93 (m, 3H), 3.77 (d, J=9.8 Hz, 2H), 3.37-3.33 (m, 2H), 2.29-2.19 (m, 2H), 2.06 (t, J=3.3 Hz, 1H).

Example 81: Preparation of 1-((3-((1R,5S,6r)-3-(4-chloropyridin-2-yl)-3-azabicyclo[3.1.0]hexan-6-yl)-1,2,4-oxadiazol-5-yl)methyl)-7-methyl-1,7-dihydro-6H-purin-6-one (Example Compound 212)

The overall Example 212 reaction scheme is as follows:

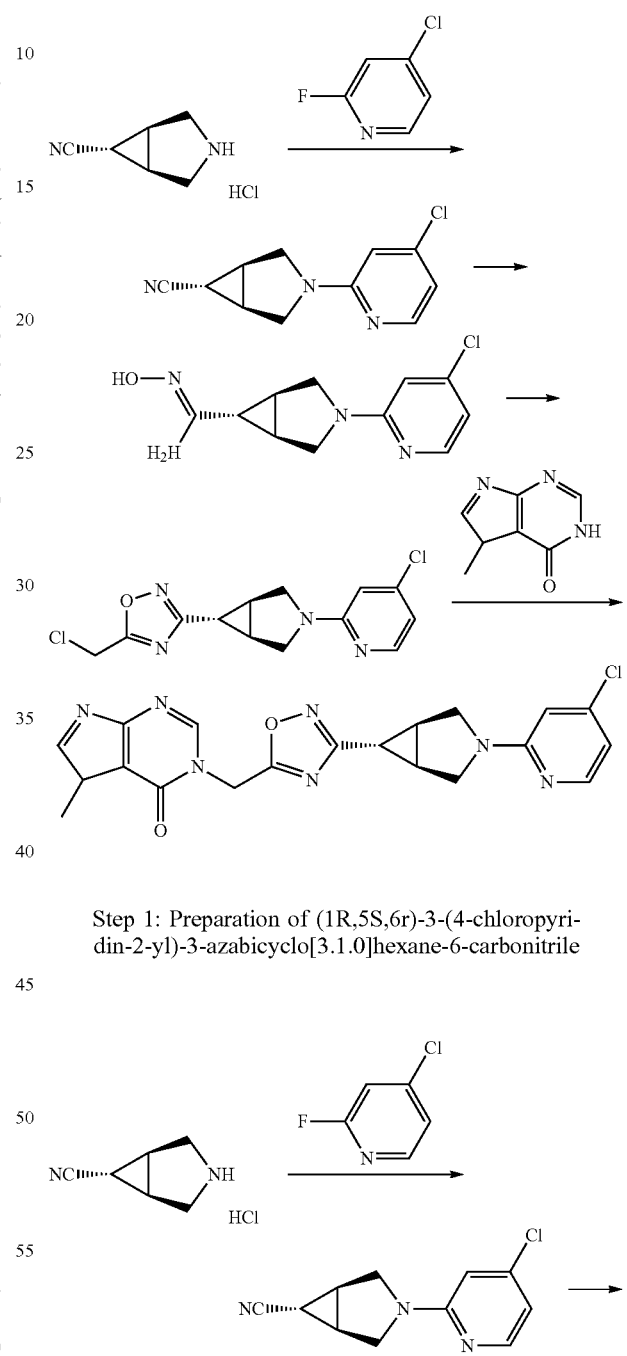

Step 1: Preparation of (1R,5S,6r)-3-(4-chloropyridin-2-yl)-3-azabicyclo[3.1.0]hexane-6-carbonitrile To a vial was added 3-azabicyclo[3.1.0]hexane-6-carbonitrile hydrochloride (2.00 g, 13.8 mmol), 1,8-diazabicyclo[5.4.0]undec-7-ene (10.6 mL, 69.2 mmol), pyridine (50 mL) and 4-chloro-2-fluoropyridine (4.10 mL, 41.5 mmol). The reaction mixture was stirred at 110° C. for 16 h. The reaction mixture was washed with water, extracted 3 times with iPrOAc, dried over sodium sulfate, filtered, and concentrated in vacuo. The residue was adsorbed onto silica and purified by flash column chromatography with 0-100% iPrOAc in heptane to afford the desired compound as a white solid (2.27 g, 75%). ¹H NMR (400 MHz, CDCl₃-d) δ 8.02 (d, J=54 Hz, 1H), 6.68 (dd, J=5.4, 1.8 Hz, 1H), 6.55 (d, J=1.6 Hz, 1H), 3.77 (d, J=11.0 Hz, 2H), 3.41-3.36 (m, 2H), 2.46-2.41 (m, 2H), 1.66 (t, J=3.5 Hz, 1H).

Step 2: Preparation of (1R,5S,6r,Z)-3-(4-chloropyridin-2-yl)-N-hydroxy-3-azabicyclo[3.1.0]hexane-6-carboximidamide

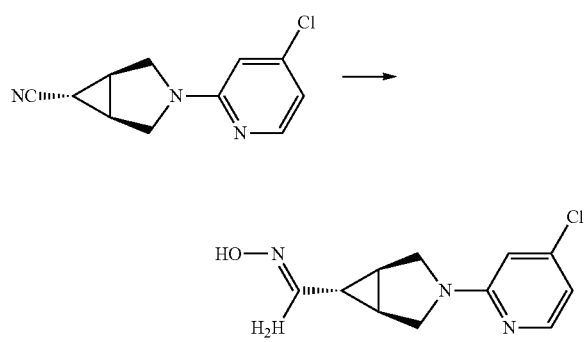

The title compound was prepared from (1R,5S,6r)-3-(4-chloropyridin-2-yl)-3-azabicyclo[3.1.0]hexane-6-carbonitrile (3.58 g, 16.3 mmol) in a manner analogous to Example 41 and 42, Step 10.

Step 3: Preparation of 5-(chloromethyl)-3-((1R,5S,6r)-3-(4-chloropyridin-2-yl)-3-azabicyclo[3.1.0]hexan-6-yl)-1,2,4-oxadiazole

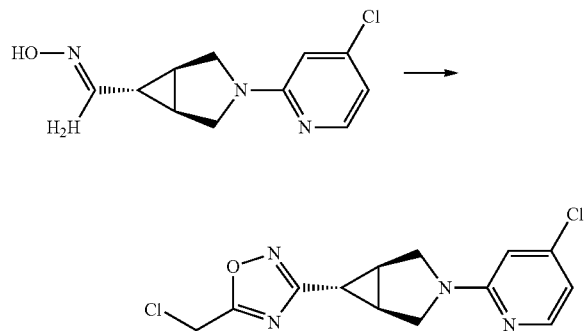

The title compound was prepared from (1R,5S,6r,Z)-3-(4-chloropyridin-2-yl)-N-hydroxy-3-azabicyclo[3.1.0]hexane-6-carboximidamide (4.12 g, 16.3 mmol) as a yellow oil (4.55 g, 90% yield) in a manner analogous to Example 41 and 42, Step 11. ¹H NMR (400 MHz, CDCl₃-d) 8.04 (d, J=5.4 Hz, 1H), 6.68 (dd, J=5.4, 1.8 Hz, 1H), 6.57 (d, J=1.7 Hz, 1H), 5.05 (s, 2H), 3.85 (d, J=10.8 Hz, 2H), 3.49 (d, J=9.2 Hz, 2H), 2.31-2.22 (m, 2H), 2.03 (t, J=3.3 Hz, 1H).

Step 4: Preparation of 1-((3-((1R,5S,6r)-3-(4-chloropyridin-2-yl)-3-azabicyclo[3.1.0]hexan-6-yl)-1,2,4-oxadiazol-5-yl)methyl)-7-methyl-1,7-dihydro-6H-purin-6-one (Example Compound 212)

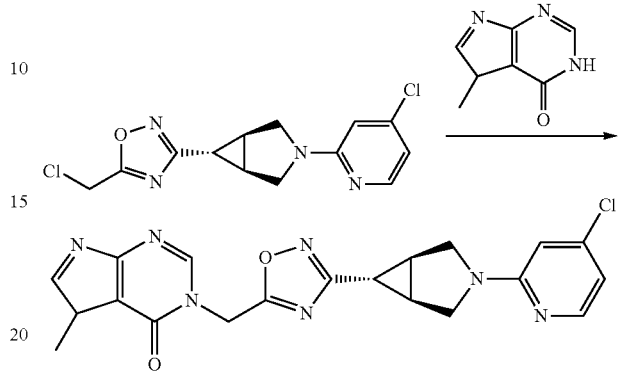

The title compound was prepared from 5-(chloromethyl)-3-((1R,5S,6r)-3-(4-chloropyridin-2-yl)-3-azabicyclo[3.1.0]hexan-6-yl)-1,2,4-oxadiazole (4.55 g, 14.6 mmol) and 7-methyl-1,7-dihydro-6H-purin-6-one (2.41 g, 16.1 mmol) as a white solid (3.14 g, 51% yield), in a manner analogous to Example 25, Step 5. LCMS [M+H⁺] 425.2. ¹H NMR (400 MHz, DMSO) δ 8.43 (s, 1H), 8.23 (d, J=0.6 Hz, 1H), 8.02 (d, J=5.4 Hz, 1H), 6.67 (dd, J=5.4, 1.7 Hz, 1H), 6.55 (d, J=1.7 Hz, 1H), 5.52 (s, 2H), 3.95 (s, 3H), 3.81 (d, J=10.8 Hz, 2H), 3.46 (dt, J=11.1, 1.8 Hz, 2H), 2.24-2.14 (m, 2H), 1.97 (t, J=3.3 Hz, 1H).

Example 82: Preparation of 6-((3-((1R,5S,6r)-3-phenyl-3-azabicyclo[3.1.0]hexan-6-yl)-1,2,4-oxadiazol-5-yl)methyl)pyrido[2,3-d]pyridazin-5(6H)-one (Example Compound 213)

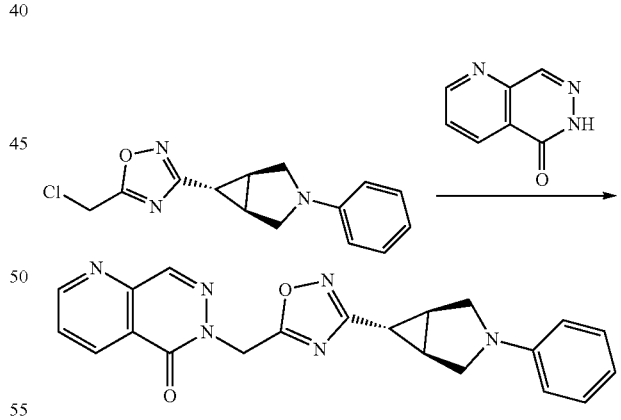

To a sealed tube was added 6-[[3-[(1R,5S)-3-azabicyclo[3.1.0]hexan-6-yl]-1,2,4-oxadiazol-5-yl]methyl]pyrido[2,3-d]pyridazin-5-one; hydrochloride (as prepared in Example 4, Step 7) (100 mg, 0.29 mmol), chloro-(2-dicyclohexylphosphino-2',6'-diisopropoxy-1,1'-biphenyl)[2-(2-aminoethyl)phenyl]palladium(II)-methyl-t-butyl ether adduct (24 mg, 0.029 mmol), cesium carbonate (280 mg, 0.87 mmol), bromobenzene (0.036 mL, 0.35 mmol) and 1,4-dioxane (1.1 mL). The headspace was flushed with N2 and the tube was sealed. The reaction mixture was stirred at 110° C. for 18 h. The reaction mixture was diluted with dichloromethane, filtered through celite, eluting with dichloromethane and the filtrate was concentrated in vacuo. The residue was adsorbed onto silica and purified by flash column chromatography with 10-80% 3:1 MeOH: iPrOAc in heptane to afford the desired compound as an orange oil. The residue was further purified by achiral SFC to yield the title compound (14.6 mg, 13%) as a white solid. LCMS [M+H⁺]: 387.1. 1H NMR (400 MHz, DMSO-d6) δ 9.20 (dd, J=4.6, 1.7 Hz, 1H), 8.67-8.62 (m, 1H), 8.60 (d, J=0.8 Hz, 1H), 7.92 (dd, J=8.1, 4.6 Hz, 1H), 7.19-7.10 (m, 2H), 6.66-6.61 (m, 1H), 6.59-6.54 (m, 2H), 5.67 (s, 2H), 3.68 (d, J=9.6 Hz, 2H), 3.25-3.21 (m, 2H), 2.24-2.17 (m, 2H), 2.03 (t, J=3.2 Hz, 1H).

Example 83: Preparation of 3-((3-((1R,5S,6r)-3-(3-chlorophenyl)-3-azabicyclo[3.1.0]hexan-6-yl)-1,2,4-oxadiazol-5-yl)methyl)pyrido[2,3-d]pyrimidin-4(3H)-one (Example Compound 216)

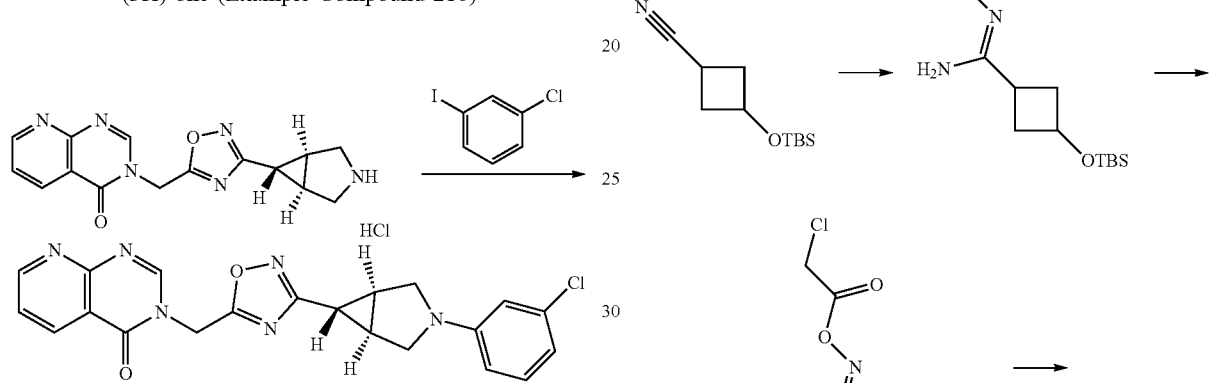

The title compound was prepared from 3-((3-((1R,5S,6r)-3-azabicyclo[3.1.0]hexan-6-yl)-1,2,4-oxadiazol-5-yl)methyl)pyrido[2,3-d]pyrimidin-4(3H)-one hydrochloride (50 mg, 0.16 mmol) and 1-chloro-3-iodobenzene (116 mg, 0.49 mmol) as a white crystalline solid (5 mg, 7%), in a manner analogous to Example 4, Step 8. LCMS [M+H⁺]: 421. ¹H NMR (300 MHz, methanol-d₄) δ 9.00 (d, J=2.1 Hz, 1H), 8.69-8.66 (m, 2H), 7.65 (dd, J=8.0, 4.7 Hz, 1H), 7.13-7.08 (m, 1H), 6.64-6.61 (m, 1H), 6.57-6.56 (m, 1H), 6.51-6.49 (m, 1H), 5.52 (s, 2H), 3.68 (d, J=9.6 Hz, 2H), 3.30-3.28 (m, 2H), 2.25-2.24 (m, 2H), 2.09-2.00 (m, 1H).

Example 84: Preparation of 1-((3-((1r,3r)-3-(4-chlorophenoxy)cyclobutyl)-1,2,4-oxadiazol-5-yl)methyl)-7-methyl-1,7-dihydro-6H-purin-6-one (Example Compound 218)

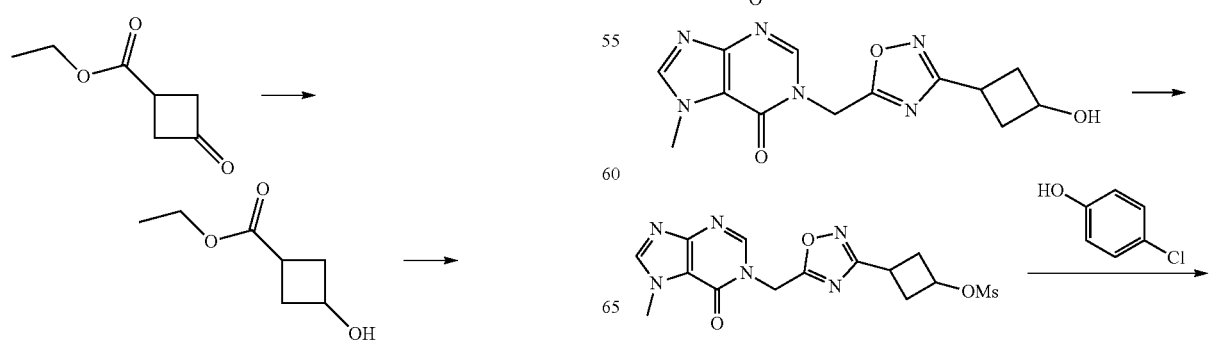

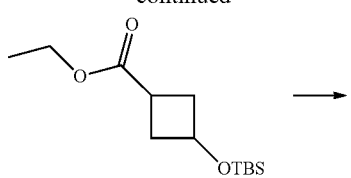

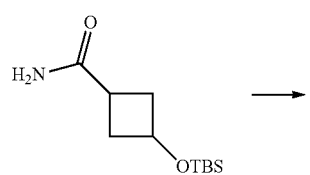

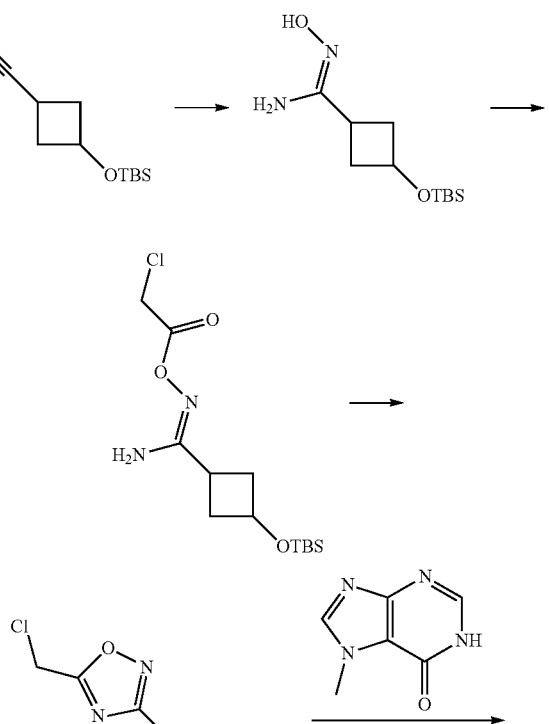

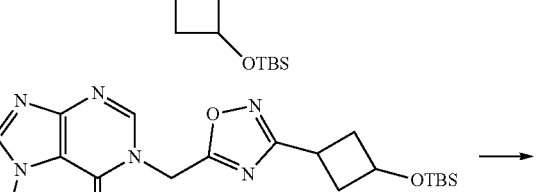

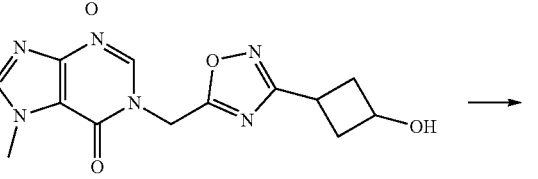

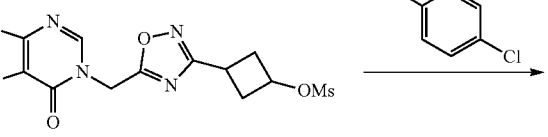

-continued

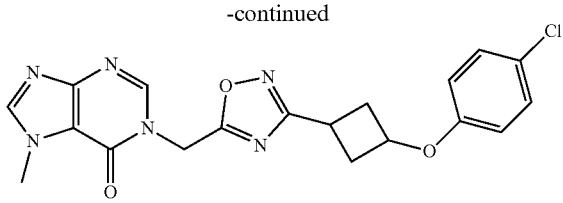

Step 1: Preparation of ethyl 3-hydroxycyclobutanecarboxylate

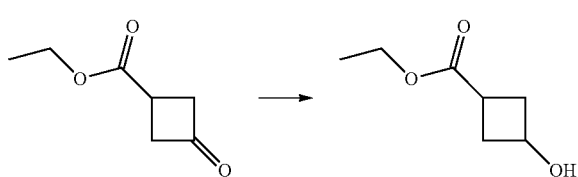

Sodium borohydride (454 mg, 12.0 mmol) was added to a solution of ethyl 3-oxocyclobutanecarboxylate (1.74 g, 12.0 mmol) in THF (60 mL) at 0° C. The reaction was stirred at room temperature for 4 h. The reaction was quenched with water at 0° C. and extracted with iPrOAc (3×). The combined organic extracts were washed with brine, dried with MgSO$_4$, filtered and concentrated. The crude mixture was adsorbed on silica gel and purified by silica gel column with 0-70% iPOAc/Heptane to afford the title compound (1.41 g, 81% Yield) as a clear oil.

Step 2: Preparation of ethyl 3-(tert-butyldimethylsilyloxy)cyclobutanecarboxylate

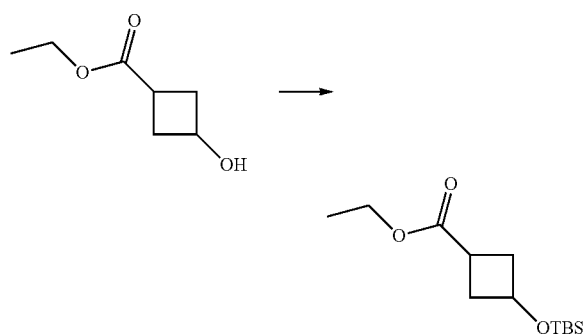

TBSCl (3.20 g, 21.0 mmol) was added to a solution of ethyl 3-hydroxycyclobutanecarboxylate (1.50 g, 10.0 mmol), imidazole (1.40 g, 21.0 mmol) and DMAP (130 mg, 1.00 mmol) in DCM (35 mL). The reaction was stirred at room temperature overnight. The reaction was quenched with sat NH$_4$Cl and partitioned in DCM. The aqueous layer was extracted with DCM (3×). The combined organic extracts were washed with brine, dried with MgSO$_4$, filtered and concentrated. The crude mixture was adsorbed on silica gel and purified by silica gel column with 0-40% iPrOAc/heptane to afford the title compound (2.90 g, 110% Yield) as a clear liquid.

Step 3: Preparation of 3-(tert-butyldimethylsilyloxy)cyclobutanecarboxamide

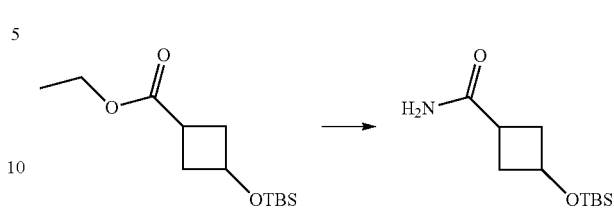

A mixture of ethyl 3-[tert-butyl(dimethyl)silyl]oxycyclobutanecarboxylate (2.80 g, 11.0 mmol) in ammonia (7 mol/L) in MeOH (27 mL) was stirred at 60° C. overnight. The crude mixture was adsorbed on silica gel and purified by silica gel a column with 40-100%, 100% iPrOAc/Heptane. 1.1 g of methyl ester was recovered. The Reaction was restarted with ammonia (7 mol/L) in MeOH (10 mL) was stirred at 60° C. for 2 days. The crude mixture was adsorbed on silica gel and purified by silica gel a column with 40-100%, 100% iPrOAc/Heptane to afford the title compound (1.34 g, 54% Yield) as a white solid.

Step 4: Preparation of 3-(tert-butyldimethylsilyloxy)cyclobutanecarbonitrile

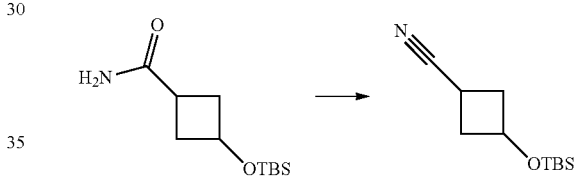

Phosphoryl chloride (506 µL, 5.37 mmol) was added to a solution of 3-[tert-butyl(dimethyl)silyl]oxycyclobutanecarboxamide (1.12 g, 4.88 mmol) and TEA (2.1 mL, 14.6 mmol) in DCM (16 mL) at 0° C. The reaction was stirred at 0° C. and allowed to warm-up to room temperature over 4 h. The reaction was partitioned with DCM/water and the aqueous layer was extracted with DCM (3×). The DCM layer was washed with brine, dried with MgSO$_4$, filtered and concentrated. The crude mixture was adsorbed on silica gel and purified by silica gel column with 0-40% iPrOAc/Heptane to afford the title compound (976 mg, 95% Yield) as a clear oil.

Step 5: Preparation of (Z)-3-(tert-butyldimethylsilyloxy)-N'-hydroxycyclobutanecarboximidamide

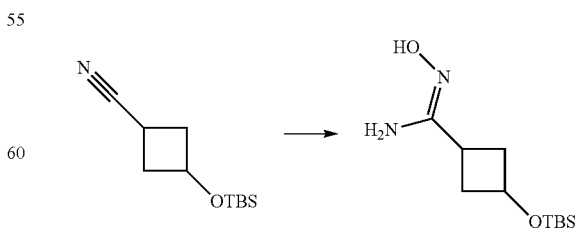

A mixture of 3-[tert-butyl(dimethyl)silyl]oxycyclobutanecarbonitrile (1.02 g, 4.83 mmol) and hydroxylamine (50 mass %) in H$_2$O (2.9 mL, 48.3 mmol) in EtOH (912 mL)

was stirred at 80° C. overnight. The reaction mixture was concentrated on the rotavap and taken up in iPrOAc. The organic layer was washed with water and brine, dried with MgSO$_4$, filtered and concentrated to afford the title compound (1.22 g, 103% Yield) as a crude white solid.

Step 6: Preparation of (Z)-3-(tert-butyldimethylsilyloxy)-N'-(2-chloroacetoxy)cyclobutanecarboximidamide

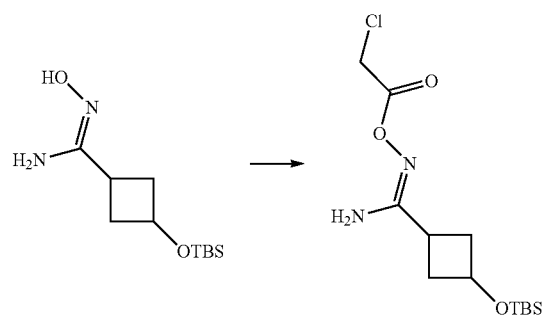 [SMILES: CC(C)(C)[Si](C)(C)OC1CC(/C(N)=N/O)C1 ; CC(C)(C)[Si](C)(C)OC1CC(/C(N)=N/OC(=O)CCl)C1]

Chloroacetyl chloride (476 µL, 5.99 mmol) was added to a solution of 3-[tert-butyl(dimethyl)silyl]oxy-N'-hydroxycyclobutanecarboxamidine (1.22 g, 4.99 mmol) and DIPEA (2.6 mL, 15.0 mmol) in DCM (33 mL). The reaction was stirred at room temperature for 2 h. The reaction mixture was concentrated on the rotavap. The residue was taken up in DCM and washed with saturated NaHCO$_3$, water and brine. The organic layer was dried with MgSO$_4$, filtered and concentrated to afford the title compound (1.78 g, 111% Yield) as a crude orange solid.

Step 7: Preparation of 3-(3-(tert-butyldimethylsilyloxy)cyclobutyl)-5-(chloromethyl)-1,2,4-oxadiazole

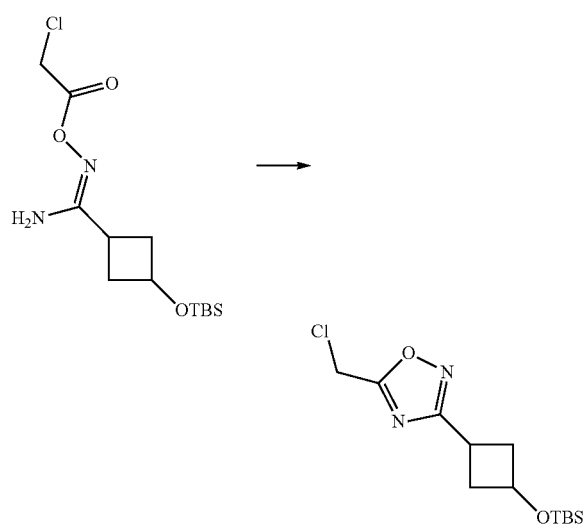

A mixture of [(Z)-[amino-[3-[tert-butyl(dimethyl)silyl]oxycyclobutyl]methylene]amino] 2-chloroacetate (1.78 g, 5.55 mmol) and MS 4 Å in toluene (56 mL) was stirred at 120° C. The reaction mixture was filtered through diatomaceous earth and concentrated on the rotavap. The crude mixture was adsorbed on silica gel and purified by silica gel column with 0-50% iPOAc/heptane to afford the title compound (1.09 g, 65% Yield) as a yellow oil.

Step 8: Preparation of 1-((3-(3-(tert-butyldimethylsilyloxy)cyclobutyl)-1,2,4-oxadiazol-5-yl)methyl)-7-methyl-1H-purin-6(7H)-one

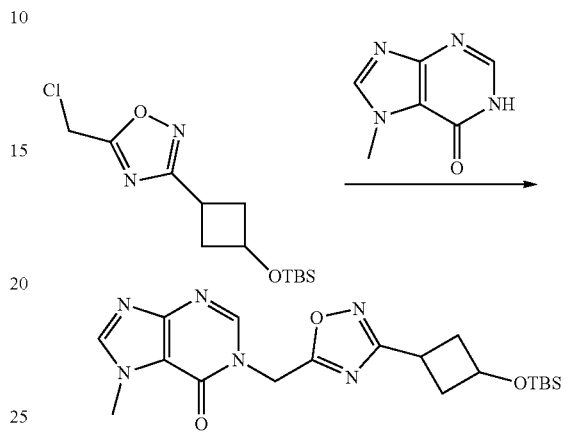

A mixture of 7-methyl-1H-purin-6(7H)-one (657 mg, 4.16 mmol), tert-butyl-[3-[5-(chloromethyl)-1,2,4-oxadiazol-3-yl]cyclobutoxy]-dimethyl-silane (1.05 g, 3.47 mmol), Cs$_2$CO$_3$ (2.26 g, 6.93 mmol) and TBAI (131 mg, 0.35 mmol) in DMF (12 mL) was stirred at 70° C. for 5 h. The reaction mixture was partitioned in water/iPrOAc and extracted with iPrOAc (3×). The combined organic extracts were washed with water and brine and they were dried over MgSO$_4$, filtered and concentrated. The crude mixture was adsorbed on silica gel and purified by silica gel column with 40-80% (3:1 iPrOAc/MeOH)/Heptane to afford the title compound (1.04 g, 72% Yield) as a pale pink solid.

Step 9: Preparation of 1-((3-(3-hydroxycyclobutyl)-1,2,4-oxadiazol-5-yl)methyl)-7-methyl-1H-purin-6(7H)-one

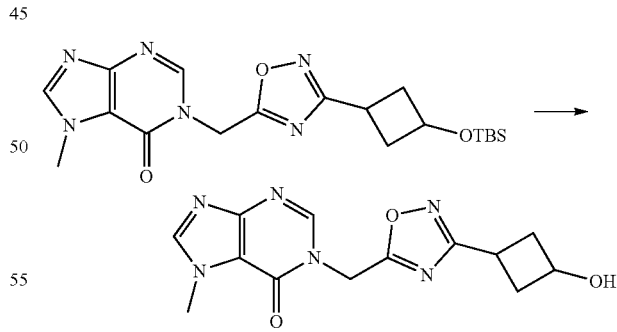

A mixture of 1-[[3-[3-[tert-butyl(dimethyl)silyl]oxycyclobutyl]-1,2,4-oxadiazol-5-yl]methyl]-7-methyl-purin-6-one (1.02 g, 2.45 mmol) and TBAF (1.0 mol/L) in THF (2.9 mL, 2.9 mmol) in THF (12 mL) was stirred at room temperature for 1 h. The reaction mixture was partitioned in water/iPrOAc and extracted with iPrOAc (3×) and with 20% MeOH/DCM (10×). The organics were dried with MgSO$_4$, filtered and concentrated. The aqueous layer still contain desired product and was concentrated on the rotavap. The crude mixture from the organic and the aqueous layers were purified by silica gel column with 0-10%, 10% MeOH/DCM to afford the title compound (628 mg, 85% Yield) as a pale yellow solid.

Step 10: Preparation of 3-(5-((7-methyl-6-oxo-6,7-dihydro-1H-purin-1-yl)methyl)-1,2,4-oxadiazol-3-yl) cyclobutyl methanesulfonate

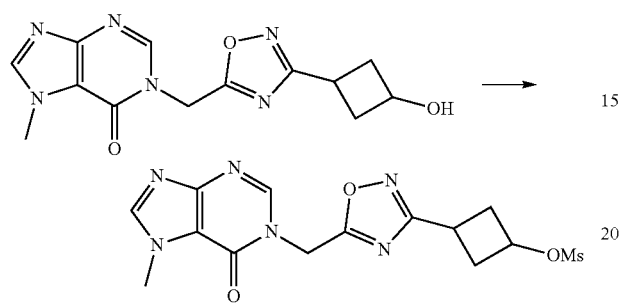

Methanesulfonic anhydride (463 mg, 2.58 mmol) was added to a solution of 1-[[3-(3-hydroxycyclobutyl)-1,2,4-oxadiazol-5-yl]methyl]-7-methyl-purin-6-one (520 mg, 1.72 mmol) and DIPEA (902 µL, 5.16 mmol) in acetonitrile (17 mL). The reaction was stirred at 80° C. overnight. Methanesulfonic anhydride (617 mg, 3.44 mmol), DIPEA (1.20 mL, 6.88 mmol) and DMAP (31.84 mg, 0.26 mmol) were added and the reaction was stirred at 60° C. overnight. The crude mixture was adsorbed on silica gel and purified by silica gel column with 0-20% MeOH/DCM. The material was triturated with 10% MeOH/DCM and the white solid was recovered by filtration to afford the title compound (529 mg, 81% Yield) as a white solid.

Step 11: Preparation of 1-((3-(((1r,3r)-3-(4-chlorophenoxy)cyclobutyl)-1,2,4-oxadiazol-5-yl)methyl)-7-methyl-1,7-dihydro-6H-purin-6-one (Example Compound 218)

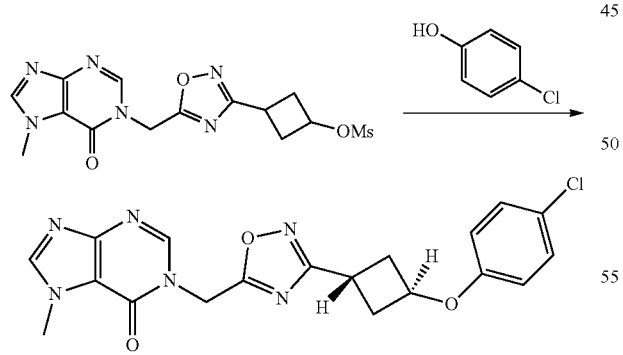

A mixture of [3-[5-[(7-methyl-6-oxo-purin-1-yl)methyl]-1,2,4-oxadiazol-3-yl]cyclobutyl] methanesulfonate (180 mg, 0.47 mmol), 4-chlorophenol (93 µL, 0.95 mmol) and Cs$_2$CO$_3$ (309 mg, 0.95 mmol) in DMSO (2.4 mL) was stirred at 80° C. overnight. The reaction mixture was partitioned in brine/iPrOAc and extracted with iPrOAc (3×). The combined organic extracts were washed with brine, dried over MgSO$_4$, filtered and concentrated. The product was purified by preparative HPLC using a Gemini-NX C18 5 µm, 110 A column with 20-60% of acetonitrile in 0.1% Ammonium Hydroxide in Water. The compound was further purified by SFC using a Torus AA column with 5-60% of 0.1% ammonium hydroxide in methanol in CO$_2$. This resulted in the titled compound (92.7 mg, 47% Yield) as a white solid. LCMS [M+H$^+$]: 413.1. 1H NMR (400 MHz, DMSO-d6) δ 8.46 (s, 1H), 8.24 (s, 1H), 7.34-7.27 (m, 2H), 6.88-6.81 (m, 2H), 5.57 (s, 2H), 4.95-4.83 (m, 1H), 3.95 (s, 3H), 3.76-3.64 (m, 1H), 2.74-2.63 (m, 2H), 2.60-2.50 (m, 2H).

Example 85: Preparation of 1-((3-(((1R,5S,6r)-3-(3-chloro-2,6-difluorophenyl)-3-azabicyclo[3.1.0] hexan-6-yl)-1,2,4-oxadiazol-5-yl)methyl)-7-methyl-1,7-dihydro-6H-purin-6-one (Example Compound 222)

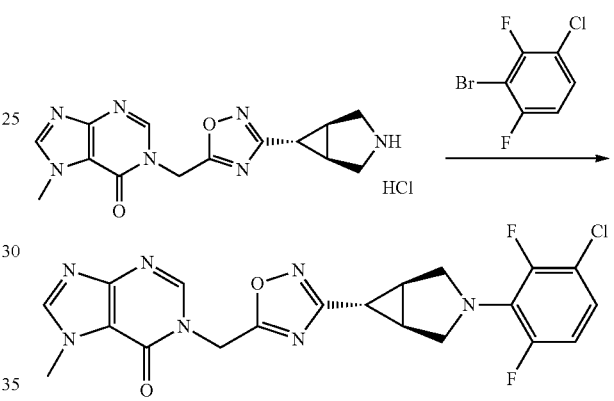

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 2-bromo-4-chloro-1,3-difluorobenzene (87.4 mg, 0.384 mmol) as a white solid (3.4 mg, 2% yield), in a manner analogous to Example 4, Step 8. LCMS [M+H$^+$] 460.1. $^1$H NMR (400 MHz, DMSO) δ 8.43 (s, 1H), 8.23 (s, 1H), 7.13 (ddd, J=9.4, 8.5, 2.0 Hz, 1H), 6.79 (td, J=9.5, 5.4 Hz, 1H), 5.52 (s, 2H), 3.95 (s, 3H), 3.74 (dd, J=9.7, 2.9 Hz, 2H), 3.29 (d, J=1.7 Hz, 2H), 2.18-2.13 (m, 2H), 2.15 (t, J=2.7 Hz, 1H).

Examples 86 and 87: Preparation of 7-methyl-1-((3-((1R,5R,6S)-3-phenylbicyclo[3.1.0]hex-2-en-6-yl)-1,2,4-oxadiazol-5-yl)methyl)-1,7-dihydro-6H-purin-6-one (Example Compound 226) and 7-methyl-1-((3-((1S,5S,6R)-3-phenylbicyclo[3.1.0] hex-2-en-6-yl)-1,2,4-oxadiazol-5-yl)methyl)-1,7-dihydro-6H-purin-6-one (Example Compound 225)

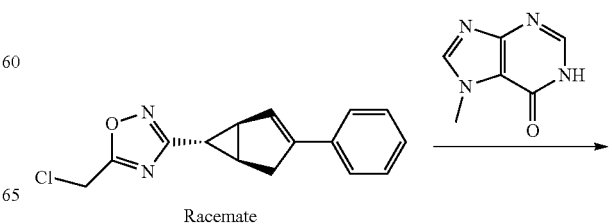

Racemate

323
-continued

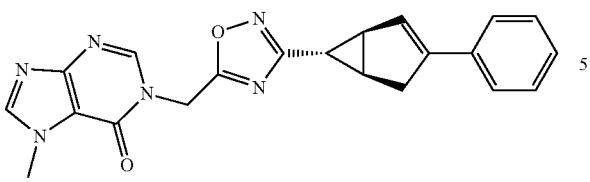

+

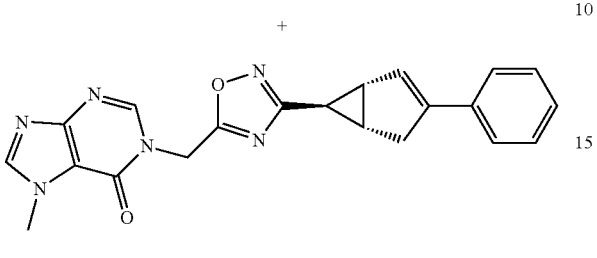

In a 50 mL RBF were charged 7-methyl-1H-purin-6-one (381 mg, 2.54 mmol), 5-(chloromethyl)-3-[rac-(1R,5R,6S)-3-(2-fluorophenyl)-6-bicyclo[3.1.0]hex-3-enyl]-1,2,4-oxadiazole (from Examples 108 and 109, Step 3) (461 mg, 1.69 mmol), tetrabutylammonium iodide (62 mg, 0.17 mmol), potassium carbonate (701 mg, 5.07 mmol) and DMF (11 mL). The reaction mixture was stirred at 20° C. for 1.5 hours and it was diluted with water (80 mL). The formed solid was collected by filtration and washed with water (25 mL). The obtained material was purified by flash column chromatography (100 g column) on silica gel using a solution of 20% MeOH/DCM in DCM (5 to 40% gradient) to afford a racemic mixture of the desired products (477 mg, 1.23 mmol, 73% yield) as a white solid. The racemic material was separated by SFC with the following conditions: Column: OJ 10×250 mm, 5 µm, Isocratic 40% MeCN+EtOH 1:1, 10 mL/min, 100 Bar, Column temperature: 35° C., Run time: 11 min.

Example 86, enantiomer 1, (Example Compound 226): white solid, Rt=7.7 min (OJ 10×250 mm, 5 µm, Isocratic 40% MeCN+EtOH 1:1, 10 mL/min, 100 Bar); LCMS [M+H$^+$]387.1; $^1$H NMR (500 MHz, DMSO-d6): δ 8.43 (s, 1H), 8.23 (d, J=0.4 Hz, 1H), 7.44-7.40 (m, 2H), 7.34-7.28 (m, 2H), 7.26-7.21 (m, 1H), 6.53 (q, J=1.9 Hz, 1H), 5.51 (s, 2H), 3.95 (d, J=0.2 Hz, 3H), 3.09 (ddd, J=17.5, 6.7, 1.4 Hz, 1H), 2.92 (dt, J=17.6, 2.2 Hz, 1H), 2.47-2.41 (m, 1H), 2.26 (td, J=6.6, 3.4 Hz, 1H), 1.64 (dd, J=3.3, 2.6 Hz, 1H).

Example 87, enantiomer 2, (Example Compound 225): white solid, Rt=9.5 min (OJ 10×250 mm, 5 µm, Isocratic 40% MeCN+EtOH 1:1, 10 mL/min, 100 Bar); LCMS [M+H$^+$]387.1; $^1$H NMR (500 MHz, DMSO-d6) δ 8.43 (s, 1H), 8.23 (s, 1H), 7.46-7.37 (m, 2H), 7.31 (t, J=7.6 Hz, 2H), 7.27-7.19 (m, 1H), 6.53 (q, J=1.8 Hz, 1H), 5.51 (s, 2H), 3.95 (s, 3H), 3.09 (ddd, J=17.8, 6.8, 1.2 Hz, 1H), 2.91 (d, J=17.8 Hz, 1H), 2.47-2.43 (m, 1H), 2.26 (td, J=6.6, 3.4 Hz, 1H), 1.64 (t, J=3.0 Hz, 1H).

324

Example 88: Preparation of 1-((3-((1R,5S,6r)-3-(4-chloro-3-fluorophenyl)-3-azabicyclo[3.1.0]hexan-6-yl)-1,2,4-oxadiazol-5-yl)methyl)-7-methyl-1,7-dihydro-6H-purin-6-one (Example Compound 229)

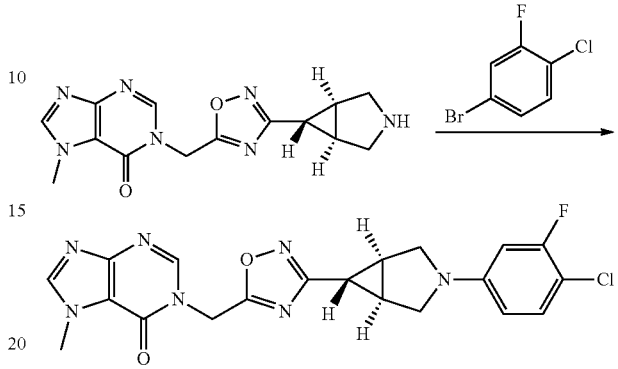

A mixture of 1-((3-[(1R,2R,3R)-2-(aminomethyl)-3-(chloromethyl) cyclopropyl]-1,2,4-oxadiazol-5-yl]methyl)-7-methyl-6,7-dihydro-1H-purin-6-one (100 mg, 0.29 mmol), 4-bromo-1-chloro-2-fluorobenzene (72 mg, 0.34 mmol), chloro-(2-dicyclohexylphosphino-2',6'-diisopropoxy-1,1'-biphenyl)[2-(2-aminoethyl)phenyl]palladium (II)-methyl-t-butyl ether adduct (26.7 mg, 0.0320 mmol), Cs$_2$CO$_3$ (280 mg, 0.86 mmol) and dioxane (2 mL) was stirred for 12 h at 110° C. under nitrogen. The solids were filtered out. The filtrate was diluted with ethyl acetate, washed with water, dried with anhydrous Na$_2$SO$_4$, and concentrated under vacuum. The residue was adsorbed onto silica gel and purified by flash column chromatography eluted with ethyl DCM/MeOH (20:1) to afford the title compound (12 mg, 10% yield) as a white solid. LCMS [M+H$^+$]: 442.1. $^1$H NMR (300 MHz, DMSO-d$_6$) δ 8.45 (s, 1H), 8.25 (s, 1H), 7.29 (t, J=8.8 Hz, 1H), 6.58 (dd, J=12.7, 2.7 Hz, 1H), 6.47-6.36 (m, 1H), 5.53 (s, 2H), 3.96 (s, 3H), 3.67 (d, J=9.9 Hz, 2H), 3.33 (s, 2H), 2.22 (t, J=2.8 Hz, 2H), 2.12-1.98 (m, 1H).

Example 89: Preparation of 3-((3-((1s,3s)-3-hydroxy-3-(naphthalen-2-yl)cyclobutyl)-1,2,4-oxadiazol-5-yl)methyl)-5-methylpyrido[3,4-d]pyrimidin-4(3H)-one (Example Compound 232)

The overall Example 89 reaction scheme is as follows:

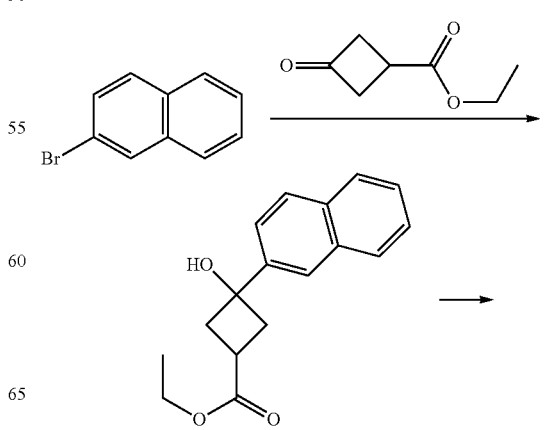

325
-continued

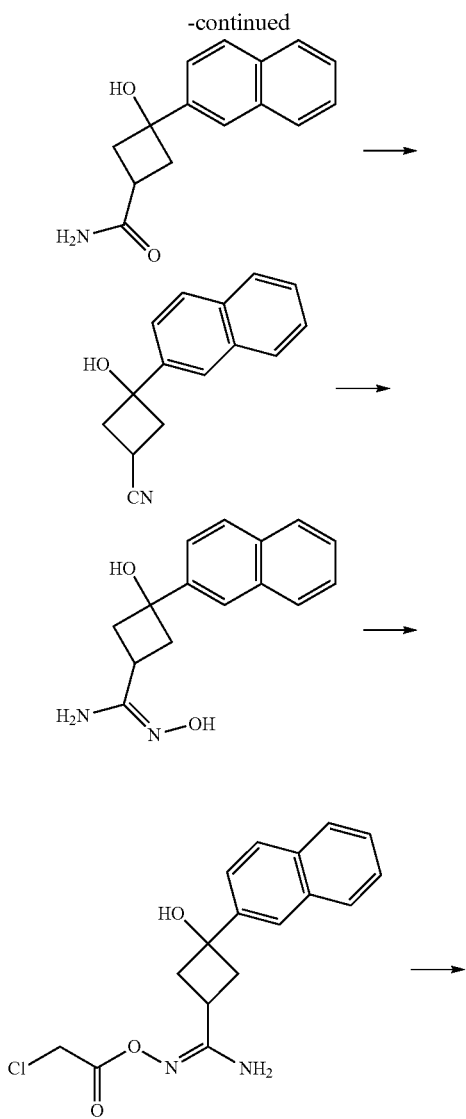

326

Step 1: Preparation of ethyl 3-hydroxy-3-(naphthalen-2-yl)cyclobutane-1-carboxylate

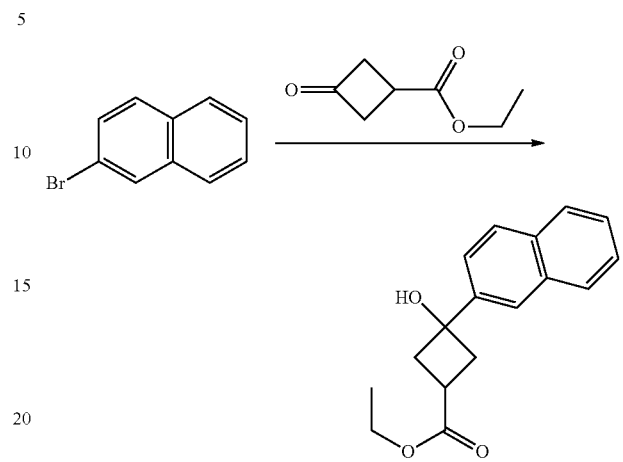

n-BuLi (23.3 mL, 247.35 mmol) was added dropwise to a solution of 2-bromonaphthalene (10 g, 48.29 mmol) in THF (200 mL) at −78° C. under $N_2$. The reaction was stirred at −78° C. for 30 min. Then ethyl 3-oxocyclobutane-1-carboxylate (6.89 g, 48.46 mmol) was added to the solution at −78° C. The resulting solution was stirred for an additional 2 h at −78° C. The reaction was quenched with saturated $NH_4Cl$, extracted with ethyl acetate, washed with brine, dried over $MgSO_4$, and concentrated under vacuum. The crude product was adsorbed onto silica gel and purified by flash column chromatography eluted with ethyl acetate/petroleum ether (1:1). This resulted in the title compound (6 g, 46%) as clear oil.

Step 2: Preparation of 3-hydroxy-3-(naphthalen-2-yl)cyclobutane-1-carboxamide

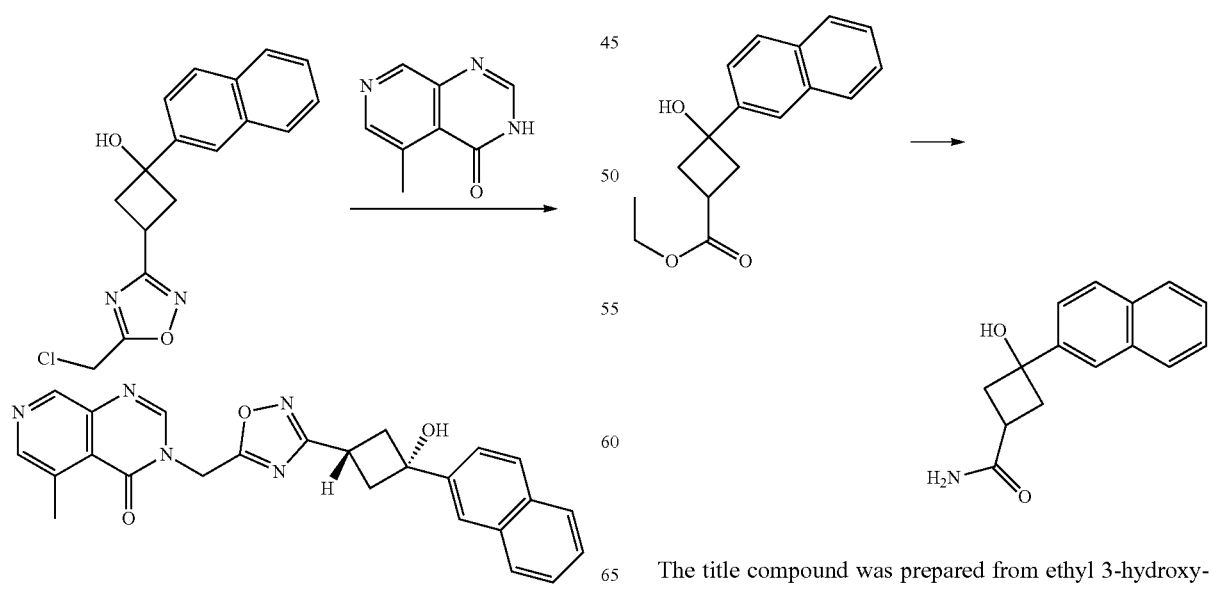

The title compound was prepared from ethyl 3-hydroxy-3-(naphthalen-2-yl) cyclobutane-1-carboxylate in a manner analogous to Example 64, Step 2.

327

Step 3: Preparation of 3-hydroxy-3-(naphthalen-2-yl)cyclobutane-1-carbonitrile

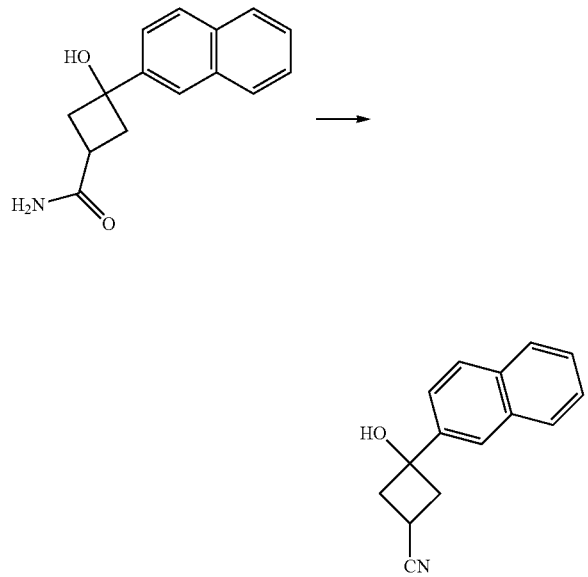

The title compound was prepared from 3-hydroxy-3-(naphthalen-2-yl) cyclobutane-1-carboxamide in a manner analogous to Example 64, Step 3.

Step 4: Preparation of N-dihydroxy-3-(naphthalen-2-yl)cyclobut-1-carboximidamide

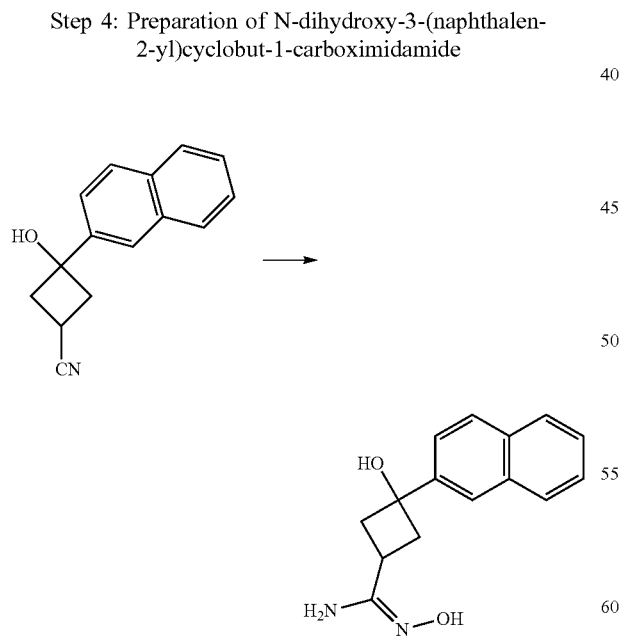

The title compound was prepared from 3-hydroxy-3-(naphthalen-2-yl) cyclobutane-1-carbonitrile in a manner analogous to Example 64, Step 4.

328

Step 5: Preparation of [amino[3-hydroxy-3-(naphthalen-2-yl)cyclobutyl]methylidene]amino 2-chloroacetate

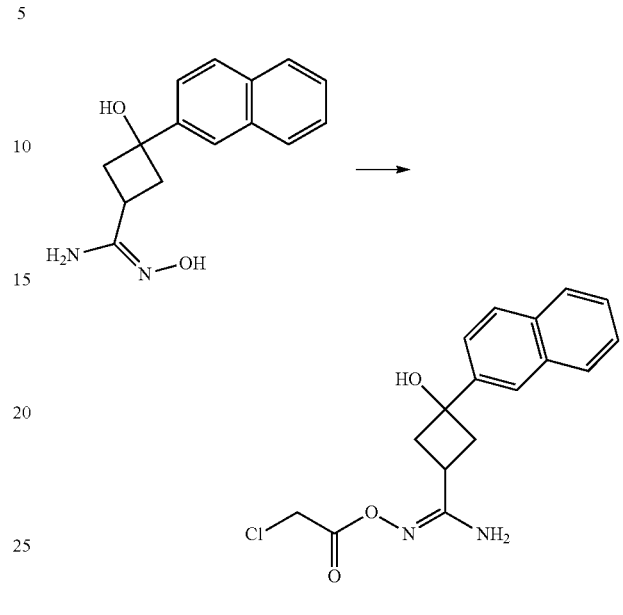

The title compound was prepared from N-dihydroxy-3-(naphthalen-2-yl) cyclobut-1-carboximidamide in a manner analogous to Example 64, Step 5.

Step 6: Preparation of 3-[5-(chloromethyl)-1,2,4-oxadiazol-3-yl]-1-(naphthalen-2-yl)cyclobutan-1-ol

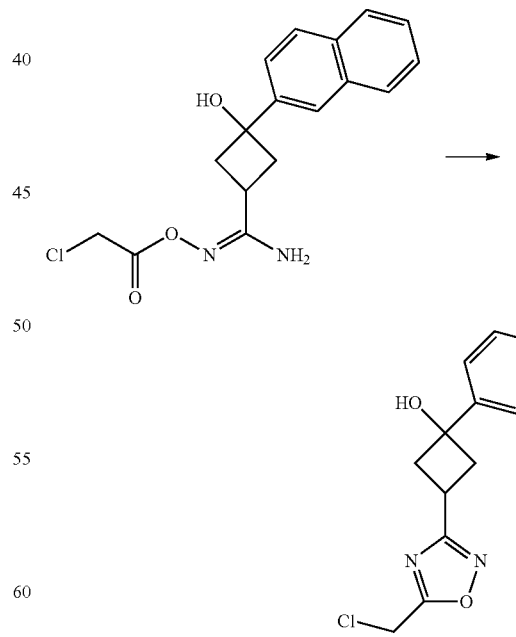

The title compound was prepared from [amino[3-hydroxy-3-(naphthalen-2-yl) cyclobutyl]methylidene]amino 2-chloroacetate in a manner analogous to Example 64, Step 6.

Step 7: Preparation of 3-((3-((1s,3s)-3-hydroxy-3-(naphthalen-2-yl)cyclobutyl)-1,2,4-oxadiazol-5-yl)methyl)-5-methylpyrido[3,4-d]pyrimidin-4(3H)-one (Example Compound 232)

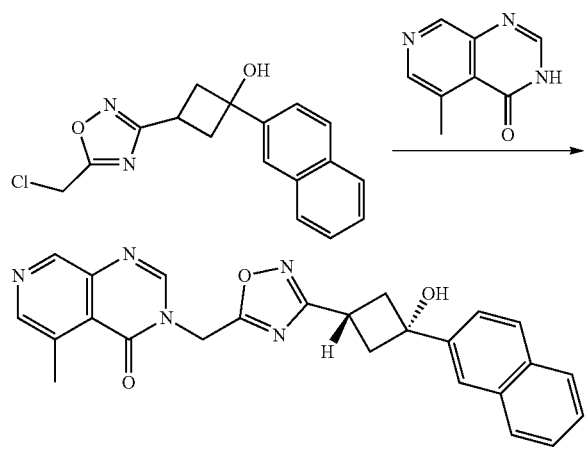

The title compound was prepared from 3-[5-(chloromethyl)-1,2,4-oxadiazol-3-yl]-1-(naphthalen-2-yl)cyclobutan-1-ol and 5-methylpyrido[3,4-d]pyrimidin-4(3H)-one in a manner analogous to Example 25, Step 5. LCMS [M+H$^+$] 440. $^1$H NMR (400 MHz, DMSO-d6) δ 8.94 (s, 1H), 8.66 (s, 1H), 8.54 (s, 1H), 8.08 (s, 1H), 7.99-7.87 (m, 3H), 7.72 (dd, J=8.6, 1.8 Hz, 1H), 7.56-7.45 (m, 2H), 5.93 (s, 1H), 5.56 (s, 2H), 3.28 (d, J=9.2 Hz, 1H), 2.99-2.89 (m, 2H), 2.71 (s, 3H), 2.68-2.63 (m, 2H).

Example 90: Preparation of 3-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile (Example compound 235)

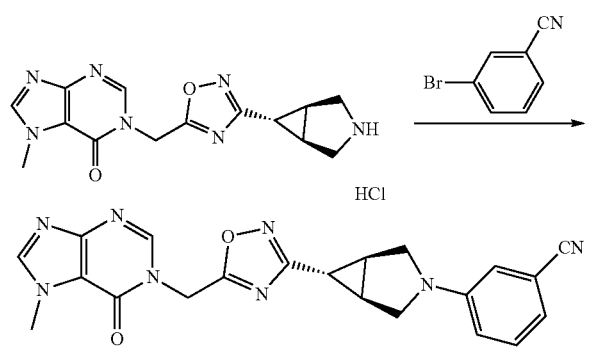

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 3-bromobenzonitrile (69.9 mg, 0.384 mmol) as a white solid (75.4 mg, 57% yield), in a manner analogous to Example 4, Step 8. LCMS [M+H$^+$] 415.2. $^1$H NMR (400 MHz, DMSO) δ 8.43 (s, 1H), 8.23 (s, 1H), 7.41-7.28 (m, 1H), 7.02 (d, J=7.6 Hz, 1H), 6.93 (s, 1H), 6.88 (dd, J=8.4, 2.1 Hz, 1H), 5.52 (s, 2H), 3.95 (s, 3H), 3.71 (d, J=10.0 Hz, 2H), 3.29 (s, 2H), 2.22 (s, 2H), 2.01 (t, J=3.3 Hz, 1H).

Example 91: Preparation of 1-((3-((1R,5S,6r)-3-(3-chloro-2-fluorophenyl)-3-azabicyclo[3.1.0]hexan-6-yl)-1,2,4-oxadiazol-5-yl)methyl)-7-methyl-1,7-dihydro-6H-purin-6-one (Example Compound 236)

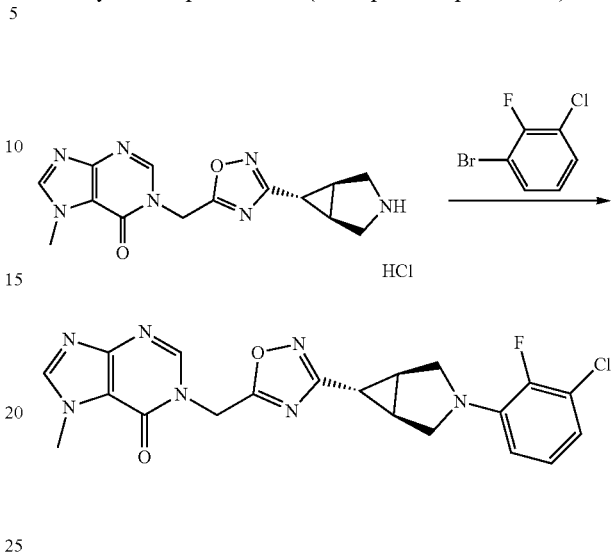

The title compound was prepared from 1-[[3-[(1R,5S)-3-azabicyclo[3.1.0]hexan-6-yl]-1,2,4-oxadiazol-5-yl]methyl]-7-methyl-purin-6-one hydrochloride (112 mg, 0.320 mmol) and 1-bromo-3-chloro-2-fluorobenzene (80.5 mg, 0.384 mmol) as a white solid (17.9 mg, 13% yield), in a manner analogous to Example 4, Step 8. LCMS [M+H$^+$] 442.1. $^1$H NMR (400 MHz, DMSO) δ 8.43 (s, 1H), 8.23 (s, 1H), 7.01 (td, J=8.2, 1.3 Hz, 1H), 6.87 (ddd, J=7.9, 6.3, 1.5 Hz, 1H), 6.73 (td, J=8.4, 1.6 Hz, 1H), 5.52 (s, 2H), 3.95 (s, 3H), 3.79 (dd, J=9.9, 3.0 Hz, 2H), 3.39 (d, J=9.6 Hz, 2H), 2.17 (td, J=2.8, 2.4, 1.2 Hz, 2H), 2.12 (t, J=3.2 Hz, 1H).

IC$_{50}$ Determinations of Exemplified Compounds

The IC$_{50}$ (effective concentration) of compounds on the human TRPA1 channel was determined using a FLIPR Tetra instrument. CHO cells expressing TRPA1 were plated into 384-well plates, incubated overnight at 37° C., and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 10 minutes or 90 minutes at room temperature prior to adding agonist. Following this incubation, about an EC$_{50}$ concentration of cinnamaldehyde (75) was added to active the channels and block of cinnamaldehyde induced calcium influx was measured.

The IC$_{50}$ results were fit with a standard Hill function, keeping the Hill coefficient (n) fixed to 1.5. Fixing the Hill coefficient will generally reduce variability of the IC$_{50}$ determination. The IC$_{50}$ results were individually examined to make sure the MIN and MAX points were set correctly prior to validation of the results.

The IC$_{50}$ (hTRPA1 IC$_{50}$ (micromolar)) results for compounds of the present disclosure are shown in Table 1 below where "hTRPA1" refers to hTRPA1 CHO Ca2+ MAX EVO (IC$_{50}$).

TABLE 1

| Ex. | Structure | Name | IC$_{50}$ (10 min) | IC$_{50}$ (90 min) |
|---|---|---|---|---|
| 1 | 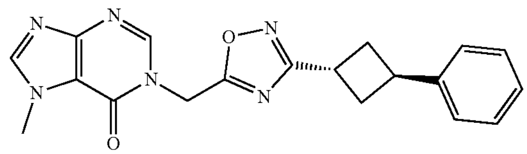 [SMILES: Cn1cnc2ncn(Cc3nc([C@H]4C[C@H](c5ccccc5)C4)no3)c(=O)c21] | 7-methyl-1-((3-((trans)-3-phenylcyclobutyl)-1,2,4-oxadiazol-5-yl)methyl)-1H-purin-6(7H)-one | 0.225 | — |
| 2 | 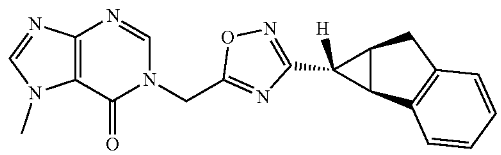 [SMILES: Cn1cnc2ncn(Cc3nc([C@@H]4[C@H]5Cc6ccccc6[C@H]54)no3)c(=O)c21] | 7-methyl-1-[[3-[rac-(1R,1aR,6aS)-1,1a,6,6a-tetrahydrocyclopropa[a]inden-1-yl]-1,2,4-oxadiazol-5-yl]methyl]purin-6-one | 0.277 | — |
| 3 | 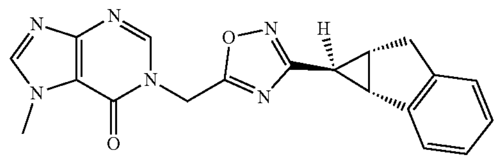 [SMILES: Cn1cnc2ncn(Cc3nc([C@H]4[C@@H]5Cc6ccccc6[C@@H]54)no3)c(=O)c21] | 7-methyl-1-[[3-[rac-(1S,1aS,6aR)-1,1a,6,6a-tetrahydrocyclopropa[a]inden-1-yl]-1,2,4-oxadiazol-5-yl]methyl]purin-6-one | 0.588 | — |
| 4 | 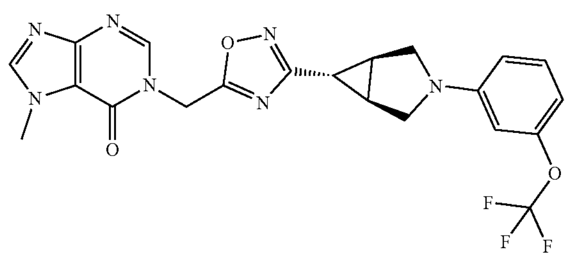 [SMILES: Cn1cnc2ncn(Cc3nc([C@H]4[C@@H]5CN(c6cccc(OC(F)(F)F)c6)C[C@@H]54)no3)c(=O)c21] | 7-methyl-1-[[3-[(1R,5S,6r)-3-(3-trifluoromethoxy)phenyl-3-azabicyclo[3.1.0]hexan-6-yl]-1,2,4-oxadiazol-5-yl]methyl]purin-6-one | 0.119 | — |
| 5 | 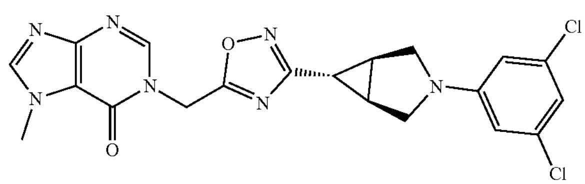 [SMILES: Cn1cnc2ncn(Cc3nc([C@H]4[C@@H]5CN(c6cc(Cl)cc(Cl)c6)C[C@@H]54)no3)c(=O)c21] | 7-methyl-1-[[3-[(1R,5S,6r)-3-(3,5-dichlorophenyl)-3-azabicyclo[3.1.0]hexan-6-yl]-1,2,4-oxadiazol-5-yl]methyl]purin-6-one | 0.272 | — |
| 6 | 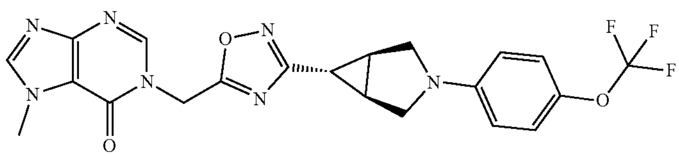 [SMILES: Cn1cnc2ncn(Cc3nc([C@H]4[C@@H]5CN(c6ccc(OC(F)(F)F)cc6)C[C@@H]54)no3)c(=O)c21] | 7-methyl-1-[[3-[(1R,5S,6 r)-3-[4-(trifluoromethoxy)phenyl]-3-azabicyclo[3.1.0]hexan-6-yl]-1,2,4-oxadiazol-5-yl]methyl]purin-6-one | 0.0424 | — |
| 7 | 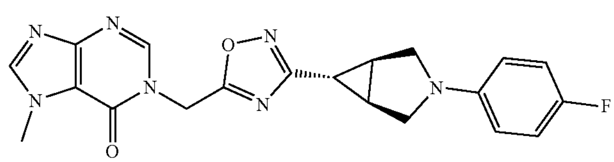 [SMILES: Cn1cnc2ncn(Cc3nc([C@H]4[C@@H]5CN(c6ccc(F)cc6)C[C@@H]54)no3)c(=O)c21] | 7-methyl-1-[[3-[(1R,5S,6 r)-3-(4-fluorophenyl)-3-azabicyclo[3.1.0]hexan-6-yl]-1,2,4-oxadiazol-5-yl]methyl]purin-6-one | 0.031 | — |
| 8 | 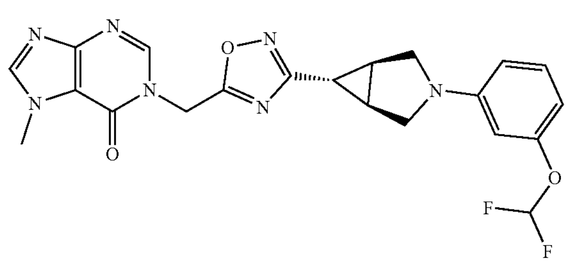 [SMILES: Cn1cnc2ncn(Cc3nc([C@H]4[C@@H]5CN(c6cccc(OC(F)F)c6)C[C@@H]54)no3)c(=O)c21] | 7-methyl-1-[[3-[(1R,5S,6 r)-3-[3-(difluoromethoxy)phenyl]-3-azabicyclo[3.1.0]hexan-6-yl]-1,2,4-oxadiazol-5-yl]methyl]purin-6-one | 0.105 | — |

TABLE 1-continued

| Ex. | Structure | Name | IC$_{50}$ (10 min) | IC$_{50}$ (90 min) |
|---|---|---|---|---|
| 9 | 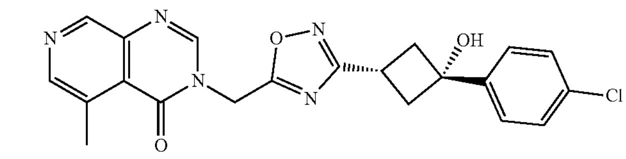 [SMILES: Cc1cncc2ncn(Cc3nc([C@H]4C[C@](O)(c5ccc(Cl)cc5)C4)no3)c(=O)c12] | 3-((3-((1s,3s)-3-(4-chlorophenyl)-3-hydroxycyclobutyl)-1,2,4-oxadiazol-5-yl)methyl)-5-methylpyrido[3,4-d]pyrimidin-4(3H)-one | 0.0309 | — |
| 10 | 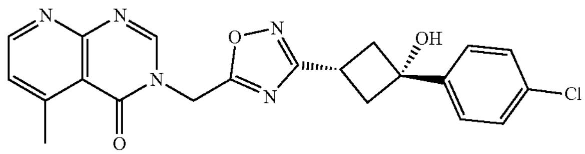 [SMILES: Cc1ccnc2ncn(Cc3nc([C@H]4C[C@](O)(c5ccc(Cl)cc5)C4)no3)c(=O)c12] | 3-((3-((1s,3s)-3-(4-chlorophenyl)-3-hydroxycyclobutyl)-1,2,4-oxadiazol-5-yl)methyl)-5-methylpyrido[2,3-d]pyrimidin-4(3H)-one | 0.141 | — |
| 11 | 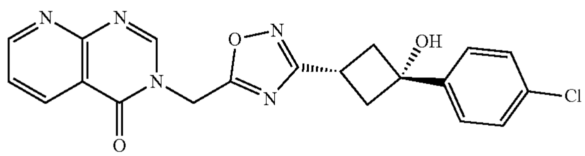 [SMILES: O=c1c2cccnc2ncn1Cc1nc([C@H]2C[C@](O)(c3ccc(Cl)cc3)C2)no1] | 3-((3-((1s,3s)-3-(4-chlorophenyl)-3-hydroxycyclobutyl)-1,2,4-oxadiazol-5-yl)methyl)pyrido[2,3-d]pyrimidin-4(3H)-one | 0.261 | — |
| 12 | 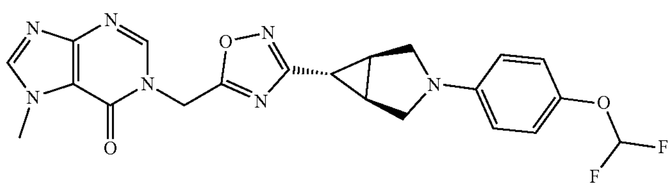 [SMILES: Cn1cnc2ncn(Cc3nc([C@H]4[C@@H]5CN(c6ccc(OC(F)F)cc6)C[C@@H]54)no3)c(=O)c21] | 7-methyl-1-[[3-[(1R,5S,6 r)-3-[4-(difluoromethoxy)phenyl]-3-azabicyclo[3.1.0]hexan-6-yl]-1,2,4-oxadiazol-5-yl]methyl]purin-6-one | 0.0504 | — |
| 13 | 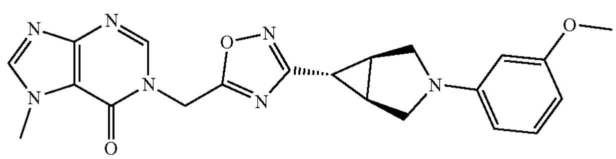 [SMILES: COc1cccc(N2C[C@@H]3[C@H](C2)[C@H]3c2noc(Cn3cnc4ncn(C)c4c3=O)n2)c1] | 7-methyl-1-[[3-[(1R,5S,6 r)-3-(3-methoxyphenyl)-3-azabicyclo[3.1.0]hexan-6-yl]-1,2,4-oxadiazol-5-yl]methyl]purin-6-one | 0.158 | — |
| 14 | 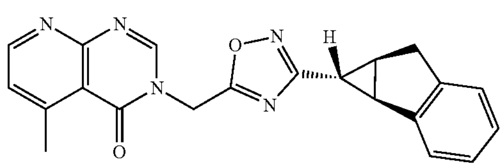 [SMILES: Cc1ccnc2ncn(Cc3nc([C@@H]4[C@H]5Cc6ccccc6[C@H]54)no3)c(=O)c12] | 5-methyl-3-[[3-[rac-(1R,1aR,6aS)-1,1a,6,6a-tetrahydrocyclopropa[a]inden-1-yl]-1,2,4-oxadiazol-5-yl]methyl]pyrido[2,3-d]pyrimidin-4-one | 0.119 | — |
| 15 | 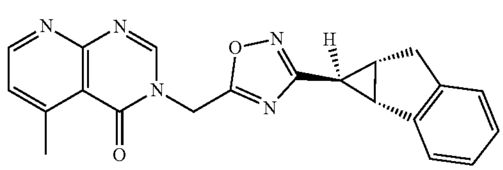 [SMILES: Cc1ccnc2ncn(Cc3nc([C@H]4[C@@H]5Cc6ccccc6[C@@H]54)no3)c(=O)c12] | 5-methyl-3-[[3-[rac-(1S,1aS,6aR)-1,1a,6,6a-tetrahydrocyclopropa[a]inden-1-yl]-1,2,4-oxadiazol-5-yl]methyl]pyrido[2,3-d]pyrimidin-4-one | 0.305 | — |
| 16 | 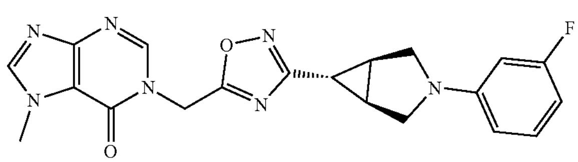 [SMILES: Cn1cnc2ncn(Cc3nc([C@H]4[C@@H]5CN(c6cccc(F)c6)C[C@@H]54)no3)c(=O)c21] | 7-methyl-1-[[3-[(1R,5S,6 r)-3-(3-fluorophenyl)-3-azabicyclo[3.1.0]hexan-6-yl]-1,2,4-oxadiazol-5-yl]methyl]purin-6-one | 0.0558 | — |
| 17 | 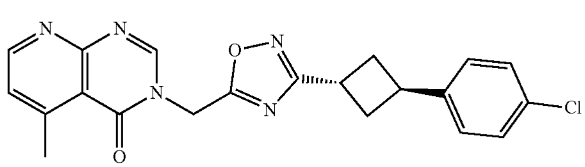 [SMILES: Cc1ccnc2ncn(Cc3nc([C@H]4C[C@H](c5ccc(Cl)cc5)C4)no3)c(=O)c12] | 3-((3-((trans)-3-(4-chlorophenyl)cyclobutyl)-1,2,4-oxadiazol-5-yl)methyl)-5-methylpyrido[2,3-d]pyrimidin-4(3H)-one d]pyrimidin-4-one | 0.0213 | — |

TABLE 1-continued

| Ex. | Structure | Name | IC$_{50}$ (10 min) | IC$_{50}$ (90 min) |
|---|---|---|---|---|
| 18 | 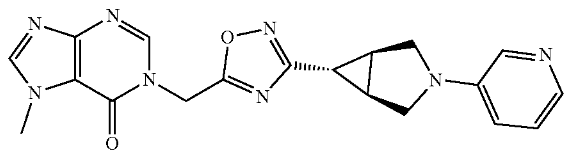 [SMILES: Cn1cnc2ncn(Cc3nc([C@H]4[C@@H]5CN(c6cccnc6)C[C@@H]54)no3)c(=O)c21] | 7-methyl-1-[[3-[(1R, 5S,6r)-3-(3-pyridyl)-3-azabicyclo[3.1.0]hexan-6-yl]-1,2,4-oxadiazol-5-yl]methyl]purin-6-one | 0.778 | — |
| 19 | 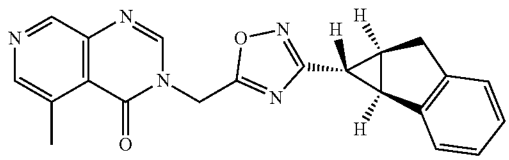 [SMILES: Cc1cncc2ncn(Cc3nc([C@@H]4[C@H]5Cc6ccccc6[C@H]54)no3)c(=O)c12] | 5-methyl-3-[[3-[rac-(1R,1aR,6aS)-1,1a,6,6a-tetrahydrocyclopropa[a]inden-1-yl]-1,2,4-oxadiazol-5-yl]methyl]pyrido[3,4-d]pyrimidin-4-one | 0.0299 | — |
| 20 | 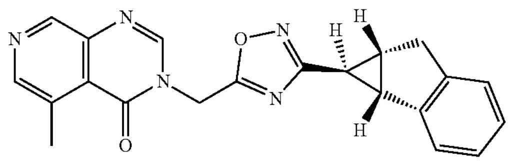 | 5-methyl-3-[[3-[rac-(1S,1aS,6aR)-1,1a,6,6a-tetrahydrocyclopropa[a]inden-1-yl]-1,2,4-oxadiazol-5-yl]methyl]pyrido[3,4-d]pyrimidin-4-one | 0.0943 | — |
| 21 | 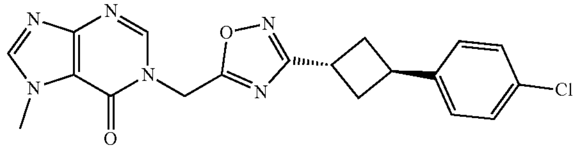 [SMILES: Cn1cnc2ncn(Cc3nc([C@H]4C[C@H](c5ccc(Cl)cc5)C4)no3)c(=O)c21] | 1-((3-((trans)-3-(4-chlorophenyl)cyclobutyl)-1,2,4-oxadiazol-5-yl)methyl)-7-methyl-1H-purin-6(7H)-one | 0.0705 | — |
| 22 | 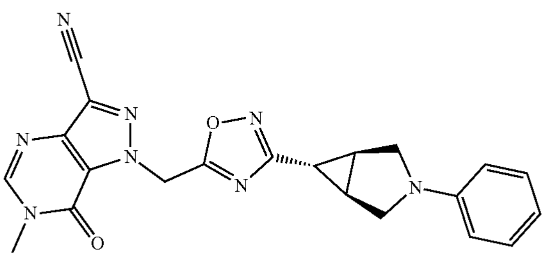 [SMILES: Cn1cnc2c(C#N)nn(Cc3nc([C@H]4[C@@H]5CN(c6ccccc6)C[C@@H]54)no3)c2c1=O] | 6-methyl-7-oxo-1-[[3-[(1R,5S,6s)-3-phenyl-3-azabicyclo[3.1.0]hexan-6-yl]-1,2,4-oxadiazol-5-yl]methyl]pyrazolo[4,3-d]pyrimidine-3-carbonitrile | 0.352 | — |
| 23 | 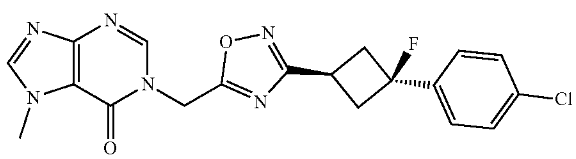 [SMILES: Cn1cnc2ncn(Cc3nc([C@H]4C[C@](F)(c5ccc(Cl)cc5)C4)no3)c(=O)c21] | 1-((3-((1s,3s)-3-(4-chlorophenyl)-3-fluorocyclobutyl)-1,2,4-oxadiazol-5-yl)methyl)-7-methyl-1H-purin-6(7H)-one | 0.0886 | — |
| 24 | 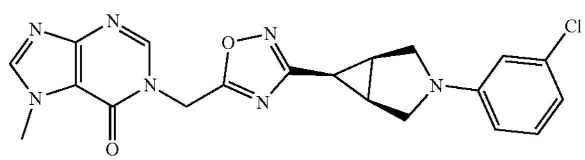 [SMILES: Cn1cnc2ncn(Cc3nc([C@@H]4[C@@H]5CN(c6cccc(Cl)c6)C[C@@H]54)no3)c(=O)c21] | 7-methyl-1-[[3-[(1R,5S,6 r)-3-(3-chlorophenyl)-3-azabicyclo[3.1.0]hexan-6-yl]-1,2,4-oxadiazol-5-yl]methyl]purin-6-one | 0.00838 | — |
| 25 | 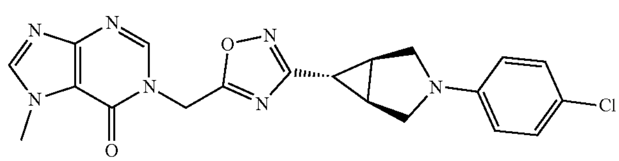 [SMILES: Cn1cnc2ncn(Cc3nc([C@H]4[C@@H]5CN(c6ccc(Cl)cc6)C[C@@H]54)no3)c(=O)c21] | 7-methyl-1-[[3-[(1R,5S,6 r)-3-(4-chlorophenyl)-3-azabicyclo[3.1.0]hexan-6-yl]-1,2,4-oxadiazol-5-yl]methyl]purin-6-one | 0.0204 | — |

TABLE 1-continued

| Ex. | Structure | Name | IC$_{50}$ (10 min) | IC$_{50}$ (90 min) |
|---|---|---|---|---|
| 26 | 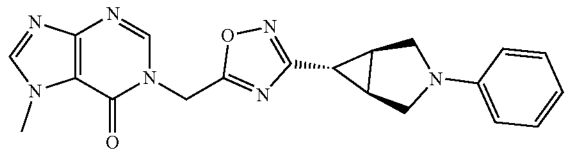 [SMILES: Cn1cnc2ncn(Cc3nc([C@H]4[C@@H]5CN(c6ccccc6)C[C@@H]54)no3)c(=O)c21] | 7-methyl-1-[[3-[(1R,5S,6 r)-3-phenyl-3-azabicyclo[3.1.0]hexan-6-yl]-1,2,4-oxadiazol-5-yl]methyl]purin-6-one | 0.0287 | — |
| 27 | 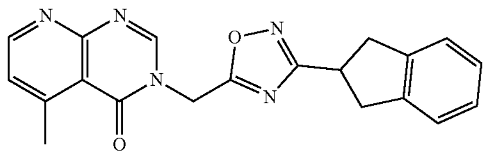 [SMILES: Cc1ccnc2ncn(Cc3nc(C4Cc5ccccc5C4)no3)c(=O)c12] | 3-((3-(2,3-dihydro-1H-inden-2-yl)-1,2,4-oxadiazol-5-yl)methyl)-5-methylpyrido[2,3-d]pyrimidin-4(3H)-one | 0.531 | — |
| 28 | 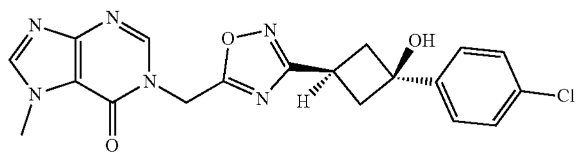 [SMILES: Cn1cnc2ncn(Cc3nc([C@H]4C[C@](O)(c5ccc(Cl)cc5)C4)no3)c(=O)c21] | 1-((3-((1s,3s)-3-(4-chlorophenyl)-3-hydroxycyclobutyl)-1,2,4-oxadiazol-5-yl)methyl)-7-methyl-1H-purin-6(7H)-one | 0.643 | — |
| 29 | 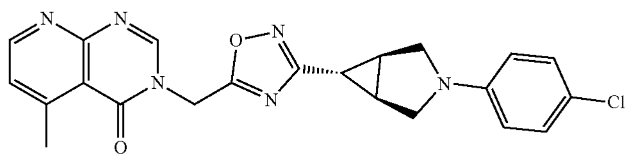 [SMILES: Cc1ccnc2ncn(Cc3nc([C@H]4[C@@H]5CN(c6ccc(Cl)cc6)C[C@@H]54)no3)c(=O)c12] | 5-methyl-3-[[3-[(1R,5S,6r)-3-(4-chlorophenyl)-3-azabicyclo[3.1.0]hexan-6-yl]-1,2,4-oxadiazol-5-yl]methyl]pyrido[2,3-d]pyrimidin-4-one | 0.290 | — |
| 30 | 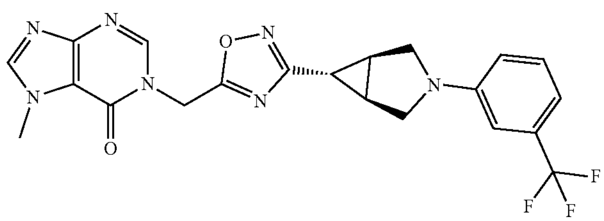 [SMILES: Cn1cnc2ncn(Cc3nc([C@H]4[C@@H]5CN(c6cccc(C(F)(F)F)c6)C[C@@H]54)no3)c(=O)c21] | 7-methyl-1-[[3-[(1R,5S,6r)-3-[3-(trifluoromethyl)phenyl]-3-azabicyclo[3.1.0]hexan-6-yl]-1,2,4-oxadiazol-5-yl]methyl]purin-6-one | 0.0527 | — |
| 31 | 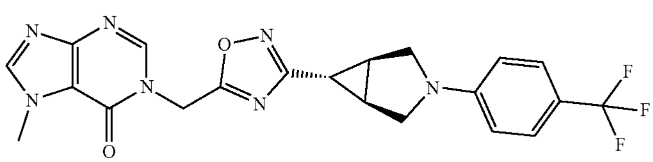 [SMILES: Cn1cnc2ncn(Cc3nc([C@H]4[C@@H]5CN(c6ccc(C(F)(F)F)cc6)C[C@@H]54)no3)c(=O)c21] | 7-methyl-1-[[3-[(1R,5S,6r)-3-[4-(trifluoromethyl)phenyl]-3-azabicyclo[3.1.0]hexan-6-yl]-1,2,4-oxadiazol-5-yl]methyl]purin-6-one | 0.0971 | — |
| 32 | 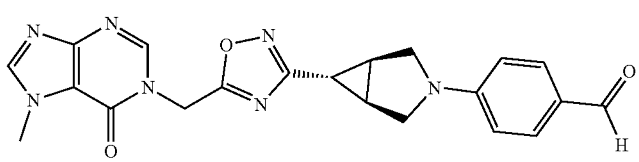 [SMILES: Cn1cnc2ncn(Cc3nc([C@H]4[C@@H]5CN(c6ccc(C=O)cc6)C[C@@H]54)no3)c(=O)c21] | 4-[(1R,5S,6r)-6-[5-[(7-methyl-6-oxo-purin-1-yl)methyl]-1,2,4-oxadiazol-3-yl]-3-azabicyclo[3.1.0]hexan-3-yl]benzaldehyde | 0.0549 | — |
| 33 | 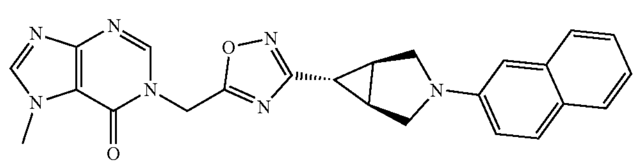 [SMILES: Cn1cnc2ncn(Cc3nc([C@H]4[C@@H]5CN(c6ccc7ccccc7c6)C[C@@H]54)no3)c(=O)c21] | 7-methyl-1-[[3-[(1R,5S,6r)-3-[2-naphthyl]-3-azabicyclo[3.1.0]hexan-6-yl]-1,2,4-oxadiazol-5-yl]methyl]purin-6-one | 0.00731 | — |
| 34 | 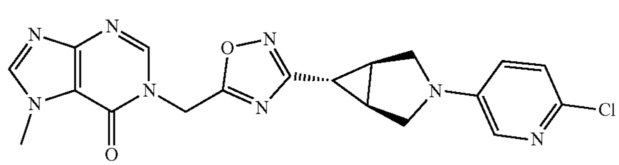 [SMILES: Cn1cnc2ncn(Cc3nc([C@H]4[C@@H]5CN(c6ccc(Cl)nc6)C[C@@H]54)no3)c(=O)c21] | 7-methyl-1-[[3-[(1R,5S,6r)-3-[6-chloro-3-pyridyl]-3-azabicyclo[3.1.0]hexan-6-yl]-1,2,4-oxadiazol-5-yl]methyl]purin-6-one | 0.464 | — |

TABLE 1-continued

| Ex. | Structure | Name | IC$_{50}$ (10 min) | IC$_{50}$ (90 min) |
|---|---|---|---|---|
| 35 | 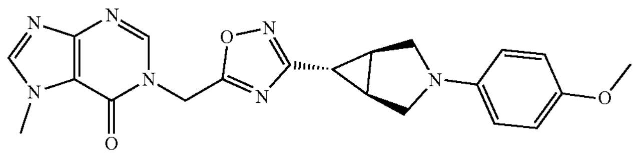 [SMILES: COc1ccc(N2C[C@@H]3[C@H](C2)[C@H]3c2noc(Cn3cnc4ncn(C)c4c3=O)n2)cc1] | 7-methyl-1-[[3-[(1R,5S,6r)-3-[4-methoxyphenyl]-3-azabicyclo[3.1.0]hexan-6-yl]-1,2,4-oxadiazol-5-yl]methyl]purin-6-one | 0.048 | — |
| 36 | 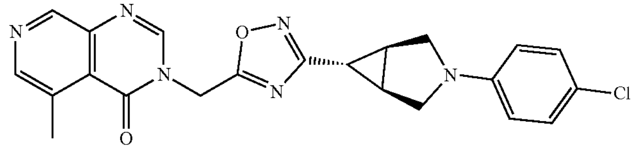 [SMILES: Cc1cncc2ncn(Cc3nc([C@H]4[C@@H]5CN(c6ccc(Cl)cc6)C[C@@H]54)no3)c(=O)c12] | 5-methyl-3-[[3-[(1R,5S,6r)-3-(4-chlorophenyl)-3-azabicyclo[3.1.0]hexan-6-yl]-1,2,4-oxadiazol-5-yl]methyl]pyrido[3,4-d]pyrimidin-4-one | 0.0714 | — |
| 37 | 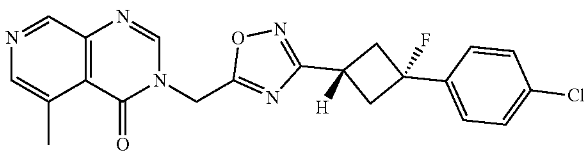 [SMILES: Cc1cncc2ncn(Cc3nc([C@H]4C[C@](F)(c5ccc(Cl)cc5)C4)no3)c(=O)c12] | 3-((3-((1s,3s)-3-(4-chlorophenyl)-3-fluorocyclobutyl)-1,2,4-oxadiazol-5-yl)methyl)-5-methylpyrido[3,4-d]pyrimidin-4(3H)-one | 0.0228 | — |
| 38 | 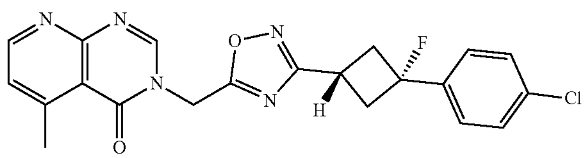 [SMILES: Cc1ccnc2ncn(Cc3nc([C@H]4C[C@](F)(c5ccc(Cl)cc5)C4)no3)c(=O)c12] | 3-((3-((1s,3s)-3-(4-chlorophenyl)-3-fluorocyclobutyl)-1,2,4-oxadiazol-5-yl)methyl)-5-methylpyrido[2,3-d]pyrimidin-4(3H)-one | 0.0289 | — |
| 39 | 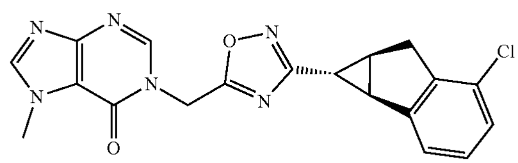 [SMILES: Cn1cnc2ncn(Cc3nc([C@@H]4[C@H]5Cc6c(Cl)cccc6[C@H]54)no3)c(=O)c21] | 7-methyl-1-[[3-[(1R,1aR,6aS)-5-chloro-1,1a,6,6a-tetrahydrocyclopropa[a]inden-1-yl]-1,2,4-oxadiazol-5-yl]methyl]purin-6-one | 0.0363 | — |
| 40 | 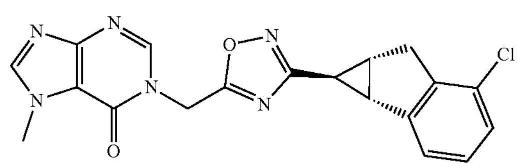 [SMILES: Cn1cnc2ncn(Cc3nc([C@H]4[C@@H]5Cc6c(Cl)cccc6[C@@H]54)no3)c(=O)c21] | 7-methyl-1-[[3-[(1S,1aS,6aR)-5-chloro-1,1a,6,6a-tetrahydrocyclopropa[a]inden-1-yl]-1,2,4-oxadiazol-5-yl]methyl]purin-6-one | 0.143 | — |
| 41 | 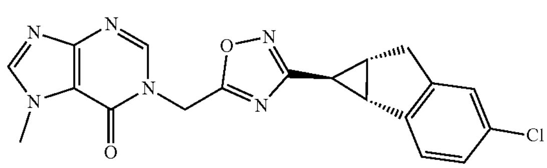 [SMILES: Cn1cnc2ncn(Cc3nc([C@H]4[C@@H]5Cc6cc(Cl)ccc6[C@@H]54)no3)c(=O)c21] | 7-methyl-1-[[3-[(1S,1aS,6aR)-4-chloro-1,1a,6,6a-tetrahydrocyclopropa[a]inden-1-yl]-1,2,4-oxadiazol-5-yl]methyl]purin-6-one | 0.377 | — |
| 42 | 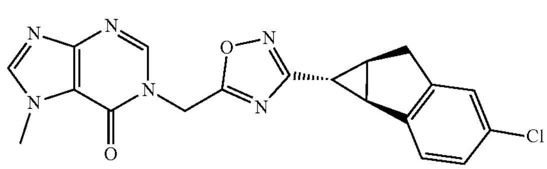 [SMILES: Cn1cnc2ncn(Cc3nc([C@@H]4[C@H]5Cc6cc(Cl)ccc6[C@H]54)no3)c(=O)c21] | 7-methyl-1-[[3-[(1R,1aR,6aS)-4-chloro-1,1a,6,6a-tetrahydrocyclopropa[a]inden-1-yl]-1,2,4-oxadiazol-5-yl]methyl]purin-6-one | 0.0737 | — |
| 43 | 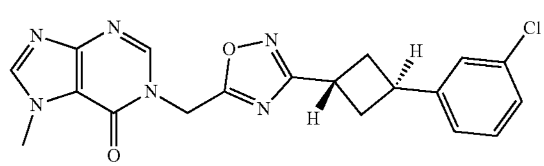 [SMILES: Cn1cnc2ncn(Cc3nc([C@H]4C[C@H](c5cccc(Cl)c5)C4)no3)c(=O)c21] | 1-((3-((1r,3r)-3-(3-chlorophenyl)cyclobutyl)-1,2,4-oxadiazol-5-yl)methyl)-7-methyl-1,7-dihydro-6H-purin-6-one | 0.0311 | — |

TABLE 1-continued

| Ex. | Structure | Name | IC$_{50}$ (10 min) | IC$_{50}$ (90 min) |
|---|---|---|---|---|
| 44 | 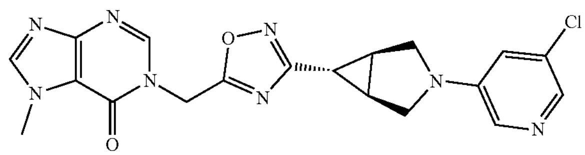 [SMILES: Cn1cnc2ncn(Cc3nc([C@H]4[C@@H]5CN(c6cncc(Cl)c6)C[C@@H]54)no3)c(=O)c21] | 7-methyl-1-[[3-[(1R,5S,6r)-3-(5-chloro-3-pyridyl)-3-azabicyclo[3.1.0]hexan-6-yl]-1,2,4-oxadiazol-5-yl]methyl]purin-6-one | 0.287 | — |
| 45 | 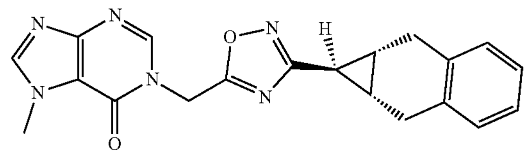 [SMILES: Cn1cnc2ncn(Cc3nc([C@H]4[C@@H]5Cc6ccccc6C[C@@H]54)no3)c(=O)c21] | 7-methyl-1-((3-((1r,1aR,7aS)-1a,2,7,7a-tetrahydro-1H-cyclopropa[b]naphthalen-1-yl)-1,2,4-oxadiazol-5-yl)methyl)-1,7-dihydro-6H-purin-6-one | 0.0766 | — |
| 46 | 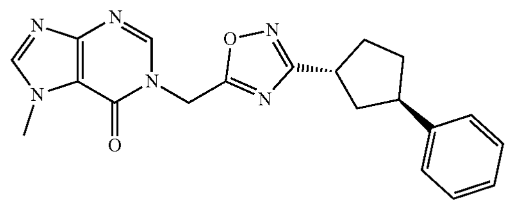 [SMILES: Cn1cnc2ncn(Cc3nc([C@@H]4CC[C@@H](c5ccccc5)C4)no3)c(=O)c21] | 7-methyl-1-[[3-[(1R,3R)-3-phenylcyclopentyl]-1,2,4-oxadiazol-5-yl]methyl]purin-6-one | 0.149 | — |
| 47 | 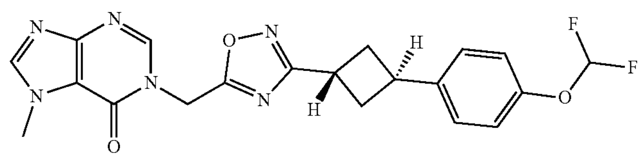 [SMILES: Cn1cnc2ncn(Cc3nc([C@H]4C[C@H](c5ccc(OC(F)F)cc5)C4)no3)c(=O)c21] | 1-((3-((1r,3r)-3-(4-(difluoromethoxy)phenyl)cyclobutyl)-1,2,4-oxadiazol-5-yl)methyl)-7-methyl-1,7-dihydro-6H-purin-6-one | 0.142 | — |
| 48 | 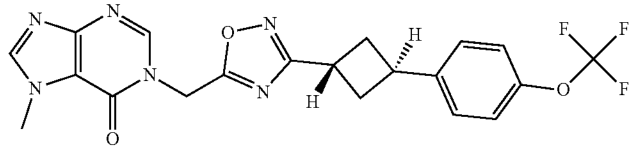 [SMILES: Cn1cnc2ncn(Cc3nc([C@H]4C[C@H](c5ccc(OC(F)(F)F)cc5)C4)no3)c(=O)c21] | 7-methyl-1-((3-((1r,3r)-3-(4-(trifluoromethoxy)phenyl)cyclobutyl)-1,2,4-oxadiazol-5-yl)methyl)-1,7-dihydro-6H-purin-6-one | 0.196 | — |
| 49 | 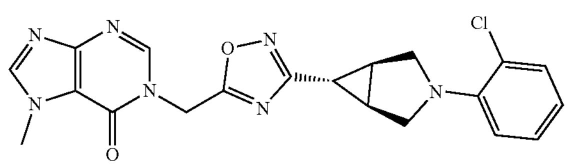 | 7-methyl-1-[[3-[(1R,5S,6r)-3-(2-chlorophenyl)-3-azabicyclo[3.1.0]hexan-6-yl]-1,2,4-oxadiazol-5-yl]methyl]purin-6-one | 0.0773 | — |
| 50 | 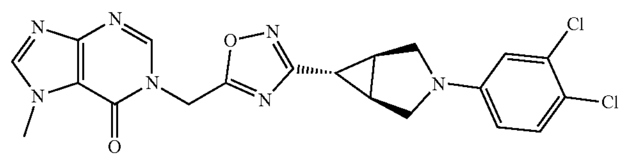 [SMILES: Cn1cnc2ncn(Cc3nc([C@H]4[C@@H]5CN(c6ccc(Cl)c(Cl)c6)C[C@@H]54)no3)c(=O)c21] | 7-methyl-1-[[3-[(1R,5S,6r)-3-(3,4-dichlorophenyl)-3-azabicyclo[3.1.0]hexan-6-yl]-1,2,4-oxadiazol-5-yl]methyl]purin-6-one | 0.0643 | — |
| 51 | 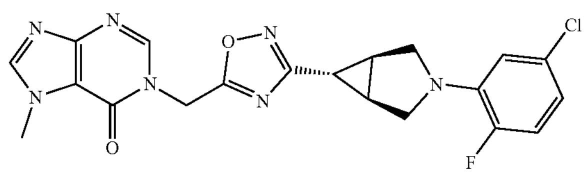 [SMILES: Cn1cnc2ncn(Cc3nc([C@H]4[C@@H]5CN(c6cc(Cl)ccc6F)C[C@@H]54)no3)c(=O)c21] | 7-methyl-1-[[3-[(1R,5S,6r)-3-(5-chloro-2-fluorophenyl)-3-azabicyclo[3.1.0]hexan-6-yl]-1,2,4-oxadiazol-5-yl]methyl]purin-6-one | 0.0125 | — |

TABLE 1-continued

| Ex. | Structure | Name | IC$_{50}$ (10 min) | IC$_{50}$ (90 min) |
|---|---|---|---|---|
| 52 | 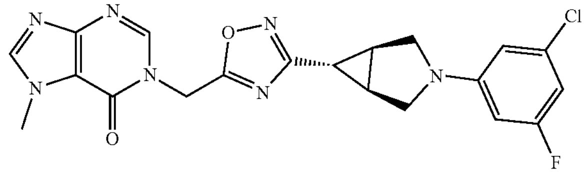 [SMILES: Cn1cnc2ncn(Cc3nc([C@H]4[C@@H]5CN(c6cc(F)cc(Cl)c6)C[C@@H]54)no3)c(=O)c21] | 7-methyl-1-[[3-[(1R,5S,6r)-3-(3-chloro-5-fluoro-phenyl)-3-azabicyclo[3.1.0]hexan-6-yl]-1,2,4-oxadiazol-5-yl]methyl]purin-6-one | 0.0205 | — |
| 53 | 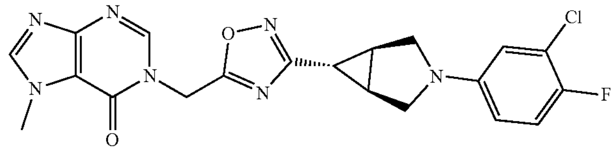 [SMILES: Cn1cnc2ncn(Cc3nc([C@H]4[C@@H]5CN(c6ccc(F)c(Cl)c6)C[C@@H]54)no3)c(=O)c21] | 7-methyl-1-[[3-[(1R,5S,6r)-3-(3-chloro-4-fluoro-phenyl)-3-azabicyclo[3.1.0]hexan-6-yl]-1,2,4-oxadiazol-5-yl]methyl]purin-6-one | 0.00978 | — |
| 54 | 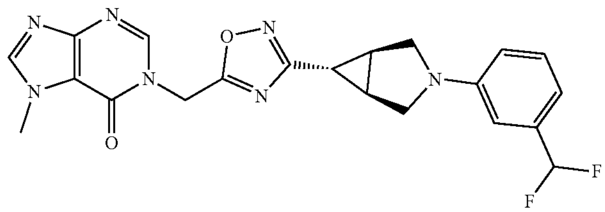 [SMILES: Cn1cnc2ncn(Cc3nc([C@H]4[C@@H]5CN(c6cccc(C(F)F)c6)C[C@@H]54)no3)c(=O)c21] | 7-methyl-1-[[3-[(1R,5S,6r)-3-[3-(difluoromethyl)phenyl]-3-azabicyclo[3.1.0]hexan-6-yl]-1,2,4-oxadiazol-5-yl]methyl]purin-6-one | 0.0644 | — |
| 55 | 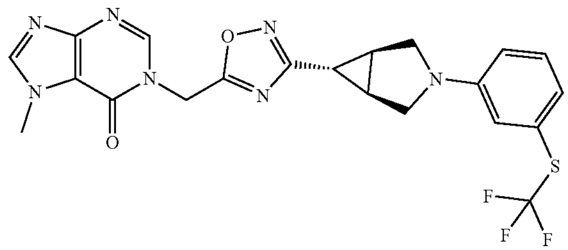 [SMILES: Cn1cnc2ncn(Cc3nc([C@H]4[C@@H]5CN(c6cccc(SC(F)(F)F)c6)C[C@@H]54)no3)c(=O)c21] | 7-methyl-1-[[3-[(1R,5S,6r)-3-[3-(trifluoromethylsulf-anyl)phenyl]-3-azabicyclo[3.1.0]hexan-6-yl]-1,2,4-oxadiazol-5-yl]methyl]purin-6-one | 0.300 | — |
| 56 | 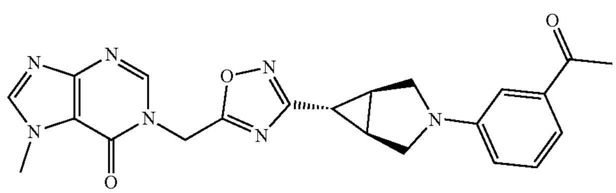 [SMILES: CC(=O)c1cccc(N2C[C@@H]3[C@H](C2)[C@H]3c2noc(Cn3cnc4ncn(C)c4c3=O)n2)c1] | 7-methyl-1-[[3-[(1R,5S,6r)-3-(3-acetylphenyl)-3-azabicyclo[3.1.0]hexan-6-yl]-1,2,4-oxadiazol-5-yl]methyl]purin-6-one | 0.295 | — |
| 57 | 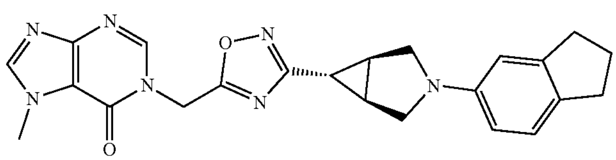 [SMILES: Cn1cnc2ncn(Cc3nc([C@H]4[C@@H]5CN(c6ccc7c(c6)CCC7)C[C@@H]54)no3)c(=O)c21] | 7-methyl-1-[[3-[(1R,5S,6r)-3-indan-5-yl-3-azabicyclo[3.1.0]hexan-6-yl]-1,2,4-oxadiazol-5-yl]methyl]purin-6-one | 0.111 | — |
| 58 | 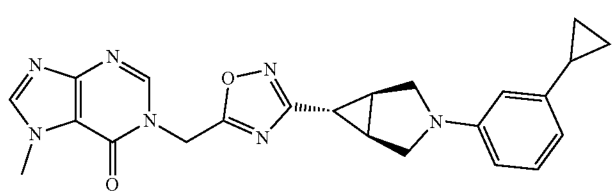 [SMILES: Cn1cnc2ncn(Cc3nc([C@H]4[C@@H]5CN(c6cccc(C7CC7)c6)C[C@@H]54)no3)c(=O)c21] | 7-methyl-1-[[3-[(1R,5S,6r)-3-(3-cyclopropylphenyl)-3-azabicyclo[3.1.0]hexan-6-yl]-1,2,4-oxadiazol-5-yl]methyl]purin-6-one | 0.112 | — |
| 59 | 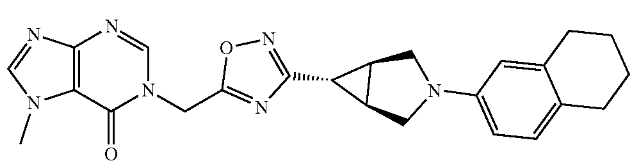 [SMILES: Cn1cnc2ncn(Cc3nc([C@H]4[C@@H]5CN(c6ccc7c(c6)CCCC7)C[C@@H]54)no3)c(=O)c21] | 7-methyl-1-[[3-[(1R,5S,6r)-3-tetralin-6-yl-3-azabicyclo[3.1.0]hexan-6-yl]-1,2,4-oxadiazol-5-yl]methyl]purin-6-one | 0.685 | — |

TABLE 1-continued

| Ex. | Structure | Name | IC$_{50}$ (10 min) | IC$_{50}$ (90 min) |
|---|---|---|---|---|
| 60 | 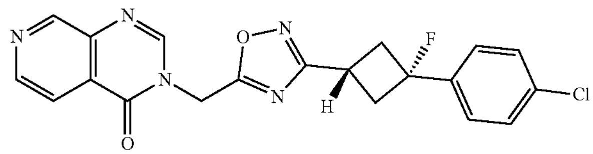 | 3-((3-((1s,3s)-3-(4-chlorophenyl)-3-fluorocyclobutyl)-1,2,4-oxadiazol-5-yl)methyl)pyrido[3,4-d]pyrimidin-4(3H)-one | 0.190 | — |
| 61 | 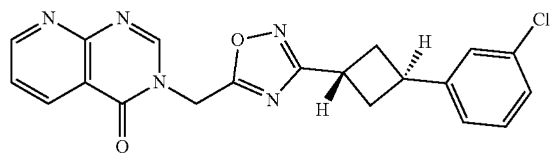 | 3-((3-((1r,3r)-3-(3-chlorophenyl)cyclobutyl)-1,2,4-oxadiazol-5-yl)methyl)pyrido[2,3-d]pyrimidin-4(3H)-one | 0.049 | — |
| 62 | 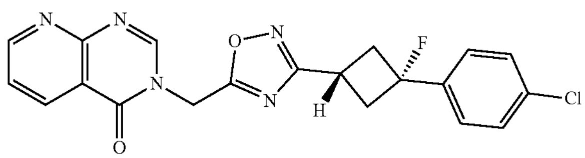 | 3-((3-((1s,3s)-3-(4-chlorophenyl)-3-fluorocyclobutyl)-1,2,4-oxadiazol-5-yl)methyl)pyrido[2,3-d]pyrimidin-4(3H)-one | 0.0202 | — |
| 63 | 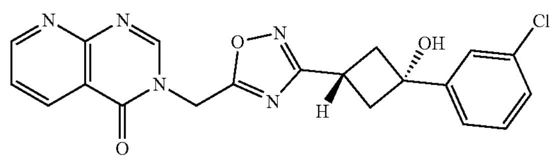 [SMILES: O=c1c2cccnc2ncn1Cc1nc([C@H]2C[C@](O)(c3cccc(Cl)c3)C2)no1] | 3-((3-((1s,3s)-3-(3-chlorophenyl)-3-hydroxycyclobutyl)-1,2,4-oxadiazol-5-yl)methyl)pyrido[2,3-d]pyrimidin-4(3H)-one | 0.281 | — |
| 65 | 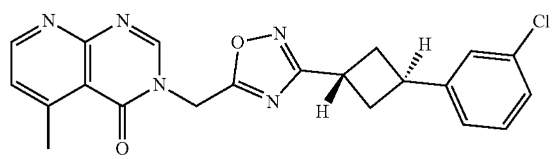 [SMILES: Cc1ccnc2ncn(Cc3nc([C@H]4C[C@H](c5cccc(Cl)c5)C4)no3)c(=O)c12] | 3-((3-((1r,3r)-3-(3-chlorophenyl)cyclobutyl)-1,2,4-oxadiazol-5-yl)methyl)-5-methylpyrido[2,3-d]pyrimidin-4(3H)-one | 0.0122 | — |
| 66 | 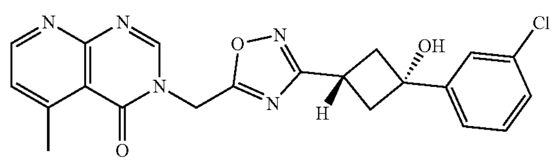 [SMILES: Cc1ccnc2ncn(Cc3nc([C@H]4C[C@](O)(c5cccc(Cl)c5)C4)no3)c(=O)c12] | 3-((3-((1s,3s)-3-(3-chlorophenyl)-3-hydroxycyclobutyl)-1,2,4-oxadiazol-5-yl)methyl)-5-methylpyrido[2,3-d]pyrimidin-4(3H)-one | 0.0578 | — |
| 68 | 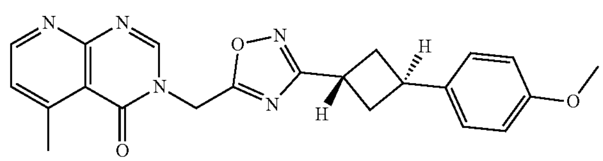 [SMILES: COc1ccc([C@H]2C[C@H](c3noc(Cn4cnc5nccc(C)c5c4=O)n3)C2)cc1] | 3-((3-((1r,3r)-3-(4-methoxyphenyl)cyclobutyl)-1,2,4-oxadiazol-5-yl)methyl)-5-methylpyrido[2,3-d]pyrimidin-4(3H)-one | 0.0387 | — |
| 69 | 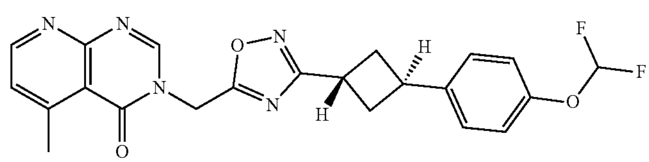 [SMILES: Cc1ccnc2ncn(Cc3nc([C@H]4C[C@H](c5ccc(OC(F)F)cc5)C4)no3)c(=O)c12] | 3-((3-((1r,3r)-3-(4-(difluoromethoxy)phenyl)cyclobutyl)-1,2,4-oxadiazol-5-yl)methyl)-5-methylpyrido[2,3-d]pyrimidin-4(3H)-one | 0.0513 | — |
| 70 | 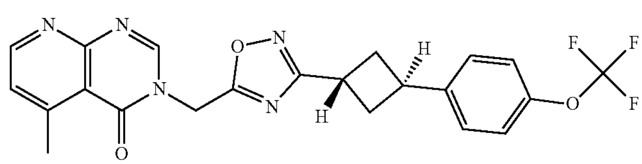 [SMILES: Cc1ccnc2ncn(Cc3nc([C@H]4C[C@H](c5ccc(OC(F)(F)F)cc5)C4)no3)c(=O)c12] | 5-methyl-3-((3-((1r,3r)-3-(4-(trifluoromethoxy)phenyl)cyclobutyl)-1,2,4-oxadiazol-5-yl)methyl)pyrido[2,3-d]pyrimidin-4(3H)-one | 0.0638 | — |

TABLE 1-continued

| Ex. | Structure | Name | IC$_{50}$ (10 min) | IC$_{50}$ (90 min) |
|---|---|---|---|---|
| 71 | 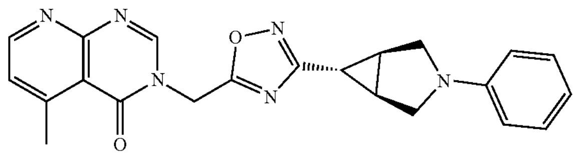 [SMILES: Cc1ccnc2ncn(Cc3nc([C@H]4[C@@H]5CN(c6ccccc6)C[C@@H]54)no3)c(=O)c12] | 5-methyl-3-[[3-[(1R,5S,6r)-3-phenyl-3-azabicyclo[3.1.0]hexan-6-yl]-1,2,4-oxadiazol-5-yl]methyl]pyrido[2,3-d]pyrimidin-R-one | 0.039 | — |
| 72 | 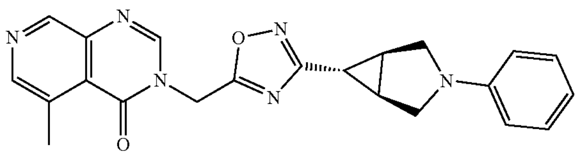 [SMILES: Cc1cncc2ncn(Cc3nc([C@H]4[C@@H]5CN(c6ccccc6)C[C@@H]54)no3)c(=O)c12] | 5-methyl-3-[[3-[(1R,5S,6r)-3-phenyl-3-azabicyclo[3.1.0]hexan-6-yl]-1,2,4-oxadiazol-5-yl]methyl]pyrido[3,4-d]pyrimidin-4-one | 0.0146 | — |
| 73 | 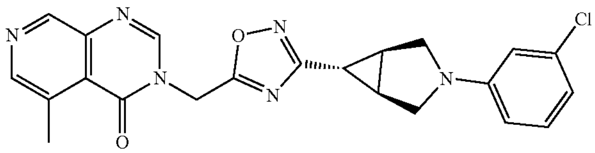 [SMILES: Cc1cncc2ncn(Cc3nc([C@H]4[C@@H]5CN(c6cccc(Cl)c6)C[C@@H]54)no3)c(=O)c12] | 5-methyl-3-[[3-[(1R,5S,6r)-3-(3-chlorophenyl)-3-azabicyclo[3.1.0]hexan-6-yl]-1,2,4-oxadiazol-5-yl]methyl]pyrido[3,4-d]pyrimidin-4-one | 0.0815 | — |
| 74 | 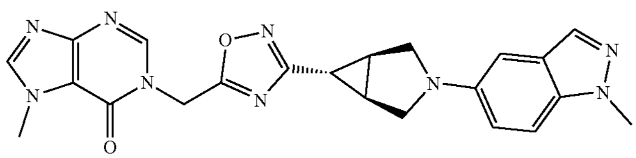 [SMILES: Cn1cnc2ncn(Cc3nc([C@H]4[C@@H]5CN(c6ccc7c(cnn7C)c6)C[C@@H]54)no3)c(=O)c21] | 7-methyl-1-[[3-[(1R,5S,6r)-3-(1-methylindazol-5-yl)-3-azabicyclo[3.1.0]hexan-6-yl]-1,2,4-oxadiazol-5-yl]methyl]purin-6-one | 0.141 | — |
| 75 | 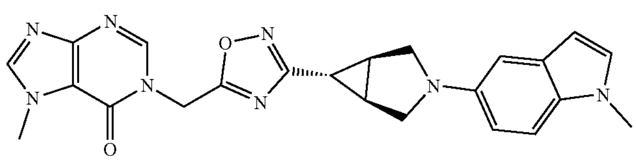 [SMILES: Cn1ccc2cc(N3C[C@@H]4[C@H](C3)[C@H]4c3noc(Cn4cnc5ncn(C)c5c4=O)n3)ccc21] | 7-methyl-1-[[3-[(1R,5S,6r)-3-(1-methylindol-5-yl)-3-azabicyclo[3.1.0]hexan-6-yl]-1,2,4-oxadiazol-5-yl]methyl]purin-6-one | 0.262 | — |
| 76 | 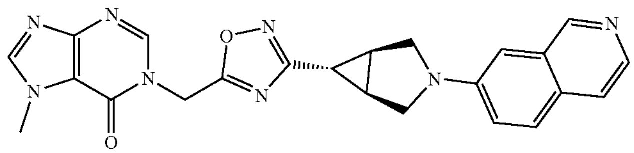 [SMILES: Cn1cnc2ncn(Cc3nc([C@H]4[C@@H]5CN(c6ccc7ccncc7c6)C[C@@H]54)no3)c(=O)c21] | 7-methyl-1-[[3-[(1R,5S,6r)-3-(7-isoquinolyl)-3-azabicyclo[3.1.0]hexan-6-yl]-1,2,4-oxadiazol-5-yl]methyl]purin-6-one | 0.0692 | — |
| 77 | 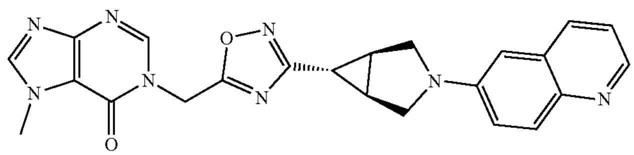 [SMILES: Cn1cnc2ncn(Cc3nc([C@H]4[C@@H]5CN(c6ccc7ncccc7c6)C[C@@H]54)no3)c(=O)c21] | 7-methyl-1-[[3-[(1R,5S,6r)-3-(6-quinolyl)-3-azabicyclo[3.1.0]hexan-6-yl]-1,2,4-oxadiazol-5-yl]methyl]purin-6-one | 0.166 | — |
| 78 | 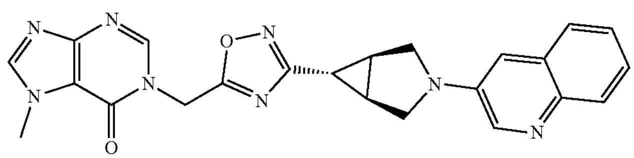 [SMILES: Cn1cnc2ncn(Cc3nc([C@H]4[C@@H]5CN(c6cnc7ccccc7c6)C[C@@H]54)no3)c(=O)c21] | 7-methyl-1-[[3-[(1R,5S,6r)-3-(3-quinolyl)-3-azabicyclo[3.1.0]hexan-6-yl]-1,2,4-oxadiazol-5-yl]methyl]purin-6-one | 0.169 | — |
| 79 | 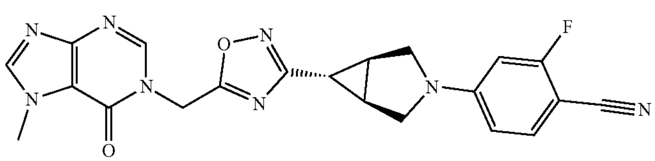 [SMILES: Cn1cnc2ncn(Cc3nc([C@H]4[C@@H]5CN(c6ccc(C#N)c(F)c6)C[C@@H]54)no3)c(=O)c21] | 2-fluoro-4-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0553 | 0.015 |

TABLE 1-continued

| Ex. | Structure | Name | IC$_{50}$ (10 min) | IC$_{50}$ (90 min) |
|---|---|---|---|---|
| 80 | 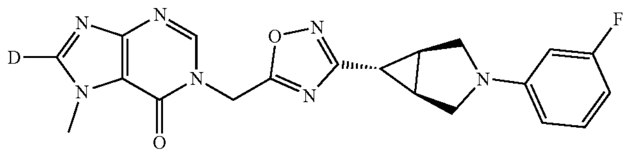 [SMILES: [2H]c1nc2ncn(Cc3nc([C@H]4[C@@H]5CN(c6cccc(F)c6)C[C@@H]54)no3)c(=O)c2n1C] | 1-((3-((1R,5S,6r)-3-(3-fluorophenyl)-3-azabicyclo[3.1.0]hexan-6-yl)-1,2,4-oxadiazol-5-yl)methyl)-7-methyl-1,7-dihydro-6H-purin-6-one-8-d | 0.0246 | 0.0052 |
| 81 | 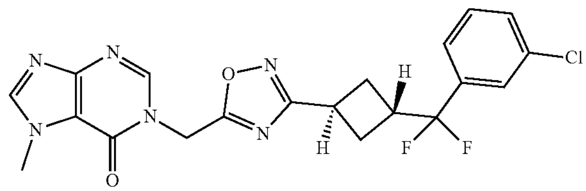 [SMILES: Cn1cnc2ncn(Cc3nc([C@H]4C[C@H](C(F)(F)c5cccc(Cl)c5)C4)no3)c(=O)c21] | 1-((3-((1r,3r)-3-((3-chlorophenyl)difluoromethyl)cyclobutyl)-1,2,4-oxadiazol-5-yl)methyl)-7-methyl-1,7-dihydro-6H-purin-6-one | 0.0264 | 0.013 |
| 82 | 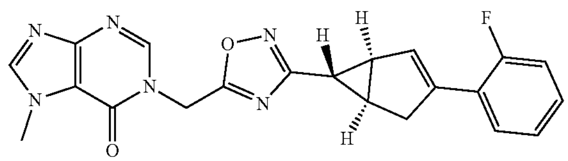 [SMILES: Cn1cnc2ncn(Cc3nc([C@@H]4[C@H]5C=C(c6ccccc6F)C[C@H]54)no3)c(=O)c21] | 7-methyl-1-[[3-[(1S,5S,6R)-3-(2-fluorophenyl)-6-bicyclo[3.1.0]hex-2-enyl]-1,2,4-oxadiazol-5-yl]methyl]purin-6-one | 0.0154 | 0.0085 |
| 83 | 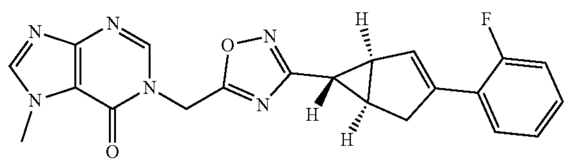 [SMILES: Cn1cnc2ncn(Cc3nc([C@@H]4[C@H]5C=C(c6ccccc6F)C[C@H]54)no3)c(=O)c21] | 7-methyl-1-[[3-[(1R,5R,6S)-3-(2-fluorophenyl)-6-bicyclo[3.1.0]hex-2-enyl]-1,2,4-oxadiazol-5-yl]methyl]purin-6-one | 0.0127 | 0.0047 |
| 84 | 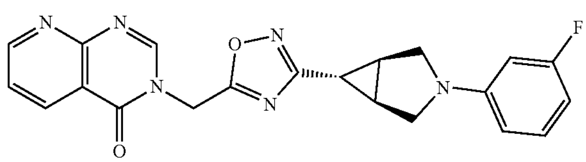 | 3-((3-((1R,5S,6r)-3-(3-fluorophenyl)-3-azabicyclo[3.1.0]hexan-6-yl)-1,2,4-oxadiazol-5-yl)methyl)pyrido[2,3-d]pyrimidin-4(3H)-one | 0.0104 | 0.0087 |
| 85 | 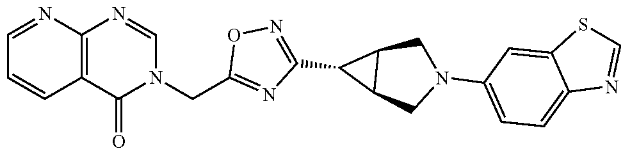 [SMILES: O=c1c2cccnc2ncn1Cc1nc([C@H]2[C@@H]3CN(c4ccc5ncsc5c4)C[C@@H]32)no1] | 3-((3-((1R,5S,6r)-3-(benzo[d]thiazol-6-yl)-3-azabicyclo[3.1.0]hexan-6-yl)-1,2,4-oxadiazol-5-yl)methyl)pyrido[2,3-d]pyrimidin-4(3H)-one | 0.024 | 0.0086 |
| 86 | 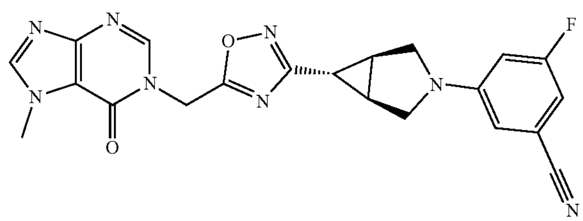 [SMILES: Cn1cnc2ncn(Cc3nc([C@H]4[C@@H]5CN(c6cc(F)cc(C#N)c6)C[C@@H]54)no3)c(=O)c21] | 3-fluoro-5-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0991 | 0.04 |
| 87 | 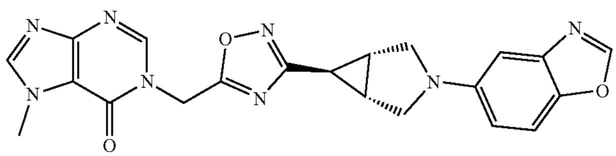 [SMILES: Cn1cnc2ncn(Cc3nc([C@H]4[C@@H]5CN(c6ccc7ocnc7c6)C[C@@H]54)no3)c(=O)c21] | 1-((3-((1R,5S,6r)-3-(benzo[d]oxazol-5-yl)-3-azabicyclo[3.1.0]hexan-6-yl)-1,2,4-oxadiazol-5-yl)methyl)-7-methyl-1,7-dihydro-6H-purin-6-one | 0.0275 | 0.018 |

TABLE 1-continued

| Ex. | Structure | Name | IC$_{50}$ (10 min) | IC$_{50}$ (90 min) |
|---|---|---|---|---|
| 88 | 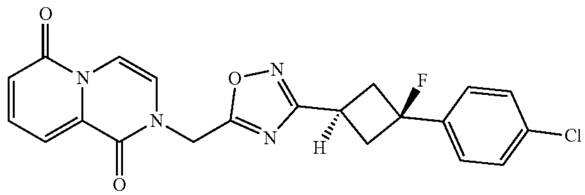 [SMILES: O=c1c2cccc(=O)n2ccn1Cc1nc([C@H]2C[C@](F)(c3ccc(Cl)cc3)C2)no1] | 2-((3-((1s,3s)-3-(4-chlorophenyl)-3-fluorocyclobutyl)-1,2,4-oxadiazol-5-yl)methyl)-2H-pyrido[1,2-a]pyrazine-1,6-dione | 0.0377 | 0.038 |
| 89 | 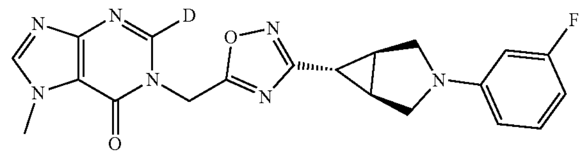 [SMILES: [2H]c1nc2ncn(C)c2c(=O)n1Cc1nc([C@H]2[C@@H]3CN(c4cccc(F)c4)C[C@@H]32)no1] | 1-((3-((1R,5S,6r)-3-(3-fluorophenyl)-3-azabicyclo[3.1.0]hexan-6-yl)-1,2,4-oxadiazol-5-yl)methyl)-7-methyl-1,7-dihydro-6H-purin-6-one-2-d | 0.0333 | 0.0048 |
| 90 | 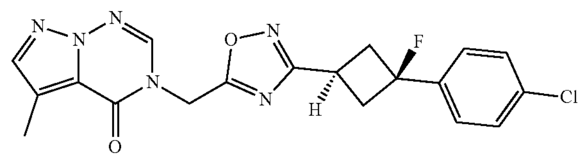 [SMILES: Cc1cnn2ncn(Cc3nc([C@H]4C[C@](F)(c5ccc(Cl)cc5)C4)no3)c(=O)c12] | 3-((3-((1s,3s)-3-(4-chlorophenyl)-3-fluorocyclobutyl)-1,2,4-oxadiazol-5-yl)methyl)-5-methylpyrazolo[5,1-f][1,2,4]triazin-4(3H)-one | 0.0649 | 0.0081 |
| 91 | 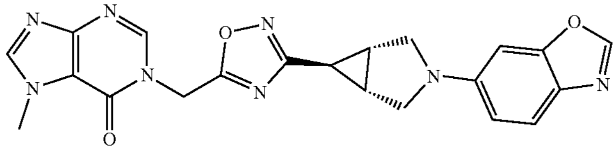 | 1-((3-((1R,5S,6r)-3-(benzo[d]oxazol-6-yl)-3-azabicyclo[3.1.0]hexan-6-yl)-1,2,4-oxadiazol-5-yl)methyl)-7-methyl-1,7-dihydro-6H-purin-6-one | 0.0384 | 0.028 |
| 92 | 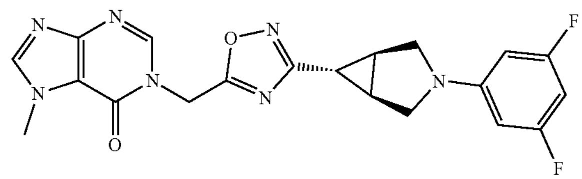 [SMILES: Cn1cnc2ncn(Cc3nc([C@H]4[C@@H]5CN(c6cc(F)cc(F)c6)C[C@@H]54)no3)c(=O)c21] | 1-((3-((1R,5S,6r)-3-(3,5-difluorophenyl)-3-azabicyclo[3.1.0]hexan-6-yl)-1,2,4-oxadiazol-5-yl)methyl)-7-methyl-1,7-dihydro-6H-purin-6-one | 0.0206 | 0.0031 |
| 93 | 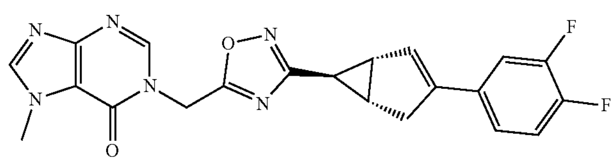 [SMILES: Cn1cnc2ncn(Cc3nc([C@H]4[C@@H]5C=C(c6ccc(F)c(F)c6)C[C@@H]54)no3)c(=O)c21] | 1-((3-((1S,5S,6R)-3-(3,4-difluorophenyl)bicyclo[3.1.0]hex-2-en-6-yl)-1,2,4-oxadiazol-5-yl)methyl)-7-methyl-1,7-dihydro-6H-purin-6-one | 0.0127 | 0.0039 |
| 94 | 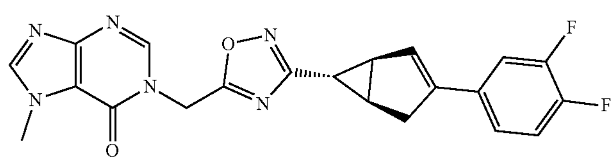 | 1-((3-((1R,5R,6S)-3-(3,4-difluorophenyl)bicyclo[3.1.0]hex-2-en-6-yl)-1,2,4-oxadiazol-5-yl)methyl)-7-methyl-1,7-dihydro-6H-purin-6-one | 0.00935 | 0.0049 |
| 95 | 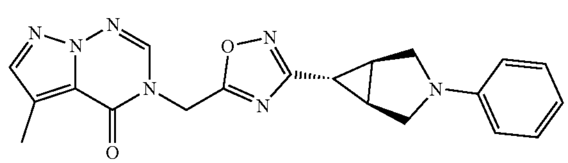 [SMILES: Cc1cnn2ncn(Cc3nc([C@H]4[C@@H]5CN(c6ccccc6)C[C@@H]54)no3)c(=O)c12] | 5-methyl-3-((3-((1R,5S,6r)-3-phenyl-3-azabicyclo[3.1.0]hexan-6-yl)-1,2,4-oxadiazol-5-yl)methyl)pyrazolo[5,1-f][1,2,4]triazin-4(3H)-one | 0.00811 | 0.0035 |

TABLE 1-continued

| Ex. | Structure | Name | IC$_{50}$ (10 min) | IC$_{50}$ (90 min) |
|---|---|---|---|---|
| 96 | 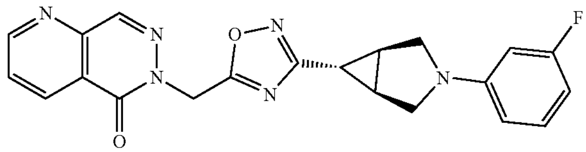 [SMILES: O=c1c2cccnc2cnn1Cc1nc([C@H]2[C@@H]3CN(c4cccc(F)c4)C[C@@H]32)no1] | 6-((3-((1R,5S,6r)-3-(3-fluorophenyl)-3-azabicyclo[3.1.0]hexan-6-yl)-1,2,4-oxadiazol-5-yl)methyl)pyrido[2,3-d]pyridazin-5(6H)-one | 0.00839 | 0.0051 |
| 97 | 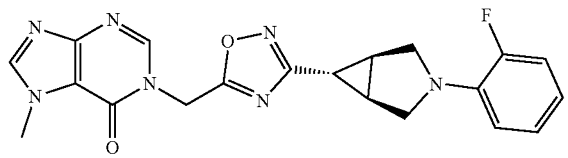 [SMILES: Cn1cnc2ncn(Cc3nc([C@H]4[C@@H]5CN(c6ccccc6F)C[C@@H]54)no3)c(=O)c21] | 1-((3-((1R,5S,6r)-3-(2-fluorophenyl)-3-azabicyclo[3.1.0]hexan-6-yl)-1,2,4-oxadiazol-5-yl)methyl)-7-methyl-1,7-dihydro-6H-purin-6-one | 0.0481 | 0.019 |
| 98 | 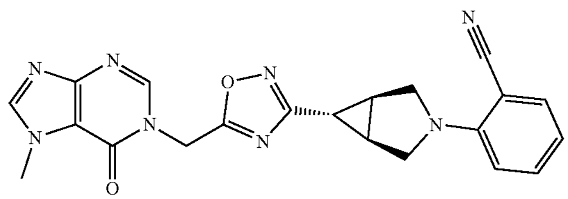 [SMILES: Cn1cnc2ncn(Cc3nc([C@H]4[C@@H]5CN(c6ccccc6C#N)C[C@@H]54)no3)c(=O)c21] | 2-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.157 | 0.1 |
| 99 | 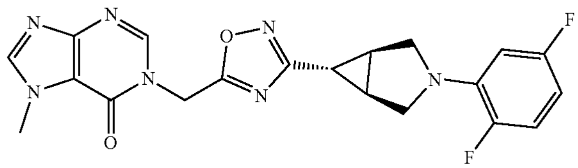 [SMILES: Cn1cnc2ncn(Cc3nc([C@H]4[C@@H]5CN(c6cc(F)ccc6F)C[C@@H]54)no3)c(=O)c21] | 1-((3-((1R,5S,6r)-3-(2,5-difluorophenyl)-3-azabicyclo[3.1.0]hexan-6-yl)-1,2,4-oxadiazol-5-yl)methyl)-7-methyl-1,7-dihydro-6H-purin-6-one | 0.0151 | 0.0063 |
| 100 | 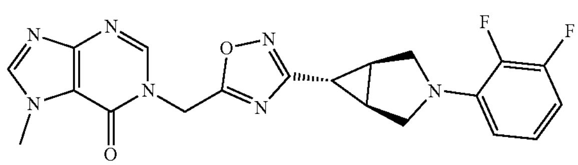 [SMILES: Cn1cnc2ncn(Cc3nc([C@H]4[C@@H]5CN(c6cccc(F)c6F)C[C@@H]54)no3)c(=O)c21] | 1-((3-((1R,5S,6r)-3-(2,3-difluorophenyl)-3-azabicyclo[3.1.0]hexan-6-yl)-1,2,4-oxadiazol-5-yl)methyl)-7-methyl-1,7-dihydro-6H-purin-6-one | 0.0128 | 0.0025 |
| 101 | 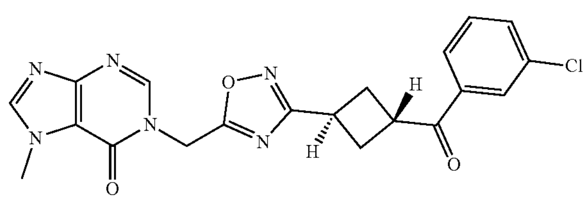 [SMILES: Cn1cnc2ncn(Cc3nc([C@H]4C[C@H](C(=O)c5cccc(Cl)c5)C4)no3)c(=O)c21] | 1-((3-((1r,3r)-3-(3-chlorobenzoyl)cyclobutyl)-1,2,4-oxadiazol-5-yl)methyl)-7-methyl-1,7-dihydro-6H-purin-6-one | 0.117 | 0.064 |
| 102 | 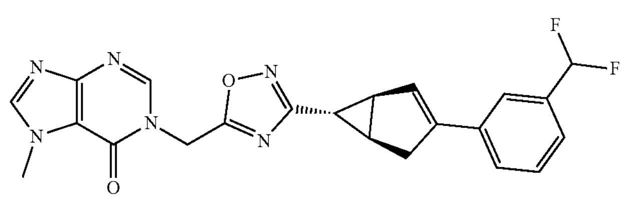 [SMILES: Cn1cnc2ncn(Cc3nc([C@@H]4[C@H]5C=C(c6cccc(C(F)F)c6)C[C@H]54)no3)c(=O)c21] | 1-((3-((1R,5R,6S)-3-(3-(difluoromethyl)phenyl)bicyclo[3.1.0]hex-2-en-6-yl)-1,2,4-oxadiazol-5-yl)methyl)-7-methyl-1,7-dihydro-6H-purin-6-one | 0.0495 | 0.037 |
| 103 | 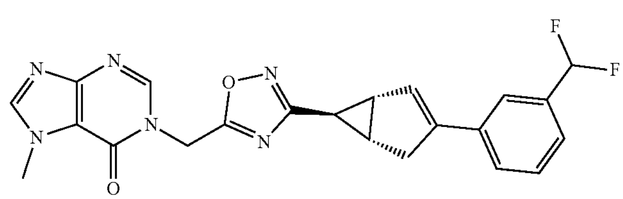 [SMILES: Cn1cnc2ncn(Cc3nc([C@H]4[C@@H]5C=C(c6cccc(C(F)F)c6)C[C@@H]54)no3)c(=O)c21] | 1-((3-((1S,5S,6R)-3-(3-(difluoromethyl)phenyl)bicyclo[3.1.0]hex-2-en-6-yl)-1,2,4-oxadiazol-5-yl)methyl)-7-methyl-1,7-dihydro-6H-purin-6-one | 0.0319 | 0.026 |

TABLE 1-continued

| Ex. | Structure | Name | IC$_{50}$ (10 min) | IC$_{50}$ (90 min) |
|---|---|---|---|---|
| 104 | 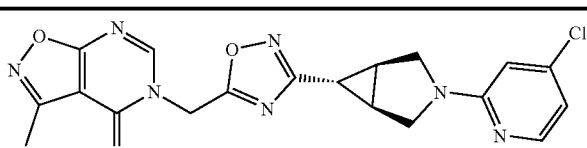 | 5-((3-((1R,5S,6r)-3-(4-chloropyridin-2-yl)-3-azabicyclo[3.1.0]hexan-6-yl)-1,2,4-oxadiazol-5-yl)methyl)-3-methyl isoxazolo[5,4-d]pyrimidin-4(5H)-one | 0.043 | 0.03 |
| 105 | 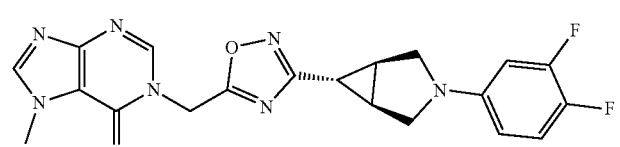 | 1-((3-((1R,5S,6r)-3-(3,4-difluorophenyl)-3-azabicyclo[3.1.0]hexan-6-yl)-1,2,4-oxadiazol-5-yl)methyl)-7-methyl-1,7-dihydro-6H-purin-6-one | 0.0215 | 0.0039 |
| 106 | 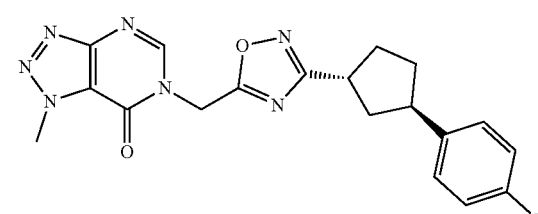 | 6-((3-((1R,3R)-3-(4-fluorophenyl)cyclopentyl)-1,2,4-oxadiazol-5-yl)methyl)-1-methyl-1,6-dihydro-7H-[1,2,3]triazolo[4,5-d]pyrimidin-7-one | 0.0403 | 0.044 |
| 107 | 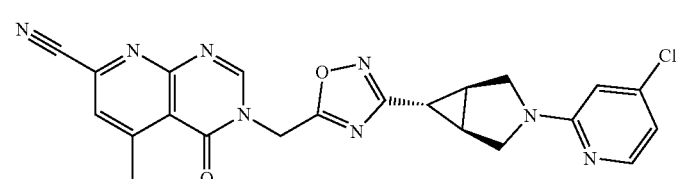 | 3-((3-((1R,5S,6r)-3-(4-chloropyridin-2-yl)-3-azabicyclo[3.1.0]hexan-6-yl)-1,2,4-oxadiazol-5-yl)methyl)-5-methyl-4-oxo-3,4-dihydropyrido[2,3-d]pyrimidine-7-carbonitrile | 0.049 | 0.0091 |
| 108 | 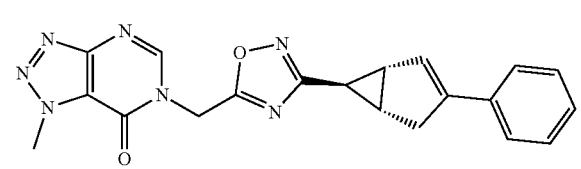 [SMILES: Cn1nnc2ncn(Cc3nc([C@H]4[C@@H]5C=C(c6ccccc6)C[C@@H]54)no3)c(=O)c21] | 1-methyl-6-((3-((1S,5S,6R)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one | 0.00612 | 0.0031 |
| 109 | 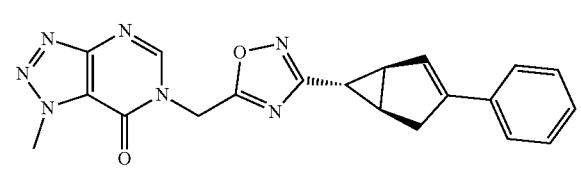 [SMILES: Cn1nnc2ncn(Cc3nc([C@@H]4[C@H]5C=C(c6ccccc6)C[C@H]54)no3)c(=O)c21] | 1-methyl-6-((3-((1R,5R,6S)-3-phenylbicyclo[3.1.0]hex-2-en-6-yl)-1,2,4-oxadiazol-5-yl)methyl)-1,6-dihydro-7H-[1,2,3]triazolo[4,5-d]pyrimidin-7-one | 0.0104 | 0.0041 |
| 110 | 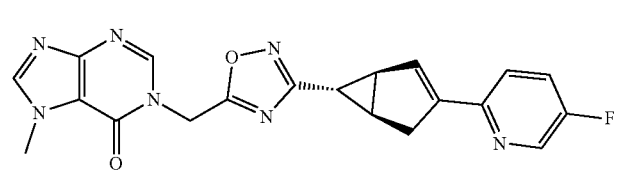 [SMILES: Cn1cnc2ncn(Cc3nc([C@@H]4[C@H]5C=C(c6ccc(F)cn6)C[C@H]54)no3)c(=O)c21] | 1-((3-((1R,5R,6S)-3-(5-fluoropyridin-2-yl)bicyclo[3.1.0]hex-2-en-6-yl)-1,2,4-oxadiazol-5-yl)methyl)-7-methyl-1,7-dihydro-6H-purin-6-one | 0.064 | 0.027 |
| 111 | 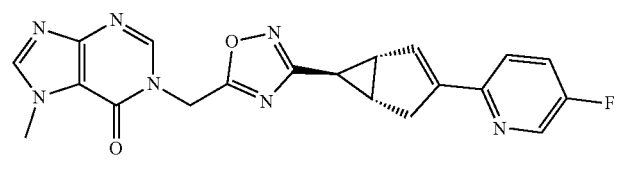 [SMILES: Cn1cnc2ncn(Cc3nc([C@H]4[C@@H]5C=C(c6ccc(F)cn6)C[C@@H]54)no3)c(=O)c21] | 1-((3-((1S,5S,6R)-3-(5-fluoropyridin-2-yl)bicyclo[3.1.0]hex-2-en-6-yl)-1,2,4-oxadiazol-5-yl)methyl)-7-methyl-1,7-dihydro-6H- | 0.116 | 0.078 |

TABLE 1-continued

| Ex. | Structure | Name | IC$_{50}$ (10 min) | IC$_{50}$ (90 min) |
|---|---|---|---|---|
| | | purin-6-one | | |
| 112 | 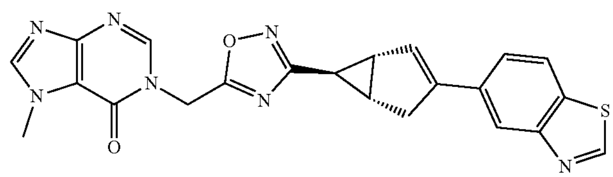 [SMILES: Cn1cnc2ncn(Cc3nc([C@H]4[C@@H]5C=C(c6ccc7scnc7c6)C[C@@H]54)no3)c(=O)c21] | 1-((3-((1S,5S,6R)-3-(benzo[d]thiazol-5-yl)bicyclo[3.1.0]hex-2-en-6-yl)-1,2,4-oxadiazol-5-yl)methyl)-7-methyl-1,7-dihydro-6H-purin-6-one | 0.036 | 0.024 |
| 113 | 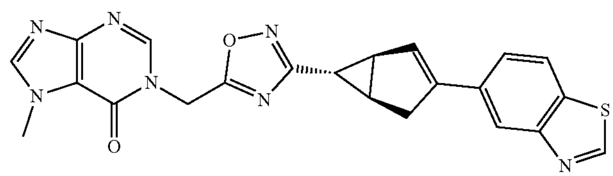 [SMILES: Cn1cnc2ncn(Cc3nc([C@@H]4[C@H]5C=C(c6ccc7scnc7c6)C[C@H]54)no3)c(=O)c21] | 1-((3-((1R,5R,6S)-3-(benzo[d]thiazol-5-yl)bicyclo[3.1.0]hex-2-en-6-yl)-1,2,4-oxadiazol-5-yl)methyl)-7-methyl-1,7-dihydro-6H-purin-6-one | 0.0362 | 0.034 |
| 114 | 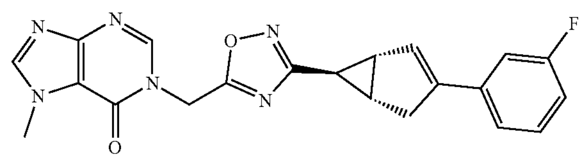 [SMILES: Cn1cnc2ncn(Cc3nc([C@H]4[C@@H]5C=C(c6cccc(F)c6)C[C@@H]54)no3)c(=O)c21] | 1-((3-((1S,5S,6R)-3-(3-fluorophenyl)bicyclo[3.1.0]hex-2-en-6-yl)-1,2,4-oxadiazol-5-yl)methyl)-7-methyl-1,7-dihydro-6H-purin-6-one | 0.0064 | 0.0017 |
| 115 | 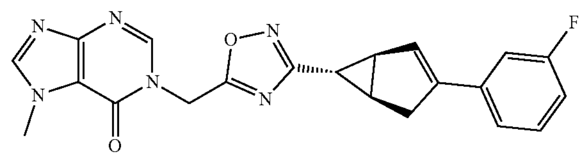 [SMILES: Cn1cnc2ncn(Cc3nc([C@@H]4[C@H]5C=C(c6cccc(F)c6)C[C@H]54)no3)c(=O)c21] | 1-((3-((1R,5R,6S)-3-(3-fluorophenyl)bicyclo[3.1.0]hex-2-en-6-yl)-1,2,4-oxadiazol-5-yl)methyl)-7-methyl-1,7-dihydro-6H-purin-6-one | 0.00973 | 0.0023 |
| 116 | 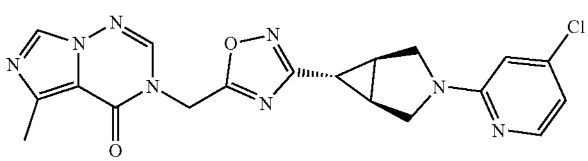 [SMILES: Cc1ncn2ncn(Cc3nc([C@H]4[C@@H]5CN(c6cc(Cl)ccn6)C[C@@H]54)no3)c(=O)c12] | 3-((3-((1R,5S,6r)-3-(4-chloropyridin-2-yl)-3-azabicyclo[3.1.0]hexan-6-yl)-1,2,4-oxadiazol-5-yl)methyl)-5-methylimidazo[5,1-f][1,2,4]triazin-4(3H)-one | 0.0611 | 0.05 |
| 117 | 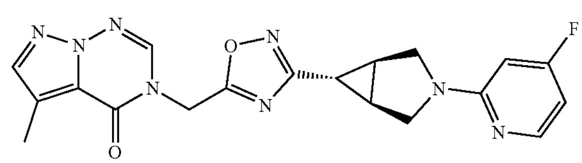 [SMILES: Cc1cnn2ncn(Cc3nc([C@H]4[C@@H]5CN(c6cc(F)ccn6)C[C@@H]54)no3)c(=O)c12] | 3-((3-((1R,5S,6r)-3-(4-fluoropyridin-2-yl)-3-azabicyclo[3.1.0]hexan-6-yl)-1,2,4-oxadiazol-5-yl)methyl)-5-methylpyrazolo[5,1-f][1,2,4]triazin-4(3H)-one | 0.0192 | 0.0075 |
| 118 | 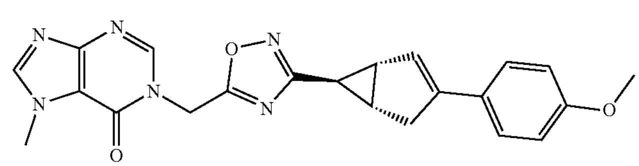 [SMILES: COc1ccc(C2=C[C@@H]3[C@H](C2)[C@H]3c2noc(Cn3cnc4ncn(C)c4c3=O)n2)cc1] | 1-((3-((1S,5S,6R)-3-(4-methoxyphenyl)bicyclo[3.1.0]hex-2-en-6-yl)-1,2,4-oxadiazol-5-yl)methyl)-7-methyl-1,7-dihydro-6H-purin-6-one | 0.0418 | 0.015 |
| 119 | 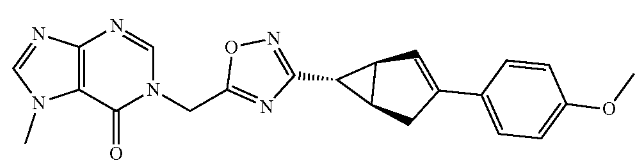 [SMILES: COc1ccc(C2=C[C@H]3[C@@H](C2)[C@@H]3c2noc(Cn3cnc4ncn(C)c4c3=O)n2)cc1] | 1-((3-((1R,5R,6S)-3-(4-methoxyphenyl)bicyclo[3.1.0]hex-2-en-6-yl)-1,2,4-oxadiazol-5-yl)methyl)-7-methyl-1,7-dihydro-6H-purin-6-one | 0.0266 | 0.016 |

TABLE 1-continued

| Ex. | Structure | Name | IC$_{50}$ (10 min) | IC$_{50}$ (90 min) |
|---|---|---|---|---|
| 120 | 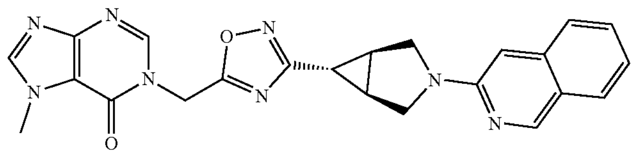 [SMILES: Cn1cnc2ncn(Cc3nc([C@H]4[C@@H]5CN(c6cc7ccccc7cn6)C[C@@H]54)no3)c(=O)c21] | 1-((3-((1R,5S,6r)-3-(isoquinolin-3-yl)-3-azabicyclo[3.1.0]hexan-6-yl)-1,2,4-oxadiazol-5-yl)methyl)-7-methyl-1,7-dihydro-6H-purin-6-one | 0.0908 | 0.081 |
| 121 | 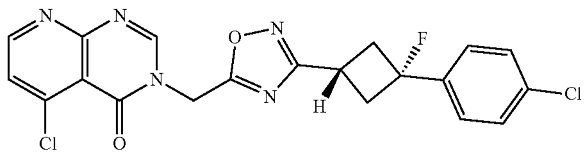 [SMILES: O=c1c2c(Cl)ccnc2ncn1Cc1nc([C@H]2C[C@](F)(c3ccc(Cl)cc3)C2)no1] | 5-chloro-3-((3-((1s,3s)-3-(4-chlorophenyl)-3-fluorocyclobutyl)-1,2,4-oxadiazol-5-yl)methyl)pyrido[2,3-d]pyrimidin-4(3H)-one | 0.0131 | 0.022 |
| 122 | 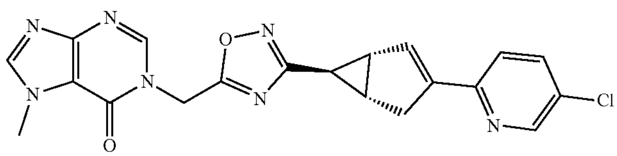 [SMILES: Cn1cnc2ncn(Cc3nc([C@H]4[C@@H]5C=C(c6ccc(Cl)cn6)C[C@@H]54)no3)c(=O)c21] | 1-((3-((1S,5S,6R)-3-(5-chloropyridin-2-yl)bicyclo[3.1.0]hex-2-en-6-yl)-1,2,4-oxadiazol-5-yl)methyl)-7-methyl-1,7-dihydro-6H-purin-6-one | 0.142 | 0.13 |
| 123 | 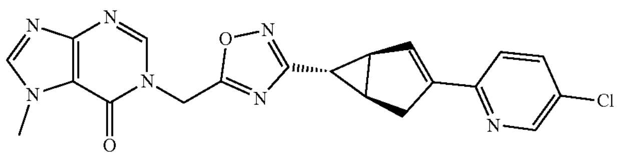 [SMILES: Cn1cnc2ncn(Cc3nc([C@@H]4[C@H]5C=C(c6ccc(Cl)cn6)C[C@H]54)no3)c(=O)c21] | 1-((3-((1R,5R,6S)-3-(5-chloropyridin-2-yl)bicyclo[3.1.0]hex-2-en-6-yl)-1,2,4-oxadiazol-5-yl)methyl)-7-methyl-1,7-dihydro-6H-purin-6-one | 0.296 | 0.36 |
| 124 | 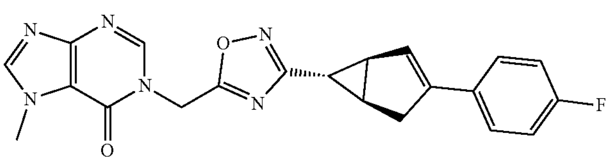 [SMILES: Cn1cnc2ncn(Cc3nc([C@@H]4[C@H]5C=C(c6ccc(F)cc6)C[C@H]54)no3)c(=O)c21] | 1-((3-((1R,5R,6S)-3-(4-fluorophenyl)bicyclo[3.1.0]hex-2-en-6-yl)-1,2,4-oxadiazol-5-yl)methyl)-7-methyl-1,7-dihydro-6H-purin-6-one | 0.0109 | 0.0075 |
| 125 | 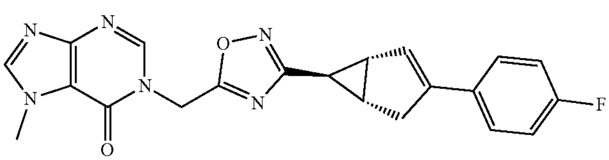 [SMILES: Cn1cnc2ncn(Cc3nc([C@H]4[C@@H]5C=C(c6ccc(F)cc6)C[C@@H]54)no3)c(=O)c21] | 1-((3-((1S,5S,6R)-3-(4-fluorophenyl)bicyclo[3.1.0]hex-2-en-6-yl)-1,2,4-oxadiazol-5-yl)methyl)-7-methyl-1,7-dihydro-6H-purin-6-one | 0.00748 | 0.003 |
| 126 | 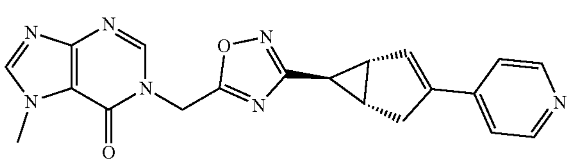 [SMILES: Cn1cnc2ncn(Cc3nc([C@H]4[C@@H]5C=C(c6ccncc6)C[C@@H]54)no3)c(=O)c21] | 7-methyl-1-((3-((1S,5S,6R)-3-(pyridin-4-yl)bicyclo[3.1.0]hex-2-en-6-yl)-1,2,4-oxadiazol-5-yl)methyl)-1,7-dihydro-6H-purin-6-one | 0.189 | 0.096 |
| 127 | 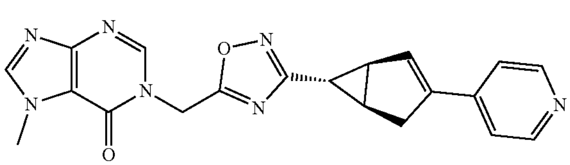 [SMILES: Cn1cnc2ncn(Cc3nc([C@@H]4[C@H]5C=C(c6ccncc6)C[C@H]54)no3)c(=O)c21] | 7-methyl-1-((3-((1R,5R,6S)-3-(pyridin-4-yl)bicyclo[3.1.0]hex-2-en-6-yl)-1,2,4-oxadiazol-5-yl)methyl)-1,7-dihydro-6H-purin-6-one | 0.129 | 0.085 |
| 128 | 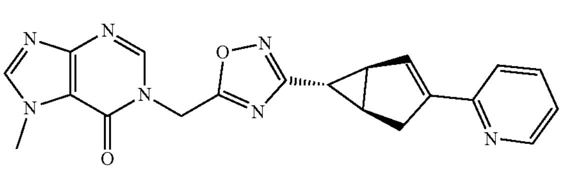 [SMILES: Cn1cnc2ncn(Cc3nc([C@@H]4[C@H]5C=C(c6ccccn6)C[C@H]54)no3)c(=O)c21] | 7-methyl-1-((3-((1R,5R,6S)-3-(pyridin-2-yl)bicyclo[3.1.0]hex-2-en-6-yl)-1,2,4-oxadiazol-5-yl)methyl)-1,7-dihydro-6H-purin-6-one | 0.118 | 0.078 |

| Ex. | Structure | Name | IC$_{50}$ (10 min) | IC$_{50}$ (90 min) |
|---|---|---|---|---|
| 129 | 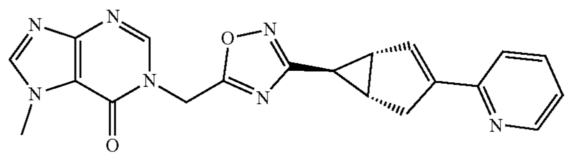 [SMILES: Cn1cnc2ncn(Cc3nc([C@H]4[C@@H]5C=C(c6ccccn6)C[C@@H]54)no3)c(=O)c21] | 7-methyl-1-((3-((1S, 5S,6R)-3-(pyridin-2-yl) bicyclo[3.1.0]hex-2-en-6-yl)-1,2,4-oxadiazol-5-yl)methyl)-1,7-dihydro-6H-purin-6-one | 0.209 | 0.21 |
| 130 | 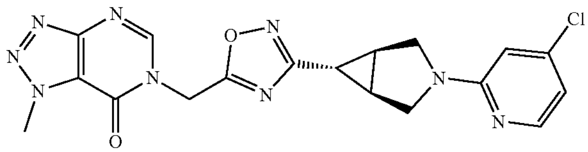 [SMILES: Cn1nnc2ncn(Cc3nc([C@H]4[C@@H]5CN(c6cc(Cl)ccn6)C[C@@H]54)no3)c(=O)c21] | 6-((3-((1R,5S,6r)-3-(4-chloropyridin-2-yl)-3-azabicyclo[3.1.0] hexan-6-yl)-1,2,4-oxadiazol-5-yl) methyl)-1-methyl-1,6-dihydro-7H-[1,2,3]triazolo[4,5-d]pyrimidin-7-one | 0.0745 | 0.044 |
| 131 | 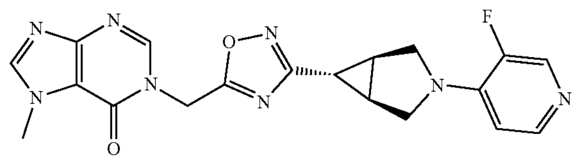 [SMILES: Cn1cnc2ncn(Cc3nc([C@H]4[C@@H]5CN(c6ccncc6F)C[C@@H]54)no3)c(=O)c21] | 1-((3-((1R,5S,6r)-3-(3-fluoropyridin-4-yl)-3-azabicyclo [3.1.0]hexan-6-yl)-1,2,4-oxadiazol-5-yl) methyl)-7-methyl-1,7-dihydro-6H-purin-6-one | 0.383 | 0.11 |
| 132 | 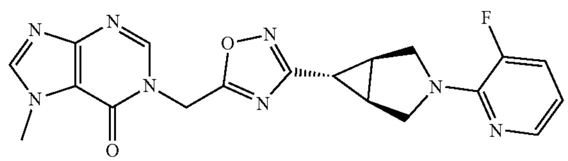 [SMILES: Cn1cnc2ncn(Cc3nc([C@H]4[C@@H]5CN(c6ncccc6F)C[C@@H]54)no3)c(=O)c21] | 1-((3-((1R,5S,6r)-3-(3-fluoropyridin-2-yl)-3-azabicyclo [3.1.0]hexan-6-yl)-1,2,4-oxadiazol-5-yl) methyl)-7-methyl-1,7-dihydro-6H-purin-6-one | 0.143 | 0.11 |
| 133 | 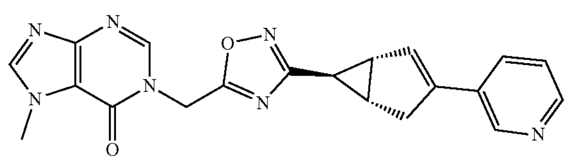 [SMILES: Cn1cnc2ncn(Cc3nc([C@H]4[C@@H]5C=C(c6cccnc6)C[C@@H]54)no3)c(=O)c21] | 7-methyl-1-((3-((1S,5S,6R)-3-(pyridin-3-yl)bicyclo [3.1.0]hex-2-en-6-yl)-1,2,4-oxadiazol-5-yl)methyl)-1,7-dihydro-6H-purin-6-one | 0.179 | 0.16 |
| 134 | 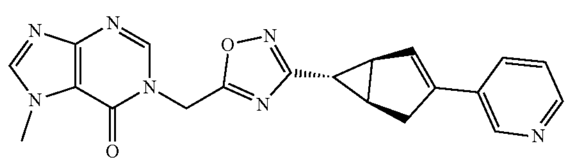 [SMILES: Cn1cnc2ncn(Cc3nc([C@@H]4[C@H]5C=C(c6cccnc6)C[C@H]54)no3)c(=O)c21] | 7-methyl-1-((3-((1R,5R,6S)-3-(pyridin-3-yl)bicyclo [3.1.0]hex-2-en-6-yl)-1,2,4-oxadiazol-5-yl)methyl)-1,7-dihydro-6H-purin-6-one | 0.348 | 0.44 |
| 135 | 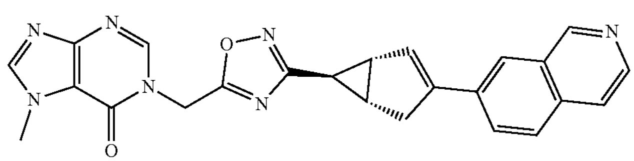 [SMILES: Cn1cnc2ncn(Cc3nc([C@H]4[C@@H]5C=C(c6ccc7ccncc7c6)C[C@@H]54)no3)c(=O)c21] | 1-((3-((1S,5S,6R)-3-(isoquinolin-7-yl)bicyclo[3.1.0]hex-2-en-6-yl)-1,2,4-oxadiazol-5-yl) methyl)-7-methyl-1,7-dihydro-6H-purin-6-one | 0.0587 | 0.048 |
| 136 | 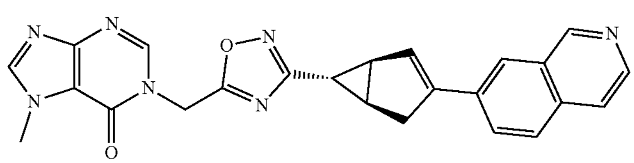 [SMILES: Cn1cnc2ncn(Cc3nc([C@@H]4[C@H]5C=C(c6ccc7ccncc7c6)C[C@H]54)no3)c(=O)c21] | 1-((3-((1R,5R,6S)-3-(isoquinolin-7-yl)bicyclo[3.1.0]hex-2-en-6-yl)-1,2,4-oxadiazol-5-yl) methyl)-7-methyl-1,7-dihydro-6H-purin-6-one | 0.0166 | 0.0076 |

TABLE 1-continued

| Ex. | Structure | Name | IC$_{50}$ (10 min) | IC$_{50}$ (90 min) |
|---|---|---|---|---|
| 137 | 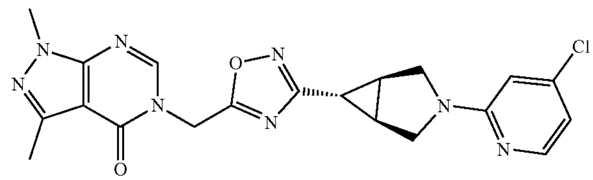 [SMILES: Cc1nn(C)c2ncn(Cc3nc([C@H]4[C@@H]5CN(c6cc(Cl)ccn6)C[C@@H]54)no3)c(=O)c12] | 5-((3-((1R,5S,6r)-3-(4-chloropyridin-2-yl)-3-azabicyclo[3.1.0]hexan-6-yl)-1,2,4-oxadiazol-5-yl)methyl)-1,3-dimethyl-1,5-dihydro-4H-pyrazolo[3,4-d]pyrimidin-4-one | 0.0585 | 0.043 |
| 138 | 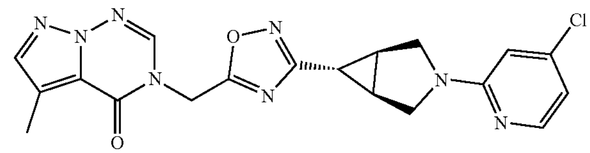 [SMILES: Cc1cnn2ncn(Cc3nc([C@H]4[C@@H]5CN(c6cc(Cl)ccn6)C[C@@H]54)no3)c(=O)c12] | 3-((3-((1R,5S,6r)-3-(4-chloropyridin-2-yl)-3-azabicyclo[3.1.0]hexan-6-yl)-1,2,4-oxadiazol-5-yl)methyl)-5-methylpyrazolo[5,1-f][1,2,4]triazin-4(3H)-one | 0.0151 | 0.0055 |
| 139 | 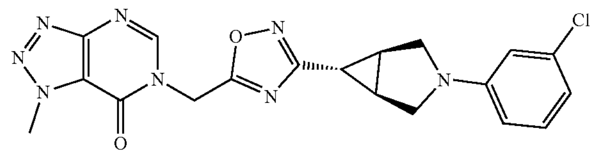 [SMILES: Cn1nnc2ncn(Cc3nc([C@H]4[C@@H]5CN(c6cccc(Cl)c6)C[C@@H]54)no3)c(=O)c21] | 6-((3-((1R,5S,6r)-3-(3-chlorophenyl)-3-azabicyclo[3.1.0]hexan-6-yl)-1,2,4-oxadiazol-5-yl)methyl)-1-methyl-1,6-dihydro-7H-[1,2,3]triazolo[4,5-d]pyrimidin-7-one | 0.0106 | 0.0036 |
| 140 | 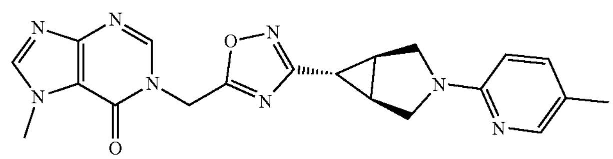 [SMILES: Cc1ccc(N2C[C@@H]3[C@H](C2)[C@H]3c2noc(Cn3cnc4ncn(C)c4c3=O)n2)nc1] | 7-methyl-1-((3-((1R,5S,6r)-3-(5-methylpyridin-2-yl)-3-azabicyclo[3.1.0]hexan-6-yl)-1,2,4-oxadiazol-5-yl)methyl)-1,7-dihydro-6H-purin-6-one | 0.222 | 0.17 |
| 141 | 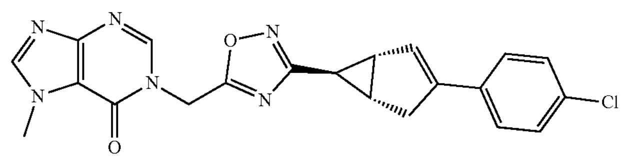 | 1-((3-((1S,5S,6R)-3-(4-chlorophenyl)bicyclo[3.1.0]hex-2-en-6-yl)-1,2,4-oxadiazol-5-yl)methyl)-7-methyl-1,7-dihydro-6H-purin-6-one | 0.00978 | 0.0051 |
| 142 | 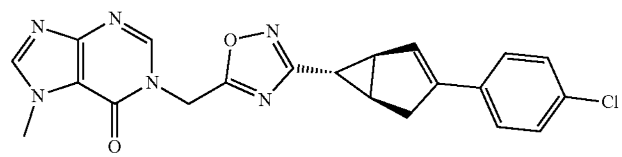 | 1-((3-((1R,5R,6S)-3-(4-chlorophenyl)bicyclo[3.1.0]hex-2-en-6-yl)-1,2,4-oxadiazol-5-yl)methyl)-7-methyl-1,7-dihydro-6H-purin-6-one | 0.0152 | 0.012 |
| 143 | 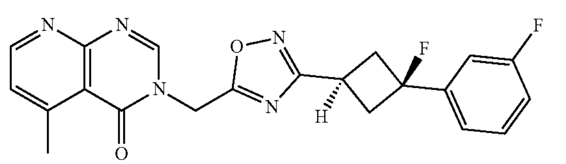 [SMILES: Cc1ccnc2ncn(Cc3nc([C@H]4C[C@](F)(c5cccc(F)c5)C4)no3)c(=O)c12] | 3-((3-((1s,3s)-3-fluoro-3-(3-fluorophenyl)cyclobutyl)-1,2,4-oxadiazol-5-yl)methyl)-5-methylpyrido[2,3-d]pyrimidin-4(3H)-one | 0.0337 | 0.028 |
| 144 | 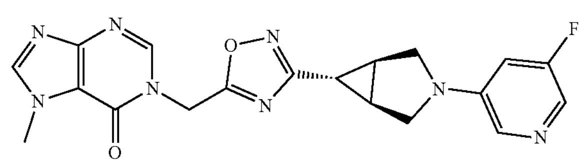 [SMILES: Cn1cnc2ncn(Cc3nc([C@H]4[C@@H]5CN(c6cncc(F)c6)C[C@@H]54)no3)c(=O)c21] | 1-((3-((1R,5S,6r)-3-(5-fluoropyridin-3-yl)-3-azabicyclo[3.1.0]hexan-6-yl)-1,2,4-oxadiazol-5-yl)methyl)-7-methyl-1,7-dihydro-6H-purin-6-one | 0.363 | 0.089 |

TABLE 1-continued

| Ex. | Structure | Name | IC$_{50}$ (10 min) | IC$_{50}$ (90 min) |
|---|---|---|---|---|
| 145 | 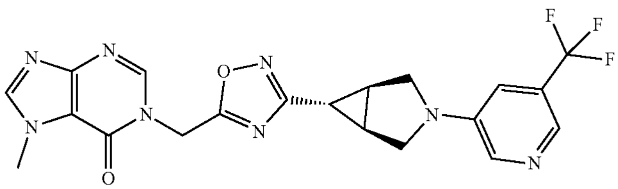 [SMILES: Cn1cnc2ncn(Cc3nc([C@H]4[C@@H]5CN(c6cncc(C(F)(F)F)c6)C[C@@H]54)no3)c(=O)c21] | 7-methyl-1-((3-((1R,5S,6r)-3-(5-(trifluoromethyl)pyridin-3-yl)-3-azabicyclo[3.1.0]hexan-6-yl)-1,2,4-oxadiazol-5-yl)methyl)-1,7-dihydro-6H-purin-6-one | 0.797 | 0.48 |
| 146 | 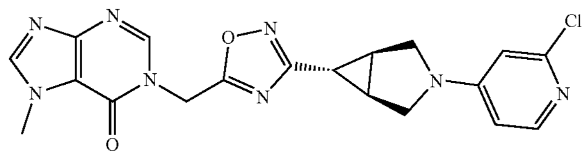 [SMILES: Cn1cnc2ncn(Cc3nc([C@H]4[C@@H]5CN(c6ccnc(Cl)c6)C[C@@H]54)no3)c(=O)c21] | 1-((3-((1R,5S,6r)-3-(2-chloropyridin-4-yl)-3-azabicyclo[3.1.0]hexan-6-yl)-1,2,4-oxadiazol-5-yl)methyl)-7-methyl-1,7-dihydro-6H-purin-6-one | 0.46 | 0.1 |
| 147 | 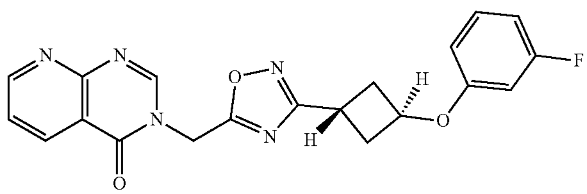 [SMILES: O=c1c2cccnc2ncn1Cc1nc([C@H]2C[C@H](Oc3cccc(F)c3)C2)no1] | 3-((3-((1r,3r)-3-(3-fluorophenoxy)cyclobutyl)-1,2,4-oxadiazol-5-yl)methyl)pyrido[2,3-d]pyrimidin-4(3H)-one | 0.232 | 0.14 |
| 148 | 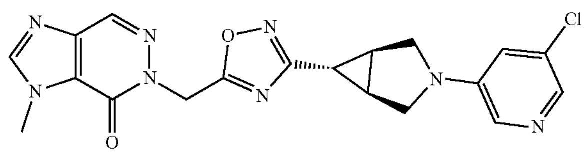 [SMILES: Cn1cnc2cnn(Cc3nc([C@H]4[C@@H]5CN(c6cncc(Cl)c6)C[C@@H]54)no3)c(=O)c21] | 5-((3-((1R,5S,6r)-3-(4-chloropyridin-2-yl)-3-azabicyclo[3.1.0]hexan-6-yl)-1,2,4-oxadiazol-5-yl)methyl)-3-methyl-3,5-dihydro-4H-imidazo[4,5-d]pyridazin-4-one | 0.305 | 0.15 |
| 149 | 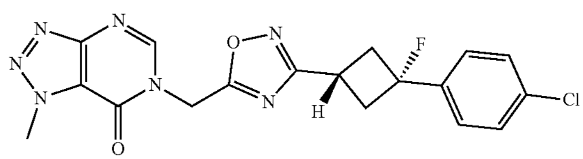 [SMILES: Cn1nnc2ncn(Cc3nc([C@H]4C[C@](F)(c5ccc(Cl)cc5)C4)no3)c(=O)c21] | 6-((3-((1s,3s)-3-(4-chlorophenyl)-3-fluorocyclobutyl)-1,2,4-oxadiazol-5-yl)methyl)-1-methyl-1,6-dihydro-7H-[1,2,3]triazolo[4,5-d]pyrimidin-7-one | 0.253 | 0.16 |
| 150 | 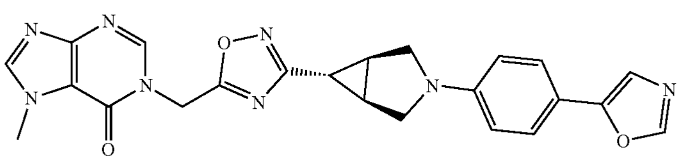 [SMILES: Cn1cnc2ncn(Cc3nc([C@H]4[C@@H]5CN(c6ccc(-c7cnco7)cc6)C[C@@H]54)no3)c(=O)c21] | 7-methyl-1-((3-((1R,5S,6r)-3-(4-(oxazol-5-yl)phenyl)-3-azabicyclo[3.1.0]hexan-6-yl)-1,2,4-oxadiazol-5-yl)methyl)-1,7-dihydro-6H-purin-6-one | 0.162 | 0.038 |
| 151 | 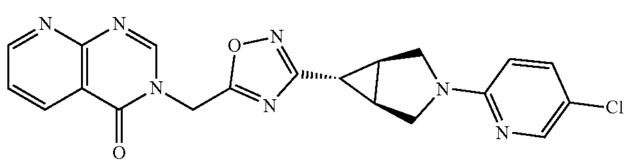 [SMILES: O=c1c2cccnc2ncn1Cc1nc([C@H]2[C@@H]3CN(c4ccc(Cl)cn4)C[C@@H]32)no1] | 3-((3-((1R,5S,6r)-3-(5-chloropyridin-2-yl)-3-azabicyclo[3.1.0]hexan-6-yl)-1,2,4-oxadiazol-5-yl)methyl)pyrido[2,3-d]pyrimidin-4(3H)one | 0.04) | 0.038 |
| 152 | 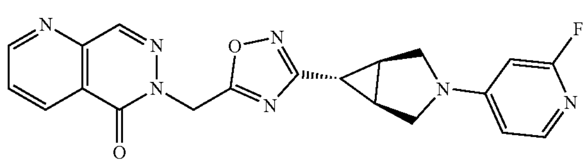 [SMILES: O=c1c2cccnc2cnn1Cc1nc([C@H]2[C@@H]3CN(c4ccnc(F)c4)C[C@@H]32)no1] | 6-((3-((1R,5S,6r)-3-(2-fluoropyridin-4-yl)-3-azabicyclo[3.1.0]hexan-6-yl)-1,2,4-oxadiazol-5-yl)methyl)pyrido[2,3-d]pyridazin-5(6H)-one | 0.0587 | 0.041 |
| 153 | 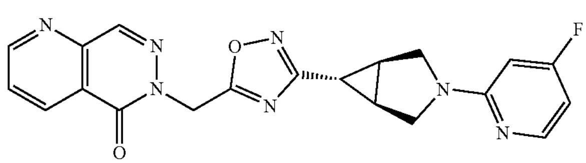 [SMILES: O=c1c2cccnc2cnn1Cc1nc([C@H]2[C@@H]3CN(c4cc(F)ccn4)C[C@@H]32)no1] | 6-((3-((1R,5S,6r)-3-(4-fluoropyridin-2-yl)-3-azabicyclo[3.1.0]hexan-6-yl)-1,2,4-oxadiazol-5-yl)methyl)pyrido[2,3-d]pyridazin-5(6H)-one | 0.0957 | 0.06 |

TABLE 1-continued

| Ex. | Structure | Name | IC$_{50}$ (10 min) | IC$_{50}$ (90 min) |
|---|---|---|---|---|
| 154 | 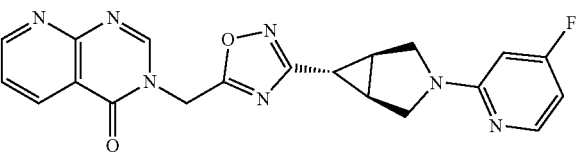 [SMILES: O=c1c2cccnc2ncn1Cc1nc([C@H]2[C@@H]3CN(c4cc(F)ccn4)C[C@@H]32)no1] | 3-((3-((1R,5S,6r)-3-(4-fluoropyridin-2-yl)-3-azabicyclo[3.1.0]hexan-6-yl)-1,2,4-oxadiazol-5-yl)methyl)pyrido[2,3-d]pyrimidin-4(3H)-one | 0.196 | 0.13 |
| 155 | 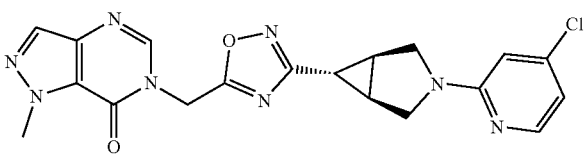 [SMILES: Cn1ncc2ncn(Cc3nc([C@H]4[C@@H]5CN(c6cc(Cl)ccn6)C[C@@H]54)no3)c(=O)c21] | 6-((3-((1R,5S,6r)-3-(4-chloropyridin-2-yl)-3-azabicyclo[3.1.0]hexan-6-yl)-1,2,4-oxadiazol-5-yl)methyl)-1-methyl-1,6-dihydro-7H-pyrazolo[4,3-d]pyrimidin-7-one | 0.0893 | 0.073 |
| 156 | 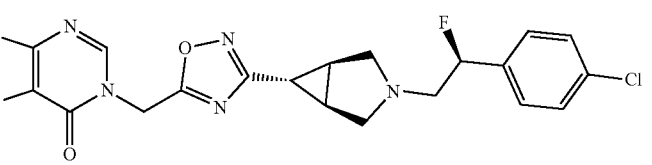 | 1-((3-((1R,5S,6S)-3-((S)-2-(4-chlorophenyl)-2-fluoroethyl)-3-azabicyclo[3.1.0]hexan-6-yl)-1,2,4-oxadiazol-5-yl)methyl)-7-methyl-1,7-dihydro-6H-purin-6-one | 0.843 | 0.86 |
| 157 | 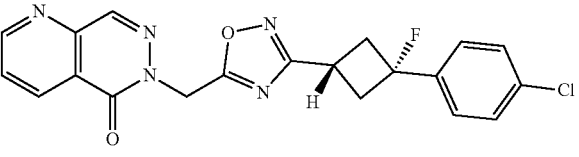 | 6-((3-((1s,3s)-3-(4-chlorophenyl)-3-fluorocyclobutyl)-1,2,4-oxadiazol-5-yl)methyl)pyrido[2,3-d]pyridazin-5(6H)-one | 0.0989 | 0.059 |
| 158 | 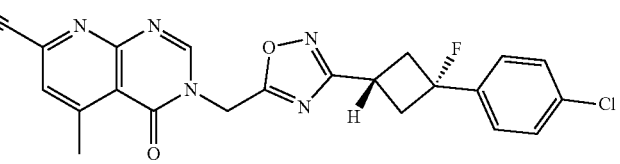 | 3-((3-((1s,3s)-3-(4-chlorophenyl)-3-fluorocyclobutyl)-1,2,4-oxadiazol-5-yl)methyl)-5-methyl-4-oxo-3,4-dihydropyrido[2,3-d]pyrimidine-7-carbonitrile | 0.0194 | 0.01 |
| 159 | 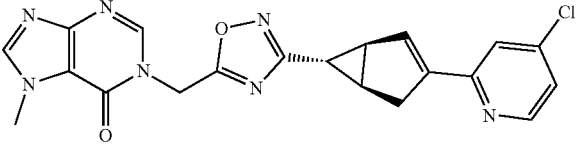 | 1-((3-((1R,5R,6S)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one | 0.119 | 0.068 |
| 160 | 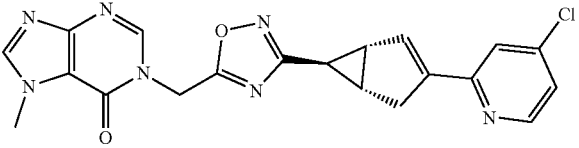 | 1-((3-((1S,5S,6R)-3-(4-chloropyridin-2-yl)bicyclo[3.1.0]hex-2-en-6-yl)-1,2,4-oxadiazol-5-yl)methyl)-7-methyl-1,7-dihydro-6H-purin-6-one | 0.0915 | 0.031 |
| 161 | 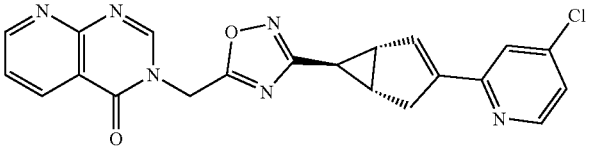 [SMILES: O=c1c2cccnc2ncn1Cc1nc([C@H]2[C@@H]3C=C(c4cc(Cl)ccn4)C[C@@H]32)no1] | 3-((3-((1S,5S,6R)-3-(4-chloropyridin-2-yl)bicyclo[3.1.0]hex-2-en-6-yl)-1,2,4-oxadiazol-5-yl)methyl)pyrido[2,3-d]pyrimidin-4(3H)-one | 0.315 | 0.2 |
| 162 | 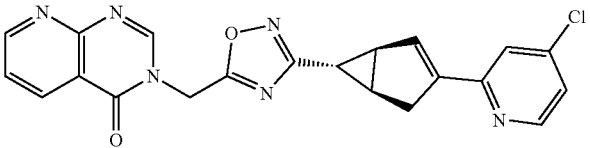 [SMILES: O=c1c2cccnc2ncn1Cc1nc([C@@H]2[C@H]3C=C(c4cc(Cl)ccn4)C[C@H]32)no1] | 3-((3-((1R,5R,6S)-3-(4-chloropyridin-2-yl)bicyclo[3.1.0]hex-2-en-6-yl)-1,2,4-oxadiazol-5-yl)methyl)pyrido[2,3-d]pyrimidin-4(3H)-one | 0.132 | 0.088 |

TABLE 1-continued

| Ex. | Structure | Name | IC$_{50}$ (10 min) | IC$_{50}$ (90 min) |
|---|---|---|---|---|
| 163 | 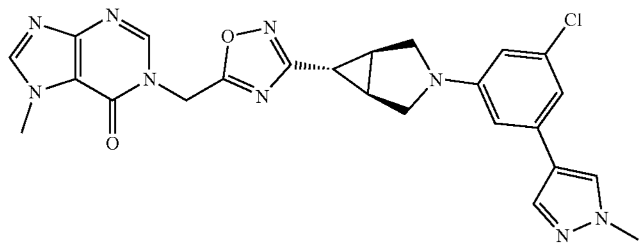 [SMILES: Cn1cc(-c2cc(Cl)cc(N3C[C@@H]4[C@H](C3)[C@H]4c3noc(Cn4cnc5ncn(C)c5c4=O)n3)c2)cn1] | 1-((3-((1R,5S,6r)-3-(3-chloro-5-(1-methyl-1H-pyrazol-4-yl)phenyl)-3-azabicyclo[3.1.0]hexan-6-yl)-1,2,4-oxadidzol-5-yl)methyl)-7-methyl-1,7-dihydro-6H-purin-6-one | 0.0713 | 0.023 |
| 164 | 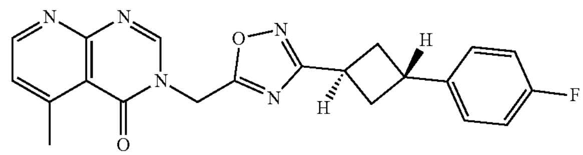 [SMILES: Cc1ccnc2ncn(Cc3nc([C@H]4C[C@H](c5ccc(F)cc5)C4)no3)c(=O)c12] | 3-((3-((1r,3r)-3-(4-fluorophenyl)cyclobutyl)-1,2,4-oxadiazol-5-yl)methyl)-5-methylpyrido[2,3-d]pyrimidin-4(3H)-one | 0.0151 | — |
| 165 | 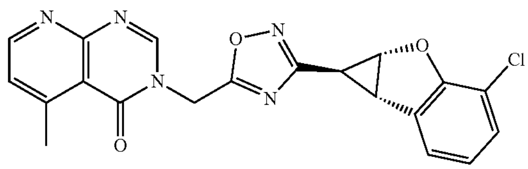 [SMILES: Cc1ccnc2ncn(Cc3nc([C@H]4[C@@H]5Oc6c(Cl)cccc6[C@@H]54)no3)c(=O)c12] | 3-((3-((1S,1aR,6bS)-3-chloro-1a,6b-dihydro-1H-cyclopropa[b]benzofuran-1-yl)-1,2,4-oxadiazol-5-yl)methyl)-5-methyl-pyrido[2,3-d]pyrimidin-4(3H)-one | 0.0222 | — |
| 166 | 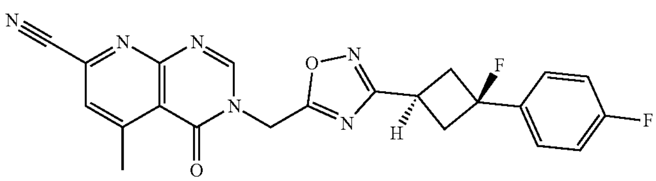 [SMILES: Cc1cc(C#N)nc2ncn(Cc3nc([C@H]4C[C@](F)(c5ccc(F)cc5)C4)no3)c(=O)c12] | 3-((3-((1s,3s)-3-fluoro-3-(4-fluorophenyl)cyclobutyl)-1,2,4-oxadiazol-5-yl)methyl)-5-methyl-4-oxo-3,4-dihydropyrido[2,3-d]pyrimidine-7-carbonitrile | 0.0376 | — |
| 167 | 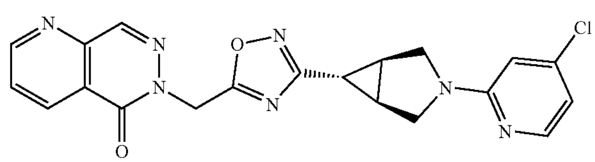 [SMILES: O=c1c2cccnc2cnn1Cc1nc([C@H]2[C@@H]3CN(c4cc(Cl)ccn4)C[C@@H]32)no1] | 6-((3-((1R,5S,6r)-3-(4-chloropyridin-2-yl)-3-azabicyclo[3.1.0]hexan-6-yl)-1,2,4-oxadiazol-5-yl)methyl)pyrido[2,3-d]pyridazin-5(6H)-one | 0.0511 | 0.046 |
| 168 | 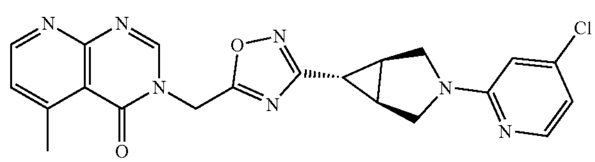 | 3-((3-((1R,5S,6r)-3-(4-chloropyridin-2-yl)-3-azabicyclo[3.1.0]hexan-6-yl)-1,2,4-oxadiazol-5-yl)methyl)-5-methylpyrido[2,3-d]pyrimidin-4(3H)-one | 0.0508 | — |
| 169 | 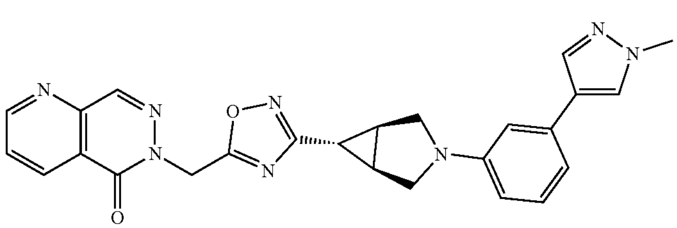 [SMILES: Cn1cc(-c2cccc(N3C[C@@H]4[C@H](C3)[C@H]4c3noc(Cn4ncc5ncccc5c4=O)n3)c2)cn1] | 6-((3-((1R,5S,6r)-3-(3-(1-methyl-1H-pyrazol-4-yl)phenyl)-3-azabicyclo[3.1.0]hexan-6-yl)-1,2,4-oxadiazol-5-yl)methyl)pyrido[2,3-d]pyridazin-5(6H)-one | 0.043 | 0.041 |
| 170 | 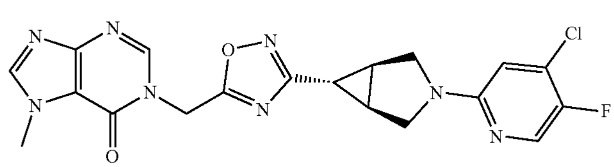 [SMILES: Cn1cnc2ncn(Cc3nc([C@H]4[C@@H]5CN(c6cc(Cl)c(F)cn6)C[C@@H]54)no3)c(=O)c21] | 1-((3-((1R,5S,6r)-3-(4-chloro-5-fluoropyridin-2-yl)-3-azabicyclo[3.1.0]hexan-6-yl)-1,2,4-oxadiazol-5-yl)methyl)-7-methyl-1,7-dihydro-6H-purin-6-one | 0.233 | 0.13 |

TABLE 1-continued

| Ex. | Structure | Name | IC$_{50}$ (10 min) | IC$_{50}$ (90 min) |
| --- | --- | --- | --- | --- |
| 171 | 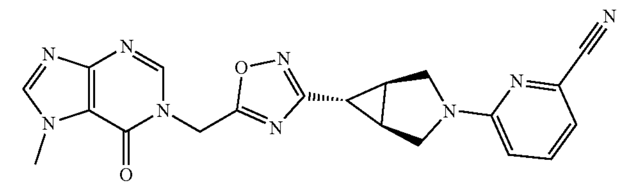 [SMILES: Cn1cnc2ncn(Cc3nc([C@H]4[C@@H]5CN(c6cccc(C#N)n6)C[C@@H]54)no3)c(=O)c21] | 6-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)picolinonitrile | 0.271 | 0.089 |
| 172 | 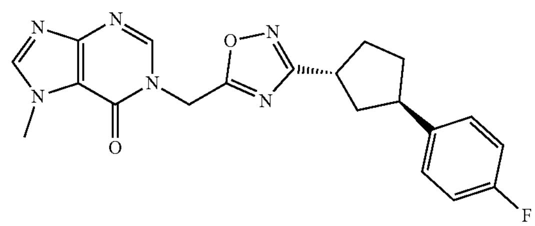 [SMILES: Cn1cnc2ncn(Cc3nc([C@@H]4CC[C@@H](c5ccc(F)cc5)C4)no3)c(=O)c21] | 1-((3-((1R,3R)-3-(4-fluorophenyl)cyclopentyl)-1,2,4-oxadiazol-5-yl)methyl)-7-methyl-1,7-dihydro-6H-purin-6-one | 0.0266 | 0.018 |
| 173 | 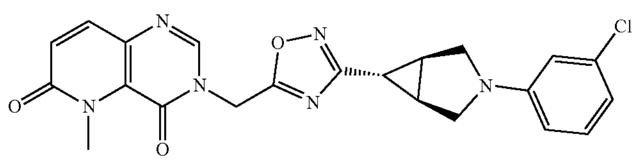 [SMILES: Cn1c(=O)ccc2ncn(Cc3nc([C@H]4[C@@H]5CN(c6cccc(Cl)c6)C[C@@H]54)no3)c(=O)c21] | 3-((3-((1R,5S,6r)-3-(3-chlorophenyl)-3-azabicyclo[3.1.0]hexan-6-yl)-1,2,4-oxadiazol-5-yl)methyl)-5-methyl-3,5-dihydropyrido[3,2-d]pyrimidine-4,6-dione | 0.00397 | — |
| 174 | 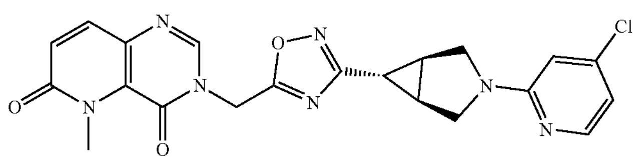 [SMILES: Cn1c(=O)ccc2ncn(Cc3nc([C@H]4[C@@H]5CN(c6cc(Cl)ccn6)C[C@@H]54)no3)c(=O)c21] | 3-((3-((1R,5S,6r)-3-(4-chloropyridin-2-yl)-3-azabicyclo[3.1.0]hexan-6-yl)-1,2,4-oxadiazol-5-yl)methyl)-5-methyl-3,5-dihydropyrido[3,2-d]pyrimidine-4,6-dione | 0.0606 | 0.05 |
| 175 | 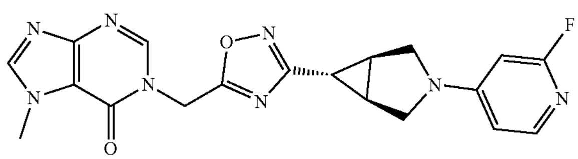 [SMILES: Cn1cnc2ncn(Cc3nc([C@H]4[C@@H]5CN(c6ccnc(F)c6)C[C@@H]54)no3)c(=O)c21] | 1-((3-((1R,5S,6r)-3-(2-fluoropyridin-4-yl)-3-azabicyclo[3.1.0]hexan-6-yl)-1,2,4-oxadiazol-5-yl)methyl)-7-methyl-1,7-dihydro-6H-purin-6-one | 0.42 | 0.073 |
| 176 | 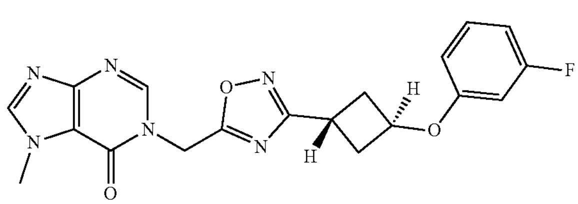 [SMILES: Cn1cnc2ncn(Cc3nc([C@H]4C[C@H](Oc5cccc(F)c5)C4)no3)c(=O)c21] | 1-((3-((1r,3r)-3-(3-fluorophenoxy)cyclobutyl)-1,2,4-oxadiazol-5-yl)methyl)-7-methyl-1,7-dihydro-6H-purin-6-one | 0.0243 | — |
| 177 | 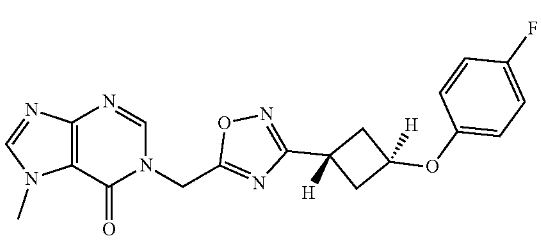 [SMILES: Cn1cnc2ncn(Cc3nc([C@H]4C[C@H](Oc5ccc(F)cc5)C4)no3)c(=O)c21] | 1-((3-((1r,3r)-3-(4-fluorophenoxy)cyclobutyl)-1,2,4-oxadiazol-5-yl)methyl)-7-methyl-1,7-dihydro-6H-purin-6-one | 0.0401 | — |

TABLE 1-continued

| Ex. | Structure | Name | IC$_{50}$ (10 min) | IC$_{50}$ (90 min) |
|---|---|---|---|---|
| 178 | 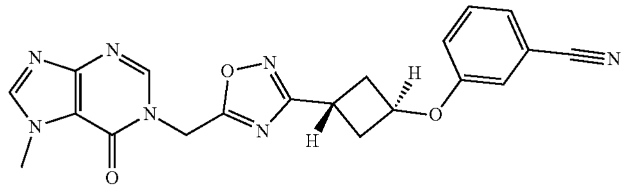 [SMILES: Cn1cnc2ncn(Cc3nc([C@H]4C[C@H](Oc5cccc(C#N)c5)C4)no3)c(=O)c21] | 3-((1r,3r)-3-(5-((7-methyl-6-oxo-6,7-dihydro-1H-purin-1-yl)methyl)-1,2,4-oxadiazol-3-yl)cyclobutoxy)benzonitrile | 0.0815 | — |
| 179 | 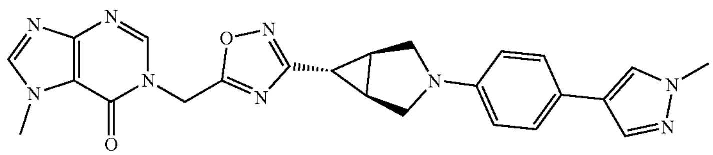 [SMILES: Cn1cc(-c2ccc(N3C[C@@H]4[C@H](C3)[C@H]4c3noc(Cn4cnc5ncn(C)c5c4=O)n3)cc2)cn1] | 7-methyl-1-((3-((1R,5S,6r)-3-(4-(1-methyl-1H-pyrazol-4-yl)phenyl)-3-azabicyclo[3.1.0]hexan-6-yl)-1,2,4-oxadiazol-5-yl)methyl)-1,7-dihydro-6H-purin-6-one | 0.134 | 0.067 |
| 180 | 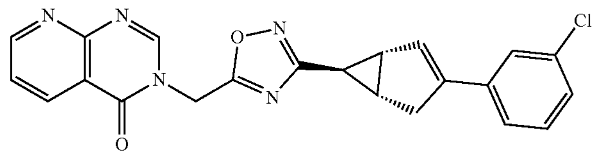 [SMILES: O=c1c2cccnc2ncn1Cc1nc([C@H]2[C@@H]3C=C(c4cccc(Cl)c4)C[C@@H]32)no1] | 3-((3-((1S,5S,6R)-3-(3-chlorophenyl)bicyclo[3.1.0]hex-2-en-6-yl)-1,2,4-oxadiazol-5-yl)methyl)pyrido[2,3-d]pyrimidin-4(3H)-one | 0.0233 | 0.024 |
| 181 | 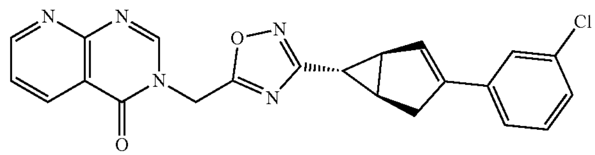 [SMILES: O=c1c2cccnc2ncn1Cc1nc([C@@H]2[C@H]3C=C(c4cccc(Cl)c4)C[C@H]32)no1] | 3-((3-((1R,5R,6S)-3-(3-chlorophenyl)bicyclo[3.1.0]hex-2-en-6-yl)-1,2,4-oxadiazol-5-yl)methyl)pyrido[2,3-d]pyrimidin-4(3H)-one | 0.0218 | 0.021 |
| 182 | 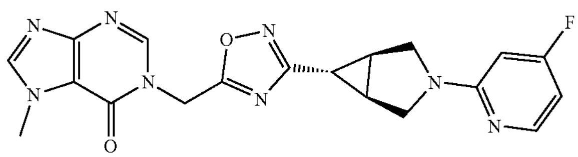 [SMILES: Cn1cnc2ncn(Cc3nc([C@H]4[C@@H]5CN(c6cc(F)ccn6)C[C@@H]54)no3)c(=O)c21] | 1-((3-((1R,5S,6r)-3-(4-fluoropyridin-2-yl)-3-azabicyclo[3.1.0]hexan-6-yl)-1,2,4-oxadiazol-5-yl)methyl)-7-methyl-1,7-dihydro-6H-purin-6-one | 0.194 | 0.043 |
| 183 | 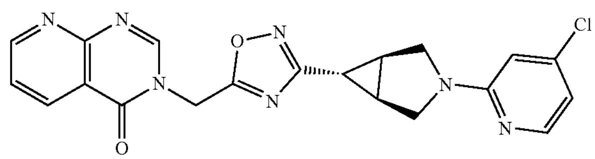 [SMILES: O=c1c2cccnc2ncn1Cc1nc([C@H]2[C@@H]3CN(c4cc(Cl)ccn4)C[C@@H]32)no1] | 3-((3-((1R,5S,6r)-3-(4-chloropyridin-2-yl)-3-azabicyclo[3.1.0]hexan-6-yl)-1,2,4-oxadiazol-5-yl)methyl)pyrido[2,3-d]pyrimidin-4(3H)-one | 0.0651 | 0.052 |
| 184 | 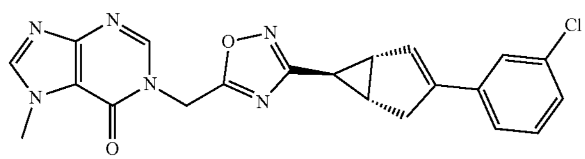 [SMILES: Cn1cnc2ncn(Cc3nc([C@H]4[C@@H]5C=C(c6cccc(Cl)c6)C[C@@H]54)no3)c(=O)c21] | 1-((3-((1S,5S,6R)-3-(3-chlorophenyl)bicyclo[3.1.0]hex-2-en-6-yl)-1,2,4-oxadiazol-5-yl)methyl)-7-methyl-1,7-dihydro-6H-purin-6-one | 0.00883 | 0.0018 |
| 185 | 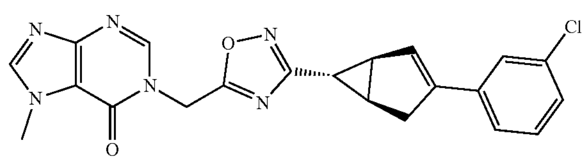 [SMILES: Cn1cnc2ncn(Cc3nc([C@@H]4[C@H]5C=C(c6cccc(Cl)c6)C[C@H]54)no3)c(=O)c21] | 1-((3-((1R,5R,6S)-3-(3-chlorophenyl)bicyclo[3.1.0]hex-2-en-6-yl)-1,2,4-oxadiazol-5-yl)methyl)-7-methyl-1,7-dihydro-6H-purin-6-one | 0.0185 | 0.0078 |

… TABLE 1-continued

| Ex. | Structure | Name | IC$_{50}$ (10 min) | IC$_{50}$ (90 min) |
|---|---|---|---|---|
| 186 | 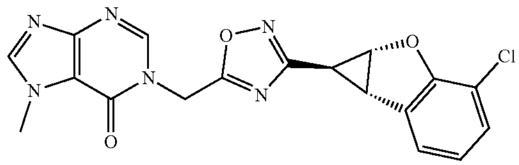 [SMILES: Cn1cnc2ncn(Cc3nc([C@H]4[C@@H]5Oc6c(Cl)cccc6[C@@H]54)no3)c(=O)c21] | 1-((3-((1S,1aR,6bS)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one | 0.0499 | 0.046 |
| 187 | 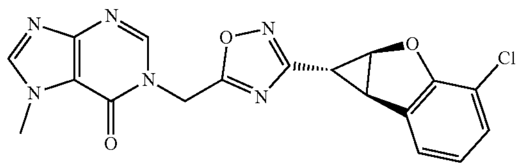 [SMILES: Cn1cnc2ncn(Cc3nc([C@@H]4[C@H]5Oc6c(Cl)cccc6[C@H]54)no3)c(=O)c21] | 1-((3-((1R,1aS,6bR)-3-chloro-1a,6b-dihydro-1H-cyclopropa[b]benzofuran-1-yl)-1,2,4-oxadiazol-5-yl)methyl)-7-methyl-1,7-dihydro-6H-purin-6-one | 0.763 | — |
| 188 | 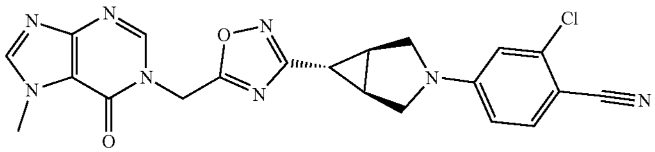 | 2-chloro-4-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0638 | 0.021 |
| 189 | 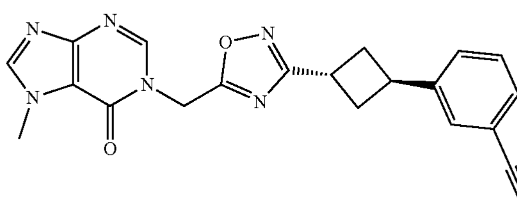 | 3-((1r,3r)-3-(5-((7-methyl-6-oxo-6,7-dihydro-1H-purin-1-yl)methyl)-1,2,4-oxadiazol-3-yl)cyclobutyl)benzonitrile | 0.0682 | — |
| 190 | 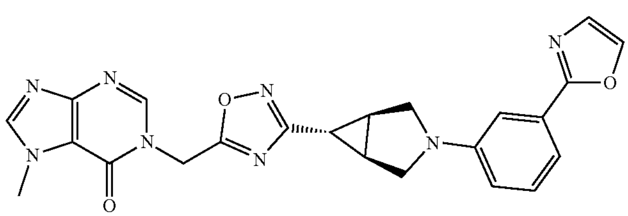 [SMILES: Cn1cnc2ncn(Cc3nc([C@H]4[C@@H]5CN(c6cccc(-c7ncco7)c6)C[C@@H]54)no3)c(=O)c21] | 7-methyl-1-((3-((1R,5S,6r)-3-(3-(oxazol-2-yl)phenyl)-3-azabicyclo[3.1.0]hexan-6-yl)-1,2,4-oxadiazol-5-yl)methyl)-1,7-dihydro-6H-purin-6-one | 0.0783 | 0.072 |
| 191 | 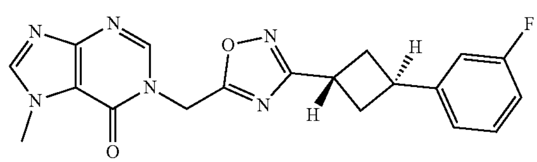 [SMILES: Cn1cnc2ncn(Cc3nc([C@H]4C[C@H](c5cccc(F)c5)C4)no3)c(=O)c21] | 1-((3-((1r,3r)-3-(3-fluorophenyl)cyclobutyl)-1,2,4-oxadiazol-5-yl)methyl)-7-methyl-1,7-dihydro-6H-purin-6-one | 0.083 | — |
| 192 | 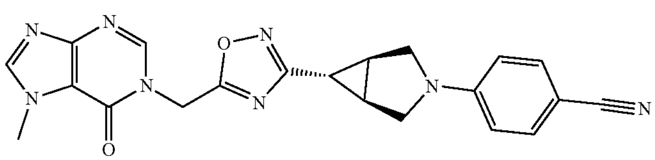 [SMILES: Cn1cnc2ncn(Cc3nc([C@H]4[C@@H]5CN(c6ccc(C#N)cc6)C[C@@H]54)no3)c(=O)c21] | 4-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0274 | 0.013 |
| 193 | 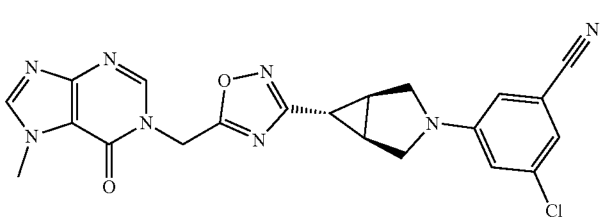 [SMILES: Cn1cnc2ncn(Cc3nc([C@H]4[C@@H]5CN(c6cc(Cl)cc(C#N)c6)C[C@@H]54)no3)c(=O)c21] | 3-chloro-5-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0371 | 0.032 |

TABLE 1-continued

| Ex. | Structure | Name | IC$_{50}$ (10 min) | IC$_{50}$ (90 min) |
|---|---|---|---|---|
| 194 | 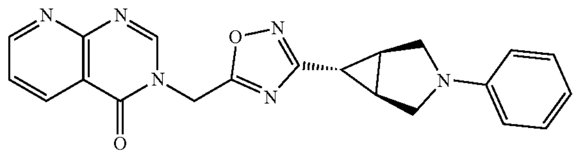 [SMILES: O=c1c2cccnc2ncn1Cc1nc([C@H]2[C@@H]3CN(c4ccccc4)C[C@@H]32)no1] | 3-(3-((1R,5S,6r)-3-phenyl-3-azabicyclo[3.1.0]hexan-6-yl)-1,2,4-oxadiazol-5-yl)methyl)pyrido[2,3-d]pyrimidin-4(3H)-one | 0.0201 | 0.015 |
| 195 | 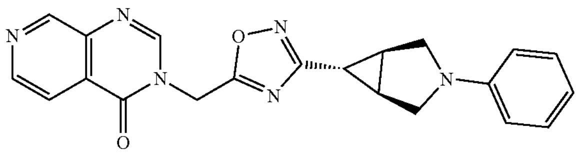 [SMILES: O=c1c2ccncc2ncn1Cc1nc([C@H]2[C@@H]3CN(c4ccccc4)C[C@@H]32)no1] | 3-(3-((1R,5S,6r)-3-phenyl-3-azabicyclo[3.1.0]hexan-6-yl)-1,2,4-oxadiazol-5-yl)methyl)pyrido[3,4-d]pyrimidin-4(3H)-one | 0.0994 | 0.11 |
| 196 | 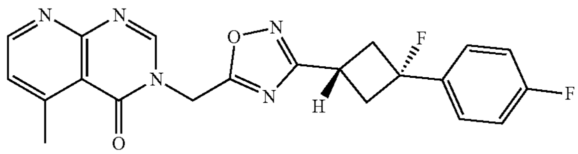 [SMILES: Cc1ccnc2ncn(Cc3nc([C@H]4C[C@](F)(c5ccc(F)cc5)C4)no3)c(=O)c12] | 3-(3-((1s,3s)-3-fluoro-3-(4-fluorophenyl)cyclobutyl)-1,2,4-oxadiazol-5-yl)methyl)-5-methyl-pyrido[2,3-d]pyrimidin-4(3H)-one | 0.013 | 0.03 |
| 197 | 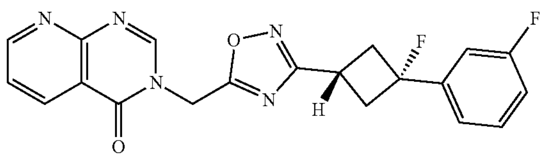 [SMILES: O=c1c2cccnc2ncn1Cc1nc([C@H]2C[C@](F)(c3cccc(F)c3)C2)no1] | 3-(3-((1s,3s)-3-fluoro-3-(3-fluorophenyl)cyclobutyl)-1,2,4-oxadiazol-5-yl)methyl)pyrido[2,3-d]pyrimidin-4(3H)-one | 0.0669 | — |
| 198 | 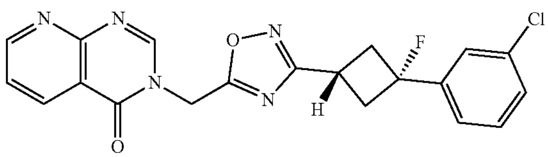 [SMILES: O=c1c2cccnc2ncn1Cc1nc([C@H]2C[C@](F)(c3cccc(Cl)c3)C2)no1] | 3-(3-((1s,3s)-3-(3-chlorophenyl)-3-fluorocyclobutyl)-1,2,4-oxadiazol-5-yl)methyl)pyrido[2,3-d]pyrimidin-4(3H)-one | 0.0587 | — |
| 199 | 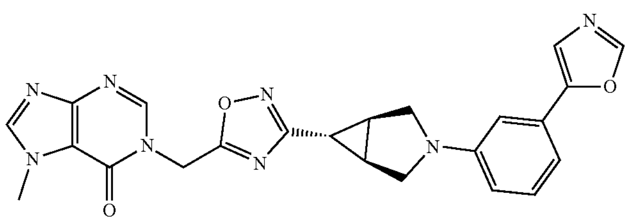 [SMILES: Cn1cnc2ncn(Cc3nc([C@H]4[C@@H]5CN(c6cccc(-c7cnco7)c6)C[C@@H]54)no3)c(=O)c21] | 7-methyl-1-((3-((1R,5S,6r)-3-(3-(oxazol-5-yl)phenyl)-3-azabicyclo[3.1.0]hexan-6-yl)-1,2,4-oxadiazol-5-yl)methyl)-1,7-dihydro-6H-purin-6-one | 0.0262 | 0.022 |
| 200 | 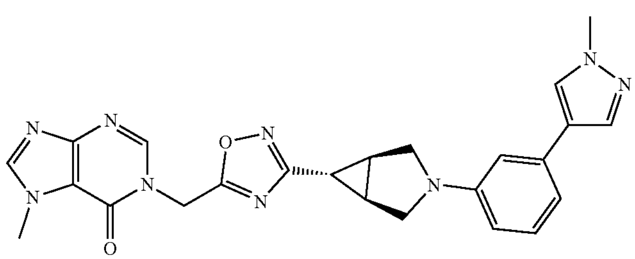 [SMILES: Cn1cc(-c2cccc(N3C[C@@H]4[C@H](C3)[C@H]4c3noc(Cn4cnc5ncn(C)c5c4=O)n3)c2)cn1] | 7-methyl-1-((3-((1R,5S,6r)-3-(3-(1-methyl-1H-pyrazol-4-yl)phenyl)-3-azabicyclo[3.1.0]hexan-6-yl)-1,2,4-oxadiazol-5-yl)methyl)-1,7-dihydro-6H-purin-6-one | 0.0384 | 0.017 |
| 201 | 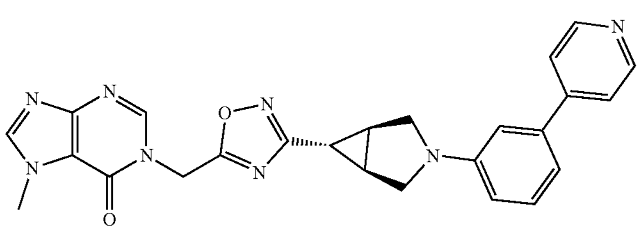 [SMILES: Cn1cnc2ncn(Cc3nc([C@H]4[C@@H]5CN(c6cccc(-c7ccncc7)c6)C[C@@H]54)no3)c(=O)c21] | 7-methyl-1-((3-((1R,5S,6r)-3-(3-(pyridin-4-yl)phenyl)-3-azabicyclo[3.1.0]hexan-6-yl)-1,2,4-oxadiazol-5-yl)methyl)-1,7-dihydro-6H-purin-6-one | 0.067 | 0.066 |

TABLE 1-continued

| Ex. | Structure | Name | IC$_{50}$ (10 min) | IC$_{50}$ (90 min) |
|---|---|---|---|---|
| 202 | 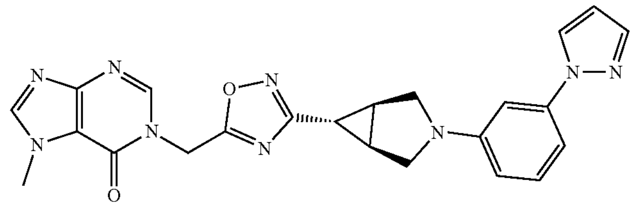 [SMILES: Cn1cnc2ncn(Cc3nc([C@H]4[C@@H]5CN(c6cccc(-n7cccn7)c6)C[C@@H]54)no3)c(=O)c21] | 1-((3-((1R,5S,6r)-3-(3-(1H-pyrazol-1-yl)phenyl)-3-azabicyclo[3.1.0]hexan-6-yl)-1,2,4-oxadiazol-5-yl)methyl)-7-methyl-1,7-dihydro-6H-purin-6-one | 0.0501 | — |
| 203 | 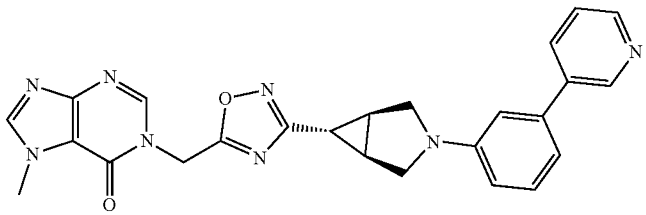 [SMILES: Cn1cnc2ncn(Cc3nc([C@H]4[C@@H]5CN(c6cccc(-c7cccnc7)c6)C[C@@H]54)no3)c(=O)c21] | 7-methyl-1-((3-((1R,5S,6r)-3-(3-(pyridin-3-yl)phenyl)-3-azabicyclo[3.1.0]hexan-6-yl)-1,2,4-oxadiazol-5-yl)methyl)-1,7-dihydro-6H-purin-6-one | 0.0463 | 0.078 |
| 204 | 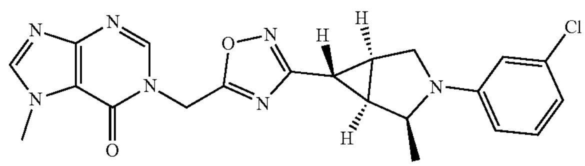 [SMILES: C[C@H]1[C@@H]2[C@H](CN1c1cccc(Cl)c1)[C@H]2c1noc(Cn2cnc3ncn(C)c3c2=O)n1] | 1-((3-((1R,2S,5S,6R)-3-(3-chlorophenyl)-2-methyl-3-azabicyclo[3.1.0]hexan-6-yl)-1,2,4-oxadiazol-5-yl)methyl)-7-methyl-1,7-dihydro-6H-purin-6-one | 0.335 | — |
| 205 | 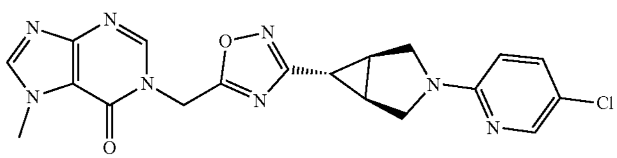 [SMILES: Cn1cnc2ncn(Cc3nc([C@H]4[C@@H]5CN(c6ccc(Cl)cn6)C[C@@H]54)no3)c(=O)c21] | 1-((3-((1R,5S,6r)-3-(5-chloropyridin-2-yl)-3-azabicyclo[3.1.0]hexan-6-yl)-1,2,4-oxadiazol-5-yl)methyl)-7-methyl-1,7-dihydro-6H-purin-6-one | 0.496 | 0.086 |
| 206 | 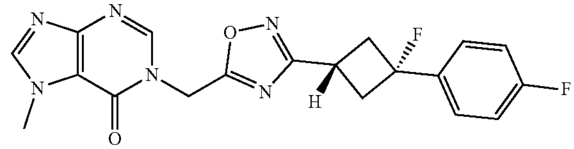 [SMILES: Cn1cnc2ncn(Cc3nc([C@H]4C[C@](F)(c5ccc(F)cc5)C4)no3)c(=O)c21] | 1-((3-((1s,3s)-3-fluoro-3-(4-fluorophenyl)cyclobutyl)-1,2,4-oxadiazol-5-yl)methyl)-7-methyl-1,7-dihydro-6H-purin-6-one | 0.313 | — |
| 207 | 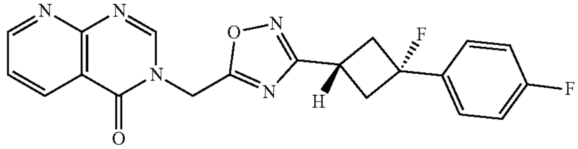 [SMILES: O=c1c2cccnc2ncn1Cc1nc([C@H]2C[C@](F)(c3ccc(F)cc3)C2)no1] | 3-((3-((1s,3s)-3-fluoro-3-(4-fluorophenyl)cyclobutyl)-1,2,4-oxadiazol-5-yl)methyl)pyrido[2,3-d]pyrimidin-4(3H)-one | 0.095 | — |
| 208 | 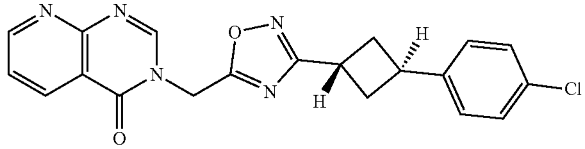 | 3-((3-((1r,3r)-3-(4-chlorophenyl)cyclobutyl)-1,2,4-oxadiazol-5-yl)methyl)pyrido[2,3-d]pyrimidin-4(3H)-one | 0.0785 | — |
| 209 | 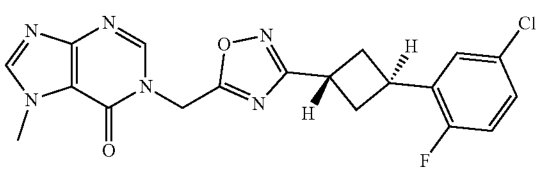 [SMILES: Cn1cnc2ncn(Cc3nc([C@H]4C[C@H](c5cc(Cl)ccc5F)C4)no3)c(=O)c21] | 1-((3-((1r,3r)-3-(5-chloro-2-fluorophenyl)cyclobutyl)-1,2,4-oxadiazol-5-yl)methyl)-7-methyl-1,7-dihydro-6H-purin-6-one | 0.886 | — |

TABLE 1-continued

| Ex. | Structure | Name | IC$_{50}$ (10 min) | IC$_{50}$ (90 min) |
|---|---|---|---|---|
| 210 | 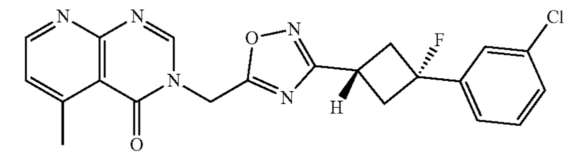 [SMILES: Cc1ccnc2ncn(Cc3nc([C@H]4C[C@](F)(c5cccc(Cl)c5)C4)no3)c(=O)c12] | 3-((3-((1s,3s)-3-(3-chlorophenyl)-3-fluorocyclobutyl)-1,2,4-oxadiazol-5-yl)methyl)-5-methyl-pyrido[2,3-d]pyrimidin-4(3H)-one | 0.0151 | — |
| 211 | 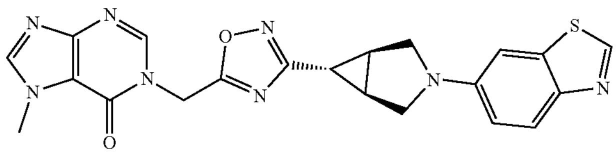 [SMILES: Cn1cnc2ncn(Cc3nc([C@H]4[C@@H]5CN(c6ccc7ncsc7c6)C[C@@H]54)no3)c(=O)c21] | 1-((3-((1R,5S,6r)-3-(benzo[d]thiazol-6-yl)-3-azabicyclo[3.1.0]hexan-6-yl)-1,2,4-oxadiazol-5-yl)methyl)-7-methyl-1,7-dihydro-6H-purin-6-one | 0.0638 | 0.01 |
| 212 | 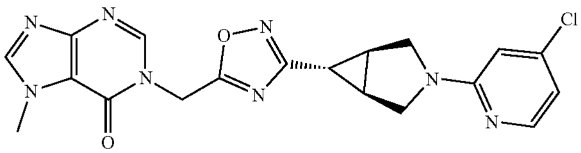 [SMILES: Cn1cnc2ncn(Cc3nc([C@H]4[C@@H]5CN(c6cc(Cl)ccn6)C[C@@H]54)no3)c(=O)c21] | 1-((3-((1R,5S,6r)-3-(4-chloropyridin-2-yl)-3-azabicyclo[3.1.0]hexan-6-yl)-1,2,4-oxadiazol-5-yl)methyl)-7-methyl-1,7-dihydro-6H-purin-6-one | 0.0847 | 0.025 |
| 213 | 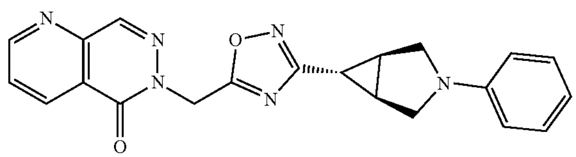 [SMILES: O=c1c2cccnc2cnn1Cc1nc([C@H]2[C@@H]3CN(c4ccccc4)C[C@@H]32)no1] | 6-((3-((1R,5S,6r)-3-phenyl-3-azabicyclo[3.1.0]hexan-6-yl)-1,2,4-oxadiazol-5-yl)methyl)pyrido[2,3-d]pyridazin-5(6H)-one | 0.00617 | 0.0051 |
| 214 | 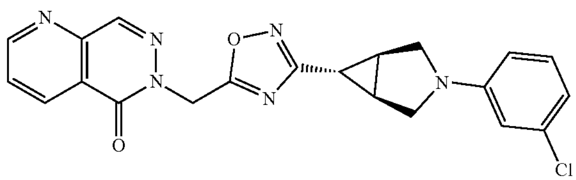 [SMILES: O=c1c2cccnc2cnn1Cc1nc([C@H]2[C@@H]3CN(c4cccc(Cl)c4)C[C@@H]32)no1] | 6-((3-((1R,5S,6r)-3-(3-chlorophenyl)-3-azabicyclo[3.1.0]hexan-6-yl)-1,2,4-oxadiazol-5-yl)methyl)pyrido[2,3-d]pyridazin-5(6H)-one | 0.00288 | — |
| 215 | 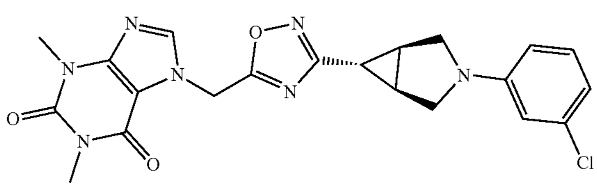 [SMILES: Cn1c(=O)c2c(ncn2Cc2nc([C@H]3[C@@H]4CN(c5cccc(Cl)c5)C[C@@H]43)no2)n(C)c1=O] | 7-((3-((1R,5S,6r)-3-(3-chlorophenyl)-3-azabicyclo[3.1.0]hexan-6-yl)-1,2,4-oxadiazol-5-yl)methyl)-1,3-dimethyl-3,7-dihydro-1H-purine-2,6-dione | 0.0565 | — |
| 216 | 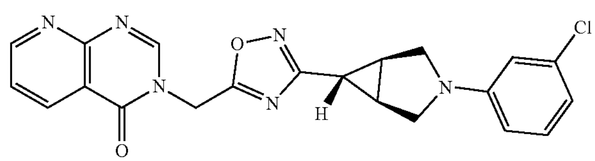 [SMILES: O=c1c2cccnc2ncn1Cc1nc([C@H]2[C@@H]3CN(c4cccc(Cl)c4)C[C@@H]32)no1] | 3-((3-((1R,5S,6r)-3-(3-chlorophenyl)-3-azabicyclo[3.1.0]hexan-6-yl)-1,2,4-oxadiazol-5-yl)methyl)pyrido[2,3-d]pyrimidin-4(3H)-one | 0.0138 | 0.013 |
| 217 | 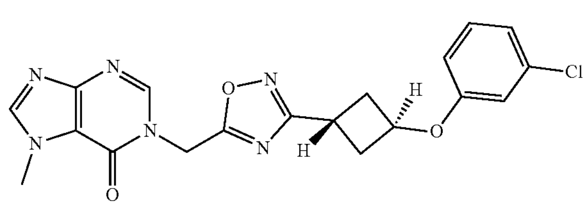 [SMILES: Cn1cnc2ncn(Cc3nc([C@H]4C[C@H](Oc5cccc(Cl)c5)C4)no3)c(=O)c21] | 1-((3-((1r,3r)-3-(3-chlorophenoxy)cyclobutyl)-1,2,4-oxadiazol-5-yl)methyl)-7-methyl-1,7-dihydro-6H-purin-6-one | 0.038 | — |

TABLE 1-continued

| Ex. | Structure | Name | IC$_{50}$ (10 min) | IC$_{50}$ (90 min) |
|---|---|---|---|---|
| 218 | 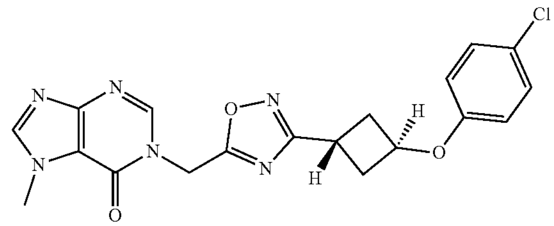 [SMILES: Cn1cnc2ncn(Cc3nc([C@H]4C[C@H](Oc5ccc(Cl)cc5)C4)no3)c(=O)c21] | 1-((3-((1r,3r)-3-(4-chlorophenoxy)cyclobutyl)-1,2,4-oxadiazol-5-yl)methyl)-7-methyl-1,7-dihydro-6H-purin-6-one | 0.0249 | 0.013 |
| 219 | 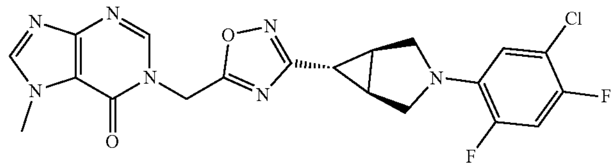 [SMILES: Cn1cnc2ncn(Cc3nc([C@H]4[C@@H]5CN(c6cc(Cl)c(F)cc6F)C[C@@H]54)no3)c(=O)c21] | 1-((3-((1R,5S,6r)-3-(5-chloro-2,4-difluorophenyl)-3-azabicyclo[3.1.0]hexan-6-yl)-1,2,4-oxadiazol-5-yl)methyl)-7-methyl-1,7-dihydro-6H-purin-6-one | 0.0293 | 0.031 |
| 220 | 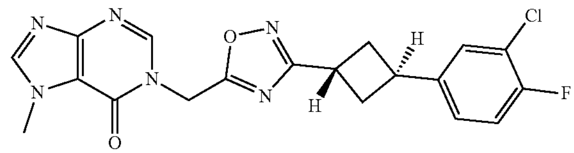 [SMILES: Cn1cnc2ncn(Cc3nc([C@H]4C[C@H](c5ccc(F)c(Cl)c5)C4)no3)c(=O)c21] | 1-((3-((1r,3r)-3-(3-chloro-4-fluorophenyl)cyclobutyl)-1,2,4-oxadiazol-5-yl)methyl)-7-methyl-1,7-dihydro-6H-purin-6-one | 0.0546 | — |
| 221 | 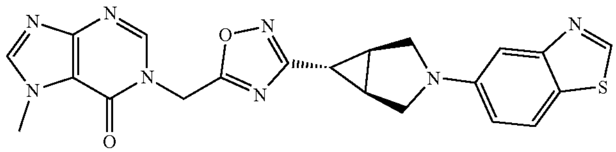 [SMILES: Cn1cnc2ncn(Cc3nc([C@H]4[C@@H]5CN(c6ccc7scnc7c6)C[C@@H]54)no3)c(=O)c21] | 1-((3-((1R,5S,6r)-3-(benzo[d]thiazol-5-yl)-3-azabicyclo[3.1.0]hexan-6-yl)-1,2,4-oxadiazol-5-yl)methyl)-7-methyl-1,7-dihydro-6H-purin-6-one | 0.094 | 0.041 |
| 222 | 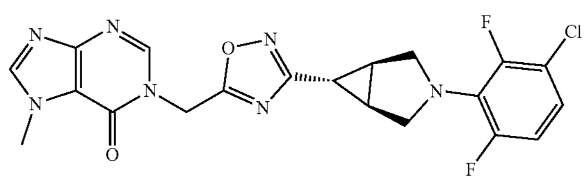 [SMILES: Cn1cnc2ncn(Cc3nc([C@H]4[C@@H]5CN(c6c(F)ccc(Cl)c6F)C[C@@H]54)no3)c(=O)c21] | 1-((3-((1R,5S,6r)-3-(3-chloro-2,6-difluorophenyl)-3-azabicyclo[3.1.0]hexan-6-yl)-1,2,4-oxadiazol-5-yl)methyl)-7-methyl-1,7-dihydro-6H-purin-6-one | 0.0297 | 0.0067 |
| 223 | 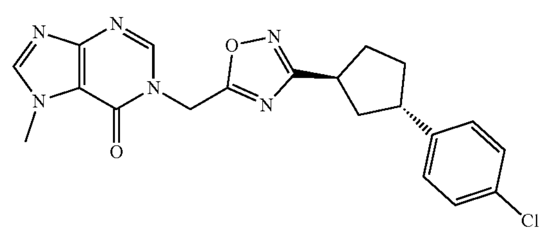 [SMILES: Cn1cnc2ncn(Cc3nc([C@H]4CC[C@H](c5ccc(Cl)cc5)C4)no3)c(=O)c21] | 1-((3-((1S,3S)-3-(4-chlorophenyl)cyclopentyl)-1,2,4-oxadiazol-5-yl)methyl)-7-methyl-1,7-dihydro-6H-purin-6-one | 0.0222 | — |
| 224 | 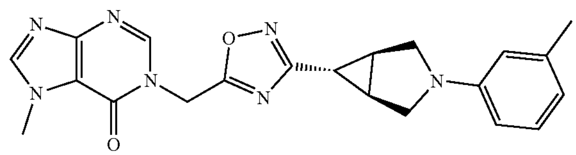 [SMILES: Cc1cccc(N2C[C@@H]3[C@H](C2)[C@H]3c2noc(Cn3cnc4ncn(C)c4c3=O)n2)c1] | 7-methyl-1-((3-((1R,5S,6r)-3-(m-tolyl)-3-azabicyclo[3.1.0]hexan-6-yl)-1,2,4-oxadiazol-5-yl)methyl)-1,7-dihydro-6H-purin-6-one | 0.0716 | 0.019 |
| 225 | 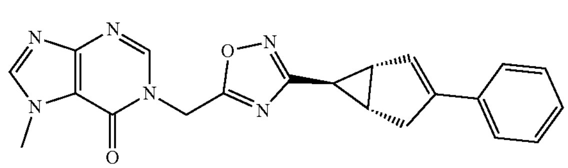 [SMILES: Cn1cnc2ncn(Cc3nc([C@H]4[C@@H]5C=C(c6ccccc6)C[C@@H]54)no3)c(=O)c21] | 7-methyl-1-((3-((1S,5S,6R)-3-phenylbicyclo[3.1.0]hex-2-en-6-yl)-1,2,4-oxadiazol-5-yl)methyl)-1,7-dihydro-6H-purin-6-one | 0.0138 | 0.0017 |

TABLE 1-continued

| Ex. | Structure | Name | IC$_{50}$ (10 min) | IC$_{50}$ (90 min) |
|---|---|---|---|---|
| 226 | 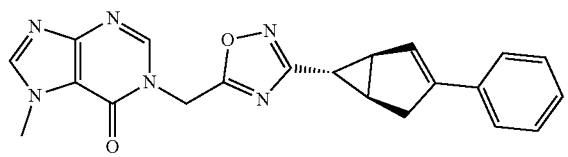 [SMILES: Cn1cnc2ncn(Cc3nc([C@@H]4[C@H]5C=C(c6ccccc6)C[C@H]54)no3)c(=O)c21] | 7-methyl-1-((3-((1R,5R,6S)-3-phenyl-bicyclo[3.1.0]hex-2-en-6-yl)-1,2,4-oxadiazol-5-yl)methyl)-1,7-dihydro-6H-purin-6-one | 0.0216 | 0.0099 |
| 227 | 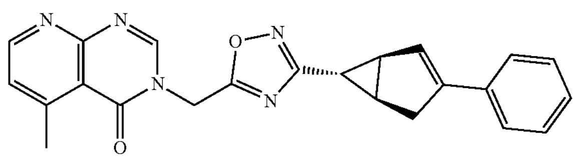 [SMILES: Cc1ccnc2ncn(Cc3nc([C@@H]4[C@H]5C=C(c6ccccc6)C[C@H]54)no3)c(=O)c12] | 5-methyl-3-((3-((1R,5R,6S)-3-phenylbicyclo[3.1.0]hex-2-en-6-yl)-1,2,4-oxadiazol-5-yl)methyl)pyrido[2,3-d]pyrimidin-4(3H)-one | 0.014 | — |
| 228 | 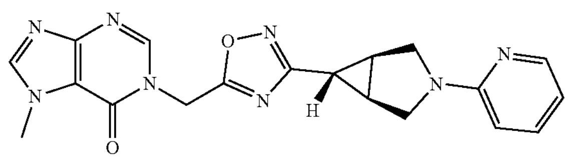 [SMILES: Cn1cnc2ncn(Cc3nc([C@H]4[C@@H]5CN(c6ccccn6)C[C@@H]54)no3)c(=O)c21] | 7-methyl-1-((3-((1R,5S,6r)-3-(pyridin-2-yl)-3-azabicyclo[3.1.0]hexan-6-yl)-1,2,4-oxadiazol-5-yl)methyl)-1,7-dihydro-6H-purin-6-one | 0.223 | 0.13 |
| 229 | 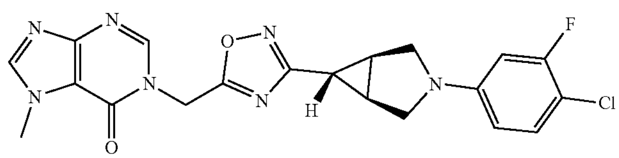 [SMILES: Cn1cnc2ncn(Cc3nc([C@H]4[C@@H]5CN(c6ccc(Cl)c(F)c6)C[C@@H]54)no3)c(=O)c21] | 1-((3-((1R,5S,6r)-3-(4-chloro-3-fluoro-phenyl)-3-azabicyclo[3.1.0]hexan-6-yl)-1,2,4-oxadiazol-5-yl)methyl)-7-methyl-1,7-dihydro-6H-purin-6-one | 0.0217 | 0.01 |
| 230 | 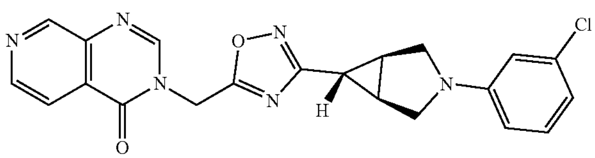 [SMILES: O=c1c2ccncc2ncn1Cc1nc([C@H]2[C@@H]3CN(c4cccc(Cl)c4)C[C@@H]32)no1] | 3-((3-((1R,5S,6r)-3-(3-chlorophenyl)-3-azabicyclo[3.1.0]hexan-6-yl)-1,2,4-oxadiazol-5-yl)methyl)pyrido[3,4-d]pyrimidin-4(3H)-one | 0.0331 | — |
| 231 | 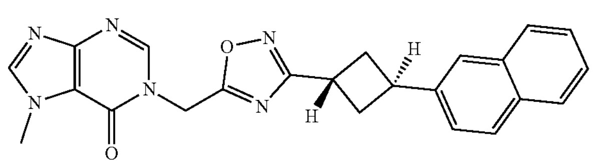 [SMILES: Cn1cnc2ncn(Cc3nc([C@H]4C[C@H](c5ccc6ccccc6c5)C4)no3)c(=O)c21] | 7-methyl-1-((3-((1r,3r)-3-(naphthalen-2-yl)cyclobutyl)-1,2,4-oxadiazol-5-yl)methyl)-1,7-dihydro-6H-purin-6-one | 0.0573 | — |
| 232 | 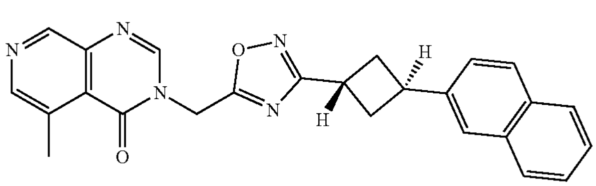 [SMILES: Cc1cncc2ncn(Cc3nc([C@H]4C[C@H](c5ccc6ccccc6c5)C4)no3)c(=O)c12] | 3-((3-((1s,3s)-3-hydroxy-3-(naphthalen-2-yl)cyclobutyl)-1,2,4-oxadiazol-5-yl)methyl)-5-methylpyrido[3,4-d]pyrimidin-4(3H)-one | 0.0145 | — |
| 233 | 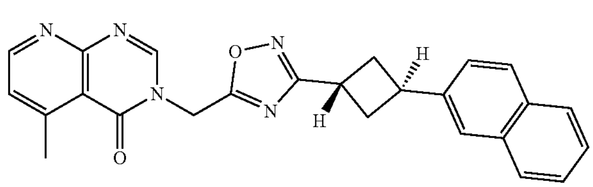 [SMILES: Cc1ccnc2ncn(Cc3nc([C@H]4C[C@H](c5ccc6ccccc6c5)C4)no3)c(=O)c12] | 3-((3-((1s,3s)-3-hydroxy-3-(naphthalen-2-yl)cyclobutyl)-1,2,4-oxadiazol-5-yl)methyl)-5-methylpyrido[2,3-d]pyrimidin-4(3H)-one | 0.0386 | — |

TABLE 1-continued

| Ex. | Structure | Name | IC$_{50}$ (10 min) | IC$_{50}$ (90 min) |
|---|---|---|---|---|
| 234 | 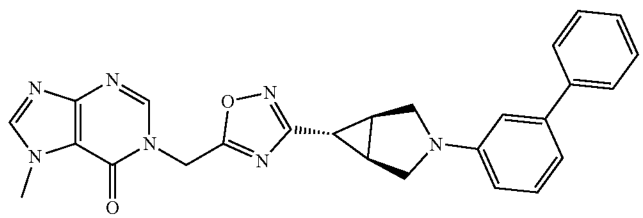 [SMILES: Cn1cnc2ncn(Cc3nc([C@H]4[C@@H]5CN(c6cccc(-c7ccccc7)c6)C[C@@H]54)no3)c(=O)c21] | 1-((3-((1R,5S,6r)-3-([1,1'-biphenyl]-3-yl)-3-azabicyclo[3.1.0]hexan-6-yl)-1,2,4-oxadiazol-5-yl)methyl)-7-methyl-1,7-dihydro-6H-purin-6-one | 0.34 | — |
| 235 | 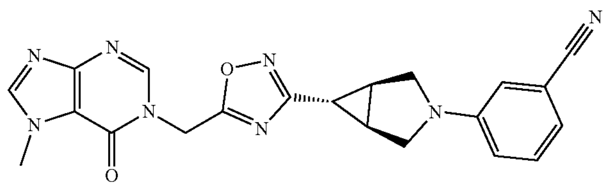 [SMILES: Cn1cnc2ncn(Cc3nc([C@H]4[C@@H]5CN(c6cccc(C#N)c6)C[C@@H]54)no3)c(=O)c21] | 3-((1R,5S,6r)-6-(5-((7-methyl-6-oxo-6,7-dihydro-1H-purin-1-yl)methyl)-1,2,4-oxadiazol-3-yl)-3-azabicyclo[3.1.0]hexan-3-yl)benzonitrile | 0.0735 | 0.017 |
| 236 | 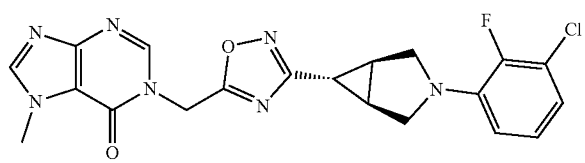 [SMILES: Cn1cnc2ncn(Cc3nc([C@H]4[C@@H]5CN(c6cccc(Cl)c6F)C[C@@H]54)no3)c(=O)c21] | 1-((3-((1R,5S,6r)-3-(3-chloro-2-fluoro-phenyl)-3-azabicyclo[3.1.0]hexan-6-yl)-1,2,4-oxadiazol-5-yl)methyl)-7-methyl-1,7-dihydro-6H-purin-6-one | 0.0213 | 0.0044 |
| 237 | 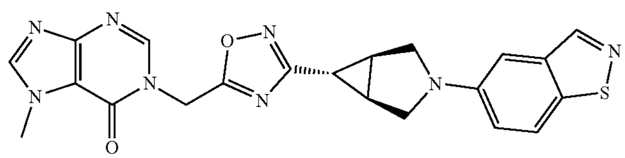 [SMILES: Cn1cnc2ncn(Cc3nc([C@H]4[C@@H]5CN(c6ccc7sncc7c6)C[C@@H]54)no3)c(=O)c21] | 1-((3-((1R,5S,6r)-3-(benzo[d]isothiazol-5-yl)-3-azabicyclo[3.1.0]hexan-6-yl)-1,2,4-oxadiazol-5-yl)methyl)-7-methyl-1,7-dihydro-6H-purin-6-one | 0.0182 | 0.0021 |
| 238 | 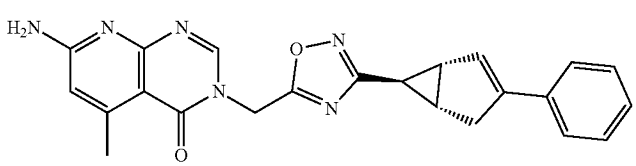 [SMILES: Cc1cc(N)nc2ncn(Cc3nc([C@H]4[C@@H]5C=C(c6ccccc6)C[C@@H]54)no3)c(=O)c12] | 7-amino-5-methyl-3-[[3-[(1S,5S,6R)-3-phenyl-6-bicyclo[3.1.0]hex-2-enyl]-1,2,4-oxadiazol-5-yl]methyl]pyrido[2,3-d]pyrimidin-4-one | 0.0113 | 0.0015 |
| 239 | 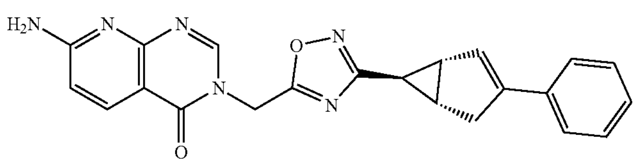 [SMILES: Nc1ccc2c(=O)n(Cc3nc([C@H]4[C@@H]5C=C(c6ccccc6)C[C@@H]54)no3)cnc2n1] | 7-amino-3-[[3-[(1S,5S,6R)-3-phenyl-6-bicyclo[3.1.0]hex-2-enyl]-1,2,4-oxadiazol-5-yl]methyl]pyrido[2,3-d]pyrimidin-4-one | 0.0105 | 0.0053 |
| 240 | 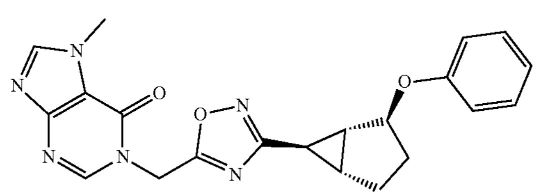 [SMILES: Cn1cnc2ncn(Cc3nc([C@@H]4[C@H]5CC[C@H](Oc6ccccc6)[C@H]54)no3)c(=O)c21] | 7-methyl-1-[[3-[(1R,2S,5R,6R)-2-phenoxy-6-bicyclo[3.1.0]hexanyl]-1,2,4-oxadiazol-5-yl]methyl]purin-6-one | 0.254 | 0.08 |
| 241 | 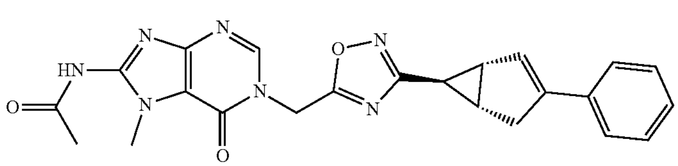 [SMILES: CC(=O)Nc1nc2ncn(Cc3nc([C@H]4[C@@H]5C=C(c6ccccc6)C[C@@H]54)no3)c(=O)c2n1C] | N-[7-methyl-6-oxo-1-[[3-[(1S,5S,6R)-3-phenyl-6-bicyclo[3.1.0]hex-2-enyl]-1,2,4-oxadiazol-5-yl]methyl]purin-8-yl]acetamide | 0.0669 | 0.018 |

TABLE 1-continued

| Ex. | Structure | Name | IC$_{50}$ (10 min) | IC$_{50}$ (90 min) |
|---|---|---|---|---|
| 242 | 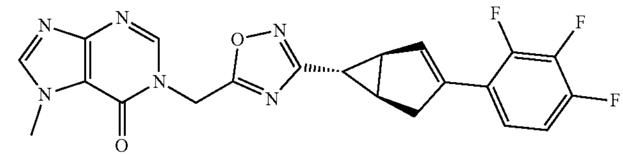 [SMILES: Cn1cnc2ncn(Cc3nc([C@@H]4[C@H]5C=C(c6ccc(F)c(F)c6F)C[C@H]54)no3)c(=O)c21] | 7-methyl-1-[[3-[(1R,5R,6S)-3-(2,3,4-trifluorophenyl)-6-bicyclo[3.1.0]hex-2-enyl]-1,2,4-oxadiazol-5-yl]methyl]purin-6-one | 0.0191 | 0.0063 |
| 243 | 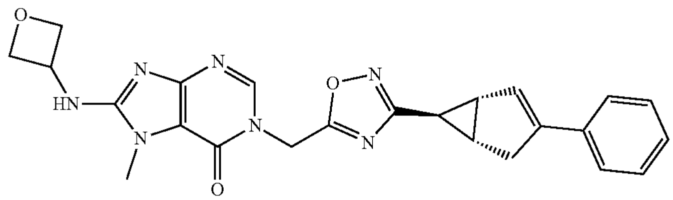 [SMILES: Cn1c(NC2COC2)nc2ncn(Cc3nc([C@H]4[C@@H]5C=C(c6ccccc6)C[C@@H]54)no3)c(=O)c21] | 7-methyl-8-(oxetan-3-ylamino)-1-[[3-[(1S,5S,6R)-3-phenyl-6-bicyclo[3.1.0]hex-2-enyl]-1,2,4-oxadiazol-5-yl]methyl]purin-6-one | 0.101 | 0.045 |
| 244 | 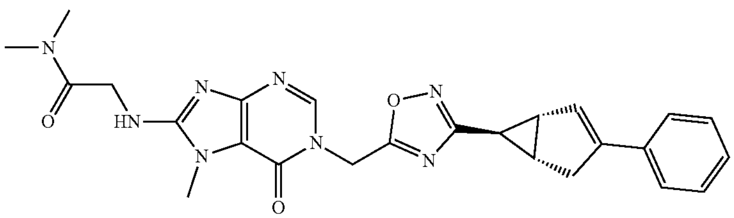 [SMILES: CN(C)C(=O)CNc1nc2ncn(Cc3nc([C@H]4[C@@H]5C=C(c6ccccc6)C[C@@H]54)no3)c(=O)c2n1C] | N,N-dimethyl-2-[[7-methyl-6-oxo-1-[[3-[(1S,5S,6R)-3-phenyl-6-bicyclo[3.1.0]hex-2-enyl]-1,2,4-oxadiazol-5-yl]methyl]purin-8-yl]amino]acetamide | 0.0687 | 0.026 |
| 245 | 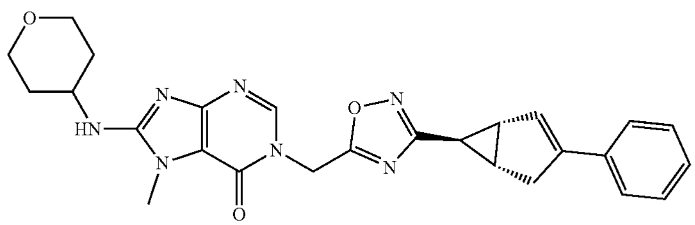 [SMILES: Cn1c(NC2CCOCC2)nc2ncn(Cc3nc([C@H]4[C@@H]5C=C(c6ccccc6)C[C@@H]54)no3)c(=O)c21] | 7-methyl-1-[[3-[(1S,5S,6R)-3-phenyl-6-bicyclo[3.1.0]hex-2-enyl]-1,2,4-oxadiazol-5-yl]methyl]-8-(tetrahydropyran-4-ylamino)purin-6-one | 0.0799 | 0.043 |
| 246 | 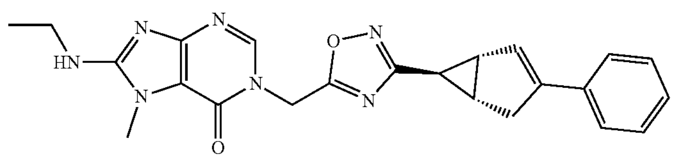 [SMILES: CCNc1nc2ncn(Cc3nc([C@H]4[C@@H]5C=C(c6ccccc6)C[C@@H]54)no3)c(=O)c2n1C] | 8-(ethylamino)-7-methyl-1-[[3-[(1S,5S,6R)-3-phenyl-6-bicyclo[3.1.0]hex-2-enyl]-1,2,4-oxadiazol-5-yl]methyl]purin-6-one | 0.0539 | 0.029 |
| 247 | 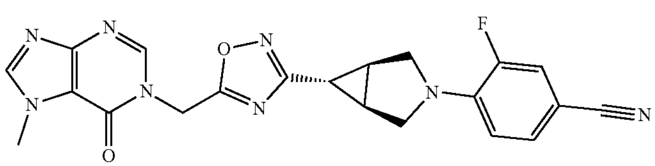 [SMILES: Cn1cnc2ncn(Cc3nc([C@H]4[C@@H]5CN(c6ccc(C#N)cc6F)C[C@@H]54)no3)c(=O)c21] | 3-fluoro-4-[(1S,5R)-6-[5-[(7-methyl-6-oxo-purin-1-yl)methyl]-1,2,4-oxadiazol-3-yl]-3-azabicyclo[3.1.0]hexan-3-yl]benzonitrile | 0.0579 | 0.023 |
| 248 | 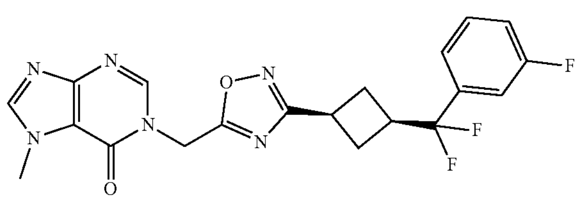 [SMILES: Cn1cnc2ncn(Cc3nc([C@H]4C[C@@H](C(F)(F)c5cccc(F)c5)C4)no3)c(=O)c21] | 1-[[3-[trans-3-[difluoro-(3-fluorophenyl)methyl]cyclobutyl]-1,2,4-oxadiazol-5-yl]methyl]-7-methyl-purin-6-one | 0.0111 | 0.0055 |
| 249 | 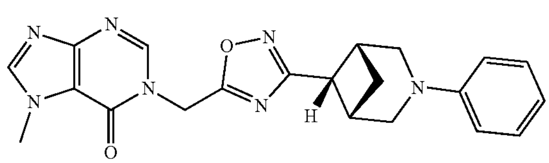 [SMILES: Cn1cnc2ncn(Cc3nc([C@H]4[C@@H]5C[C@H]4CN(c4ccccc4)C5)no3)c(=O)c21] | 7-methyl-1-((3-((1R,5S,6s)-3-phenyl-3-azabicyclo[3.1.1]heptan-6-yl)-1,2,4-oxadiazol-5-yl)methyl)-1,7-dihydro-6H-purin-6-one | 0.0834 | 0.072 |

TABLE 1-continued

| Ex. | Structure | Name | IC$_{50}$ (10 min) | IC$_{50}$ (90 min) |
|---|---|---|---|---|
| 250 | 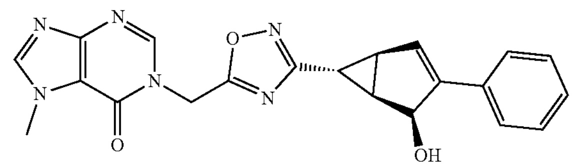 [SMILES: Cn1cnc2ncn(Cc3nc([C@@H]4[C@H]5C=C(c6ccccc6)[C@@H](O)[C@H]54)no3)c(=O)c21] | 7-methyl-1-[[3-[(1R, 4S,5R,6R)-4-hydroxy-3-phenyl-6-bicyclo[3.1.0]hex-2-enyl]-1,2,4-oxadiazol-5-yl]methyl]purin-6-one | 0.312 | 0.04 |
| 251 | 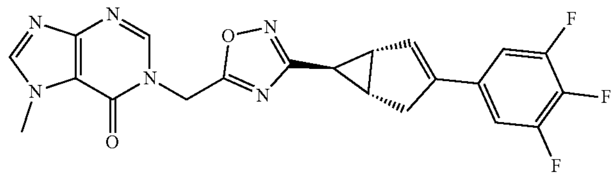 [SMILES: Cn1cnc2ncn(Cc3nc([C@H]4[C@@H]5C=C(c6cc(F)c(F)c(F)c6)C[C@@H]54)no3)c(=O)c21] | 7-methyl-1-[[3-[(1S,5S,6R)-3-(3,4,5-trifluorophendyl)-6-bicyclo[3.1.0]hex-2-enyl]-1,2,4-oxadiazol-5-yl]methyl]purin-6-one | 0.0149 | 0.002 |
| 252 | 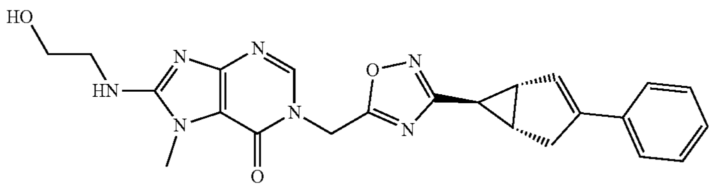 [SMILES: Cn1c(NCCO)nc2ncn(Cc3nc([C@H]4[C@@H]5C=C(c6ccccc6)C[C@@H]54)no3)c(=O)c21] | 8-(2-hydroxyethyl amino)-7-methyl-1-[[3-[(1S,5S,6R)-3-phenyl-6-bicyclo[3.1.0]hex-2-enyl]-1,2,4-oxadiazol-5-yl]methyl]purin-6-one | 0.304 | 0.068 |
| 253 | 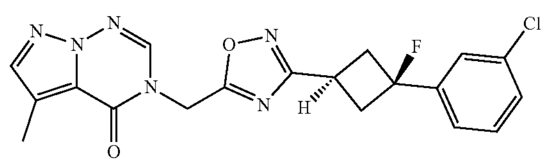 [SMILES: Cc1cnn2ncn(Cc3nc([C@H]4C[C@](F)(c5cccc(Cl)c5)C4)no3)c(=O)c12] | 3-[[3-[trans-3-(3-chlorophenyl)-3-fluoro-cyclobutyl]-1,2,4-oxadiazol-5-yl]methyl]-5-methyl-pyrazolo[5,1-f][1,2,4]triazin-4-one | 0.0435 | 0.031 |
| 254 | 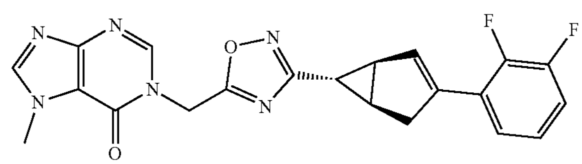 [SMILES: Cn1cnc2ncn(Cc3nc([C@@H]4[C@H]5C=C(c6cccc(F)c6F)C[C@H]54)no3)c(=O)c21] | 7-methyl-1-[[3-[(1R,5R,6S)-3-(2,3-difluorophenyl)-6-bicyclo[3.1.0]hex-2-enyl]-1,2,4-oxadiazol-5-yl]methyl]purin-6-one | 0.0123 | 0.0021 |
| 255 | 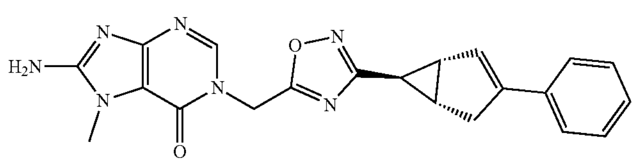 [SMILES: Cn1c(N)nc2ncn(Cc3nc([C@H]4[C@@H]5C=C(c6ccccc6)C[C@@H]54)no3)c(=O)c21] | 8-amino-7-methyl-1-[[3-[(1S,5S,6R)-3-phenyl-6-bicyclo[3.1.0]hex-2-enyl]-1,2,4-oxadiazol-5-yl]methyl]purin-6-one | 0.0333 | 0.0038 |
| 256 | 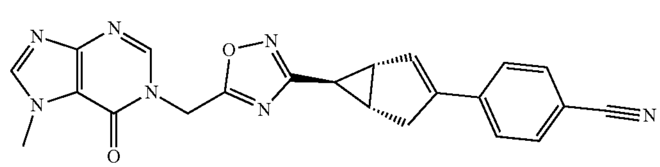 [SMILES: Cn1cnc2ncn(Cc3nc([C@H]4[C@@H]5C=C(c6ccc(C#N)cc6)C[C@@H]54)no3)c(=O)c21] | 4-[(1S,5S,6R)-6-[5-[(7-methyl-6-oxo-purin-1-yl)methyl]-1,2,4-oxadiazol-3-yl]-3-bicyclo[3.1.0]hex-2-enyl]benzonitrile | 0.0217 | 0.0066 |
| 257 | 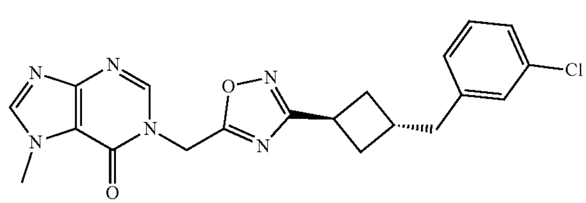 [SMILES: Cn1cnc2ncn(Cc3nc([C@H]4C[C@H](Cc5cccc(Cl)c5)C4)no3)c(=O)c21] | 1-[[3-[trans-3-[(3-chlorophenyl)methyl]cyclobutyl]-1,2,4-oxadiazol-5-yl]methyl]-7-methyl-purin-6-one | 0.0166 | 0.019 |

TABLE 1-continued

| Ex. | Structure | Name | IC$_{50}$ (10 min) | IC$_{50}$ (90 min) |
|---|---|---|---|---|
| 258 | 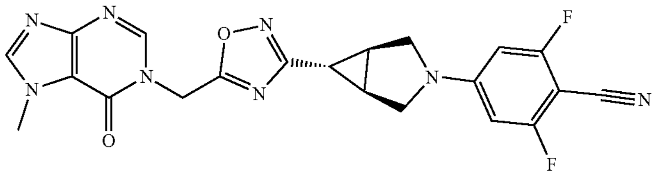 [SMILES: Cn1cnc2ncn(Cc3nc([C@H]4[C@@H]5CN(c6cc(F)c(C#N)c(F)c6)C[C@@H]54)no3)c(=O)c21] | 2,6-difluoro-4-[(1S,5R)-6-[5-[(7-methyl-6-oxo-purin-1-yl)methyl]-1,2,4-oxadiazol-3-yl]-3-azabicyclo[3.1.0]hexan-3-yl]benzonitrile | 0.0782 | 0.018 |
| 259 | 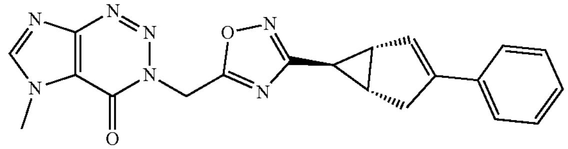 [SMILES: Cn1cnc2nnn(Cc3nc([C@H]4[C@@H]5C=C(c6ccccc6)C[C@@H]54)no3)c(=O)c21] | 5-methyl-3-[[3-[(1S,5S,6R)-3-phenyl-6-bicyclo[3.1.0]hex-2-enyl]-1,2,4-oxadiazol-5-yl]methyl]imidazo[4,5-d]triazin-4-one | 0.0251 | 0.016 |
| 260 | 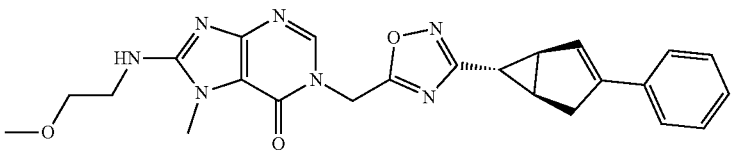 [SMILES: COCCNc1nc2ncn(Cc3nc([C@@H]4[C@H]5C=C(c6ccccc6)C[C@H]54)no3)c(=O)c2n1C] | 8-(2-methoxyethylamino)-7-methyl-1-[[3-[(1R,5R,6S)-3-phenyl-6-bicyclo[3.1.0]hex-2-enyl]-1,2,4-oxadiazol-5-yl]methyl]purin-6-one | 0.0426 | 0.035 |
| 261 | 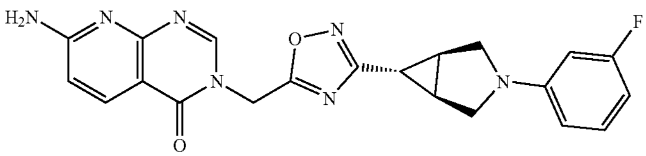 [SMILES: Nc1ccc2c(=O)n(Cc3nc([C@H]4[C@@H]5CN(c6cccc(F)c6)C[C@@H]54)no3)cnc2n1] | 7-amino-3-[[3-[(1R,5S)-3-(3-fluorophenyl)-3-azabicyclo[3.1.0]hexan-6-yl]-1,2,4-oxadiazol-5-yl]methyl]pyrido[2,3-d]pyrimidin-4-one | 0.00973 | 0.0043 |
| 262 | 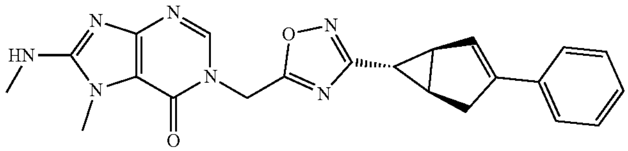 [SMILES: CNc1nc2ncn(Cc3nc([C@@H]4[C@H]5C=C(c6ccccc6)C[C@H]54)no3)c(=O)c2n1C] | 7-methyl-8-(methylamino)-1-[[3-[(1R,5R,6S)-3-phenyl-6-bicyclo[3.1.0]hex-2-enyl]-1,2,4-oxadiazol-5-yl]methyl]purin-6-one | 0.0335 | 0.014 |
| 263 | 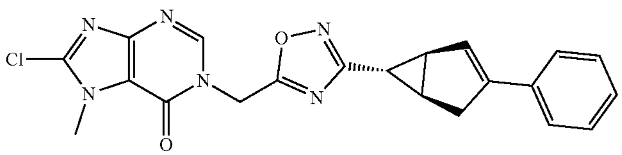 [SMILES: Cn1c(Cl)nc2ncn(Cc3nc([C@@H]4[C@H]5C=C(c6ccccc6)C[C@H]54)no3)c(=O)c21] | 8-chloro-7-methyl-1-[[3-[(1R,5R,6S)-3-phenyl-6-bicyclo[3.1.0]hex-2-enyl]-1,2,4-oxadiazol-5-yl]methyl]purin-6-one | 0.0158 | 0.0065 |
| 264 | 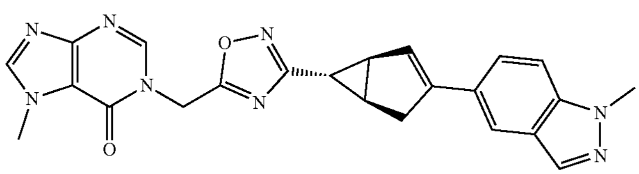 [SMILES: Cn1cnc2ncn(Cc3nc([C@@H]4[C@H]5C=C(c6ccc7c(cnn7C)c6)C[C@H]54)no3)c(=O)c21] | 7-methyl-1-[[3-[(1R,5R,6S)-3-(1-methylindazol-5-yl)-6-bicyclo[3.1.0]hex-2-enyl]-1,2,4-oxadiazol-5-yl]methyl]purin-6-one | 0.029 | 0.014 |
| 265 | 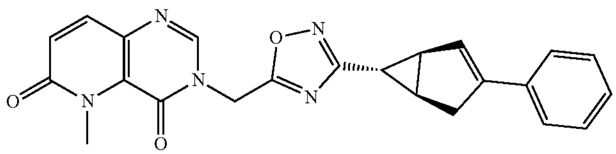 [SMILES: Cn1c(=O)ccc2ncn(Cc3nc([C@@H]4[C@H]5C=C(c6ccccc6)C[C@H]54)no3)c(=O)c21] | 5-methyl-3-[[3-[(1R,5R,6S)-3-phenyl-6-bicyclo[3.1.0]hex-2-enyl]-1,2,4-oxadiazol-5-yl]methyl]pyrido[3,2-d]pyrimidine-3,6-dione | 0.0161 | 0.012 |
| 266 | 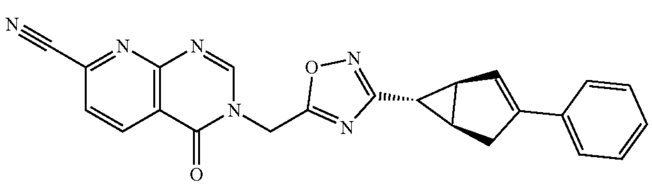 [SMILES: N#Cc1ccc2c(=O)n(Cc3nc([C@@H]4[C@H]5C=C(c6ccccc6)C[C@H]54)no3)cnc2n1] | 4-oxo-3-[[3-[(1R,5R,6S)-3-phenyl-6-bicyclo[3.1.0]hex-2-enyl]-1,2,4-oxadiazol-5-yl]methyl]pyrido[2,3-d]pyrimidine-7-carbonitrile | 0.0546 | 0.039 |

TABLE 1-continued

| Ex. | Structure | Name | IC$_{50}$ (10 min) | IC$_{50}$ (90 min) |
| --- | --- | --- | --- | --- |
| 267 | 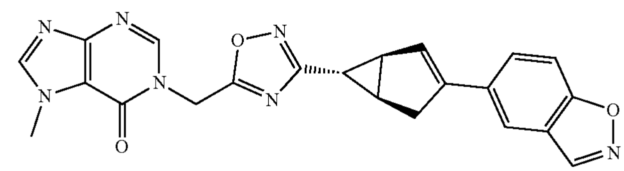 [SMILES: Cn1cnc2ncn(Cc3nc([C@@H]4[C@H]5C=C(c6ccc7oncc7c6)C[C@H]54)no3)c(=O)c21] | 7-methyl-1-[[3-[(1R,5R,6S)-3-(1,3-benzoxazol-5-yl)-6-bicyclo[3.1.0]hex-2-enyl]-1,2,4-oxadiazol-5-yl]methyl]purin-6-one | 0.0139 | 0.0044 |
| 268 | 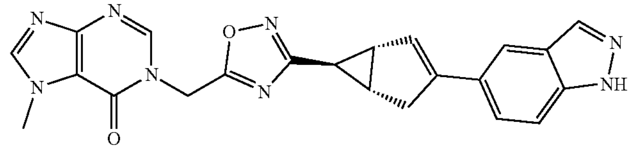 [SMILES: Cn1cnc2ncn(Cc3nc([C@H]4[C@@H]5C=C(c6ccc7[nH]ncc7c6)C[C@@H]54)no3)c(=O)c21] | 7-methyl-1-[[3-[(1S,5S,6R)-3-(1H-indazol-5-yl)-6-bicyclo[3.1.0]hex-2-enyl]-1,2,4-oxadiazol-5-yl]methyl]purin-6-one | 0.02 | 0.012 |
| 269 | 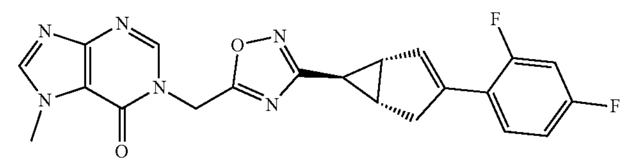 [SMILES: Cn1cnc2ncn(Cc3nc([C@H]4[C@@H]5C=C(c6ccc(F)cc6F)C[C@@H]54)no3)c(=O)c21] | 7-methyl-1-[[3-[(1S,5S,6R)-3-(2,4-difluorophenyl)-6-bicyclo[3.1.0]hex-2-enyl]-1,2,4-oxadiazol-5-yl]methyl]purin-6-one | 0.00696 | 0.0046 |
| 270 | 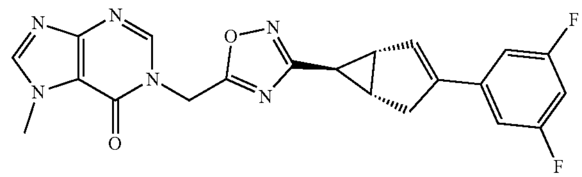 [SMILES: Cn1cnc2ncn(Cc3nc([C@H]4[C@@H]5C=C(c6cc(F)cc(F)c6)C[C@@H]54)no3)c(=O)c21] | 7-methyl-1-[[3-[(1S,5S,6R)-3-(3,5-difluorophenyl)-6-bicyclo[3.1.0]hex-2-enyl]-1,2,4-oxadiazol-5-yl]methyl]purin-6-one | 0.013 | 0.0024 |
| 271 | 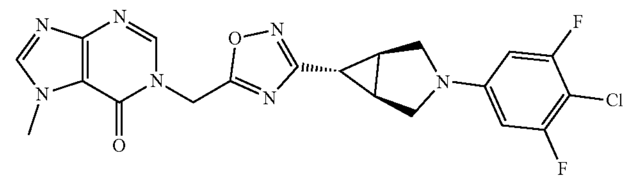 [SMILES: Cn1cnc2ncn(Cc3nc([C@H]4[C@@H]5CN(c6cc(F)c(Cl)c(F)c6)C[C@@H]54)no3)c(=O)c21] | 7-methyl-1-[[3-[(1S,5R)-3-(4-chloro-3,5-difluorophenyl)-3-azabicyclo[3.1.0]hexan-6-yl]-1,2,4-oxadiazol-5-yl]methyl]purin-6-one | 0.0347 | 0.011 |
| 272 | 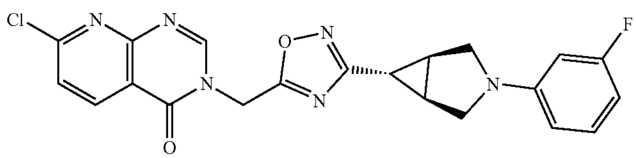 [SMILES: O=c1c2ccc(Cl)nc2ncn1Cc1nc([C@H]2[C@@H]3CN(c4cccc(F)c4)C[C@@H]32)no1] | 7-chloro-3-[[3-[(1R,5S)-3-(3-fluorophenyl)-3-azabicyclo[3.1.0]hexan-6-yl]-1,2,4-oxadiazol-5-yl]methyl]pyrido[2,3-d]pyrimidin-4-one | 0.0583 | 0.035 |
| 273 | 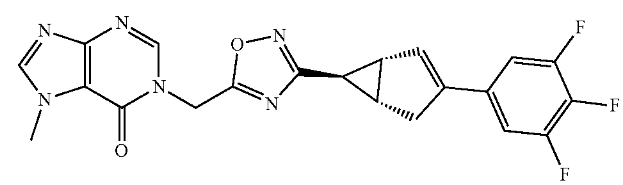 [SMILES: Cn1cnc2ncn(Cc3nc([C@H]4[C@@H]5C=C(c6cc(F)c(F)c(F)c6)C[C@@H]54)no3)c(=O)c21] | 7-methyl-1-[[3-[(1S,5S,6R)-3-(3,4,5-trifluorophenyl)-6-bicyclo[3.1.0]hex-2-enyl]-1,2,4-oxadiazol-5-yl]methyl]purin-6-one | 0.0149 | 0.002 |
| 274 | 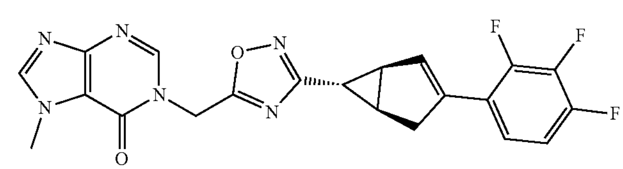 [SMILES: Cn1cnc2ncn(Cc3nc([C@@H]4[C@H]5C=C(c6ccc(F)c(F)c6F)C[C@H]54)no3)c(=O)c21] | 7-methyl-1-[[3-[(1R,5R,6S)-3-(2,3,4-trifluorophenyl)-6-bicyclo[3.1.0]hex-2-enyl]-1,2,4-oxadiazol-5-yl]methyl]purin-6-one | 0.0191 | 0.0063 |

TABLE 1-continued

| Ex. | Structure | Name | IC$_{50}$ (10 min) | IC$_{50}$ (90 min) |
| --- | --- | --- | --- | --- |
| 275 | 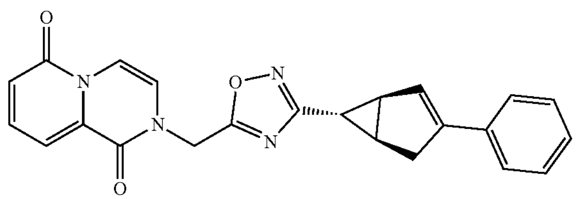 [SMILES: O=c1c2cccc(=O)n2ccn1Cc1nc([C@@H]2[C@H]3C=C(c4ccccc4)C[C@H]32)no1] | 2-[[3-[(1R,5R,6S)-3-phenyl-6-bicyclo[3.1.0]hex-2-enyl]-1,2,4-oxadiazol-5-yl]methyl]pyrido[1,2-a]pyrazine-1,6-dione | 0.0119 | 0.0065 |
| 276 | 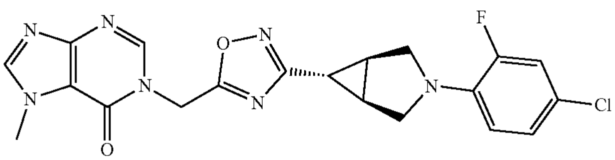 [SMILES: Cn1cnc2ncn(Cc3nc([C@H]4[C@@H]5CN(c6ccc(Cl)cc6F)C[C@@H]54)no3)c(=O)c21] | 7-methyl-1-[[3-[(1S,5R)-3-(4-chloro-2-fluorophenyl)-3-azabicyclo[3.1.0]hexan-6-yl]-1,2,4-oxadiazol-5-yl]methyl]purin-6-one | 0.015 | 0.0074 |
| 277 | 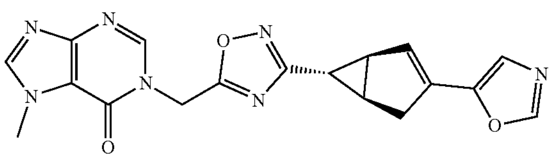 [SMILES: Cn1cnc2ncn(Cc3nc([C@@H]4[C@H]5C=C(c6cnco6)C[C@H]54)no3)c(=O)c21] | 7-methyl-1-[[3-[(1R,5R,6S)-3-(4-oxazol-5-ylphenyl)-6-bicyclo[3.1.0]hex-2-enyl]-1,2,4-oxadiazol-5-yl]methyl]purin-6-one | 0.0168 | 0.011 |
| 278 | 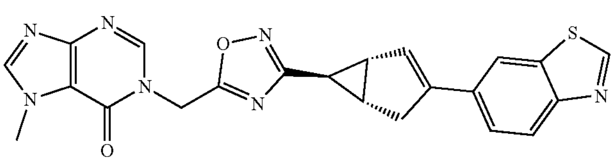 [SMILES: Cn1cnc2ncn(Cc3nc([C@H]4[C@@H]5C=C(c6ccc7ncsc7c6)C[C@@H]54)no3)c(=O)c21] | 7-methyl-1-[[3-[(1S,5S,6R)-3-(1,3-benzothiazol-6-yl)-6-bicyclo[3.1.0]hex-2-enyl]-1,2,4-oxadiazol-5-yl]methyl]purin-6-one | 0.0158 | 0.0031 |
| 279 | 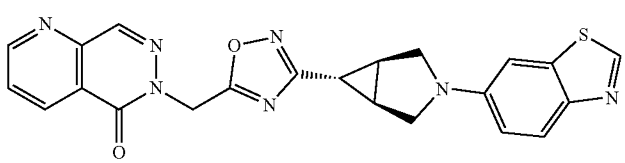 [SMILES: O=c1c2cccnc2cnn1Cc1nc([C@H]2[C@@H]3CN(c4ccc5ncsc5c4)C[C@@H]32)no1] | 6-[[3-[(1R,5S)-3-(1,3-benzothiazol-6-yl)-3-azabicyclo[3.1.0]hexan-6-yl]-1,2,4-oxadiazol-5-yl]methyl]pyrido[2,3-d]pyridazin-5-one | 0.0112 | 0.0056 |
| 280 | 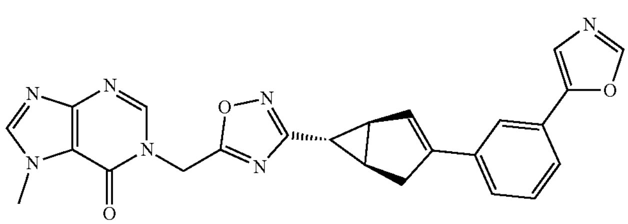 [SMILES: Cn1cnc2ncn(Cc3nc([C@@H]4[C@H]5C=C(c6cccc(-c7cnco7)c6)C[C@H]54)no3)c(=O)c21] | 7-methyl-1-[[3-[(1R,5R,6S)-3-(3-oxazol-5-ylphenyl)-6-bicyclo[3.1.0]hex-2-enyl]-1,2,4-oxadiazol-5-yl]methyl]purin-6-one | 0.0461 | 0.04 |
| 281 | 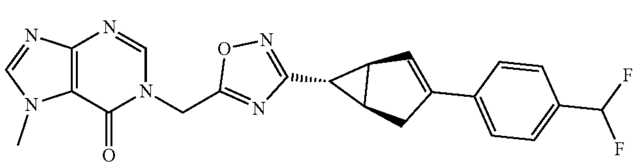 [SMILES: Cn1cnc2ncn(Cc3nc([C@@H]4[C@H]5C=C(c6ccc(C(F)F)cc6)C[C@H]54)no3)c(=O)c21] | 7-methyl-1-[[3-[(1R,5R,6S)-3-[4-(difluoromethyl)phenyl]-6-bicyclo[3.1.0]hex-2-enyl]-1,2,4-oxadiazol-5-yl]methyl]purin-6-one | 0.0679 | 0.035 |
| 282 | 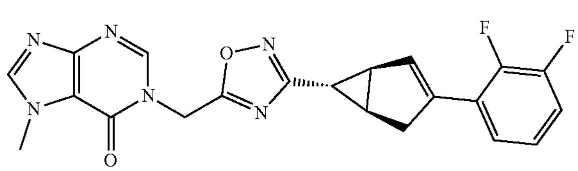 [SMILES: Cn1cnc2ncn(Cc3nc([C@@H]4[C@H]5C=C(c6cccc(F)c6F)C[C@H]54)no3)c(=O)c21] | 7-methyl-1-[[3-[(1R,5R,6S)-3-(2,3-difluorophenyl)-6-bicyclo[3.1.0]hex-2-enyl]-1,2,4-oxadiazol-5-yl]methyl]purin-6-one | 0.0169 | 0.0031 |

TABLE 1-continued

| Ex. | Structure | Name | IC$_{50}$ (10 min) | IC$_{50}$ (90 min) |
|---|---|---|---|---|
| 283 | 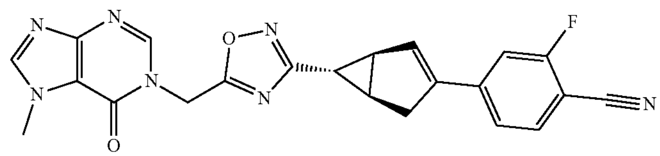 [SMILES: Cn1cnc2ncn(Cc3nc([C@@H]4[C@H]5C=C(c6ccc(C#N)c(F)c6)C[C@H]54)no3)c(=O)c21] | 2-fluoro-4-[(1R,5R,6S)-6-[5-[(7-methyl-6-oxo-purin-1-yl)methyl]-1,2,4-oxadiazol-3-yl]-3-bicyclo[3.1.0]hex-2-enyl]benzonitrile | 0.0196 | 0.0053 |

Proton NMR and LCMS M+1 data for the compounds 1 to 283 of Table 1 are shown below in Table 2.

TABLE 2

| Ex. | 1H NMR (ppm) | M + H |
|---|---|---|
| 1 | $^1$H NMR (400 MHz, DMSO-d6) δ 8.47 (s, 1H), 8.26-8.20 (m, 1H), 7.37-7.27 (m, 4H), 7.27-7.15 (m, 1H), 5.58 (s, 2H), 3.96 (s, 3H), 3.80-3.58 (m, 2H), 2.65-2.51 (m, 4H). | 363.1 |
| 2 | $^1$H NMR (300 MHz, CD$_3$OD) δ 8.38 (s, 1H), 8.13 (s, 1H), 7.32-7.27 (m, 1H), 7.19-7.09 (m, 3H), 5.51 (s, 2H), 4.05 (s, 3H), 3.29-3.24 (m, 1H), 3.12-3.06 (m, 1H), 2.90-2.88 (m, 1H), 2.42-2.37 (m, 1H), 1.52 (t, J = 4.0 Hz, 1H). | 361.1 |
| 3 | $^1$H NMR (300 MHz, CD$_3$OD) δ 8.38 (s, 1H), 8.13 (s, 1H), 7.32-7.29 (m, 1H), 7.19-7.09 (m, 3H), 5.51 (s, 2H), 4.06 (s, 3H), 3.29-3.25 (m, 1H), 3.13-3.07 (m, 1H), 2.91-2.89 (m, 1H), 2.42-2.37 (m, 1H), 1.53 (t, J = 3.6 Hz, 1H). | 361.1 |
| 4 | $^1$H NMR (400 MHz, DMSO) δ 8.43 (s, 1H), 8.23 (s, 1H), 7.24 (t, J = 8.2 Hz, 1H), 6.57 (dd, J = 8.3, 2.1 Hz, 2H), 6.44 (s, 1H), 5.52 (s, 2H), 3.95 (s, 3H), 3.68 (d, J = 9.8 Hz, 2H), 3.30-3.26 (m, 2H), 2.27-2.13 (m, 2H), 2.03 (t, J = 3.2 Hz, 1H). | 474.1 |
| 5 | $^1$H NMR (400 MHz, DMSO) δ 8.43 (s, 1H), 8.23 (s, 1H), 6.73 (t, J = 1.7 Hz, 1H), 6.55 (d, J = 1.8 Hz, 2H), 5.52 (s, 2H), 3.95 (s, 3H), 3.68 (d, J = 10.1 Hz, 2H), 3.36-3.31 (m, 2H), 2.25-2.15 (m, 2H), 1.99 (t, J = 3.3 Hz, 1H). | 458.1 |
| 6 | $^1$H NMR (400 MHz, DMSO) δ 8.43 (s, 1H), 8.23 (s, 1H), 7.14 (d, J = 8.4 Hz, 2H), 6.65-6.53 (m, 2H), 5.52 (s, 2H), 3.95 (s, 3H), 3.67 (d, J = 9.7 Hz, 2H), 3.30-3.25 (m, 2H), 2.28-2.14 (m, 2H), 2.03 (t, J = 3.2 Hz, 1H). | 474.1 |
| 7 | $^1$H NMR (400 MHz, DMSO) δ 8.43 (s, 1H), 8.27-8.19 (m, 1H), 7.08-6.92 (m, 2H), 6.63-6.48 (m, 2H), 5.52 (s, 2H), 3.95 (s, 3H), 3.66 (d, J = 9.5 Hz, 2H), 3.22-3.17 (m, 2H), 2.19 (t, J = 2.1 Hz, 2H), 2.05 (t, J = 3.2 Hz, 1H). | 408.1 |
| 8 | $^1$H NMR (400 MHz, DMSO) δ 8.43 (s, 1H), 8.23 (s, 1H), 7.38-6.96 (m, 2H), 6.43 (ddd, J = 7.3, 4.7, 2.1 Hz, 2H), 6.31 (t, J = 2.1 Hz, 1H), 5.52 (s, 2H), 3.95 (s, 3H), 3.67 (d, J = 9.8 Hz, 2H), 3.28 (d, J = 9.0 Hz, 2H), 2.24-2.16 (m, 2H), 2.01 (t, J = 3.2 Hz, 1H). | 456.1 |
| 9 | $^1$H NMR (400 MHz, DMSO-d6) δ 8.93 (s, 1H), 8.64 (s, 1H), 8.53 (d, J = 1.0 Hz, 1H), 7.62-7.54 (m, 2H), 7.44-7.37 (m, 2H), 5.89 (s, 1H), 5.53 (s, 2H), 3.28-3.18 (m, 1H), 2.84-2.73 (m, 2H), 2.70 (s, 3H), 2.59 (td, J = 9.5, 2.6 Hz, 2H). | 424.1 |
| 10 | $^1$H NMR (400 MHz, DMSO-d6) δ 8.79 (d, J = 4.8 Hz, 1H), 8.72 (s, 1H), 7.62-7.52 (m, 2H), 7.44-7.36 (m, 3H), 5.89 (s, 1H), 5.52 (s, 2H), 3.41-3.17 (m, 1H), 2.84-2.71 (m, 5H), 2.65-2.52 (m, 2H). | 424.1 |
| 11 | $^1$H NMR (400 MHz, DMSO-d6) δ 9.03 (dd, J = 4.6, 2.0 Hz, 1H), 8.78 (s, 1H), 8.57 (dd, J = 7.9, 2.0 Hz, 1H), 7.63 (dd, J = 7.9, 4.6 Hz, 1H), 7.61-7.54 (m, 2H), 7.43-7.36 (m, 2H), 5.89 (s, 1H), 5.58 (s, 2H), 3.30-3.17 (m, 1H), 2.84-2.71 (m, 2H), 2.64-2.53 (m, 2H). | 410.1 |
| 12 | $^1$H NMR (400 MHz, DMSO) δ 8.43 (s, 1H), 8.23 (s, 1H), 7.00 (d, J = 8.9 Hz, 2H), 6.97 (t, J = 75.1 Hz, 1H), 6.58 (d, J = 9.1 Hz, 2H), 5.52 (s, 2H), 3.95 (s, 3H), 3.66 (d, J = 9.6 Hz, 2H), 3.26-3.19 (m, 2H), 2.20 (s, 2H), 2.03 (t, J = 3.2 Hz, 1H). | 456.1 |
| 13 | $^1$H NMR (400 MHz, DMSO) δ 8.43 (s, 1H), 8.23 (s, 1H), 7.04 (t, J = 8.1 Hz, 1H), 6.24 (dd, J = 8.1, 2.1 Hz, 1H), 6.17 (dd, J = 8.2, 1.8 Hz, 1H), 6.09 (t, J = 2.2 Hz, 1H), 5.52 (s, 2H), 3.95 (s, 3H), 3.69 (s, 3H), 3.66 (d, J = 9.7 Hz, 2H), 3.26-3.21 (m, 2H), 2.19 (s, 2H), 2.00 (t, J = 3.2 Hz, 1H). | 420.1 |
| 14 | $^1$H NMR (400 MHz, DMSO-d$_6$) δ 8.79 (d, J = 4.8 Hz, 1H), 8.70 (s, 1H), 7.41 (d, J = 5.2 Hz, 1H), 7.39-7.37 (m, 1H), 7.23-7.21 (m, 1H), 7.16-7.12 (m, 2H), 5.49 (s, 2H), 3.27-3.23 (m, 1H), 3.12-3.08 (m, 1H), 2.90-2.88 (m, 1H), 2.77 (s, 3H), 2.40-2.36 (m, 1H), 1.60 (t, J = 2.8 Hz, 1H). | 372.1 |
| 15 | $^1$H NMR (400 MHz, DMSO-d$_6$) δ 8.79 (d, J = 4.8 Hz, 1H), 8.70 (s, 1H), 7.41 (d, J = 5.2 Hz, 1H), 7.39-7.37 (m, 1H), 7.23-7.21 (m, 1H), 7.14-7.12 (m, 2H), 5.49 (s, 2H), 3.27-3.23 (m, 1H), 3.12-3.08 (m, 1H), 2.90-2.89 (m, 1H), 2.77 (s, 3H), 2.40-2.36 (m, 1H), 1.60 (t, J = 3.2 Hz, 1H). | 372.1 |

TABLE 2-continued

| Ex. | 1H NMR (ppm) | M + H |
|---|---|---|
| 16 | ¹H NMR (400 MHz, DMSO) δ 8.43 (s, 1H), 8.23 (s, 1H), 7.15 (q, J = 7.9 Hz, 1H), 6.46-6.30 (m, 3H), 5.52 (s, 2H), 3.95 (s, 3H), 3.66 (d, J = 9.8 Hz, 2H), 3.29 (d, J = 3.2 Hz, 2H), 2.20 (s, 2H), 2.01 (t, J = 3.2 Hz, 1H). | 408.1 |
| 17 | ¹H NMR (400 MHz, DMSO-d6) δ 8.79 (d, J = 4.8 Hz, 1H), 8.73 (s, 1H), 7.41 (d, J = 4.7 Hz, 1H), 7.39-7.31 (m, 4H), 5.55 (s, 2H), 3.73 (p, J = 8.7 Hz, 1H), 3.68-3.59 (m, 1H), 2.77 (s, 3H), 2.64-2.50 (m, 4H). | 408.1 |
| 18 | ¹H NMR (400 MHz, DMSO) δ 8.43 (s, 1H), 8.27-8.19 (m, 1H), 7.95 (d, J = 2.8 Hz, 1H), 7.88 (dd, J = 4.6, 1.2 Hz, 1H), 7.15 (dd, J = 8.3, 4.5 Hz, 1H), 6.93 (ddd, J = 8.5, 2.9, 1.3 Hz, 1H), 5.52 (s, 2H), 3.95 (s, 3H), 3.72 (d, J = 9.7 Hz, 2H), 3.31-3.24 (m, 2H), 2.27-2.18 (m, 2H), 2.04 (t, J = 3.3 Hz, 1H). | 391.1 |
| 19 | ¹H NMR (300 MHz, DMSO-d₆) δ 8.92 (s, 1H), 8.61 (s, 1H), 8.52 (s, 1H), 7.39-7.36 (m, 1H), 7.21-7.20 (m, 1H), 7.14-7.12 (m, 2H), 5.50 (s, 2H), 3.28-3.22 (m, 1H), 3.12-3.07 (m, 1H), 2.90-2.88 (m, 1H), 2.70 (s, 3H), 2.40-2.37 (m, 1H), 1.59 (s, 1H). | 372.1 |
| 20 | ¹H NMR (300 MHz, DMSO-d₆) δ 8.92 (s, 1H), 8.61 (s, 1H), 8.52 (s, 1H), 7.39-7.36 (m, 1H), 7.23-7.20 (m, 1H), 7.16-7.11 (m, 2H), 5.50 (s, 2H), 3.28-3.22 (m, 1H), 3.12-3.06 (m, 1H), 2.90-2.88 (m, 1H), 2.70 (s, 3H), 2.40-2.36 (m, 1H), 1.59 (t, J = 3.0 Hz, 1H). | 372.1 |
| 21 | ¹H NMR (400 MHz, DMSO-d6) δ 8.47 (s, 1H), 8.24 (s, 1H), 7.41-7.30 (m, 4H), 5.58 (s, 2H), 3.96 (s, 3H), 3.73 (p, J = 8.8 Hz, 1H), 3.68-3.58 (m, 1H), 2.64-2.50 (m, 4H). | 397.1 |
| 22 | ¹H NMR (300 MHz, CDCl₃) δ 8.03 (s, 1H), 7.25-7.20 (m, 2H), 6.73 (t, J = 7.2 Hz, 1H), 6.60 (d, J = 7.8 Hz, 2H), 6.08 (s, 2H), 3.73 (d, J = 9.3 Hz, 2H), 3.64 (s, 3H), 3.34-3.31 (m, 2H), 2.24-2.23 (m, 2H), 2.16-2.14 (m, 1H). | 415.1 |
| 23 | ¹H NMR (400 MHz, DMSO-d6) δ 8.46 (s, 1H), 8.24 (s, 1H), 7.65-7.56 (m, 2H), 7.58-7.47 (m, 2H), 5.58 (s, 2H), 3.95 (s, 3H), 3.49-3.37 (m, 1H), 3.11-2.97 (m, 2H), 2.93-2.75 (m, 2H). | 415.0 |
| 24 | ¹H NMR (400 MHz, DMSO-d6) δ 8.43 (s, 1H), 8.23 (s, 1H), 7.15 (t, J = 8.1 Hz, 1H), 6.65 (dd, J = 7.5, 1.9 Hz, 1H), 6.56 (t, J = 2.2 Hz, 1H), 6.54-6.49 (m, 1H), 5.52 (s, 2H), 3.95 (s, 3H), 3.67 (d, J = 9.9 Hz, 2H), 3.30-3.25 (m, 2H), 2.23-2.18 (m, 2H), 2.01 (t, J = 3.3 Hz, 1H). | 424.1 |
| 25 | ¹H NMR (400 MHz, DMSO-d6) δ 8.43 (s, 1H), 8.23 (s, 1H), 7.21-7.13 (m, 2H), 6.60-6.53 (m, 2H), 5.52 (s, 2H), 3.95 (s, 3H), 3.66 (d, J = 9.7 Hz, 2H), 3.26-3.20 (m, 2H), 2.23-2.17 (m, 2H), 2.02 (t, J = 3.2 Hz, 1H). | 424.1 |
| 26 | ¹H NMR (400 MHz, DMSO-d6) δ 8.43 (s, 1H), 8.23 (s, 1H), 7.20-7.11 (m, 2H), 6.68-6.59 (m, 1H), 6.64-6.52 (m, 2H), 5.52 (s, 2H), 3.95 (s, 3H), 3.67 (d, J = 9.7 Hz, 2H), 3.26-3.21 (m, 2H), 2.22-2.17 (m, 2H), 2.03 (t, J = 3.3 Hz, 1H). | 390.1 |
| 27 | ¹H NMR (400 MHz, DMSO-d6) δ 8.78 (d, J = 4.8 Hz, 1H), 8.70 (s, 1H), 7.40 (dd, J = 4.8, 1.0 Hz, 1H), 7.28-7.18 (m, 2H), 7.22-7.10 (m, 2H), 5.51 (s, 2H), 3.88-3.71 (m, 1H), 3.33-3.20 (m, 2H), 3.13 (dd, J = 15.7, 7.4 Hz, 2H), 2.76 (d, J = 0.8 Hz, 3H). | 360.1 |
| 28 | ¹H NMR (400 MHz, DMSO-d6) δ 8.46 (s, 1H), 8.24 (s, 1H), 7.61-7.56 (m, 2H), 7.43-7.37 (m, 2H), 5.91 (s, 1H), 5.56 (s, 2H), 3.95 (s, 3H), 3.29-3.20 (quin, J = 9.0 Hz, 1H), 2.83-2.74 (m, 2H), 2.64-2.54 (m, 2H). | 413 |
| 29 | ¹H NMR (400 MHz, DMSO) δ 8.79 (d, J = 4.8 Hz, 1H), 8.69 (s, 1H), 7.40 (d, J = 4.8 Hz, 1H), 7.17 (d, J = 8.9 Hz, 2H), 6.56 (d, J = 9.0 Hz, 2H), 5.48 (s, 2H), 3.65 (d, J = 9.7 Hz, 2H), 3.26-3.21 (m, 2H), 2.77 (s, 3H), 2.20 (s, 2H), 2.03 (t, J = 3.2 Hz, 1H). | 435.1 |
| 30 | ¹H NMR (400 MHz, DMSO) δ 8.43 (s, 1H), 8.26-8.17 (m, 1H), 7.36 (t, J = 7.9 Hz, 1H), 6.93 (d, J = 7.6 Hz, 1H), 6.83 (d, J = 8.4 Hz, 1H), 6.76 (s, 1H), 5.52 (s, 2H), 3.95 (s, 3H), 3.74 (d, J = 9.8 Hz, 2H), 3.36-3.33 (m, 2H), 2.28-2.16 (m, 2H), 2.04 (t, J = 3.2 Hz, 1H). | 458.1 |
| 31 | ¹H NMR (400 MHz, DMSO) δ 8.43 (s, 1H), 8.23 (s, 1H), 7.45 (d, J = 8.7 Hz, 2H), 6.67 (d, J = 8.7 Hz, 2H), 5.52 (s, 2H), 3.95 (s, 3H), 3.72 (d, J = 10.0 Hz, 2H), 3.41-3.35 (m, 2H), 2.24 (s, 2H), 2.02 (t, J = 3.3 Hz, 1H). | 458.1 |
| 32 | ¹H NMR (400 MHz, DMSO) δ 9.68 (s, 1H), 8.43 (s, 1H), 8.27-8.19 (m, 1H), 7.68 (d, J = 8.8 Hz, 2H), 6.67 (d, J = 8.8 Hz, 2H), 5.52 (s, 2H), 3.95 (s, 3H), 3.77 (d, J = 10.5 Hz, 2H), 3.54-3.42 (m, 2H), 2.26 (s, 2H), 2.02 (t, J = 3.3 Hz, 1H). | 418.1 |
| 33 | ¹H NMR (400 MHz, DMSO) δ 8.44 (s, 1H), 8.24 (s, 1H), 7.71 (t, J = 9.0 Hz, 2H), 7.63 (d, J = 8.1 Hz, 1H), 7.33 (ddd, J = 8.2, 6.8, 1.2 Hz, 1H), 7.15 (ddd, J = 8.0, 6.9, 1.1 Hz, 1H), 7.06 (dd, J = 9.0, 2.4 Hz, 1H), 6.81 (d, J = 2.2 Hz, 1H), 5.53 (s, 2H), 3.96 (s, 3H), 3.82 (d, J = 9.8 Hz, 2H), 3.43-3.35 (m, 2H), 2.30-2.18 (m, 2H), 2.12-2.04 (m, 1H). | 440.1 |
| 34 | ¹H NMR (400 MHz, DMSO) δ 8.43 (s, 1H), 8.23 (s, 1H), 7.71 (d, J = 3.0 Hz, 1H), 7.24 (d, J = 8.7 Hz, 1H), 7.03 (dd, J = 8.8, 3.2 Hz, 1H), 5.52 (s, 2H), 3.95 (s, 3H), 3.70 (d, J = 9.8 Hz, 2H), 3.33-3.25 (m, 2H), 2.22 (d, J = 2.3 Hz, 2H), 2.03 (t, J = 3.3 Hz, 1H). | 425.1 |
| 35 | ¹H NMR (400 MHz, DMSO) δ 8.43 (s, 1H), 8.23 (s, 1H), 6.87-6.69 (m, 2H), 6.63-6.45 (m, 2H), 5.52 (s, 2H), 3.95 (s, 3H), 3.64 (d, J = 8.0 Hz, 5H), 3.12 (d, J = 9.0 Hz, 2H), 2.24-2.10 (m, 2H), 2.06 (t, J = 3.2 Hz, 1H). | 420.1 |
| 36 | ¹H NMR (400 MHz, DMSO) δ 8.95-8.89 (m, 1H), 8.61 (s, 1H), 8.55-8.49 (m, 1H), 7.21-7.13 (m, 2H), 6.60-6.52 (m, 2H), 5.49 (s, 2H), 3.65 (d, J = 9.7 Hz, 2H), 3.26-3.21 (m, 2H), 2.70 (s, 3H), 2.24-2.16 (m, 2H), 2.03 (t, J = 3.2 Hz, 1H). | 435.1 |

TABLE 2-continued

| Ex. | 1H NMR (ppm) | M + H |
|---|---|---|
| 37 | ¹H NMR (300 MHz, DMSO-d₆) δ 8.95 (s, 1H), 8.66 (s, 1H), 8.54 (s, 1H), 7.62 (d, J = 8.1 Hz, 2H), 7.52 (d, J = 8.4 Hz, 2H), 5.57 (s, 2H), 3.51-3.38 (m, 1H), 3.13-2.98 (m, 2H), 2.95-2.78 (m, 2H), 2.71 (s, 3H). | 426.2 |
| 38 | ¹H NMR (300 MHz, DMSO-d₆) δ 8.81 (d, J = 4.8 Hz, 1H), 8.74 (s, 1H), 7.62 (d, J = 8.5 Hz, 2H), 7.52 (d, J = 8.3 Hz, 2H), 7.42 (d, J = 5.1 Hz, 1H), 5.56 (s, 2H), 3.43 (m, 1H), 3.05 (m, 2H), 2.96-2.80 (m, 2H), 2.78 (s, 3H). | 426.2 |
| 79 | ¹H NMR (400 MHz, DMSO-d₆) δ 8.44 (s, 1H), 8.23 (s, 1H), 7.55 (t, J = 8.3 Hz, 1H), 6.55 (dd, J = 13.3, 2.2 Hz, 1H), 6.47 (dd, J = 8.9, 2.2 Hz, 1H), 5.52 (s, 2H), 3.95 (s, 3H), 3.72 (d, J = 10.7 Hz, 2H), 3.46 (d, J = 10.7, 1.9 Hz, 2H), 2.29-2.19 (m, 2H), 2.02 (t, J = 3.3 Hz, 1H) | 433.1 |
| 80 | ¹H NMR (400 MHz, DMSO-d₆) δ 8.44 (s, 1H), 7.16-7.12 (m, 1H), 6.44-6.36 (m, 3H), 5.52 (s, 2H), 3.95 (s, 3H), 3.68 (d, J = 10.0 Hz, 2H), 3.31-3.26 (m, 2H), 2.20 (m, 2H), 2.01 (t, J = 3.2 Hz, 1H) | 409.2 |
| 81 | ¹H NMR (400 MHz, DMSO-d₆) δ 8.44 (s, 1H), 8.24 (s, 1H), 7.59 (s, 2H), 7.55-7.51 (d, J = 7.1 Hz, 2H), 5.55 (s, 2H), 3.94 (s, 3H), 3.59 (s, 1H), 3.33-3.32 (m, 1H), 2.57-2.53 (m, 2H), 2.31-2.27 (m, 2H) | 447.1 |
| 82 | ¹H NMR (400 MHz, DMSO-d6) δ 8.44 (s, 1H), 8.24 (s, 1H), 7.43-7.34 (m, 1H), 7.33-7.24 (m, 1H), 7.23-7.12 (m, 2H), 6.56 (s, 1H), 5.52 (s, 2H), 3.95 (s, 3H), 3.20-3.09 (m, 1H), 3.02-2.90 (m, 1H), 2.54-2.46 (m, 1H), 2.31-2.16 (m, 1H), 1.70-1.64 (m, 1H) | 405.1 |
| 83 | ¹H NMR (400 MHz, DMSO-d6) δ 8.44 (s, 1H), 8.24 (s, 1H), 7.41-7.34 (m, 1H), 7.32-7.25 (m, 1H), 7.23-7.13 (m, 2H), 6.56 (s, 1H), 5.51 (s, 2H), 3.95 (s, 3H), 3.19-3.09 (m, 1H), 3.02-2.92 (m, 1H), 2.53-2.47 (m, 1H), 2.31-2.20 (m, 1H), 1.70-1.64 (m, 1H) | 405.1 |
| 84 | ¹H NMR (400 MHz, DMSO-d6) δ 9.03 (dd, J = 4.6, 2.0 Hz, 1H), 8.75 (s, 1H), 8.56 (dd, J = 7.8, 2.0 Hz, 1H), 7.63 (dd, J = 8.0, 4.6 Hz, 1H), 7.20-7.09 (m, 1H), 6.45-6.29 (m, 3H), 5.54 (s, 2H), 3.65 (d, J = 9.8 Hz, 2H), 3.30-3.18 (m, 2H), 2.21-2.17 (m, 2H), 2.01 (t, J = 3.3 Hz, 1H) | 405.2 |
| 85 | ¹H NMR (400 MHz, DMSO-d6) δ 9.03 (dd, J = 4.5, 2.0 Hz, 1H), 8.96 (s, 1H), 8.75 (s, 1H), 8.57 (dd, J = 7.9, 2.0 Hz, 1H), 7.84 (d, J = 9.0 Hz, 1H), 7.64 (dd, J = 7.9, 4.6 Hz, 1H), 7.20 (d, J = 2.3 Hz, 1H), 6.85 (dd, J = 9.0, 2.4 Hz, 1H), 5.55 (s, 2H), 3.76 (d, J = 9.8 Hz, 2H), 3.38-3.32 (m, 2H), 2.25-2.22 (m, 2H), 2.06 (t, J = 3.3 Hz, 1H) | 444.1 |
| 86 | ¹H NMR (400 MHz, DMSO-d₆) δ 8.43 (s, 1H), 8.24 (s, 1H), 6.94 (dd, J = 8.2, 2.0 Hz, 1H), 6.83 (t, J = 1.7 Hz, 1H), 6.71 (dd, J = 12.4, 2.4 Hz, 1H), 5.52 (s, 2H), 3.95 (s, 3H), 3.71 (d, J = 10.2 Hz, 2H), 3.38-3.33 (m, 2H), 2.22 (d, J = 3.3 Hz, 2H), 2.00 (t, J = 3.3 Hz, 1H) | 433.1 |
| 87 | ¹H NMR (400 MHz, DMSO-d₆) δ 8.55 (s, 1H), 8.45 (d, J = 4.6 Hz, 1H), 8.24 (s, 1H), 7.54 (d, J = 8.9 Hz, 1H), 6.89 (s, 1H), 6.72 (d, J = 9.0 Hz, 1H), 5.53 (s, 2H), 3.96 (s, 3H), 3.75 (d, J = 9.6 Hz, 2H), 3.28-3.26 (m, 2H), 2.22 (s, 2H), 2.08 (s, 1H) | 431.1 |
| 88 | ¹H NMR (300 MHz, DMSO-d₆) δ 8.46 (s, 1H), 8.24 (s, 1H), 7.51-7.45 (m, 1H), 7.42-7.38 (m, 1H), 7.29-7.28 (m, 1H), 7.21-7.17 (m, 1H), 5.58 (s, 2H), 4.99-4.95 (m, 1H), 3.97 (s, 3H), 3.73-3.68 (m, 1H), 2.78-2.70 (m, 2H), 2.59-2.53 (m, 2H) | 427.1 |
| 89 | ¹H NMR (400 MHz, DMSO-d₆) δ 8.24 (s, 1H), 7.21-7.10 (m, 1H), 6.49-6.27 (m, 3H), 5.52 (s, 2H), 3.95 (s, 3H), 3.66 (d, J = 9.8 Hz, 2H), 3.30-3.25 (m, 2H), 2.20 (d, J = 3.1 Hz, 2H), 2.01 (t, J = 3.3 Hz, 1H) | 409.1 |
| 90 | ¹H NMR (400 MHz, DMSO-d₆) δ 8.43 (s, 1H), 7.77 (s, 1H), 7.61 (d, J = 8.4 Hz, 2H), 7.51 (d, J = 8.4 Hz, 2H), 5.50 (s, 2H), 3.46-3.39 (m, 1H), 3.09-3.00 (m, 2H), 2.91-2.77 (m, 2H), 2.36 (s, 3H) | 416.1 |
| 91 | ¹H NMR (300 MHz, DMSO-d₆) δ 8.43 (s, 2H), 8.23 (s, 1H), 7.55 (s, 1H), 6.86 (s, 1H), 6.69-6.67 (m, 1H), 5.53 (s, 2H), 4.05-3.95 (m, 6H), 2.34-2.06 (m, 4H) | 413.0 |
| 92 | ¹H NMR (400 MHz, DMSO-d₆) δ 8.43 (s, 1H), 8.24 (s, 1H), 6.37-6.21 (m, 1H), 6.29-6.18 (m, 2H), 5.52 (s, 2H), 3.95 (s, 3H), 3.65 (d, J = 10.0 Hz, 2H), 3.30 (d, J = 2.5 Hz, 2H), 2.21 (s, 2H), 1.99 (t, J = 3.3 Hz, 1H) | 426.1 |
| 93 | ¹H NMR (400 MHz, DMSO-d6) 8.42 (s, 1H), 8.22 (s, 1H), 7.50 (ddd, J = 12.3, 7.8, 2.0 Hz, 1H), 7.40-7.30 (m, 1H), 7.23 (s, 1H), 6.59 (d, J = 1.7 Hz, 1H), 5.49 (s, 2H), 3.93 (s, 3H), 3.04 (dd, J = 18.0, 5.9 Hz, 1H), 2.88 (d, J = 17.6 Hz, 1H), 2.43 (dd, J = 6.3, 2.4 Hz, 1H), 2.24 (dt, J = 9.9, 5.2 Hz, 1H), 1.65-1.61 (m, 1H) | 423.1 |
| 94 | ¹H NMR (400 MHz, DMSO-d6) 8.42 (s, 1H), 8.22 (s, 1H), 7.50 (ddd, J = 12.3, 7.9, 2.0 Hz, 1H), 7.36 (dt, J = 10.6, 8.6 Hz, 1H), 7.23 (s, 1H), 6.58 (d, J = 1.6 Hz, 1H), 5.49 (s, 2H), 3.93 (s, 3H), 3.04 (dd, J = 17.9, 5.9 Hz, 1H), 2.88 (d, J = 17.7 Hz, 1H), 2.43 (dd, J = 6.3, 2.4 Hz, 1H), 2.24 (td, J = 6.5, 3.5 Hz, 1H), 1.63 (dd, J = 7.6, 4.6 Hz, 1H) | 423.1 |
| 95 | ¹H NMR (400 MHz, DMSO-d6) δ 8.39 (s, 1H), 7.76 (s, 1H), 7.20-7.10 (m, 2H), 6.68-6.59 (m, 1H), 6.61-6.52 (m, 2H), 5.43 (s, 2H), 3.68 (d, J = 9.7 Hz, 2H), 3.25-3.21 (m, 2H), 2.36 (s, 3H), 2.23-2.18 (m, 2H), 2.04 (t, J = 3.2 Hz, 1H) | 390.2 |
| 96 | ¹H NMR (400 MHz, DMSO-d6) δ 9.20 (dd, J = 4.7, 1.7 Hz, 1H), 8.67-8.62 (m, 1H), 8.61-8.59 (m, 1H), 7.92 (dd, J = 8.1, 4.6 Hz, 1H), 7.20-7.10 (m, 1H), 6.46-6.30 (m, 3H), 5.67 (s, 2H), 3.66 (d, J = 9.8 Hz, 2H), 3.29-3.26 (m, 2H), 2.26-2.16 (m, 2H), 2.01 (t, J = 3.2 Hz, 1H) | 405.2 |
| 99 | ¹H NMR (400 MHz, DMSO-d₆) δ 8.43 (s, 1H), 8.24 (s, 1H), 7.10-7.03 (m, 1H), 6.58-6.53 (m, 1H), 6.51-6.47 (m, 1H), 5.52 (s, 2H), 3.95 (s, 3H), | 426.1 |

TABLE 2-continued

| Ex. | 1H NMR (ppm) | M + H |
|---|---|---|
|  | 3.78 (dd, J = 9.9, 2.9 Hz, 2H), 3.37 (d, J = 10.1 Hz, 2H), 2.16 (d, J = 2.9 Hz, 2H), 2.10 (t, J = 3.2 Hz, 1H) |  |
| 100 | ¹H NMR (400 MHz, DMSO-d₆) δ 8.44 (s, 1H), 8.24 (s, 1H), 7.03-6.94 (m, 1H), 6.74-6.65 (m, 1H), 6.56 (t, J = 8.3 Hz, 1H), 5.52 (s, 2H), 3.95 (s, 3H), 3.81-3.77 (m, 2H), 3.41-3.31 (m, 2H), 2.17 (d, J = 2.8 Hz, 2H), 2.12-2.11 (m, 1H) | 426.0 |
| 101 | ¹H NMR (300 MHz, DMSO-d₆) δ 8.47 (s, 1H), 8.25 (s, 1H), 7.88-7.83 (m, 2H), 7.77-7.70 (m, 1H), 7.59-7.54 (m, 1H), 5.58 (s, 2H), 4.29-4.19 (m, 1H), 3.96 (s, 3H), 3.57-3.54 (m, 1H), 2.72-2.50 (m, 4H) | 425.1 |
| 104 | ¹H NMR (400 MHz, DMSO-d6) δ 8.85 (s, 1H), 8.02 (d, J = 5.5 Hz, 1H), 6.67 (dd, J = 5.5, 1.7 Hz, 1H), 6.55 (d, J = 1.8 Hz, 1H), 5.54 (s, 2H), 3.82 (d, J = 10.9 Hz, 2H), 3.52-3.40 (m, 2H), 2.48 (s, 3H), 2.23-2.17 (m, 2H), 1.98 (t, J = 3.3 Hz, 1H) | 426.1 |
| 105 | ¹H NMR (400 MHz, DMSO) δ 8.43 (s, 1H), 8.23 (s, 1H), 7.19 (dt, J = 10.8, 9.2 Hz, 1H), 6.63-6.50 (m, 1H), 6.37-6.28 (m, 1H), 5.52 (s, 2H), 3.95 (s, 3H), 3.64 (d, J = 9.8 Hz, 2H), 3.27-3.19 (m, 2H), 2.23-2.15 (m, 2H), 2.02 (t, J = 3.3 Hz, 1H) | — |
| 107 | 1H NMR (400 MHz, DMSO-d6) δ 8.80 (s, 1H), 8.06-8.04 (m, 1H), 8.02 (d, J = 5.5 Hz, 1H), 6.66 (dd, J = 5.5, 1.7 Hz, 1H), 6.54 (d, J = 1.8 Hz, 1H), 5.50 (s, 2H), 3.81 (d, J = 10.9 Hz, 2H), 3.48-3.43 (m, 2H), 2.81 (s, 3H), 2.22-2.18 (m, 2H), 1.98 (t, J = 3.3 Hz, 1H) | 461.1 |
| 108 | ¹H NMR (400 MHz, CDCl₃) δ 8.06 (s, 1H), 7.35-7.11 (m, 5H), 6.30 (s, 1H), 5.30 (s, 2H), 4.39 (s, 3H), 3.08 (dd, J = 17.6, 6.5 Hz, 1H), 2.83 (d, J = 17.6 Hz, 1H), 2.49-2.39 (m, 1H), 2.29-2.19 (m, 1H), 1.65-1.56 (m, 1H) | 388.1 |
| 109 | ¹H NMR (400 MHz, CDCl₃) δ 8.10 (s, 1H), 7.39-7.14 (m, 5H), 6.34 (s, 1H), 5.34 (s, 2H), 4.43 (s, 3H), 3.12 (dd, J = 17.7, 6.7 Hz, 1H), 2.87 (d, J = 17.7 Hz, 1H), 2.53-2.45 (m, 1H), 2.34-2.24 (m, 1H), 1.68-1.61 (m, 1H) | 388.1 |
| 110 | ¹H NMR (400 MHz, DMSO-d6) δ 8.49 (d, J = 2.9 Hz, 1H), 8.44 (s, 1H), 8.24 (s, 1H), 7.71-7.64 (m, 1H), 7.64-7.59 (m, 1H), 6.84-6.77 (m, 1H), 5.52 (s, 2H), 3.96 (s, 3H), 3.30-3.24 (m, 1H), 3.16-3.07 (m, 1H), 3.03-2.94 (m, 1H), 2.33-2.24 (m, 1H), 1.72-1.66 (m, 1H) | 406.1 |
| 111 | ¹H NMR (400 MHz, DMSO-d6) δ 8.49 (d, J = 2.8 Hz, 1H), 8.44 (s, 1H), 8.24 (s, 1H), 7.71-7.65 (m, 1H), 7.65-7.59 (m, 1H), 6.84-6.77 (m, 1H), 5.52 (s, 2H), 3.96 (s, 3H), 3.40-3.35 (m, 1H), 3.16-3.08 (m, 1H), 3.04-2.93 (m, 1H), 2.33-2.24 (m, 1H), 1.73-1.66 (m, 1H) | 406.1 |
| 114 | ¹H NMR (400 MHz, DMSO-d6) δ 8.44 (s, 1H), 8.24 (s, 1H), 7.39-7.31 (m, 1H), 7.29-7.23 (m, 2H), 7.11-7.03 (m, 1H), 6.66-6.62 (m, 1H), 5.51 (s, 2H), 3.95 (s, 3H), 3.08 (dd, J = 18.5, 6.5 Hz, 1H), 2.95-2.87 (m, 1H), 2.48-2.43 (m, 1H), 2.26 (td, J = 6.4, 3.4 Hz, 1H), 1.67-1.64 (m, 1H) | 405.1 |
| 115 | ¹H NMR (400 MHz, DMSO-d6) δ 8.44 (s, 1H), 8.24 (s, 1H), 7.39-7.31 (m, 1H), 7.29-7.23 (m, 2H), 7.11-7.03 (m, 1H), 6.66-6.62 (m, 1H), 5.51 (s, 2H), 3.95 (s, 3H), 3.08 (dd, J = 18.5, 6.5 Hz, 1H), 2.95-2.87 (m, 1H), 2.48-2.43 (m, 1H), 2.26 (td, J = 6.4, 3.4 Hz, 1H), 1.67-1.64 (m, 1H) | 405.3 |
| 116 | ¹H NMR (400 MHz, DMSO-d₆) δ 8.39 (s, 1H), 8.21 (s, 1H), 8.02 (d, J = 5.5 Hz, 1H), 6.67 (dd, J = 5.2, 1.6 Hz, 1H), 6.55 (d, J = 1.2 Hz, 1H), 5.36 (s, 2H), 3.82 (d, J = 10.8 Hz, 2H), 3.46 (d, J = 10.8 Hz, 2H), 2.47 (s, 3H), 2.22-2.20 (m, 2H), 1.99 (t, J = 3.3 Hz, 1H) | 425.1 |
| 117 | ¹H NMR (400 MHz, DMSO-d₆) δ 8.40 (s, 1H), 8.07 (dd, J = 9.7, 5.7 Hz, 1H), 7.77 (s, 1H), 6.52-6.48 (m,1H), 6.31 (dd, J = 12.6, 2.2 Hz, 1H), 5.44 (s, 2H), 3.81 (d, J = 10.8 Hz, 2H), 3.50-3.42 (m, 2H), 2.36 (s, 3H), 2.25-2.18 (m, 2H), 2.00 (t, J = 3.3 Hz, 1H) | 409.1 |
| 120 | ¹H NMR (400 MHz, DMSO-d₆) δ 8.93 (s, 1H), 8.44 (s, 1H), 8.24 (d, J = 0.6 Hz, 1H), 7.84 (d, J = 8.2 Hz, 1H), 7.62 (d, J = 8.4 Hz, 1H), 7.53-7.49 (m, 1H), 7.23-7.19 (m, 1H), 6.64 (s, 1H), 5.53 (s, 2H), 3.96 (s, 3H), 3.92 (d, J = 10.5 Hz, 2H), 3.50 (d, J = 10.4 Hz, 2H), 2.24 (s, 2H), 2.05 (t, J = 3.3 Hz, 1H) | 441.0 |
| 121 | ¹H NMR (400 MHz, DMSO-d₆) δ 8.87 (d, J = 5.1 Hz, 1H), 8.81 (s, 1H), 7.71 (d, J = 5.1 Hz, 1H), 7.65-7.56 (m, 2H), 7.55-7.47 (m, 2H), 5.56 (s, 2H), 3.60-3.41 (m, 1H), 3.08-3.00 (m, 2H), 2.94-2.77 (m, 2H) | 446.1 |
| 124 | ¹H NMR (400 MHz, DMSO-D6) δ 8.43 (s, 1H), 8.26-8.22 (m, 1H), 7.51-7.41 (m, 2H), 7.18-7.10 (m, 2H), 6.50 (d, J = 1.7 Hz, 1H), 5.51 (s, 2H), 3.95 (s, 3H), 3.08 (dd, J = 19.0, 6.9 Hz, 1H), 2.90 (d, J = 17.6 Hz, 1H), 2.47-2.41 (m, 1H), 2.25 (td, J = 6.5, 3.4 Hz, 1H), 1.66-1.61 (m, 1H) | 405.2 |
| 125 | ¹H NMR (400 MHz, DMSO-D6) δ 8.44 (s, 1H), 8.27-8.22 (m, 1H), 7.50-7.41 (m, 2H), 7.19-7.10 (m, 2H), 6.50 (d, J = 1.7 Hz, 1H), 5.51 (s, 2H), 3.95 (s, 3H), 3.07 (dd, J = 18.2, 6.0 Hz, 1H), 2.90 (d, J = 17.7 Hz, 1H), 2.47-2.41 (m, 1H), 2.25 (td, J = 6.5, 3.4 Hz, 1H), 1.67-1.62 (m, 1H) | 405.3 |
| 135 | ¹H NMR (400 MHz, DMSO-d6) δ 9.27 (s, 1H), 8.48-8.41 (m, 2H), 8.24 (s, 1H), 8.03-7.94 (m, 2H), 7.92-7.85 (m, 1H), 7.77 (d, J = 5.4 Hz, 1H), 6.81-6.76 (m, 1H), 5.52 (s, 2H), 3.96 (s, 3H), 3.28-3.16 (m, 1H), 3.13-3.02 (m, 1H), 2.57-2.49 (m, 1H), 2.38-2.29 (m, 1H), 1.76-1.70 (m, 1H) | 438.0 |
| 136 | ¹H NMR (400 MHz, DMSO-d6) δ 9.27 (s, 1H), 8.48-8.41 (m, 2H), 8.24 (s, 1H), 8.04-7.95 (m, 2H), 7.92-7.85 (m, 1H), 7.78 (d, J = 5.5 Hz, 1H), 6.81-6.76 (m, 1H), 5.52 (s, 2H), 3.96 (s, 3H), 3.28-3.16 (m, 1H), 3.13-3.02 (m, 1H), 2.57-2.49 (m, 1H), 2.38-2.29 (m, 1H), 1.74 (t, J = 2.9 Hz, 1H) | 438.0 |
| 137 | ¹H NMR (400 MHz, DMSO-d6) δ 8.49 (s, 1H), 8.02 (d, J = 5.5 Hz, 1H), 6.67 (dd, J = 5.5, 1.7 Hz, 1H), 6.55 (d, J = 1.9 Hz, 1H), 5.46 (s, 2H), 3.85 (s, | 439.2 |

TABLE 2-continued

| Ex. | 1H NMR (ppm) | M + H |
|---|---|---|
| | 3H), 3.81 (d, J = 10.8 Hz, 2H), 3.49-3.43 (m, 2H), 2.41 (s, 3H), 2.24-2.14 (m, 2H), 1.97 (t, J = 3.3 Hz, 1H) | |
| 138 | ¹H NMR (400 MHz, DMSO-d₆) δ 8.40 (s, 1H), 8.03 (d, J = 5.4 Hz, 1H), 7.77 (s, 1H), 6.67 (dd, J = 5.4, 1.7 Hz, 1H), 6.55 (d, J = 1.8 Hz, 1H), 5.44 (s, 2H), 3.82 (d, J = 10.8 Hz, 2H), 3.48-3.45 (m, 2H), 2.39-2.34 (m, 3H), 2.25-2.18 (m, 2H), 2.00 (t, J = 3.3 Hz, 1H). | 425.1 |
| 139 | ¹H NMR (400 MHz, DMSO-d6) δ 8.57 (s, 1H), 7.15 (t, J = 8.1 Hz, 1H), 6.65 (dd, J = 7.6, 1.9 Hz, 1H), 6.57-6.55 (m, 1H), 6.53-6.49 (m, 1H), 5.57 (s, 2H), 4.36 (s, 3H), 3.67 (d, J = 9.9 Hz, 2H), 3.30-3.25 (m, 2H), 2.22-2.19 (m, 2H), 2.01 (t, J = 3.3 Hz, 1H) | 425.1 |
| 140 | ¹H NMR (400 MHz, DMSO) δ 8.43 (s, 1H), 8.23 (s, 1H), 7.92-7.85 (m, 1H), 7.33 (dd, J = 8.6, 2.2 Hz, 1H), 6.40 (d, J = 8.5 Hz, 1H), 5.51 (s, 2H), 3.95 (s, 3H), 3.78 (d, J = 10.5 Hz, 2H), 3.40-3.34 (m, 2H), 2.17 (d, J = 2.3 Hz, 2H), 2.12 (s, 3H), 1.97 (t, J = 3.2 Hz, 1H) | — |
| 141 | ¹H NMR (400 MHz, DMSO-d6) δ 8.43 (s, 1H), 8.24 (s, 1H), 7.44 (d, J = 8.5 Hz, 2H), 7.37 (d, J = 8.5 Hz, 2H), 6.58 (s, 1H), 5.51 (s, 2H), 3.95 (s, 3H), 3.12-3.02 (m, 1H), 2.95-2.86 (m, 1H), 2.48-2.42 (m, 1H), 2.29-2.22 (m, 1H), 1.68-1.64 (m, 1H) | 421.2 |
| 142 | ¹H NMR (400 MHz, DMSO-d6) δ 8.43 (s, 1H), 8.24 (s, 1H), 7.44 (d, J = 8.6 Hz, 2H), 7.37 (d, J = 8.6 Hz, 2H), 6.58 (s, 1H), 5.51 (s, 2H), 3.95 (s, 3H), 3.11-3.02 (m, 1H), 2.94-2.85 (m, 1H), 2.48-2.42 (m, 1H), 2.30-2.20 (m, 1H), 1.65 (t, J = 2.9 Hz, 1H) | 421.1 |
| 143 | ¹H NMR (400 MHz, CDCl3) δ 8.84 (d, J = 4.9 Hz, 1H), 8.42 (s, 1H), 7.44-7.39 (m, 1H), 7.30-7.28 (m,2H), 7.24-7.21 (m, 1H), 7.10-7.05 (m, 1H), 5.41 (s, 2H), 3.43-3.34 (m, 1H), 3.14-3.03 (m, 2H), 3.02-2.94 (m, 2H), 2.92 (s, 3H) | 410.2 |
| 144 | ¹H NMR (400 MHz, DMSO-d6) δ 8.43 (s, 1H), 8.23 (s, 1H), 7.85-7.79 (m, 2H), 6.84 (dt, J = 12.2, 2.4 Hz, 1H), 5.52 (s, 2H), 3.95 (s, 3H), 3.72 (d, J = 10.0 Hz, 2H), 3.34 (s, 2H), 2.25-2.21 (m, 2H), 2.02 (t, J = 3.3 Hz, 1H) | 409.2 |
| 145 | ¹H NMR (400 MHz, DMSO-d6) δ 8.43 (s, 1H), 8.23 (s, 1H), 8.21 (d, J = 2.8 Hz, 1H), 8.18 (d, J = 1.6 Hz, 1H), 7.14 (s, 1H), 5.52 (s, 2H), 3.95 (s, 3H), 3.80 (d, J = 10.0 Hz, 2H), 3.43-3.37 (m, 2H), 2.28-2.21 (m, 2H), 2.05 (t, J = 3.3 Hz, 1H) | 459.2 |
| 147 | ¹H NMR (300 MHz, DMSO-d₆) δ 9.04-9.02 (m, 1H), 8.79 (s, 1H), 8.59-8.55 (m, 1H), 7.65-7.61 (m, 1H), 7.33-7.25 (m, 1H), 6.79-6.75 (m, 1H), 6.73-6.64 (m, 2H), 5.62 (s, 2H), 4.93-4.89.(m, 1H), 3.72-3.69 (m, 1H), 2.74-2.66 (m, 2H), 2.58-2.53 (m, 2H) | 394.2 |
| 148 | 1H NMR (400 MHz, DMSO-d6) δ 8.51 (s, 1H), 8.41 (s, 1H), 8.02 (d, J = 5.4 Hz, 1H), 6.67 (dd, J = 5.5, 1.7 Hz, 1H), 6.56 (d, J = 1.8 Hz, 1H), 5.64 (s, 2H), 4.04 (s, 3H), 3.82 (d, J = 10.8 Hz, 2H), 3.49-3.44 (m, 2H), 2.22-2.19 (m, 2H), 1.98 (t, J = 3.3 Hz, 1H) | 425.2 |
| 149 | ¹H NMR (400 MHz, DMSO-d6) δ 8.60 (s, 1H), 7.67-7.56 (m, 2H), 7.56-7.47 (m, 2H), 5.63 (s, 2H), 4.36 (s, 3H), 3.50-3.38 (m, 1H), 3.11-2.97 (m, 2H), 2.93-2.76 (m, 2H) | 416.1 |
| 151 | ¹H NMR (400 MHz, DMSO-d6) δ 9.03 (dd, J = 4.6, 2.0 Hz, 1H), 8.74 (s, 1H), 8.56 (dd, J = 8.0, 2.0 Hz, 1H), 8.01 (d, J = 5.5 Hz, 1H), 7.63 (dd, J = 7.9, 4.6 Hz, 1H), 6.66 (dd, J = 5.3, 1.7 Hz, 1H), 6.54 (d, J = 1.7 Hz, 1H), 5.54 (s, 2H), 3.80 (d, J = 10.8 Hz, 2H), 3.45 (ddd, J = 10.9, 2.6, 1.4 Hz, 2H), 2.21-2.16 (m, 2H), 1.98 (t, J = 3.3 Hz, 1H) | 422.1 |
| 152 | ¹H NMR (400 MHz, DMSO-d6) δ 9.21 (dd, J = 4.6, 1.7 Hz, 1H), 8.65 (dd, J = 8.0, 1.6 Hz, 1H), 8.60 (s, 1H), 8.07 (dd, J = 9.7, 5.7 Hz, 1H), 7.93 (dd, J = 8.1, 4.6 Hz, 1H), 6.54-6.45 (m, 1H), 6.31 (dd, J = 12.5, 2.2 Hz, 1H), 5.67 (s, 2H), 3.81 (d, J = 10.8 Hz, 2H), 3.49-3.43 (m, 2H), 2.24-2.18 (m, 2H), 1.98 (t, J = 3.3 Hz, 1H) | 406.2 |
| 153 | ¹H NMR (400 MHz, DMSO-d6) δ 9.20 (dd, J = 4.6, 1.7 Hz, 1H), 8.64 (dd, J = 8.4, 1.8 Hz, 1H), 8.60 (s, 1H), 7.92 (dd, J = 8.1, 4.6 Hz, 1H), 7.76 (d, J = 6.0 Hz, 1H), 6.48-6.41 (m, 1H), 6.13-6.08 (m, 1H), 5.67 (s, 2H), 3.70 (d, J = 10.5 Hz, 2H), 3.47-3.41 (m, 2H), 2.27-2.21 (m, 2H), 2.00 (t, J = 3.3 Hz, 1H) | 406.2 |
| 154 | ¹H NMR (400 MHz, DMSO-d6) δ 9.03 (dd, J = 4.6, 2.0 Hz, 1H), 8.74 (s, 1H), 8.56 (dd, J = 7.9, 2.0 Hz, 1H), 7.75 (d, J = 5.9 Hz, 1H), 7.63 (dd, J = 7.9, 4.6 Hz, 1H), 6.48-6.40 (m, 1H), 6.12-6.07 (m, 1H), 5.54 (s, 2H), 3.69 (d, J = 10.5 Hz, 2H), 3.45-3.40 (m, 2H), 2.25-2.20 (m, 2H), 2.00 (t, J = 3.3 Hz, 1H) | 406.1 |
| 155 | ¹H NMR (400 MHz, DMSO-d6) δ 8.31 (s, 1H), 8.06 (s, 1H), 8.02 (d, J = 5.5 Hz, 1H), 6.67 (dd, J = 5.5, 1.7 Hz, 1H), 6.55 (d, J = 1.7 Hz, 1H), 5.53 (s, 2H), 4.19 (s, 3H), 3.81 (d, J = 10.8 Hz, 2H), 3.49-3.43 (m, 2H), 2.21-2.18 (m, 2H), 1.98 (t, J = 3.3 Hz, 1H) | 425.1 |
| 156 | ¹H NMR (400 MHz, DMSO-d₆) δ 8.42 (s, 1H), 8.24 (s, 1H), 7.50-7.33 (m, 4H), 5.72-5.57 (m, 1H), 5.49 (s, 2H), 3.95 (s, 3H), 3.16-3.02 (m, 2H), 3.00-2.76 (m, 2H), 2.53 (d, J = 9.9 Hz, 2H), 2.17 (t, J = 3.1 Hz, 1H), 1.89 (q, J = 2.5 Hz, 2H) | 470.1 |
| 157 | ¹H NMR (400 MHz, DMSO-d6) δ 9.21 (dd, J = 4.6, 1.7 Hz, 1H), 8.65 (dd, J = 8.4, 1.8 Hz, 1H), 8.61 (s, 1H), 7.92 (dd, J = 8.1, 4.6 Hz, 1H), 7.61 (dd, J = 8.6, 1.2 Hz, 2H), 7.54-7.47 (m, 2H), 5.73 (s, 2H), 3.50-3.39 (m, 1H), 3.10-2.97 (m, 2H), 2.93-2.77 (m, 2H) | 412.1 |

TABLE 2-continued

| Ex. | 1H NMR (ppm) | M + H |
|---|---|---|
| 158 | $^1$H NMR (400 MHz, DMSO-d6) δ 8.84 (s, 1H), 8.04 (s, 1H), 7.64-7.57 (m, 2H), 7.51 (d, J = 8.3 Hz, 2H), 5.57 (s, 2H), 3.50-3.36 (m, 1H), 3.04 (tdd, J = 10.7, 8.5, 2.8 Hz, 2H), 2.91-2.77 (m, 5H) | 451.1 |
| 159 | $^1$H NMR (500 MHz, DMSO-d6) δ 8.47 (dd, J = 5.4, 0.4 Hz, 1H), 8.43 (s, 1H), 8.23 (d, J = 0.4 Hz, 1H), 7.67 (d, J = 1.6 Hz, 1H), 7.36 (dd, J = 5.3, 2.0 Hz, 1H), 6.97 (q, J = 1.7 Hz, 1H), 5.51 (s, 2H), 3.95 (s, 3H), 3.11 (ddd, J = 8.3, 6.5, 1.2 Hz, 1H), 2.99 (d, J = 18.3 Hz, 1H), 2.29 (td, J = 6.6, 3.7 Hz, 1H), 1.70 (dd, J = 3.4, 2.6 Hz, 1H). 1H hidden by DMSO signal | 422.0 |
| 160 | $^1$H NMR (500 MHz, DMSO-d6) δ 8.47 (dd, J = 5.3, 0.3 Hz, 1H), 8.43 (s, 1H), 8.24-8.22 (m, 1H), 7.67 (d, J = 1.6 Hz, 1H), 7.36 (dd, J = 5.3, 2.0 Hz, 1H), 6.97 (q, J = 1.8 Hz, 1H), 5.51 (s, 2H), 3.95 (s, 3H), 3.11 (ddd, J = 17.9, 6.7, 1.5 Hz, 1H), 2.99 (d, J = 18.2 Hz, 1H), 2.29 (td, J = 6.4, 3.5 Hz, 1H), 1.70 (dd, J = 3.3, 2.6 Hz, 1H). 1H hidden by DMSO signal | 422.0 |
| 164 | $^1$H NMR (400 MHz, DMSO-$d_6$) δ 8.79 (d, J = 4.8 Hz, 1H), 8.74 (s, 1H), 7.43-7.39 (m, 1H), 7.38-7.32 (m, 2H), 7.19-7.08 (m, 2H), 5.56 (s, 2H), 3.80-3.59 (m, 2H), 2.78 (s, 3H), 2.64-2.51 (m, 4H) | 392 |
| 166 | $^1$H NMR (300 MHz, DMSO-$d_6$) δ 8.84 (s, 1H), 8.05 (s, 1H), 7.65-7.61 (m, 2H), 7.27 (t, J = 8.8 Hz, 2H), 5.56 (s, 2H), 3.45-3.39 (m, 1H), 3.05-3.00 (m, 2H), 2.94-2.73 (m, 2H), 2.81 (s, 3H) | 435.1 |
| 167 | $^1$H NMR (400 MHz, DMSO-d6) δ 9.21 (dd, J = 4.6, 1.7 Hz, 1H), 8.65 (dd, J = 8.5, 1.8 Hz, 1H), 8.60 (s, 1H), 8.03 (d, J = 5.4 Hz, 1H), 7.93 (dd, J = 8.1, 4.6 Hz, 1H), 6.67 (dd, J = 5.5, 1.7 Hz, 1H), 6.55 (d, J = 1.8 Hz, 1H), 5.67 (s, 2H), 3.82 (d, J = 10.9 Hz, 2H), 3.47 (dt, J = 11.0, 1.9 Hz, 2H), 2.23-2.19 (m, 2H), 1.99 (t, J = 3.3 Hz, 1H) | 422.1 |
| 168 | $^1$H NMR (400 MHz, DMSO-d6) δ 8.79 (d, J = 4.8 Hz, 1H), 8.70 (s, 1H), 8.03 (d, J = 5.5 Hz, 1H), 7.41 (dd, J = 4.8, 1.0 Hz, 1H), 6.67 (dd, J = 5.5, 1.7 Hz, 1H), 6.55 (d, J = 1.7 Hz, 1H), 5.49 (s, 2H), 3.82 (d, J = 10.8 Hz, 2H), 3.49-3.44 (m, 2H), 2.77 (d, J = 0.7 Hz, 3H), 2.23-2.19 (m, 2H), 1.99 (t, J = 3.3 Hz, 1H) | 436.1 |
| 169 | $^1$H NMR (400 MHz, DMSO-d6) δ 9.21 (dd, J = 4.6, 1.7 Hz, 1H), 8.66 (dd, J = 7.9, 1.8 Hz, 1H), 8.61 (s, 1H), 8.07 (s, 1H), 7.93 (dd, J = 8.1, 4.6 Hz, 1H), 7.80 (d, J = 0.8 Hz, 1H), 7.13 (t, J = 7.8 Hz, 1H), 6.88-6.81 (m, 1H), 6.74 (t, J = 2.0 Hz, 1H), 6.42 (dd, J = 7.8, 2.2 Hz, 1H), 5.68 (s, 2H), 3.85 (s, 3H), 3.74 (d, J = 9.7 Hz, 2H), 3.30-3.25 (m, 3H), 2.23 (s, 1H), 2.06 (t, J = 3.2 Hz, 1H) | 467.2 |
| 176 | $^1$H NMR (300 MHz, DMSO-$d_6$) δ 8.46 (s, 1H), 8.24 (s, 1H), 7.34-7.26 (m, 1H), 6.79-6.73 (m, 1H), 6.68-6.65 (m, 2H), 5.59 (s, 2H), 4.93-4.87 (m, 1H), 3.97 (s, 3H), 3.74-3.68 (m, 1H), 2.72-2.66 (m, 2H), 2.59-2.54 (m, 2H) | 397.4 |
| 178 | $^1$H NMR (300 MHz, DMSO-$d_6$) δ 8.46 (s, 1H), 8.24 (s, 1H), 7.51-7.45 (m, 1H), 7.42-7.38 (m, 1H), 7.29-7.28 (m, 1H), 7.21-7.17 (m, 1H), 5.58 (s, 2H), 4.99-4.95 (m, 1H), 3.97 (s, 3H), 3.73-3.68 (m, 1H), 2.78-2.70 (m, 2H), 2.59-2.53 (m, 2H) | 404.2 |
| 182 | $^1$H NMR (400 MHz, DMSO) δ 8.43 (s, 1H), 8.23 (d, J = 0.6 Hz, 1H), 8.06 (dd, J = 9.7, 5.7 Hz, 1H), 6.49 (ddd, J = 8.7, 5.7, 2.2 Hz, 1H), 6.30 (dd, J = 12.5, 2.2 Hz, 1H), 5.52 (s, 2H), 3.98-3.93 (m, 3H), 3.80 (d, J = 10.8 Hz, 2H), 3.45 (dt, J = 10.9, 1.8 Hz, 2H), 2.24-2.14 (m, 2H), 1.97 (t, J = 3.3 Hz, 1H) | — |
| 183 | $^1$H NMR (400 MHz, DMSO-d6) δ 9.03 (dd, J = 4.7, 2.0 Hz, 1H), 8.74 (s, 1H), 8.56 (dd, J = 8.0, 2.0 Hz, 1H), 8.01 (d, J = 5.4 Hz, 1H), 7.63 (dd, J = 7.9, 4.6 Hz, 1H), 6.66 (dd, J = 5.5, 1.7 Hz, 1H), 6.54 (d, J = 1.7 Hz, 1H), 5.54 (s, 2H), 3.81 (d, J = 10.8 Hz, 2H), 3.47-3.42 (m, 2H), 2.21-2.16 (m, 2H), 1.98 (t, J = 3.3 Hz, 1H) | 422.1 |
| 184 | $^1$H NMR (500 MHz, DMSO-d6) δ 8.43 (s, 1H), 8.22 (s, 1H), 7.46 (t, J = 1.7 Hz, 1H), 7.38 (dt, J = 7.7, 1.4 Hz, 1H), 7.34 (t, J = 7.7 Hz, 1H), 7.30-7.27 (m, 1H), 6.64 (q, J = 1.8 Hz, 1H), 5.51 (s, 2H), 3.95 (s, 3H), 3.07 (ddd, J = 17.5, 6.7, 1.3 Hz, 1H), 2.91 (d, J = 17.8 Hz, 1H), 2.45 (dt, J = 8.7, 2.4 Hz, 1H), 2.26 (td, J = 6.5, 3.4 Hz, 1H), 1.65 (dd, J = 3.2, 2.6 Hz, 1H) | 421.0 |
| 185 | $^1$H NMR (500 MHz, DMSO-d6) δ 8.43 (s, 1H), 8.23 (s, J = 6.8 Hz, 1H), 7.47 (t, J = 1.7 Hz, 1H), 7.39 (dt, J = 7.7, 1.4 Hz, 1H), 7.34 (t, J = 7.8 Hz, 1H), 7.31-7.27 (m, 1H), 6.65 (q, J = 1.9 Hz, 1H), 5.51 (s, 2H), 3.95 (s, 3H), 3.12-3.03 (m, 1H), 2.92 (d, J = 17.8 Hz, 1H), 2.46 (dq, J = 4.8, 2.5 Hz, 1H), 2.26 (td, J = 6.5, 3.4 Hz, 1H), 1.68-1.63 (m, 1H) | 421.0 |
| 186 | $^1$H NMR (500 MHz, DMSO-d6) δ 8.44 (s, 1H), 8.24 (s, 1H), 7.46 (dd, J = 7.5, 1.0 Hz, 1H), 7.28 (dd, J = 8.1, 1.1 Hz, 1H), 7.00-6.92 (m, 1H), 5.55 (s, 2H), 5.39 (dd, J = 5.4, 1.3 Hz, 1H), 3.95 (s, 3H), 3.43 (dd, J = 5.4, 3.4 Hz, 1H), 2.05 (dd, J = 3.4, 1.3 Hz, 1H) | 397.0 |
| 187 | $^1$H NMR (500 MHz, DMSO-d6) δ 8.45 (s, 1H), 8.24 (s, 1H), 7.47 (dd, J = 7.5, 1.0 Hz, 1H), 7.28 (dd, J = 8.1, 1.1 Hz, 1H), 6.99-6.95 (m, 1H), 5.56 (s, 2H), 5.39 (dd, J = 5.4, 1.3 Hz, 1H), 3.96 (s, 3H), 3.43 (dd, J = 5.4, 3.4 Hz, 1H), 2.06 (dd, J = 3.4, 1.3 Hz, 1H) | 397.0 |
| 188 | $^1$H NMR (400 MHz, DMSO) δ 8.43 (s, 1H), 8.23 (s, 1H), 7.61 (d, J = 8.8 Hz, 1H), 6.76 (d, J = 2.3 Hz, 1H), 6.60 (dd, J = 8.9, 2.3 Hz, 1H), 5.52 (s, 2H), 3.95 (s, 3H), 3.74 (d, J = 10.6 Hz, 2H), 3.47 (d, J = 6.6 Hz, 2H), 2.26-2.24 (m, 2H), 2.01 (t, J = 3.3 Hz, 1H) | — |
| 191 | $^1$H NMR (400 MHz, DMSO-$d_6$) δ 8.48 (s, 1H), 8.25 (s, 1H), 7.35-7.17 (m, 1H), 7.23-7.12 (m, 2H), 7.08-6.98 (m, 1H), 5.59 (s, 2H), 3.96 (s, 3H), 3.82-3.60 (m, 2H), 2.58 (dd, J = 8.6, 6.9 Hz, 4H) | 381.1 |

TABLE 2-continued

| Ex. | 1H NMR (ppm) | M + H |
|---|---|---|
| 192 | ¹H NMR (400 MHz, DMSO) δ 8.43 (s, 1H), 8.23 (s, 1H), 7.58-7.49 (m, 2H), 6.68-6.59 (m, 2H), 5.52 (s, 2H), 3.95 (s, 3H), 3.72 (d, J = 10.3 Hz, 2H), 3.42 (dt, J = 10.4, 1.9 Hz, 2H), 2.29-2.20 (m, 2H), 2.01 (t, J = 3.3 Hz, 1H) | — |
| 194 | ¹H NMR (400 MHz, DMSO-d6) δ 9.03 (dd, J = 4.6, 2.0 Hz, 1H), 8.75 (s, 1H), 8.57 (dd, J = 7.9, 2.0 Hz, 1H), 7.63 (dd, J = 8.0, 4.6 Hz, 1H), 7.19-7.10 (m, 2H), 6.68-6.57 (m, 2H), 6.60-6.52 (m, 2H), 5.54 (s, 2H), 3.67 (d, J = 9.7 Hz, 2H), 3.24-3.19 (m, 2H), 2.22-2.16 (m, 2H), 2.03 (t, J = 3.2 Hz, 1H) | 387.2 |
| 195 | ¹H NMR (400 MHz, DMSO-d6) δ 9.16 (s, 1H), 8.76 (d, J = 5.2 Hz, 1H), 8.67 (s, 1H), 8.05-7.99 (m, 1H), 7.20-7.11 (m, 2H), 6.69-6.60 (m, 1H), 6.60-6.53 (m, 2H), 5.56 (s, 2H), 3.67 (d, J = 9.7 Hz, 2H), 3.25-3.20 (m, 2H), 2.22-2.17 (m, 2H), 2.03 (t, J = 3.2 Hz, 1H) | 387.1 |
| 196 | ¹H NMR (300 MHz, DMSO-d₆) δ 8.79 (d, J = 4.8 Hz, 1H), 8.73 (s, 1H), 7.66-7.61 (m, 2H), 7.42 (dd, J = 4.8, 1.0 Hz, 1H), 7.34-7.22 (m, 2H), 5.55 (s, 2H), 3.38-3.32 (m, 1H), 3.12-3.02 (m, 2H), 2.95-2.74 (m, 2H), 2.73 (s, 3H) | 410.1 |
| 197 | ¹H NMR (400 MHz, DMSO-d₆)) δ 9.0-9.02 (m, 1H), 8.79 (s, 1H), 8.58-8.56 (m, 1H), 7.64 (dd, J = 8.0, 4.6 Hz, 1H), 7.51 (dd, J = 14.2, 8.0 Hz, 1H), 7.42 (d, J = 7.7 Hz, 2H), 7.24 (t, J = 8.4 Hz, 1H), 5.61 (s, 2H), 3.54-3.41 (m, 1H), 3.09-3.00 (m, 2H), 2.93-2.77 (m, 2H) | 396.1 |
| 198 | ¹H NMR (300 MHz, DMSO-d₆) δ 9.04 (dd, J = 4.6, 2.0 Hz, 1H), 8.79 (s, 1H), 8.58 (dd, J = 7.9, 2.0 Hz, 1H), 7.68-7.60 (m, 2H), 7.58-7.44 (m, 3H), 5.61 (s, 2H), 3.53-3.42 (m, 1H), 3.12-3.01 (m, 2H), 2.95-2.73 (m, 2H) | 412.1 |
| 204 | ¹H NMR (400 MHz, DMSO-d6) δ 8.43 (s, 1H), 8.23 (s, 1H), 7.13 (t, J = 8.0 Hz, 1H), 6.60 (dd, J = 7.6, 1.9 Hz, 1H), 6.56-6.49 (m, 2H), 5.51 (s, 2H), 4.21 (q, J = 6.1 Hz, 1H), 3.95 (s, 3H), 3.53 (d, J = 10.0 Hz, 1H), 3.38-3.34 (m, 1H), 2.15 (dt, J = 7.0, 3.5 Hz, 1H), 1.97 (dd, J = 7.3, 3.3 Hz, 1H), 1.93 (t, J = 3.2 Hz, 1H), 1.07 (d, J = 6.1 Hz, 3H) | 438.1 |
| 206 | ¹H NMR (300 MHz, DMSO-d₆) δ 8.48 (s, 1H), 8.25 (s, 1H), 7.67-7.61 (m, 2H), 7.31-7.25 (m, 2H), 5.59 (s, 2H), 3.96 (s, 3H), 3.49-3.32 (m, 1H), 3.11-2.97 (m, 2H), 2.96-2.76 (m, 2H) | 399.1 |
| 207 | ¹H NMR (300 MHz, DMSO-d₆) δ 9.05 (dd, J = 4.6, 2.0 Hz, 1H), 8.80 (s, 1H), 8.59 (dd, J = 7.9, 2.0 Hz, 1H), 7.71-7.58 (m, 3H), 7.36-7.22 (m, 2H), 5.62 (s, 2H), 3.49-3.28 (m, 1H), 3.18-2.98 (m, 2H), 2.90-2.84 (m, 2H) | — |
| 208 | ¹H NMR (300 MHz, DMSO-d6) δ 9.05 (dd, J = 4.6, 2.0 Hz, 1H), 8.80 (s, 1H), 8.59 (dd, J = 7.9, 2.0 Hz, 1H), 7.71-7.58 (m, 3H), 7.36-7.22 (m, 2H), 5.62 (s, 2H), 3.49-3.28 (m, 1H), 3.18-2.98 (m, 2H), 2.90-2.84 (m, 2H) | 394.1 |
| 209 | ¹H NMR (300 MHz, DMSO-d₆) δ 8.48 (s, 1H), 8.25 (s, 1H), 7.56-7.53 (m, 1H), 7.36-7.31 (m, 1H), 7.23-7.17 (m, 1H), 5.60 (s, 2H), 3.96 (s, 3H), 3.94-3.85 (m, 1H), 3.70-3.61 (m, 1H), 2.70-2.08 (m, 4H) | 415.0 |
| 210 | ¹H NMR (300 MHz, DMSO-d₆) δ 8.80 (d, J = 4.8 Hz, 1H), 8.73 (s, 1H), 7.63 (s, 1H), 7.59-7.51 (m, 1H), 7.50-7.46 (m, 2H), 7.42 (d, J = 4.9 Hz, 1H), 5.56 (s, 2H), 3.50-3.32 (m, 1H), 3.13-3.02 (m, 2H), 2.92-2.77 (m, 2H), 2.77 (s, 3H) | 426.1 |
| 211 | ¹H NMR (400 MHz, DMSO) δ 8.96 (s, 1H), 8.44 (s, 1H), 8.23 (d, J = 0.7 Hz, 1H), 7.85 (d, J = 8.9 Hz, 1H), 7.21 (d, J = 2.4 Hz, 1H), 6.86 (dd, J = 9.0, 2.5 Hz, 1H), 5.53 (s, 2H), 3.98-3.93 (m, 3H), 3.77 (d, J = 9.8 Hz, 2H), 3.37-3.33 (m, 2H), 2.29-2.19 (m, 2H), 2.06 (t, J = 3.3 Hz, 1H) | — |
| 212 | ¹H NMR (400 MHz, DMSO) δ 8.43 (s, 1H), 8.23 (d, J = 0.6 Hz, 1H), 8.02 (d, J = 5.4 Hz, 1H), 6.67 (dd, J = 5.4, 1.7 Hz, 1H), 6.55 (d, J = 1.7 Hz, 1H), 5.52 (s, 2H), 3.95 (s, 3H), 3.81 (d, J = 10.8 Hz, 2H), 3.46 (dt, J = 11.1, 1.8 Hz, 2H), 2.24-2.14 (m, 2H), 1.97 (t, J = 3.3 Hz, 1H) | — |
| 213 | ¹H NMR (400 MHz, DMSO-d6) δ 9.20 (dd, J = 4.6, 1.7 Hz, 1H), 8.67-8.62 (m, 1H), 8.60 (d, J = 0.8 Hz, 1H), 7.92 (dd, J = 8.1, 4.6 Hz, 1H), 7.19-7.10 (m, 2H), 6.66-6.61 (m, 1H), 6.59-6.54 (m, 2H), 5.67 (s, 2H), 3.68 (d, J = 9.6 Hz, 2H), 3.25-3.21 (m, 2H), 2.24-2.17 (m, 2H), 2.03 (t, J = 3.2 Hz, 1H) | 387.1 |
| 214 | ¹H NMR (400 MHz, DMSO-d6) δ 9.20 (dd, J = 4.5, 1.7 Hz, 1H), 8.64 (dd, J = 8.1, 1.8 Hz, 1H), 8.60 (s, 1H), 7.92 (dd, J = 8.1, 4.6 Hz, 1H), 7.15 (t, J = 8.0 Hz, 1H), 6.64 (dd, J = 7.6, 1.9 Hz, 1H), 6.56 (t, J = 2.2 Hz, 1H), 6.51 (dd, J = 8.4, 2.3 Hz, 1H), 5.67 (s, 2H), 3.67 (d, J = 9.8 Hz, 2H), 3.28-3.23 (m, 2H), 2.25-2.18 (m, 2H), 2.01 (t, J = 3.3 Hz, 1H) | 421.1 |
| 215 | ¹H NMR (400 MHz, DMSO-d6) δ 8.23 (s, 1H), 7.15 (t, J = 8.1 Hz, 1H), 6.65 (dd, J = 7.5, 1.9 Hz, 1H), 6.56 (t, J = 2.1 Hz, 1H), 6.54-6.49 (m, 1H), 5.89 (s, 2H), 3.67 (d, J = 9.9 Hz, 2H), 3.46 (s, 3H), 3.29-3.27 (m, 2H), 3.19 (s, 3H), 2.20-2.17 (m, 2H), 2.01 (t, J = 3.2 Hz, 1H) | 454.1 |
| 216 | ¹H NMR (300 MHz, CD₃OD) δ 9.00 (d, J = 2.1 Hz, 1H), 8.69-8.66 (m, 2H), 7.65 (dd, J = 8.0, 4.7 Hz, 1H), 7.13-7.08 (m, 1H), 6.64-6.61 (m, 1H), 6.57-6.56 (m, 1H), 6.51-6.49 (m, 1H), 5.52 (s, 2H), 3.68 (d, J = 9.6 Hz, 2H), 3.30-3.28 (m, 2H), 2.25-2.24 (m, 2H), 2.09-2.00 (m, 1H) | 421.1 |
| 217 | ¹H NMR (400 MHz, DMSO-d6) δ 8.46 (s, 1H), 8.24 (s, 1H), 7.30 (t, J = 8.2 Hz, 1H), 7.00 (ddd, J = 7.9, 2.0, 0.9 Hz, 1H), 6.87 (t, J = 2.2 Hz, 1H), 6.81 (ddd, J = 8.4, 2.5, 0.9 Hz, 1H), 5.58 (s, 2H), 4.98-4.88 (m, 1H), 3.95 (s, 2H), 3.77-3.65 (m, 1H), 2.76-2.64 (m, 2H), 2.61-2.52 (m, 2H) | 413.1 |
| 218 | ¹H NMR (400 MHz, DMSO-d6) δ 8.46 (s, 1H), 8.24 (s, 1H), 7.34-7.27 (m, 2H), 6.88-6.81 (m, 2H), 5.57 (s, 2H), 4.95-4.83 (m, 1H), 3.95 (s, 3H), 3.76-3.64 (m, 1H), 2.74-2.63 (m, 2H), 2.60-2.50 (m, 2H) | 413.1 |

TABLE 2-continued

| Ex. | 1H NMR (ppm) | M + H |
|---|---|---|
| 220 | $^1$H NMR (400 MHz, DMSO-d$_6$) δ 8.48 (s, 1H), 8.25 (s, 1H), 7.57-7.55 (m, 1H), 7.41-7.29 (m, 2H), 5.59 (s, 2H), 3.96 (s, 3H), 3.81-3.59 (m, 2H), 2.59-2.49 (m, 4H) | 415.1 |
| 222 | $^1$H NMR (400 MHz, DMSO) δ 8.43 (s, 1H), 8.23 (s, 1H), 7.13 (ddd, J = 9.4, 8.5, 2.0 Hz, 1H), 6.79 (td, J = 9.5, 5.4 Hz, 1H), 5.52 (s, 2H), 3.95 (s, 3H), 3.74 (dd, J = 9.7, 2.9 Hz, 2H), 3.29 (d, J = 1.7 Hz, 2H), 2.18-2.13 (m, 2H), 2.15 (t, J = 2.7 Hz, 1H) | — |
| 225 | $^1$H NMR (500 MHz, DMSO-d6) δ 8.43 (s, 1H), 8.23 (s, 1H), 7.46-7.37 (m, 2H), 7.31 (t, J = 7.6 Hz, 2H), 7.27-7.19 (m, 1H), 6.53 (q, J = 1.8 Hz, 1H), 5.51 (s, 2H), 3.95 (s, 3H), 3.09 (ddd, J = 17.8, 6.8, 1.2 Hz, 1H), 2.91 (d, J = 17.8 Hz, 1H), 2.47-2.43 (m, 1H), 2.26 (td, J = 6.6, 3.4 Hz, 1H), 1.64 (t, J = 3.0 Hz, 1H) | 387.1 |
| 226 | $^1$H NMR (500 MHz, DMSO-d6): δ 8.43 (s, 1H), 8.23 (d, J = 0.4 Hz, 1H), 7.44-7.40 (m, 2H), 7.34-7.28 (m, 2H), 7.26-7.21 (m, 1H), 6.53 (q, J = 1.9 Hz, 1H), 5.51 (s, 2H), 3.95 (d, J = 0.2 Hz, 3H), 3.09 (ddd, J = 17.5, 6.7, 1.4 Hz, 1H), 2.92 (dt, J = 17.6, 2.2 Hz, 1H), 2.47-2.41 (m, 1H), 2.26 (td, J = 6.6, 3.4 Hz, 1H), 1.64 (dd, J = 3.3, 2.6 Hz, 1H) | 387.1 |
| 228 | $^1$H NMR (300 MHz, DMSO-d$_6$) δ 8.44 (s, 1H), 8.24 (s, 1H), 8.07-8.05 (m, 1H), 7.52-7.46 (m, 1H), 6.61-6.57 (m, 1H), 6.47-6.45 (m, 1H), 5.53 (s, 2H), 3.96 (s, 3H), 3.81 (d, J = 10.6 Hz, 2H), 3.44-3.40 (m, 2H), 2.19-2.13 (m, 2H), 1.98 (t, J = 3.3 Hz, 1H) | 391.1 |
| 229 | $^1$H NMR (300 MHz, DMSO-d$_6$) δ 8.45 (s, 1H), 8.25 (s, 1H), 7.29 (t, J = 8.8 Hz, 1H), 6.58 (dd, J = 12.7, 2.7 Hz, 1H), 6.47-6.36 (m, 1H), 5.53 (s, 2H), 3.96 (s, 3H), 3.67 (d, J = 9.9 Hz, 2H), 3.33 (s, 2H), 2.22 (t, J = 2.8 Hz, 2H), 2.12-1.98 (m, 1H) | 442.1 |
| 230 | $^1$H NMR (300 MHz, DMSO-d$_6$) δ 9.16 (d, J = 0.6 Hz, 1H), 8.76-8.75 (m, 1H), 8.66 (s, 1H), 8.02 (dd, J = 5.1, 0.9 Hz, 1H), 7.15 (t, J = 8.1 Hz, 1H), 6.66-6.63 (m, 1H), 6.56-6.49 (m, 2H), 5.56 (s, 2H), 3.67 (d, J = 9.9 Hz, 2H), 3.28-3.25 (m, 2H), 2.20 (t, J = 3.0 Hz, 1H), 2.01 (t, J = 3.2 Hz, 1H) | 421.1 |
| 231 | $^1$H NMR (300 MHz, DMSO-d$_6$) δ 8.49 (s, 1H), 8.25 (s, 1H), 7.89-7.86 (m, 3H), 7.81 (s, 1H), 7.50-7.42 (m, 3H), 5.60 (s, 2H), 3.96 (s, 3H), 3.93-3.87 (m, 1H), 3.74-3.67 (m, 1H), 2.73-2.48 (m, 4H) | 413.1 |
| 232 | $^1$H NMR (400 MHz, DMSO-d$_6$) δ 8.94 (s, 1H), 8.66 (s, 1H), 8.54 (s, 1H), 8.08 (s, 1H), 7.99-7.87 (m, 3H), 7.72 (dd, J = 8.6, 1.8 Hz, 1H), 7.56-7.45 (m, 2H), 5.93 (s, 1H), 5.56 (s, 2H), 3.28 (d, J = 9.2 Hz, 1H), 2.99-2.89 (m, 2H), 2.71 (s, 3H), 2.68-2.63 (m, 2H) | 440.0 |
| 233 | $^1$H NMR (300 MHz, DMSO-d$_6$) δ 8.80 (d, J = 4.8 Hz, 1H), 8.74 (s, 1H), 8.08 (s, 1H), 8.01-7.84 (m, 3H), 7.73-7.69 (m, 1H), 7.60-7.45 (m, 2H), 7.41 (d, J = 4.8 Hz, 1H), 5.94 (s, 1H), 5.55 (s, 2H), 3.36-3.24 (m, 1H), 3.00-2.85 (m, 2H), 2.77 (s, 3H), 2.69-2.49 (m, 2H) | 440.0 |
| 235 | $^1$H NMR (400 MHz, DMSO) δ 8.43 (s, 1H), 8.23 (s, 1H), 7.41-7.28 (m, 1H), 7.02 (d, J = 7.6 Hz, 1H), 6.93 (s, 1H), 6.88 (dd, J = 8.4, 2.1 Hz, 1H), 5.52 (s, 2H), 3.95 (s, 3H), 3.71 (d, J = 10.0 Hz, 2H), 3.29 (s, 2H), 2.22 (s, 2H), 2.01 (t, J = 3.3 Hz, 1H) | — |
| 236 | $^1$H NMR (400 MHz, DMSO) δ 8.43 (s, 1H), 8.23 (s, 1H), 7.01 (td, J = 8.2, 1.3 Hz, 1H), 6.87 (ddd, J = 7.9, 6.3, 1.5 Hz, 1H), 6.73 (td, J = 8.4, 1.6 Hz, 1H), 5.52 (s, 2H), 3.95 (s, 3H), 3.79 (dd, J = 9.9, 3.0 Hz, 2H), 3.39 (d, J = 9.6 Hz, 2H), 2.17 (td, J = 2.8, 2.4, 1.2 Hz, 2H), 2.12 (t, J = 3.2 Hz, 1H) | — |
| 238 | $^1$H NMR (400 MHz, DMSO-d$_6$) δ 8.46 (s, 1H), 7.42 (d, J = 7.2 Hz, 2H), 7.33-7.29 (m, 2H), 7.25 (d, J = 7.2 Hz, 1H), 6.97 (s, 2H), 6.53 (s, 1H), 6.37 (s, 1H), 5.36 (s, 2H), 3.14-3.06 (m, 1H), 2.94-2.86 (m, 1H), 2.54-2.50 (m, 4H), 2.32-2.27 (m, 1H), 1.67-1.63 (m, 1H) | 413 |
| 239 | $^1$H NMR (400 MHz, DMSO-d$_6$) δ 8.49 (s, 1H), 8.01 (d, J = 8.8 Hz, 1H), 7.42 (d, J = 7.4 Hz, 2H), 7.31 (t, J = 7.6 Hz, 2H), 7.28-7.16 (m, 3H), 6.61 (d, J = 8.7 Hz, 1H), 6.53 (s, 1H), 5.41 (s, 2H), 3.11-3.05 (m, 1H), 2.93-2.89 (m, 1H), 2.47-2.43 (m, 1H), 2.28-2.24 (m, 1H), 1.63 (t, J = 2.9 Hz, 1H) | 399 |
| 240 | $^1$H NMR (500 MHz, DMSO-d6) δ 8.41 (s, 1H), 8.23 (s, 1H), 7.30-7.25 (m, 2H), 6.96-6.90 (m, 3H), 5.49 (s, 2H), 4.92 (d, J = 4.5 Hz, 1H), 3.94 (s, 3H), 2.06 (t, J = 3.2 Hz, 1H), 2.04-1.90 (m, 3H), 1.85 (dd, J = 12.5, 7.2 Hz, 1H), 1.79-1.66 (m, 2H) | 405 |
| 241 | $^1$H NMR (500 MHz, DMSO-d6) δ 10.78 (s, 1H), 8.43 (s, 1H), 7.42 (d, J = 7.6 Hz, 2H), 7.31 (t, J = 7.7 Hz, 2H), 7.23 (t, J = 7.1 Hz, 1H), 6.53 (s, 1H), 5.51 (s, 2H), 3.73 (s, 3H), 3.09 (dd, J = 17.9, 6.7 Hz, 1H), 2.92 (d, J = 18.1 Hz, 1H), 2.48-2.44 (m, 1H), 2.27 (td, J = 6.6, 3.7 Hz, 1H), 2.15 (s, 3H), 1.64 (t, J = 2.7 Hz, 1H) | 444 |
| 242 | $^1$H NMR (500 MHz, DMSO-d6) δ 8.43 (s, 1H), 8.23 (d, J = 0.4 Hz, 1H), 7.35-7.18 (m, 2H), 6.59 (s, 1H), 5.51 (s, 2H), 3.95 (s, 3H), 3.14 (dd, J = 18.2, 6.1 Hz, 1H), 2.97 (d, J = 17.8 Hz, 1H), 2.54-2.51 (m, 1H), 2.30-2.24 (m, 1H), 1.69 (dd, J = 3.3, 2.6 Hz, 1H) | 441 |
| 243 | $^1$H NMR (500 MHz, DMSO-d6) δ 8.28 (s, 1H), 7.66 (d, J = 6.2 Hz, 1H), 7.44-7.41 (m, 2H), 7.33-7.29 (m, 2H), 7.25-7.22 (m, 1H), 6.54-6.53 (m, 1H), 5.44 (s, 2H), 4.93-4.86 (m, 1H), 4.82 (t, J = 6.7 Hz, 2H), 4.58 (t, J = 6.3 Hz, 2H), 3.69 (s, 3H), 3.09 (dd, J = 18.7, 6.1 Hz, 1H), 2.95-2.88 (m, 1H), 2.47-2.43 (m, 1H), 2.26 (td, J = 6.6, 3.4 Hz, 1H), 1.64-1.62 (m, 1H) | 458 |
| 244 | $^1$H NMR (500 MHz, DMSO-d6) δ 8.27 (s, 1H), 7.44-7.40 (m, 2H), 7.33-7.30 (m, 2H), 7.25-7.21 (m, 1H), 7.10 (t, J = 5.9 Hz, 1H), 6.54-6.52 (m, 1H), 5.44 (s, 2H), 4.17 (d, J = 5.8 Hz, 2H), 3.69 (s, 3H), 3.12-3.06 (m, 1H), | 487 |

TABLE 2-continued

| Ex. | 1H NMR (ppm) | M + H |
|---|---|---|
| | 3.03 (s, 3H), 2.94-2.89 (m, 1H), 2.86 (s, 3H), 2.47-2.44 (m, 1H), 2.26 (td, J = 6.6, 3.5 Hz, 1H), 1.65-1.62 (m, 1H) | |
| 245 | $^1$H NMR (500 MHz, DMSO-d6) δ 8.26 (s, 1H), 7.44-7.41 (m, 2H), 7.34-7.29 (m, 2H), 7.26-7.22 (m, 1H), 6.83 (d, J = 7.6 Hz, 1H), 6.55-6.52 (m, 1H), 5.43 (s, 2H), 3.94-3.85 (m, 3H), 3.64 (s, 3H), 3.40 (td, J = 11.7, 2.0 Hz, 2H), 3.13-3.06 (m, 1H), 2.94-2.88 (m, 1H), 2.47-2.42 (m, 1H), 2.26 (td, J = 6.6, 3.4 Hz, 1H), 1.94-1.87 (m, 1H), 1.65-1.62 (m, 1H), 1.61-1.52 (m, 2H) | 486 |
| 246 | $^1$H NMR (400 MHz, DMSO-d6) δ 8.21 (s, 1H), 7.38 (d, J = 7.4 Hz, 2H), 7.27 (t, J = 7.4 Hz, 2H), 7.22-7.16 (m, 1H), 6.93 (t, J = 5.4 Hz, 1H), 6.50-6.47 (m, 1H), 5.39 (s, 2H), 3.57 (s, 3H), 3.36-3.31 (m, 2H), 3.05 (dd, J = 18.1, 6.7 Hz, 1H), 2.91-2.84 (m, 1H), 2.42-2.38 (m, 1H), 2.24-2.19 (m, 1H), 1.60-1.57 (m, 1H), 1.14 (t, J = 7.1 Hz, 3H) | 430 |
| 247 | $^1$H NMR (400 MHz, DMSO) δ 8.43 (s, 1H), 8.23 (s, 1H), 7.58 (dd, J = 14.4, 2.0 Hz, 1H), 7.44 (dd, J = 8.6, 2.0 Hz, 1H), 6.79 (t, J = 8.9 Hz, 1H), 5.52 (s, 2H), 3.95 (s, 3H), 3.88 (dd, J = 10.4, 3.4 Hz, 2H), 3.57 (d, J = 9.2 Hz, 2H), 2.25-2.15 (m, 2H), 2.12-2.04 (m, 1H) | 433.1 |
| 248 | $^1$H NMR (400 MHz, CDCl$_3$) δ 8.15 (s, 1H), 7.87 (s, 1H), 7.46-7.38 (m, 1H), 7.24 (s, 1H), 7.19-7.12 (m, 2H), 5.41 (s, 2H), 4.10 (s, 3H), 3.66-3.63 (m, 1H), 3.23-3.15 (m, 1H), 2.68-2.61 (m, 2H), 2.42-2.35 (m, 2H) | 431 |
| 249 | $^1$H NMR (400 MHz, DMSO-d$_6$) δ 8.48 (s, 1H), 8.24 (s, 1H), 7.23-7.19 (m, 2H), 6.70-6.64 (m, 3H), 5.60 (s, 2H), 3.96 (s, 3H), 3.65-3.53 (m, 4H), 3.03 (d, J = 5.6 Hz, 1H), 2.84 (d, J = 6 Hz, 2H), 2.50-2.47 (m, 1H), 1.49-1.45 (m, 1H) | 404 |
| 250 | $^1$H NMR (500 MHz, DMSO-d6) δ 8.44 (s, 1H), 8.24 (s, 1H), 7.58-7.55 (m, 2H), 7.33-7.29 (m, 2H), 7.24-7.20 (m, 1H), 6.62-6.60 (m, 1H), 5.53 (s, 2H), 5.45 (d, J = 7.6 Hz, 1H), 4.95 (dd, J = 7.5, 2.6 Hz, 1H), 3.96 (s, 3H), 2.49-2.46 (m, 1H), 2.23 (dd, J = 5.6, 3.6 Hz, 1H), 1.67 (dd, J = 3.6, 2.4 Hz, 1H) | 403 |
| 251 | $^1$H NMR (500 MHz, DMSO-d6) δ 8.43 (s, 1H), 8.23 (s, 1H), 7.39 (dd, J = 9.5, 6.8 Hz, 2H), 6.70 (d, J = 1.9 Hz, 1H), 5.51 (s, 2H), 3.95 (s, 3H), 3.04 (dd, J = 18.0, 7.8 Hz, 1H), 2.90 (d, J = 17.7 Hz, 1H), 2.48-2.44 (m, 1H), 2.30-2.24 (m, 1H), 1.68-1.64 (m, 1H) | 441 |
| 252 | $^1$H NMR (500 MHz, DMSO-d6) δ 8.26 (s, 1H), 7.44-7.40 (m, 2H), 7.34-7.29 (m, 2H), 7.26-7.21 (m, 1H), 7.03 (t, J = 5.7 Hz, 1H), 6.55-6.52 (m, 1H), 5.43 (s, 2H), 4.82-4.73 (m, 1H), 3.63 (s, 3H), 3.60-3.54 (m, 1H), 3.40 (q, J = 6.9 Hz, 2H), 3.10 (dd, J = 17.7, 6.9 Hz, 1H), 2.94-2.89 (m, 1H), 2.47-2.42 (m, 1H), 2.26 (td, J = 6.6, 3.4 Hz, 1H), 1.64-1.62 (m, 1H) | 446 |
| 253 | $^1$H NMR (400 MHz, DMSO-d$_6$) δ 8.44 (s, 1H), 7.78 (s, 1H), 7.63 (s, 1H), 7.57-7.56 (d, J = 6.8 Hz, 1H), 7.53-7.47 (m, 2H), 5.50 (s, 2H), 3.56-3.42 (m, 1H), 3.15-3.01 (m, 2H), 2.91-2.83 (m, 2H), 2.37 (s, 3H) | 415 |
| 254 | $^1$H NMR (500 MHz, DMSO-d6) δ 8.43 (s, 1H), 8.24 (d, J = 0.4 Hz, 1H), 7.35-7.28 (m, 1H), 7.23-7.14 (m, 2H), 6.63 (s, 1H), 5.52 (s, 2H), 3.95 (s, 3H), 3.15 (dd, J = 17.0, 6.7 Hz, 1H), 2.98 (d, J = 17.7 Hz, 1H), 2.55-2.51 (m, 1H), 2.32-2.23 (m, 1H), 1.72-1.66 (m, 1H) | 423 |
| 255 | $^1$H NMR (500 MHz, DMSO-d6) δ 8.25 (s, 1H), 7.44-7.41 (m, 2H), 7.33-7.29 (m, 2H), 7.25-7.22 (m, 1H), 6.83 (s, 2H), 6.54 (dd, J = 3.7, 1.8 Hz, 1H), 5.43 (s, 2H), 3.62 (s, 3H), 3.10 (ddd, J = 17.8, 6.9, 1.6 Hz, 1H), 2.92 (d, J = 17.6 Hz, 1H), 2.47-2.44 (m, 1H), 2.26 (td, J = 6.5, 3.3 Hz, 1H), 1.63 (dd, J = 3.3, 2.6 Hz, 1H) | 402 |
| 256 | $^1$H NMR (500 MHz, DMSO-d6) δ 8.43 (s, 1H), 8.23 (d, J = 0.4 Hz, 1H), 7.80-7.74 (m, 2H), 7.65-7.56 (m, 2H), 6.81 (d, J = 1.9 Hz, 1H), 5.51 (s, 2H), 3.97-3.93 (m, 3H), 3.30 (d, J = 11.9 Hz, 1H), 3.15-3.06 (m, 1H), 2.96 (d, J = 17.8 Hz, 1H), 2.31 (td, J = 6.5, 3.4 Hz, 1H), 1.70 (dd, J = 3.4, 2.6 Hz, 1H) | 412 |
| 257 | $^1$H NMR (400 MHz, DMSO-d$_6$) δ 8.44 (s, 1H), 8.23 (s, 1H), 7.30-7.17 (m, 4H), 5.53 (s, 2H), 3.94 (s, 3H), 3.72-3.62 (m, 1H), 2.81 (d, J = 7.9 Hz, 2H), 2.68-2.67 (m, 1H), 2.33-2.18 (m, 2H), 2.17-2.05 (m, 2H) | 411 |
| 258 | $^1$H NMR (400 MHz, DMSO) δ 8.43 (s, 1H), 8.23 (s, 1H), 6.49 (d, J = 11.9 Hz, 2H), 5.52 (s, 2H), 3.95 (s, 3H), 3.73 (d, J = 10.9 Hz, 2H), 3.55-3.45 (m, 2H), 2.29-2.19 (m, 2H), 2.02 (t, J = 3.4 Hz, 1H) | 451.1 |
| 259 | $^1$H NMR (500 MHz, DMSO-d6) δ 8.55 (s, 1H), 7.46-7.40 (m, 2H), 7.36-7.29 (m, 2H), 7.28-7.21 (m, 1H), 6.54 (q, J = 1.9 Hz, 1H), 5.94 (s, 2H), 4.04 (s, 3H), 3.10 (ddd, J = 17.6, 6.4, 1.5 Hz, 1H), 2.93 (d, J = 18.0 Hz, 1H), 2.49-2.44 (m, 1H), 2.28 (td, J = 6.4, 3.1 Hz, 1H), 1.66 (dd, J = 3.2, 2.6 Hz, 1H) | 388 |
| 260 | $^1$H NMR (500 MHz, DMSO-d6) δ 8.27 (s, 1H), 7.44-7.41 (m, 2H), 7.34-7.29 (m, 2H), 7.26-7.22 (m, 1H), 7.11 (t, J = 5.3 Hz, 1H), 6.55-6.52 (m, 1H), 5.43 (s, 2H), 3.63 (s, 3H), 3.54-3.48 (m, 4H), 3.28 (s, 3H), 3.13-3.06 (m, 1H), 2.95-2.89 (m, 1H), 2.45 (dq, J = 6.5, 2.4 Hz, 1H), 2.26 (td, J = 6.6, 3.4 Hz, 1H), 1.63 (dd, J = 3.3, 2.6 Hz, 1H) | 460 |
| 261 | $^1$H NMR (400 MHz, DMSO-d$_6$) δ 8.49 (s, 1H), 8.00 (d, J = 8.7 Hz, 1H), 7.22-7.10 (m, 3H), 6.61 (d, J = 8.7 Hz, 1H), 6.46-6.30 (m, 2H), 5.42 (s, 2H), 3.66 (d, J = 9.8 Hz, 2H), 3.27 (d, J = 10.0 Hz, 2H), 2.20 (t, J = 2.6 Hz, 2H), 2.00 (t, J = 3.3 Hz, 1H) | 420 |
| 262 | $^1$H NMR (500 MHz, DMSO-d6) δ 8.26 (s, 1H), 7.44-7.40 (m, 2H), 7.34-7.29 (m, 2H), 7.26-7.22 (m, 1H), 6.95 (q, J = 4.6 Hz, 1H), 6.55-6.53 (m, 1H), 5.43 (s, 2H), 3.61 (s, 3H), 3.10 (dd, J = 18.7, 6.7 Hz, 1H), | 416 |

TABLE 2-continued

| Ex. | 1H NMR (ppm) | M + H |
|---|---|---|
|  | 2.94-2.89 (m, 1H), 2.90 (d, J = 4.6 Hz, 3H), 2.47-2.43 (m, 1H), 2.28-2.24 (m, 1H), 1.64-1.62 (m, 1H) |  |
| 263 | ¹H NMR (500 MHz, DMSO-d6) δ 8.49 (s, 1H), 7.44-7.40 (m, 2H), 7.33-7.29 (m, 2H), 7.26-7.21 (m, 1H), 6.55-6.52 (m, 1H), 5.53 (s, 2H), 3.91 (s, 3H), 3.09 (dd, J = 17.8, 5.4 Hz, 1H), 2.95-2.89 (m, 1H), 2.47-2.43 (m, 1H), 2.26 (td, J = 6.6, 3.4 Hz, 1H), 1.65-1.63 (m, 1H) | 421 |
| 264 | ¹H NMR (500 MHz, DMSO-d6) δ 8.44 (s, 1H), 8.24 (s, 1H), 8.00 (d, J = 0.8 Hz, 1H), 7.65 (s, 1H), 7.61 (dd, J = 8.9, 1.5 Hz, 1H), 7.57 (dt, J = 8.9 Hz, 1H), 6.52 (d, J = 1.8 Hz, 1H), 5.52 (s, 2H), 4.02 (s, 3H), 3.96 (s, 3H), 3.16 (dd, J = 17.3, 6.6 Hz, 1H), 2.99 (d, J = 17.6 Hz, 1H), 2.46 (dt, J = 4.7, 2.4 Hz, 1H), 2.27 (td, J = 6.5, 3.4 Hz, 1H), 1.67-1.64 (m, 1H) | 441 |
| 265 | ¹H NMR (500 MHz, DMSO-d6) δ 8.47 (s, 1H), 7.75 (d, J = 9.6 Hz, 1H), 7.44-7.40 (m, 2H), 7.33-7.29 (m, 2H), 7.25-7.22 (m, 1H), 6.97 (d, J = 9.6 Hz, 1H), 6.55-6.52 (m, 1H), 5.49 (s, 2H), 3.87 (s, 3H), 3.13-3.06 (m, 1H), 2.95-2.89 (m, 1H), 2.48-2.44 (m, 1H), 2.27 (td, J = 6.6, 3.4 Hz, 1H), 1.66-1.64 (m, 1H) | 414 |
| 266 | ¹H NMR (500 MHz, DMSO-d6) δ 8.86 (s, 1H), 8.79 (d, J = 8.0 Hz, 1H), 8.17 (d, J = 8.0 Hz, 1H), 7.43-7.38 (m, 2H), 7.34-7.28 (m, 2H), 7.26-7.20 (m, 1H), 6.53 (d, J = 1.9 Hz, 1H), 5.55 (s, 2H), 3.12-3.04 (m, 1H), 2.91 (d, J = 17.9 Hz, 1H), 2.47-2.41 (m, 1H), 2.28-2.22 (m, 1H), 1.65-1.63 (m, 1H) | 409 |
| 267 | ¹H NMR (500 MHz, DMSO-d6) δ 8.72 (s, 1H), 8.44 (s, 1H), 8.25-8.23 (m, 1H), 7.81 (d, J = 1.6 Hz, 1H), 7.72-7.68 (m, 1H), 7.56 (dd, J = 8.6, 1.6 Hz, 1H), 6.62-6.59 (m, 1H), 5.51 (s, 2H), 3.96 (s, 3H), 3.22-3.12 (m, 1H), 3.04-2.96 (m, 1H), 2.49-2.45 (m, 1H), 2.31-2.25 (m, 1H), 1.70-1.65 (m, 1H) | 428 |
| 268 | ¹H NMR (500 MHz, DMSO-d6) δ 8.44 (s, 1H), 8.24 (s, 1H), 8.02 (s, 1H), 7.66 (s, 1H), 7.58-7.53 (m, 1H), 7.47 (s, 1H), 6.48 (d, J = 1.9 Hz, 1H), 5.52 (s, 2H), 3.96 (s, 3H), 3.20-3.13 (m, 1H), 2.98 (d, J = 17.2 Hz, 1H), 2.47-2.44 (m, 1H), 2.30-2.24 (m, 1H), 1.67-1.64 (m, 1H) | 427 |
| 269 | ¹H NMR (500 MHz, DMSO-d6) δ 8.43 (s, 1H), 8.23 (d, J = 0.4 Hz, 1H), 7.42 (td, J = 8.9, 6.7 Hz, 1H), 7.24 (ddd, J = 11.9, 9.3, 2.6 Hz, 1H), 7.06 (ddd, J = 8.4, 2.8, 1.4 Hz, 1H), 6.53-6.50 (m, 1H), 5.51 (s, 2H), 3.95 (s, 3H), 3.13 (dd, J = 18.0, 6.8 Hz, 1H), 2.95 (d, J = 17.8 Hz, 1H), 2.49 (dd, J = 4.7, 2.3 Hz, 1H), 2.25 (td, J = 6.6, 3.4 Hz, 1H), 1.66 (dd, J = 3.3, 2.6 Hz, 1H) | 423 |
| 270 | ¹H NMR (500 MHz, DMSO-d6) δ 8.43 (s, 1H), 8.23 (d, J = 0.5 Hz, 1H), 7.18-7.13 (m, 2H), 7.09 (tt, J = 9.3, 2.3 Hz, 1H), 6.74 (d, J = 1.9 Hz, 1H), 5.51 (s, 2H), 3.95 (s, 3H), 3.06 (ddd, J = 17.7, 6.7, 1.4 Hz, 1H), 2.91 (d, J = 17.9 Hz, 1H), 2.47 (dq, J = 4.8, 2.4 Hz, 1H), 2.27 (td, J = 6.5, 3.4 Hz, 1H), 1.67 (dd, J = 3.4, 2.5 Hz, 1H) | 423 |
| 271 | ¹H NMR (400 MHz, DMSO) δ 8.43 (s, 1H), 8.23 (s, 1H), 6.52-6.41 (m, 2H), 5.52 (s, 2H), 3.95 (s, 3H), 3.65 (d, J = 10.2 Hz, 2H), 3.36-3.31 (m, 2H), 2.26-2.16 (m, 2H), 1.99 (t, J = 3.3 Hz, 1H) | 460 |
| 272 | ¹H NMR (400 MHz, DMSO-d₆) δ 8.80 (s, 1H), 8.56 (d, J = 8.3 Hz, 1H), 7.71 (d, J = 8.3 Hz, 1H), 7.18-7.12 (m, 1H), 6.46-6.31 (m, 3H), 5.54 (s, 2H), 3.66 (d, J = 9.9 Hz, 2H), 3.27 (d, J = 10.3 Hz, 2H), 2.21-2.17 (m, 2H), 2.01 (t, J = 3.3 Hz, 1H) | 439 |
| 273 | ¹H NMR (400 MHz, DMSO-d6) δ 8.43 (s, 1H), 8.24 (s, 1H), 7.48-7.31 (m, 2H), 6.70 (s, 1H), 5.51 (s, 2H), 3.95 (s, 3H), 3.04 (dd, J = 17.7, 6.8 Hz, 1H), 2.89 (d, J = 17.9 Hz, 1H), 2.49-2.42 (m, 1H), 2.33-2.20 (m, 1H), 1.72-1.61 (m, 1H) | 441 |
| 274 | ¹H NMR (400 MHz, DMSO-d6) δ 8.43 (s, 1H), 8.24 (s, 1H), 7.35-7.18 (m, 2H), 6.59 (s, 1H), 5.51 (s, 2H), 3.95 (s, 3H), 3.14 (dd, J = 18.1, 6.6 Hz, 1H), 2.96 (d, J = 17.9 Hz, 1H), 2.55-2.51 (m, 1H), 2.27 (td, J = 6.5, 3.4 Hz, 1H), 1.72-1.67 (m, 1H) | 441 |
| 275 | ¹H NMR (400 MHz, DMSO-d6) δ 7.72 (dd, J = 9.2, 7.2 Hz, 1H), 7.69-7.66 (m, 1H), 7.42-7.38 (m, 2H), 7.29 (dd, J = 10.2, 4.8 Hz, 2H), 7.24-7.18 (m, 3H), 6.80 (dd, J = 9.2, 1.2 Hz, 1H), 6.52 (d, J = 1.8 Hz, 1H), 5.35 (s, 2H), 3.07 (dd, J = 19.0, 6.5 Hz, 1H), 2.94-2.83 (m, 1H), 2.43 (dt, J = 8.0, 4.0 Hz, 1H), 2.25 (td, J = 6.5, 3.3 Hz, 1H), 1.62 (dd, J = 5.9, 2.7 Hz, 1H) | 399 |
| 276 | ¹H NMR (400 MHz, DMSO) δ 8.43 (s, 1H), 8.23 (s, 1H), 7.24 (dd, J = 13.7, 2.5 Hz, 1H), 7.08 (ddd, J = 8.8, 2.5, 1.0 Hz, 1H), 6.76 (dd, J = 9.8, 8.9 Hz, 1H), 5.52 (s, 2H), 3.95 (s, 3H), 3.75 (dd, J = 9.8, 2.9 Hz, 2H), 3.40-3.32 (m, 2H), 2.19-2.14 (m, 2H), 2.12 (t, J = 3.2 Hz, 1H) | 442 |
| 277 | ¹H NMR (400 MHz, DMSO-d6) δ 8.44 (s, 2H), 8.24 (d, J = 0.5 Hz, 1H), 7.70 (s, 1H), 7.67 (d, J = 8.5 Hz, 2H), 7.53 (d, J = 8.5 Hz, 2H), 6.64 (d, J = 1.8 Hz, 1H), 5.52 (s, 2H), 3.95 (s, 3H), 3.11 (dd, J = 17.8, 5.7 Hz, 1H), 2.94 (d, J = 17.6 Hz, 1H), 2.48-2.43 (m, 1H), 2.28 (td, J = 6.5, 3.4 Hz, 1H), 1.71-1.65 (m, 1H) | 454 |
| 278 | ¹H NMR (400 MHz, DMSO-d6) δ 9.34 (s, 1H), 8.44 (s, 1H), 8.24 (s, 1H), 8.17 (d, J = 1.5 Hz, 1H), 8.00 (d, J = 8.6 Hz, 1H), 7.68 (dd, J = 8.6, 1.7 Hz, 1H), 6.67 (d, J = 1.6 Hz, 1H), 5.52 (s, 2H), 3.96 (s, 3H), 3.18 (dd, J = 17.7, 6.7 Hz, 1H), 3.01 (d, J = 17.9 Hz, 1H), 2.49-2.47 (m, 1H), 2.36-2.26 (m, 1H), 1.74-1.66 (m, 1H) | 444 |
| 279 | ¹H NMR (400 MHz, DMSO) δ 9.21 (dd, J = 4.6, 1.6 Hz, 1H), 8.96 (s, 1H), 8.68-8.63 (m, 1H), 8.60 (s, 1H), 7.92 (dd, J = 8.1, 4.6 Hz, 1H), 7.84 (d, J = 8.9 Hz, 1H), 7.21 (d, J = 2.2 Hz, 1H), 6.86 (dd, J = 9.0, 2.3 Hz, 1H), 5.68 (s, | 444.1 |

TABLE 2-continued

| Ex. | 1H NMR (ppm) | M + H |
|---|---|---|
| | 2H), 3.77 (d, J = 9.8 Hz, 2H), 3.37-3.32 (m, 2H), 2.28-2.23 (m, 2H), 2.07 (t, J = 3.2 Hz, 1H) | |
| 280 | $^1$H NMR (400 MHz, DMSO-d6) δ 8.43 (d, J = 4.3 Hz, 2H), 8.22 (s, 1H), 7.73 (s, 2H), 7.57 (dd, J = 5.3, 2.0 Hz, 1H), 7.41 (d, J = 5.0 Hz, 2H), 6.65 (d, J = 1.6 Hz, 1H), 5.50 (s, 2H), 3.94 (s, 3H), 3.12 (dd, J = 17.7, 5.7 Hz, 1H), 2.95 (d, J = 17.5 Hz, 1H), 2.45 (d, J = 2.3 Hz, 1H), 2.27 (dd, J = 9.9, 6.4 Hz, 1H), 1.68-1.64 (m, 1H) | 454 |
| 281 | $^1$H NMR (400 MHz, DMSO-d6) δ 8.44 (s, 1H), 8.24 (s, 1H), 7.62-7.46 (m, 4H), 7.00 (t, J = 56.0 Hz, 1H), 6.70-6.63 (m, 1H), 5.51 (s, 2H), 3.95 (s, 3H), 3.16-3.04 (m, 1H), 3.00-2.89 (m, 1H), 2.50-2.45 (m, 1H), 2.33-2.23 (m, 1H), 1.7H.64 (m, 1H) | 437 |
| 282 | $^1$H NMR (400 MHz, DMSO-d6) δ 8.44 (s, 1H), 8.25-8.22 (m, 1H), 7.36-7.27 (m, 1H), 7.24-7.13 (m, 2H), 6.67-6.60 (m, 1H), 5.52 (s, 2H), 3.95 (s, 3H), 3.20-3.11 (m, 1H), 2.98 (d, J = 17.7 Hz, 1H), 2.55-2.51 (m, 1H), 2.28 (td, J = 6.6, 3.5 Hz, 1H), 1.72-1.68 (m, 1H) | 423 |
| 283 | $^1$H NMR (400 MHz, DMSO-d6) δ 8.43 (s, 1H), 8.24 (s, 1H), 7.89-7.82 (m, 1H), 7.59 (dd, J = 11.2, 1.3 Hz, 1H), 7.45 (dd, J = 8.2, 1.4 Hz, 1H), 6.92 (d, J = 1.9 Hz, 1H), 5.51 (s, 2H), 3.95 (s, 3H), 3.08 (dd, J = 18.2, 6.2 Hz, 1H), 2.95 (d, J = 17.8 Hz, 1H), 2.54-2.51 (m, 1H), 2.35-2.27 (m, 1H), 1.75-1.69 (m, 1H) | 430 |

Based on experimental evidence to date, without being bound to any particular theory, it is believed that oxadiazol compounds of the present disclosure comprising a bicycle [3.1.0]hexene linker of the structure

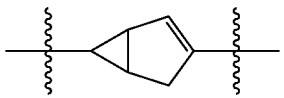 [SMILES: *C1=CC2C(*)C2C1]

that is substituted with a 3-halo phenyl (see example compounds 114, 115, 184 and 185) provide for improved TRPA1 IC$_{50}$ values as compared to oxadiazol compounds of the present disclosure comprising a 3-azabicyclo[3.1.0]hexene linker of the structure

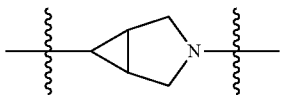 [SMILES: *C1C2CN(*)CC12]

that is substituted with a 3-halo phenyl (see example compound 16) and as compared to oxadiazol compounds of the present disclosure comprising a cyclobutylene linker of the structure

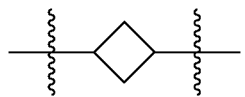 [SMILES: *C1CC(*)C1]

that is substituted with a 3-halo phenyl (see example compound 191).

Further based on experimental evidence to date, without being bound to any particular theory, it is believed that oxadiazol compounds of the present disclosure comprising a bicycle[3.1.0]hexene linker that is substituted with phenyl (see example compounds 225 and 226) provide for improved TRPA1 IC$_{50}$ values as compared to oxadiazol compounds of the present disclosure comprising a 3-azabicyclo[3.1.0]hexene linker that is substituted with phenyl (see example compound 26) and as compared to oxadiazol compounds of the present disclosure comprising a cyclobutylene linker that is substituted with a phenyl (see example compound 1).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of formula (I):

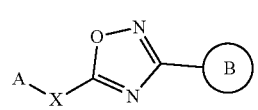

wherein:

(i) A is selected from

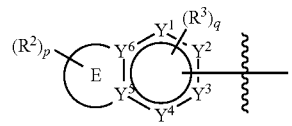

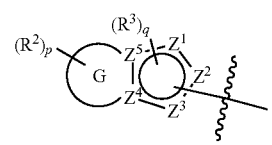

(ii) X is selected from a bond, $C_{1-4}$ alkylene, —O—, —S—, —SO$_2$—, and —N(R$^1$)—, wherein R$^1$ is selected from H and $C_{1-6}$ alkyl;

(iii) B is selected from:
  (a) substituted and unsubstituted $C_{4-6}$ cycloalkyl wherein, when substituted, the bond to the oxadiazole moiety and the bond to the substituent are on other than adjacent ring carbon atoms;
  (b) substituted and unsubstituted fused bicyclic bound to the oxadiazole moiety by a carbon-carbon bond; and
  (c) substituted and unsubstituted fused tricyclic;

(iv) E is a five membered or a six membered heteroaryl ring wherein one ring carbon atom is optionally substituted with oxo;

(v) G is a six membered heteroaryl ring having one ring carbon atom substituted with oxo;

(vi) one of $Y^1$, $Y^2$, $Y^3$ and $Y^4$ is —C(O)—, one to three of $Y^1$, $Y^2$, $Y^3$, $Y^4$, $Y^5$ and $Y^6$ are nitrogen, and the other of $Y^1$, $Y^2$, $Y^3$, $Y^4$, $Y^5$ and $Y^6$ are carbon;

(vii) one or two of $Z^1$, $Z^2$, $Z^3$, $Z^4$ and $Z^5$ are nitrogen and the other of $Z^1$, $Z^2$, $Z^3$, $Z^4$ and $Z^5$ are carbon;

(viii) each R$^2$ is independently selected from H, deuterium, —$C_{1-4}$ alkyl, —$C_{1-4}$ haloalkyl, —CN, halo, $C_{1-4}$ haloalkoxy, $C_{1-4}$ alkoxy, —OH, —SO$_2$—$C_{1-4}$alkyl, —$C_{1-4}$CN, $C_{1-4}$ aldehyde, $C_{1-4}$ ketone, and —NR$^{14}$R$^{15}$, and p is 0, 1 or 2, wherein R$^{14}$ and R$^{15}$ are independently selected from H, substituted and unsubstituted —$C_{1-4}$ alkyl, substituted and unsubstituted —C(O)—$C_{1-4}$ alkyl, substituted and unsubstituted $C_{3-6}$ cycloalkyl, substituted and unsubstituted 3- to 6-membered heterocycloalkyl, substituted and unsubstituted —$C_{1-4}$ heteroalkyl, and substituted and unsubstituted —$C_{1-4}$ alkyl-C(O)NR$^{16}$R$^{17}$ wherein R$^{16}$ and R$^{17}$ are independently selected from H and $C_{1-4}$ alkyl; and (ix) R$^3$ is selected from H, —$C_{1-4}$ alkyl, —$C_{1-4}$ haloalkyl, —CN, and halo, and q is 0 or 1; or a pharmaceutical salt thereof.

2. The compound of claim 1 wherein A is selected from:

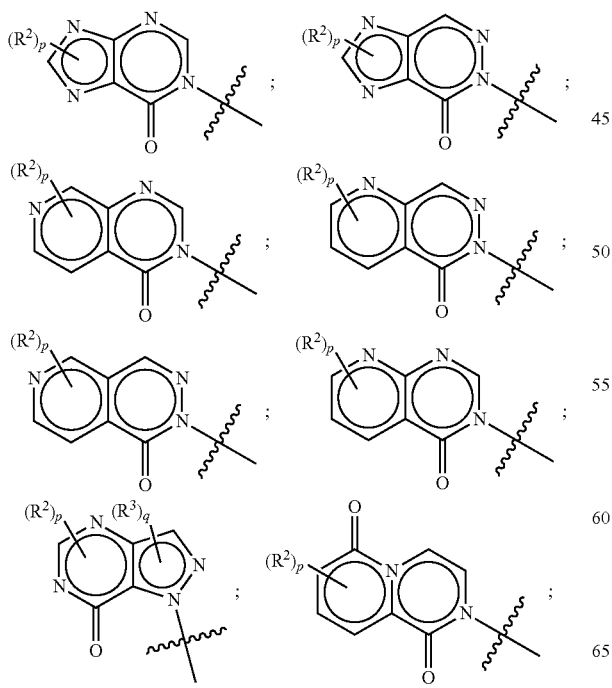

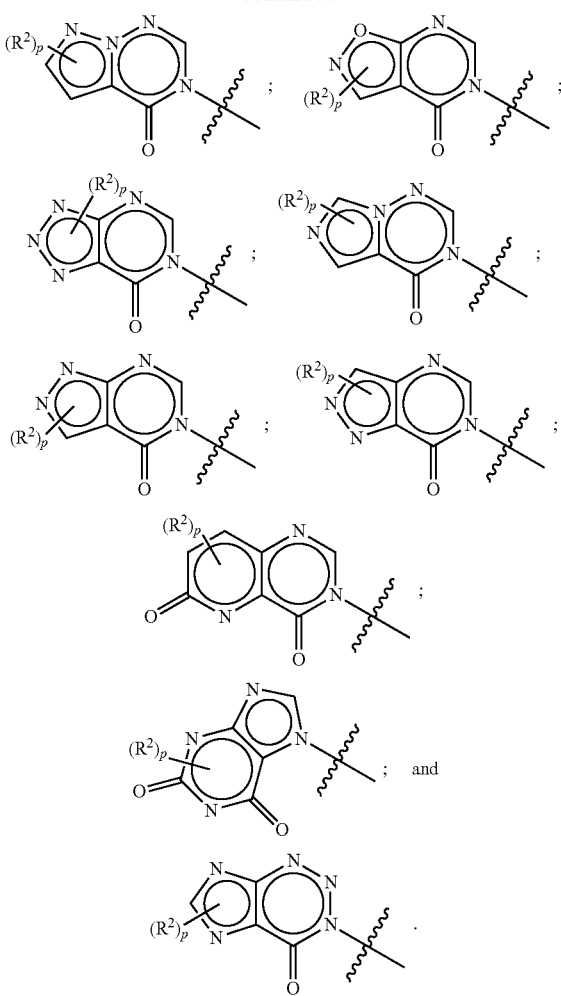

3. The compound of claim 2 wherein:

R$^2$ is selected from H, -D, —CH$_3$, —CN, -halo, —NH$_2$, —NHCH$_3$, NHCH$_2$CH$_3$, —NHCH$_2$CH$_2$CH$_2$OH, —NHCH$_2$CH$_2$OCH$_3$, —NHC(O)CH$_3$, —NHCH$_2$C(O)N(CH$_3$)$_2$,

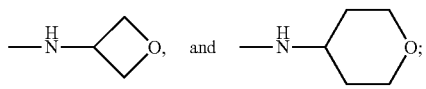

and

R$^3$ is selected from H, -D and —CN.

4. The compound of claim 3 wherein A is selected from:

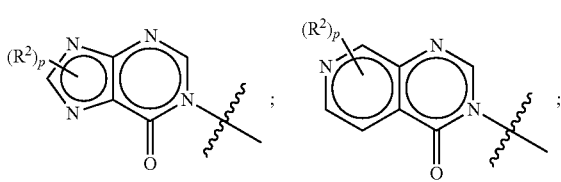

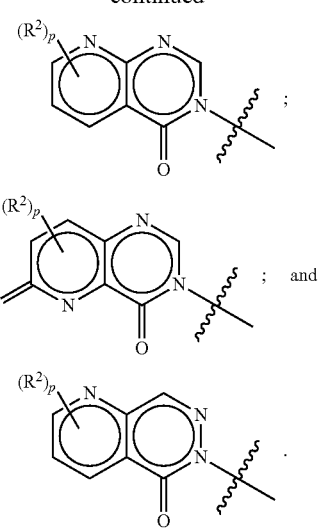
5. The compound of claim 1 wherein A is selected from:
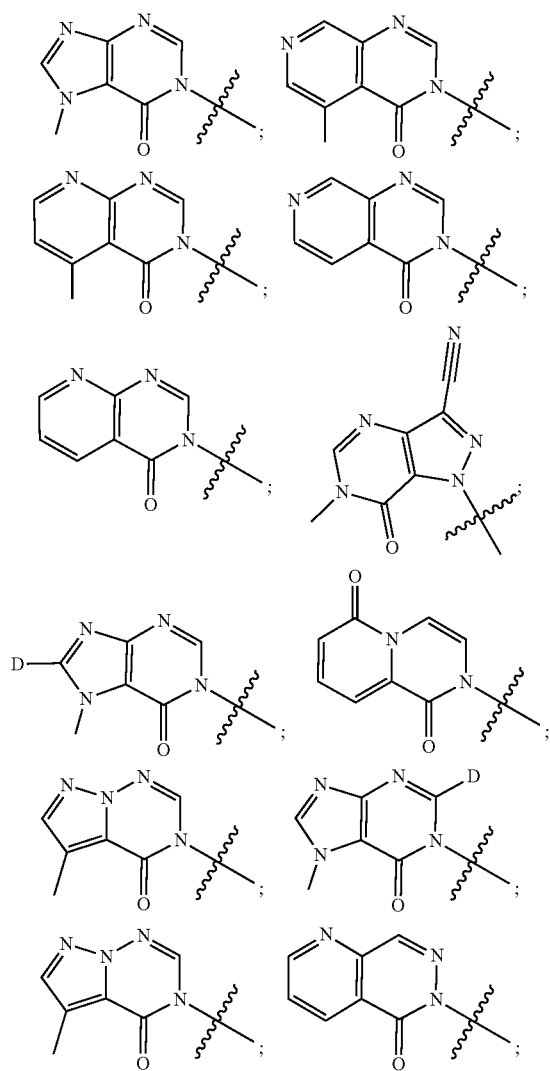
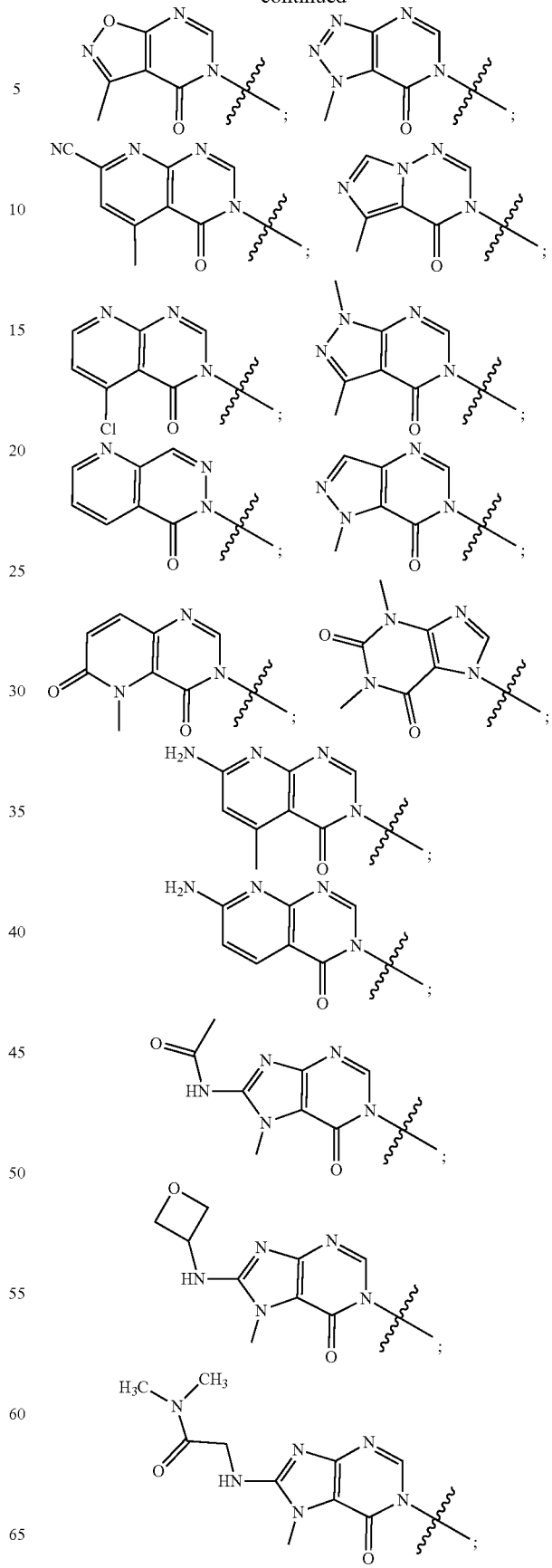

425

-continued

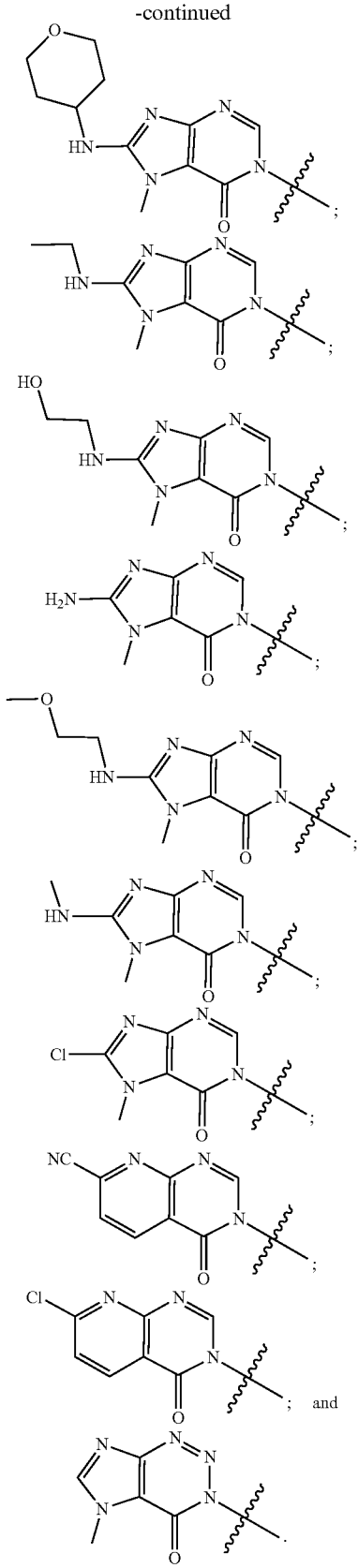

6. The compound of claim 1 wherein the B moiety substituted or unsubstituted cycloalkyl is

426

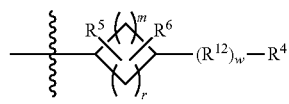

wherein:
R$^4$ is selected from substituted or unsubstituted aryl, substituted or unsubstituted heteroaryl, and substituted or unsubstituted naphthyl;
R$^5$ and R$^6$ are independently selected from H, —C$_{1-4}$ alkyl, halogen and —OH;
R$^{12}$ is selected from substituted and unsubstituted C$_{1-4}$ alkylene and —O—;
m is 1 or 2;
r is 1 or 2; and
w is 0 or 1.

7. The compound of claim 6 wherein B is

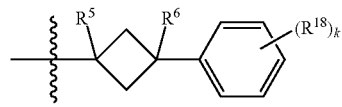

wherein:
each R$^{18}$ is independently selected from H, halogen, —OH, —C$_{1-4}$ alkyl, —C$_{1-4}$ haloalkyl, —CN, halo, C$_{1-4}$ haloalkoxy, C$_{1-4}$ alkoxy, —SO$_2$—C$_{1-4}$alkyl, —C$_{1-4}$CN, C$_{1-4}$ aldehyde, C$_{1-4}$ ketone, and fused aryl; and
k is from 0 to 2.

8. The compound of claim 7 wherein B is selected from:

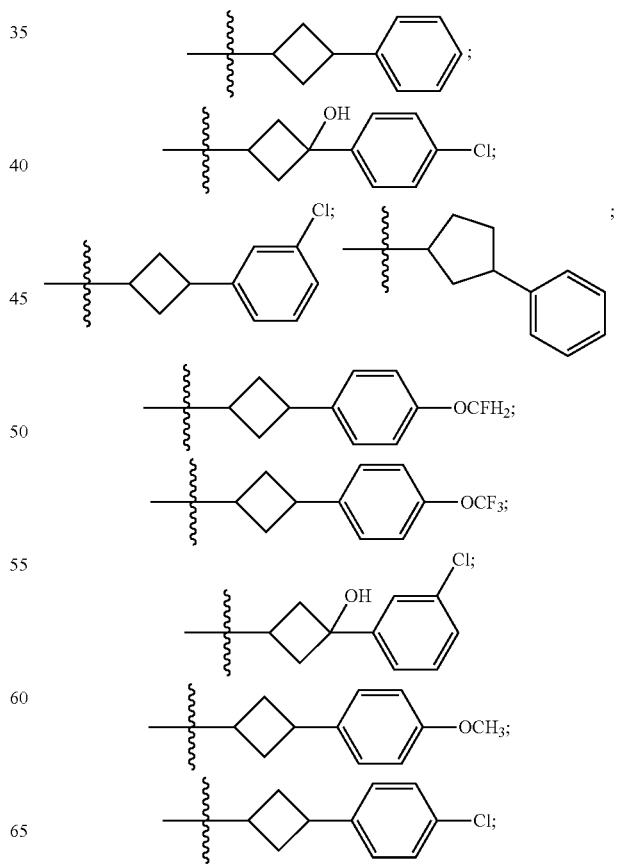

-continued
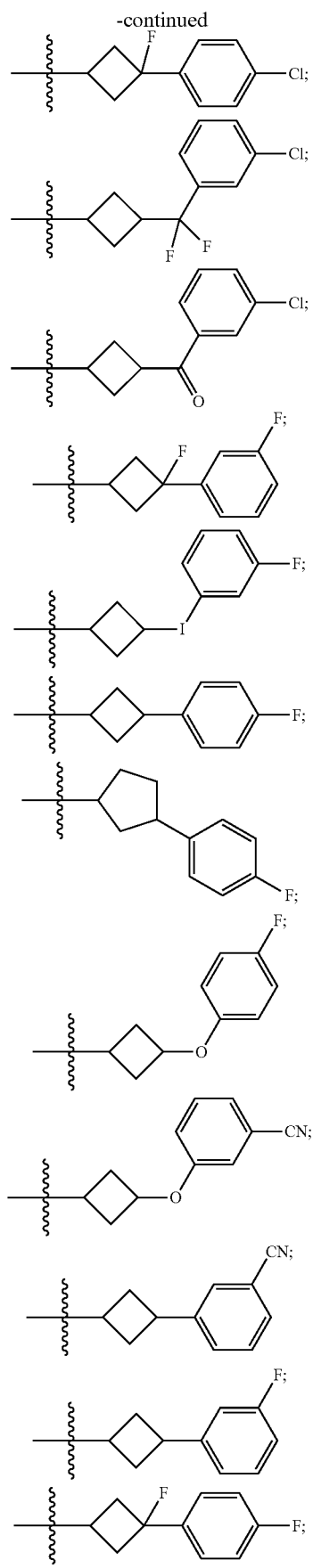
-continued
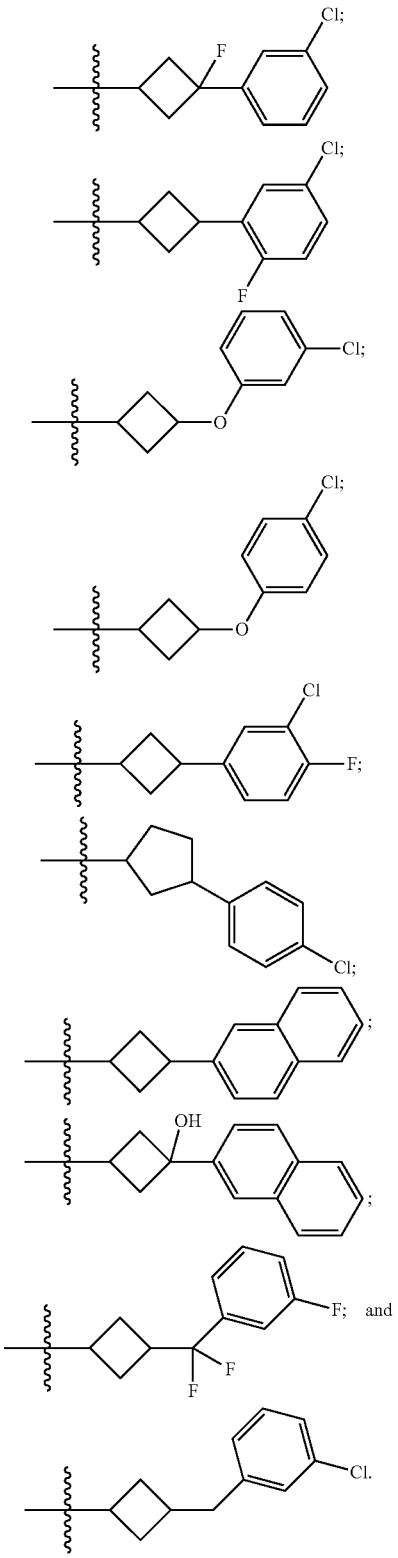
9. The compound of claim 1 wherein the B moiety substituted or unsubstituted fused tricyclic is $C_{3-6}$ cycloalkyl-$C_{3-6}$ cycloalkyl-$C_{5-6}$ aryl.
10. The compound of claim 1 wherein B is substituted or unsubstituted $C_3$ cycloalkyl-$C_5$ cycloalkyl-$C_6$ aryl.

11. The compound of claim 10 wherein B is

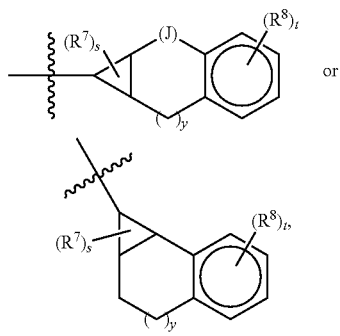

or

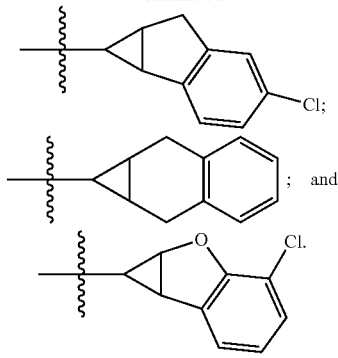

and wherein:

R⁷ is selected from H, —C$_{1-4}$ alkyl, halogen and —OH;

J is selected from —CH$_2$— and —O—;

s is 0 or 1;

y is 0 or 1;

each R⁸ is independently selected from —H, —OH, —C$_{1-4}$ alkyl, —C$_{1-4}$ haloalkyl, —CN, halo, C$_{1-4}$ haloalkoxy, C$_{1-4}$ alkoxy, —SO$_2$—C$_{1-4}$alkyl, —C$_{1-4}$CN, C$_{1-4}$ aldehyde, C$_{1-4}$ ketone; and t is 0, 1 or 2.

12. The compound of claim 11 wherein B is selected from:

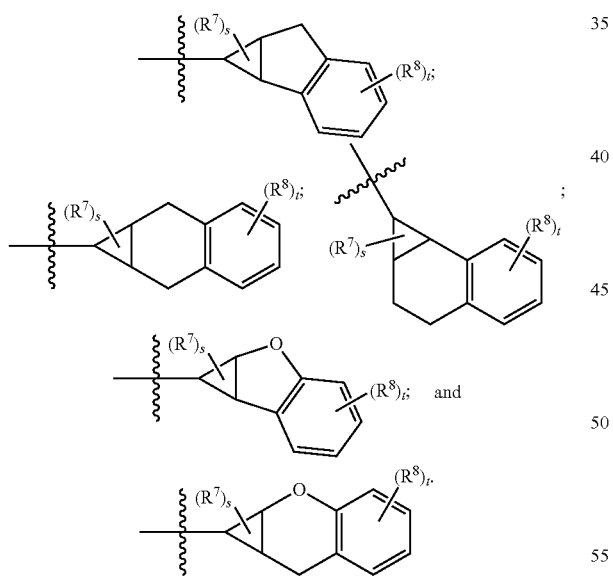

13. The compound of claim 12 wherein B is selected from:

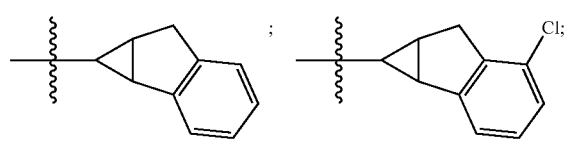

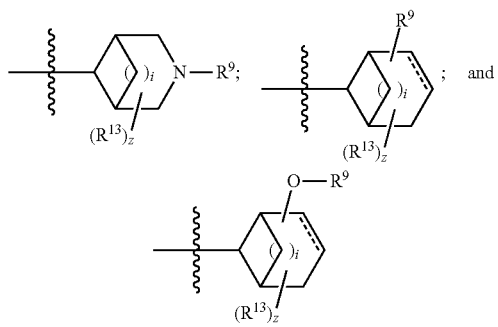

14. The compound of claim 1 wherein the B moiety is fused (C$_{3-6}$ cycloalkyl)-(4-6 membered heterocycloalkyl) or bridged 6- or 7-membered cycloalkyl or heterocycloalkyl.

15. The compound of claim 14 wherein B is selected from:

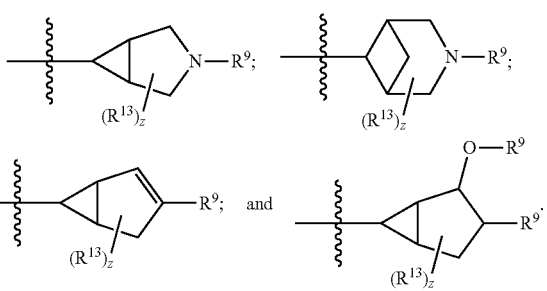

wherein

R⁹ is selected from substituted or unsubstituted aryl, substituted or unsubstituted heteroaryl, substituted or unsubstituted fused bicyclic aryl, substituted or unsubstituted fused bicyclic heteroaryl, substituted or unsubstituted fused bicyclic aryl-heteroaryl, substituted or unsubstituted fused bicyclic aryl-cycloalkyl, substituted or unsubstituted fused bicyclic aryl-heterocycle, unsubstituted fused bicyclic heteroaryl-cycloalkyl, and substituted or unsubstituted fused bicyclic heteroaryl-heterocycle;

R¹³ is selected from C$_{1-4}$ alkyl and —OH;

i is 0 or 1;

z is 0 or 1; and the dashed line represents an optional bond.

16. The compound of claim 15 wherein B is selected from:

17. The compound of claim 16 wherein $R^9$ is selected from:

18. The compound of claim 17, wherein $R^9$ is selected from:

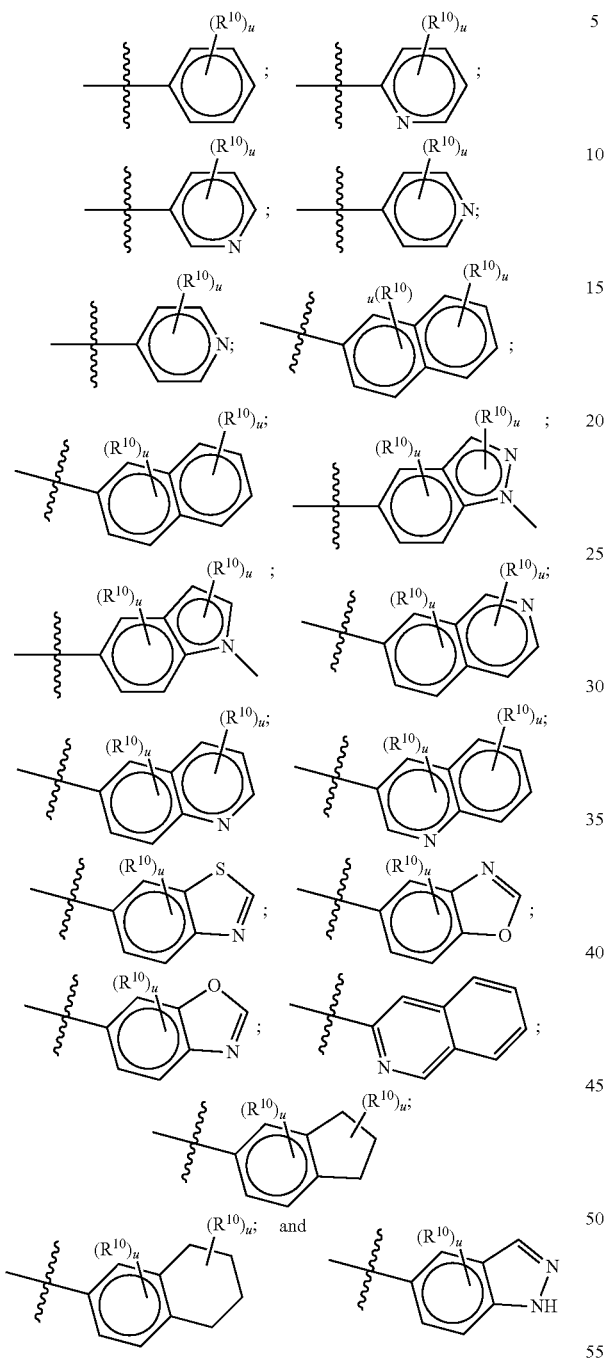
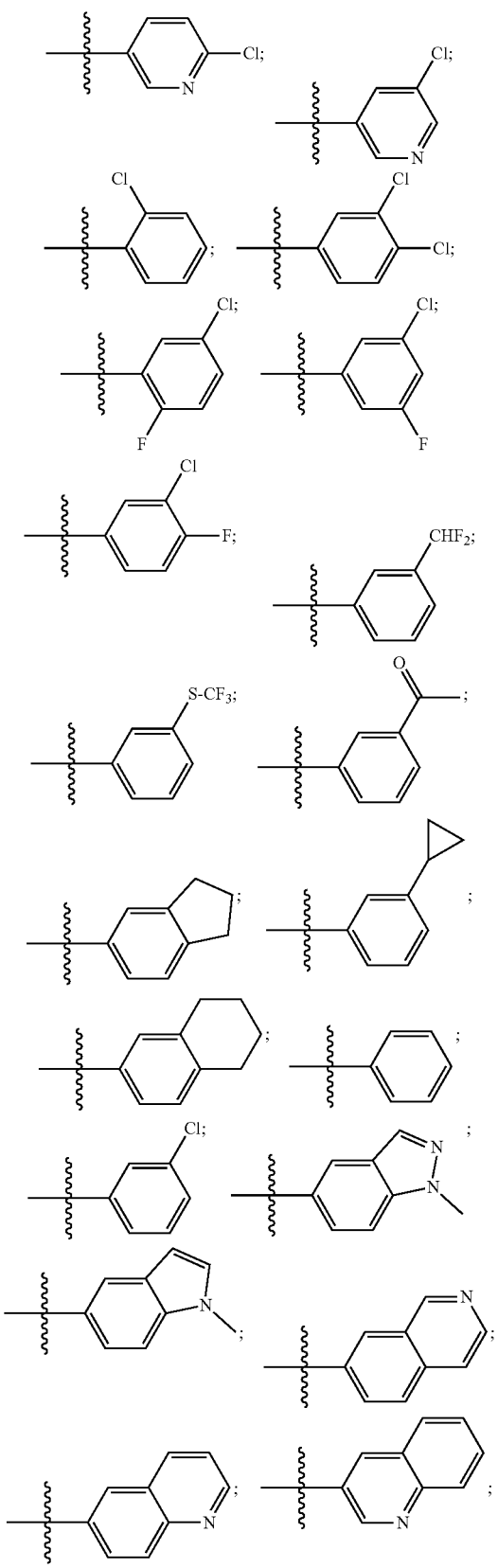

wherein
each $R^{10}$ is independently selected from H, halogen, —CN, —OH, $C_{1-4}$ alkyl, $C_{1-6}$ cycloalkyl, $C_{1-4}$ haloalkyl, $C_{1-4}$ haloalkoxy, $C_{1-4}$ alkoxy, —SO$_2$—$C_{1-4}$ alkyl, —$C_{1-4}$ CN, $C_{1-4}$ aldehyde, $C_{1-4}$ ketone, —S—$C_{1-4}$ haloalkyl, substituted or unsubstituted 5- to 6-membered heteroaryl, substituted or unsubstituted 4- to 6-membered heterocycloalkyl, and substituted or unsubstituted $C_{5-6}$ aryl, and each u is independently 0, 1, 2 or 3.

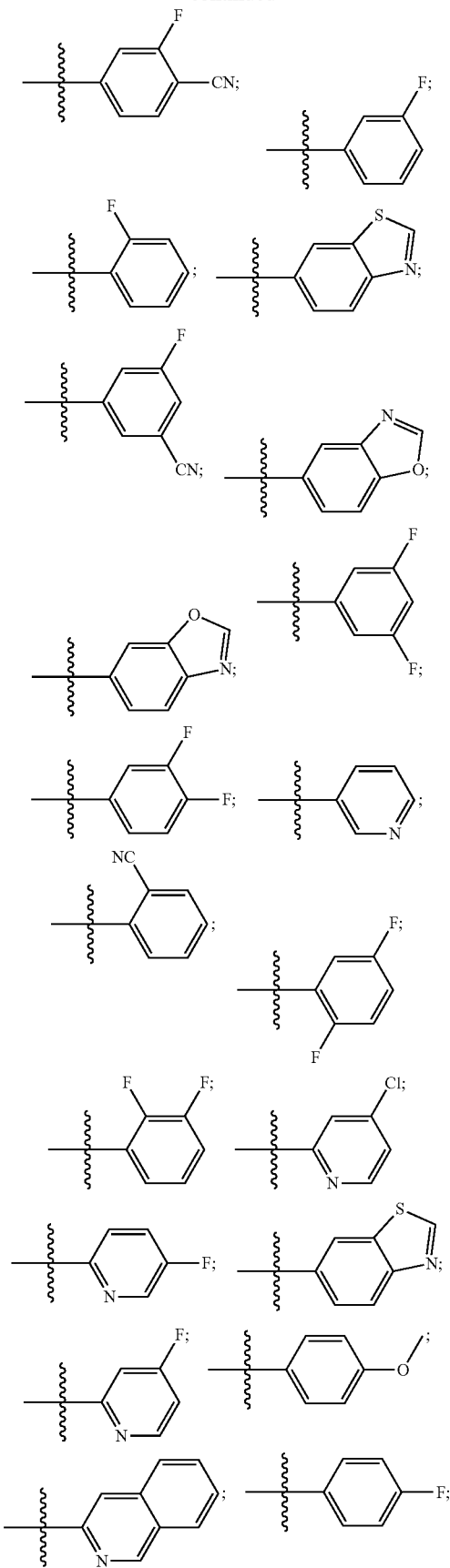
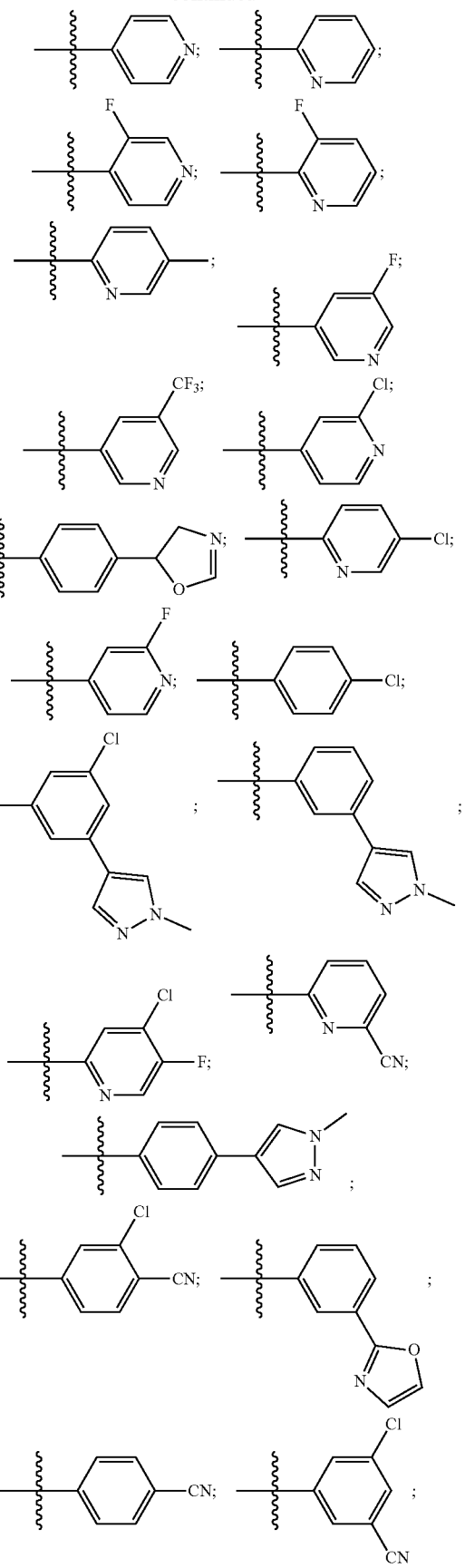

-continued
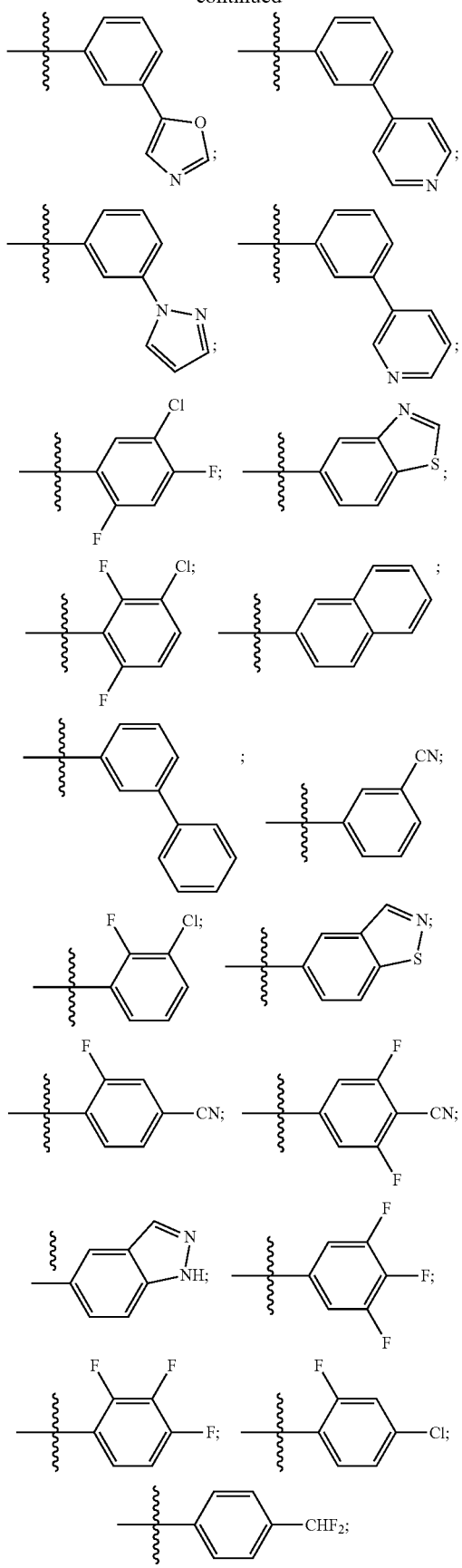
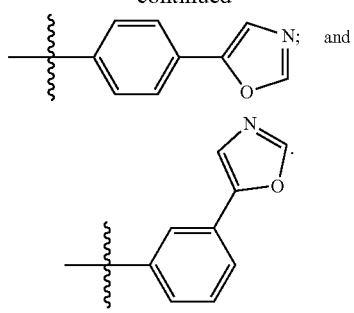
19. The compound of claim 5 wherein B is selected from:

437
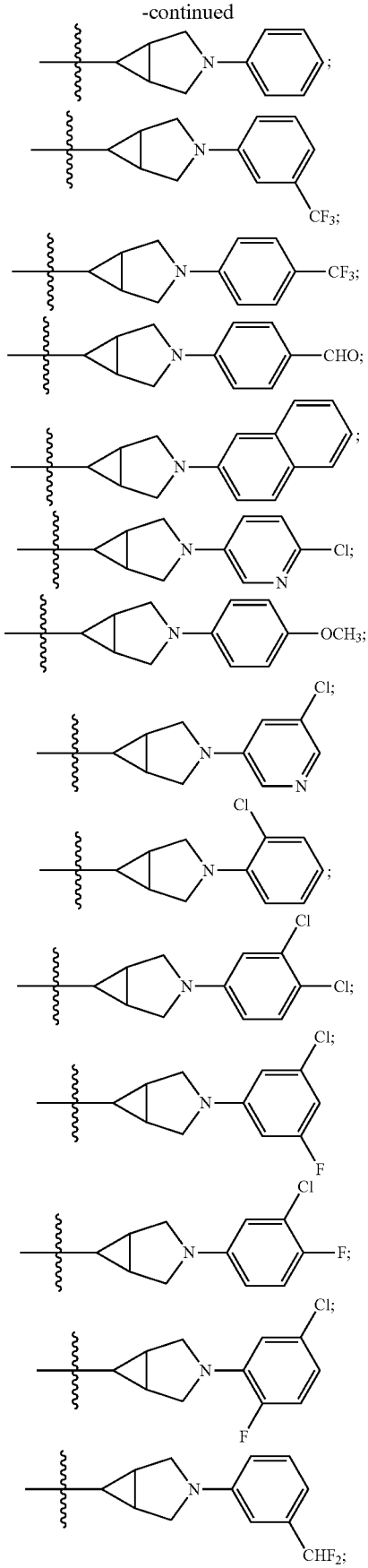
438
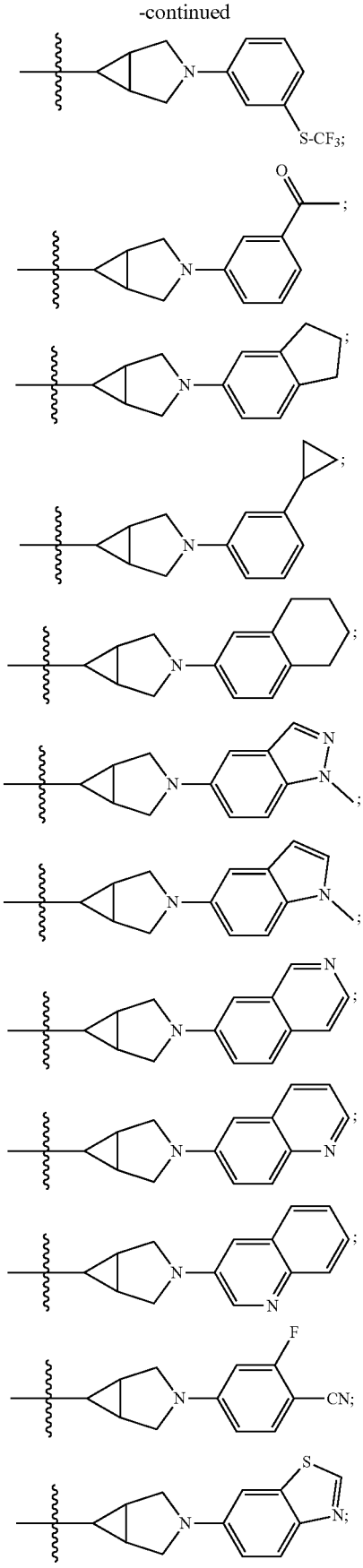

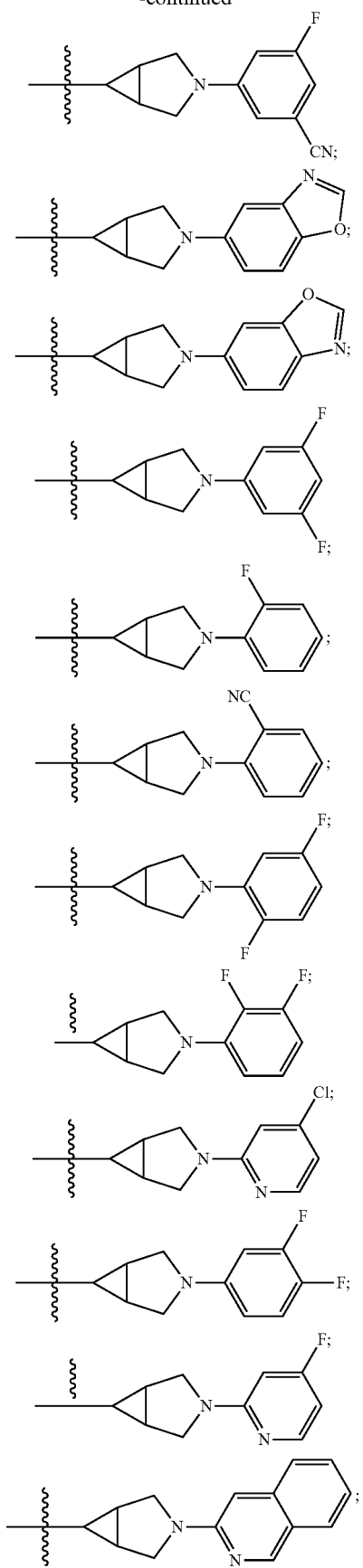
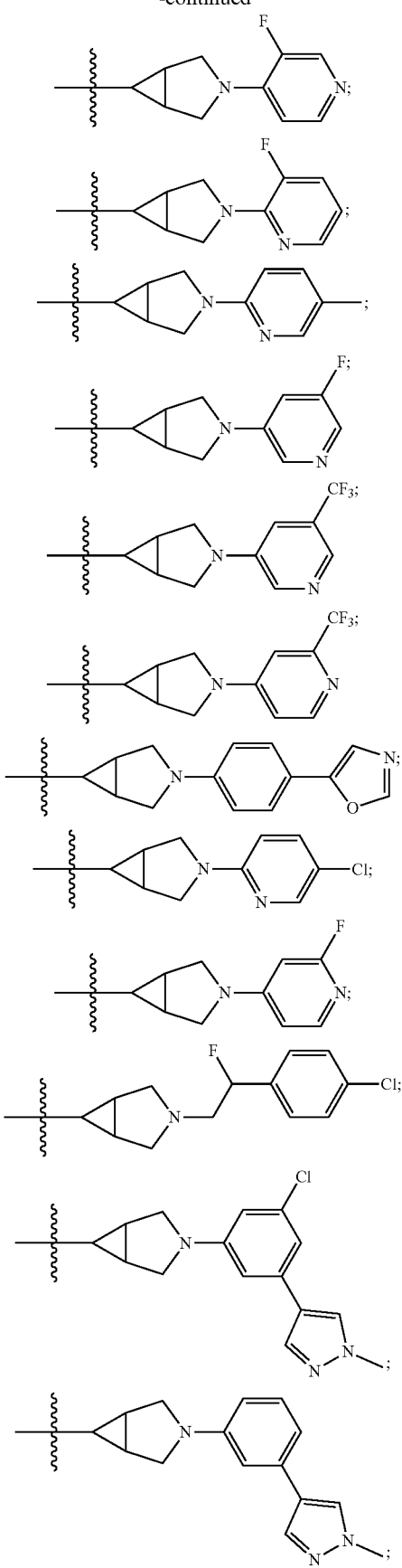

441
-continued
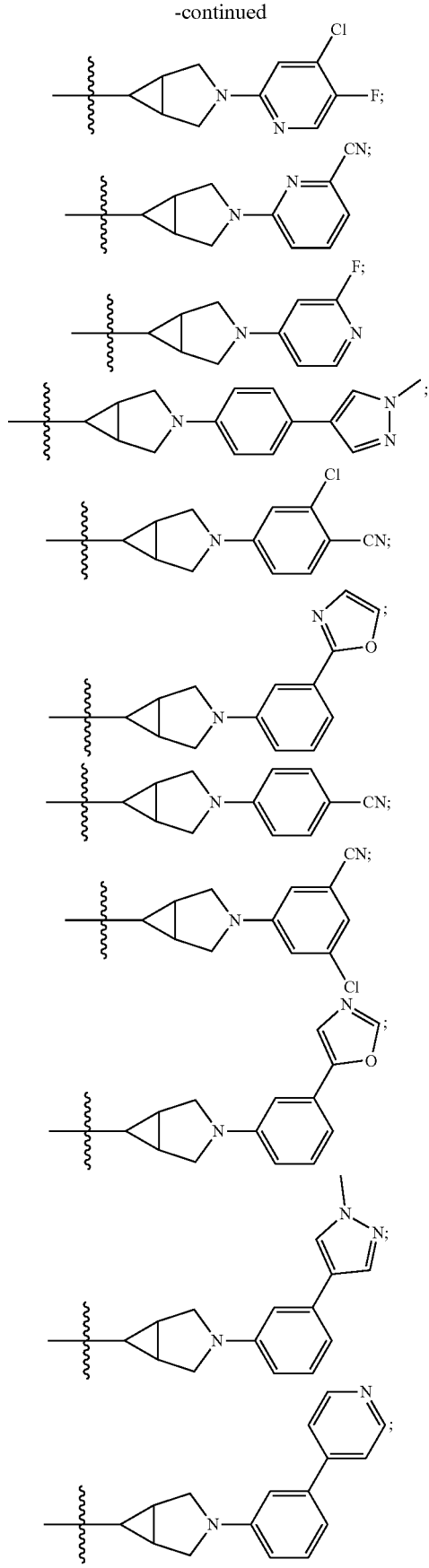
442
-continued
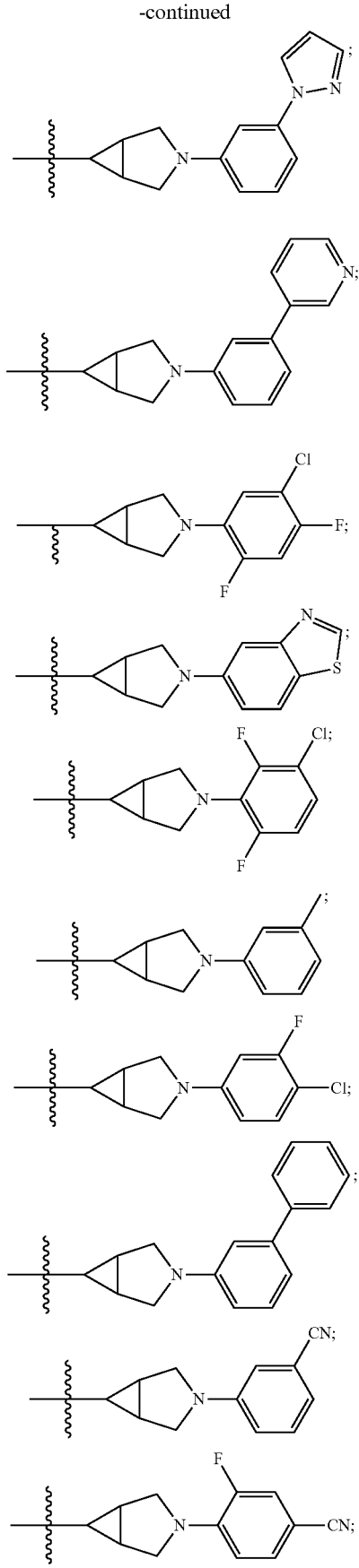

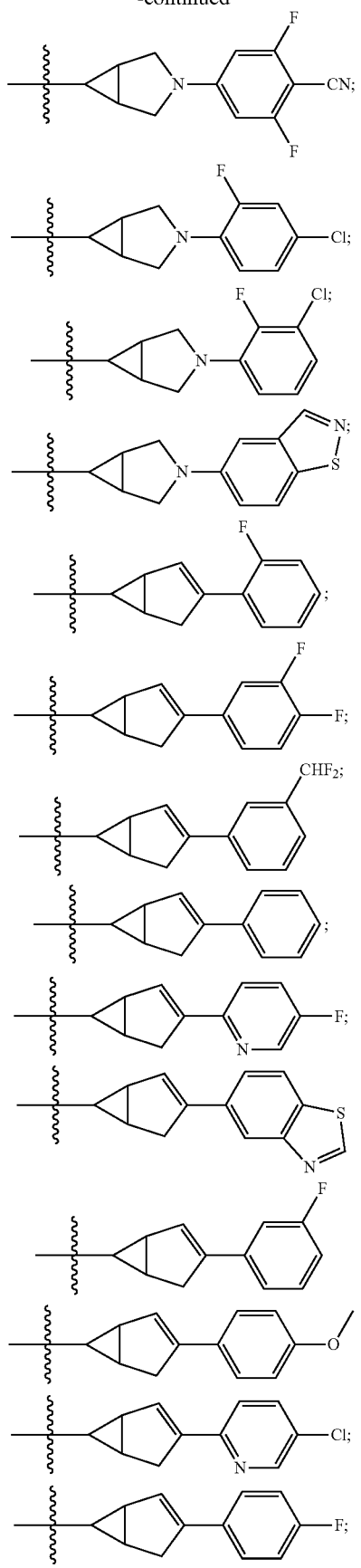
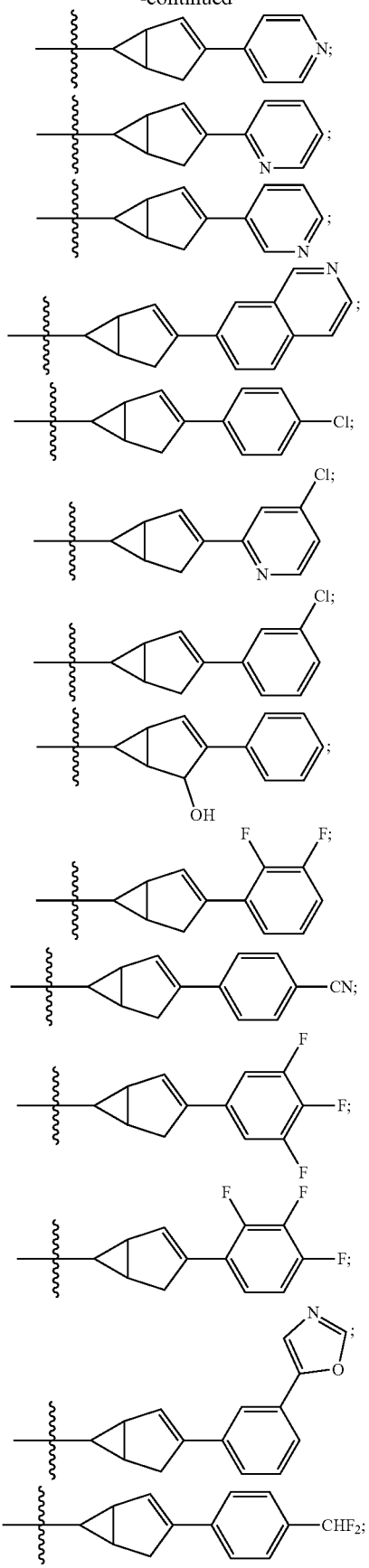

445
-continued
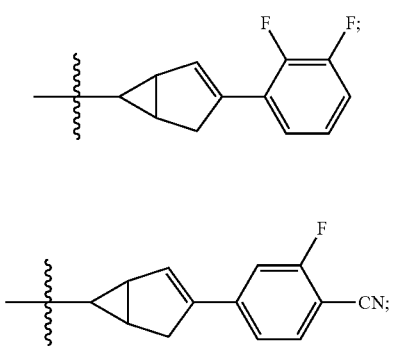
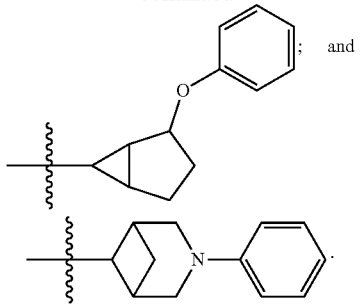
20. A compound of claim 1 selected from the following compounds, stereoisomers thereof, and pharmaceutically acceptable salts thereof:
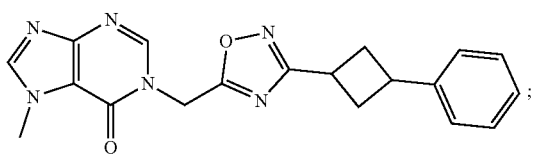
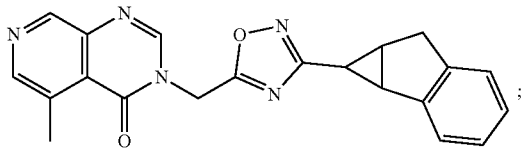
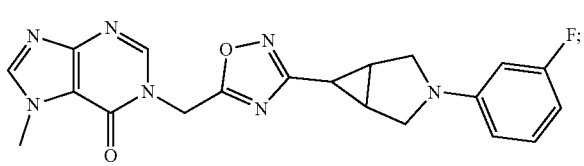
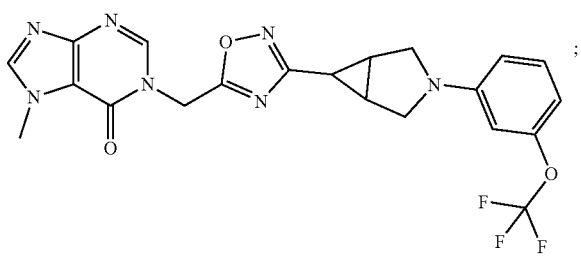
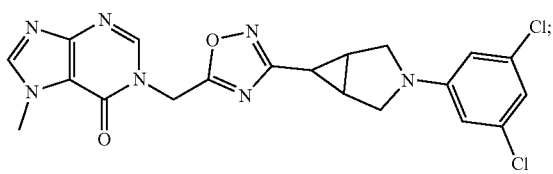
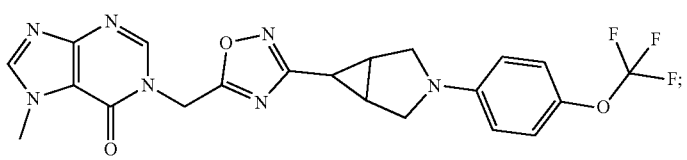
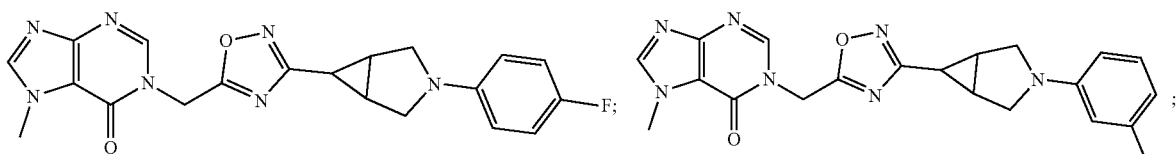
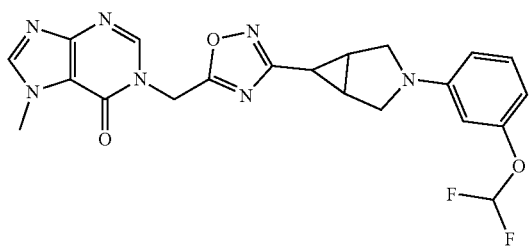
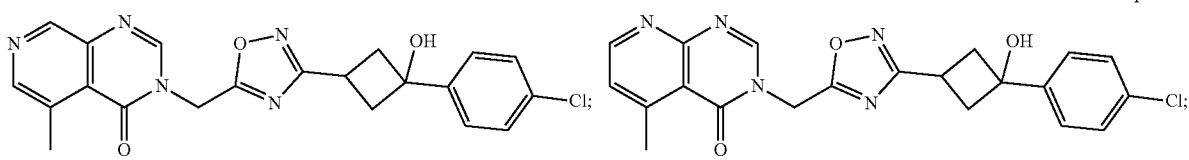

-continued
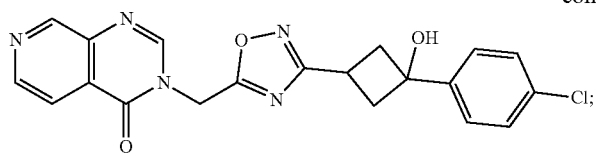
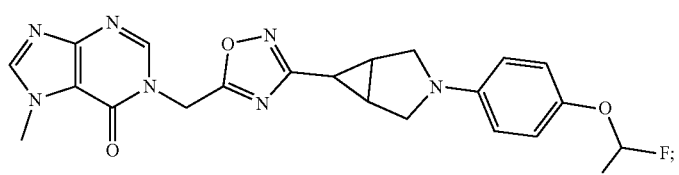
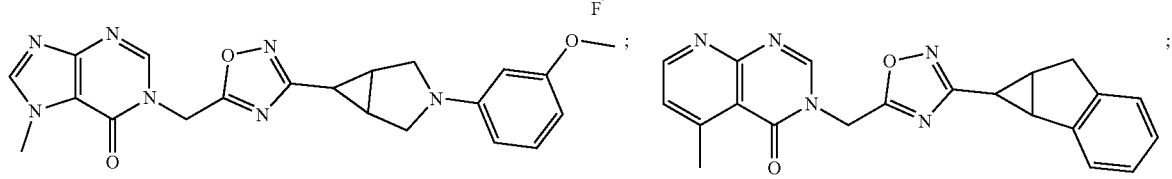
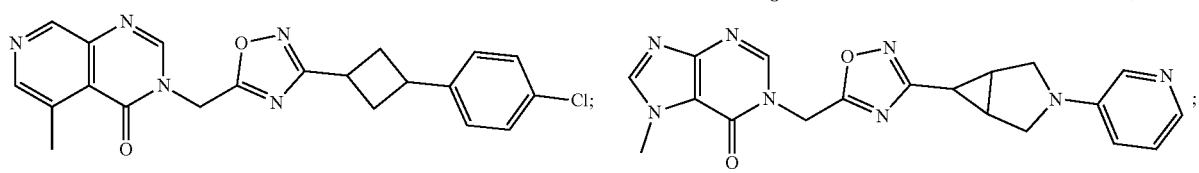
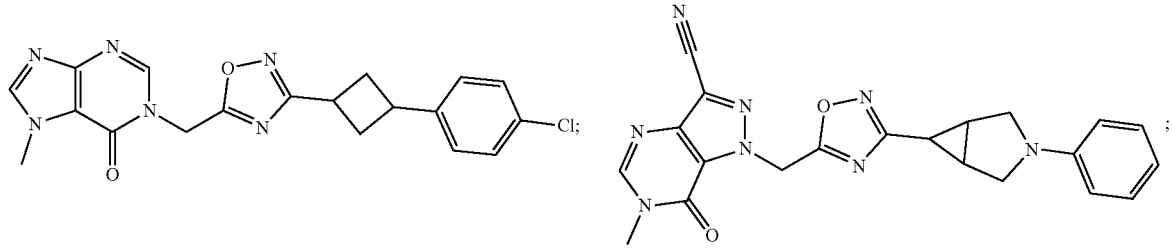
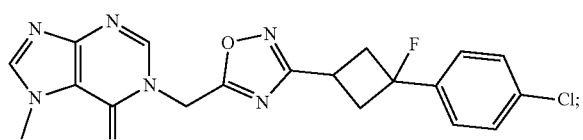
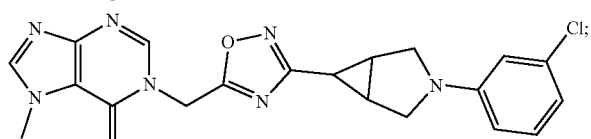
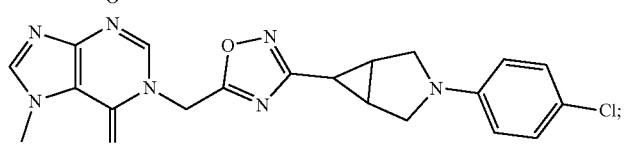
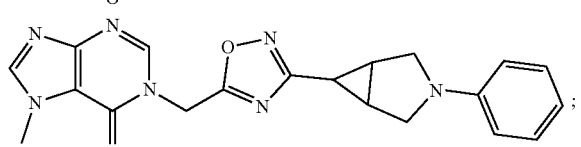
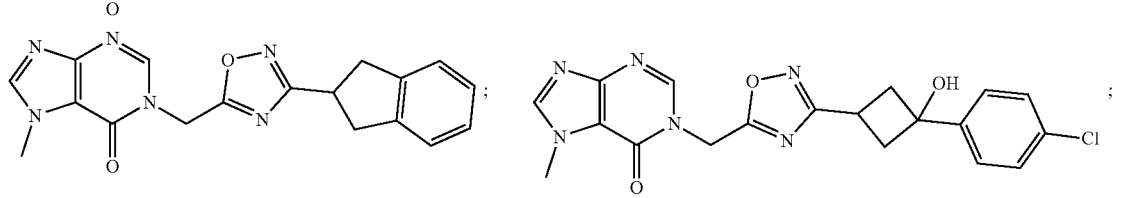

-continued
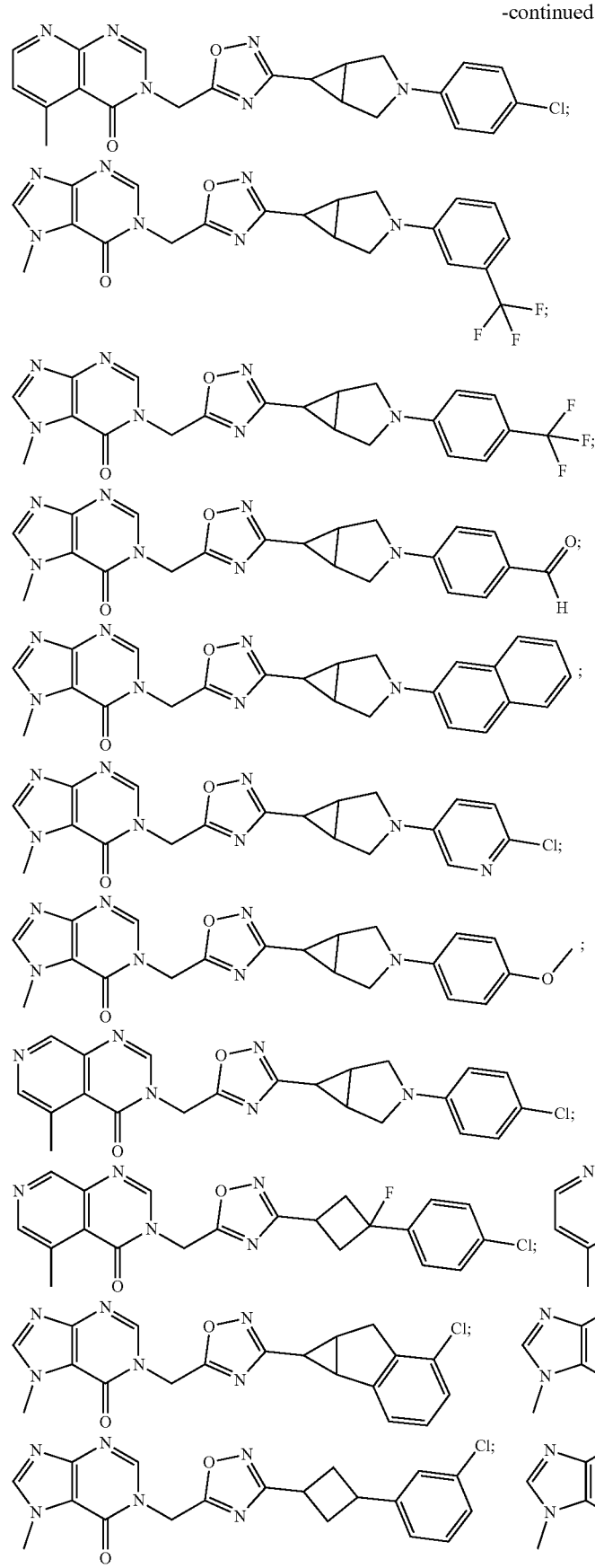

451              452
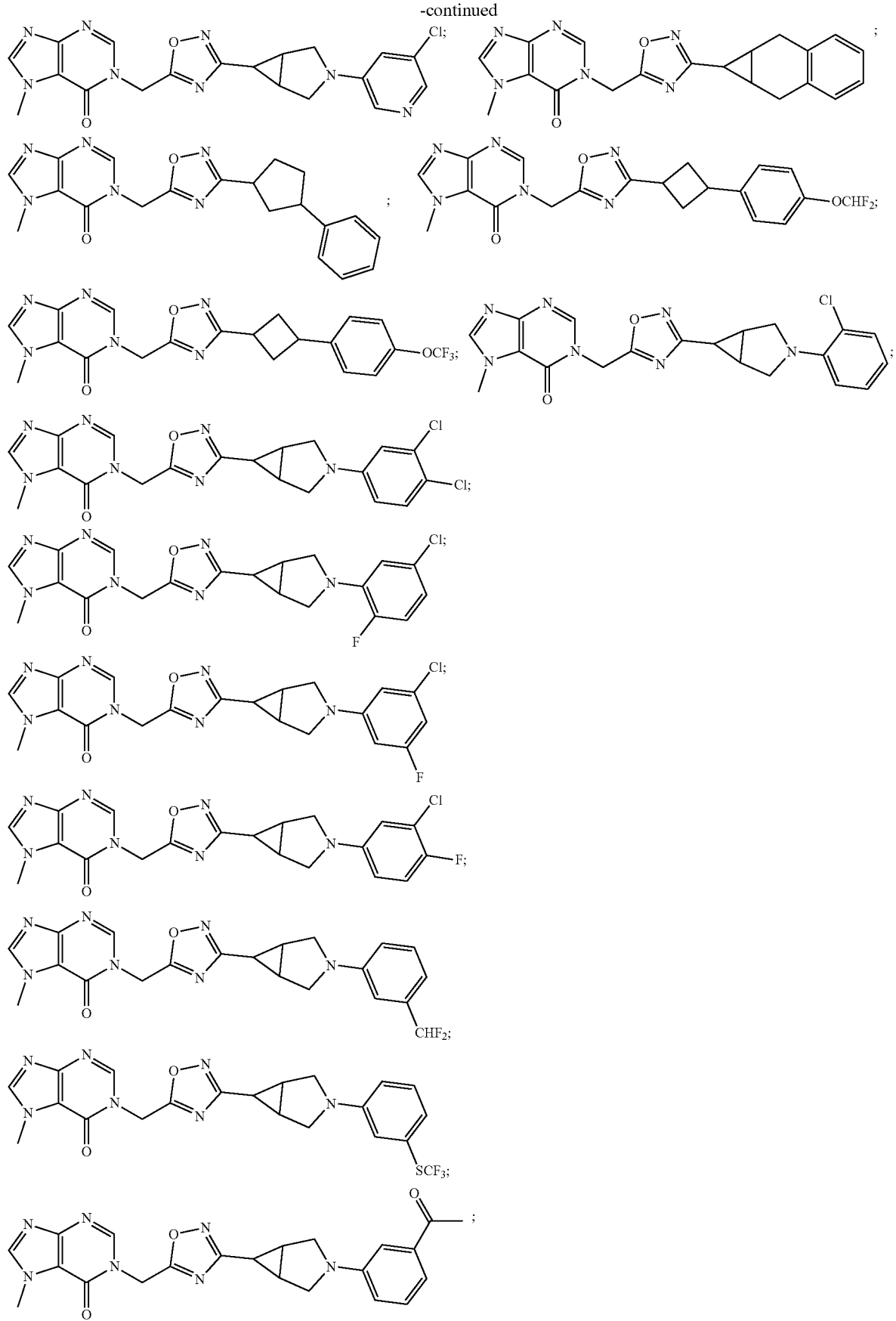
-continued

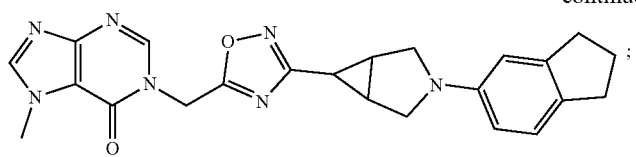
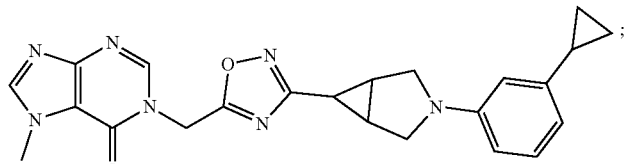
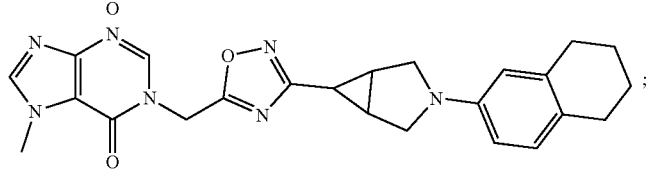
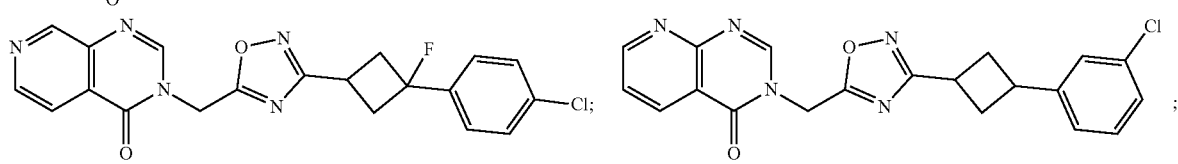
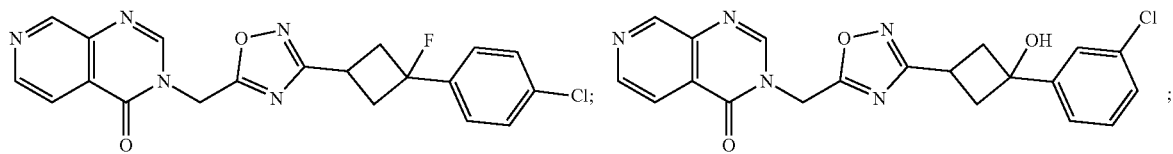
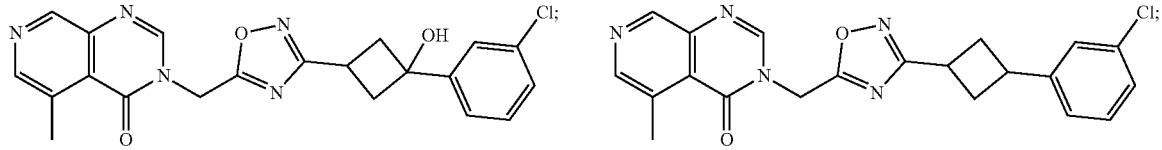
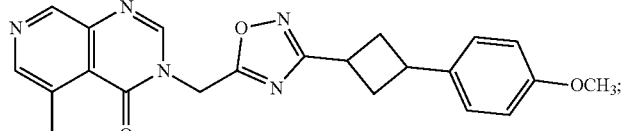
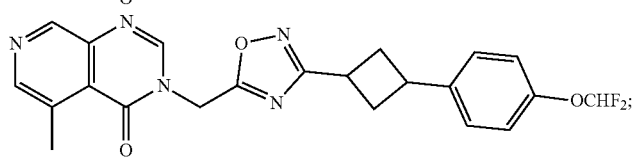
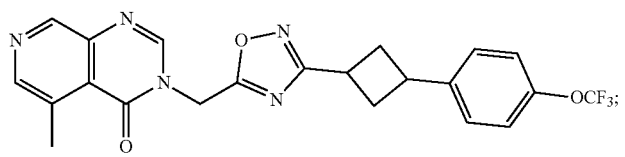
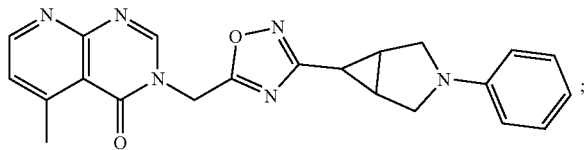
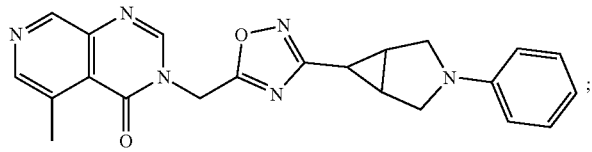

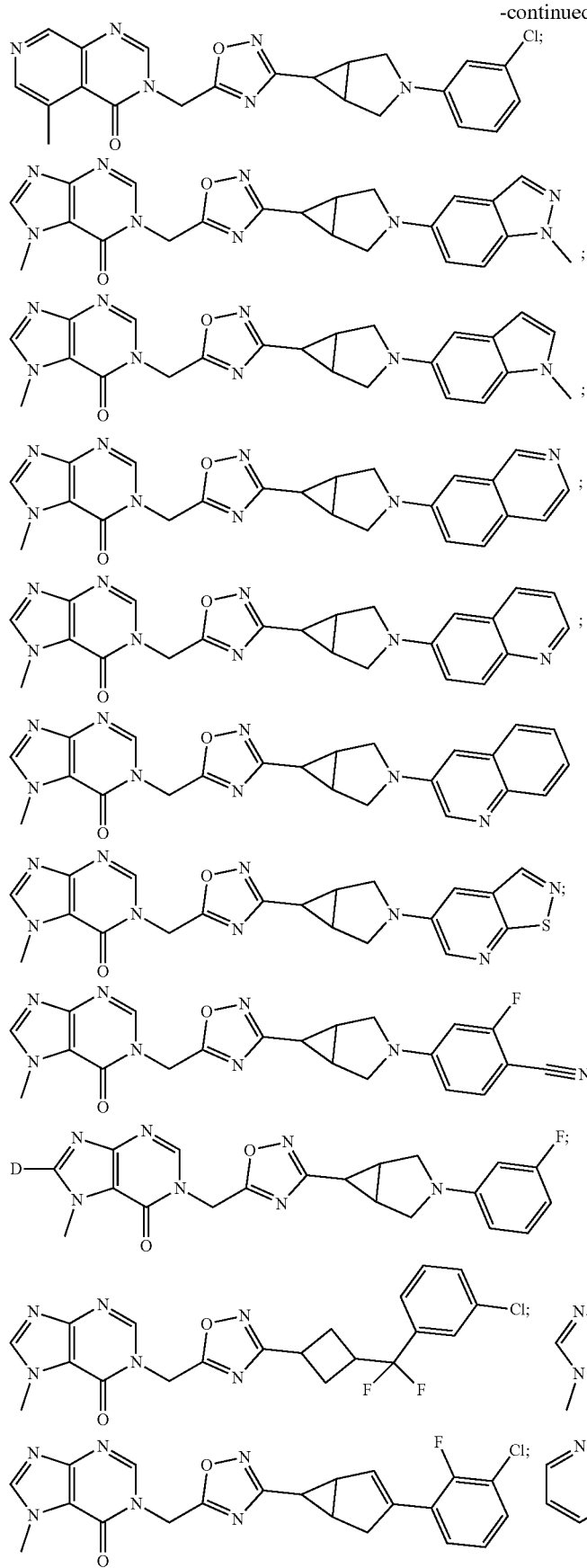

-continued
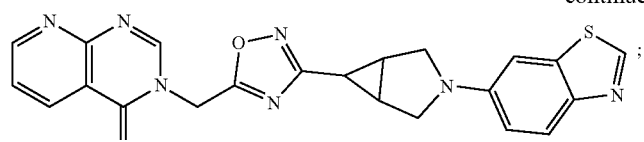
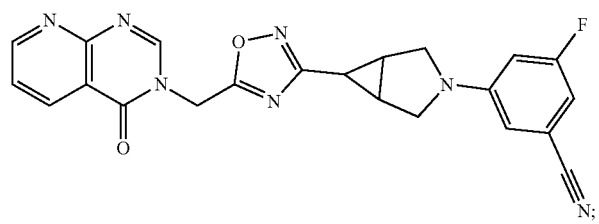
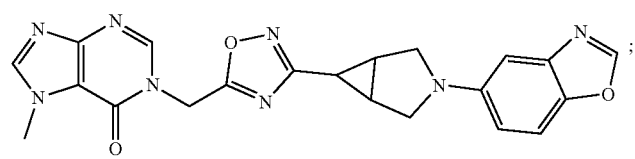
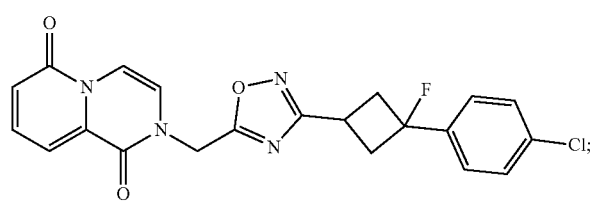
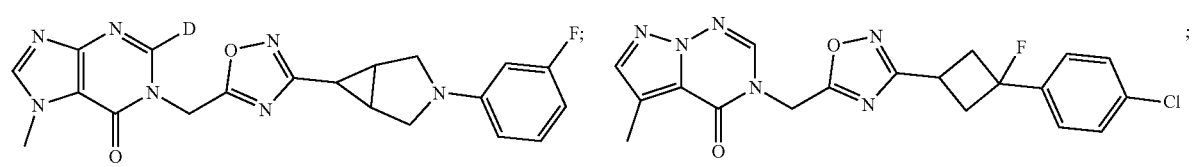
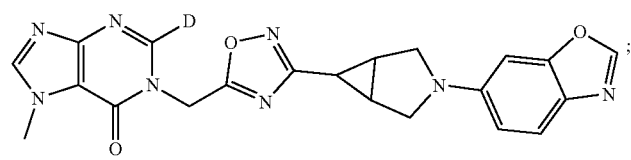
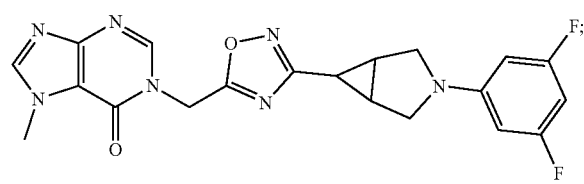
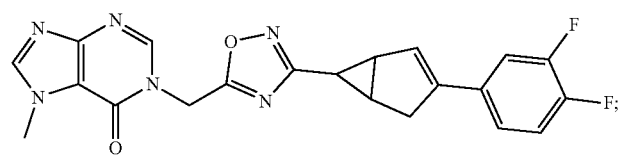
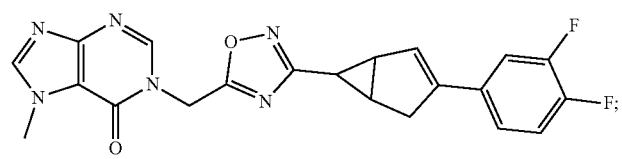
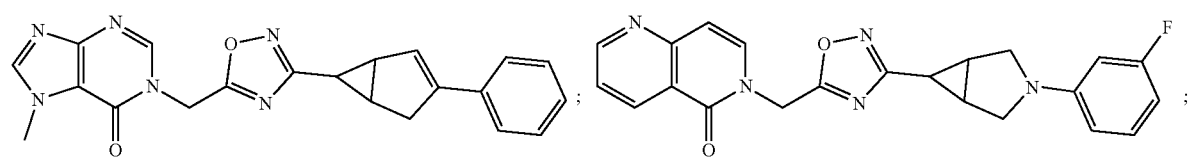

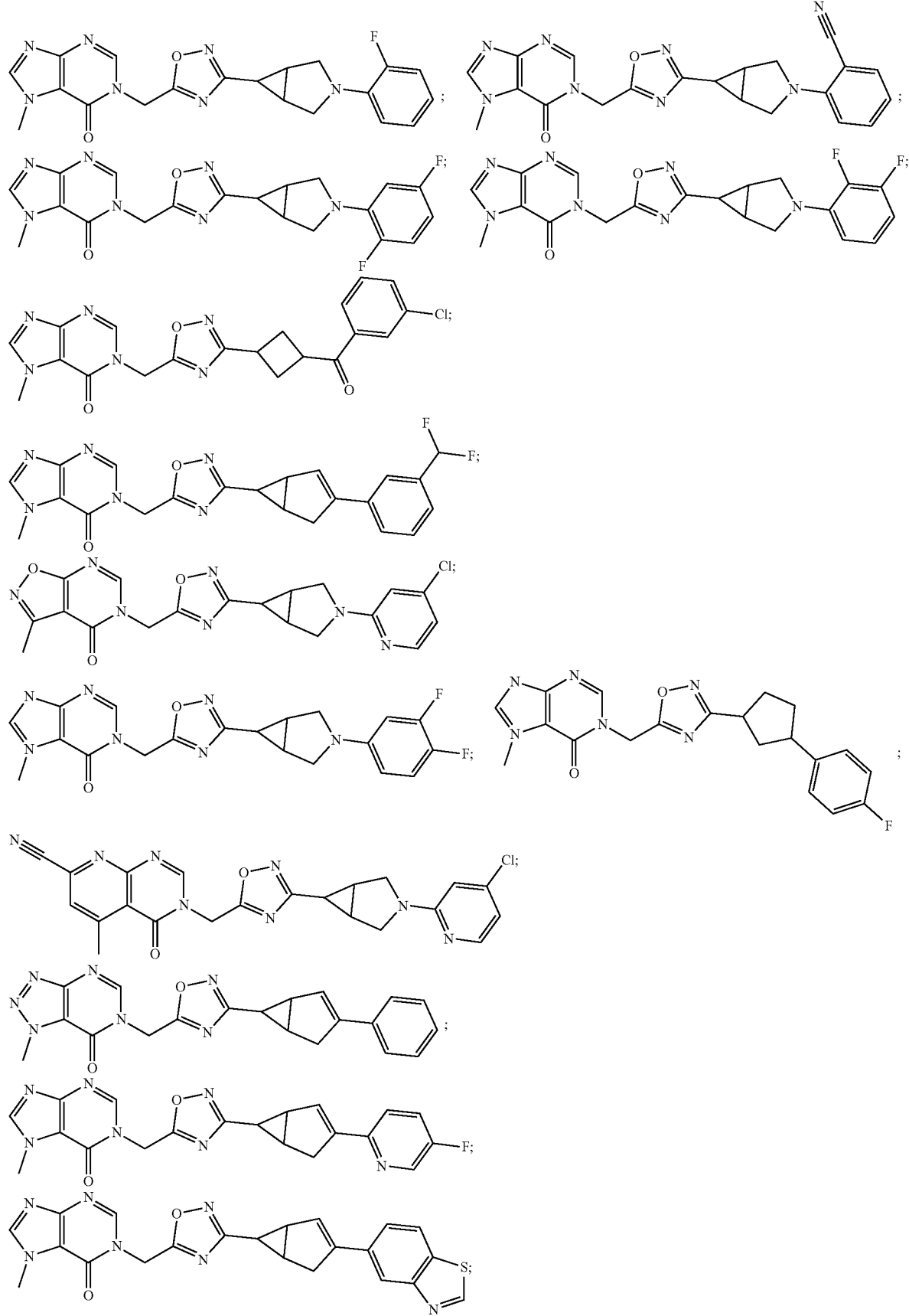

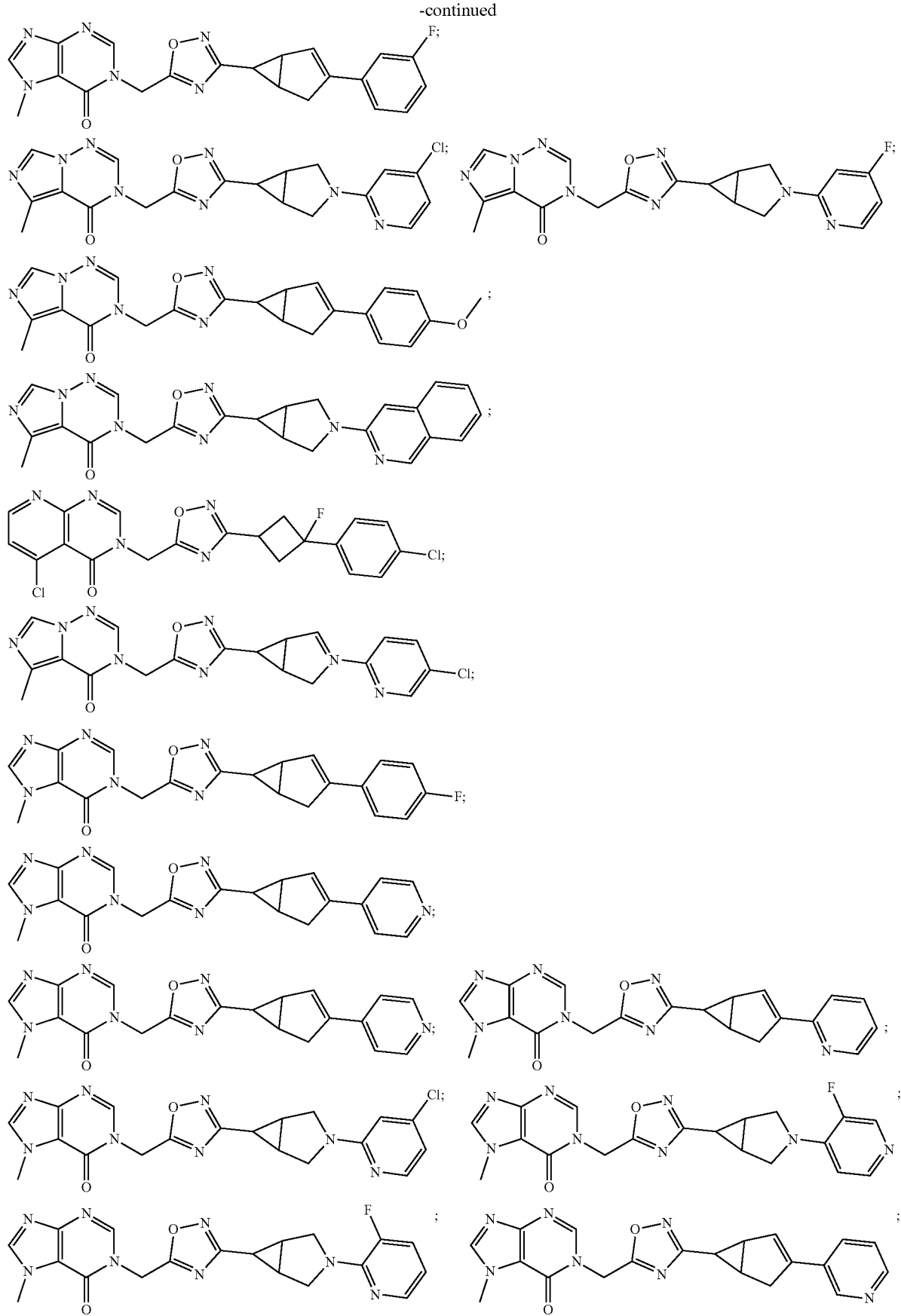

-continued
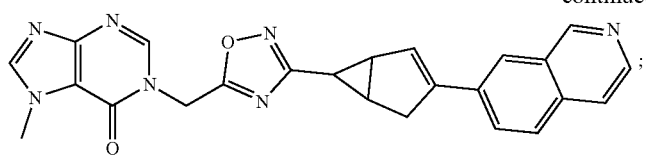
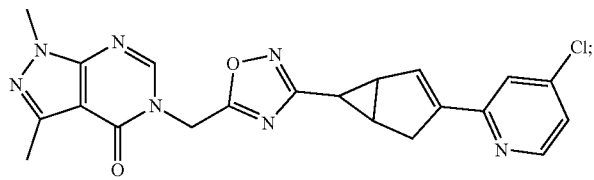
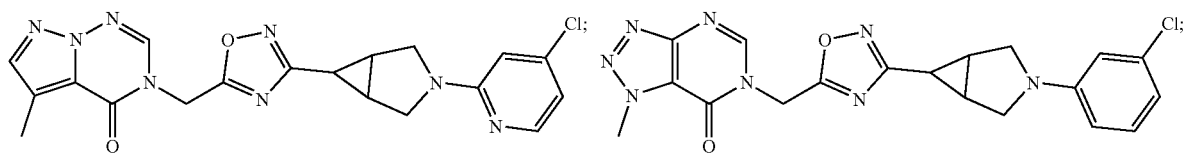
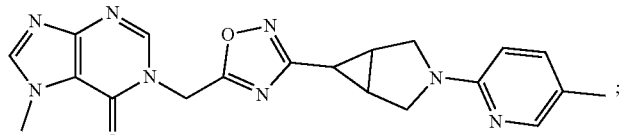
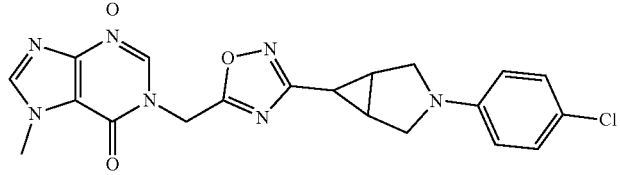
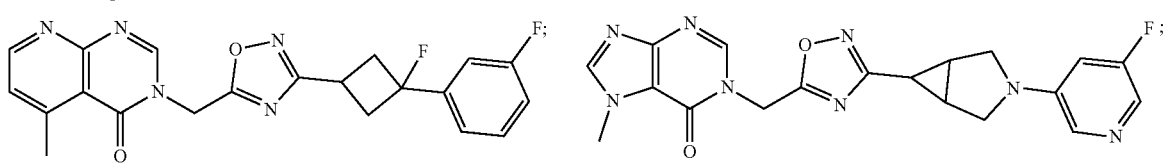
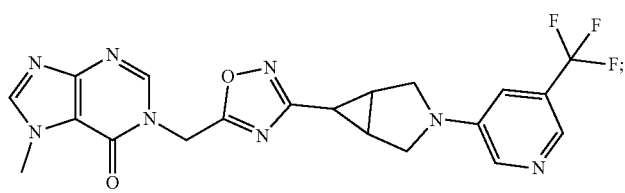
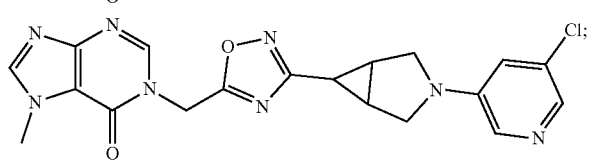
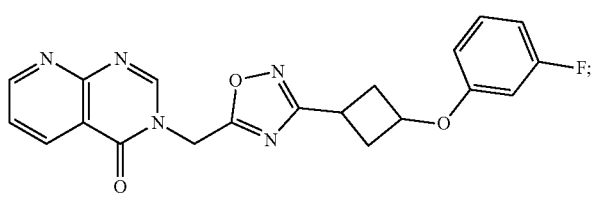
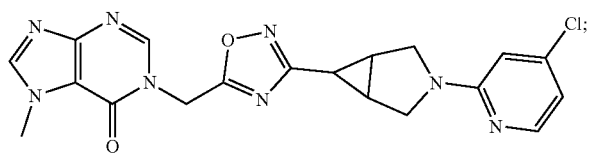

-continued
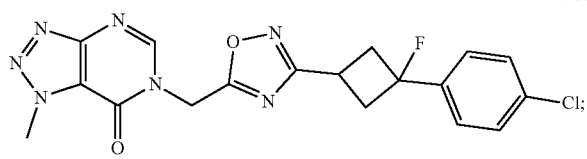
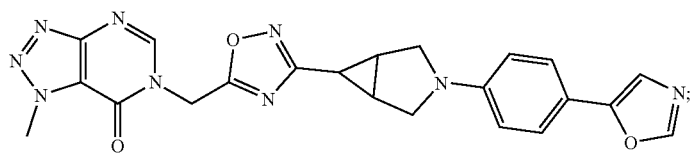
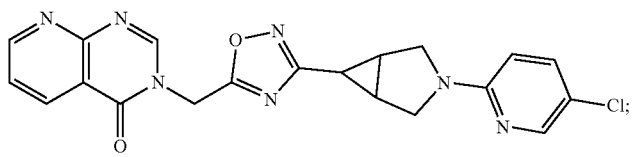
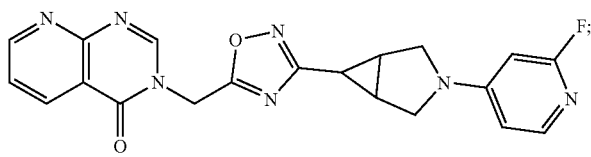
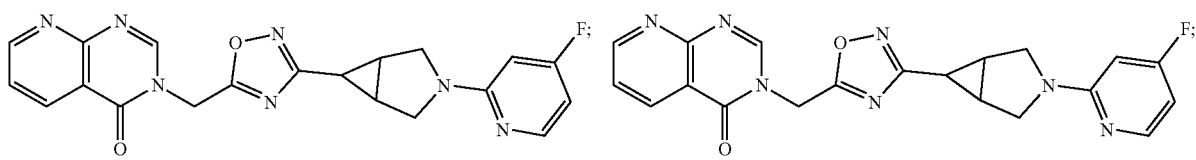
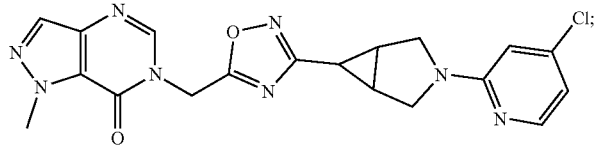
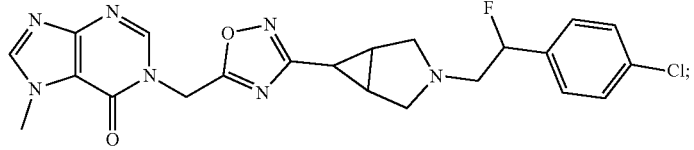
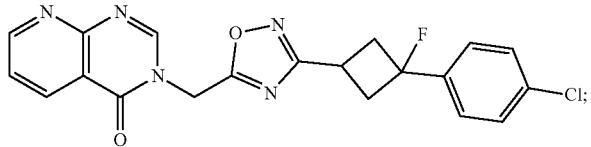
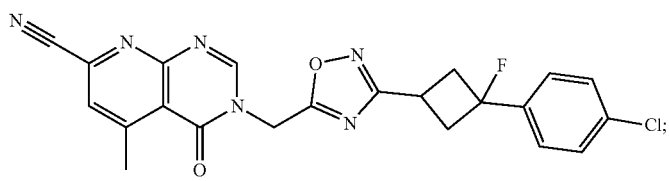
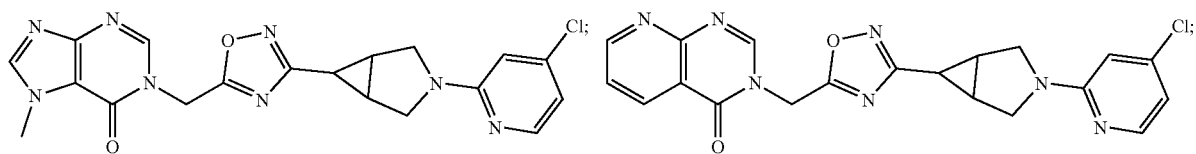

-continued
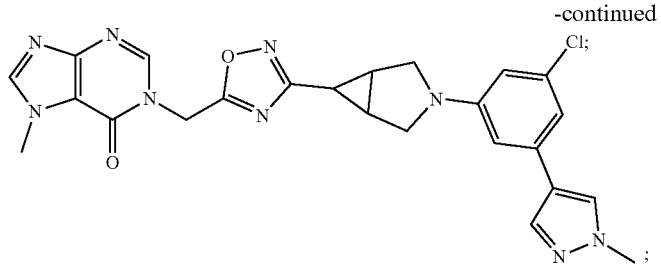
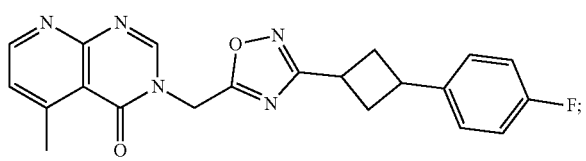
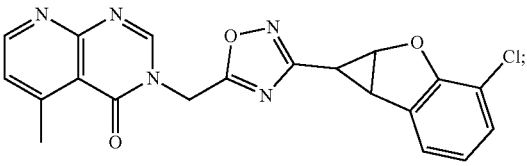
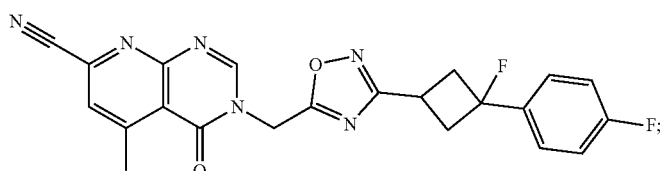
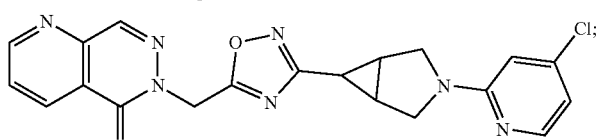
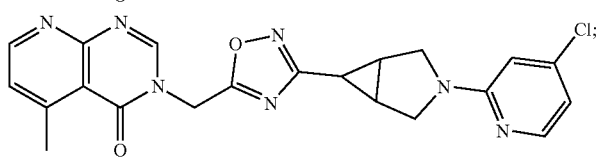
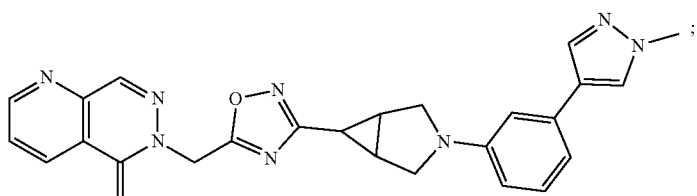
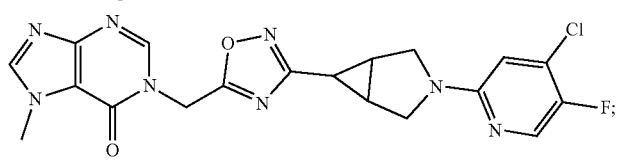
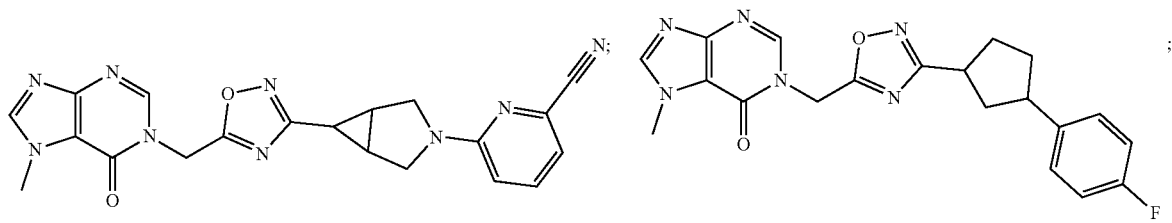
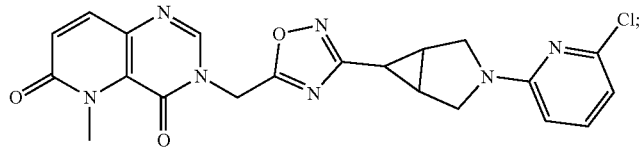

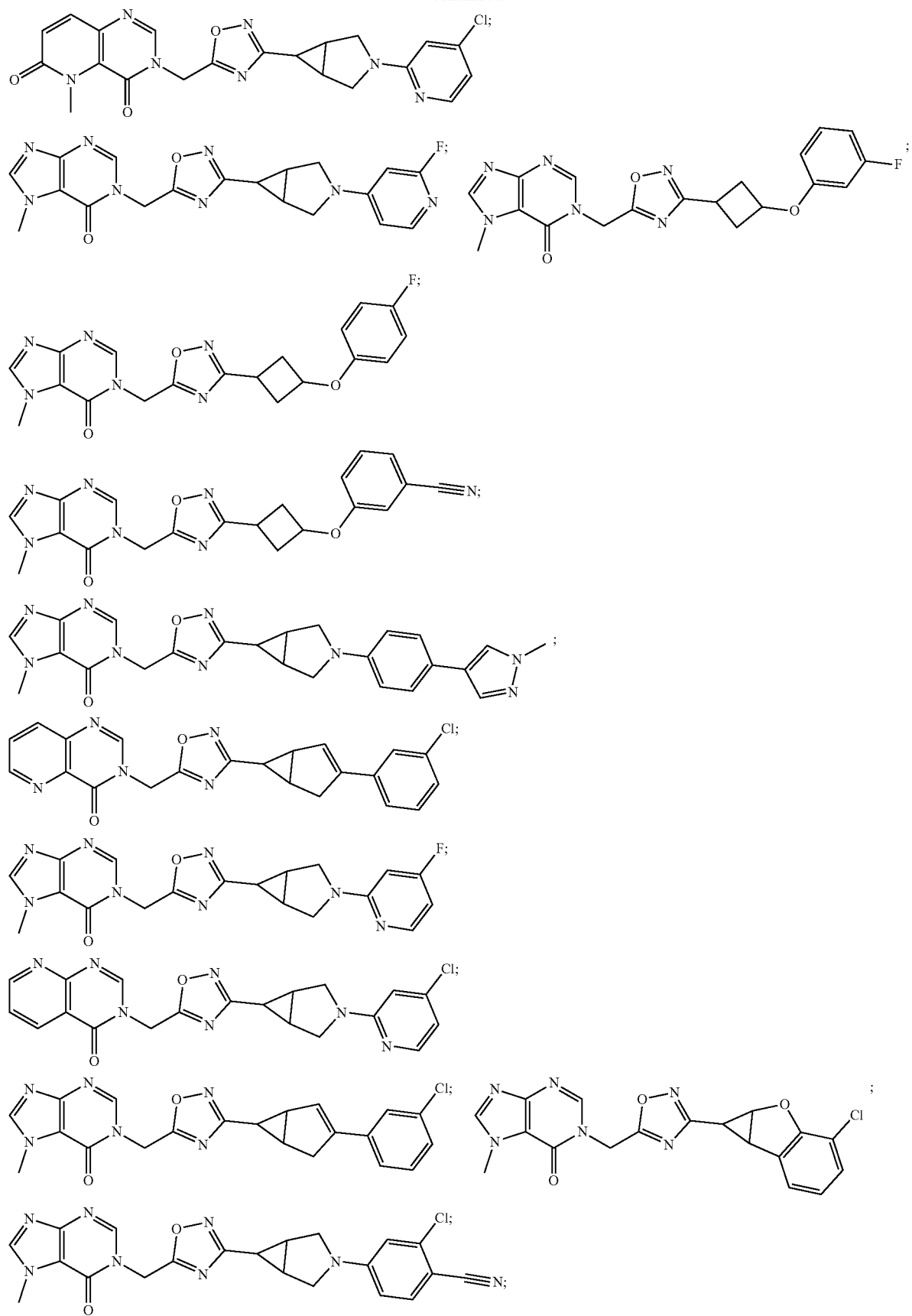

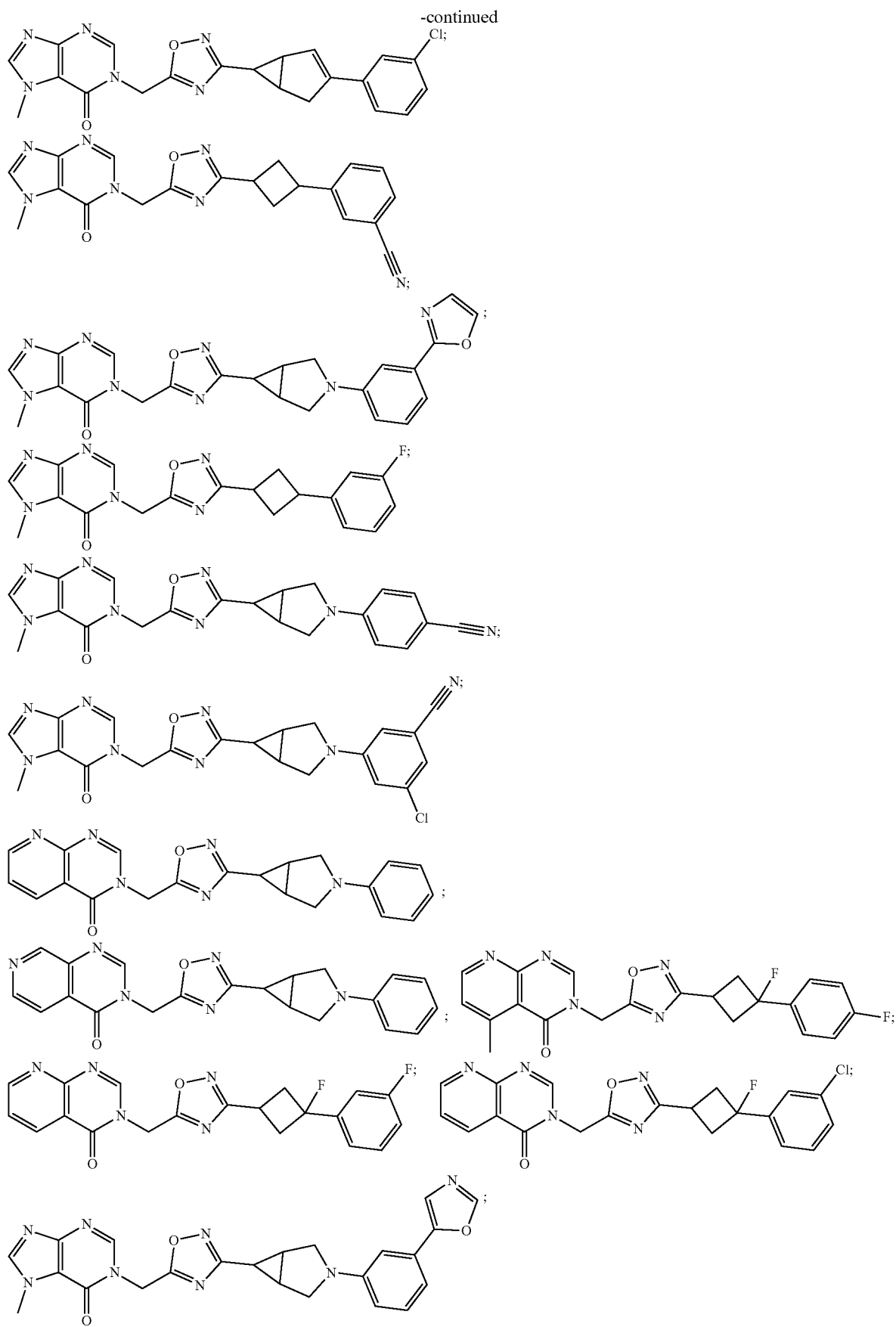

-continued
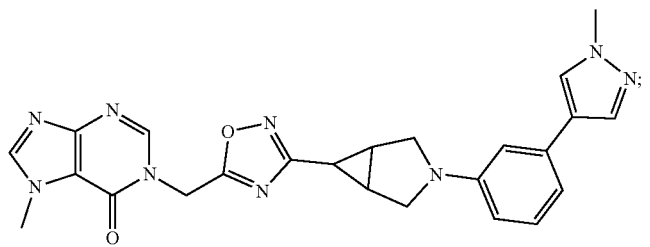
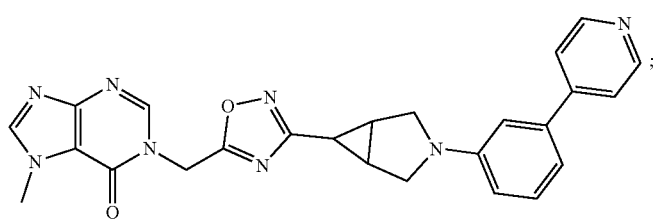
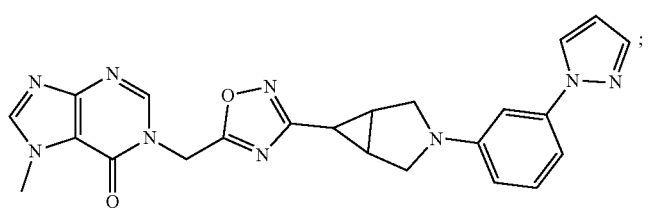
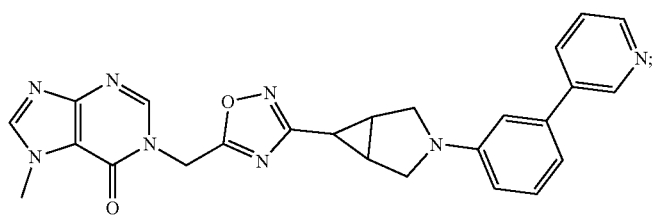
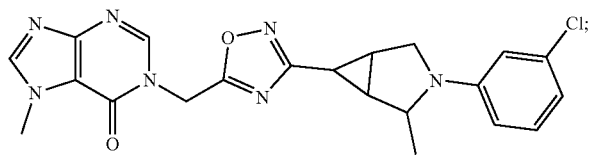
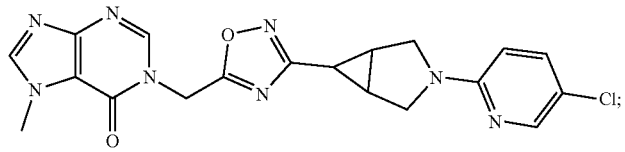
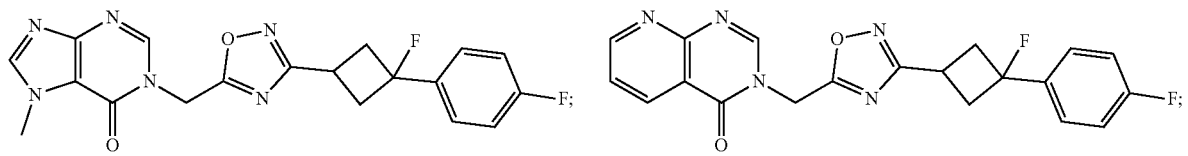
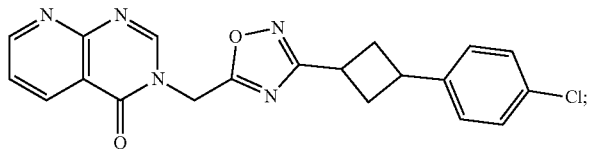
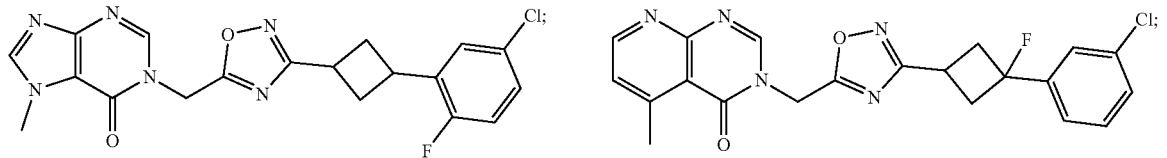

-continued
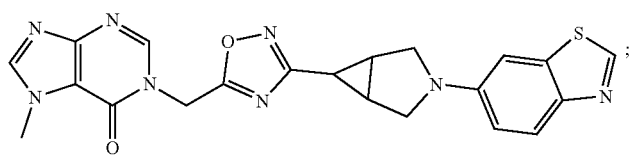
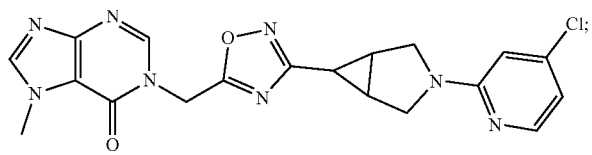
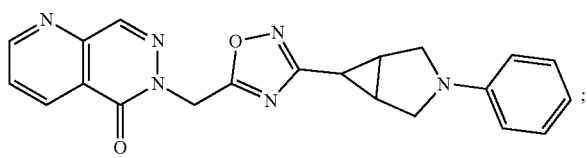
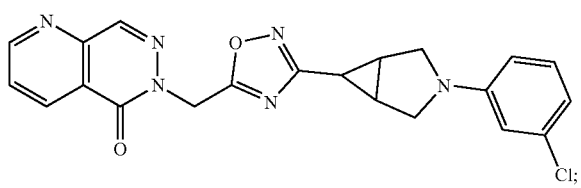
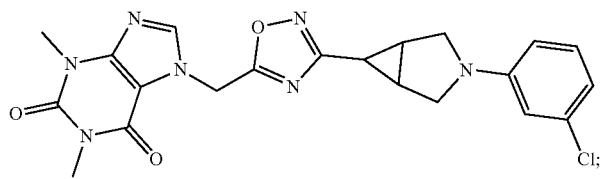
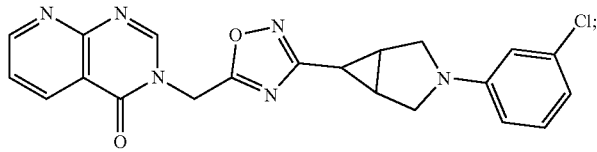
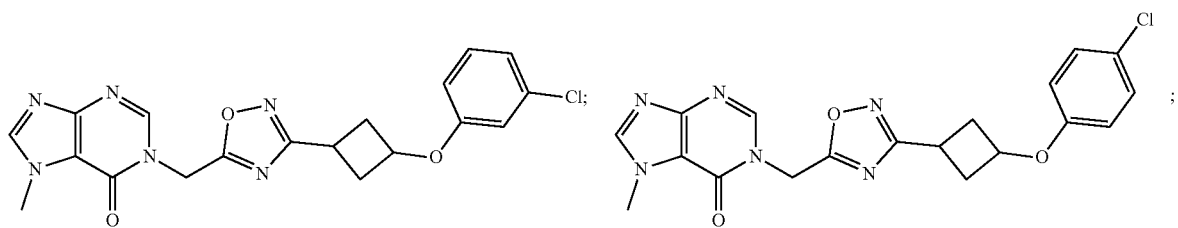
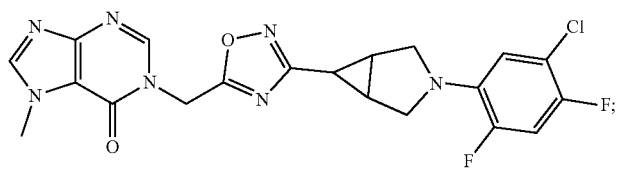
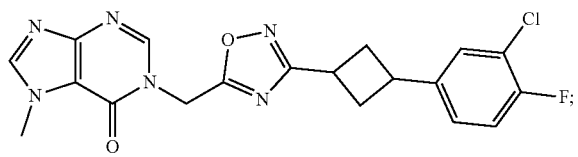
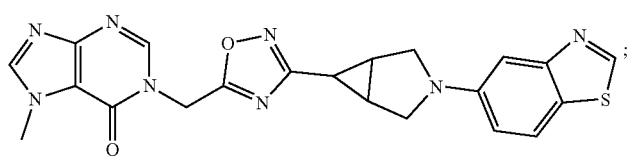

-continued
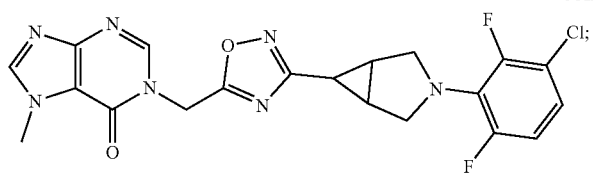
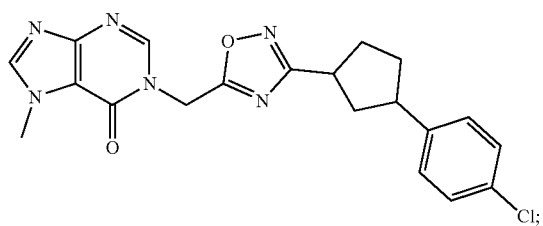
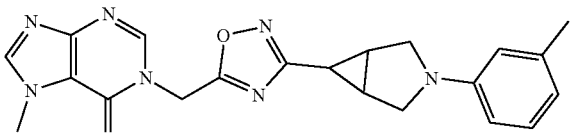
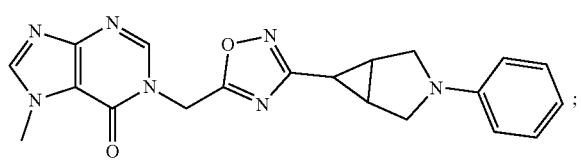
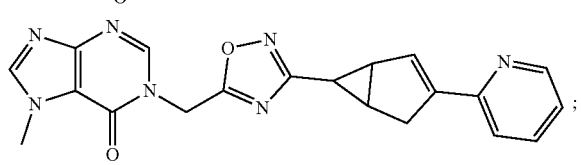
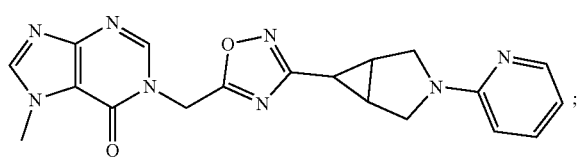
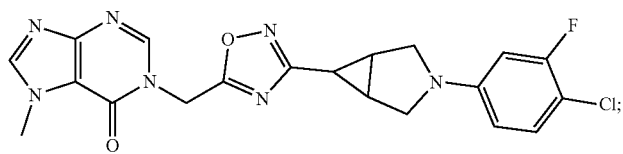
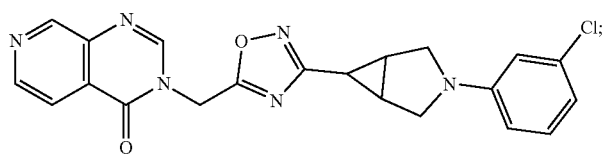
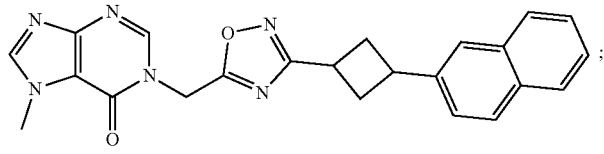
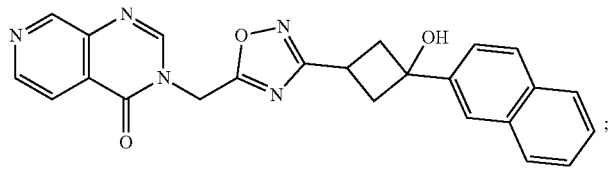

-continued
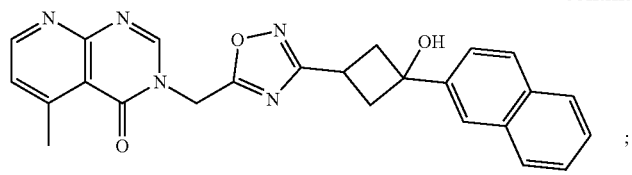
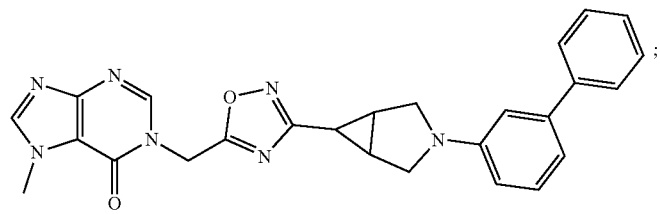
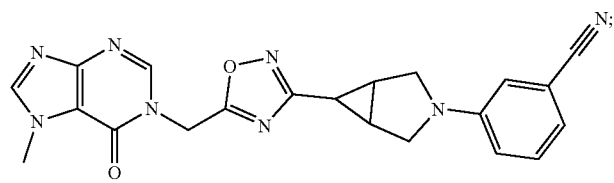
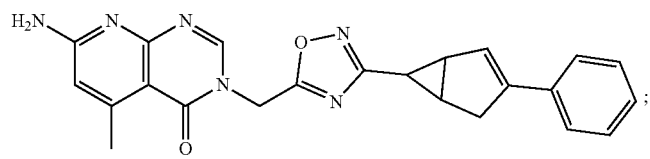
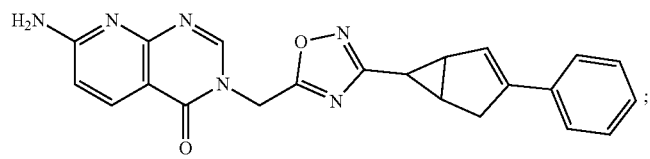
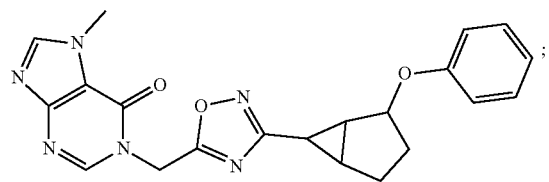
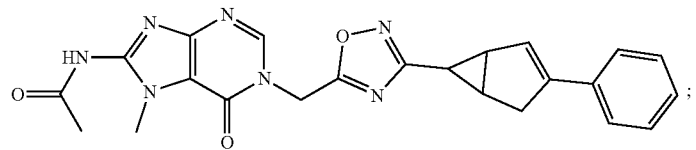
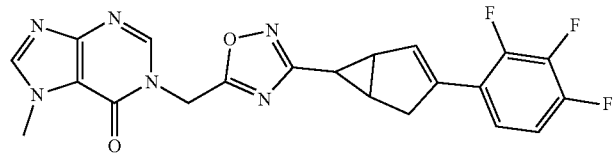
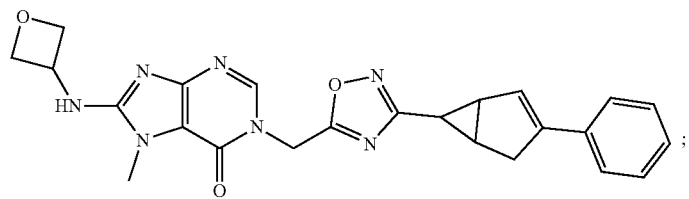

-continued
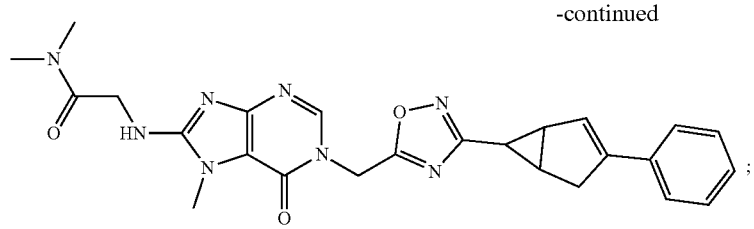
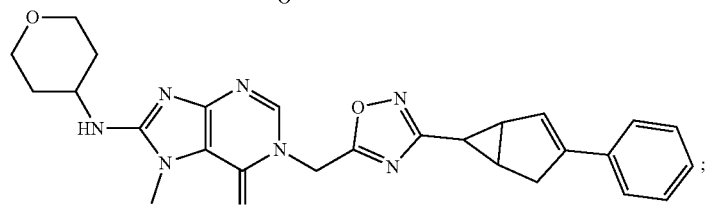
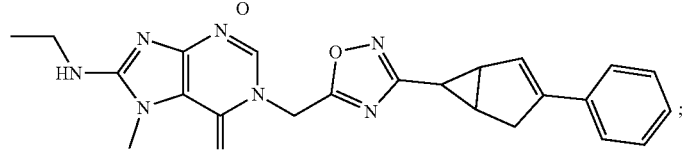
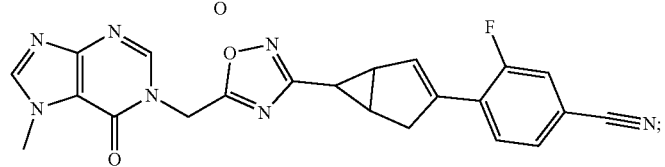
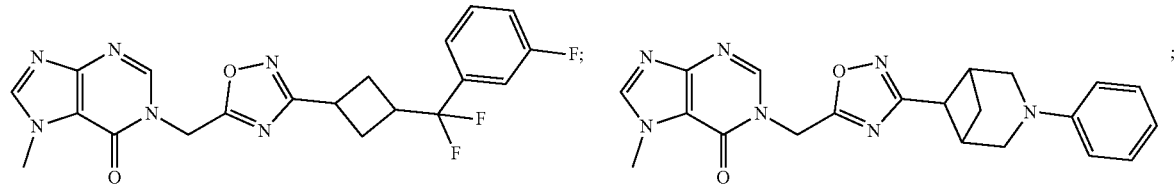
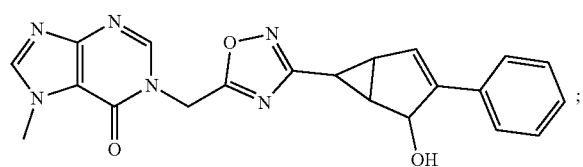
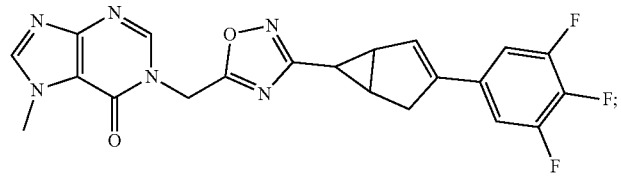
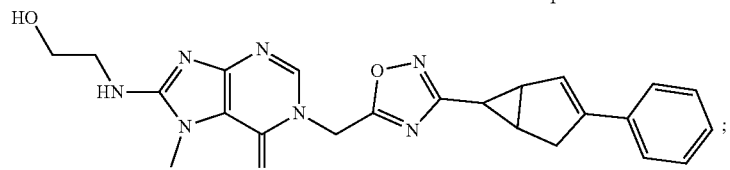
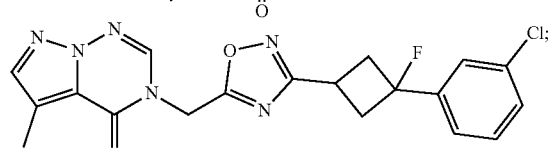
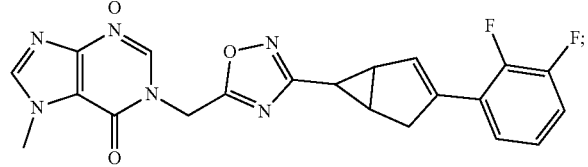

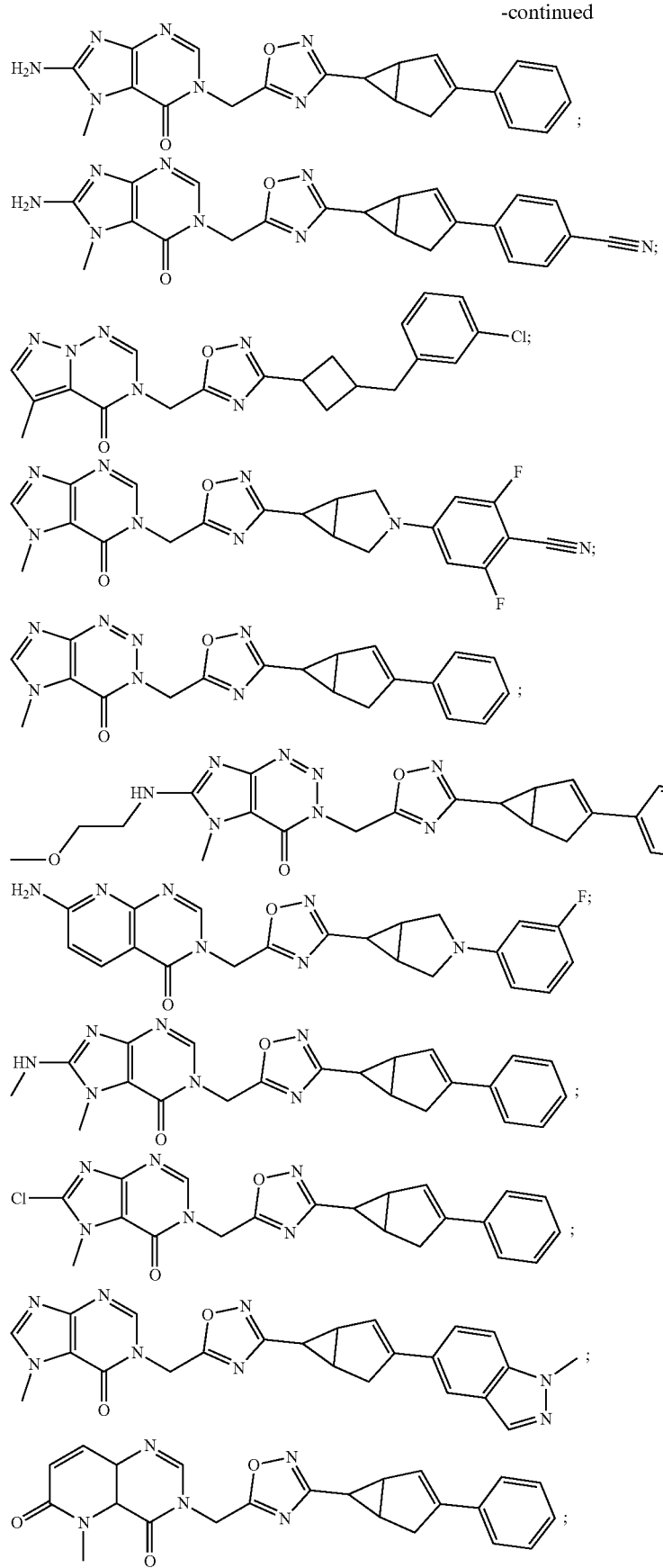

-continued
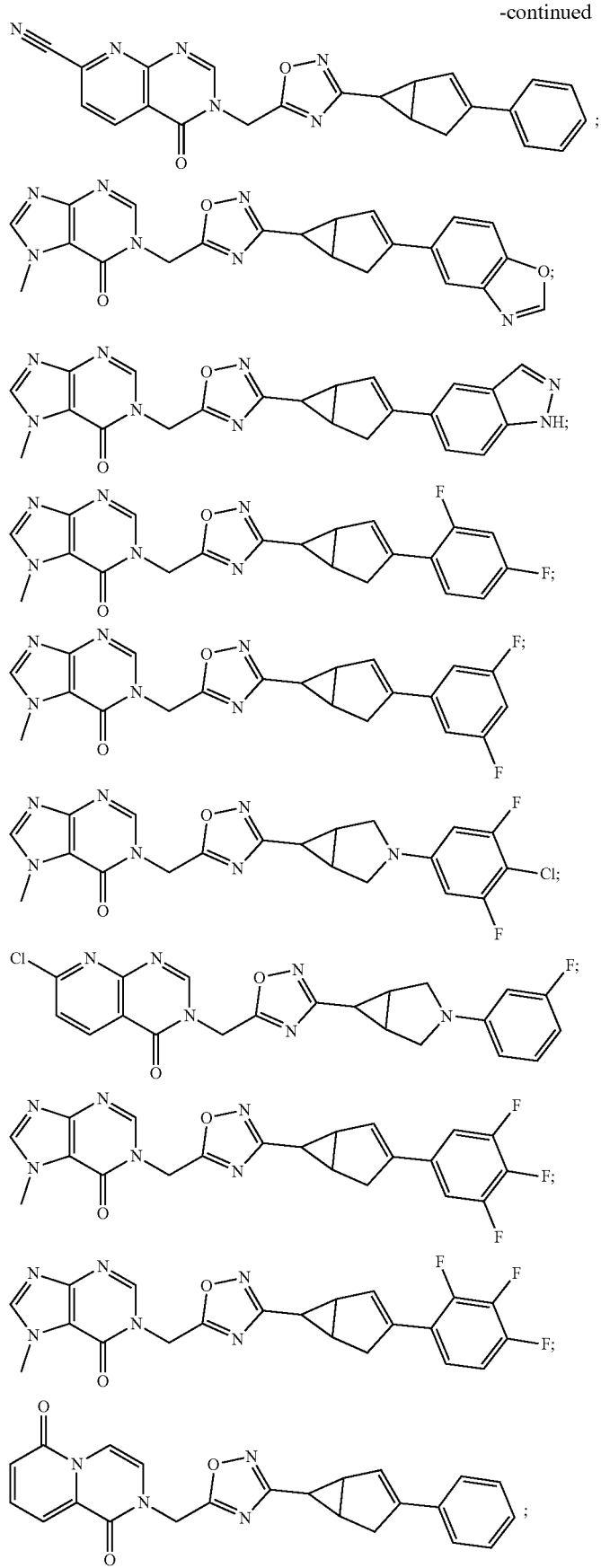

-continued
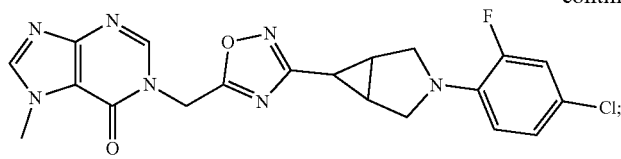
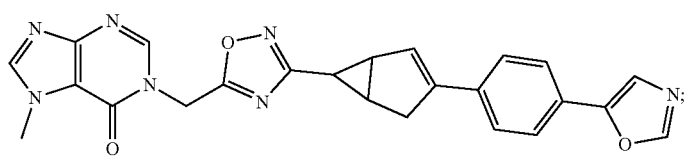
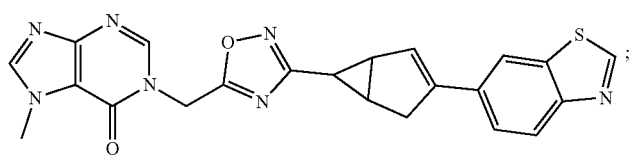
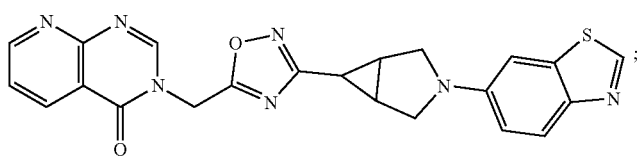
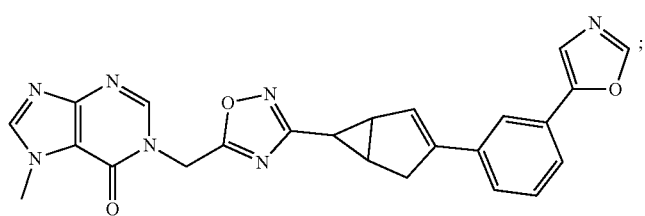
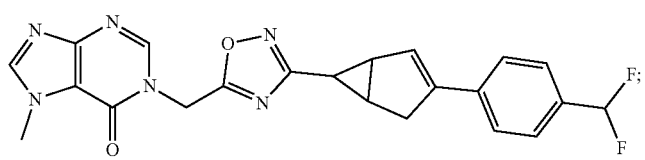
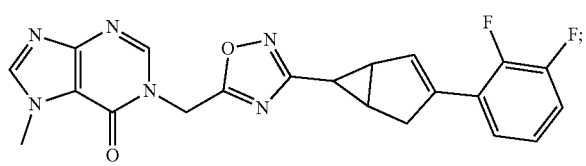
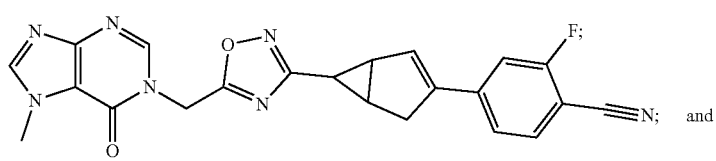
and
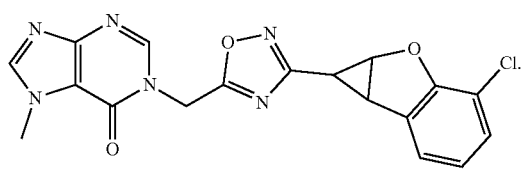

21. A stereoisomer of a compound of claim 1 selected from the following compounds and pharmaceutically acceptable salts thereof:
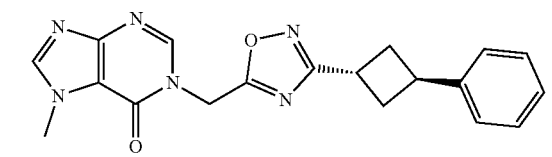
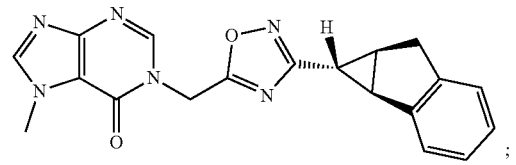
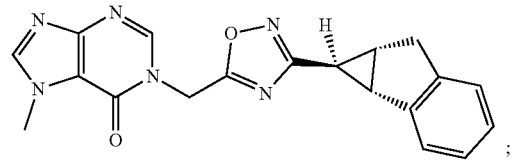
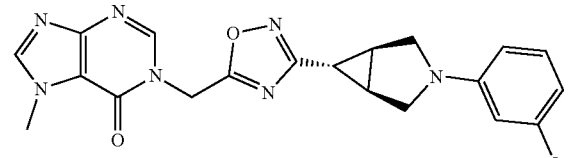
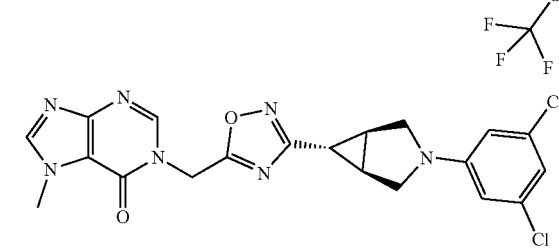
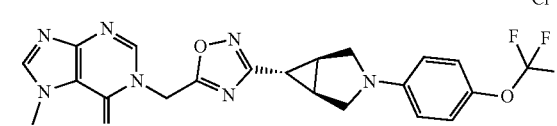
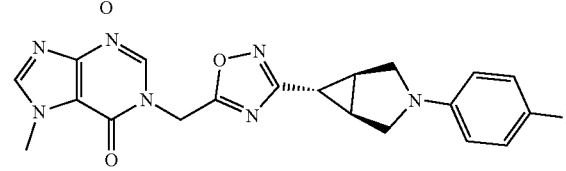
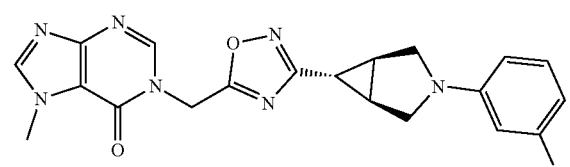
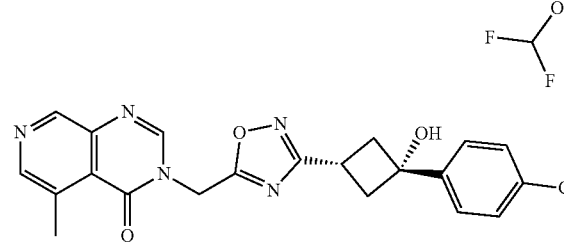
-continued
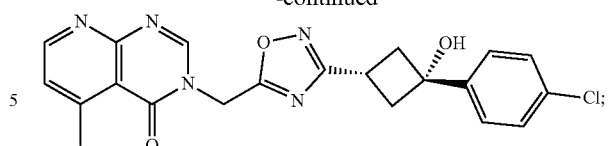
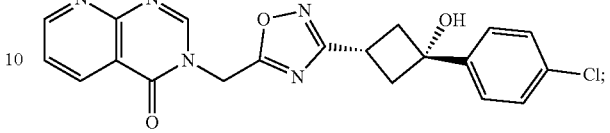
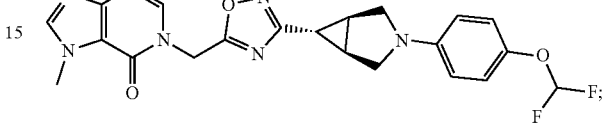
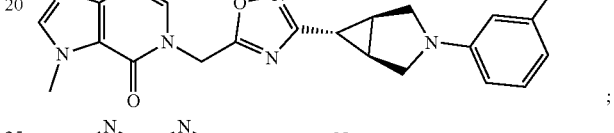
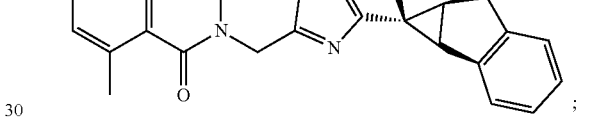
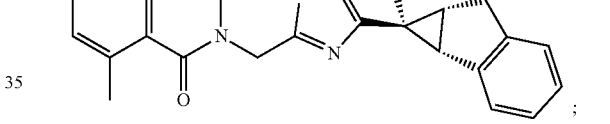
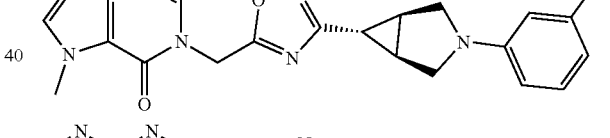
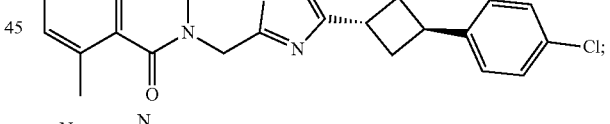
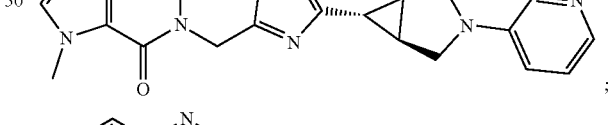
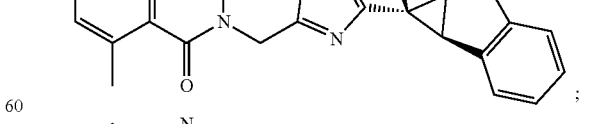
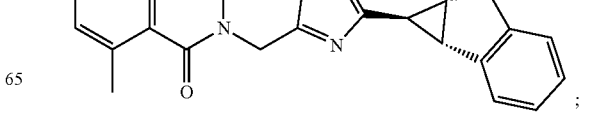

491
-continued
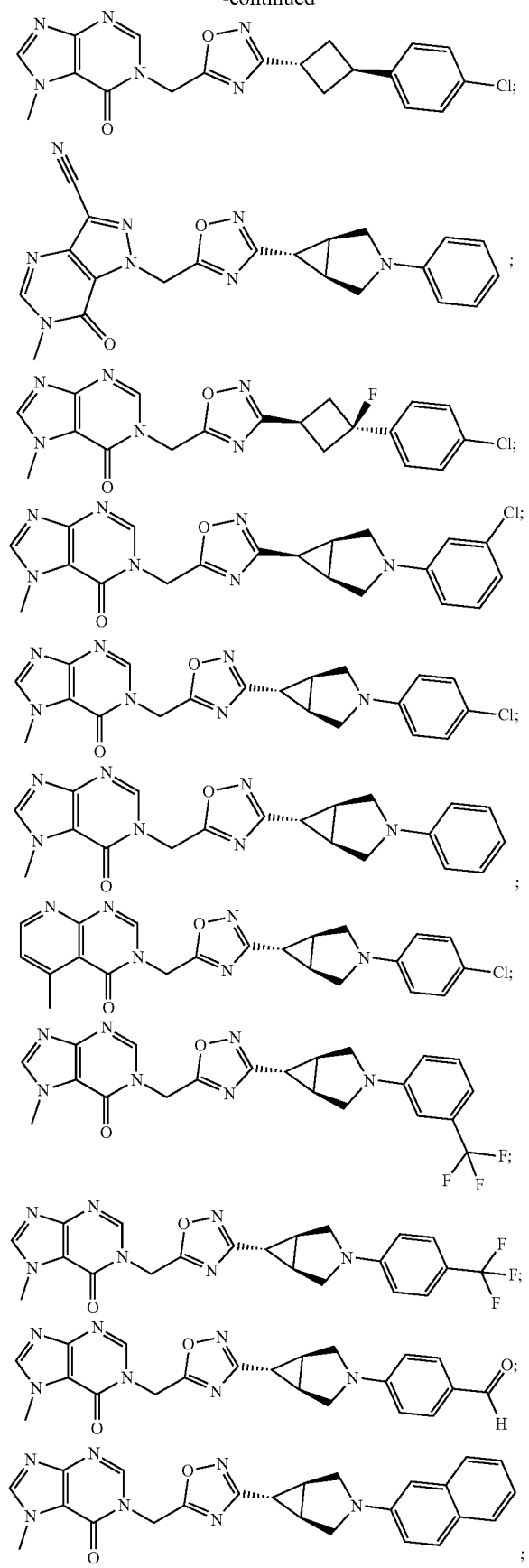
492
-continued
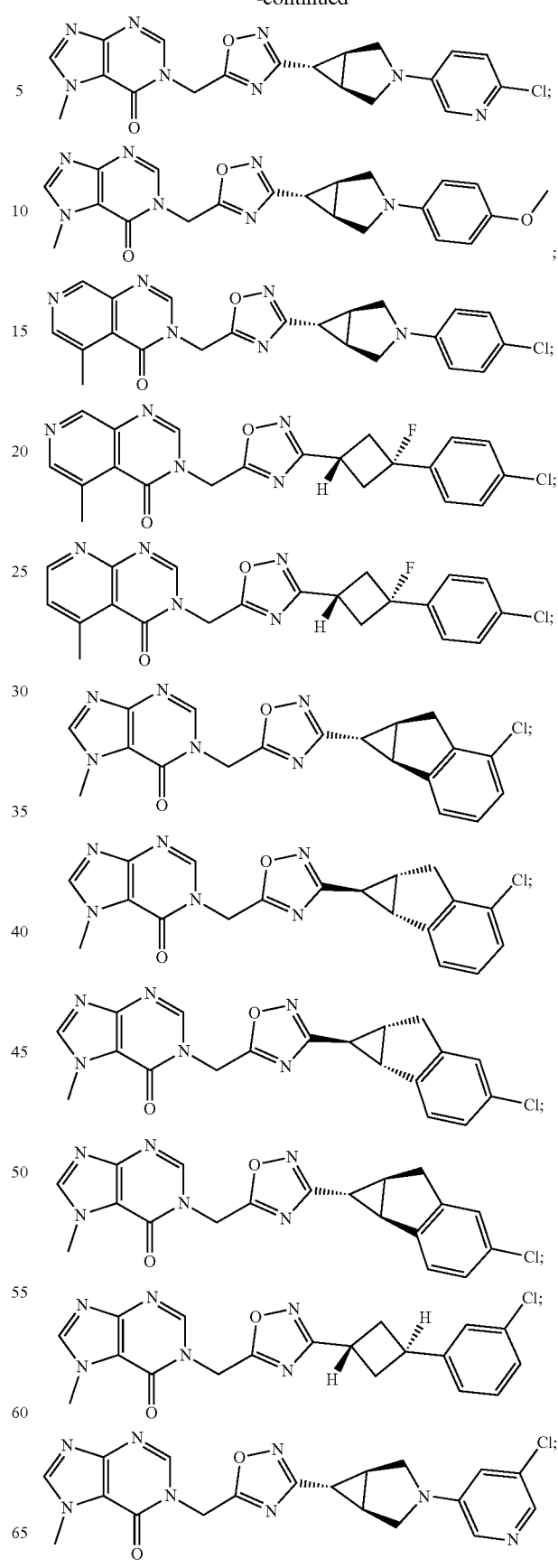

493
-continued
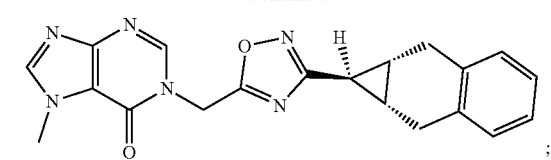
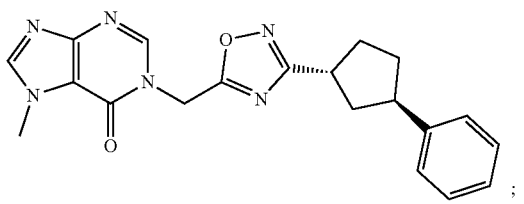
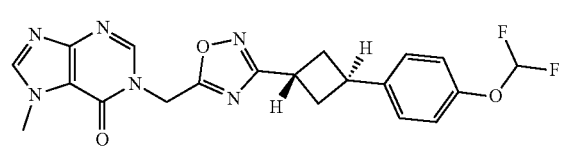
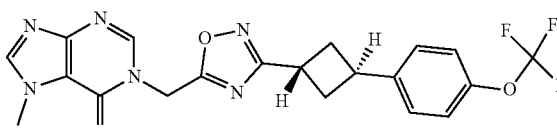
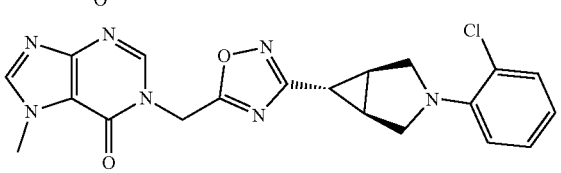
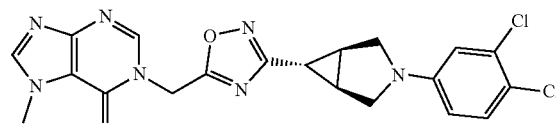
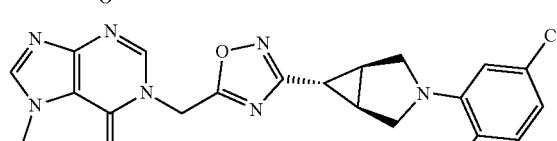
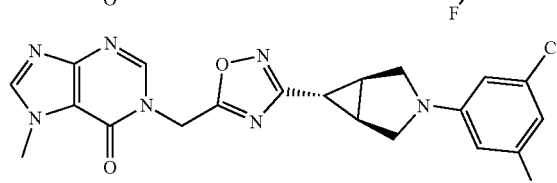
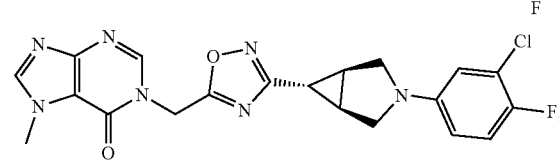
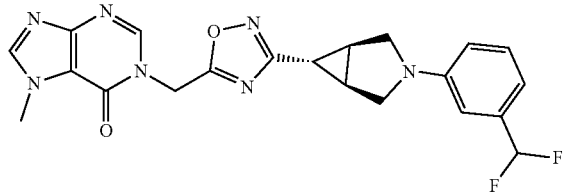
494
-continued
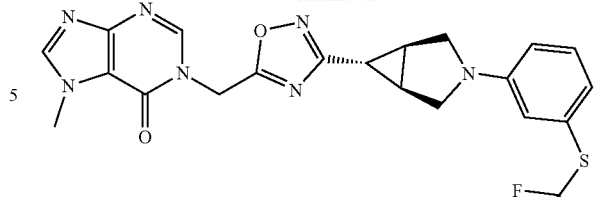
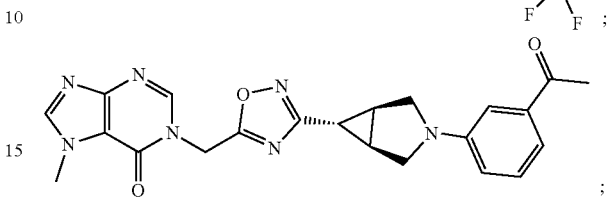
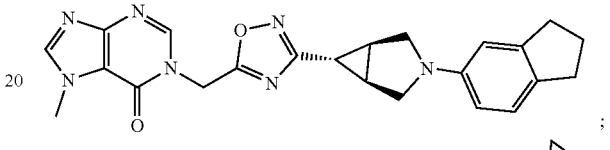
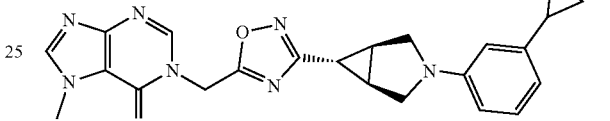
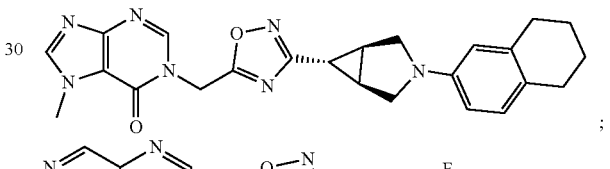
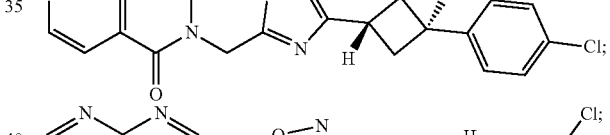
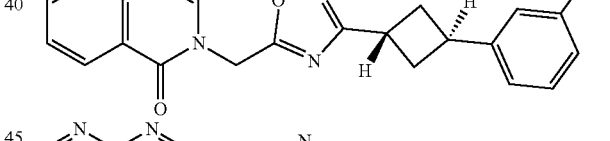
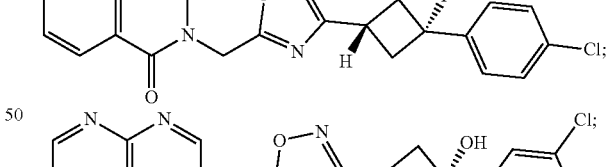
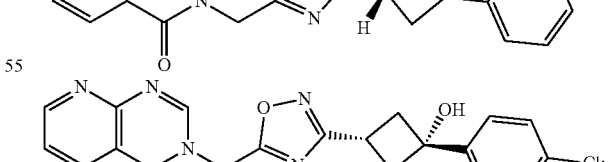
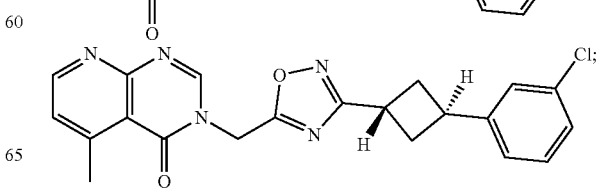

495
-continued
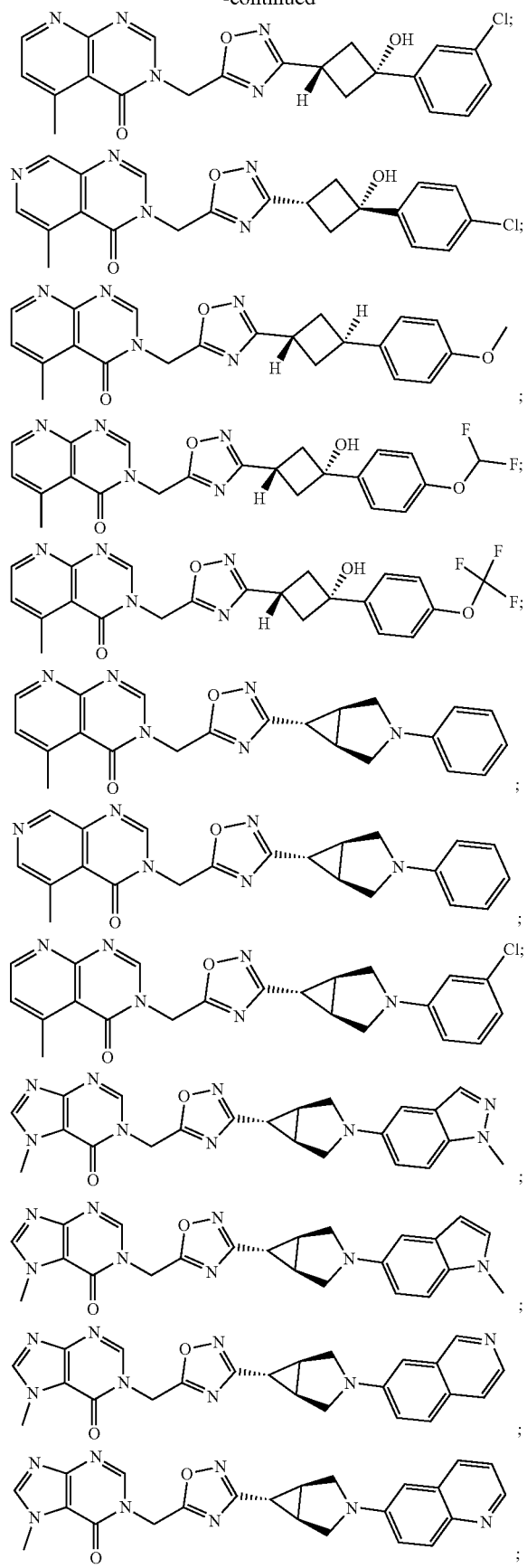
496
-continued
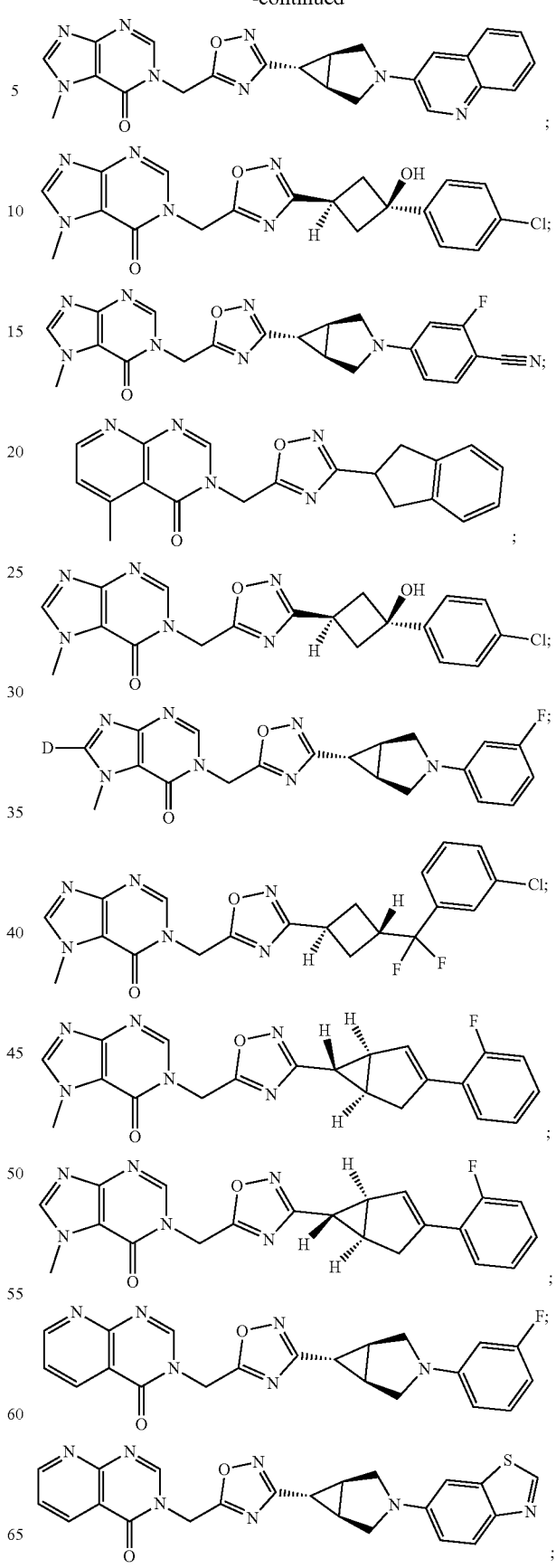

497
-continued
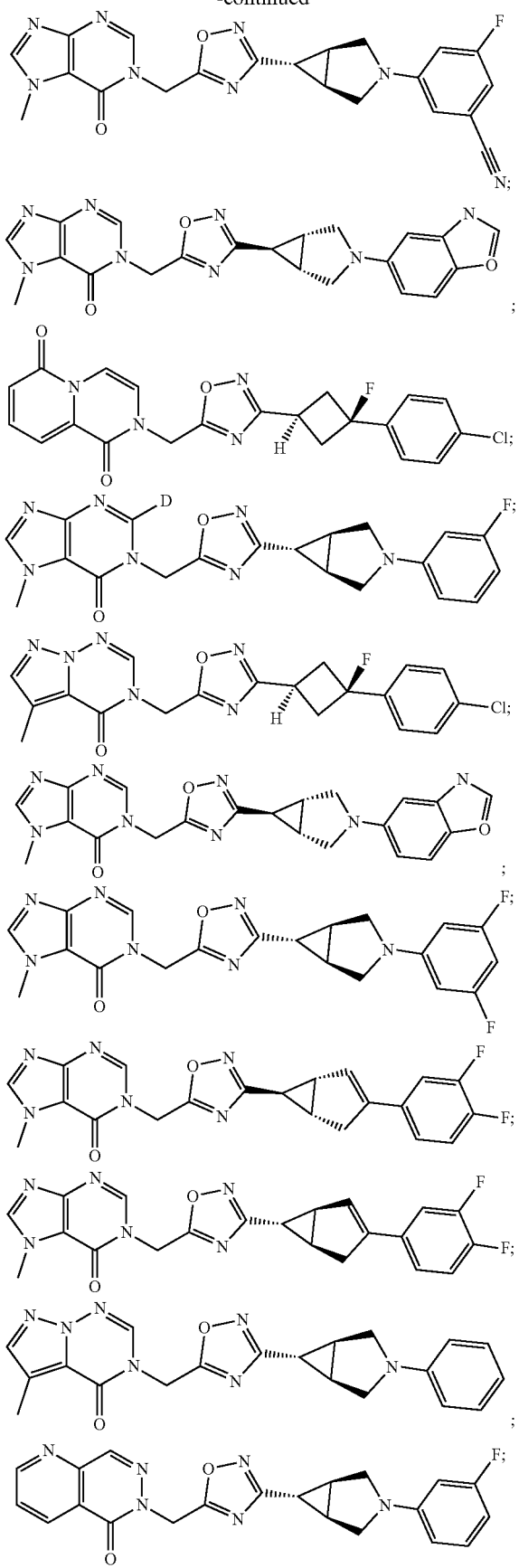
498
-continued
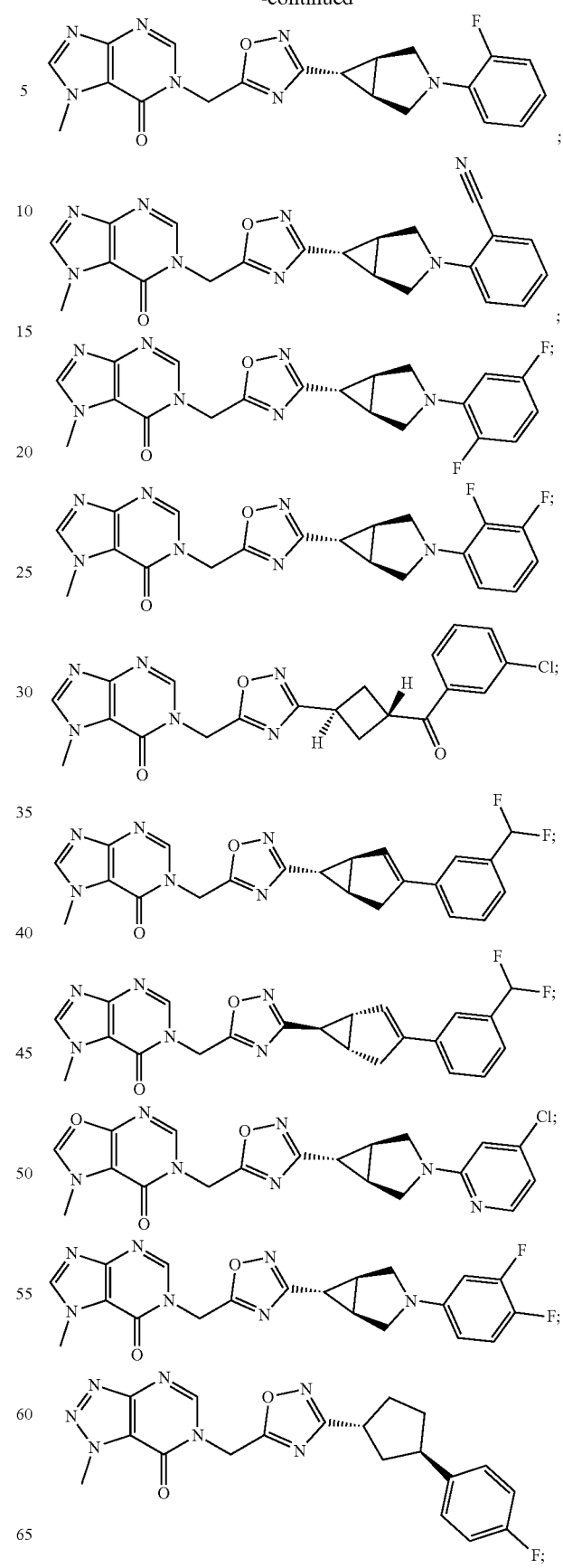

499
-continued
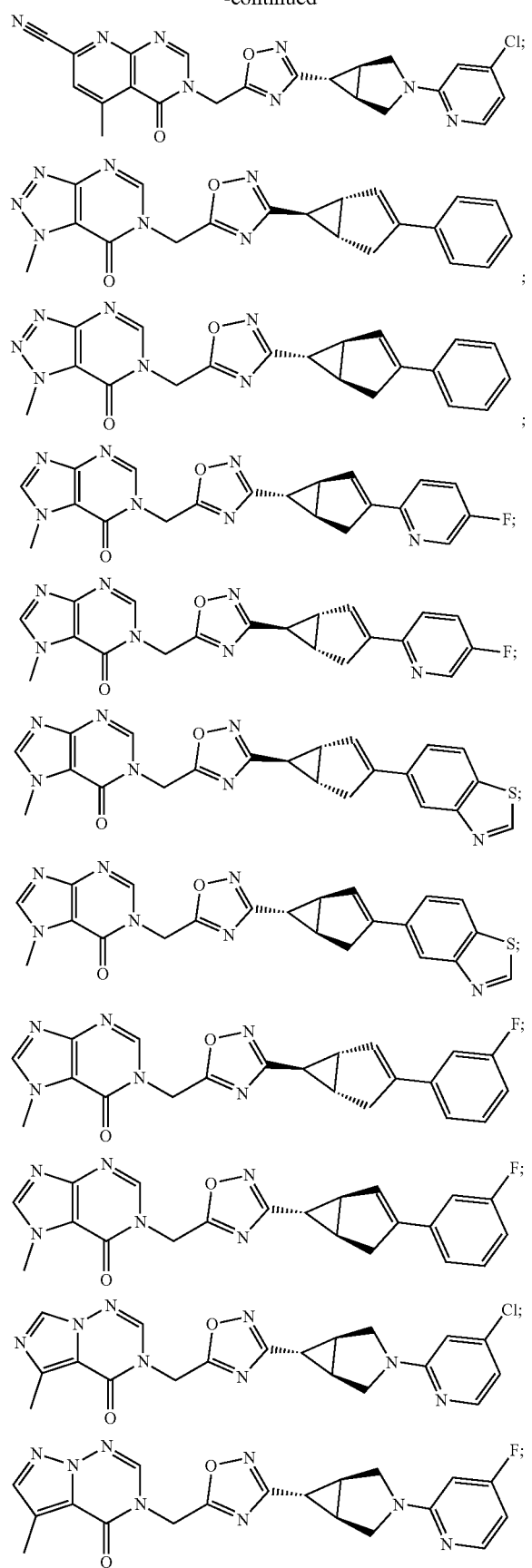
500
-continued
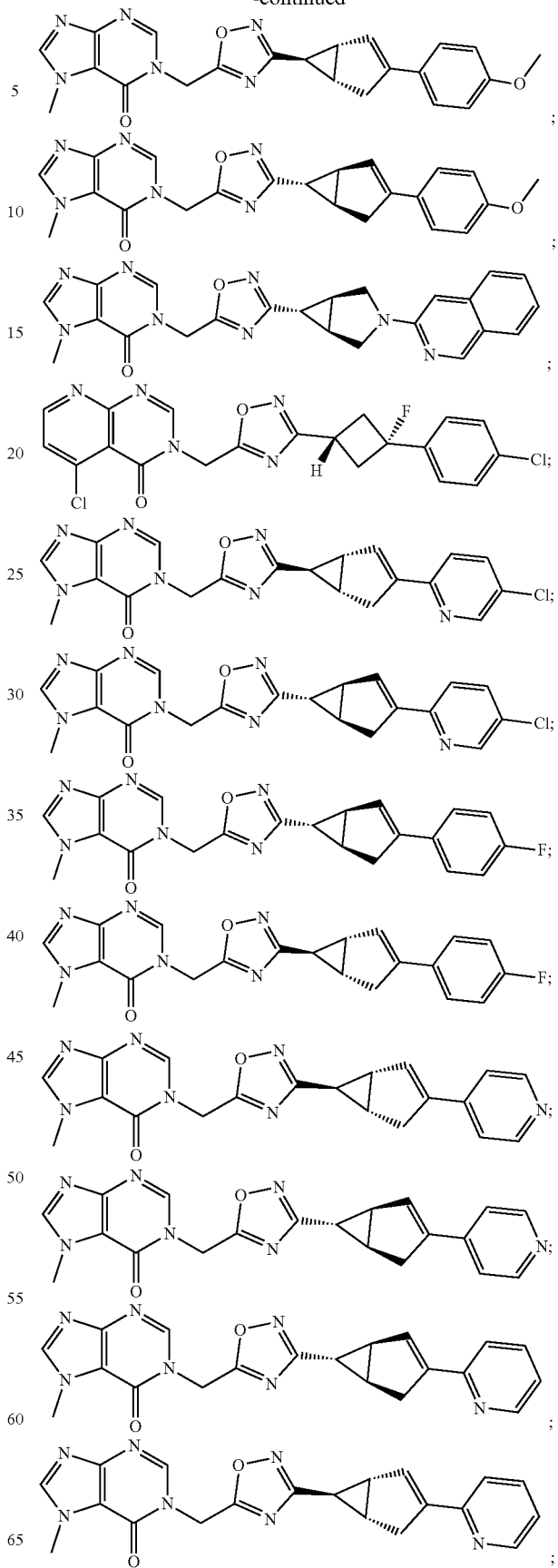

501
-continued
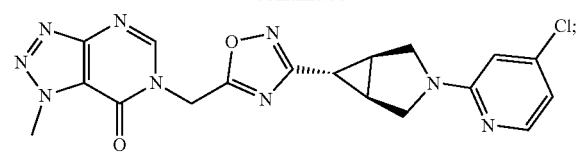
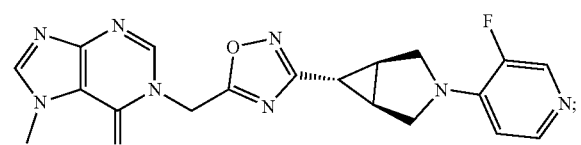
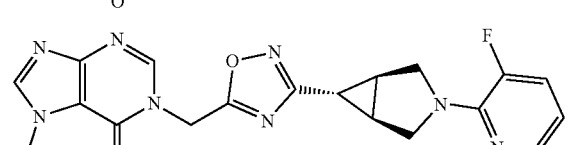
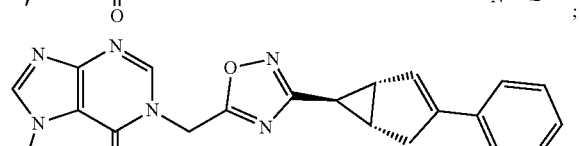
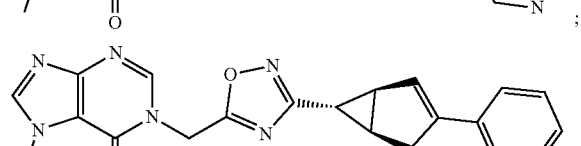
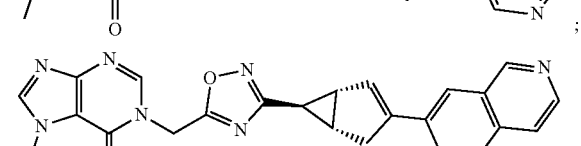
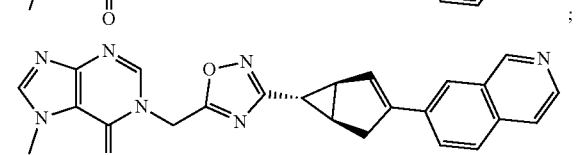
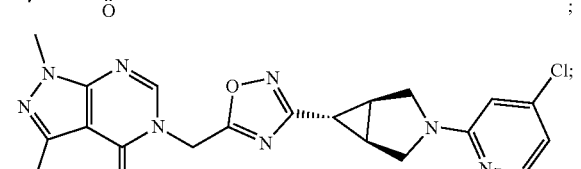
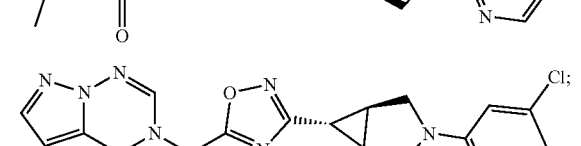
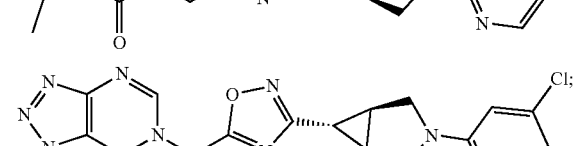
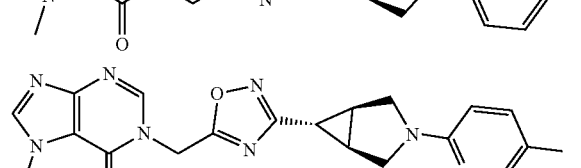
502
-continued
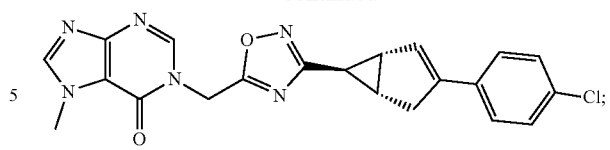
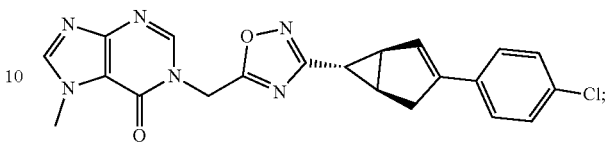
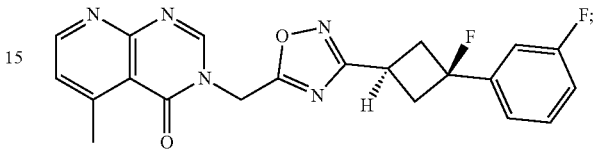
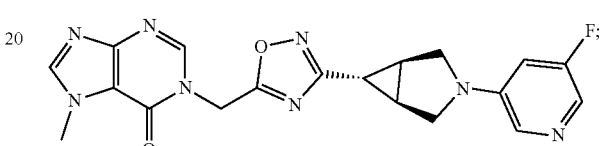
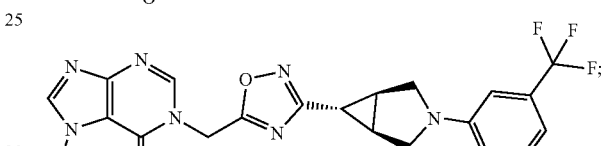
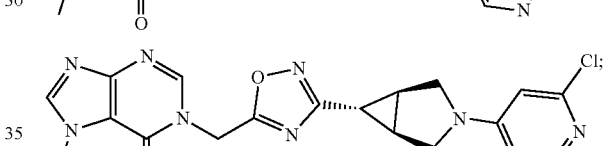
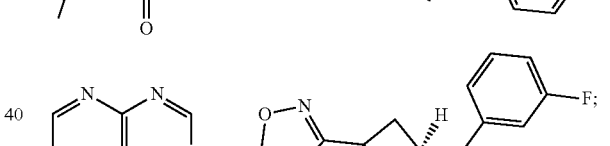
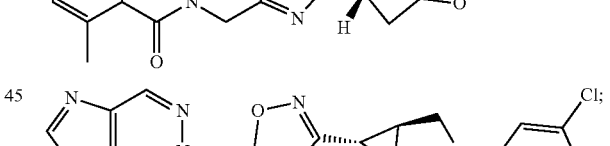
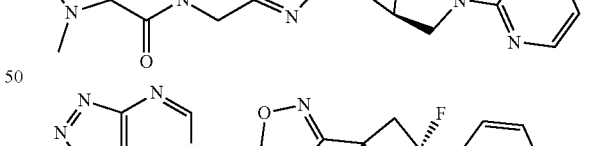
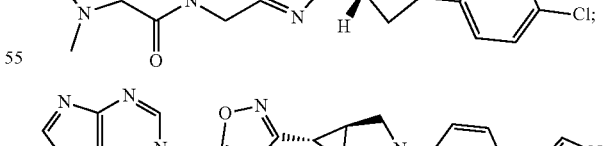
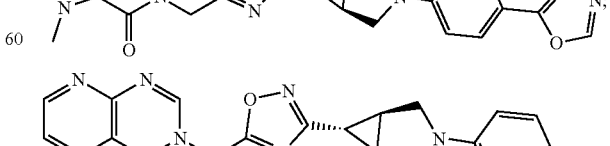
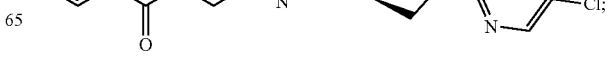

503
-continued
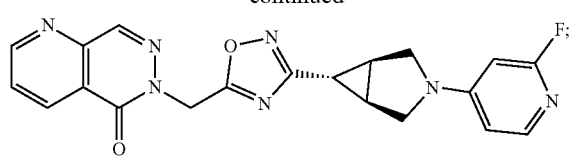
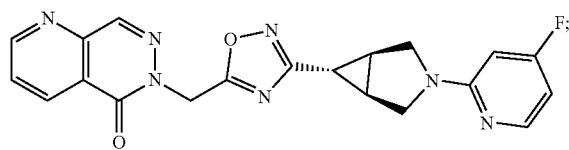
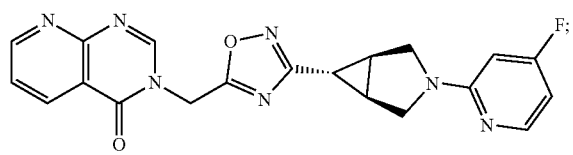
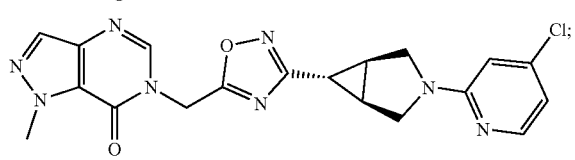
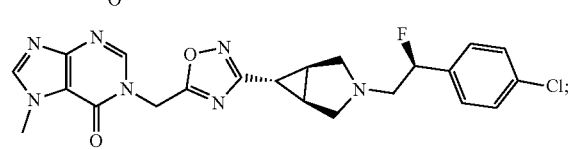
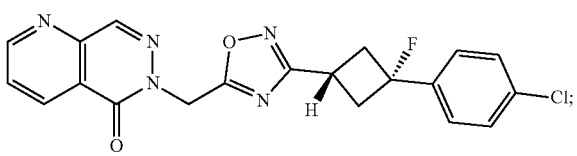
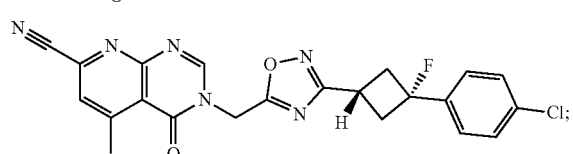
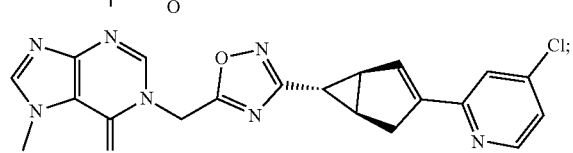
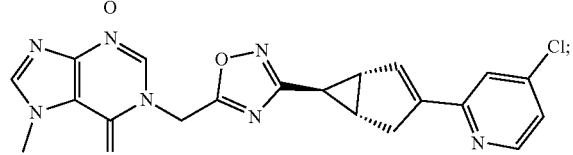
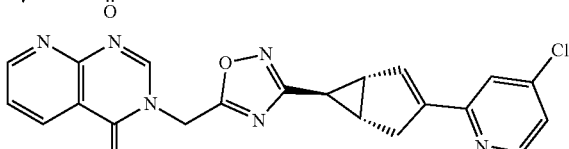
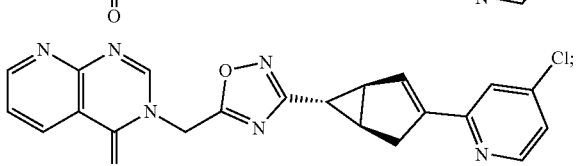
504
-continued
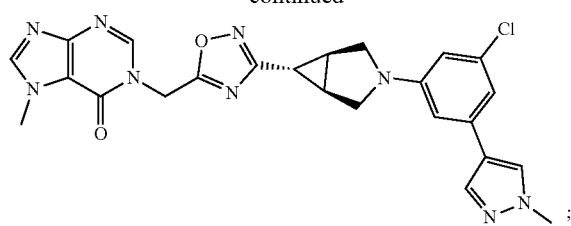
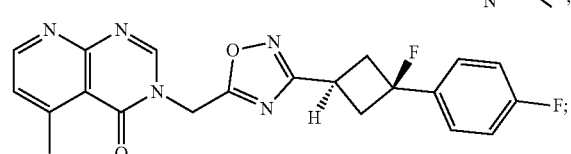
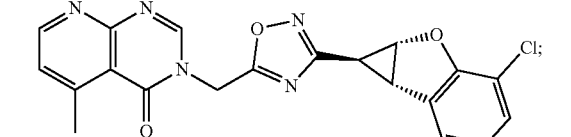
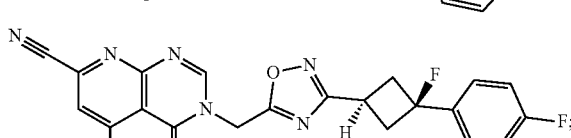
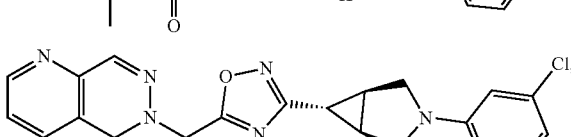
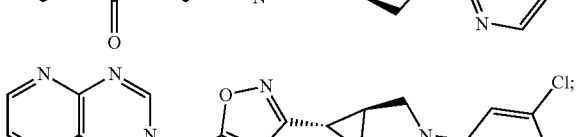
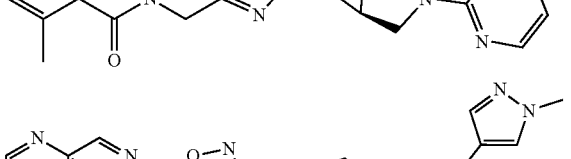
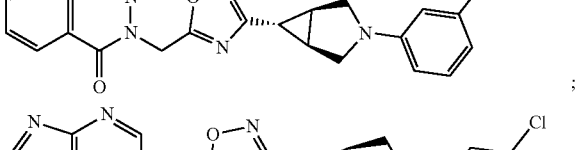
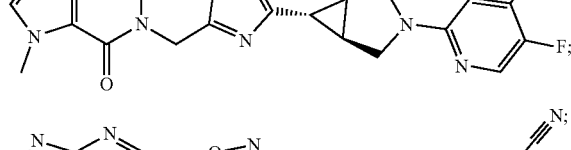
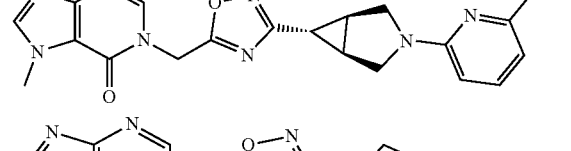
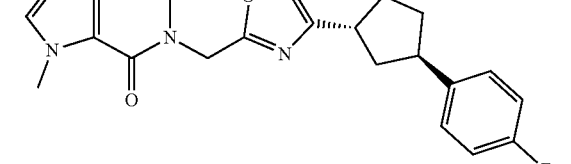

505
-continued
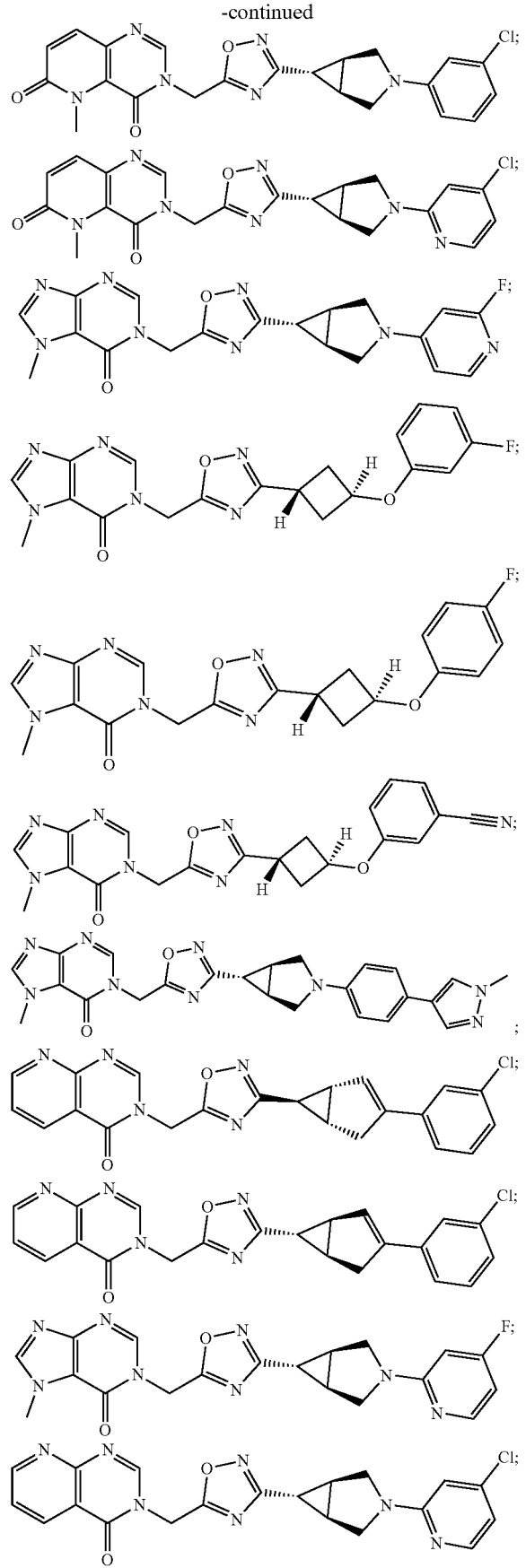
506
-continued
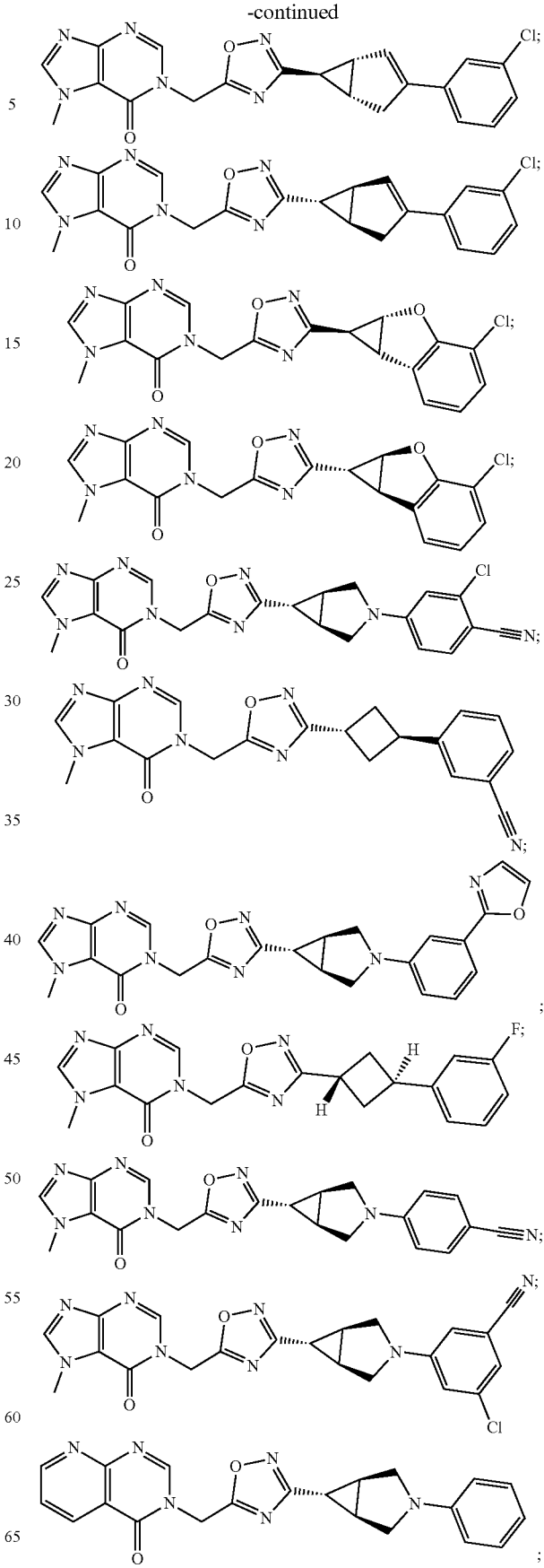

507
-continued
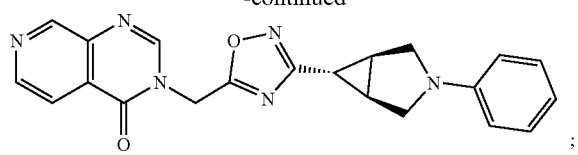
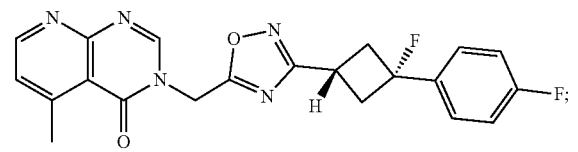
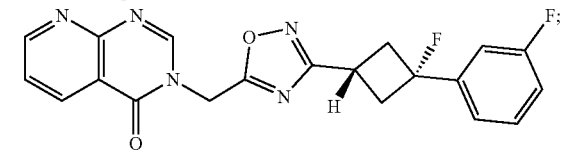
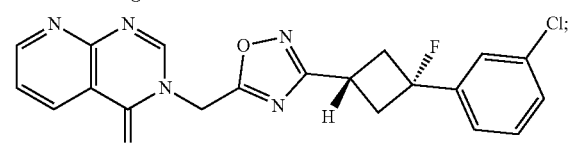
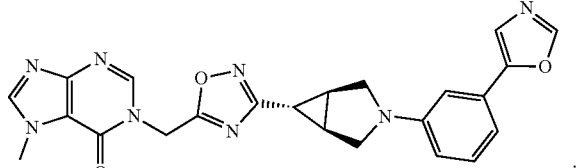
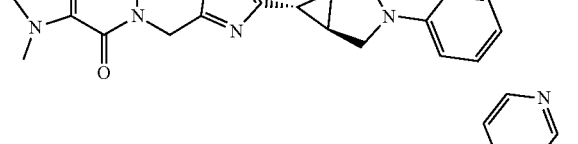
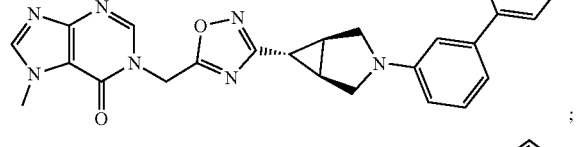
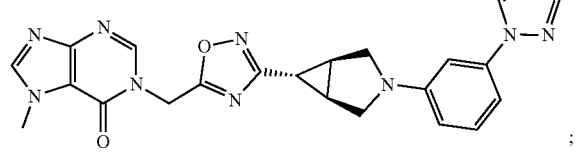
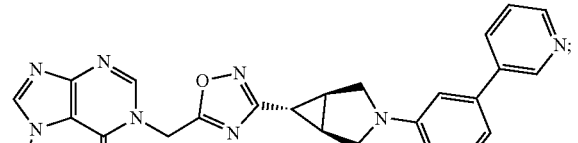
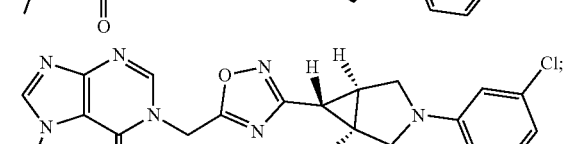
508
-continued
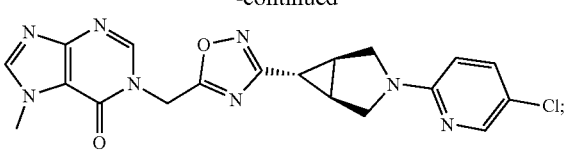
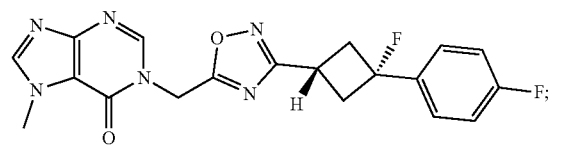
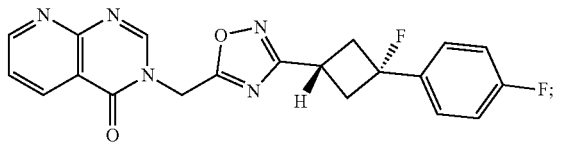
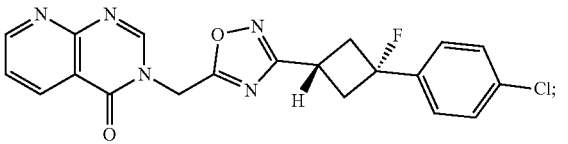
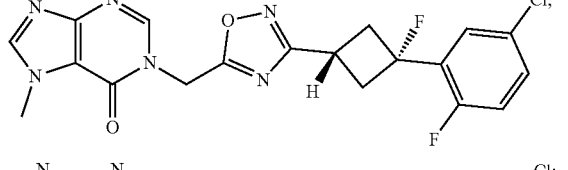
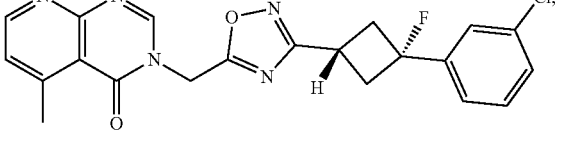
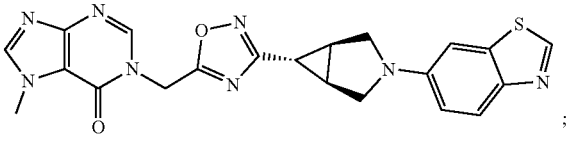
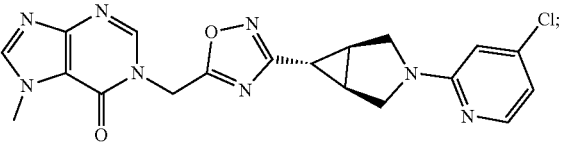
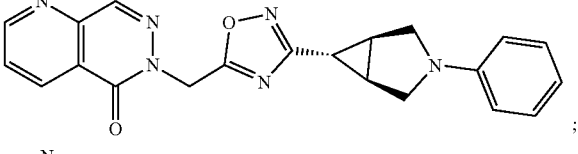
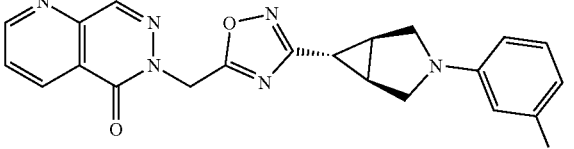
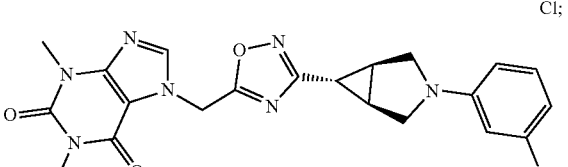

509
-continued
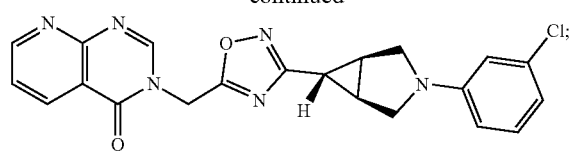
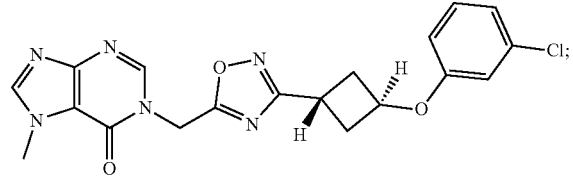
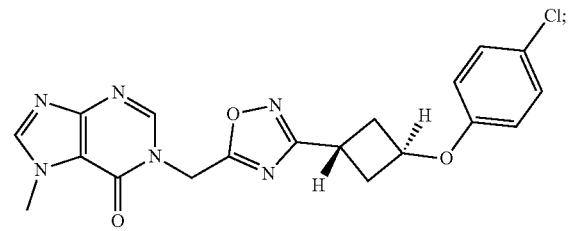
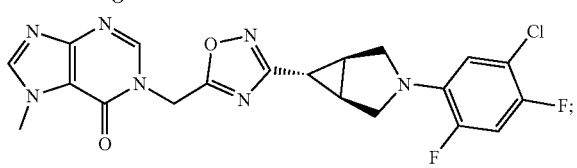
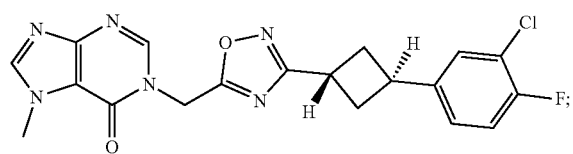
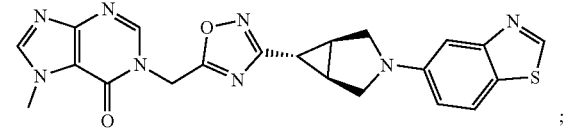
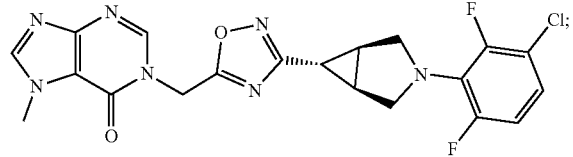
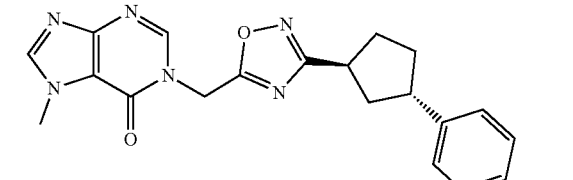
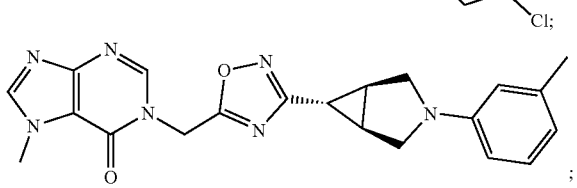
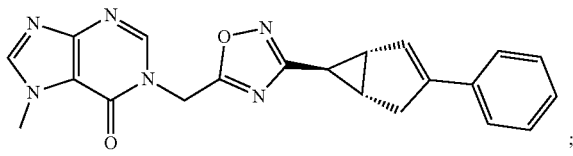
510
-continued
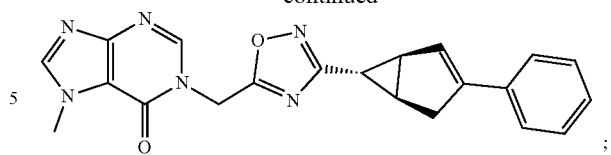
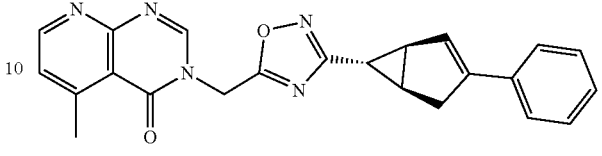
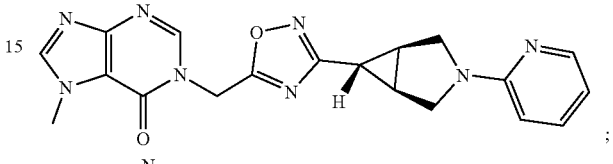
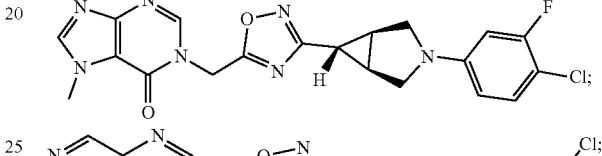
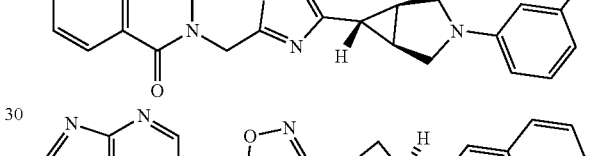
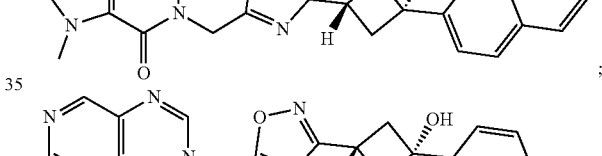
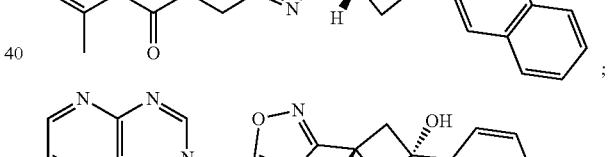
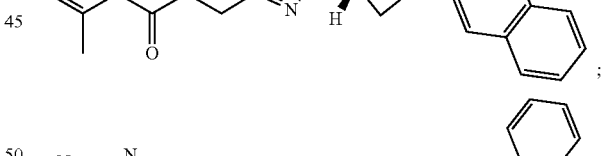
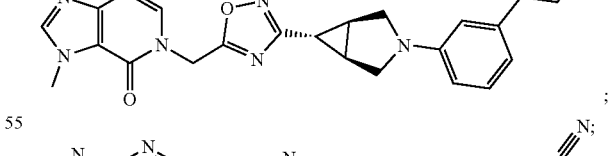
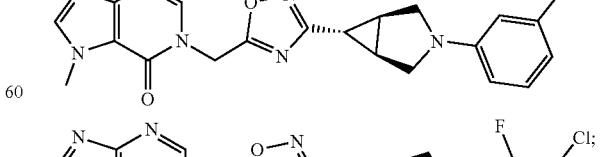
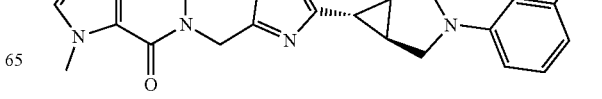

511
-continued
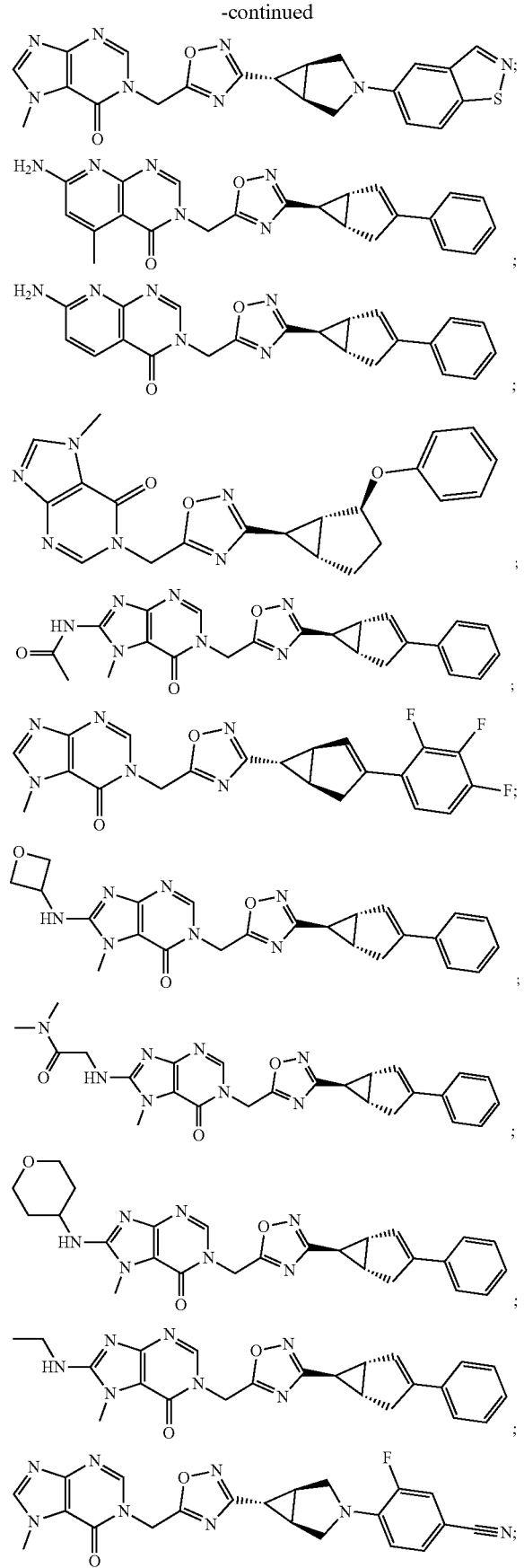
512
-continued
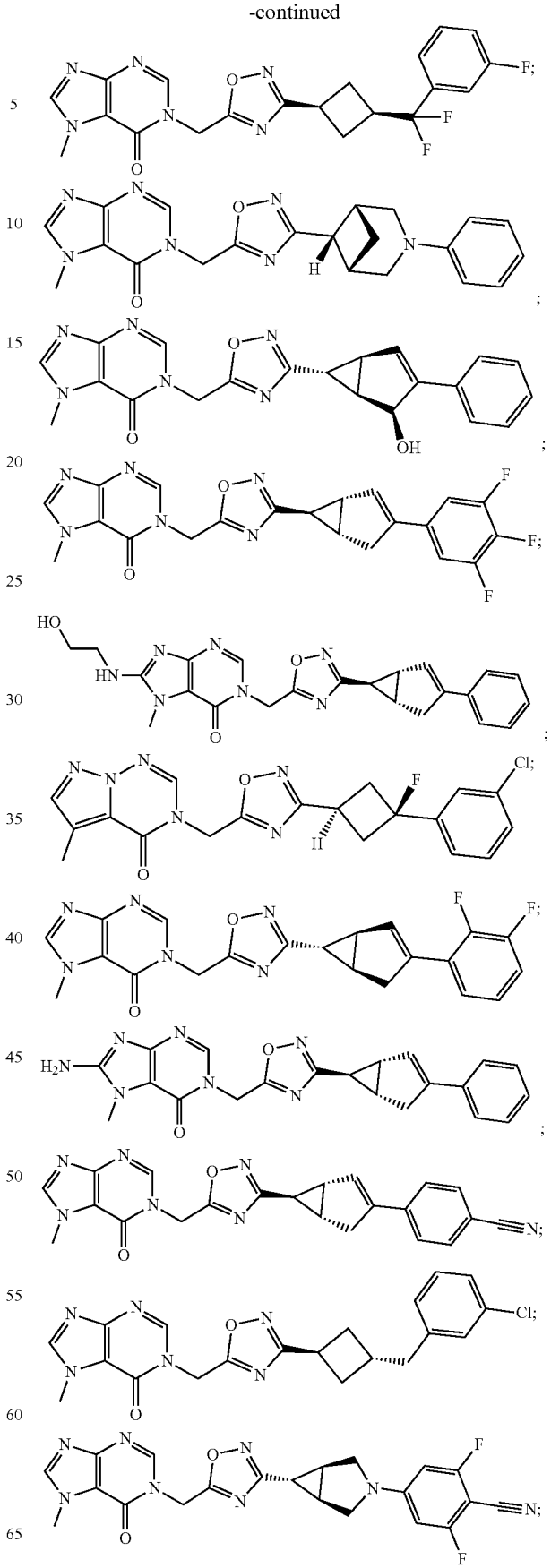

513
-continued
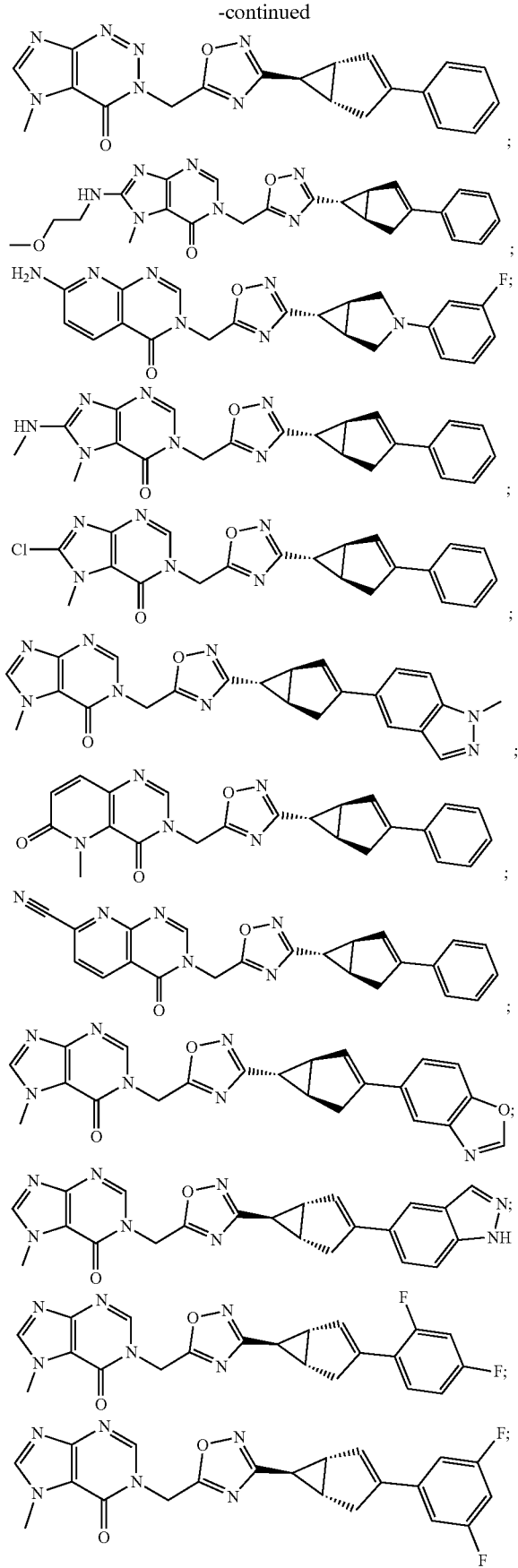
514
-continued
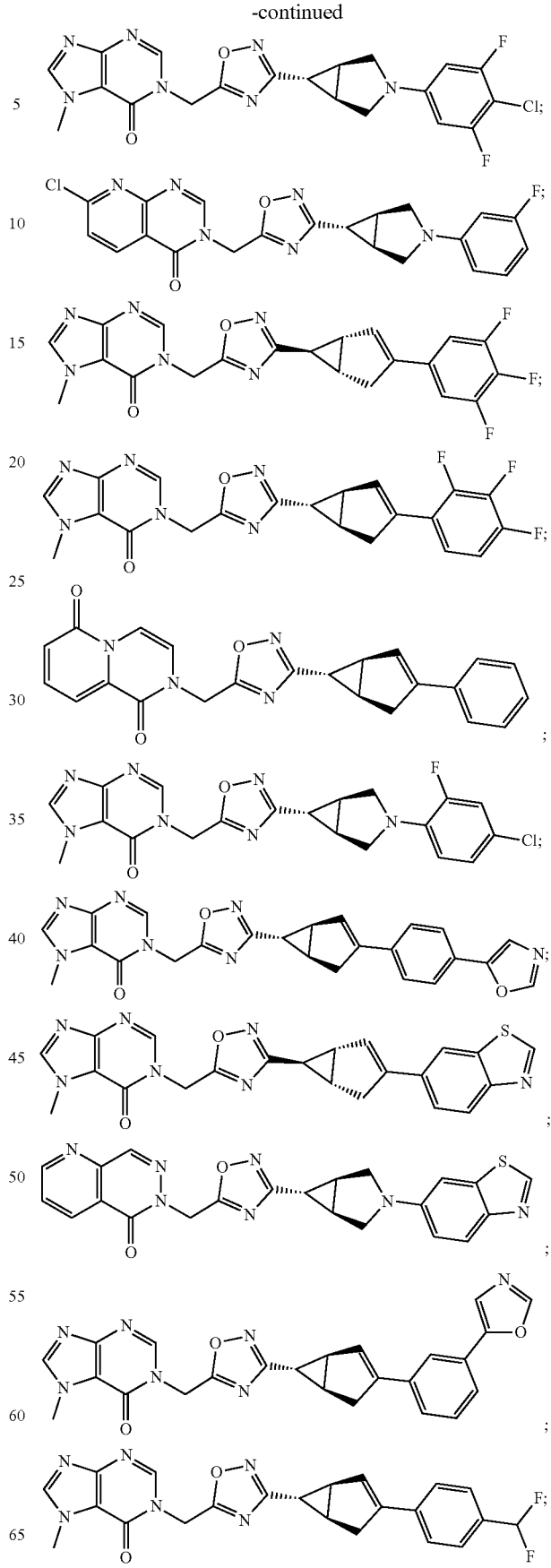

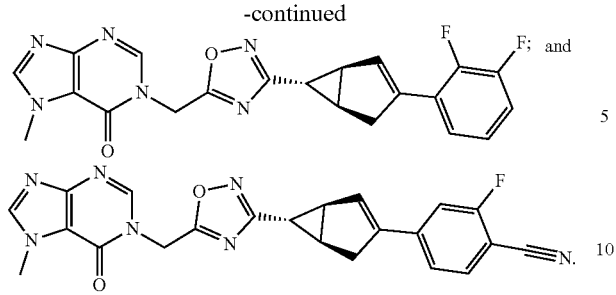

22. A pharmaceutical composition, comprising a compound as described in claim 1 or a pharmaceutically acceptable salt thereof, and a pharmaceutically acceptable carrier, diluent or excipient.

23. A method for treating a respiratory disorder in a mammal comprising, administering a compound as described in claim 1 or a pharmaceutically acceptable salt thereof to the mammal.

* * * * *